US009339510B2

(12) United States Patent
Hartman et al.

(10) Patent No.: US 9,339,510 B2
(45) Date of Patent: May 17, 2016

(54) AZEPANE DERIVATIVES AND METHODS OF TREATING HEPATITIS B INFECTIONS

(71) Applicant: Novira Therapeutics, Inc., Doylestown, PA (US)

(72) Inventors: George D. Hartman, Landsdale, PA (US); Scott Kuduk, Harleysville, PA (US)

(73) Assignee: NOVIRA THERAPEUTICS, INC., Doylestown, PA (US)

( * ) Notice: Subject to any disclaimer, the term of this patent is extended or adjusted under 35 U.S.C. 154(b) by 0 days.

(21) Appl. No.: 14/856,761

(22) Filed: Sep. 17, 2015

(65) Prior Publication Data

US 2016/0000812 A1 Jan. 7, 2016

Related U.S. Application Data

(60) Division of application No. 14/597,814, filed on Jan. 15, 2015, now Pat. No. 9,181,288, which is a continuation-in-part of application No. 14/511,964, filed on Oct. 10, 2014, now Pat. No. 9,169,212.

(60) Provisional application No. 61/928,130, filed on Jan. 16, 2014.

(51) Int. Cl.
| | |
|---|---|
| A61K 31/55 | (2006.01) |
| C07D 223/08 | (2006.01) |
| C07D 267/10 | (2006.01) |
| A61K 31/675 | (2006.01) |
| A61K 38/21 | (2006.01) |
| A61K 39/29 | (2006.01) |
| A61K 45/06 | (2006.01) |

(52) U.S. Cl.
CPC ............... *A61K 31/675* (2013.01); *A61K 38/21* (2013.01); *A61K 38/212* (2013.01); *A61K 38/215* (2013.01); *A61K 38/217* (2013.01); *A61K 39/292* (2013.01); *A61K 45/06* (2013.01)

(58) Field of Classification Search
CPC ............................ C07D 223/08; C07D 267/10
See application file for complete search history.

(56) References Cited

U.S. PATENT DOCUMENTS

| | | | |
|---|---|---|---|
| 4,569,940 A | 2/1986 | Watts | |
| 5,272,167 A | 12/1993 | Girijavallabhan et al. | |
| 5,607,929 A | 3/1997 | Nicol | |
| 5,919,970 A | 7/1999 | Song et al. | |
| 5,939,423 A | 8/1999 | Karlin | |
| 6,650,463 B2 | 11/2003 | Obikawa et al. | |
| 7,186,735 B2 | 3/2007 | Strobel et al. | |
| 7,338,956 B2 | 3/2008 | Strobel et al. | |
| 7,595,322 B2 | 9/2009 | Morgan et al. | |
| 7,750,158 B2 | 7/2010 | Shankar et al. | |
| 7,888,373 B2 | 2/2011 | Morgan et al. | |
| 8,084,457 B2 | 12/2011 | Choidas et al. | |
| 8,097,728 B2 | 1/2012 | Gu et al. | |
| 8,101,620 B2 | 1/2012 | Morgan et al. | |
| 8,153,803 B2 | 4/2012 | Kazantsev | |
| 8,404,747 B2 | 3/2013 | Kazantsev et al. | |
| 8,609,668 B2 | 12/2013 | Cuconati et al. | |
| 8,629,274 B2 | 1/2014 | Hartman et al. | |
| 8,993,771 B2 | 3/2015 | Hartman et al. | |
| 9,061,008 B2 | 6/2015 | Hartman et al. | |
| 9,066,932 B2 | 6/2015 | Hartman et al. | |
| 9,169,212 B2 | 10/2015 | Hartman et al. | |
| 9,181,288 B2 | 11/2015 | Hartman et al. | |
| 2004/0039009 A1 | 2/2004 | Prakash et al. | |
| 2005/0009871 A1 | 1/2005 | Ramesh et al. | |
| 2005/0054850 A1 | 3/2005 | Wu et al. | |
| 2005/0239833 A1 | 10/2005 | Kazantsev et al. | |
| 2006/0100228 A1 | 5/2006 | Shankar et al. | |
| 2007/0142440 A1 | 6/2007 | Burgdorf et al. | |
| 2009/0036420 A1 | 2/2009 | Galley et al. | |
| 2009/0105218 A1 | 4/2009 | Ulven et al. | |
| 2009/0163545 A1 | 6/2009 | Goldfarb | |
| 2009/0259044 A1 | 10/2009 | Kazantsev | |
| 2011/0009622 A1 | 1/2011 | Jitsuoka et al. | |
| 2011/0184019 A1 | 7/2011 | Zitzmann et al. | |
| 2011/0189771 A1 | 8/2011 | Block et al. | |
| 2011/0275630 A1 | 11/2011 | Matulenko et al. | |
| 2013/0142827 A1 | 6/2013 | Block et al. | |
| 2013/0203733 A1 | 8/2013 | Kazantsev et al. | |
| 2013/0267517 A1 | 10/2013 | Guo et al. | |
| 2013/0303552 A1 | 11/2013 | Xu et al. | |
| 2015/0152073 A1 | 6/2015 | Hartman et al. | |
| 2015/0174115 A1 | 6/2015 | Hartman et al. | |
| 2015/0197533 A1 | 7/2015 | Hartman et al. | |
| 2015/0216938 A1 | 8/2015 | Hartman | |

(Continued)

FOREIGN PATENT DOCUMENTS

| | | |
|---|---|---|
| CN | 102093320 A | 6/2011 |
| EP | 0 742 200 B1 | 7/1999 |

(Continued)

OTHER PUBLICATIONS

[Online] Registry via STN, May 6, 2011, RN 1291044-81-9.
[Online] Registry via STN, Oct. 7, 2008, RN 1057788-44-9.
[Online] Registry via STN, Oct. 7, 2008, RN 1057871-39-2.
[Online] Registry via STN, Aug. 15, 2011, RN 1317923-24-2.
[Online] Registry via STN, Aug. 15, 2011, RN 1318022-74-0.
[Online] Registry via STN, May 18, 2011, RN 1296380-95-4.
[Online] Registry via STN, Oct. 18, 2000, RN 296894-70-7.
[Online] Registry via STN, Sep. 20, 2013, RN 1452780-00-5.
Campagna et al. (Apr. 10, 2013) "Sulfamoylbenzamide Derivatives Inhibit the Assembly of Hepatitis B Virus Nucleocapsids," Journal of Virology. 87(12):6931-6942.
Duan et al. (2009) "2-Phenylquinazolin-4(3H)-one, a class of potent PDE5 inhibitors with high selectivity versus PDE6," Bioorganic and Medicinal Chemistry. 19(10):2777-2779.

(Continued)

*Primary Examiner* — Brian McDowell
(74) *Attorney, Agent, or Firm* — Lathrop & Gage LLP; Brian C. Trinque; Benjamin D. Heuberger

(57) ABSTRACT

Provided herein are compounds useful for the treatment of HBV infection in a subject in need thereof, pharmaceutical compositions thereof, and methods of inhibiting, suppressing, or preventing HBV infection in the subject.

20 Claims, No Drawings

(56) References Cited

U.S. PATENT DOCUMENTS

| | | |
|---|---|---|
| 2015/0225355 A1 | 8/2015 | Hartman |
| 2015/0259324 A1 | 9/2015 | Hartman et al. |

FOREIGN PATENT DOCUMENTS

| | | | |
|---|---|---|---|
| EP | 2 280 001 A1 | 2/2011 | |
| WO | 84/03281 A1 | 8/1984 | |
| WO | 99/23285 A1 | 6/1998 | |
| WO | 99/38845 A1 | 8/1999 | |
| WO | 99/48492 A1 | 9/1999 | |
| WO | 99/65906 A1 | 12/1999 | |
| WO | 01/05390 A2 | 1/2001 | |
| WO | 01/19788 A2 | 3/2001 | |
| WO | 01/55121 A1 | 8/2001 | |
| WO | 01/85694 A1 | 11/2001 | |
| WO | 02/051410 A2 | 7/2002 | |
| WO | 03/007955 A2 | 1/2003 | |
| WO | 03/044016 A1 | 5/2003 | |
| WO | 2004/022060 A2 | 3/2004 | |
| WO | 2004/058709 A1 | 7/2004 | |
| WO | 2004/086865 A1 | 10/2004 | |
| WO | 2004/099192 A2 | 11/2004 | |
| WO | 2004/100947 A2 | 11/2004 | |
| WO | 2005/016922 A2 | 2/2005 | |
| WO | 2005/044797 A1 | 5/2005 | |
| WO | 2005/087217 A1 | 9/2005 | |
| WO | 2005/105785 A2 | 11/2005 | |
| WO | 2005/115374 A1 | 12/2005 | |
| WO | 2006/002133 A1 | 1/2006 | |
| WO | 2006/024834 A1 | 3/2006 | |
| WO | 2006/053109 A1 | 5/2006 | |
| WO | 2006/067445 A2 | 6/2006 | |
| WO | 2006/067446 A1 | 6/2006 | |
| WO | 2006/123257 A2 | 11/2006 | |
| WO | 2006/128129 A2 | 11/2006 | |
| WO | 2006/128172 A2 | 11/2006 | |
| WO | 2007/031791 A1 | 3/2007 | |
| WO | 2008/011476 A2 | 1/2008 | |
| WO | 2008/022171 A1 | 2/2008 | |
| WO | 2008/093614 A1 | 8/2008 | |
| WO | 2008/137794 A1 | 11/2008 | |
| WO | 2009/016088 A1 | 2/2009 | |
| WO | 2009/062402 A1 | 5/2009 | |
| WO | 2009/086303 A2 | 7/2009 | |
| WO | 2009/131065 A1 | 10/2009 | |
| WO | 2010/018113 A2 | 2/2010 | |
| WO | 2010/043592 A1 | 4/2010 | |
| WO | 2010/088000 A2 | 8/2010 | |
| WO | 2010/123139 A1 | 10/2010 | |
| WO | 2011/002635 A1 | 1/2011 | |
| WO | 2011/088015 A1 | 7/2011 | |
| WO | 2011/088561 A1 | 7/2011 | |
| WO | 2011/109237 A2 | 9/2011 | |
| WO | 2011/112191 A1 | 9/2011 | |
| WO | 2011/123609 A1 | 10/2011 | |
| WO | 2011/155898 A1 | 12/2011 | |
| WO | 2012/016133 A2 | 2/2012 | |
| WO | 2012/018635 A2 | 2/2012 | |
| WO | 2012/075235 A1 | 6/2012 | |
| WO | 2012/080050 A1 | 6/2012 | |
| WO | 2012/136834 A1 | 10/2012 | |
| WO | 2013/006394 A1 | 1/2013 | |
| WO | 2013/096744 A1 | 6/2013 | |
| WO | 2013/102655 A1 | 7/2013 | |
| WO | 2013/130703 A2 | 9/2013 | |
| WO | 2013/181584 A2 | 12/2013 | |
| WO | 2014/033167 A1 | 3/2014 | |
| WO | 2014/033170 A1 | 3/2014 | |
| WO | 2014/033176 A1 | 3/2014 | |
| WO | 2014/037480 A1 | 3/2014 | |

OTHER PUBLICATIONS

Ei-Sharief et al. (1987) "Synthesis of different types of chlorinated sulfonamides with expected insecticidal and bactericidal activities," Proceedings of the Indian National Science Academy, Part A: Physical Sciences. 53 (1):179-188.

Ermann et al. (2008) "Arylsulfonamide CB2 receptor agonists: SAR and optimization of CB2 selectivity," Bioorganic & Medicinal Chemistry Letters. 18(5):1725-1729.

International Search Report corresponding to International Patent Application No. PCT/US2012/071195, mailed Dec. 21, 2012.

International Search Report with Written Opinion corresponding to International Patent Application No. PCT/US2015/011663, mailed Apr. 29, 2015.

International Search Report with Written Opinion corresponding to International Patent Application No. PCT/US2015/014663, mailed Apr. 29, 2015.

Kim et al. (Apr. 9, 2011) "Discovery of novel HCV polymerase inhibitors using pharmacophore-based virtual screening," Bioorganic and Medicinal Chemistry. 21(11):3329-3334.

Lambeng et al. (2007) "Arylsulfonamides as a new class of cannabinoid CB1 receptor ligands: Identification of a lead and initial SAR studies," Bioorganic & Medicinal Chemistry Letters. 17(1):272-277.

Mohamed et al. (1986) "Synthesis of different types of chlorinated sulfonamides with expected insecticidal and antimicrobial activities," Acta Pharmaceutica Jugoslavica. 36(3):301-310.

Search Report with Written Opinion corresponding to Singapore Patent Application No. 11201402660Y, completed May 22, 2015.

Supplementary European Search Report corresponding to European Patent Application No. 12859684, dated May 27, 2015.

Taylor et al. (Mar. 3, 2011) "A Brain-Permeable Small Molecule Reduces Neuronal Cholesterol by Inhibiting Activity of Sirtuin 2 Deacetylase," ACS Chemical Biology. 6(6):540-546.

Lau et al. (2005) "Peginterferon Alfa-2a, Lamivudine, and the Combination for HBeAg-Positive Chronic Hepatitis B," The New England Journal of Medicine. 352(26):2682-2695.

Liaw et al. (2009) "Hepatitis B virus infection," Lancet. 373:582-592.

Patani et al. (1996) "Bioisosterism: A Rational Approach in Drug Design," Chem. Rev. 96:3147-3176.

Thompson et al. (2007) "Toll-like receptors, RIG-I-like RNA helicases and the antiviral innate immune response," Immunology and Cell Biology. 85:435-445.

AZEPANE DERIVATIVES AND METHODS OF TREATING HEPATITIS B INFECTIONS

RELATED APPLICATIONS

This application is a divisional of U.S. application Ser. No. 14/597,814, filed Jan. 15, 2015, which is a continuation-in-part of U.S. application Ser. No. 14/511,964, filed Oct. 10, 2014 which claims priority to U.S. Provisional Application No. 61/928,130, filed Jan. 16, 2014. The entire contents of these applications are incorporated herein by reference in their entirety.

BACKGROUND

Chronic hepatitis B virus (HBV) infection is a significant global health problem, affecting over 5% of the world population (over 350 million people worldwide and 1.25 million individuals in the U.S.).

Despite the availability of a prophylactic HBV vaccine, the burden of chronic HBV infection continues to be a significant unmet worldwide medical problem, due to suboptimal treatment options and sustained rates of new infections in most parts of the developing world. Current treatments do not provide a cure and are limited to only two classes of agents (interferon and nucleoside analogues/inhibitors of the viral polymerase); drug resistance, low efficacy, and tolerability issues limit their impact. The low cure rates of HBV are attributed at least in part to the presence and persistence of covalently closed circular DNA (cccDNA) in the nucleus of infected hepatocytes. However, persistent suppression of HBV DNA slows liver disease progression and helps to prevent hepatocellular carcinoma. Current therapy goals for HBV-infected patients are directed to reducing serum HBV DNA to low or undetectable levels, and to ultimately reducing or preventing the development of cirrhosis and hepatocellular carcinoma.

There is a need in the art for therapeutic agents that treat, ameliorate or prevent HBV infection. Administration of these therapeutic agents to an HBV infected patient, either as monotherapy or in combination with other HBV treatments or ancillary treatments, will lead to significantly improved prognosis, diminished progression of the disease, and enhanced seroconversion rates.

SUMMARY OF THE INVENTION

Provided herein are compounds useful for the treatment of HBV infection in a subject in need thereof.

In one aspect, provided herein are compounds having the Formula I:

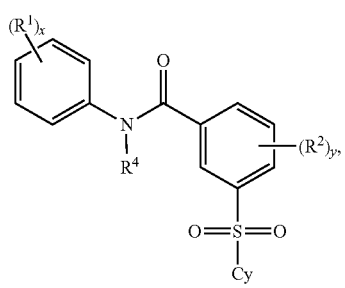

I or a pharmaceutically acceptable salt thereof.

In one embodiment, the compound of Formula I has the Formula II,

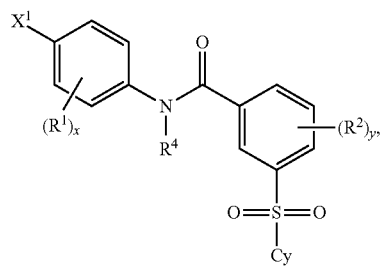

II or a pharmaceutically acceptable salt thereof.

In another embodiment, the compound of Formula I has the Formula III,

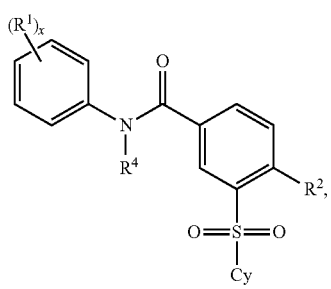

III or a pharmaceutically acceptable salt thereof.

In another aspect, provided herein are compounds having the Formula IV:

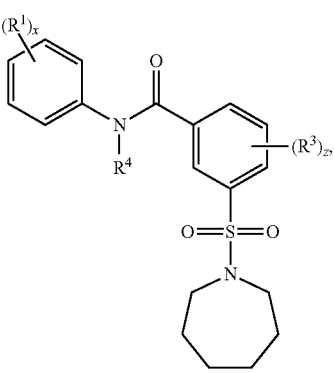

IV or a pharmaceutically acceptable salt thereof.

In another aspect, provided herein are compounds having the Formula V:

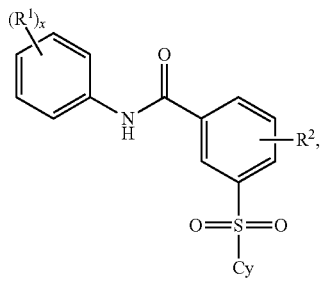

V or a pharmaceutically acceptable salt thereof.

In another aspect, provided herein are pharmaceutical compositions comprising a compound of Formula I, Ia, Ib, II, III, IV, V, Vx, or Va, or a pharmaceutically acceptable salt thereof, together with a pharmaceutically acceptable carrier.

In one aspect, provided herein is a method of treating an HBV infection in an individual in need thereof, comprising administering to the individual a therapeutically effective amount of a compound of Formula I, Ia, Ib, II, III, IV, V, Vx, or Va.

In another aspect, provided herein is a method of eradicating an HBV infection in an individual in need thereof, comprising administering to the individual a therapeutically effective amount of a compound of Formula I, Ia, Ib, II, III, IV, V, Vx, or Va.

In another aspect, provided herein is a method of reducing viral load associated with an HBV infection in an individual in need thereof, comprising administering to the individual a therapeutically effective amount of a compound of Formula I, Ia, Ib, II, III, IV, V, Vx, or Va.

In still another aspect, provided herein is a method of reducing reoccurrence of an HBV infection in an individual in need thereof, comprising administering to the individual a therapeutically effective amount of a compound of Formula I, Ia, Ib, II, III, IV, V, Vx, or Va.

In yet another aspect, provided herein is a method of reducing an adverse physiological impact of an HBV infection in an individual in need thereof, comprising administering to the individual a therapeutically effective amount of a compound of Formula I, Ia, Ib, II, III, IV, V, Vx, or Va.

Also provided herein are methods of inducing remission of hepatic injury from an HBV infection in an individual in need thereof, comprising administering to the individual a therapeutically effective amount of a compound of Formula I, Ia, Ib, II, III, IV, V, Vx, or Va.

In another aspect, provided herein is a method of reducing the physiological impact of long-term antiviral therapy for HBV infection in an individual in need thereof, comprising administering to the individual a therapeutically effective amount of a compound of Formula I, Ia, Ib, II, III, IV, V, Vx, or Va.

In another aspect, provided herein is method of prophylactically treating an HBV infection in an individual in need thereof, wherein the individual is afflicted with a latent HBV infection, comprising administering to the individual a therapeutically effective amount of a compound of Formula I, Ia, Ib, II, III, IV, V, Vx, or Va.

Any of the above methods may further comprise administration to the individual at least one additional therapeutic agent. In an embodiment, the additional therapeutic agent may be selected from, but not limited to, the group consisting of a HBV polymerase inhibitor, immunomodulatory agents, pegylated interferon, viral entry inhibitor, viral maturation inhibitor, capsid assembly modulator, reverse transcriptase inhibitor, a cyclophilin/TNF inhibitor, a TLR-agonist, an HBV vaccine, and agents of distinct or unknown mechanism, and a combination thereof.

In another embodiment, the additional therapeutic agent is selected from the group consisting of a HBV polymerase inhibitor, interferon, viral entry inhibitor, viral maturation inhibitor, capsid assembly modulator, reverse transcriptase inhibitor, a TLR-agonist, and agents of distinct or unknown mechanism, and a combination thereof.

In another embodiment, the additional therapeutic agent is a reverse transcriptase inhibitor and is at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, cidofovir, Efavirenz, Nevirapine, Delavirdine, or Etravirine.

In another embodiment of the combination therapy, the additional therapeutic agent is a TLR agonist. In a preferred embodiment, the TLR agonist is a TLR-7 agonist selected from the group consisting of SM360320 (9-benzyl-8-hydroxy-2-(2-methoxy-ethoxy)adenine) and AZD 8848 (methyl[3-({[3-(6-amino-2-butoxy-8-oxo-7,8-dihydro-9H-purin-9-yl)propyl][3-(4-morpholinyl)propyl]amino}methyl)phenyl]acetate).

In a further embodiment of the combination therapy, the additional therapeutic agent is an interferon, wherein the interferon is any interferon, which may be optionally pegylated. In yet a further embodiment, the interferon is interferon alpha (IFN-α), interferon beta (IFN-β), interferon lambda (IFN-λ), or interferon gamma (IFN-γ). In a preferred embodiment, the interferon is interferon-alpha-2a, interferon-alpha-2b, interferon-alpha-n1, pegylated interferon-alpha-2a, or pegylated interferon-alpha-2b.

In any of the methods provided herein, the method may further comprise administering to the individual at least one HBV vaccine, a nucleoside HBV inhibitor, or any combination thereof. In an embodiment, the HBV vaccine is at least one of RECOMBIVAX HB, ENGERIX-B, ELOVAC B, GENEVAC-B, or SHANVAC B.

In another embodiment of the methods provided herein, administering the compound of Formula I, Ia, Ib, II, III, IV, V, Vx, or Va allows for administering of the at least one additional therapeutic agent at a lower dose or frequency as compared to the administering of the at least one additional therapeutic agent alone that is required to achieve similar results in prophylactically treating an HBV infection in an individual in need thereof.

In another embodiment of the methods provided herein, administering the compound of Formula I, Ia, Ib, II, III, IV, V, Vx, or Va reduces the viral load in the individual to a greater extent or at a faster rate compared to the administering of a compound selected from the group consisting of a HBV polymerase inhibitor, interferon, viral entry inhibitor, viral maturation inhibitor, distinct capsid assembly modulator, antiviral compounds of distinct or unknown mechanism, and any combination thereof.

In another embodiment of the methods provided herein, the administering of the compound of Formula I, Ia, Ib, II, III, IV, V, Vx, or Va causes a lower incidence of viral mutation and/or viral resistance than the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In another aspect, provided herein is method of treating an HBV infection in an individual in need thereof, comprising reducing the HBV viral load by administering to the individual a therapeutically effective amount of a compound of Formula I, Ia, Ib, II, III, IV, V, Vx, or Va alone or in combination with a reverse transcriptase inhibitor; and further administering to the individual a therapeutically effective amount of HBV vaccine. In an embodiment, the reverse transcriptase inhibitor is at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, cidofovir, Efavirenz, Nevirapine, Delavirdine, or Etravirine In another embodiment of the methods provided herein, the method further comprises monitoring the HBV viral load, and wherein the method is carried out for a period of time such that the HBV virus is undetectable.

DETAILED DESCRIPTION OF THE INVENTION

Provided herein are compounds that are useful in the treatment and prevention of HBV infection in man. In a non-limiting aspect, these compounds may modulate or disrupt HBV assembly and other HBV core protein functions necessary for the generation of infectious particles by interacting with HBV capsid to afford defective viral particles with greatly reduced virulence. The compounds of the invention have potent antiviral activity, exhibit favorable metabolic, tissue distribution, safety and pharmaceutical profiles, and are suitable for use in man.

The HBV capsid protein plays essential functions during the viral life cycle. HBV capsid/core proteins form metastable viral particles or protein shells that protect the viral genome during intercellular passage, and also play a central role in viral replication processes, including genome encapsidation, genome replication, and virion morphogenesis and egress. Capsid structures also respond to environmental cues to allow un-coating after viral entry. Consistently, proper capsid assembly and function of core protein have been found to be critical for viral infectivity.

The crucial function of HBV capsid proteins imposes stringent evolutionary constraints on the viral capsid protein sequence, leading to the observed low sequence variability and high conservation. Consistently, mutations in HBV capsid that disrupt its assembly are lethal, and mutations that perturb capsid stability severely attenuate viral replication. The more conserved a drug target is, the fewer replication-competent resistance mutations are acquired by patients. Indeed, natural mutations in HBV capsid for chronically infected patients accumulate in only four out of 183 residues in the full length protein. Thus, HBV capsid assembly and function inhibitors may elicit lower drug resistance emergence rates relative to existing HBV antivirals. Further, drug therapy that targets HBV capsid could be less prone to drug-resistant mutations when compared to drugs that target traditional neuraminidase enzyme active sites. Reports describing compounds that bind viral capsids and inhibit replication of HIV, rhinovirus and HBV provide strong pharmacological proof of concept for viral capsid proteins as antiviral drug targets.

In one aspect, the compounds of the invention are useful in HBV treatment by disrupting, accelerating, reducing, delaying and/or inhibiting normal viral capsid assembly and/or disassembly of immature or mature particles, thereby inducing aberrant capsid morphology and leading to antiviral effects such as disruption of virion assembly and/or disassembly, virion maturation, and/or virus egress. In one embodiment, a disruptor of capsid assembly interacts with mature or immature viral capsid to perturb the stability of the capsid, thus affecting assembly and/or disassembly. In another embodiment, a disruptor of capsid assembly perturbs protein folding and/or salt bridges required for stability, function and/or normal morphology of the viral capsid, thereby disrupting and/or accelerating capsid assembly and/or disassembly. In yet another embodiment, the compounds of the invention bind capsid and alter metabolism of cellular polyproteins and precursors, leading to abnormal accumulation of protein monomers and/or oligomers and/or abnormal particles, which causes cellular toxicity and death of infected cells. In another embodiment, the compounds of the invention cause failure of the formation of capsid of optimal stability, affecting efficient uncoating and/or disassembly of viruses (e.g., during infectivity).

In one embodiment, the compounds of the invention disrupt and/or accelerate capsid assembly and/or disassembly when the capsid protein is immature. In another embodiment, the compounds of the invention disrupt and/or accelerate capsid assembly and/or disassembly when the capsid protein is mature. In yet another embodiment, the compounds of the invention disrupt and/or accelerate capsid assembly and/or disassembly during vial infectivity. In yet another embodiment, the disruption and/or acceleration of capsid assembly and/or disassembly attenuates HBV viral infectivity and/or reduces viral load. In yet another embodiment, disruption, acceleration, inhibition, delay and/or reduction of capsid assembly and/or disassembly eradicates the virus from the host organism. In yet another embodiment, eradication of the HBV from a host advantageously obviates the need for chronic long-term therapy and/or reduces the duration of long-term therapy.

In one embodiment, the compounds described herein are suitable for monotherapy and are effective against natural or native HBV strains and against HBV strains resistant to currently known drugs. In another embodiment, the compounds described herein are suitable for use in combination therapy.

In another embodiment, the compounds of the invention can be used in methods of modulating (e.g., inhibit or disrupt) the activity, stability, function, and viral replication properties of HBV cccDNA. In yet another embodiment, the compounds of the invention can be used in methods of diminishing or preventing the formation of HBV cccDNA.

In another embodiment, the compounds of the invention can be used in methods of modulating (e.g., inhibit or disrupt) the activity of HBV cccDNA. In yet another embodiment, the compounds of the invention can be used in methods of diminishing or preventing the formation of HBV cccDNA.

Definitions

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "capsid assembly modulator" refers to a compound that disrupts or accelerates or inhibits or hinders or delays or reduces or modifies normal capsid assembly (e.g., during maturation) or normal capsid disassembly (e.g., during infectivity) or perturbs capsid stability, thereby inducing aberrant capsid morphology and function. In one embodiment, a capsid assembly modulator accelerates capsid assembly or disassembly, thereby inducing aberrant capsid morphology. In another embodiment, a capsid assembly modulator interacts (e.g. binds at an active site, binds at an allosteric site, modifies and/or hinders folding and the like) with the major capsid assembly protein (CA), thereby disrupting capsid assembly or disassembly. In yet another embodiment, a capsid assembly modulator causes a perturbation in structure or function of CA (e.g., ability of CA to assemble, disassemble, bind to a substrate, fold into a suitable conformation, or the like), which attenuates viral infectivity and/or is lethal to the virus.

As used herein, the term "treatment" or "treating," is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has HBV infection, a symptom of HBV infection or the potential to develop HBV infection, with the purpose to cure, heal, alleviate, relieve, alter, remedy, ameliorate, improve or affect HBV infection, the symptoms of HBV infection or the potential to develop HBV infection. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject or individual is human.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "alkyl," by itself or as part of another substituent means, unless otherwise stated, a straight or branched chain hydrocarbon having the number of carbon atoms designated (i.e., $C_{1-6}$ means one to six carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is $(C_{1-6})$alkyl, particularly ethyl, methyl, isopropyl, isobutyl, n-pentyl, n-hexyl and cyclopropylmethyl.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e., skeletal atoms) is a carbon atom. In one embodiment, the cycloalkyl group is saturated or partially unsaturated. In another embodiment, the cycloalkyl group is fused with an aromatic ring. Cycloalkyl groups include groups having 3 to 10 ring atoms ($C_{3-10}$ cycloalkyl), or groups having 3 to 7 ring atoms ($C_{3-7}$ cycloalkyl). Illustrative examples of cycloalkyl groups include, but are not limited to, the following moieties:

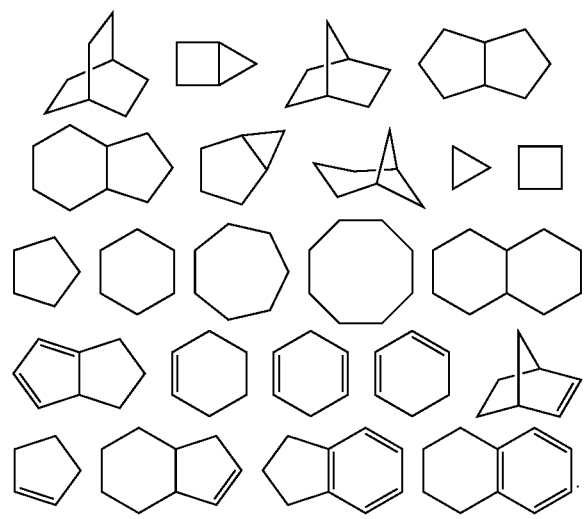

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

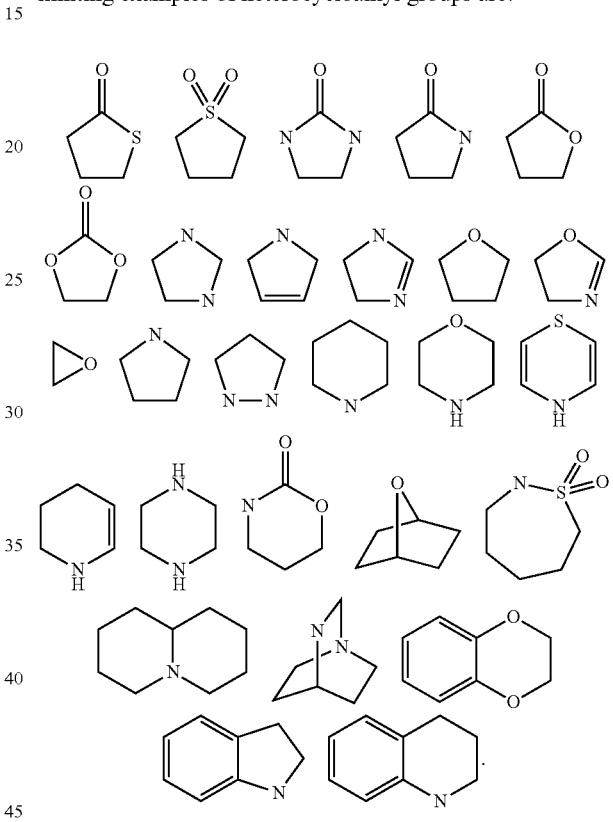

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl. In some embodiments, aryl groups have six carbon atoms. In some embodiments, aryl groups have from six to ten carbon atoms. In some embodiments, aryl groups have from six to sixteen carbon atoms.

As used herein, the term "heteroaryl" or "heteroaromatic" refers to a heterocycle having aromatic character. In some embodiments, heteroaryl or heteroaromatic groups have two to five carbon atoms. In some embodiments, heteroaryl or heteroaromatic groups have from tow to ten carbon atoms. In some embodiments, heteroaryl or heteroaromatic groups have from two to sixteen carbon atoms. A polycyclic heteroaryl may include one or more rings that are partially saturated. In some embodiments, polycyclic heteroaryl groups have two to five carbon atoms. In some embodiments, polycyclic heteroaryl groups have from tow to ten carbon atoms. In some embodiments, polycyclic heteroaryl groups have from two to sixteen carbon atoms. Examples include the following moieties:

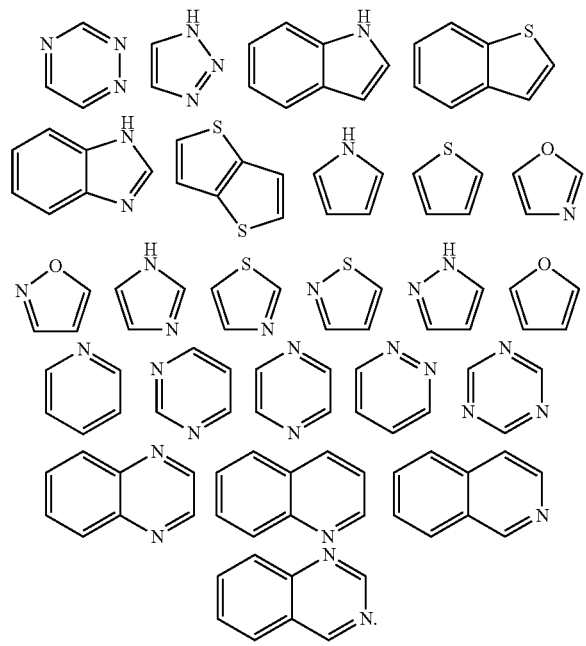

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "ddA" refers to 2',3'-dideoxyadenosine.

Compounds of the Invention

The present invention relates to the discovery of compounds that are useful in the treatment and prevention of HBV infection in man. In one aspect, the compounds of the invention are useful in HBV treatment by disrupting, accelerating, reducing delaying or inhibiting normal viral capsid assembly or disassembly of immature or mature particles, thereby inducing aberrant capsid morphology and leading to antiviral effects such as disruption of virion assembly or disassembly or virion maturation, or virus egress.

In another aspect, compounds of the invention bind to core protein thereby inducing aberrant virion and leading to antiviral effects such as disruption of virion assembly, disassembly, maturation, or virus egress.

The capsid assembly disruptors disclosed herein may be used as monotherapy or in cross-class combination regimens for treating HBV infection in man. Combination therapy with drugs exhibiting different mechanism of action (MOA) that act at different steps in the virus life cycle may deliver greater efficacy due to additive or synergistic antiviral effects. Clinically evaluated HIV treatment regimens have shown that combination therapy improves the efficacy of viral load reduction, and dramatically reduces emergence of antiviral resistance. Combination therapy for the treatment of Hepatitis C (HCV) virus infection has also resulted in significant improvement in sustained antiviral response and eradication rates. Thus, use of the HBV capsid assembly inhibitors of the present invention in combination with, for example, neuraminidase drugs, is likely to deliver a more profound antiviral effect and greater disease eradication rates than current standards of care.

Capsid assembly plays a central role in HBV genome replication. HBV polymerase binds pre-genomic HBV RNA (pgRNA), and pgRNA encapsidation must occur prior to HBV DNA synthesis. Moreover, it is well established that nuclear accumulation of the cccDNA replication intermediate, which is responsible for maintenance of chronic HBV replication in the presence of nucleoside suppressive therapy, requires the capsid for shuttling HBV DNA to the nuclei. Therefore, the HBV capsid assembly disruptors of the invention have the potential to increase HBV eradication rates through synergistic or additive suppression of viral genome replication and to further reduce accumulation of cccDNA when used alone or in combination with existing nucleoside drugs. The capsid assembly disruptors of the present invention may also alter normal core protein function or degradation, potentially leading to altered MHC-1 antigen presentation, which may in turn increase seroconversion/eradication rates through immuno-stimulatory activity, more effectively clearing infected cells.

In one aspect, drug resistance poses a major threat to current therapies for chronic HBV infection, and cross-class combination therapy is a proven strategy for delaying emergence of drug resistance strains. The capsid assembly disruptors of the present invention can, when administered alone or in combination with other HBV therapy, offer enhanced drug resistant profiles and improved management of chronic HBV.

The compounds useful within the invention can be synthesized using techniques well-known in the art of organic synthesis. The starting materials and intermediates required for the synthesis may be obtained from commercial sources or synthesized according to methods known to those skilled in the art.

In one aspect, the compound of the invention is a compound of Formula I:

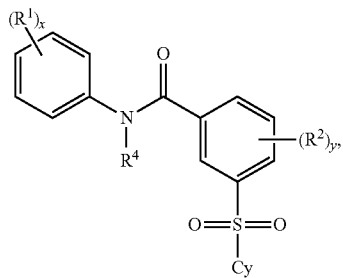

I or a pharmaceutically acceptable salt thereof;
wherein
$R^4$ is H or $C_1$-$C_3$ alkyl;

each $R^1$ is, independently at each occurrence, OH, halo, —CN, —NO$_2$, —C$_1$-C$_6$ alkyl, —O—C$_1$-C$_6$ alkyl, —C$_1$-C$_6$ heteroalkyl, —O—C$_1$-C$_6$ heteroalkyl, —C$_3$-C$_{10}$ cycloalkyl, —C$_3$-C$_{10}$ heterocycloalkyl, aryl, heteroaryl, —C$_1$-C$_4$ alkyl-(C$_3$-C$_{10}$ cycloalkyl), —C$_1$-C$_4$ alkyl-(C$_3$-C$_{10}$ heterocycloalkyl), —C$_1$-C$_4$ alkyl-(aryl), or —C$_1$-C$_4$ alkyl-(heteroaryl), wherein the alkyl, heteroalkyl, cycloalkyl, heterocycloalkyl, aryl and heteroaryl groups are optionally substituted 1-5 times with halo, —OH, —CN, or —NO$_2$;

each $R^2$ is, independently at each occurrence, OH, halo, —CN, —NO$_2$, $R^6$, or OR$^6$, wherein $R^6$ is, independently at each occurrence, —C$_1$-C$_6$ alkyl, —C$_1$-C$_6$ heteroalkyl, —C$_3$-C$_{10}$ cycloalkyl, —C$_3$-C$_{10}$ heterocycloalkyl, aryl, heteroaryl, —C$_1$-C$_4$ alkyl-(C$_3$-C$_{10}$ cycloalkyl), —C$_1$-C$_4$ alkyl-(C$_3$-C$_{10}$ heterocycloalkyl), —C$_1$-C$_4$ alkyl-(aryl), or —C$_1$-C$_4$ alkyl-(heteroaryl), wherein the alkyl, heteroalkyl, cycloalkyl, heterocycloalkyl, aryl and heteroaryl groups are optionally substituted 1-5 times with halo, —OH, —CN, or —NO$_2$;
Cy is

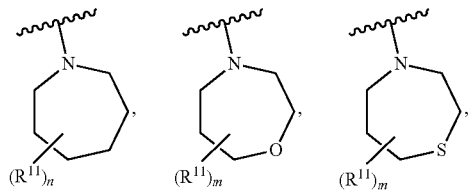

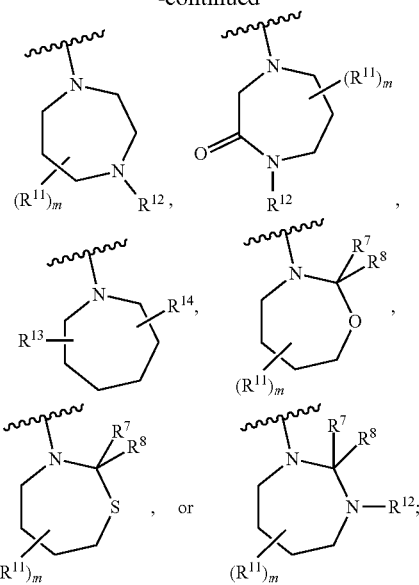

$R^7$ and $R^8$ are, independently at each occurrence, —C$_1$-C$_6$ alkyl, aryl, heteroaryl, —C$_1$-C$_4$ alkyl-(aryl), or —C$_1$-C$_4$ alkyl-(heteroaryl), wherein the aryl or heteroaryl groups are optionally substituted with C$_1$-C$_3$ alkyl;
or $R^7$ and $R^8$ join to form a 3- to 10-membered ring;
$R^{11}$ is, independently at each occurrence, OH, halo, —CN, —NO$_2$, —C$_1$-C$_6$ alkyl, —O—C$_1$-C$_6$ alkyl, —C$_1$-C$_6$ heteroalkyl, —O—C$_1$-C$_6$ heteroalkyl, —C$_3$-C$_{10}$ cycloalkyl, —C$_3$-C$_{10}$ heterocycloalkyl, aryl, heteroaryl, —C$_1$-C$_4$ alkyl-(C$_3$-C$_{10}$ cycloalkyl), —C$_1$-C$_4$ alkyl-(C$_3$-C$_{10}$ heterocycloalkyl), —C$_1$-C$_4$ alkyl-(aryl), or —C$_1$-C$_4$ alkyl-(heteroaryl), wherein the alkyl, heteroalkyl, cycloalkyl, heterocycloalkyl, aryl and heteroaryl groups are optionally substituted 1-5 times with halo, —OH, —CN, or —NO$_2$;
$R^{12}$ is, independently at each occurrence, H or —C$_1$-C$_6$ alkyl;
$R^{13}$ and $R^{14}$ join to form a CH$_2$ bridge;
m is 0, 1, 2, 3, or 4;
n is 1, 2, 3, or 4;
x is 0, 1, 2, 3, 4, or 5; and
y is 0, 1, 2, 3, or 4.

In another aspect, the compound of the invention is a compound of Formula Ia:

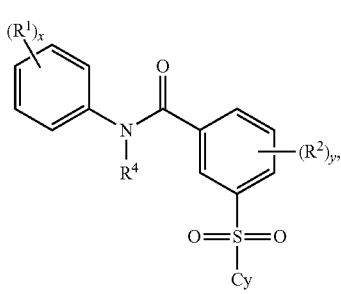

Ia or a pharmaceutically acceptable salt thereof;
wherein
$R^4$ is H or $C_1$-$C_3$ alkyl;
each $R^1$ is, independently at each occurrence, OH, halo, —CN, —NO$_2$, —C$_1$-C$_6$ alkyl, —O—C$_1$-C$_6$ alkyl, —C$_1$-C$_6$ heteroalkyl, —O—C$_1$-C$_6$ heteroalkyl, —C$_3$-C$_{10}$ cycloalkyl, —C$_3$-C$_{10}$ heterocycloalkyl, aryl, heteroaryl, —C$_1$-C$_4$ alkyl-(C$_3$-C$_{10}$ cycloalkyl), —C$_1$-C$_4$ alkyl-(C$_3$-C$_{10}$ heterocycloalkyl), —C$_1$-C$_4$ alkyl-(aryl), or —C$_1$-C$_4$ alkyl-(heteroaryl), wherein the alkyl, heteroalkyl, cycloalkyl, heterocycloalkyl, aryl and heteroaryl groups are optionally substituted 1-5 times with halo, —OH, —CN, or —NO$_2$;

each R$^2$ is, independently at each occurrence, OH, halo, —CN, —NO$_2$, R$^6$, or OR$^6$, wherein R$^6$ is, independently at each occurrence, —C$_1$-C$_6$ alkyl, —C$_1$-C$_6$ heteroalkyl, —C$_3$-C$_{10}$ cycloalkyl, —C$_3$-C$_{10}$ heterocycloalkyl, aryl, heteroaryl, —C$_1$-C$_4$ alkyl-(C$_3$-C$_{10}$ cycloalkyl), —C$_1$-C$_4$ alkyl-(C$_3$-C$_{10}$ heterocycloalkyl), —C$_1$-C$_4$ alkyl-(aryl), or —C$_1$-C$_4$ alkyl-(heteroaryl), wherein the alkyl, heteroalkyl, cycloalkyl, heterocycloalkyl, aryl and heteroaryl groups are optionally substituted 1-5 times with halo, —OH, —CN, or —NO$_2$;

or two R$^2$ groups, and the phenyl ring to which they are attached, join to form benzimidazole;

Cy is

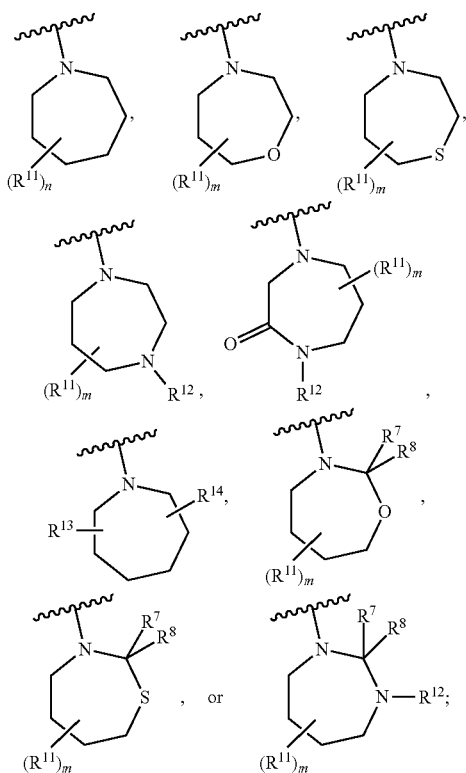

R$^7$ and R$^8$ are, independently at each occurrence, —C$_1$-C$_6$ alkyl, aryl, heteroaryl, —C$_1$-C$_4$ alkyl-(aryl), or —C$_1$-C$_4$ alkyl-(heteroaryl), wherein the aryl or heteroaryl groups are optionally substituted with C$_1$-C$_3$ alkyl;

or R$^7$ and R$^8$ join to form a 3- to 10-membered ring;

R$^{11}$ is, independently at each occurrence, OH, halo, —CN, —NO$_2$, =O, —OC(O)CH$_3$, —C$_1$-C$_6$ alkyl, —O—C$_1$-C$_6$ alkyl, —C$_1$-C$_6$ heteroalkyl, —O—C$_1$-C$_6$ heteroalkyl, —C$_3$-C$_{10}$ cycloalkyl, —O—C$_3$-C$_{10}$ cycloalkyl, —C$_3$-C$_{10}$ heterocycloalkyl, aryl, heteroaryl, —C$_1$-C$_4$ alkyl-(C$_3$-C$_{10}$ cycloalkyl), —C$_1$-C$_4$ alkyl-(C$_3$-C$_{10}$ heterocycloalkyl), —C$_1$-C$_4$ alkyl-(aryl), or —C$_1$-C$_4$ alkyl-(heteroaryl), wherein the alkyl, heteroalkyl, cycloalkyl, heterocycloalkyl, aryl and heteroaryl groups are optionally substituted 1-5 times with halo, —OH, —CN, or —NO$_2$;

R$^{12}$ is, independently at each occurrence, H or —C$_1$-C$_6$ alkyl;

R$^{13}$ and R$^{14}$, together with the carbons to which they are attached, join to form a cyclopropyl ring;

m is 0, 1, 2, 3, or 4;
n is 1, 2, 3, or 4;
x is 0, 1, 2, 3, 4, or 5; and
y is 0, 1, 2, 3, or 4.

In still another aspect, the compound of the invention is a compound of Formula Ib:

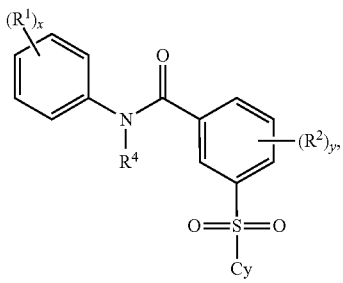

Ib or a pharmaceutically acceptable salt thereof;
wherein
R$^4$ is H or C$_1$-C$_3$ alkyl;

each R$^1$ is, independently at each occurrence, OH, halo, —CN, —NO$_2$, —C$_1$-C$_6$ alkyl, —O—C$_1$-C$_6$ alkyl, —C$_1$-C$_6$ heteroalkyl, —O—C$_1$-C$_6$ heteroalkyl, —C$_3$-C$_{10}$ cycloalkyl, —C$_3$-C$_{10}$ heterocycloalkyl, aryl, heteroaryl, —C$_1$-C$_4$ alkyl-(C$_3$-C$_{10}$ cycloalkyl), —C$_1$-C$_4$ alkyl-(C$_3$-C$_{10}$ heterocycloalkyl), —C$_1$-C$_4$ alkyl-(aryl), or —C$_1$-C$_4$ alkyl-(heteroaryl), wherein the alkyl, heteroalkyl, cycloalkyl, heterocycloalkyl, aryl and heteroaryl groups are optionally substituted 1-5 times with halo, —OH, —CN, or —NO$_2$;

each R$^2$ is, independently at each occurrence, OH, halo, —CN, —NO$_2$, R$^6$, or OR$^6$, wherein R$^6$ is, independently at each occurrence, —C$_1$-C$_6$ alkyl, —C$_1$-C$_6$ heteroalkyl, —C$_3$-C$_{10}$ cycloalkyl, —C$_3$-C$_{10}$ heterocycloalkyl, aryl, heteroaryl, —C$_1$-C$_4$ alkyl-(C$_3$-C$_{10}$ cycloalkyl), —C$_1$-C$_4$ alkyl-(C$_3$-C$_{10}$ heterocycloalkyl), —C$_1$-C$_4$ alkyl-(aryl), or —C$_1$-C$_4$ alkyl-(heteroaryl), wherein the alkyl, heteroalkyl, cycloalkyl, heterocycloalkyl, aryl and heteroaryl groups are optionally substituted 1-5 times with halo, —OH, —CN, or —NO$_2$;

or two R$^2$ groups, and the phenyl ring to which they are attached, join to form benzimidazole;

Cy is

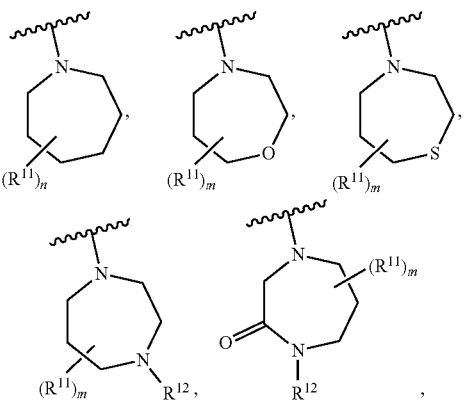

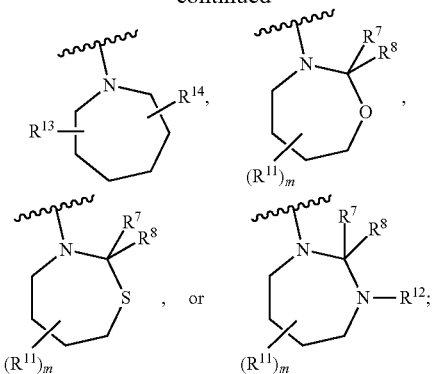

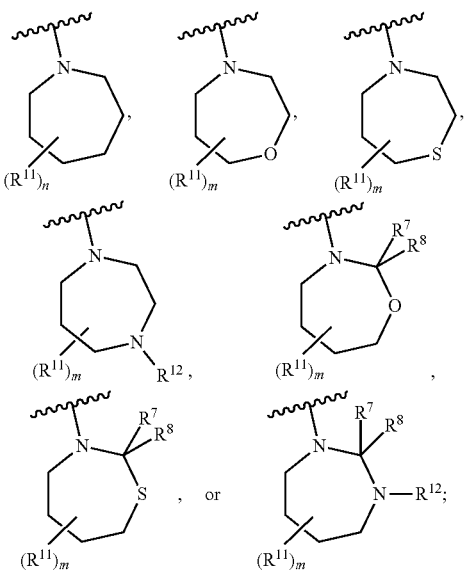

R⁷ and R⁸ are, independently at each occurrence, —$C_1$-$C_6$ alkyl, aryl, heteroaryl, —$C_1$-$C_4$ alkyl-(aryl), or —$C_1$-$C_4$ alkyl-(heteroaryl), wherein the aryl or heteroaryl groups are optionally substituted with $C_1$-$C_3$ alkyl;

or $R^7$ and $R^8$ join to form a 3- to 10-membered ring;

$R^{11}$ is, independently at each occurrence, OH, halo, —CN, —$NO_2$, =O, —$OC(O)CH_3$, —$H_2PO_4$, —$C_1$-$C_6$ alkyl, —O—$C_1$-$C_6$ alkyl, —$C_1$-$C_6$ heteroalkyl, —O—$C_1$-$C_6$ heteroalkyl, —$C_3$-$C_{10}$ cycloalkyl, —O—$C_3$-$C_{10}$ cycloalkyl, —$C_3$-$C_{10}$ heterocycloalkyl, aryl, heteroaryl, —$C_1$-$C_4$ alkyl-($C_3$-$C_{10}$ cycloalkyl), —$C_1$-$C_4$ alkyl-($C_3$-$C_{10}$ heterocycloalkyl), —$C_1$-$C_4$ alkyl-(aryl), or —$C_1$-$C_4$ alkyl-(heteroaryl), wherein the alkyl, heteroalkyl, cycloalkyl, heterocycloalkyl, aryl and heteroaryl groups are optionally substituted 1-5 times with halo, —OH, —CN, or —$NO_2$;

$R^{12}$ is, independently at each occurrence, H or —$C_1$-$C_6$ alkyl;

$R^{13}$ and $R^{14}$, together with the carbons to which they are attached, join to form a cyclopropyl ring;

m is 0, 1, 2, 3, or 4;

n is 1, 2, 3, or 4;

x is 0, 1, 2, 3, 4, or 5; and y is 0, 1, 2, 3, or 4.

In one embodiment of Formula Ib provided herein, x is 0, 1, 2, or 3.

In another embodiment of Formula Ib provided herein, x is 1, 2, or 3.

In one embodiment of Formula I provided herein, $R^4$ is H or $C_1$-$C_3$ alkyl;

each $R^1$ is, independently at each occurrence, OH, halo, —CN, —$NO_2$, —$C_1$-$C_6$ alkyl, —O—$C_1$-$C_6$ alkyl, —$C_1$-$C_6$ heteroalkyl, —O—$C_1$-$C_6$ heteroalkyl, —$C_3$-$C_{10}$ cycloalkyl, —$C_3$-$C_{10}$ heterocycloalkyl, —$C_1$-$C_4$ alkyl-($C_3$-$C_{10}$ cycloalkyl), or —$C_1$-$C_4$ alkyl-($C_3$-$C_{10}$ heterocycloalkyl), wherein the alkyl, heteroalkyl, cycloalkyl, and heterocycloalkyl groups are optionally substituted 1-3 times with halo, —OH, —CN, or —$NO_2$;

each $R^2$ is, independently at each occurrence, OH, halo, —CN, —$NO_2$, $R^6$, or $OR^6$, wherein $R^6$ is, independently at each occurrence, —$C_1$-$C_6$ alkyl, —$C_1$-$C_6$ heteroalkyl, —$C_3$-$C_{10}$ cycloalkyl, —$C_3$-$C_{10}$ heterocycloalkyl, —$C_1$-$C_4$ alkyl-($C_3$-$C_{10}$ cycloalkyl), or —$C_1$-$C_4$ alkyl-($C_3$-$C_{10}$ heterocycloalkyl), wherein the alkyl, heteroalkyl, cycloalkyl, and heterocycloalkyl groups are optionally substituted 1-3 times with halo, —OH, —CN, or —$NO_2$;

Cy is $R^7$ and $R^8$ are, independently at each occurrence, —$C_1$-$C_6$ alkyl, aryl, heteroaryl, —$C_1$-$C_4$ alkyl-(aryl), or —$C_1$-$C_4$ alkyl-(heteroaryl);

or $R^7$ and $R^8$ join to form a 3- to 7-membered ring;

$R^{11}$ is, independently at each occurrence, OH, halo, —CN, —$NO_2$, —$C_1$-$C_6$ alkyl, —O—$C_1$-$C_6$ alkyl, —$C_1$-$C_6$ hetero alkyl, —O—$C_1$-$C_6$ hetero alkyl, —$C_3$-$C_{10}$ cycloalkyl, —$C_3$-$C_{10}$ heterocycloalkyl, —$C_1$-$C_4$ alkyl-($C_3$-$C_{10}$ cyclo alkyl), or —$C_1$-$C_4$ alkyl-($C_3$-$C_{10}$ hetero cyclo alkyl), wherein the alkyl, heteroalkyl, cycloalkyl, and heterocycloalkyl groups are optionally substituted 1-3 times with halo, —OH, —CN, or —$NO_2$;

$R^{12}$ is, independently at each occurrence, H or —$C_1$-$C_6$ alkyl;

m is 0, 1, 2, or 3;

n is 1, 2, or 3;

x is 0, 1, 2, or 3; and y is 0, 1, 2, or 3.

In another embodiment of Formula I provided herein, $R^4$ is H or $C_1$-$C_3$ alkyl;

each $R^1$ is, independently at each occurrence, OH, halo, —$C_1$-$C_6$ alkyl, —O—$C_1$-$C_6$ alkyl, —$C_1$-$C_6$ heteroalkyl, or —O—$C_1$-$C_6$ heteroalkyl, wherein the alkyl group is optionally substituted 1-3 times with halo or —OH;

each $R^2$ is, independently at each occurrence, OH, halo, $R^6$, or $OR^6$, wherein $R^6$ is, independently at each occurrence, —$C_1$-$C_6$ alkyl, —$C_3$-$C_{10}$ cycloalkyl, —$C_1$-$C_4$ alkyl-($C_3$-$C_{10}$ cycloalkyl), wherein the alkyl and cycloalkyl groups are optionally substituted 1-3 times with halo or —OH;

Cy is

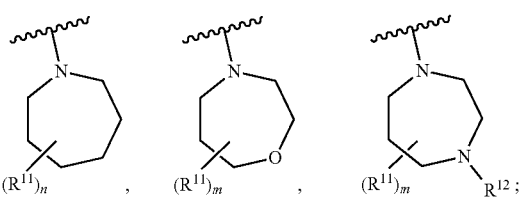

$R^{11}$ is, independently at each occurrence, OH, halo, —$C_1$-$C_6$ alkyl, —O—$C_1$-$C_6$ alkyl, —$C_1$-$C_6$ heteroalkyl, or —O—$C_1$-$C_6$ heteroalkyl, wherein the alkyl group is optionally substituted 1-3 times with halo or —OH;

$R^{12}$ is, independently at each occurrence, H or —$C_1$-$C_6$ alkyl;

m is 0, 1, 2, or 3;
n is 1, 2, or 3;
x is 0, 1, 2, or 3; and
y is 0, 1, 2, or 3.

In one embodiment of Formula I provided herein, $R^4$ is H.

In another embodiment of Formula I provided herein, $R^7$ and $R^8$ are, independently at each occurrence, —$C_1$-$C_6$ alkyl, phenyl, pyridyl, benzyl, or pyridylmethyl.

In another embodiment of Formula I provided herein, $R^7$ and $R^8$ are, independently at each occurrence, —$C_1$-$C_6$ alkyl, wherein the —$C_1$-$C_6$ alkyl groups join to form a 3- to 7-membered ring.

In another embodiment of Formula I provided herein, each $R^1$ is, independently at each occurrence, halo, and x is 1, 2, or 3.

In a further embodiment of Formula I provided herein, the compound is of the Formula II:

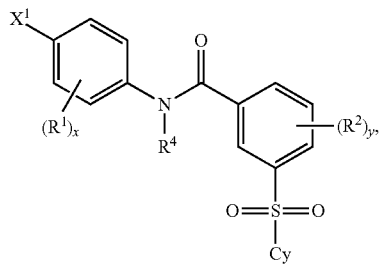

II or a pharmaceutically acceptable salt thereof, wherein $X^1$ is halo.

In another embodiment of Formula I and Formula II provided herein, each $R^2$ is, independently at each occurrence, halo, OH, —$C_1$-$C_6$ alkyl, or —O—$C_1$-$C_6$ alkyl, wherein the alkyl group is optionally substituted 1-3 times with halo or OH.

In one specific embodiment, each $R^2$ is, independently at each occurrence, halo or —$C_1$-$C_3$ alkyl-OH, and y is 1 or 2.

In still another embodiment of Formula I and Formula II provided herein, each $R^2$ is, independently at each occurrence, $OR^6$, wherein $R^6$ is, independently at each occurrence, —$C_1$-$C_6$ alkyl or —$C_3$-$C_{10}$ cyclo alkyl, wherein the alkyl and cycloalkyl groups are optionally substituted 1-2 times with halo or OH.

In a further embodiment of Formula I and Formula II provided herein, the compound is of Formula III:

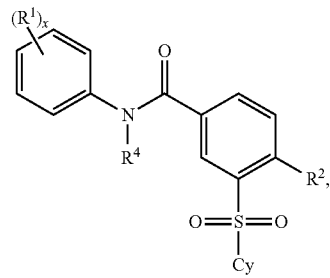

III or a pharmaceutically acceptable salt thereof.

In still another embodiment of Formulas I-III provided herein, Cy is

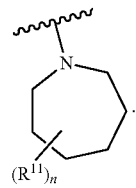

In one specific embodiment, each $R^{11}$ is, independently at each occurrence, halo, OH, —$C_1$-$C_6$ alkyl, or —O—$C_1$-$C_6$ alkyl, wherein the alkyl group is optionally substituted 1-3 times with halo or OH.

In yet another embodiment of Formulas I-III provided herein, Cy is

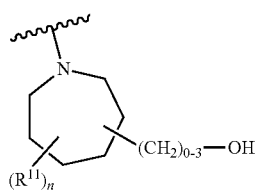

and n is 0, 1, or 2. In one specific embodiment, $R^{11}$ is —O—$C_1$-$C_3$ alkyl, and n is 1. In another specific embodiment, $R^{11}$ is OH or —$C_1$-$C_3$ alkyl-OH, and n is 1. In another specific embodiment, n is 0. In another specific embodiment, $R^{11}$ is halo, and n is 1. In still another specific embodiment, $R^{11}$ is —$C_1$-$C_3$ alkyl, and n is 1.

In a further embodiment of Formulas I-III provided herein, Cy is

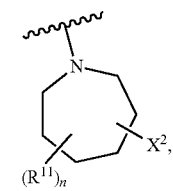

wherein $X^2$ is halo and n is 0, 1, or 2. In one specific embodiment, n is 0.

In another embodiment of Formulas I-III provided herein, Cy is

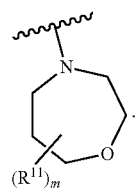

In one specific embodiment, each $R^{11}$ is, independently at each occurrence, OH or —$C_1$-$C_3$ alkyl, wherein the alkyl group is optionally substituted 1-3 times with halo or OH, and m is 1 or 2. In another specific embodiment, m is 0.

In another aspect, provided herein is a compound of Formula IV:

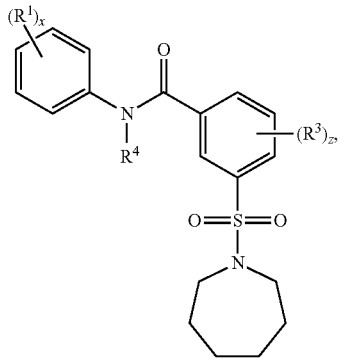

or a pharmaceutically acceptable salt thereof;
wherein
$R^4$ is H or $C_1$-$C_3$ alkyl;
each $R^1$ is, independently at each occurrence, OH, halo, —CN, —$NO_2$, —$C_1$-$C_6$ alkyl, —O—$C_1$-$C_6$ alkyl, —$C_1$-$C_6$ hetero alkyl, —O—$C_1$-$C_6$ hetero alkyl, —$C_3$-$C_{10}$ cycloalkyl, —$C_3$-$C_{10}$ heterocycloalkyl, aryl, heteroaryl, —$C_1$-$C_4$ alkyl-($C_3$-$C_{10}$ cyclo alkyl), —$C_1$-$C_4$ alkyl-($C_3$-$C_{10}$ hetero cyclo alkyl), —$C_1$-$C_4$ alkyl-(aryl), or —$C_1$-$C_4$ alkyl-(heteroaryl), wherein the alkyl, heteroalkyl, cycloalkyl, heterocycloalkyl, aryl and heteroaryl groups are optionally substituted 1-5 times with halo, —OH, —CN, or —$NO_2$;
each $R^3$ is, independently at each occurrence, OH, —CN, —$NO_2$, —$C_1$-$C_6$ alkyl, —$C_1$-$C_6$ alkoxy, $R^9$, or $OR^9$, wherein $R^9$ is, independently at each occurrence, —$C_1$-$C_6$ heteroalkyl, —$C_3$-$C_{10}$ cycloalkyl, —$C_3$-$C_{10}$ heterocycloalkyl, aryl, heteroaryl, —$(CH_2)_{1-4}$—($C_3$-$C_{10}$ cyclo alkyl), —$(CH_2)_{1-4}$—($C_3$-$C_{10}$ heterocycloalkyl), —$(CH_2)_{1-4}$-(aryl), or —$(CH_2)_{1-4}$-(heteroaryl), wherein the alkyl group is substituted 1-5 times with halo, —OH, —CN, or —$NO_2$; and the alkoxy, —$(CH_2)_{1-4}$—, heteroalkyl, cycloalkyl, heterocycloalkyl, aryl and heteroaryl groups are optionally substituted 1-5 times with halo, —OH, —CN, or —$NO_2$;
x is 0, 1, 2, 3, 4, or 5; and
z is 1, 2, 3, or 4.

In one embodiment of Formula IV provided herein,
$R^4$ is H or $C_1$-$C_3$ alkyl;
each $R^1$ is, independently at each occurrence, OH, halo, —CN, —$NO_2$, —$C_1$-$C_6$ alkyl, —O—$C_1$-$C_6$ alkyl, —$C_1$-$C_6$ heteroalkyl, —O—$C_1$-$C_6$ heteroalkyl, —$C_3$-$C_{10}$ cycloalkyl, —$C_3$-$C_{10}$ heterocycloalkyl, —$C_1$-$C_4$ alkyl-($C_3$-$C_{10}$ cycloalkyl), or —$C_1$-$C_4$ alkyl-($C_3$-$C_{10}$ heterocycloalkyl), wherein the alkyl, heteroalkyl, cycloalkyl, and heterocycloalkyl groups are optionally substituted 1-3 times with halo, —OH, —CN, or —$NO_2$;
each $R^3$ is, independently at each occurrence, OH, —CN, —$NO_2$, —$C_1$-$C_6$ alkyl, —$C_1$-$C_6$ alkoxy, $R^9$, or $OR^9$, wherein $R^9$ is, independently at each occurrence, —$C_1$-$C_6$ heteroalkyl, —$C_3$-$C_{10}$ cycloalkyl, —$C_3$-$C_{10}$ heterocycloalkyl, —$(CH_2)_{1-4}$—($C_3$-$C_{10}$ cycloalkyl), or —$(CH_2)_{1-4}$—($C_3$-$C_{10}$ heterocycloalkyl), wherein the alkyl group is substituted 1-3 times with halo, —OH, —CN, or —$NO_2$; and the alkoxy, —$(CH_2)_{1-4}$—, heteroalkyl, cyclo alkyl, and heterocycloalkyl groups are optionally substituted 1-3 times with halo, —OH, —CN, or —$NO_2$;
x is 0, 1, 2, or 3; and
z is 1, 2, or 3.

In another embodiment of Formula IV provided herein,
$R^4$ is H or $C_1$-$C_3$ alkyl;
each $R^1$ is, independently at each occurrence, OH, halo, —$C_1$-$C_6$ alkyl, —O—$C_1$-$C_6$ alkyl, —$C_1$-$C_6$ heteroalkyl, or —O—$C_1$-$C_6$ heteroalkyl, wherein the alkyl group is optionally substituted 1-3 times with halo or —OH;
each $R^3$ is, independently at each occurrence, OH, —$C_1$-$C_6$ alkyl, —$C_1$-$C_6$ alkoxy, $R^9$, or $OR^9$, wherein $R^9$ is, independently at each occurrence, —$C_3$-$C_{10}$ cycloalkyl or —$(CH_2)_{1-4}$—($C_3$-$C_{10}$ cycloalkyl), wherein the alkyl group is substituted 1-3 times with halo or —OH; and the alkoxy, —$(CH_2)_{1-4}$—, and cycloalkyl groups are optionally substituted 1-3 times with halo or —OH;
x is 0, 1, 2, or 3; and
z is 1, 2, or 3.

In another embodiment of Formula IV provided herein, $R^4$ is H.

In another embodiment of Formula IV provided herein, each $R^1$ is, independently at each occurrence, halo and x is 1, 2, or 3.

In still another embodiment of Formula IV provided herein, each $R^3$ is, independently at each occurrence, OH or —$C_1$-$C_6$ alkyl, wherein the alkyl group is substituted 1-3 times with halo or —OH and z is 1, 2, or 3.

In yet another embodiment of Formula IV provided herein, $R^3$ is —$C_1$-$C_3$ alkyl-OH and z is 1.

In another embodiment of Formula I provided herein, the compound is of Formula V:

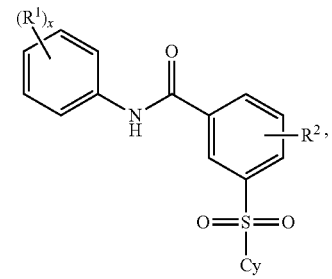

or a pharmaceutically acceptable salt thereof;
wherein
each $R^1$ is, independently at each occurrence, halo, OH, —$C_1$-$C_6$ alkyl, or —O—$C_1$-$C_6$ alkyl, wherein the alkyl group is optionally substituted 1-3 times with halo or OH;
each $R^2$ is, independently at each occurrence, halo, OH, —$C_1$-$C_6$ alkyl, or —O—$C_1$-$C_6$ alkyl, wherein the alkyl group is optionally substituted 1-3 times with halo or OH;
Cy is

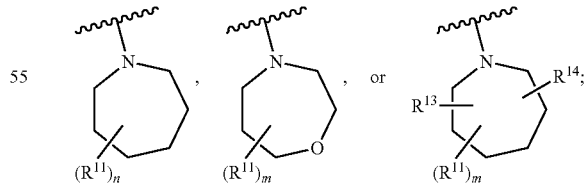

$R^{11}$ is, independently at each occurrence, —OH, halo, —$C_1$-$C_6$ alkyl, —$OC(O)CH_3$, or —$C_3$-$C_{10}$ cycloalkyl;
$R^{13}$ and $R^{14}$, together with the carbons to which they are attached, join to form a cyclopropyl ring;
m is 1, 2, or 3;
n is 1, 2, or 3; and
x is 2 or 3.

In another embodiment of Formula I provided herein, the compound is of Formula Vx:

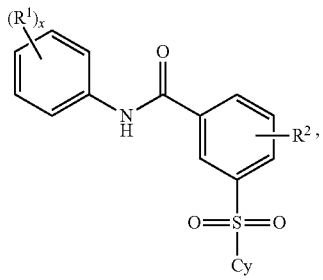

or a pharmaceutically acceptable salt thereof;
wherein
each $R^1$ is, independently at each occurrence, halo, OH, —$C_1$-$C_6$ alkyl, or —O—$C_1$-$C_6$ alkyl, wherein the alkyl group is optionally substituted 1-3 times with halo or OH;
each $R^2$ is, independently at each occurrence, halo, OH, —$C_1$-$C_6$ alkyl, or —O—$C_1$-$C_6$ alkyl, wherein the alkyl group is optionally substituted 1-3 times with halo or OH;
Cy is

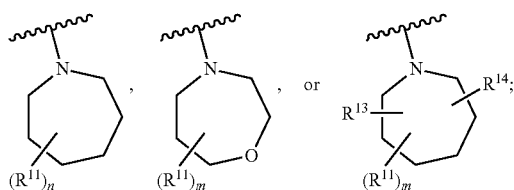

$R^{11}$ is, independently at each occurrence, —OH, halo, —$C_1$-$C_6$ alkyl, —OC(O)CH$_3$, or —$C_3$-$C_{10}$ cycloalkyl;
$R^{13}$ and $R^{14}$, together with the carbons to which they are attached, join to form a cyclopropyl ring;
m is 1, 2, or 3;
n is 1, 2, or 3; and
x is 1, 2, or 3.

In a specific embodiment of Formula V provided herein, each $R^1$ is, independently at each occurrence, halo.

In another specific embodiment of Formula V provided herein, each $R^2$ is, independently at each occurrence, halo or —$C_1$-$C_6$ alkyl, wherein the alkyl is optionally substituted 1-3 times with halo.

In yet another embodiment of Formula I provided herein, the compound is of Formula Va:

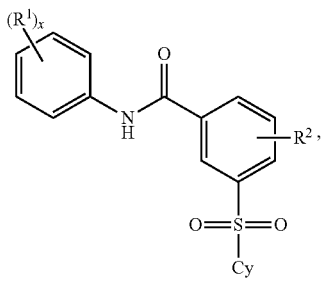

or a pharmaceutically acceptable salt thereof;

wherein
each $R^1$ is, independently at each occurrence, halo, OH, —$C_1$-$C_6$ alkyl, or —O—$C_1$-$C_6$ alkyl, wherein the alkyl group is optionally substituted 1-3 times with halo or OH;
each $R^2$ is, independently at each occurrence, halo, OH, —$C_1$-$C_6$ alkyl, or —O—$C_1$-$C_6$ alkyl, wherein the alkyl group is optionally substituted 1-3 times with halo or OH;
Cy is

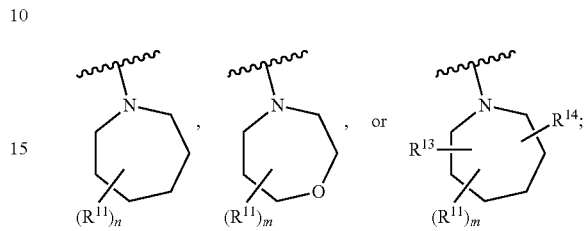

$R^{11}$ is, independently at each occurrence, —OH, halo, —$C_1$-$C_6$ alkyl, —OC(O)CH$_3$, —H$_2$PO$_4$, or —$C_3$-$C_{10}$ cycloalkyl;
$R^{13}$ and $R^{14}$, together with the carbons to which they are attached, join to form a cyclopropyl ring;
m is 1, 2, or 3;
n is 1, 2, or 3; and
x is 1, 2, or 3.

In one specific embodiment of Formula Va provided herein, x is 2 or 3.

In another specific embodiment of Formula Va provided herein, each $R^1$ is, independently at each occurrence, halo.

In still another specific embodiment of Formula Va provided herein, each $R^2$ is, independently at each occurrence, halo or —$C_1$-$C_6$ alkyl, wherein the alkyl is optionally substituted 1-3 times with halo.

In yet another specific embodiment of Formula Va provided herein, Cy is

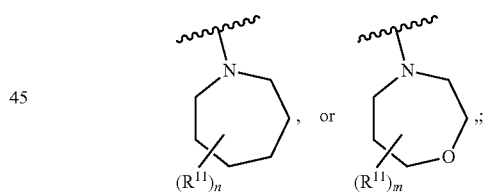

and $R^{11}$ is, independently at each occurrence, —OH, halo, —$C_1$-$C_6$ alkyl, —OC(O)CH$_3$, or —H$_2$PO$_4$, wherein n and m are 1, 2, or 3, and at least one $R^{11}$ is H$_2$PO$_4$.

Certain preferred embodiments of Formulas I, Ia, Ib, II, III, IV, V, Vx, and Va, including pharmaceutically acceptable salts thereof, are shown below in Table 1 and in Table 2. All compounds of Formulas I, Ia, Ib, II, III, IV, V, Vx, and Va as well as pharmaceutically acceptable salts thereof, and the compounds of Table 1 and Table 2, as well as pharmaceutically acceptable salts thereof, are considered to be "compounds of the invention."

Synthetic method codes refer to the synthesis methodologies provided in the experimental section. For example, "A01B01C01D01" refers the use of intermediate A01 for region A, intermediate B01 for region B, intermediate C01 for region C, and intermediate D01 for region D.

TABLE 1
| Structure | Compound ID | ¹H NMR | MS(M + H)⁺ | Synthetic method |
|---|---|---|---|---|
| 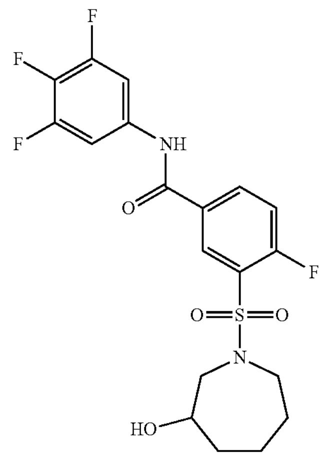 [SMILES: O=C(Nc1cc(F)c(F)c(F)c1)c1ccc(F)c(S(=O)(=O)N2CCCCC(O)C2)c1] | 1762 | ¹H NMR (400 MHz, MeOD) δ 8.46 (dd, J = 2.4, 6.7 Hz, 1H), 8.26-8.22 (m, 1H), 7.66-7.56 (m, 2H), 7.51 (dd, J = 8.7, 10.0 Hz, 1H), 3.96-3.86 (m, 1H), 3.77 (dd, J = 4.3, 14.2 Hz, 1H), 3.64-3.54 (m, 1H), 3.25-3.14 (m, 1H), 3.02 (dd, J = 8.4, 14.3 Hz, 1H), 2.01-1.97 (m, J = 4.3, 8.3, 12.7 Hz, 1H), 1.92-1.50 (m, 5H). | 447 | GENERAL PROCEDURE A A01B02C02 |
| 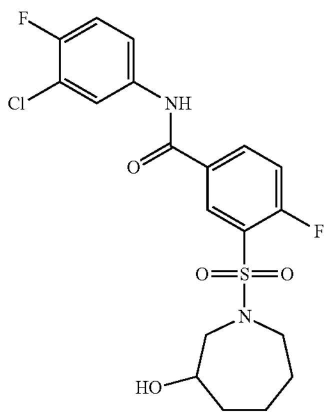 [SMILES: O=C(Nc1ccc(F)c(Cl)c1)c1ccc(F)c(S(=O)(=O)N2CCCCC(O)C2)c1] | 1763 | | 445/447 | GENERAL PROCEDURE A A01B02C01 |
| 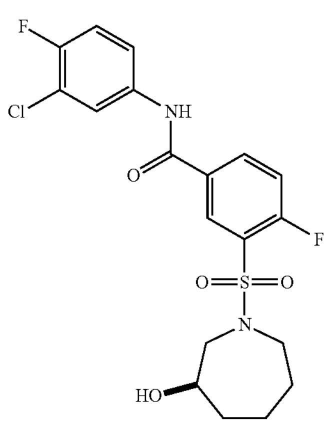 | 1763_E1 | ¹H NMR (400 MHz, DMSO-d6) δ = 10.69 (s, 1H), 8.40-8.45 (m, 1H), 8.25-8.35 (m, 1H), 8.00-8.05 (m, 1H), 7.70-7.80 (m, 2H), 7.40-7.50 (m, 1H), 4.90-4.92 (m, 1H), 3.60-3.80 (m, 2H), 3.45-3.55 (m, 1H), 3.05-3.15 (m, 1H), 2.85-2.95 (m, 1H), 1.35-1.85 (m, 6H). | 445/447 | Separated from 1763 through Supercritical Fluid Chromatography |

TABLE 1-continued

| Structure | Compound ID | ¹H NMR | MS(M + H)⁺ | Synthetic method |
|---|---|---|---|---|
| (structure) | 1763_E2 | ¹H NMR (400 MHz, DMSO-d6) δ = 10.69 (s, 1H), 8.40-8.45 (m, 1H), 8.25-8.35 (m, 1H), 8.00-8.05 (m, 1H), 7.70-7.80 (m, 2H), 7.40-7.50 (m, 1H), 4.90-4.92 (m, 1H), 3.60-3.80 (m, 2H), 3.45-3.55 (m, 1H), 3.05-3.15 (m, 1H), 2.85-2.95 (m, 1H), 1.35-1.85 (m, 6H). | 445/447 | Separated from 1763 through Supercritical Fluid Chromatography |
| (structure) | 1764 | | 429 | GENERAL PROCEDURE A A01B02C03 |
| (structure) | 1765 | | 447 | GENERAL PROCEDURE A A02B02C02 |

TABLE 1-continued

| Structure | Compound ID | ¹H NMR | MS(M + H)⁺ | Synthetic method |
|---|---|---|---|---|
| (structure) | 1766 | ¹H NMR (400 MHz, MeOD) δ 8.49-8.41 (m, 1H), 8.28-8.20 (m, 1H), 7.99 (dd, J = 2.5, 6.7 Hz, 1H), 7.63 (d, J = 1.5 Hz, 1H), 7.50 (dd, J = 8.7, 9.9 Hz, 1H), 7.31-7.21 (m, 1H), 3.92-3.83 (m, 1H), 3.54-3.44 (m, 2H), 3.42-3.35 (m, 2H), 2.08-1.88 (m, 3H), 1.81-1.66 (m, 3H) | 445/447 | GENERAL PROCEDURE A A02B02C01 |
| (structure) | 1766_E1 | ¹H NMR (400 MHz, METHANOL-d4) δ = 8.44-8.46 (m, 1H), 8.20-8.25 (m, 1H), 7.96-7.99 (m, 1H), 7.60-7.65 (m, 1H), 7.47-7.52 (m, 1H), 7.24-7.29 (m, 1H), 3.85-3.92 (m, 1H), 3.45-3.55 (m, 2H), 3.35-3.41 (m, 2H), 1.90-2.05 (m, 3H), 1.65-1.80 (m, 3H). | 445/447 | Separated from 1763 through Supercritical Fluid Chromatography |
| (structure) | 1766_E2 | ¹H NMR (400 MHz, METHANOL-d4) δ = 8.44-8.46 (m, 1H), 8.20-8.25 (m, 1H), 7.96-7.99 (m, 1H), 7.60-7.65 (m, 1H), 7.47-7.52 (m, 1H), 7.24-7.29 (m, 1H), 3.85-3.92 (m, 1H), 3.45-3.55 (m, 2H), 3.35-3.41 (m, 2H), 1.90-2.05 (m, 3H), 1.65-1.80 (m, 3H). | 445/447 | Separated from 1766 through Supercritical Fluid Chromatography |

TABLE 1-continued

| Structure | Compound ID | ¹H NMR | MS(M + H)⁺ | Synthetic method |
|---|---|---|---|---|
| 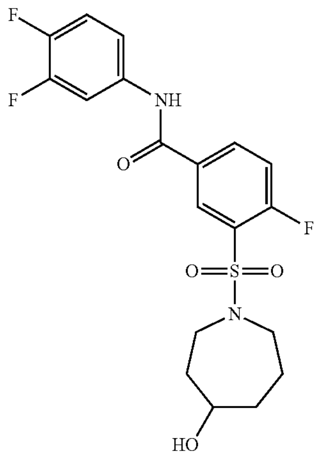 [SMILES: O=C(Nc1ccc(F)c(F)c1)c1ccc(F)c(S(=O)(=O)N2CCCC(O)CC2)c1] | 1767 | ¹HNMR (400 MHz, MeOD) δ 8.45 (dd, J = 2.4, 6.7 Hz, 1H), 8.26-8.22 (m, 1H), 7.87-7.81 (m, 1H), 7.55-7.40 (m, 2H), 7.32-7.24 (m, 1H), 3.93-3.81 (m, 1H), 3.54-3.44 (m, 2H), 3.42-3.34 (m, 2H), 2.10-1.87 (m, 3H), 1.83-1.61 (m, 3H) | 429 | GENERAL PROCEDURE A A01B02C03 |
| 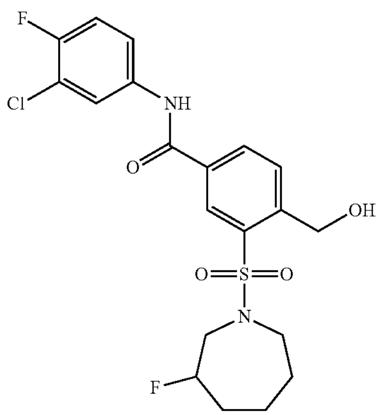 [SMILES: O=C(Nc1ccc(F)c(Cl)c1)c1ccc(CO)c(S(=O)(=O)N2CCCCC(F)C2)c1] | 1768 | ¹H NMR (400 MHz, MeOD) δ 8.34 (d, J = 1.76 Hz, 1H), 8.16-8.22 (m, 1H), 7.95-8.05 (m, 2H), 7.60-7.66 (m, 1H), 7.21-7.29 (m, 1H), 5.02 (d, J = 6.27 Hz, 2H), 4.73-4.80 (m, 1H), 3.66-3.79 (m, 1H), 3.51-3.63 (m, 1H), 3.41-3.51 (m, 1H), 3.33-3.39 (m, 1H), 1.91-2.10 (m, 2H), 1.72-1.89 (m, 3H), 1.50-1.67 (m, 1H) | 459/461 | GENERAL PROCEDURE B A03B03C01 |
| 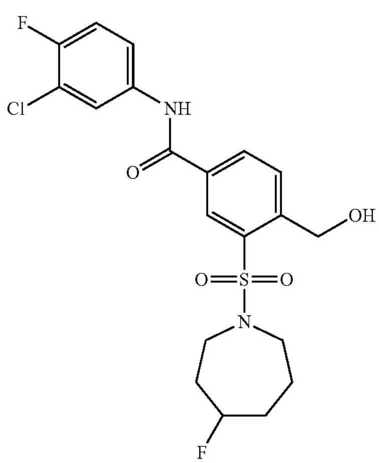 [SMILES: O=C(Nc1ccc(F)c(Cl)c1)c1ccc(CO)c(S(=O)(=O)N2CCCC(F)CC2)c1] | 1769 | ¹H NMR (400 MHz, MeOD) δ 8.40-8.49 (m, 1H), 8.18-8.29 (m, 1H), 7.93-8.01 (m, 1H), 7.58-7.67 (m, 1H), 7.49 (dd, J = 8.72, 9.98 Hz, 1H), 7.26 (t, J = 8.97 Hz, 1H), 3.34-3.55 (m, 2H), 3.15-3.28 (m, 2H), 1.67-1.89 (m, 5H), 1.48-1.62 (m, 1H), 1.28 (s, 3H) | 459/461 | GENERAL PROCEDURE B A04B03C01 |

TABLE 1-continued

| Structure | Compound ID | ¹H NMR | MS(M + H)⁺ | Synthetic method |
|---|---|---|---|---|
| 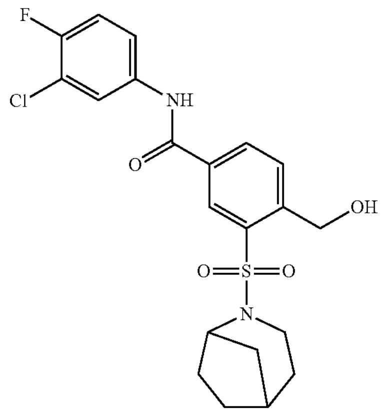 [SMILES: O=C(Nc1ccc(F)c(Cl)c1)c1ccc(CO)c(S(=O)(=O)N2CCC3CCC2C3)c1] | 1784 | ¹H NMR (400 MHz, MeOD) δ 8.47 (d, J = 1.9 Hz, 1H), 8.19 (dd, J = 8.1, 1.8 Hz, 1H), 7.94-8.04 (m, 2H), 7.67-7.63 (m, 1H), 7.27 (t, J = 8.9 Hz, 1H), 5.10 (s, 2H), 4.27-4.18 (m, 1H), 2.94 (t, J = 7.3 Hz, 2H), 2.18-2.01 (m, 1H), 1.95-1.80 (m, 2H), 1.70 (dd, J = 12.7, 7.3 Hz, 1H), 1.56-1.42 (m, 3H), 1.28-1.23 (m, 1H), 1.13-0.99 (m, 1H) | 453/455 | GENERAL PROCEDURE B A14B03C01 |
| 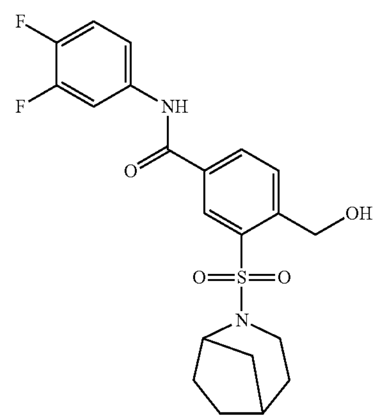 [SMILES: O=C(Nc1ccc(F)c(F)c1)c1ccc(CO)c(S(=O)(=O)N2CCC3CCC2C3)c1] | 1791 | | 437 | GENERAL PROCEDURE B A14B03C03 |
| 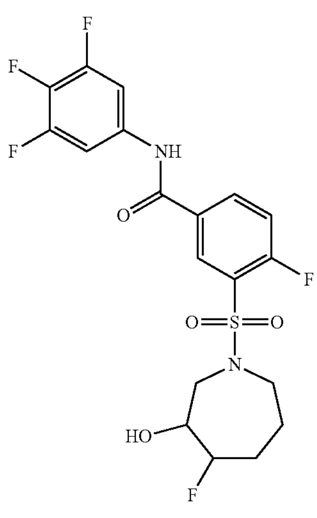 [SMILES: O=C(Nc1cc(F)c(F)c(F)c1)c1ccc(F)c(S(=O)(=O)N2CCCC(F)C(O)C2)c1] | 1820 | ¹H NMR (400 MHz, MeOD) δ 8.45-8.47 (m, 1H), 8.24-8.26 (m, 1H), 7.48-7.63 (m, 3H), 3.78-3.91 (m, 1H), 3.75-3.76 (m, 1H), 3.51-3.60 (m, 1H), 3.18-3.33 (m, 1H), 2.99-3.05 (m, 1H), 1.58-2.03 (m, 5H). | 465 | GENERAL PROCEDURE A A07B02C02 |

TABLE 1-continued

| Structure | Compound ID | ¹H NMR | MS(M + H)⁺ | Synthetic method |
|---|---|---|---|---|
| 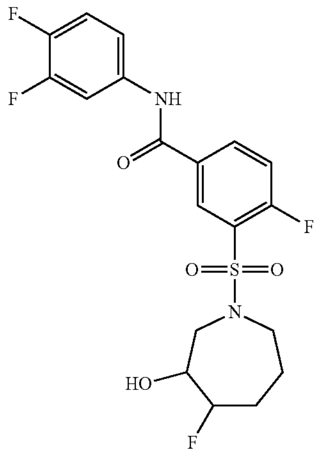 [SMILES: O=C(Nc1ccc(F)c(F)c1)c1ccc(F)c(S(=O)(=O)N2CCCC(F)C(O)C2)c1] | 1821 | | 447 | GENERAL PROCEDURE A A07B02C03 |
| 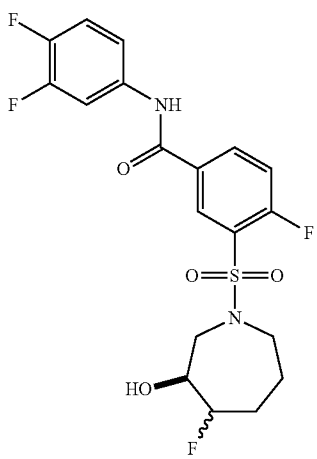 [SMILES: O=C(Nc1ccc(F)c(F)c1)c1ccc(F)c(S(=O)(=O)N2CCCC(F)[C@@H](O)C2)c1] | 1821_D1 | ¹H NMR (400 MHz, DMSO-d6) δ = 10.73 (s, 1H), 8.36-8.46 (m, 1H), 8.25-8.35 (m, 1H), 7.87-7.95 (m, 1H), 7.65-7.76 (m, 1H), 7.45-7.55 (m, 2H), 5.54-5.56 (m, 2H), 4.25-4.41 (m, 1H), 3.50-3.70 (m, 2H), 3.40-3.45 (m, 1H), 2.98-3.10 (m, 2H), 1.55-2.10 (m, 4H). | 447 | Separated from 1821 through Supercritical Fluid Chromatography |
| 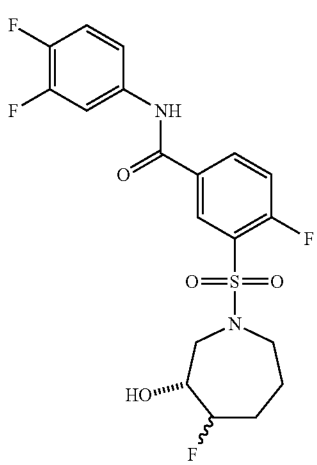 [SMILES: O=C(Nc1ccc(F)c(F)c1)c1ccc(F)c(S(=O)(=O)N2CCCC(F)[C@H](O)C2)c1] | 1821_D2 | ¹H NMR (400 MHz, DMSO-d6) δ = 10.72 (s, 1H), 8.39-8.45 (m, 1H), 8.30-8.37 (m, 1H), 7.87-7.95 (m, 1H), 7.60-7.70 (m, 1H), 7.45-7.55 (m, 2H), 5.39-5.41 (m, 1H), 4.60-4.70 (m, 1H), 3.85-3.95 (m, 1H), 3.45-3.55 (m, 2H), 3.07-3.20 (m, 2H), 2.05-2.15 (m, 1H), 1.61-1.85 (m, 3H).. | 447 | Separated from 1821 through Supercritical Fluid Chromatography |

TABLE 1-continued

| Structure | Compound ID | ¹H NMR | MS(M + H)⁺ | Synthetic method |
|---|---|---|---|---|
| 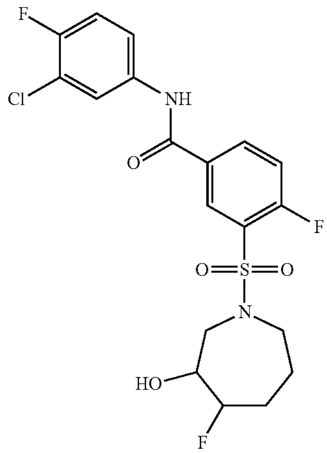 [SMILES: O=C(Nc1ccc(F)c(Cl)c1)c1ccc(F)c(S(=O)(=O)N2CCCC(F)C(O)C2)c1] | 1822 | | 463/465 | GENERAL PROCEDURE A A07B02C01 |
| 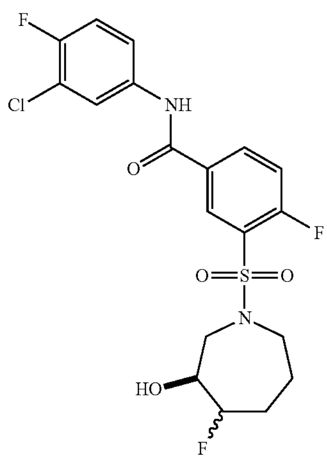 [SMILES: O=C(Nc1ccc(F)c(Cl)c1)c1ccc(F)c(S(=O)(=O)N2CCCC(F)[C@@H](O)C2)c1] | 1822_D1 | ¹H NMR (400 MHz, DMSO-d6) δ = 10.70 (s, 1H), 8.38-8.41 (m, 1H), 8.26-8.37 (m, 1H), 8.03-8.06 (m, 1H), 7.70-7.73 (m, 2H), 7.43-7.48 (m, 1H), 5.54-5.56 (m, 1H), 4.25-4.40 (m, 1H), 3.35-3.65 (m, 3H), 3.01-3.08 (m, 2H), 1.64-1.90 (m, 4H). | 463/465 | Separated from 1822 through Supercritical Fluid Chromatography |
| 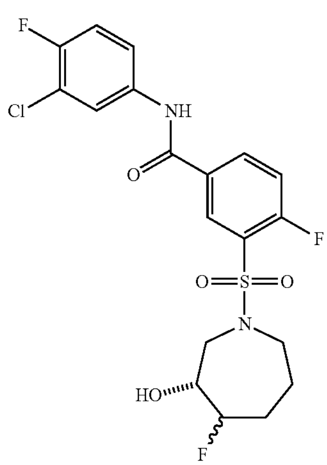 [SMILES: O=C(Nc1ccc(F)c(Cl)c1)c1ccc(F)c(S(=O)(=O)N2CCCC(F)[C@H](O)C2)c1] | 1822_D2 | ¹H NMR (400 MHz, DMSO-d6) δ = 10.70 (s, 1H), 8.38-8.41 (m, 1H), 8.26-8.37 (m, 1H), 8.03-8.06 (m, 1H), 7.67-7.72 (m, 2H), 7.43-7.48 (m, 1H), 5.38-5.40 (m, 1H), 4.68-4.83 (m, 1H), 3.85-3.92 (m, 1H), 3.50-3.57 (m, 2H), 3.09-3.19 (m, 2H), 2.07-2.10 (m, 1H), 1.65-1.85 (m, 3H). | 463/465 | Separated from 1822 through Supercritical Fluid Chromatography |

TABLE 1-continued
| Structure | Compound ID | $^1$H NMR | MS(M + H)$^+$ | Synthetic method |
|---|---|---|---|---|
| 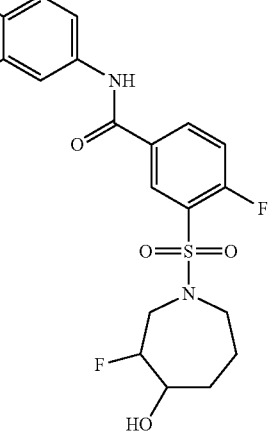 | 1829 | | 465 | GENERAL PROCEDURE A A08B02C02 |
| 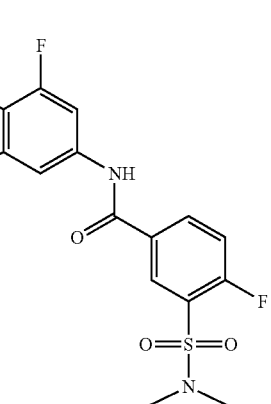 | 1829_D1 | $^1$H NMR (400 MHz, DMSO-d6) δ = 10.81 (s, 1H), 8.38-8.45 (m, 1H), 8.25-8.35 (m, 1H), 7.69-7.74 (m, 3H), 5.09-5.29 (m, 1H), 4.25-4.78 (m, 1H), 3.44-3.90 (m, 3H), 3.05-3.20 (m, 1H), 1.50-1.90 (m, 4H). | 465 | Separated from 1821 through Supercritical Fluid Chromatography |
| 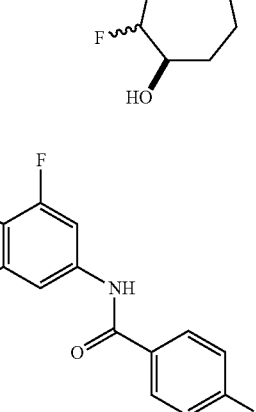 | 1829_D2 | $^1$H NMR (400 MHz, DMSO-d6) δ = 10.82 (s, 1H), 8.40-8.43 (m, 1H), 8.25-8.35 (m, 1H), 7.69-7.74 (m, 3H), 5.09-5.25 (m, 1H), 4.40-4.78 (m, 1H), 3.48-3.90 (m, 3H), 3.05-3.17 (m, 1H), 1.50-1.90 (m, 4H). | 465 | Separated from 1821 through Supercritical Fluid Chromatography |

TABLE 1-continued

| Structure | Compound ID | ¹H NMR | MS(M + H)⁺ | Synthetic method |
|---|---|---|---|---|
| (structure) | 1830 | | 447 | GENERAL PROCEDURE A A08B02C03 |
| (structure) | 1831 | ¹H NMR (400 MHz, MeOD) δ 8.46-8.48 (m, 1H), 8.23-8.28 (m, 1H), 7.97-7.99 (m, 1H), 7.62-7.63 (m, 1H), 7.49-7.54 (m, 1H), 7.24-7.29 (m, 1H), 4.33-4.46 (m, 1H), 3.60-3.75 (m, 3H), 3.35-3.45 (m, 1H), 3.17-3.21 (m, 1H), 1.85-1.95 (m, 2H), 1.68-1.76 (m, 2H). | 463/465 | GENERAL PROCEDURE A A08B02C01 |
| (structure) | 1832 | | 465 | GENERAL PROCEDURE A A09B02C02 |

TABLE 1-continued

| Structure | Compound ID | ¹H NMR | MS(M + H)⁺ | Synthetic method |
|---|---|---|---|---|
| 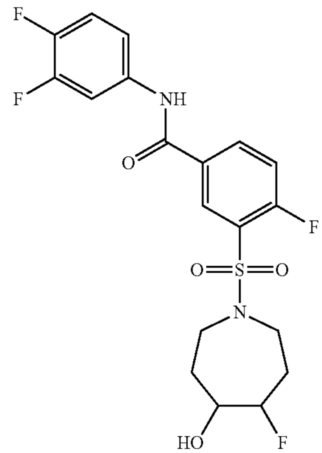 [SMILES: O=C(Nc1ccc(F)c(F)c1)c1ccc(F)c(S(=O)(=O)N2CCC(O)C(F)CC2)c1] | 1833 | ¹H NMR (400 MHz, MeOD) δ 8.43-8.46 (m, 1H), 8.23-8.25 (m, 1H), 7.80-7.86 (m, 1H), 7.44-7.53 (m, 2H), 7.26-7.31 (m, 1H), 4.41-4.53 (m, 1H), 3.77-3.81 (m, 1H), 3.41-3.72 (m, 4H), 1.73-2.25 (m, 4H). | 447 | GENERAL PROCEDURE A A08B02C03 |
| 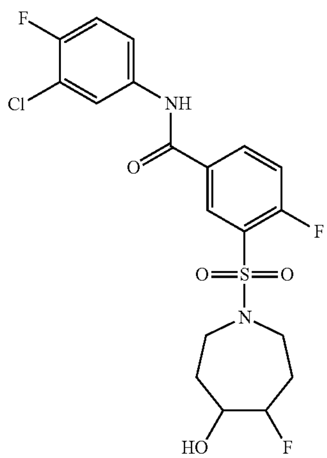 [SMILES: O=C(Nc1ccc(F)c(Cl)c1)c1ccc(F)c(S(=O)(=O)N2CCC(O)C(F)CC2)c1] | 1834 | | 463/465 | GENERAL PROCEDURE A A08B02C01 |
| 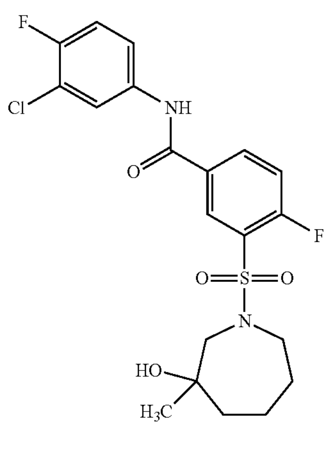 [SMILES: CC1(O)CCCCN(S(=O)(=O)c2cc(C(=O)Nc3ccc(F)c(Cl)c3)ccc2F)C1] | 1890 | ¹H NMR (400 MHz, MeOD) δ 8.17-8.34 (m, 1H), 7.61-7.74 (m, 2H), 7.27 (s, 4H), 4.08 (s., 2H), 3.22-3.29 (m, 1H), 2.55-2.81 (m, 2H), 1.77-2.26 (m, 5H), 0.57-0.77 (m, 4H) | 459/461 | GENERAL PROCEDURE A A05B02C01 |

TABLE 1-continued
| Structure | Compound ID | ¹H NMR | MS(M + H)⁺ | Synthetic method |
|---|---|---|---|---|
| 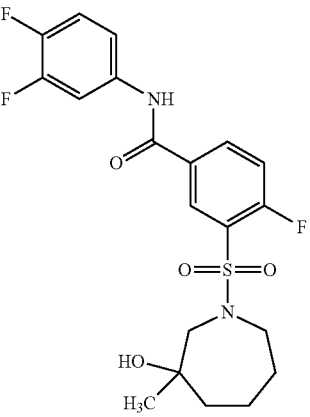 [SMILES: CC1(O)CCCCN(S(=O)(=O)c2cc(C(=O)Nc3ccc(F)c(F)c3)ccc2F)C1] | 1891 | ¹H NMR (400 MHz, MeOD) δ 8.42-8.47 (m, 1H), 8.20-8.26 (m, 1H), 7.79-7.87 (m, 1H), 7.40-7.53 (m, 2H), 7.22-7.32 (m, 1H), 3.36-3.53 (m, 2H), 3.17-3.28 (m, 2H), 1.70-1.83 (m, 5H), 1.51-1.61 (m, 1H), 1.28 (s, 3H) | 443 | GENERAL PROCEDURE A A05B02C03 |
| 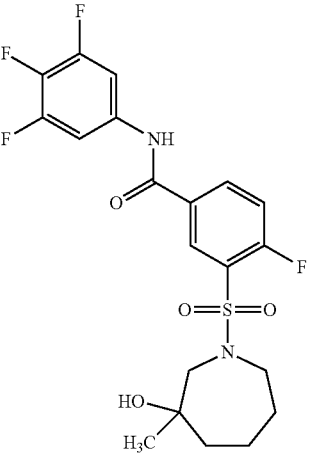 [SMILES: CC1(O)CCCCN(S(=O)(=O)c2cc(C(=O)Nc3cc(F)c(F)c(F)c3)ccc2F)C1] | 1892 | ¹H NMR (400 MHz, MeOD) δ 8.43-8.47 (m, 1H), 8.19-8.27 (m, 1H), 7.56-7.64 (m, 2H), 7.46-7.53 (m, 1H), 3.37-3.52 (m, 3H), 3.19-3.27 (m, 1H), 1.70-1.82 (m, 5H), 1.46-1.64 (m, 1H), 1.28 (s, 3H) | 461 | GENERAL PROCEDURE A A05B02C02 |
| 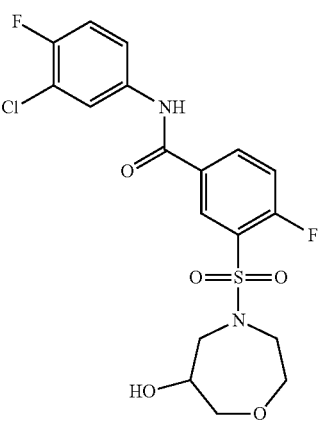 [SMILES: O=C(Nc1ccc(F)c(Cl)c1)c1ccc(F)c(S(=O)(=O)N2CCOCC(O)C2)c1] | 1893 | ¹H NMR (400 MHz, MeOD) δ = 8.51-8.27 (m, 2H), 8.03-7.98 (m, 1H), 7.71-7.52 (m, 2H), 7.27 (t, J = 8.8 Hz, 1H), 4.11-3.62 (m, 7H), 3.43-3.17 (m, 2H). | 447/449 | GENERAL PROCEDURE A A13B02C01 |

TABLE 1-continued

| Structure | Compound ID | ¹H NMR | MS(M + H)⁺ | Synthetic method |
|---|---|---|---|---|
| 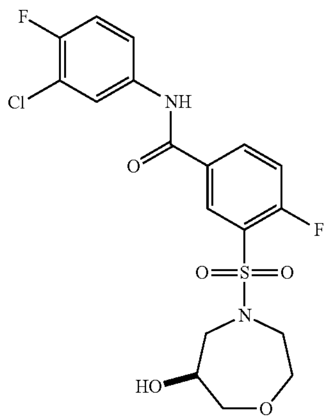 [SMILES: O=C(Nc1ccc(F)c(Cl)c1)c1ccc(F)c(S(=O)(=O)N2CCOC[C@@H](O)C2)c1] | 1893_E1 | | 447/449 | Separated from 1893 through Supercritical Fluid Chromatography |
| 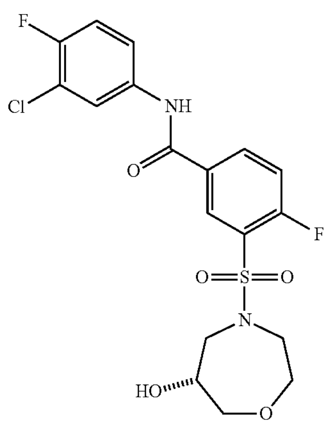 [SMILES: O=C(Nc1ccc(F)c(Cl)c1)c1ccc(F)c(S(=O)(=O)N2CCOC[C@H](O)C2)c1] | 1893_E2 | | 447/449 | Separated from 1893 through Supercritical Fluid Chromatography |
| 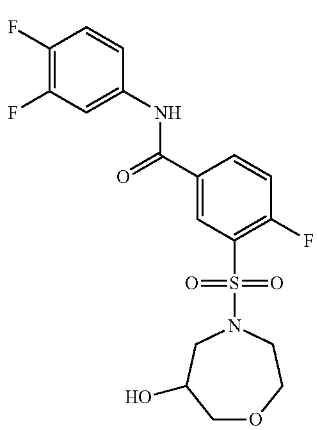 [SMILES: O=C(Nc1ccc(F)c(F)c1)c1ccc(F)c(S(=O)(=O)N2CCOCC(O)C2)c1] | 1894 | | 431 | GENERAL PROCEDURE A A13B02C03 |

TABLE 1-continued

| Structure | Compound ID | ¹H NMR | MS(M + H)⁺ | Synthetic method |
|---|---|---|---|---|
| (structure) | 1895 | | 449 | GENERAL PROCEDURE A A13B02C02 |
| (structure) | 1896 | ¹H NMR (400 MHz, MeOD) δ 8.51-8.26 (m, 2H), 8.06-7.98 (m, 1H), 7.71-7.52 (m, 2H), 7.27 (t, J = 8.8 Hz, 1H), 4.26-4.17 (m, 1H), 3.81-3.03 (m, 8H), 2.83 (s, 3H). | 460/462 | GENERAL PROCEDURE A A10B02C01 |
| (structure) | 1897 | | 444 | GENERAL PROCEDURE A A10B02C03 |

TABLE 1-continued

| Structure | Compound ID | ¹H NMR | MS(M + H)⁺ | Synthetic method |
|---|---|---|---|---|
| 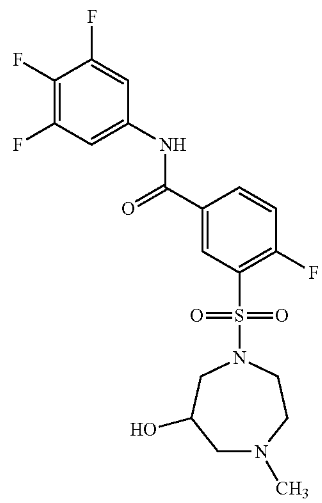 [SMILES: CN1CCN(S(=O)(=O)c2cc(C(=O)Nc3cc(F)c(F)c(F)c3)ccc2F)CC(O)C1] | 1898 | ¹H NMR (400 MHz, MeOD) δ 8.49-8.21 (m, 2H), 7.68-7.52 (m, 3H), 4.27-4.18 (m, 1H), 3.79-3.02 (m, 8H), 2.78 (s, 3H). | 462 | GENERAL PROCEDURE A A10B02C02 |
| 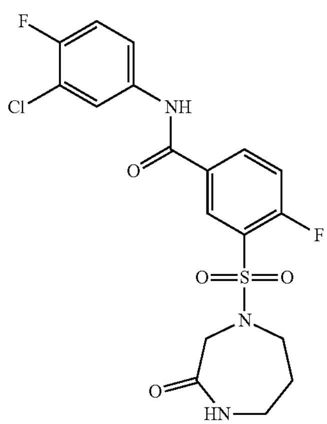 [SMILES: O=C1CN(S(=O)(=O)c2cc(C(=O)Nc3ccc(F)c(Cl)c3)ccc2F)CCCN1] | 1899 | | 444/446 | GENERAL PROCEDURE A A11B02C01 |
| 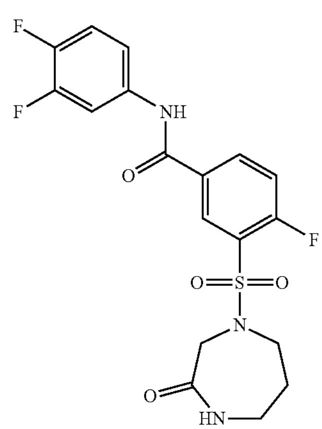 [SMILES: O=C1CN(S(=O)(=O)c2cc(C(=O)Nc3ccc(F)c(F)c3)ccc2F)CCCN1] | 1900 | ¹H NMR (400 MHz, CD₃OD) δ 8.47-8.49 (m, 1H), 8.25-8.27 (m, 1H), 7.78-7.85 (m, 1H), 7.46-7.54 (m, 2H), 7.28-7.32 (m, 1H), 4.14 (s, 2H), 3.67 (t, J = 6.0 Hz, 2H), 3.35-3.37 (m, 2H), 1.90-2.03 (m, 2H). | 428 | GENERAL PROCEDURE A A11B02C03 |

TABLE 1-continued

| Structure | Compound ID | ¹H NMR | MS(M + H)⁺ | Synthetic method |
|---|---|---|---|---|
| 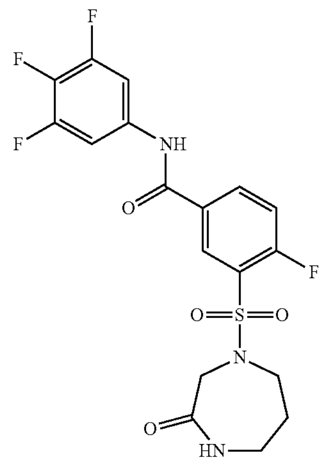 [SMILES: O=C1CN(S(=O)(=O)c2cc(C(=O)Nc3cc(F)c(F)c(F)c3)ccc2F)CCCN1] | 1901 | | 446 | GENERAL PROCEDURE A A11B02C02 |
| 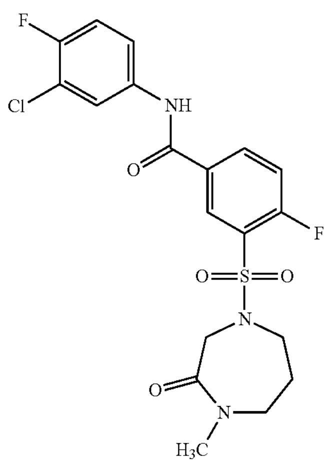 [SMILES: CN1CCCN(S(=O)(=O)c2cc(C(=O)Nc3ccc(F)c(Cl)c3)ccc2F)CC1=O] | 1902 | ¹H NMR (400 MHz, CD₃OD) δ 8.46-8.48 (m, 1H), 8.23-8.27 (m, 1H), 8.00-8.02 (m, 1H), 7.64-7.67 (m, 1H), 7.52 (t, J = 8.4 Hz, 1H), 7.28 (t, J = 8.8 Hz, 1H), 4.20 (s, 2H), 3.65 (t, J = 5.6 Hz, 2H), 3.57 (t, J = 5.2 Hz, 2H), 2.89 (s, 3H), 1.92-1.96 (m, 2H). | 458/460 | GENERAL PROCEDURE A A12B02C01 |
| 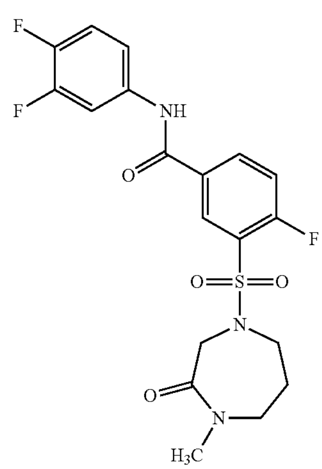 [SMILES: CN1CCCN(S(=O)(=O)c2cc(C(=O)Nc3ccc(F)c(F)c3)ccc2F)CC1=O] | 1903 | | 442 | GENERAL PROCEDURE A A12B02C03 |

TABLE 1-continued

| Structure | Compound ID | ¹H NMR | MS(M + H)⁺ | Synthetic method |
|---|---|---|---|---|
| 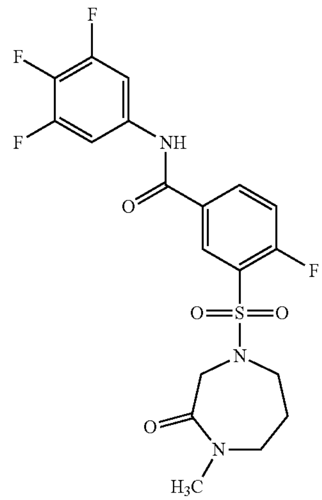 [SMILES: CN1CCCN(S(=O)(=O)c2cc(C(=O)Nc3cc(F)c(F)c(F)c3)ccc2F)CC1=O] | 1904 | | 460 | GENERAL PROCEDURE A A12B02C02 |
| 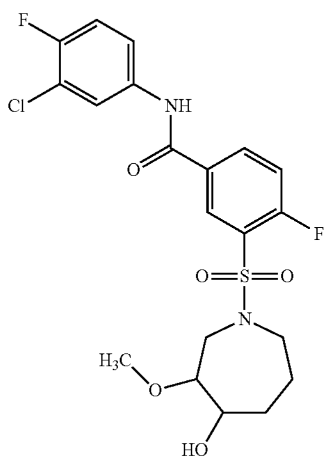 [SMILES: COC1CN(S(=O)(=O)c2cc(C(=O)Nc3ccc(F)c(Cl)c3)ccc2F)CCCC1O] | 1907 | 1H NMR (400 MHz, MeOD) δ 8.40-8.51 (m, 1H), 8.22-8.31 (m, 1H), 7.95-8.02 (m, 1H), 7.59-7.69 (m, 1H), 7.46-7.56 (m, 1H), 7.21-7.34 (m, 1H), 3.65-3.75 (m, 1H), 3.46 (s, 3H), 3.36-3.41 (m, 2H), 3.20-3.31 (m, 2H), 3.10-3.19 (m, 1H), 1.85-2.21 (m, 2H), 1.43-1.83 ppm (m, 2H) | 474/476 | GENERAL PROCEDURE A A16B02C01 |
| 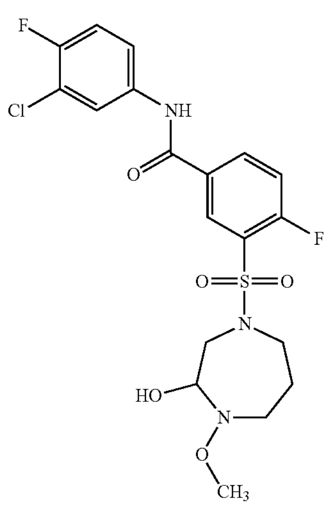 [SMILES: CON1CCCN(S(=O)(=O)c2cc(C(=O)Nc3ccc(F)c(Cl)c3)ccc2F)CC1O] | 1908 | 1H NMR (400 MHz, MeOD) δ 8.45 (s, 1H), 8.29-8.19 (m, 1H), 8.03-7.93 (m, 1H), 7.68-7.57 (m, 1H), 7.54-7.46 (m, 1H), 7.30-7.23 (m, 1H), 3.71-3.56 (m, 2H), 3.49-3.42 (m, 1H), 3.41 (s, 3H), 3.29-3.16 (m, 2H), 3.16-3.08 (m, 1H), 2.05-1.88 (m, 2H), 1.74-1.56 (m, 2H) | 474/476 | GENERAL PROCEDURE A A17B02C01 |

TABLE 1-continued

| Structure | Compound ID | ¹H NMR | MS(M + H)⁺ | Synthetic method |
|---|---|---|---|---|
| 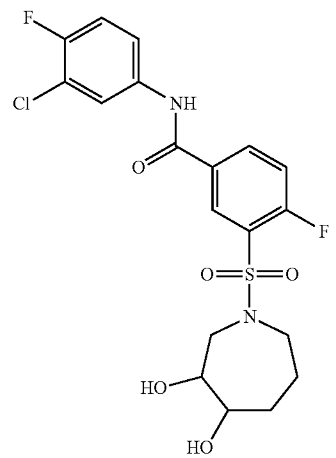 [SMILES: O=C(Nc1ccc(F)c(Cl)c1)c1ccc(F)c(S(=O)(=O)N2CCCC(O)C(O)C2)c1] | 1909 | 1H NMR (400 MHz, MeOD) δ 8.49-8.41 (m, 1H), 8.29-8.20 (m, 1H), 8.03-7.94 (m, 1H), 7.67-7.59 (m, 1H), 7.55-7.46 (m, 1H), 7.31-7.22 (m, 1H), 4.01-3.94 (m, 1H), 3.89-3.82 (m, 1H), 3.71-3.59 (m, 2H), 3.26-3.09 (m, 2H), 2.08-1.92 (m, 2H), 1.81-1.63 (m, 2H) | 460/462 | GENERAL PROCEDURE A A18B02C01 |
| 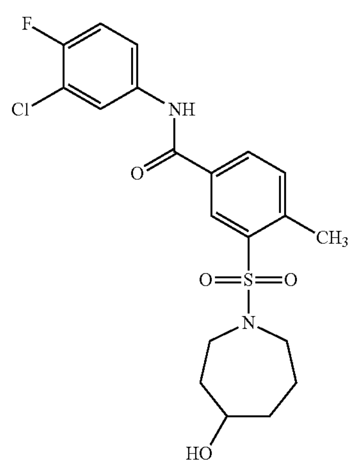 [SMILES: Cc1ccc(C(=O)Nc2ccc(F)c(Cl)c2)cc1S(=O)(=O)N1CCCC(O)CC1] | 1910 | ¹H NMR (400 MHz, MeOD) δ 8.38 (d, J = 1.9 Hz, 1H), 8.08-8.04 (m, 1H), 8.00-7.96 (m, 1H), 7.67-7.61 (m, 1H), 7.59-7.55 (m, 1H), 7.27 (s, 1H), 3.96-3.86 (m, 1H), 3.56-3.35 (m, 4H), 2.68 (s, 3H), 2.10-1.89 (m, 3H), 1.85-1.65 (m, 3H) | 441/443 | GENERAL PROCEDURE A A02B04C01 |
| 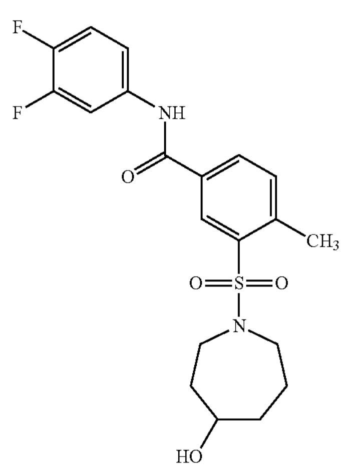 [SMILES: Cc1ccc(C(=O)Nc2ccc(F)c(F)c2)cc1S(=O)(=O)N1CCCC(O)CC1] | 1911 | ¹H NMR (400 MHz, MeOD) δ 8.39-8.36 (m, 1H), 8.09-8.04 (m, 1H), 8.01-7.96 (m, 1H), 7.67-7.61 (m, 1H), 7.59-7.54 (m, 1H), 7.30-7.24 (m, 1H), 3.95-3.84 (m, 1H), 3.55-3.35 (m, 4H), 2.68 (s, 3H), 2.10-1.91 (m, 3H), 1.85-1.65 (m, 3H) | 425 | GENERAL PROCEDURE A A02B04C03 |

TABLE 1-continued

| Structure | Compound ID | ¹H NMR | MS(M + H)⁺ | Synthetic method |
|---|---|---|---|---|
| 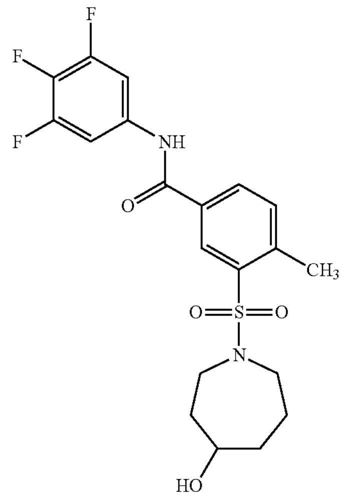 [SMILES: Cc1ccc(C(=O)Nc2cc(F)c(F)c(F)c2)cc1S(=O)(=O)N1CCCC(O)CC1] | 1912 | | 443 | GENERAL PROCEDURE A A02B04C02 |
| 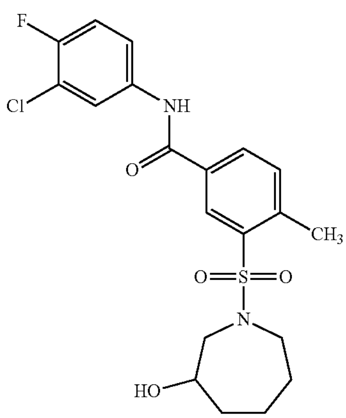 [SMILES: Cc1ccc(C(=O)Nc2ccc(F)c(Cl)c2)cc1S(=O)(=O)N1CCCCC(O)C1] | 1913 | | 441 | GENERAL PROCEDURE A A01B04C01 |
| 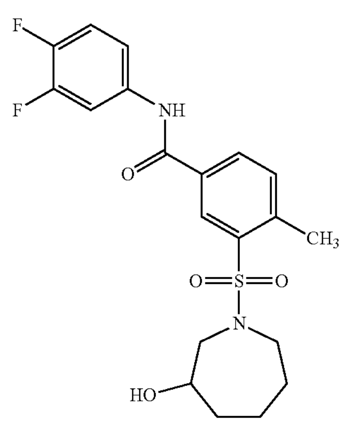 [SMILES: Cc1ccc(C(=O)Nc2ccc(F)c(F)c2)cc1S(=O)(=O)N1CCCCC(O)C1] | 1914 | | 425 | GENERAL PROCEDURE A A01B04C03 |

TABLE 1-continued

| Structure | Compound ID | ¹H NMR | MS(M + H)⁺ | Synthetic method |
|---|---|---|---|---|
| (structure) | 1915 | | 443 | GENERAL PROCEDURE A<br>A01B04C02 |
| (structure) | 1917 | | 443 | GENERAL PROCEDURE F<br>A02B05C03 |
| (structure) | 1918 | | 461 | GENERAL PROCEDURE F<br>A02B05C02 |

TABLE 1-continued

| Structure | Compound ID | ¹H NMR | MS(M + H)⁺ | Synthetic method |
|---|---|---|---|---|
| 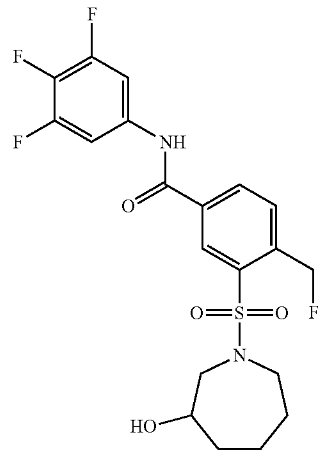 [SMILES: O=C(Nc1cc(F)c(F)c(F)c1)c1ccc(CF)c(S(=O)(=O)N2CCCCC(O)C2)c1] | 1921 | | 461 | GENERAL PROCEDURE F A01B05C02 |
| 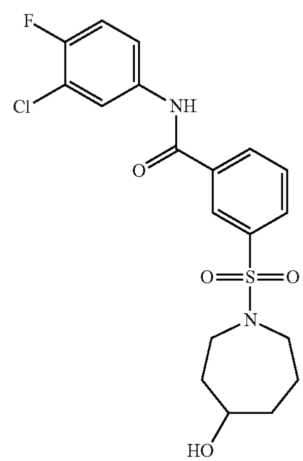 [SMILES: O=C(Nc1ccc(F)c(Cl)c1)c1cccc(S(=O)(=O)N2CCCC(O)CC2)c1] | 1928 | | 427/429 | GENERAL PROCEDURE A A02B01C01 |
| 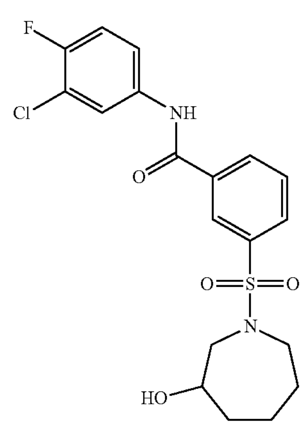 [SMILES: O=C(Nc1ccc(F)c(Cl)c1)c1cccc(S(=O)(=O)N2CCCCC(O)C2)c1] | 1929 | ¹H NMR (400 MHz, MeOD) δ 8.38 (s, 1H), 8.21 (d, J = 7.8 Hz, 1H), 7.95-8.08 (m, 2H), 7.77 (t, J = 7.8 Hz, 1H), 7.61-7.69 (m, 1H), 7.28 (t, J = 9.0 Hz, 1H), 3.85-3.94 (m, 1H), 3.69 (dd, J = 4.5, 14.0 Hz, 1H), 3.54 (td, J = 6.5, 13.2 Hz, 1H), 3.09-3.20 (m, 1H), 2.96 (dd, J = 8.3, 14.0 Hz, 1H), 1.43-2.03 (m, 6H). | 427/429 | GENERAL PROCEDURE A A01B01C01 |

TABLE 1-continued

| Structure | Compound ID | ¹H NMR | MS(M + H)⁺ | Synthetic method |
|---|---|---|---|---|
| (structure) | 1932 | | 459/561 | GENERAL PROCEDURE A A06B02C01 |
| (structure) | 1938 | ¹H NMR (400 MHz, MeOD) δ 8.44 (dd, J = 2.3, 6.6 Hz, 1H), 8.25-8.23 (m, 1H), 7.85-7.84 (m, 1H), 7.55-7.41 (m, 2H), 7.35-7.23 (m, 1H), 3.62-3.49 (m, 2H), 3.32-3.26 (m, 2H), 2.11-1.94 (m, 1H), 1.85-1.62 (m, 5H), 1.26 (s, 3H) | 443 | GENERAL PROCEDURE A A06B02C03 |
| (structure) | 1944 | | 461 | GENERAL PROCEDURE A A06B02C02 |

TABLE 1-continued

| Structure | Compound ID | ¹H NMR | MS(M + H)⁺ | Synthetic method |
|---|---|---|---|---|
| 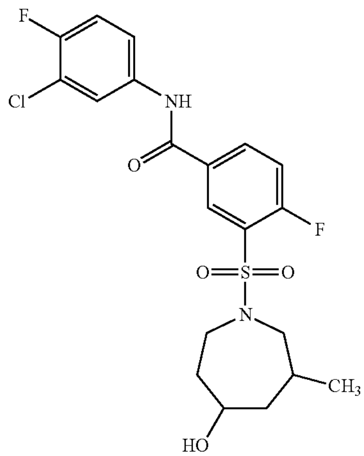 [SMILES: CC1CC(O)CCN(S(=O)(=O)c2cc(C(=O)Nc3ccc(F)c(Cl)c3)ccc2F)C1] | 1934_D1 | | 459/461 | GENERAL PROCEDURE A A30B02C01 |
| 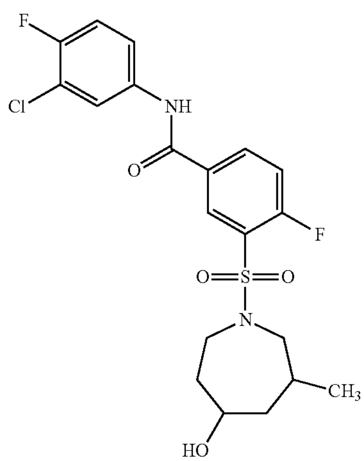 [SMILES: CC1CC(O)CCN(S(=O)(=O)c2cc(C(=O)Nc3ccc(F)c(Cl)c3)ccc2F)C1] | 1934_D2 | NMR | 459/461 | GENERAL PROCEDURE A A30B02C01 |
| 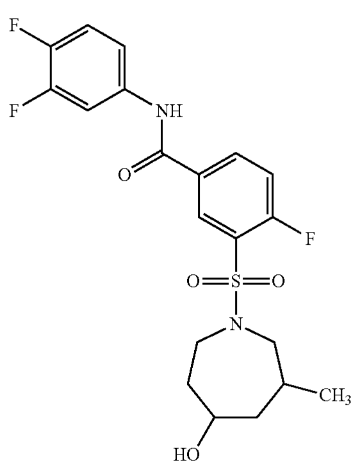 [SMILES: CC1CC(O)CCN(S(=O)(=O)c2cc(C(=O)Nc3ccc(F)c(F)c3)ccc2F)C1] | 1940_D1 | NMR | 443 | GENERAL PROCEDURE A A30B02C03 |

TABLE 1-continued

| Structure | Compound ID | ¹H NMR | MS(M + H)⁺ | Synthetic method |
|---|---|---|---|---|
| 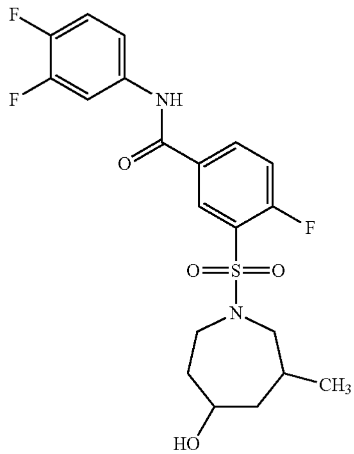 [SMILES: CC1CC(O)CCN(S(=O)(=O)c2cc(C(=O)Nc3ccc(F)c(F)c3)ccc2F)C1] | 1940_D2 | | 443 | GENERAL PROCEDURE A A30B02C03 |
| 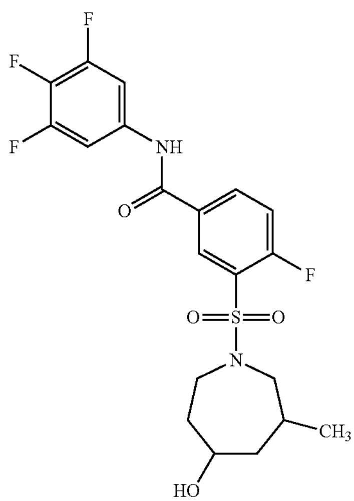 [SMILES: CC1CC(O)CCN(S(=O)(=O)c2cc(C(=O)Nc3cc(F)c(F)c(F)c3)ccc2F)C1] | 1946_D1 | | 461 | GENERAL PROCEDURE A A30B02C02 |
| 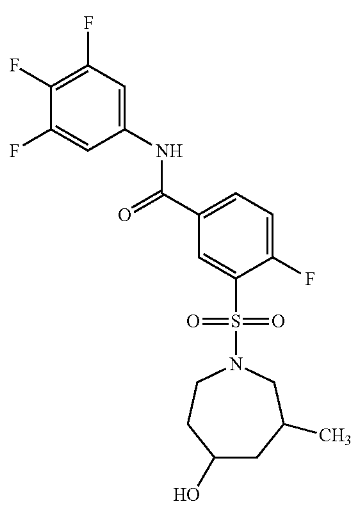 [SMILES: CC1CC(O)CCN(S(=O)(=O)c2cc(C(=O)Nc3cc(F)c(F)c(F)c3)ccc2F)C1] | 1946_D2 | | 461 | GENERAL PROCEDURE A A30B02C02 |

TABLE 1-continued

| Structure | Compound ID | ¹H NMR | MS(M + H)⁺ | Synthetic method |
|---|---|---|---|---|
| (structure) | 2041 | | 459/461 | GENERAL PROCEDURE A A30B02C01 |
| (structure) | 2042 | | 443 | GENERAL PROCEDURE A A31B02C03 |
| (structure) | 2043 | | 461 | GENERAL PROCEDURE A A31B02C02 |

TABLE 1-continued

| Structure | Compound ID | ¹H NMR | MS(M + H)⁺ | Synthetic method |
|---|---|---|---|---|
| 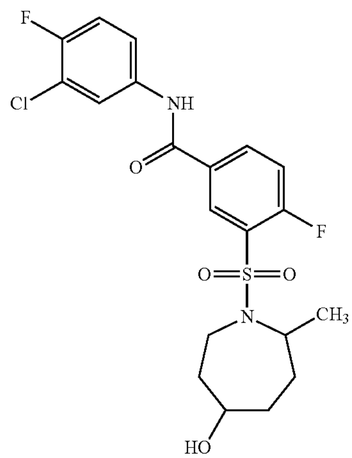 [SMILES: CC1CCC(O)CCN1S(=O)(=O)c1cc(C(=O)Nc2ccc(F)c(Cl)c2)ccc1F] | _1935_D1 | | 459/461 | GENERAL PROCEDURE A A32B02C01 |
| 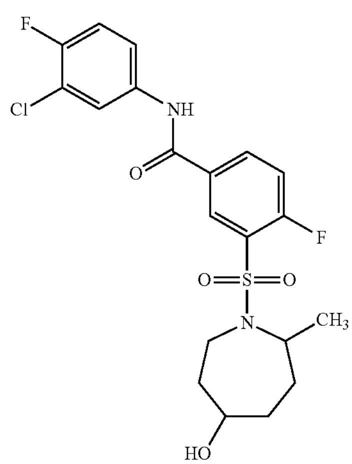 [SMILES: CC1CCC(O)CCN1S(=O)(=O)c1cc(C(=O)Nc2ccc(F)c(Cl)c2)ccc1F] | _1935_D2 | | 459/461 | GENERAL PROCEDURE A A32B02C01 |
| 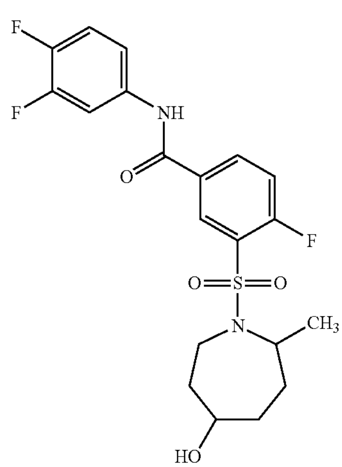 [SMILES: CC1CCC(O)CCN1S(=O)(=O)c1cc(C(=O)Nc2ccc(F)c(F)c2)ccc1F] | _1941_D1 | ¹H NMR (400 MHz, MeOD) δ 8.48 (dd, J = 6.65, 2.13 Hz, 1H), 8.26 (d, J = 2.51 Hz, 1H), 7.81 (ddd, J = 12.49, 7.34, 2.26 Hz, 1H), 7.53 (t, J = 9.29 Hz, 1H), 7.45 (d, J = 9.03 Hz, 1H), 7.26-7.36 (m, 1H), 4.06-4.17 (m, 1H), 3.83 (d, J = 15.81 Hz, 1H), 3.56-3.66 (m, 1H), 3.08-3.18 (m, 1H), 1.84-2.07 (m, 3H), 1.29-1.62 (m, 3H), 0.91 (d, J = 6.27 Hz, 3H). | 443 | GENERAL PROCEDURE A A32B02C03 |

TABLE 1-continued

| Structure | Compound ID | ¹H NMR | MS(M + H)⁺ | Synthetic method |
|---|---|---|---|---|
| (structure) | _1941_D2 | ¹H NMR (400 MHz, MeOD) δ 8.49 (dd, J = 6.78, 2.26 Hz, 1H), 8.20-8.29 (m, 1H), 7.84 (ddd, J = 12.74, 7.34, 2.51 Hz, 1H), 7.41-7.57 (m, 2H), 7.25-7.34 (m, 1H), 3.98-4.14 (m, 2H), 3.74 (d, J = 15.31 Hz, 1H), 3.38 (d, J = 4.77 Hz, 1H), 1.87-1.99 (m, 2H), 1.61-1.84 (m, 4H), 0.92 (d, J = 6.27 Hz, 3H). | 443 | GENERAL PROCEDURE A A32B02C03 |
| (structure) | _1947_D1 | | 461 | GENERAL PROCEDURE A A32B02C02 |
| (structure) | _1947_D2 | | 461 | GENERAL PROCEDURE A A32B02C02 |

TABLE 1-continued

| Structure | Compound ID | ¹H NMR | MS(M + H)⁺ | Synthetic method |
|---|---|---|---|---|
| 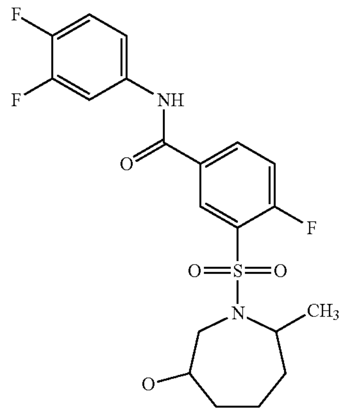 [SMILES: CC1CCCC(O)CN1S(=O)(=O)c1cc(C(=O)Nc2ccc(F)c(F)c2)ccc1F] | _2065_D1 | | 459/461 | GENERAL PROCEDURE A A33B02C01 |
| 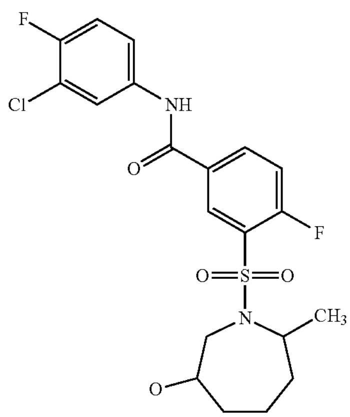 [SMILES: CC1CCCC(O)CN1S(=O)(=O)c1cc(C(=O)Nc2ccc(F)c(Cl)c2)ccc1F] | _2065_D2 | | 459/461 | GENERAL PROCEDURE A A33B02C01 |
| 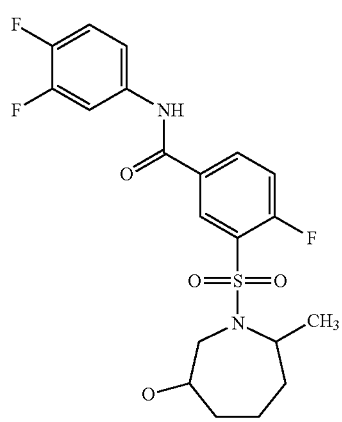 [SMILES: CC1CCCC(O)CN1S(=O)(=O)c1cc(C(=O)Nc2ccc(F)c(F)c2)ccc1F] | _2066_D1 | | 443 | GENERAL PROCEDURE A A33B02C03 |

TABLE 1-continued

| Structure | Compound ID | ¹H NMR | MS(M + H)⁺ | Synthetic method |
|---|---|---|---|---|
| 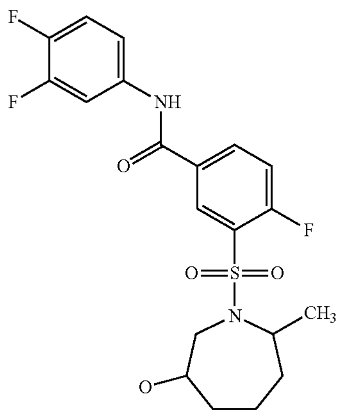 [SMILES: CC1CCCC(O)CN1S(=O)(=O)c1cc(C(=O)Nc2ccc(F)c(F)c2)ccc1F] | _2066_D2 | | 443 | GENERAL PROCEDURE A A33B02C03 |
| 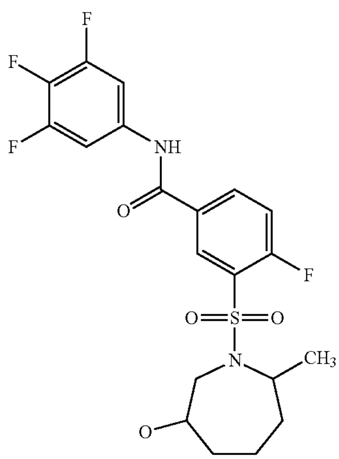 [SMILES: CC1CCCC(O)CN1S(=O)(=O)c1cc(C(=O)Nc2cc(F)c(F)c(F)c2)ccc1F] | _2067_D1 | | 461 | GENERAL PROCEDURE A A33B02C02 |
| 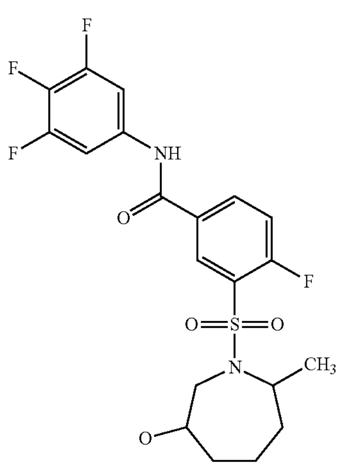 [SMILES: CC1CCCC(O)CN1S(=O)(=O)c1cc(C(=O)Nc2cc(F)c(F)c(F)c2)ccc1F] | _2067_D2 | | 461 | GENERAL PROCEDURE A A33B02C02 |

TABLE 1-continued

| Structure | Compound ID | ¹H NMR | MS(M + H)⁺ | Synthetic method |
|---|---|---|---|---|
| (structure of 1950_D1) | 1950_D1 | | 475/477 | GENERAL PROCEDURE A A21B02C01 |
| (structure of 1950_D2) | 1950_D2 | | 475/477 | GENERAL PROCEDURE A A21B02C01 |
| (structure of 1951_D1) | 1951_D1 | | 459 | GENERAL PROCEDURE A A21B02C03 |

TABLE 1-continued

| Structure | Compound ID | ¹H NMR | MS(M + H)⁺ | Synthetic method |
|---|---|---|---|---|
| 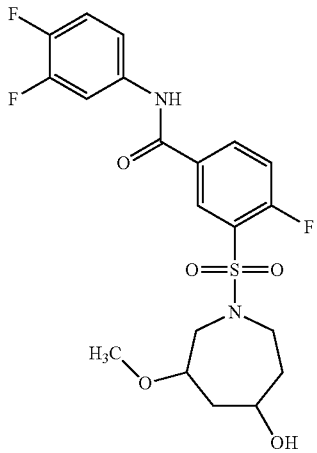 [SMILES: COC1CC(O)CCN(S(=O)(=O)c2cc(C(=O)Nc3ccc(F)c(F)c3)ccc2F)C1] | 1951_D2 | | 459 | GENERAL PROCEDURE A A21B02C03 |
| 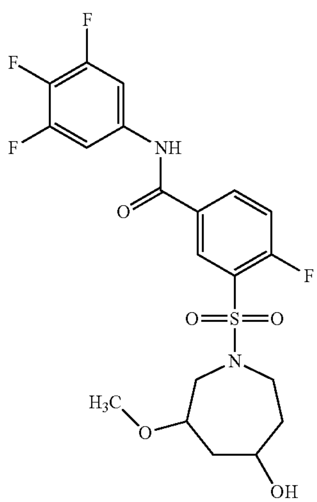 [SMILES: COC1CC(O)CCN(S(=O)(=O)c2cc(C(=O)Nc3cc(F)c(F)c(F)c3)ccc2F)C1] | 1952_D1 | ¹H NMR (400 MHz, METHANOL-d4) δ = 8.45-8.48 (m, 1H), 8.24-8.26 (m, 1H), 7.59-7.64 (m, 2H), 7.49-7.55 (m, 1H), 3.80-3.85 (m, 1H), 3.60-3.65 (m, 1H), 3.30-3.55 (m, 7H), 2.26-2.29 (m, 1H), 2.05-2.10 (m, 1H), 1.70-1.84 (m, 2H). | 477 | GENERAL PROCEDURE A A21B02C02 |
| 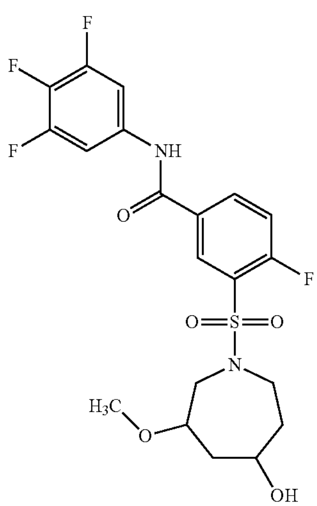 [SMILES: COC1CC(O)CCN(S(=O)(=O)c2cc(C(=O)Nc3cc(F)c(F)c(F)c3)ccc2F)C1] | 1952_D2 | ¹H NMR (400 MHz, METHANOL-d4) δ = 8.45-8.48 (m, 1H), 8.23-8.26 (m, 1H), 7.59-7.64 (m, 2H), 7.48-7.54 (m, 1H), 4.02-4.07 (m, 1H), 3.66-3.72 (m, 2H), 3.55-3.60 (m, 1H), 3.32-3.39 (m, 5H), 1.96-2.18 (m, 3H), 1.75-1.79 (m, 1H). | 477 | GENERAL PROCEDURE A A21B02C02 |

| Structure | Compound ID | ¹H NMR | MS(M + H)⁺ | Synthetic method |
|---|---|---|---|---|
| (structure) | 1956_D1 | | 475/477 | GENERAL PROCEDURE A A21B02C01 |
| (structure) | 1956_D2 | | 475/477 | GENERAL PROCEDURE A A21B02C01 |
| (structure) | 1957_D1 | ¹H NMR (400 MHz, METHANOL-d4) δ = 8.47-8.49 (m, 1H), 8.25-8.27 (m, 1H), 7.80-7.85 (m, 1H), 7.44-7.54 (m, 2H), 7.27-7.31 (m, 1H), 3.93-3.95 (m, 1H), 3.45-3.64 (m, 4H), 3.34 (s, 3H), 3.06-3.09 (m, 1H), 2.04-2.07 (m, 2H), 1.52-1.61 (m, 2H). | 459 | GENERAL PROCEDURE A A20B02C03 |

TABLE 1-continued

| Structure | Compound ID | ¹H NMR | MS(M + H)⁺ | Synthetic method |
|---|---|---|---|---|
| 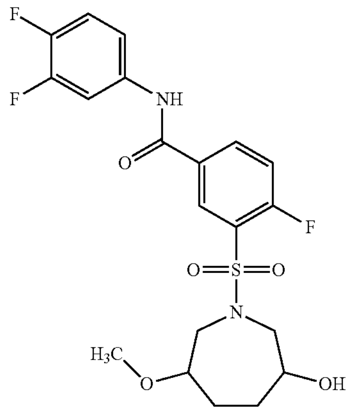 [SMILES: COC1CCC(O)CN(S(=O)(=O)c2cc(C(=O)Nc3ccc(F)c(F)c3)ccc2F)C1] | 1957_D2 | ¹H NMR (400 MHz, METHANOL-d4) δ = 8.46-8.48 (m, 1H), 8.24-8.27 (m, 1H), 7.80-7.85 (m, 1H), 7.44-7.55 (m, 2H), 7.27-7.33 (m, 1H), 3.86-3.92 (m, 3H), 3.60-3.65 (m, 1H), 3.34 (s, 3H), 2.99-3.03 (m, 1H), 2.88-2.91 (m, 1H), 1.98-2.01 (m, 1H), 1.77-1.84 (m, 3H). | 459 | GENERAL PROCEDURE A A20B02C03 |
| 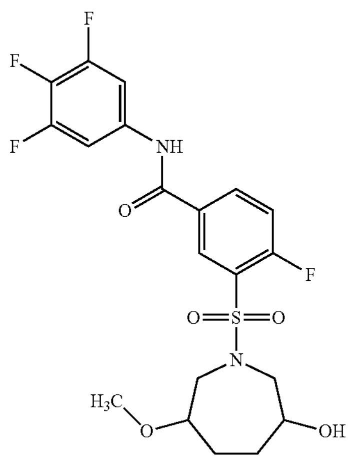 [SMILES: COC1CCC(O)CN(S(=O)(=O)c2cc(C(=O)Nc3cc(F)c(F)c(F)c3)ccc2F)C1] | 1958_D1 | | 477 | GENERAL PROCEDURE A A20B02C02 |
| 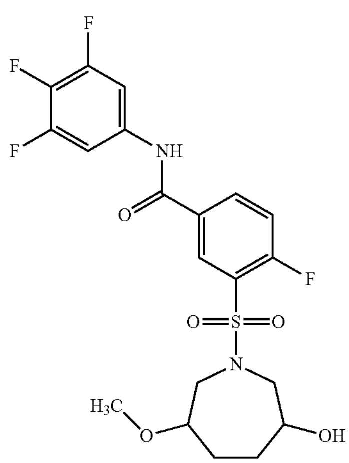 [SMILES: COC1CCC(O)CN(S(=O)(=O)c2cc(C(=O)Nc3cc(F)c(F)c(F)c3)ccc2F)C1] | 1958_D2 | | 477 | GENERAL PROCEDURE A A20B02C02 |

TABLE 1-continued

| Structure | Compound ID | ¹H NMR | MS(M + H)⁺ | Synthetic method |
|---|---|---|---|---|
| 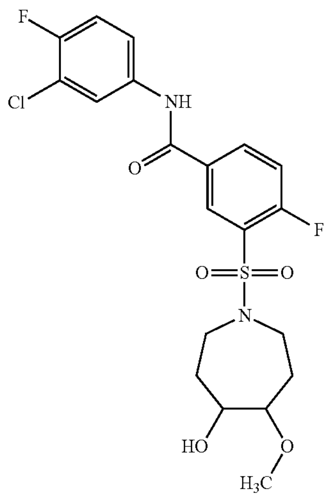 [SMILES: COC1CCN(S(=O)(=O)c2cc(C(=O)Nc3ccc(F)c(Cl)c3)ccc2F)CCC1O] | 1959 | ¹H NMR (400 MHz, MeOD) δ 8.45 (dd, J = 2.3, 6.7 Hz, 1H), 8.25 (ddd, J = 2.4, 4.6, 8.6 Hz, 1H), 7.98 (dd, J = 2.6, 6.8 Hz, 1H), 7.64 (ddd, J = 2.6, 4.2, 9.0 Hz, 1H), 7.50 (dd, J = 8.7, 9.9 Hz, 1H), 7.27 (t, J = 9.0 Hz, 1H), 3.77-3.68 (m, 1H), 3.64-3.49 (m, 2H), 3.44-3.37 (m, 5H), 3.27-3.20 (m, 1H), 2.10 (tdd, J = 2.9, 7.6, 15.2 Hz, 1H), 2.05-1.97 (m, 1H), 1.84-1.70 (m, 2H) | 475/477 | GENERAL PROCEDURE A A15B02C01 |
| 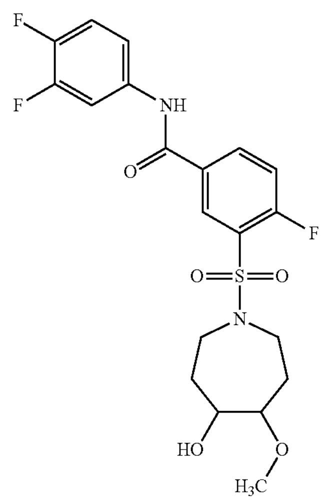 [SMILES: COC1CCN(S(=O)(=O)c2cc(C(=O)Nc3ccc(F)c(F)c3)ccc2F)CCC1O] | 1960 | | 459 | GENERAL PROCEDURE A A15B02C03 |
| 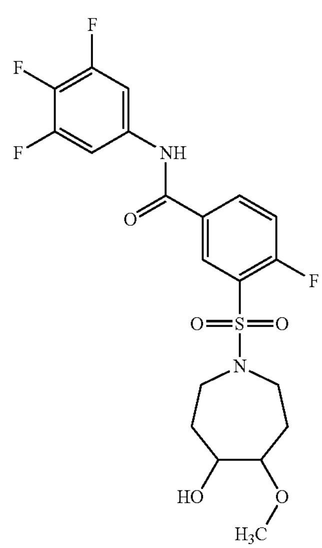 [SMILES: COC1CCN(S(=O)(=O)c2cc(C(=O)Nc3cc(F)c(F)c(F)c3)ccc2F)CCC1O] | 1961 | | 477 | GENERAL PROCEDURE A A15B02C02 |

TABLE 1-continued

| Structure | Compound ID | ¹H NMR | MS(M + H)⁺ | Synthetic method |
|---|---|---|---|---|
| (structure) | 1971 | | 458 | GENERAL PROCEDURE A A16B02C03 |
| (structure) | 1972 | | 458 | GENERAL PROCEDURE A A17B02C03 |
| (structure) | 1973 | | 476 | GENERAL PROCEDURE A A16B02C02 |

TABLE 1-continued

| Structure | Compound ID | ¹H NMR | MS(M + H)⁺ | Synthetic method |
|---|---|---|---|---|
| 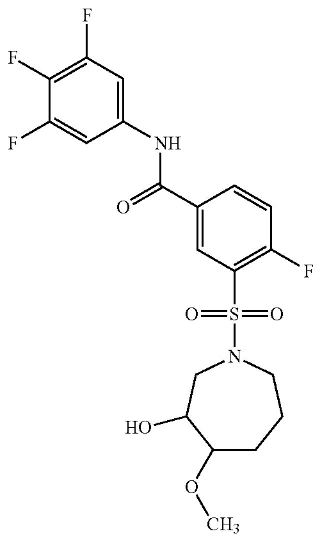 [SMILES: COC1CCCN(S(=O)(=O)c2cc(C(=O)Nc3cc(F)c(F)c(F)c3)ccc2F)CC1O] | 1974 | | 476 | GENERAL PROCEDURE A A17B02C02 |
| 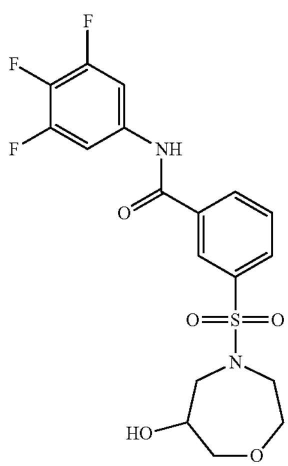 [SMILES: O=C(Nc1cc(F)c(F)c(F)c1)c1cccc(S(=O)(=O)N2CCOCC(O)C2)c1] | 1975 | | 431 | GENERAL PROCEDURE A A13B01C02 |
| 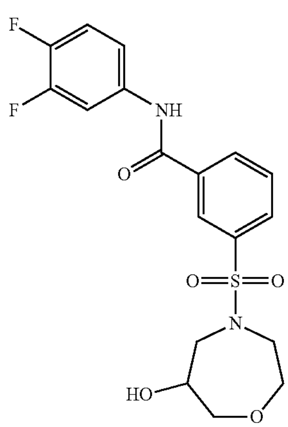 [SMILES: O=C(Nc1ccc(F)c(F)c1)c1cccc(S(=O)(=O)N2CCOCC(O)C2)c1] | 1976 | | 413 | GENERAL PROCEDURE A A13B01C03 |

TABLE 1-continued

| Structure | Compound ID | ¹H NMR | MS(M + H)⁺ | Synthetic method |
|---|---|---|---|---|
| 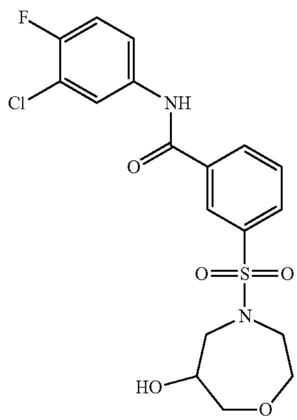 [SMILES: O=C(Nc1ccc(F)c(Cl)c1)c1cccc(S(=O)(=O)N2CCOCC(O)C2)c1] | 1977 | ¹H NMR (400 MHz, METHANOL-d₄) δ = 8.40 (t, J = 1.6 Hz, 1H), 8.23 (d, J = 8.2 Hz, 1H), 8.10-8.05 (m, 1H), 8.00 (dd, J = 2.6, 6.8 Hz, 1H), 7.78 (t, J = 7.8 Hz, 1H), 7.69-7.63 (m, 1H), 7.28 (t, J = 9.0 Hz, 1H), 4.06-3.98 (m, 1H), 3.93-3.84 (m, 2H), 3.80-3.59 (m, 4H), 3.27 (ddd, J = 3.6, 8.2, 13.8 Hz, 1H), 3.15 (dd, J = 7.3, 14.1 Hz, 1H) | 429/431 | GENERAL PROCEDURE A A13B01C01 |
| 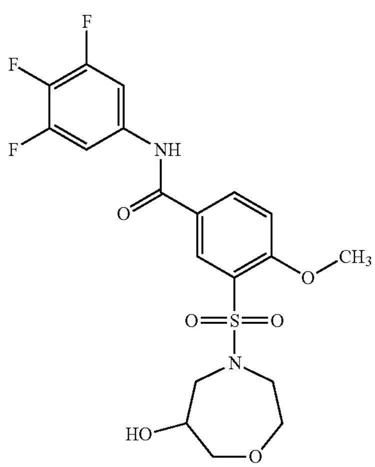 | 1978 | | 461 | GENERAL PROCEDURE A A13B06C02 |
| 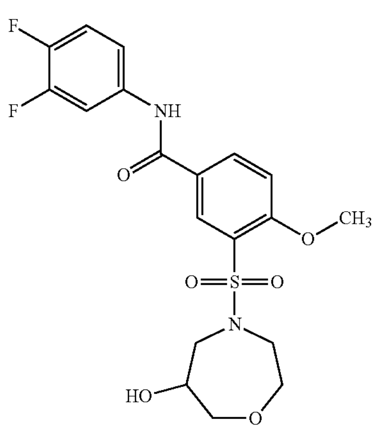 | 1979 | ¹H NMR (400 MHz, METHANOL-d₄) δ = 8.50 (d, J = 2.3 Hz, 1H), 8.22 (dd, J = 2.4, 8.8 Hz, 1H), 7.83 (ddd, J = 2.5, 7.4, 12.8 Hz, 1H), 7.47-7.42 (m, 1H), 7.37 (d, J = 8.7 Hz, 1H), 7.32-7.23 (m, 1H), 4.07 (s, 3H), 4.06-3.99 (m, 1H), 3.96-3.88 (m, 2H), 3.88-3.79 (m, 2H), 3.74-3.64 (m, 2H), 3.30-3.24 (m, 1H), 3.13 (dd, J = 7.5, 14.6 Hz, 1H) | 443 | GENERAL PROCEDURE A A13B06C03 |

TABLE 1-continued

| Structure | Compound ID | $^1$H NMR | MS(M + H)$^+$ | Synthetic method |
|---|---|---|---|---|
| 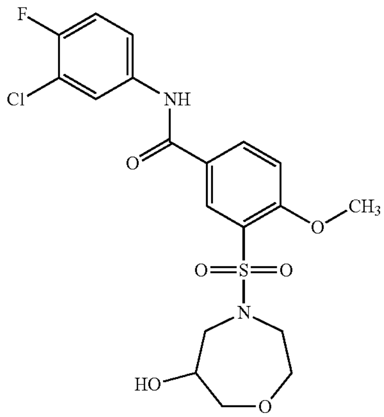 [SMILES: COc1ccc(C(=O)Nc2ccc(F)c(Cl)c2)cc1S(=O)(=O)N1CCOCC(O)C1] | 1980 | $^1$H NMR (400 MHz, METHANOL-d$_4$) δ = 8.50 (d, J = 2.3 Hz, 1H), 8.22 (dd, J = 2.4, 8.7 Hz, 1H), 7.97 (dd, J = 2.6, 6.7 Hz, 1H), 7.65-7.59 (m, 1H), 7.37 (d, J = 8.7 Hz, 1H), 7.26 (t, J = 9.0 Hz, 1H), 4.07 (s, 3H), 4.05-3.98 (m, 1H), 3.96-3.88 (m, 2H), 3.87-3.78 (m, 2H), 3.73-3.64 (m, 2H), 3.31-3.24 (m, 1H), 3.13 (dd, J = 7.6, 14.5 Hz, 1H) | 459/461 | GENERAL PROCEDURE A A13B06C01 |
| 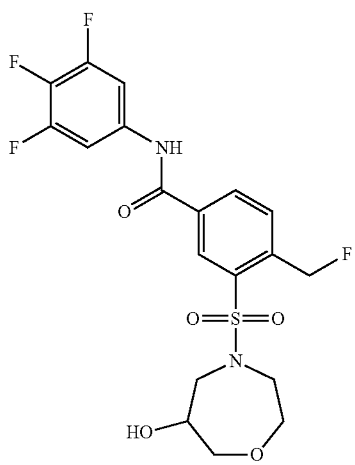 [SMILES: O=C(Nc1cc(F)c(F)c(F)c1)c1ccc(CF)c(S(=O)(=O)N2CCOCC(O)C2)c1] | 1981 | | 463 | GENERAL PROCEDURE F A13B05C02 |
| 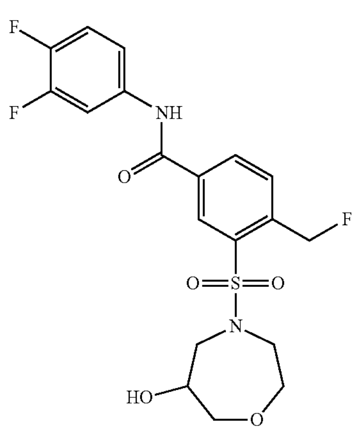 [SMILES: O=C(Nc1ccc(F)c(F)c1)c1ccc(CF)c(S(=O)(=O)N2CCOCC(O)C2)c1] | 1982 | $^1$H NMR (400 MHz, METHANOL-d$_4$) δ 8.41-8.50 (m, 1H), 8.20-8.28 (m, 1H), 7.80-7.95 (m, 2H), 7.40-7.51 (m, 1H), 7.19-7.34 (m, 1H), 5.90-5.99 (m, 1H), 5.76-5.85 (m, 1H), 3.99-4.06 (m, 1H), 3.84-3.95 (m, 2H), 3.59-3.83 (m, 4H), 3.38-3.47 (m, 1H), 3.33-3.36 (m, 1H) | 445 | GENERAL PROCEDURE F A13B05C03 |

TABLE 1-continued
| Structure | Compound ID | ¹H NMR | MS(M + H)⁺ | Synthetic method |
|---|---|---|---|---|
| 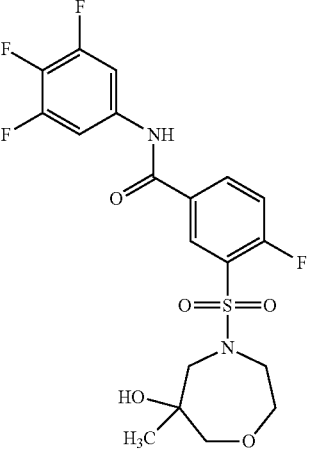 [SMILES: CC1(O)COCCN(S(=O)(=O)c2cc(C(=O)Nc3cc(F)c(F)c(F)c3)ccc2F)C1] | 1984 | | 463 | GENERAL PROCEDURE A A35B02C02 |
| 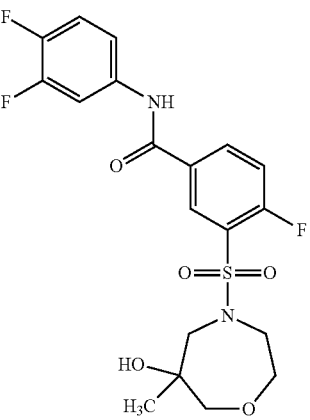 [SMILES: CC1(O)COCCN(S(=O)(=O)c2cc(C(=O)Nc3ccc(F)c(F)c3)ccc2F)C1] | 1985 | | 445 | GENERAL PROCEDURE A A35B02C03 |
| 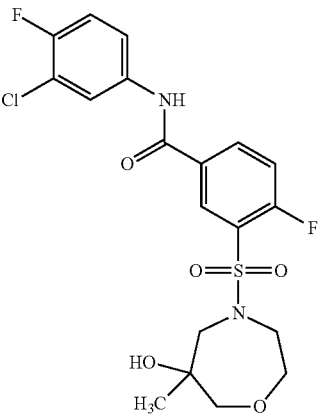 | 1986 | | 461/463 | GENERAL PROCEDURE A A35B02C01 |

TABLE 1-continued

| Structure | Compound ID | ¹H NMR | MS(M + H)⁺ | Synthetic method |
|---|---|---|---|---|
| 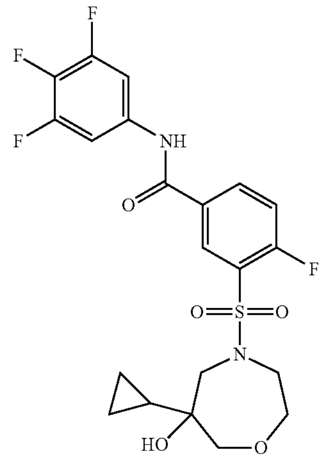 [SMILES: O=C(Nc1cc(F)c(F)c(F)c1)c1ccc(F)c(S(=O)(=O)N2CCOCC(O)(C3CC3)C2)c1] | 1987 | | 489 | GENERAL PROCEDURE A A36B02C02 |
| 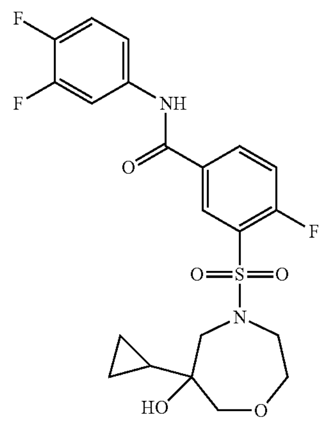 [SMILES: O=C(Nc1ccc(F)c(F)c1)c1ccc(F)c(S(=O)(=O)N2CCOCC(O)(C3CC3)C2)c1] | 1988 | | 471 | GENERAL PROCEDURE A A36B02C03 |
| 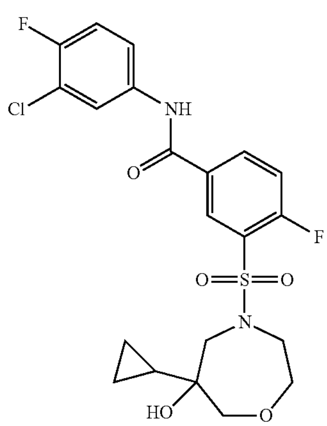 [SMILES: O=C(Nc1ccc(F)c(Cl)c1)c1ccc(F)c(S(=O)(=O)N2CCOCC(O)(C3CC3)C2)c1] | 1989 | | 487/489 | GENERAL PROCEDURE A A36B02C01 |

TABLE 1-continued

| Structure | Compound ID | ¹H NMR | MS(M + H)⁺ | Synthetic method |
|---|---|---|---|---|
| 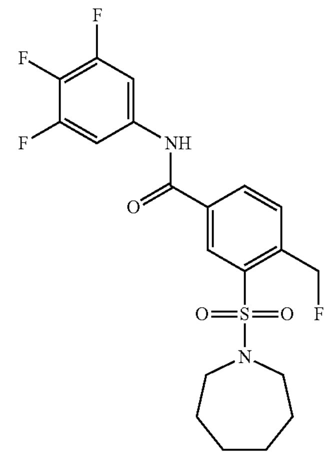 [SMILES: O=C(Nc1cc(F)c(F)c(F)c1)c1ccc(CF)c(S(=O)(=O)N2CCCCCC2)c1] | 2002 |  | 445 | GENERAL PROCEDURE F A53B05C02 |
| 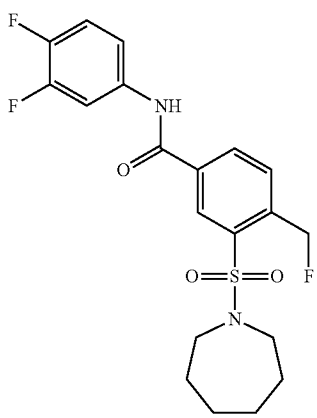 [SMILES: O=C(Nc1ccc(F)c(F)c1)c1ccc(CF)c(S(=O)(=O)N2CCCCCC2)c1] | 2003 |  | 427 | GENERAL PROCEDURE F A53B05C03 |
| 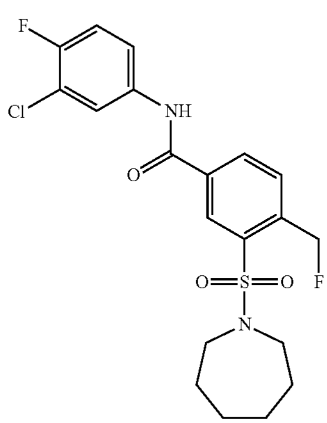 [SMILES: O=C(Nc1ccc(F)c(Cl)c1)c1ccc(CF)c(S(=O)(=O)N2CCCCCC2)c1] | 2004 |  | 443 | GENERAL PROCEDURE F A53B05C01 |

TABLE 1-continued

| Structure | Compound ID | $^1$H NMR | MS(M + H)$^+$ | Synthetic method |
|---|---|---|---|---|
| 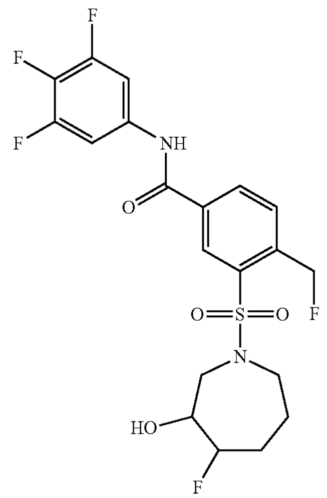 [SMILES: O=C(Nc1cc(F)c(F)c(F)c1)c1ccc(CF)c(S(=O)(=O)N2CCCC(F)C(O)C2)c1] | 2005 | | 479 | GENERAL PROCEDURE F A07B05C02 |
| 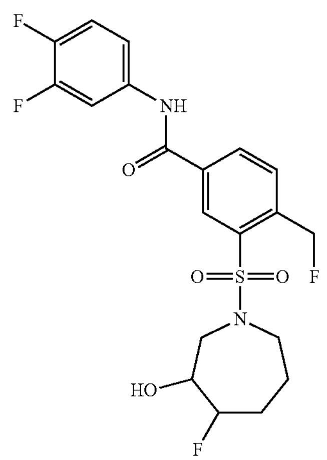 [SMILES: O=C(Nc1ccc(F)c(F)c1)c1ccc(CF)c(S(=O)(=O)N2CCCC(F)C(O)C2)c1] | 2006 | | 461 | GENERAL PROCEDURE F A07B05C03 |
| 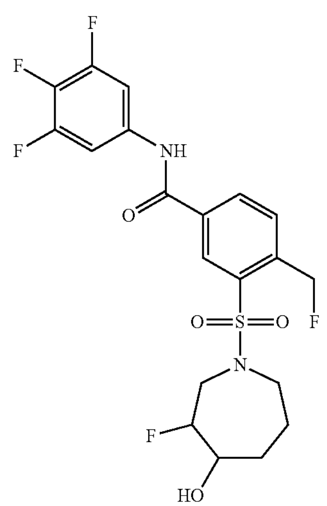 [SMILES: O=C(Nc1cc(F)c(F)c(F)c1)c1ccc(CF)c(S(=O)(=O)N2CCCC(O)C(F)C2)c1] | 2008 | $^1$H NMR (400 MHz, METHANOL-d$_4$) δ 8.34-8.45 (m, 1H), 8.16-8.28 (m, 1H), 7.84-7.97 (m, 1H), 7.53-7.69 (m, 2H), 5.88-5.94 (m, 1H), 5.77-5.82 (m, 1H), 4.77-4.82 (m, 1H), 4.64-4.71 (m, 1H), 4.41-4.49 (m, 1H), 4.30-4.37 (m, 1H), 3.99-4.10 (m, 1H), 3.34-3.83 (m, 5H), 3.17-3.28 (m, 1H), 1.82-2.08 (m, 2H), 1.65-1.80 (m, 2H) | 479 | GENERAL PROCEDURE F A08B05C02 |

TABLE 1-continued

| Structure | Compound ID | ¹H NMR | MS(M + H)⁺ | Synthetic method |
|---|---|---|---|---|
| 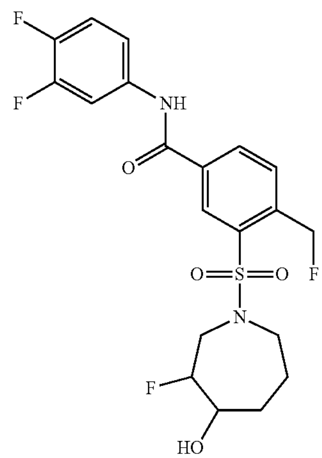 [SMILES: O=C(Nc1ccc(F)c(F)c1)c1ccc(CF)c(S(=O)(=O)N2CCCC(O)C(F)C2)c1] | 2009 | | 461 | GENERAL PROCEDURE F A08B05C03 |
| 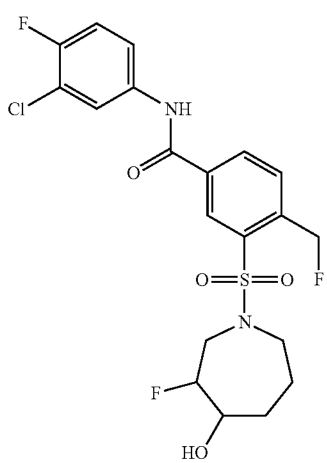 [SMILES: O=C(Nc1ccc(F)c(Cl)c1)c1ccc(CF)c(S(=O)(=O)N2CCCC(O)C(F)C2)c1] | 2010 | ¹H NMR (400 MHz, METHANOL-d₄) δ 8.36-8.42 (m, 1H), 8.21-8.27 (m, 1H), 7.95-8.01 (m, 1H), 7.86-7.93 (m, 1H), 7.60-7.68 (m, 1H), 7.26 (s, 1H), 5.88-5.95 (m, 1H), 5.75-5.82 (m, 1H), 4.77-4.82 (m, 1H), 4.65-4.72 (m, 1H), 4.40-4.49 (m, 1H), 4.30-4.38 (m, 1H), 3.97-4.12 (m, 1H), 3.49-3.83 (m, 3H), 3.34-3.43 (m, 1H), 3.19-3.28 (m, 1H), 1.80-2.07 (m, 2H), 1.65-1.80 (m, 2H) | 477 | GENERAL PROCEDURE F A08B05C01 |
| 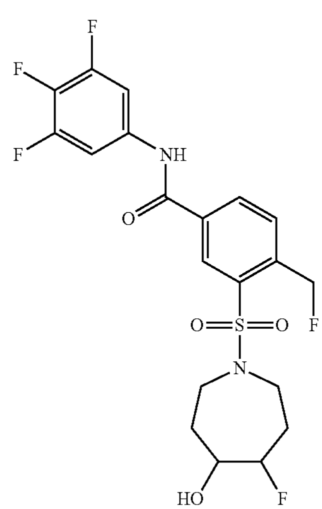 [SMILES: O=C(Nc1cc(F)c(F)c(F)c1)c1ccc(CF)c(S(=O)(=O)N2CCC(O)C(F)CC2)c1] | 2011 | ¹H NMR (400 MHz, METHANOL-d₄) δ 8.34-8.41 (m, 1H), 8.19-8.25 (m, 1H), 7.86-7.94 (m, 1H), 7.56-7.67 (m, 2H), 5.90 (s, 1H), 5.78 (s, 1H), 4.71-4.78 (m, 1H), 4.49-4.57 (m, 1H), 4.37-4.46 (m, 1H), 4.04-4.16 (m, 1H), 3.82-3.93 (m, 1H), 3.46 (s, 4H), 1.93-2.29 (m, 3H), 1.73-1.92 (m, 1H) | 447 | GENERAL PROCEDURE F A09B05C02 |

TABLE 1-continued

| Structure | Compound ID | ¹H NMR | MS(M + H)⁺ | Synthetic method |
|---|---|---|---|---|
| 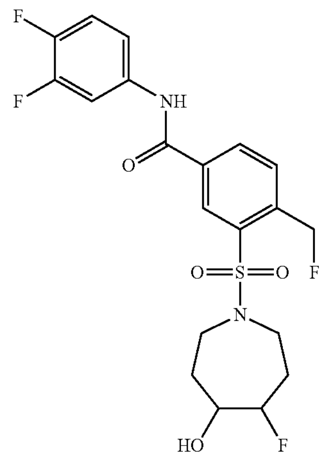 [SMILES: O=C(Nc1ccc(F)c(F)c1)c1ccc(CF)c(S(=O)(=O)N2CCC(O)C(F)CC2)c1] | 2012 | | 461 | GENERAL PROCEDURE F A08B05C03 |
| 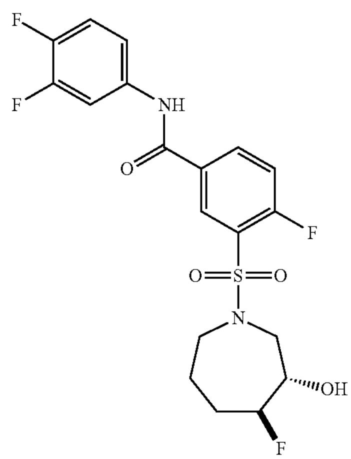 [SMILES: O=C(Nc1ccc(F)c(F)c1)c1ccc(F)c(S(=O)(=O)N2CCC[C@H](F)[C@@H](O)C2)c1] | 1821_Trans | ¹HNMR (MeOD-d4, 400 MHz) 8.47 (dd, J = 6.7, 2.3 Hz, 1H), 8.24-8.28 (m, 1H), 7.81-7.87 (m, 1H), 7.41-7.56 (m, 2H), 7.23-7.34 (m, 1H), 4.24-4.50 (m, 1H), 3.64-3.91 (m, 2H), 3.45-3.59 (m, 1H), 3.07-3.26 (m, 2H), 1.63-2.16 (m, 4H) | 447 | GENERAL PROCEDURE A A07_transB02C03 |
| 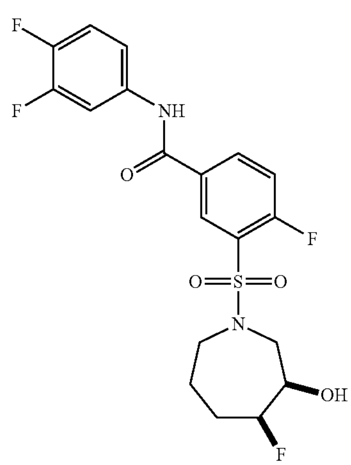 [SMILES: O=C(Nc1ccc(F)c(F)c1)c1ccc(F)c(S(=O)(=O)N2CCC[C@H](F)[C@H](O)C2)c1] | 1821_Cis | | 447 | GENERAL PROCEDURE A A07_CisB02C03 |

TABLE 1-continued

| Structure | Compound ID | ¹H NMR | MS(M + H)⁺ | Synthetic method |
|---|---|---|---|---|
| 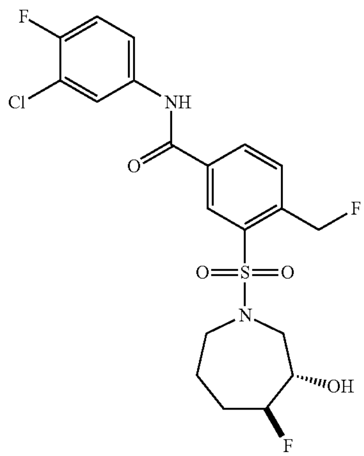 [SMILES: O=C(Nc1ccc(F)c(Cl)c1)c1ccc(CF)c(S(=O)(=O)N2CCC[C@H](F)[C@@H](O)C2)c1] | 2007_Trans | | 477/479 | GENERAL PROCEDURE A A07_transB05C01 |
| 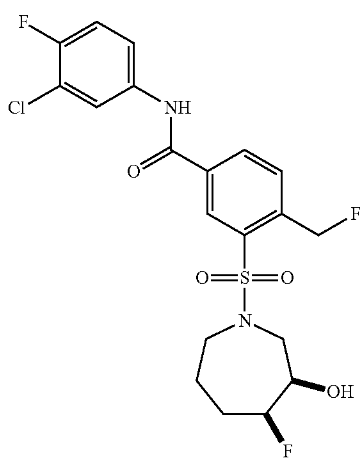 [SMILES: O=C(Nc1ccc(F)c(Cl)c1)c1ccc(CF)c(S(=O)(=O)N2CCC[C@H](F)[C@H](O)C2)c1] | 2007_Cis | ¹HNMR (MeOD-d4, 400 MHz) 8.40 (s, 1H), 8.25 (dd, J = 8.1, 1.6 Hz, 1H), 7.99 (dd, J = 6.7, 2.6 Hz, 1H), 7.91 (d, J = 8.2 Hz, 1H), 7.61-7.71 (m, 1H), 7.25-7.30 (m, 1H), 5.75-6.00 (m, 2H), 3.90-4.10 (m, 1H), 3.57-3.72 (m, 2H), 3.36 (s, 1H), 3.30 (s, 1H), 3.18-3.27 (m, 1H), 2.15-2.31 (m, 1H), 1.69-2.06 (m, 3H) | 477/479 | GENERAL PROCEDURE A A07_CisB05C01 |
| 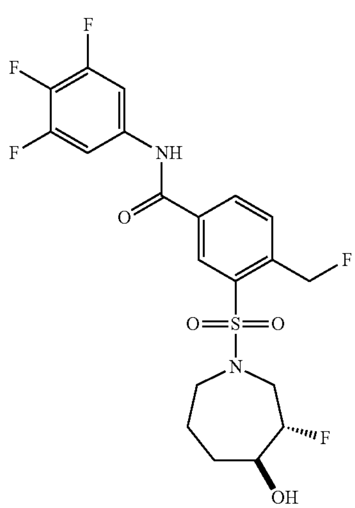 [SMILES: O=C(Nc1cc(F)c(F)c(F)c1)c1ccc(CF)c(S(=O)(=O)N2CCC[C@H](O)[C@@H](F)C2)c1] | 2008_Trans | ¹HNMR (MeOD-d4, 400 MHz) 8.41 (s, 1H), 8.25 (dd, J = 8.0, 1.8 Hz, 1H), 7.92 (d, J = 8.2 Hz, 1H), 7.57-7.68 (m, 2H), 5.93 (s, 1H), 5.81 (s, 1H), 4.29-4.52 (m, 1H), 3.60-3.85 (m, 3H), 3.36-3.44 (m, 1H), 3.24-3.32 (m, 1H), 1.62-2.03 (m, 4H) | 479 | GENERAL PROCEDURE A A08_transB05C02 |

TABLE 1-continued
| Structure | Compound ID | ¹H NMR | MS(M + H)⁺ | Synthetic method |
|---|---|---|---|---|
| 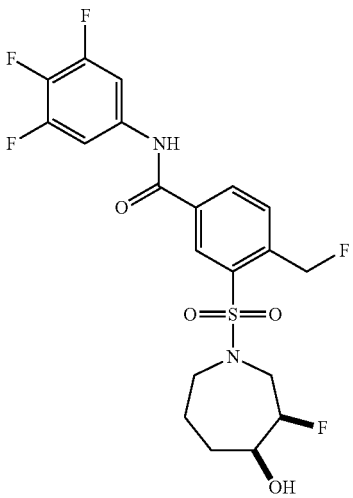 [SMILES: O=C(Nc1cc(F)c(F)c(F)c1)c1ccc(CF)c(S(=O)(=O)N2CCC[C@H](O)[C@H](F)C2)c1] | 2008_Cis | ¹HNMR (MeOD-d4, 400 MHz) 8.40 (s, 1H), 8.25 (dd, J = 8.0, 1.8 Hz, 1H), 7.92 (d, J = 8.2 Hz, 1H), 7.54-7.71 (m, 2H), 5.75-5.98 (m, 2H), 4.66-4.85 (m, 1H), 4.00-4.13 (m, 1H), 3.49-3.79 (m, 3H), 3.22-3.29 (m, 1H), 1.86-2.13 (m, 2H), 1.64-1.81 (m, 2H) | 479 | GENERAL PROCEDURE A A08_CisB05C02 |
| 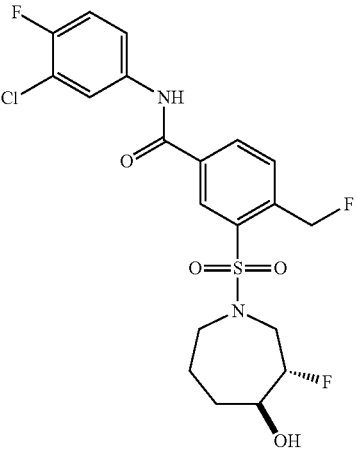 [SMILES: O=C(Nc1ccc(F)c(Cl)c1)c1ccc(CF)c(S(=O)(=O)N2CCC[C@H](O)[C@@H](F)C2)c1] | 2010_Trans | | 477/479 | GENERAL PROCEDURE A A08_transB05C01 |
| 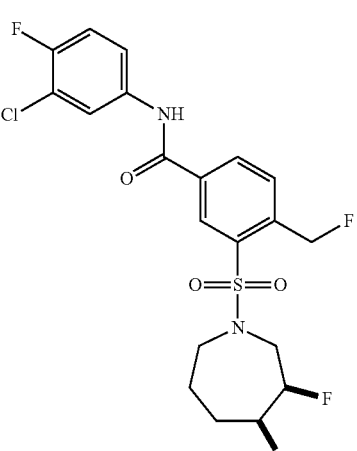 | 2010_Cis | | 477/479 | GENERAL PROCEDURE A A08_CisB05C01 |

TABLE 1-continued

| Structure | Compound ID | ¹H NMR | MS(M + H)⁺ | Synthetic method |
|---|---|---|---|---|
| 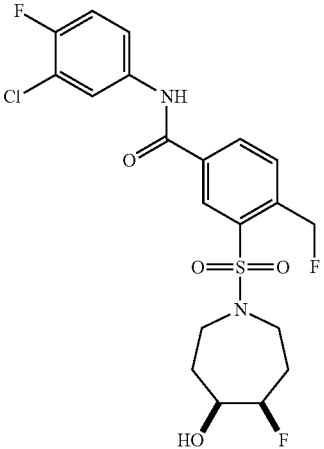 [SMILES: O=C(Nc1ccc(F)c(Cl)c1)c1ccc(CF)c(S(=O)(=O)N2CC[C@@H](F)[C@@H](O)CC2)c1] | 2013_Cis | ¹HNMR (400 MHz, METHANOL-d₄) δ = 8.36 (s, 1H), 8.23 (d, J = 8.0 Hz, 1H), 7.98 (dd, J = 2.5, 6.8 Hz, 1H), 7.89 (d, J = 8.0 Hz, 1H), 7.68-7.60 (m, 1H), 7.26 (t, J = 8.9 Hz, 1H), 5.90 (s, 1H), 5.78 (s, 1H), 4.86-4.71 (m, 1H), 4.16-4.03 (m, 1H), 3.65-3.52 (m, 2H), 3.34 (d, J = 4.3 Hz, 2H), 2.31-2.18 (m, 1H), 2.15-1.83 (m, 3H) | 477/479 | GENERAL PROCEDURE F A08_cisB05C01 |
| 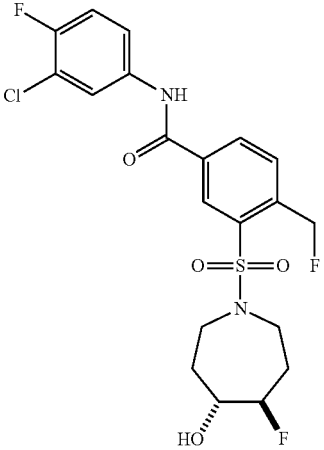 [SMILES: O=C(Nc1ccc(F)c(Cl)c1)c1ccc(CF)c(S(=O)(=O)N2CC[C@@H](O)[C@H](F)CC2)c1] | 2013_Trans | ¹HNMR (400 MHz, METHANOL-d₄) δ = 8.38 (s, 1H), 8.23 (d, J = 8.0 Hz, 1H), 7.98 (dd, J = 2.5, 6.5 Hz, 1H), 7.89 (d, J = 8.0 Hz, 1H), 7.67-7.60 (m, 1H), 7.26 (t, J = 8.9 Hz, 1H), 5.90 (s, 1H), 5.79 (s, 1H), 4.56-4.38 (m, 1H), 3.92-3.81 (m, 1H), 3.58 (m, 1H), 3.52-3.42 (m, 2H), 3.41-3.33 (m, 2H), 2.25-2.10 (m, 1H), 2.09-1.93 (m, 2H), 1.85-1.74 (m, 1H) | 477/479 | GENERAL PROCEDURE F A08_transB05C01 |
| 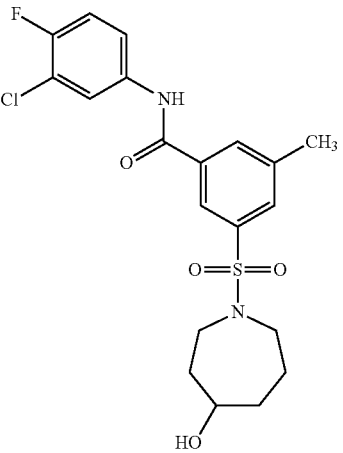 [SMILES: Cc1cc(C(=O)Nc2ccc(F)c(Cl)c2)cc(S(=O)(=O)N2CCCC(O)CC2)c1] | 2018 | ¹H NMR (400 MHz, DMSO-d6) δ = 10.62 (s, 1H), 8.11 (s, 1H), 8.04-8.07 (m, 2H), 7.82 (s, 1H), 7.72-7.74 (m, 1H), 7.43-7.48 (m, 1H), 4.57-4.58 (m, 1H), 3.60-3.70 (m, 1H), 3.25-3.34 (m, 2H), 3.17-3.20 (m, 2H), 2.52 (s, 3H), 1.49-1.82 (m, 6H). | 441/443 | GENERAL PROCEDURE E A02B07C01 |

TABLE 1-continued

| Structure | Compound ID | ¹H NMR | MS(M + H)⁺ | Synthetic method |
|---|---|---|---|---|
| (structure) | 2020 | | 443 | GENERAL PROCEDURE E A02B07C02 |
| (structure) | 2021 | 1H NMR (400 MHz, DMSO-d6) δ = 10.73-10.69 (m, 1H), 8.43-8.38 (m, 1H), 8.34-8.28 (m, 1H), 8.08-8.03 (m, 1H), 7.75-7.66 (m, 2H), 7.50-7.42 (m, 1H), 5.28-5.22 (m, 1H), 4.95-4.88 (m, 1H), 3.95-3.84 (m, 1H), 3.62-3.51 (m, 2H), 3.17-3.09 (m, 2H), 2.02 (s, 4H), 1.81-1.53 (m, 3H) | 503/505 | GENERAL PROCEDURE A A54B02C01 |
| (structure) | 2022 | 1H NMR (400 MHz, DMSO-d6) δ = 10.82-10.68 (m, 1H), 8.42-8.35 (m, 1H), 8.34-8.28 (m, 1H), 8.08-8.03 (m, 1H), 7.76-7.65 (m, 2H), 7.50-7.42 (m, 1H), 5.11-4.79 (m, 2H), 3.94-3.81 (m, 1H), 3.57-3.50 (m, 1H), 3.47-3.41 (m, 2H), 3.31-3.28 (m, 1H), 2.02 (s, 3H), 1.95-1.54 (m, 4H) | 503/505 | GENERAL PROCEDURE A A55B02C01 |

TABLE 1-continued

| Structure | Compound ID | ¹H NMR | MS(M + H)⁺ | Synthetic method |
|---|---|---|---|---|
| 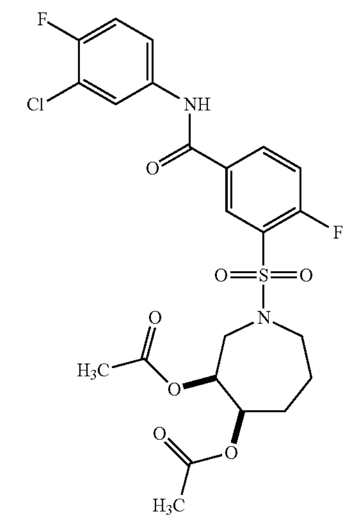 [SMILES: CC(=O)O[C@H]1CN(S(=O)(=O)c2cc(C(=O)Nc3ccc(F)c(Cl)c3)ccc2F)CCC[C@H]1OC(C)=O] | 2023 | 1H NMR (400 MHz, DMSO-d6) δ = 10.71-10.68 (m, 1H), 8.41-8.37 (m, 1H), 8.34-8.28 (m, 1H), 8.08-8.03 (m, 1H), 7.74-7.69 (m, 2H), 7.49-7.43 (m, 1H), 5.09-5.00 (m, 2H), 3.62-3.57 (m, 2H), 3.42-3.38 (m, 2H), 3.32-3.30 (m, 1H), 3.19-3.16 (m, 1H), 2.03 (s, 3H), 2.01-2.00 (m, 3H), 1.91-1.67 (m, 2H) | 545/546 | GENERAL PROCEDURE A A56B02C01 |
| 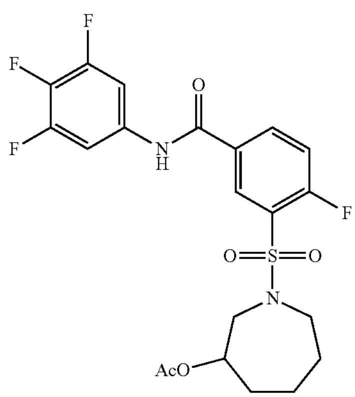 [SMILES: CC(=O)OC1CCCCN(S(=O)(=O)c2cc(C(=O)Nc3cc(F)c(F)c(F)c3)ccc2F)C1] | 2024 | ¹H NMR (400 MHz, DMSO-d6) δ = 10.81 (s, 1H), 8.37-8.39 (m, 1H), 8.27-8.30 (m, 1H), 7.69-7.74 (m, 3H), 4.86-4.90 (m, 1H), 3.53-3.55 (m, 1H), 3.30-3.40 (m, 1H), 3.15-3.25 (m, 1H), 2.33 (s, 3H), 1.80-1.90 (m, 1H), 1.65-1.75 (m, 4H), 1.45-1.55 (m, 4H). | 489 | GENERAL PROCEDURE A A56B02C02 |
| 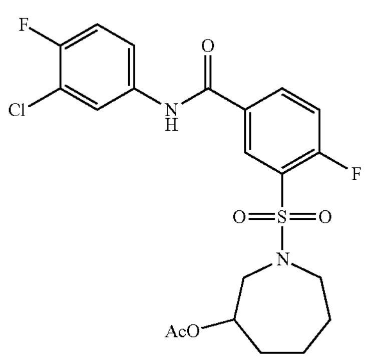 [SMILES: CC(=O)OC1CCCCN(S(=O)(=O)c2cc(C(=O)Nc3ccc(F)c(Cl)c3)ccc2F)C1] | 2025 | ¹H NMR (400 MHz, DMSO-d6) δ = 10.71 (s, 1H), 8.40-8.45 (m, 1H), 8.27-8.35 (m, 1H), 8.00-8.05 (m, 1H), 7.65-7.75 (m, 2H), 7.43-7.48 (m, 1H), 4.87-4.90 (m, 1H), 3.53-3.55 (m, 2H), 3.30-3.40 (m, 1H), 3.20-3.25 (m, 1H), 1.99 (s, 3H), 1.45-1.90 (m, 6H). | 487/489 | GENERAL PROCEDURE A A56B02C01 |

TABLE 1-continued

| Structure | Compound ID | ¹H NMR | MS(M + H)⁺ | Synthetic method |
|---|---|---|---|---|
| 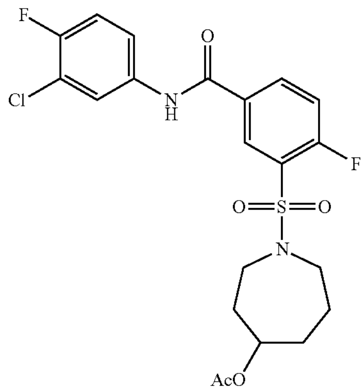 [SMILES: CC(=O)OC1CCCN(S(=O)(=O)c2cc(C(=O)Nc3ccc(F)c(Cl)c3)ccc2F)CC1] | 2026 | | 487/489 | GENERAL PROCEDURE A A57B02C01 |
| 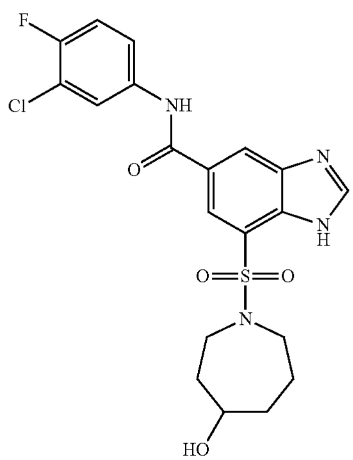 [SMILES: O=C(Nc1ccc(F)c(Cl)c1)c1cc(S(=O)(=O)N2CCCC(O)CC2)c2[nH]cnc2c1] | 2033 | 1H NMR (400 MHz, METHANOL-d4) δ 8.53-8.61 (m, 1H), 8.39-8.46 (m, 1H), 8.25-8.33 (m, 1H), 7.95-8.03 (m, 1H), 7.59-7.71 (m, 1H), 7.20-7.34 (m, 1H), 3.73-3.85 (m, 1H), 3.35-3.59 (m, 4H), 1.78-2.05 (m, 3H), 1.54-1.77 (m, 3H) | 467/469 | GENERAL PROCEDURE G A02B08C01 |
| 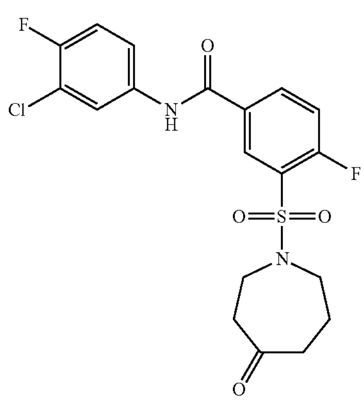 [SMILES: O=C1CCCN(S(=O)(=O)c2cc(C(=O)Nc3ccc(F)c(Cl)c3)ccc2F)CC1] | 2044 | ¹H NMR (400 MHz, DMSO-d6) δ = 10.70 (s, 1H), 8.40-8.43 (m, 1H), 8.27-8.35 (m, 1H), 8.04-8.06 (m, 1H), 7.69-7.74 (m, 2H), 7.43-7.48 (m, 1H), 3.58-3.61 (m, 2H), 3.47-3.49 (m, 2H), 2.50-2.62 (m, 4H), 1.75-1.78 (m, 2H). | 443/445 | GENERAL PROCEDURE A A58B02C01 |

TABLE 1-continued

| Structure | Compound ID | ¹H NMR | MS(M + H)⁺ | Synthetic method |
|---|---|---|---|---|
| 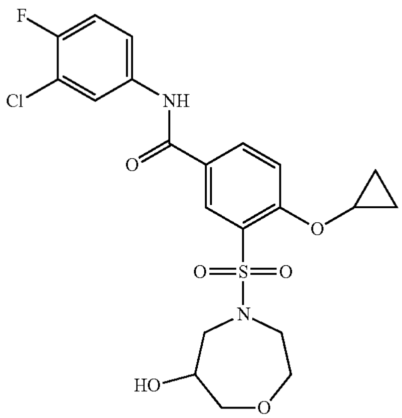 [SMILES: O=C(Nc1ccc(F)c(Cl)c1)c1ccc(OC2CC2)c(S(=O)(=O)N2CCOCC(O)C2)c1] | 2081 | 1H NMR (400 MHz, MeOD) δ 8.48 (d, J = 2.01 Hz, 1H), 8.23 (dd, J = 8.66, 2.13 Hz, 1H), 7.96 (dd, J = 6.78, 2.51 Hz, 1H), 7.70 (d, J = 8.78 Hz, 1H), 7.59-7.65 (m, 1H), 7.27 (t, J = 8.91 Hz, 1H), 4.07-4.13 (m, 1H), 4.03 (t, J = 6.53 Hz, 1H), 3.77-3.97 (m, 4H), 3.61-3.73 (m, 2H), 3.21-3.30 (m, 1H), 3.11 (dd, J = 14.56, 7.53 Hz, 1H), 0.84-1.04 (m, 4H). | 485/487 | GENERAL PROCEDURE C A13B09C01 |
| 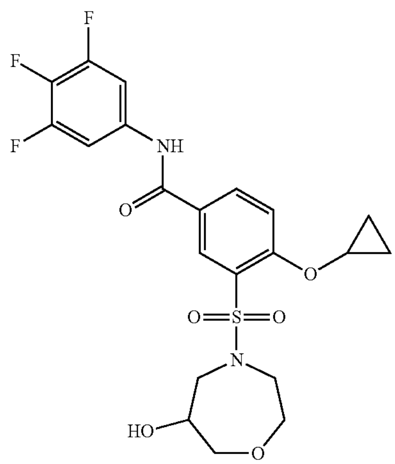 [SMILES: O=C(Nc1cc(F)c(F)c(F)c1)c1ccc(OC2CC2)c(S(=O)(=O)N2CCOCC(O)C2)c1] | 2082 | | 487 | GENERAL PROCEDURE C A13B09C02 |
| 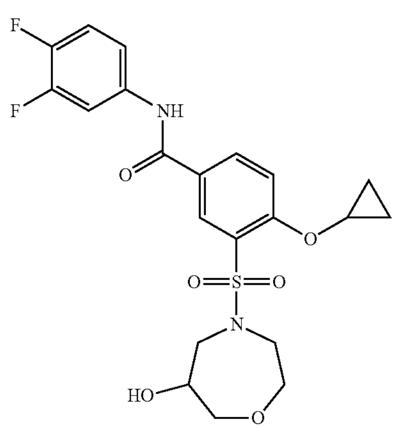 [SMILES: O=C(Nc1ccc(F)c(F)c1)c1ccc(OC2CC2)c(S(=O)(=O)N2CCOCC(O)C2)c1] | 2083 | | 469 | GENERAL PROCEDURE C A13B09C03 |

| Structure | Compound ID | ¹H NMR | MS(M + H)⁺ | Synthetic method |
|---|---|---|---|---|
| 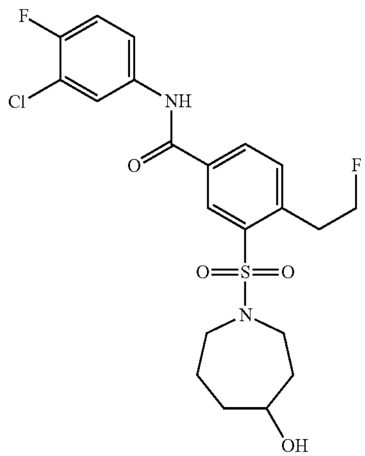 [SMILES: O=C(Nc1ccc(F)c(Cl)c1)c1ccc(CCF)c(S(=O)(=O)N2CCCC(O)CC2)c1] | 2205 | 1H NMR (400 MHz, MeOD) δ 8.32 (s, 1H), 8.24 (d, J = 7.2 Hz, 1H), 7.99 (d, J = 6.8 Hz, 1H), 7.92 (d, J = 8.0 Hz, 1H), 7.64-7.65 (m, 1H), 7.27 (t, J = 7.2 Hz, 1H), 4.57-4.73 (m, 2H), 3.95-3.96 (m, 1H), 3.56-3.62 (m, 2H), 3.00-3.15 (m, 2H), 2.85-2.93 (m, 2H), 1.31-1.85 (m, 6H). | 473/475 | GENERAL PROCEDURE D A02B12C01 |
| 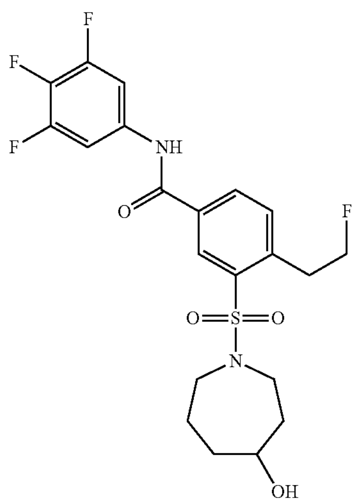 [SMILES: O=C(Nc1cc(F)c(F)c(F)c1)c1ccc(CCF)c(S(=O)(=O)N2CCCC(O)CC2)c1] | 2206 | | 475 | GENERAL PROCEDURE D A02B12C02 |
| 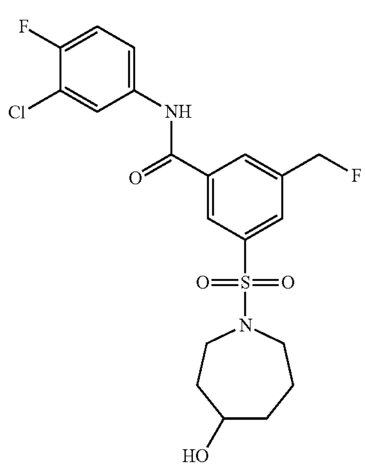 [SMILES: O=C(Nc1ccc(F)c(Cl)c1)c1cc(CF)cc(S(=O)(=O)N2CCCC(O)CC2)c1] | 2207 | 1H NMR (400 MHz, METHANOL-d₄) δ = 8.44-8.34 (m, 1H), 8.29-8.21 (m, 1H), 8.10-8.06 (m, 1H), 8.03-7.98 (m, 1H), 7.69-7.63 (m, 1H), 7.32-7.24 (m, 1H), 5.71-5.63 (m, 1H), 5.58-5.50 (m, 1H), 4.07-3.98 (m, 1H), 3.92-3.85 (m, 2H), 3.80-3.58 (m, 5H), 3.31-3.24 (m, 1H), 3.21-3.13 (m, 1H) | 459/461 | GENERAL PROCEDURE F A02B10C01 |

TABLE 1-continued

| Structure | Compound ID | ¹H NMR | MS(M + H)⁺ | Synthetic method |
|---|---|---|---|---|
| 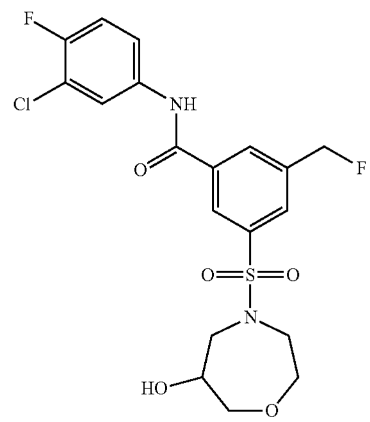 [SMILES: O=C(Nc1ccc(F)c(Cl)c1)c1cc(CF)cc(S(=O)(=O)N2CCOCC(O)C2)c1] | 2208 | ¹H NMR (400 MHz, METHANOL-d₄) δ = 8.37-8.32 (m, 1H), 8.28-8.22 (m, 1H), 8.08-7.96 (m, 2H), 7.72-7.61 (m, 1H), 7.34-7.22 (m, 1H), 5.67-5.62 (m, 1H), 5.56-5.51 (m, 1H), 3.91-3.78 (m, 1H), 3.47-3.38 (m, 2H), 3.31-3.25 (m, 2H), 2.05-1.59 (m, 6H) | 461/463 | GENERAL PROCEDURE F A13B10C01 |
| 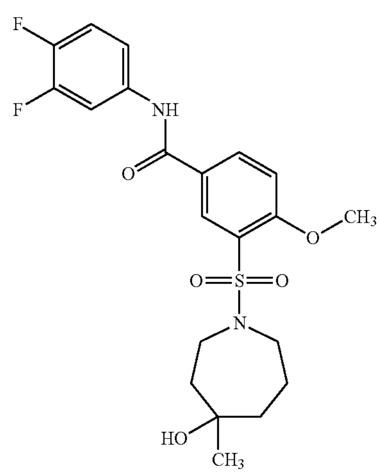 [SMILES: COc1ccc(C(=O)Nc2ccc(F)c(F)c2)cc1S(=O)(=O)N1CCCC(C)(O)CC1] | 2113 | | 455 | GENERAL PROCEDURE A A06B06C03 |
| 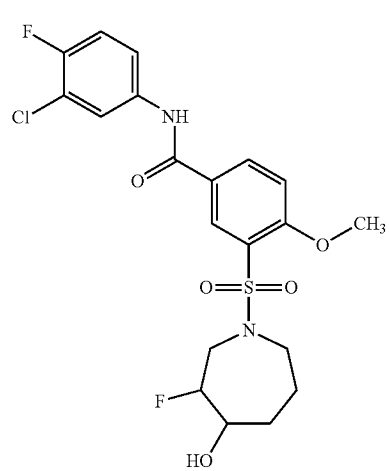 [SMILES: COc1ccc(C(=O)Nc2ccc(F)c(Cl)c2)cc1S(=O)(=O)N1CCCC(O)C(F)C1] | 2114_D1 | | 475/477 | GENERAL PROCEDURE A A08B06C01 |

TABLE 1-continued

| Structure | Compound ID | ¹H NMR | MS(M + H)⁺ | Synthetic method |
|---|---|---|---|---|
| (structure) | 2114_D2 | | 475/477 | GENERAL PROCEDURE A A08B06C01 |
| (structure) | 2115_D1 | | 477 | GENERAL PROCEDURE A A08B06C02 |
| (structure) | 2115_D2 | | 477 | GENERAL PROCEDURE A A08B06C02 |

TABLE 1-continued

| Structure | Compound ID | ¹H NMR | MS(M + H)⁺ | Synthetic method |
|---|---|---|---|---|
| 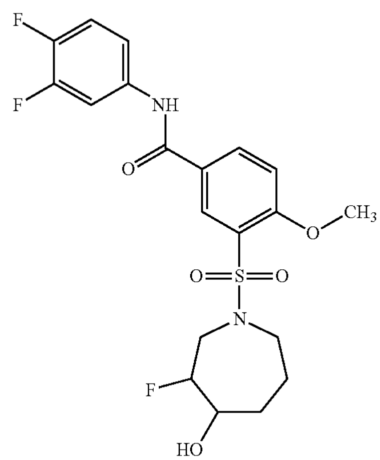 [SMILES: COc1ccc(C(=O)Nc2ccc(F)c(F)c2)cc1S(=O)(=O)N1CCCC(O)C(F)C1] | 2116_D1 | | 459 | GENERAL PROCEDURE A A08B06C03 |
| 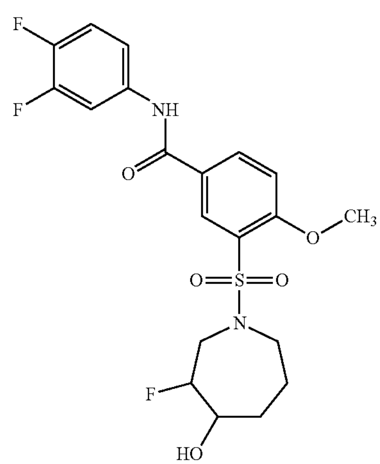 [SMILES: COc1ccc(C(=O)Nc2ccc(F)c(F)c2)cc1S(=O)(=O)N1CCCC(O)C(F)C1] | 2116_D2 | | 459 | GENERAL PROCEDURE A A08B06C03 |
| 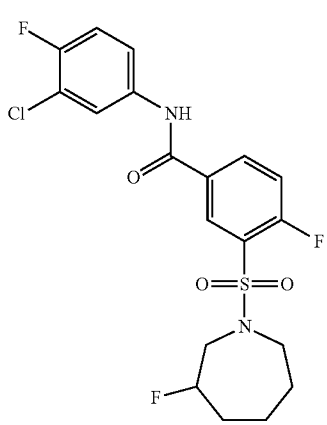 [SMILES: O=C(Nc1ccc(F)c(Cl)c1)c1ccc(F)c(S(=O)(=O)N2CCCCC(F)C2)c1] | 2117 | | 447/449 | GENERAL PROCEDURE A A03B02C01 |

TABLE 1-continued

| Structure | Compound ID | ¹H NMR | MS(M + H)⁺ | Synthetic method |
|---|---|---|---|---|
| 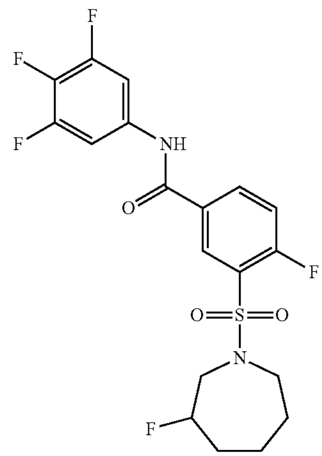 [SMILES: O=C(Nc1cc(F)c(F)c(F)c1)c1ccc(F)c(S(=O)(=O)N2CCCCC(F)C2)c1] | 2118 | ¹H NMR (400 MHz, METHANOL-d4) δ = 8.45-8.48 (m, 1H), 8.24-8.27 (m, 1H), 7.59-7.64 (m, 2H), 7.47-7.53 (m, 1H), 4.70-4.90 (m, 1H), 3.70-3.81 (m, 1H), 3.40-3.60 (m, 2H), 3.25-3.35 (m, 1H), 1.75-2.05 (m, 5H), 1.55-1.65 (m, 1H). | 449 | GENERAL PROCEDURE A A03B02C02 |
| 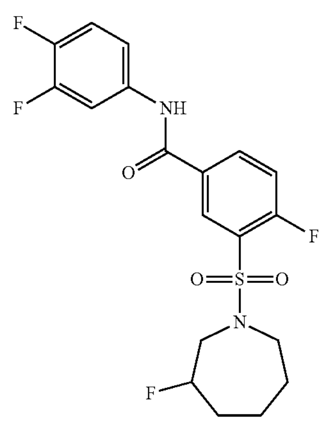 [SMILES: O=C(Nc1ccc(F)c(F)c1)c1ccc(F)c(S(=O)(=O)N2CCCCC(F)C2)c1] | 2119 | | 431 | GENERAL PROCEDURE A A03B02C03 |
| 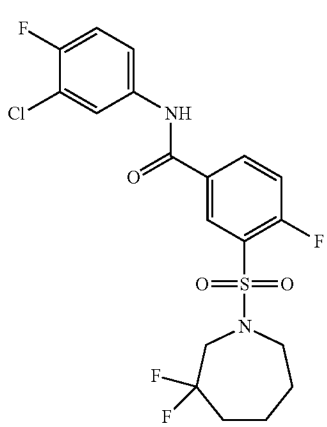 [SMILES: O=C(Nc1ccc(F)c(Cl)c1)c1ccc(F)c(S(=O)(=O)N2CCCCC(F)(F)C2)c1] | 2120 | | 465/467 | GENERAL PROCEDURE A A19B02C01 |

TABLE 1-continued
| Structure | Compound ID | ¹H NMR | MS(M + H)⁺ | Synthetic method |
|---|---|---|---|---|
| 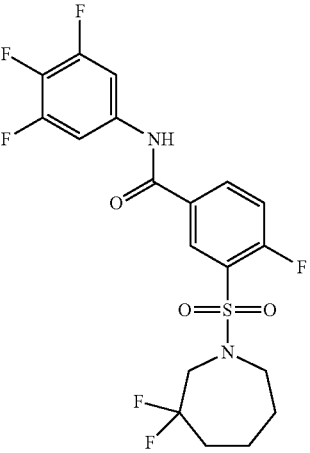 [SMILES: O=C(Nc1cc(F)c(F)c(F)c1)c1ccc(F)c(S(=O)(=O)N2CCCCC(F)(F)C2)c1] | 2121 | ¹H NMR (400 MHz, METHANOL-d4) δ = 8.46-8.49 (m, 1H), 8.27-8.29 (m, 1H), 7.53-7.64 (m, 3H), 3.82-3.89 (m, 2H), 3.33-3.42 (m, 2H), 2.13-2.17 (m, 2H), 1.85-1.89 (m, 2H), 1.74-1.78 (m, 2H). | 467 | GENERAL PROCEDURE A A03B02C02 |
| 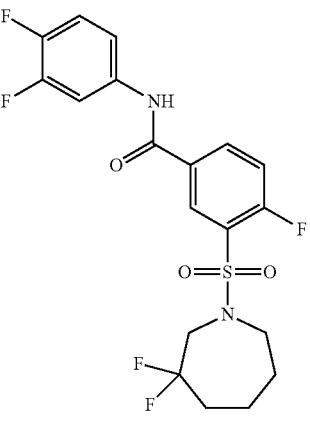 [SMILES: O=C(Nc1ccc(F)c(F)c1)c1ccc(F)c(S(=O)(=O)N2CCCCC(F)(F)C2)c1] | 2122 | | 449 | GENERAL PROCEDURE A A03B02C03 |
| 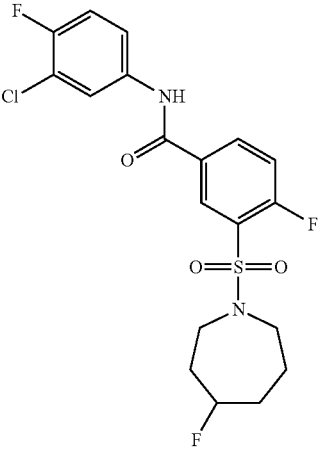 [SMILES: O=C(Nc1ccc(F)c(Cl)c1)c1ccc(F)c(S(=O)(=O)N2CCCC(F)CC2)c1] | 2123 | | 447/449 | GENERAL PROCEDURE A A04B02C01 |

TABLE 1-continued

| Structure | Compound ID | ¹H NMR | MS(M + H)⁺ | Synthetic method |
|---|---|---|---|---|
| 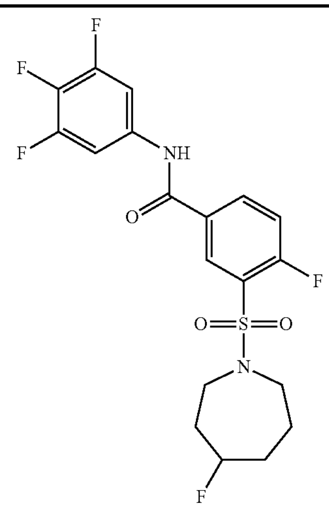 | 2124 | | 449 | GENERAL PROCEDURE A A04B02C02 |
| 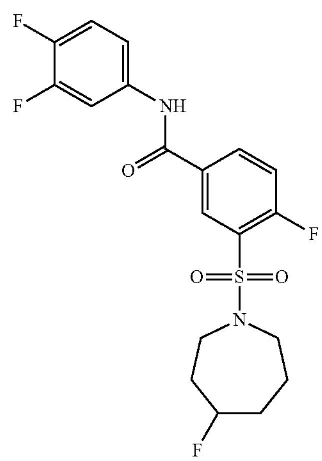 [SMILES: O=C(Nc1ccc(F)c(F)c1)c1ccc(F)c(S(=O)(=O)N2CCCC(F)CC2)c1] | 2125 | | 431 | GENERAL PROCEDURE A A04B02C03 |
| 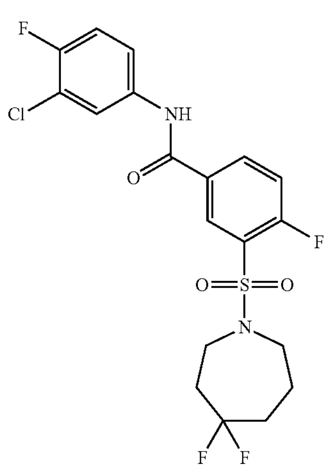 [SMILES: O=C(Nc1ccc(F)c(Cl)c1)c1ccc(F)c(S(=O)(=O)N2CCCC(F)(F)CC2)c1] | 2126 | | 465/467 | GENERAL PROCEDURE A A60B02C01 |

TABLE 1-continued

| Structure | Compound ID | ¹H NMR | MS(M + H)⁺ | Synthetic method |
|---|---|---|---|---|
| 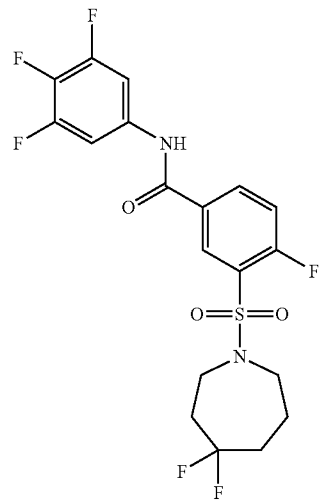 [SMILES: O=C(Nc1cc(F)c(F)c(F)c1)c1ccc(F)c(S(=O)(=O)N2CCCC(F)(F)CC2)c1] | 2127 | ¹H NMR (400 MHz, METHANOL-d4) δ = 8.50-8.41 (m, 1H), 8.30-8.21 (m, 1H), 7.69-7.42 (m, 3H), 3.56-3.43 (m, 4H), 2.44-2.10 (m, 4H), 2.02-1.80 (m, 2H) | 467 | GENERAL PROCEDURE A A60B02C02 |
| 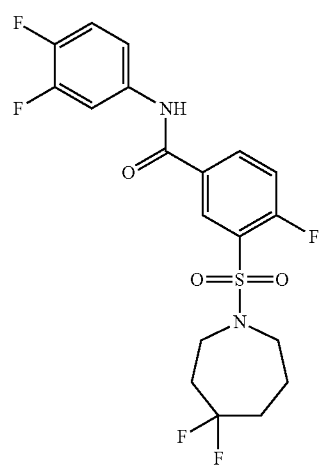 [SMILES: O=C(Nc1ccc(F)c(F)c1)c1ccc(F)c(S(=O)(=O)N2CCCC(F)(F)CC2)c1] | 2128 | ¹H NMR (400 MHz, METHANOL-d₄) δ = 8.52-8.41 (m, 1H), 8.31-8.20 (m, 1H), 7.90-7.76 (m, 1H), 7.59-7.42 (m, 2H), 7.36-7.20 (m, 1H), 3.59-3.44 (m, 4H), 2.34-2.10 (m, 4H), 1.98-1.85 (m, 2H) | 449 | GENERAL PROCEDURE A A60B02C03 |
| 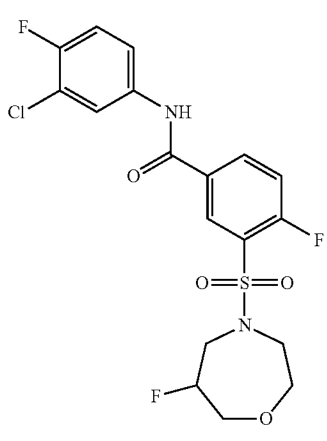 [SMILES: O=C(Nc1ccc(F)c(Cl)c1)c1ccc(F)c(S(=O)(=O)N2CCOCC(F)C2)c1] | 2129 | | 449/451 | GENERAL PROCEDURE A A60B02C01 |

TABLE 1-continued

| Structure | Compound ID | ¹H NMR | MS(M + H)⁺ | Synthetic method |
|---|---|---|---|---|
| (structure) | 2130 | | 451 | GENERAL PROCEDURE A A60B02C02 |
| (structure) | 2131 | | 433 | GENERAL PROCEDURE A A60B02C03 |
| (structure) | 2132 | | 467 | GENERAL PROCEDURE A A61B02C01 |

TABLE 1-continued

| Structure | Compound ID | ¹H NMR | MS(M + H)⁺ | Synthetic method |
|---|---|---|---|---|
| 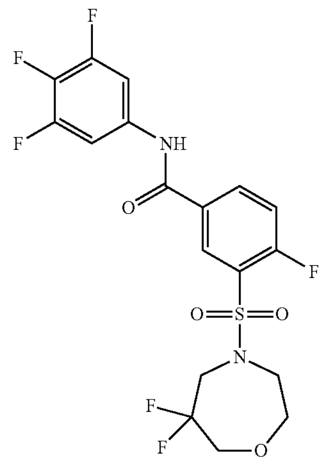 [SMILES: O=C(Nc1cc(F)c(F)c(F)c1)c1ccc(F)c(S(=O)(=O)N2CCOCC(F)(F)C2)c1] | 2133 | ¹H NMR (400 MHz, METHANOL-d₄) δ ppm 3.50-3.61 (m, 2H) 3.86-4.10 (m, 6H) 7.49-7.68 (m, 3H) 8.26-8.34 (m, 1H) 8.46-8.54 (m, 1H) | 469 | GENERAL PROCEDURE A A61B02C02 |
| 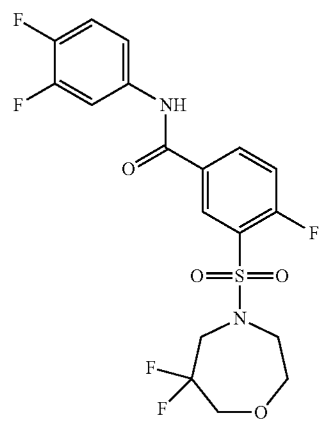 [SMILES: O=C(Nc1ccc(F)c(F)c1)c1ccc(F)c(S(=O)(=O)N2CCOCC(F)(F)C2)c1] | 2134 | ¹H NMR (400 MHz, METHANOL-d₄) δ = 8.53-8.47 (m, 1H), 8.34-8.26 (m, 1H), 7.91-7.80 (m, 1H), 7.60-7.52 (m, 1H), 7.49-7.42 (m, 1H), 7.34-7.24 (m, 1H), 4.08-3.89 (m, 6H), 3.59-3.51 (m, 2H) | 451 | GENERAL PROCEDURE A A61B02C03 |
| 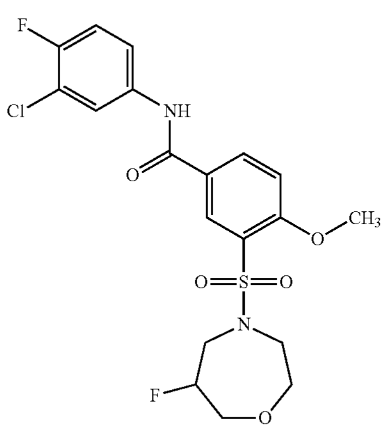 [SMILES: COc1ccc(C(=O)Nc2ccc(F)c(Cl)c2)cc1S(=O)(=O)N1CCOCC(F)C1] | 2179 | ¹H NMR (400 MHz, METHANOL-d₄) δ = 8.52-8.48 (m, 1H), 8.26-8.18 (m, 1H), 8.01-7.93 (m, 1H), 7.65-7.58 (m, 1H), 7.40-7.35 (m, 1H), 7.30-7.22 (m, 1H), 5.01-4.94 (m, 1H), 4.88-4.80 (m, 1H), 4.19-4.07 (m, 4H), 4.04-3.88 (m, 3H), 3.71-3.62 (m, 2H), 3.52-3.40 (m, 1H) | 461/463 | GENERAL PROCEDURE A A60B06C01 |

TABLE 1-continued

| Structure | Compound ID | ¹H NMR | MS(M + H)⁺ | Synthetic method |
|---|---|---|---|---|
| 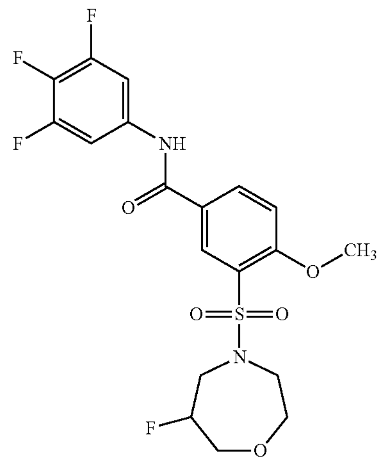 [SMILES: COc1ccc(C(=O)Nc2cc(F)c(F)c(F)c2)cc1S(=O)(=O)N1CCOCC(F)C1] | 2180 | | 463 | GENERAL PROCEDURE A A60B06C02 |
| 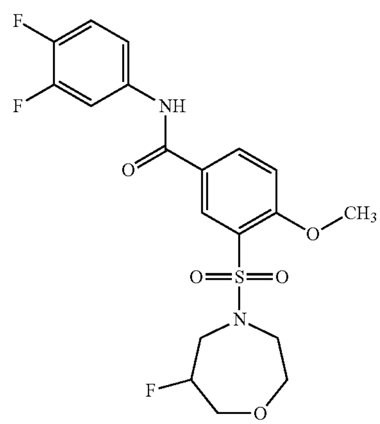 [SMILES: COc1ccc(C(=O)Nc2ccc(F)c(F)c2)cc1S(=O)(=O)N1CCOCC(F)C1] | 2181 | | 445 | GENERAL PROCEDURE A A60B06C03 |
| 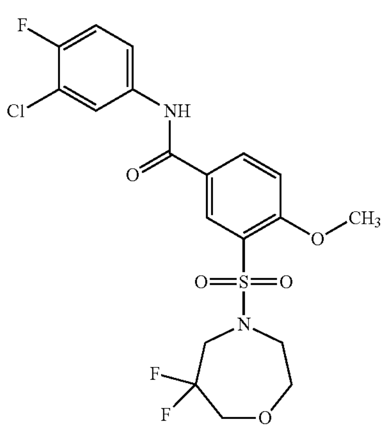 [SMILES: COc1ccc(C(=O)Nc2ccc(F)c(Cl)c2)cc1S(=O)(=O)N1CCOCC(F)(F)C1] | 2182 | | 479/481 | GENERAL PROCEDURE A A61B06C01 |

TABLE 1-continued

| Structure | Compound ID | ¹H NMR | MS(M + H)⁺ | Synthetic method |
|---|---|---|---|---|
| 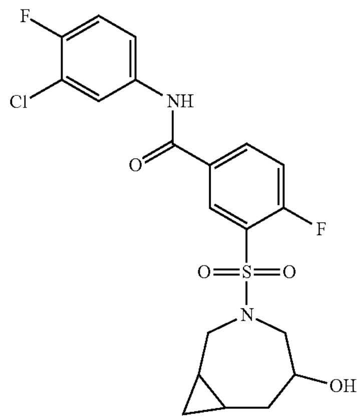 [SMILES: O=C(Nc1ccc(F)c(Cl)c1)c1ccc(F)c(S(=O)(=O)N2CC(O)CC3CC3C2)c1] | 2492 | 1H NMR (400 MHz, MeOD) δ 8.48 (dd, J = 6.78, 2.26 Hz, 1H), 8.24 (ddd, J = 8.60, 4.58, 2.38 Hz, 1H), 7.99 (dd, J = 6.53, 2.51 Hz, 1H), 7.64 (ddd, J = 8.91, 4.14, 2.51 Hz, 1H), 7.50 (dd, J = 9.79, 8.78 Hz, 1H), 7.27 (t, J = 9.03 Hz, 1H), 4.28 (dd, J = 15.18, 5.90 Hz, 1H), 4.07 (d, J = 13.30 Hz, 1H), 3.89 (t, J = 9.54 Hz, 1H), 2.57 (dd, J = 13.18, 9.91 Hz, 1H), 2.37-2.50 (m, 2H), 1.25-1.36 (m, 2H), 0.83-1.01 (m, 2H), 0.37 (q, J = 5.02 Hz, 1H). | 457/459 | GENERAL PROCEDURE A A25B02C01 |
| 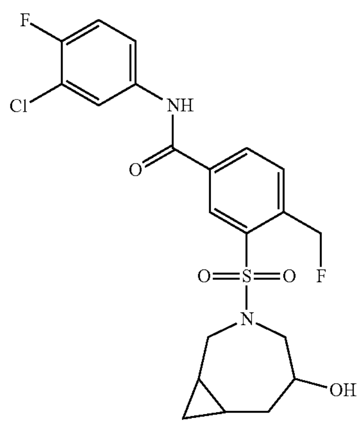 [SMILES: O=C(Nc1ccc(F)c(Cl)c1)c1ccc(CF)c(S(=O)(=O)N2CC(O)CC3CC3C2)c1] | 2493 | 1H NMR (400 MHz, MeOD) δ 8.41 (s, 1H), 8.22 (d, J = 6.78 Hz, 1H), 7.94-8.02 (m, 1H), 7.83-7.92 (m, 1H), 7.59-7.68 (m, 1H), 7.20-7.30 (m, 1H), 5.85-5.94 (m, 1H), 5.73-5.82 (m, 1H), 4.25 (dd, J = 15.06, 5.52 Hz, 1H), 3.81-3.97 (m, 2H), 2.50-2.70 (m, 2H), 2.42 (dd, J = 14.18, 6.15 Hz, 1H), 1.29-1.38 (m, 2H), 0.84-1.03 (m, 2H), 0.37 (d, J = 4.52 Hz, 1H). | 471/473 | GENERAL PROCEDURE F A25B005C01 |
| 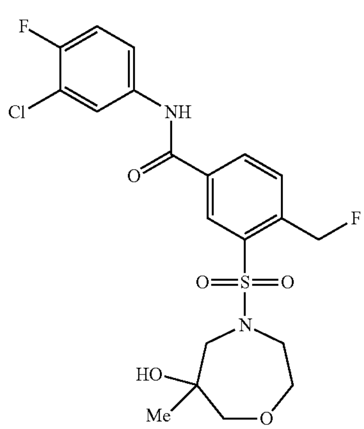 [SMILES: CC1(O)COCCN(S(=O)(=O)c2cc(C(=O)Nc3ccc(F)c(Cl)c3)ccc2CF)C1] | 2495 | | 475/477 | GENERAL PROCEDURE F A35B05C01 |

TABLE 1-continued

| Structure | Compound ID | ¹H NMR | MS(M + H)⁺ | Synthetic method |
|---|---|---|---|---|
| 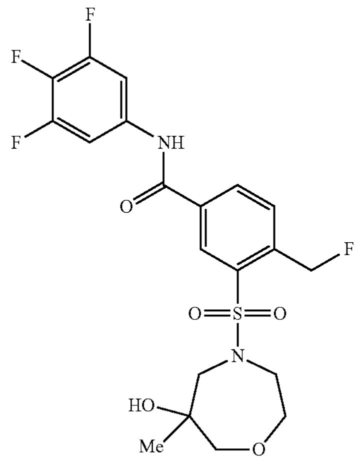 [SMILES: CC1(O)COCCN(S(=O)(=O)c2cc(C(=O)Nc3cc(F)c(F)c(F)c3)ccc2CF)C1] | 2496 | ¹H NMR (400 MHz, MeOD) δ 8.49-8.41 (m, 1H), 8.28-8.20 (m, 1H), 7.99 (dd, J = 2.5, 6.7 Hz, 1H), 7.63 (d, J = 1.5 Hz, 1H), 7.50 (dd, J = 8.7, 9.9 Hz, 1H), 7.31-7.21 (m, 1H), 3.92-3.83 (m, 1H), 3.54-3.44 (m, 2H), 3.42-3.35 (m, 2H), 2.08-1.88 (m, 3H), 1.81-1.66 (m, 3H) | 477 | GENERAL PROCEDURE F A25B02C02 |
| 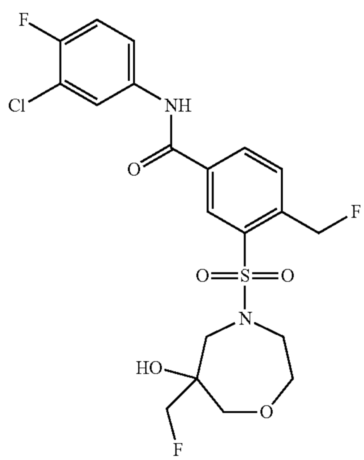 [SMILES: O=C(Nc1ccc(F)c(Cl)c1)c1ccc(CF)c(S(=O)(=O)N2CCOCC(O)(CF)C2)c1] | 2498 | ¹HNMR (400 MHz, MeOD) δ 8.45 (dd, J = 2.4, 6.7 Hz, 1H), 8.26-8.22 (m, 1H), 7.87-7.81 (m, 1H), 7.55-7.40 (m, 2H), 7.32-7.24 (m, 1H), 3.93-3.81 (m, 1H), 3.54-3.44 (m, 2H), 3.42-3.34 (m, 2H), 2.10-1.87 (m, 3H), 1.83-1.61 (m, 3H) | 493/495 | GENERAL PROCEDURE F A34B05C01 |
| 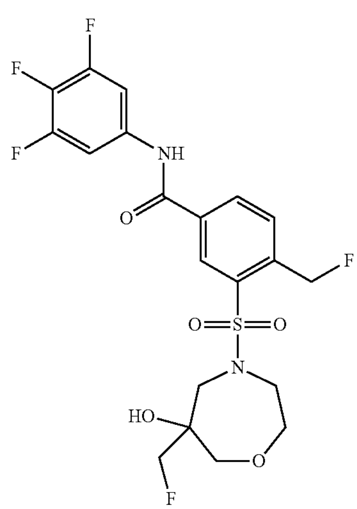 [SMILES: O=C(Nc1cc(F)c(F)c(F)c1)c1ccc(CF)c(S(=O)(=O)N2CCOCC(O)(CF)C2)c1] | 2499 | ¹H NMR (400 MHz, MeOD) δ 8.34 (d, J = 1.76 Hz, 1H), 8.16-8.22 (m, 1H), 7.95-8.05 (m, 2H), 7.60-7.66 (m, 1H), 7.21-7.29 (m, 1H), 5.02 (d, J = 6.27 Hz, 2H), 4.73-4.80 (m, 1H), 3.66-3.79 (m, 1H), 3.51-3.63 (m, 1H), 3.41-3.51 (m, 1H), 3.33-3.39 (m, 1H), 1.91-2.10 (m, 2H), 1.72-1.89 (m, 3H), 1.50-1.67 (m, 1H) | 495/517 | GENERAL PROCEDURE F A34B05C02 |

TABLE 1-continued

| Structure | Compound ID | ¹H NMR | MS(M + H)⁺ | Synthetic method |
|---|---|---|---|---|
| 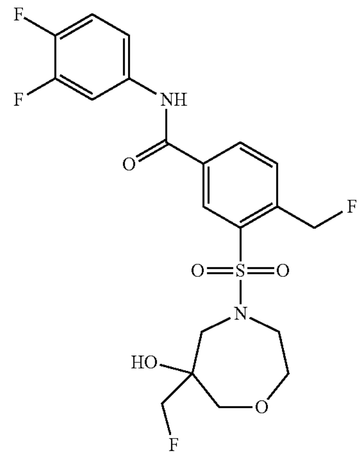 [SMILES: O=C(Nc1ccc(F)c(F)c1)c1ccc(CF)c(S(=O)(=O)N2CCOCC(O)(CF)C2)c1] | 2500 | ¹H NMR (400 MHz, MeOD) δ 8.40-8.49 (m, 1H), 8.18-8.29 (m, 1H), 7.93-8.01 (m, 1H), 7.58-7.67 (m, 1H), 7.49 (dd, J = 8.72, 9.98 Hz, 1H), 7.26 (t, J = 8.97 Hz, 1H), 3.34-3.55 (m, 2H), 3.15-3.28 (m, 2H), 1.67-1.89 (m, 5H), 1.48-1.62 (m, 1H), 1.28 (s, 3H) | 477 | GENERAL PROCEDURE F A34B05C03 |
| 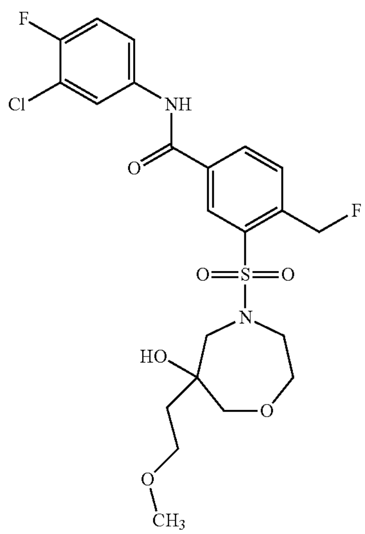 [SMILES: COCCC1(O)COCCN(S(=O)(=O)c2cc(C(=O)Nc3ccc(F)c(Cl)c3)ccc2CF)C1] | 2501 | | 519/521 | GENERAL PROCEDURE F A62B05C01 |
| 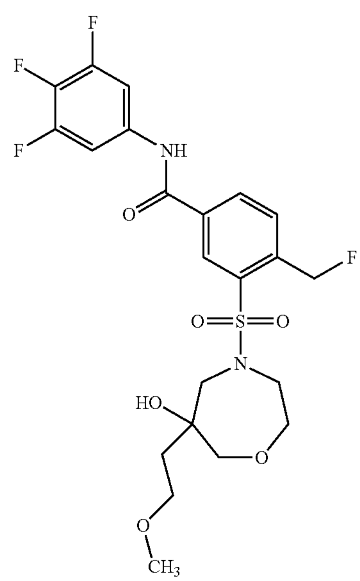 [SMILES: COCCC1(O)COCCN(S(=O)(=O)c2cc(C(=O)Nc3cc(F)c(F)c(F)c3)ccc2CF)C1] | 2502 | ¹HNMR (MeOD-d4, 400 MHz) 8.46 (s, 1H), 8.26 (d, J = 7.9 Hz, 1H), 7.92 (d, J = 8.2 Hz, 1H), 7.57-7.71 (m, 2H), 5.77-6.00 (m, 2H), 3.41-3.93 (m, 10H), 3.33-3.36 (m, 3H), 1.83 (t, J = 6.5 Hz, 2H) | 521 | GENERAL PROCEDURE F A62B05C02 |

TABLE 1-continued

| Structure | Compound ID | ¹H NMR | MS(M + H)⁺ | Synthetic method |
|---|---|---|---|---|
| (structure) | 2503 | | 503 | GENERAL PROCEDURE F A62B05C03 |
| (structure) | 2510 | | 479/451 | GENERAL PROCEDURE A A34B02C01 |
| (structure) | 2511 | | 481 | GENERAL PROCEDURE A A34B02C02 |

TABLE 1-continued

| Structure | Compound ID | ¹H NMR | MS(M + H)+ | Synthetic method |
|---|---|---|---|---|
| 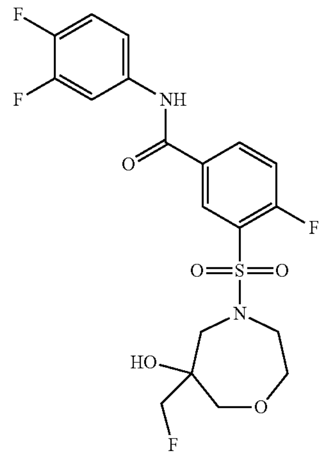 [SMILES: O=C(Nc1ccc(F)c(F)c1)c1ccc(F)c(S(=O)(=O)N2CCOCC(O)(CF)C2)c1] | 2512 | ¹H NMR (400 MHz, MeOD) δ 8.45-8.47 (m, 1H), 8.24-8.26 (m, 1H), 7.48-7.63 (m, 3H), 3.78-3.91 (m, 1H), 3.75-3.76 (m, 1H), 3.51-3.60 (m, 1H), 3.18-3.33 (m, 1H), 2.99-3.05 (m, 1H), 1.58-2.03 (m, 5H). | 463 | GENERAL PROCEDURE A A34B02C03 |
| 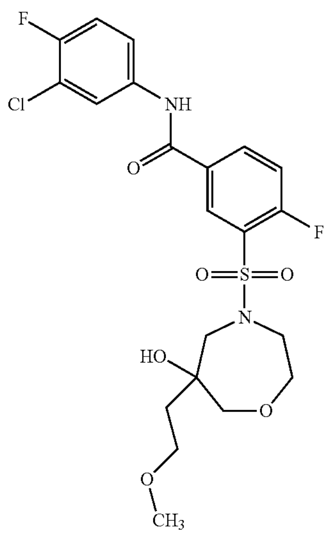 [SMILES: COCCC1(O)COCCN(S(=O)(=O)c2cc(C(=O)Nc3ccc(F)c(Cl)c3)ccc2F)C1] | 2513 | | 505/507 | GENERAL PROCEDURE A A62B02C01 |
| 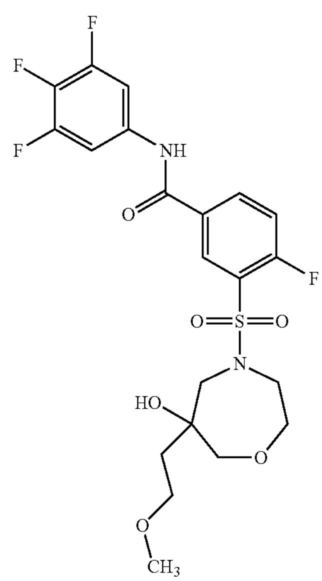 [SMILES: COCCC1(O)COCCN(S(=O)(=O)c2cc(C(=O)Nc3cc(F)c(F)c(F)c3)ccc2F)C1] | 2514 | | 507 | GENERAL PROCEDURE A A62B02C02 |

TABLE 1-continued

| Structure | Compound ID | ¹H NMR | MS(M + H)⁺ | Synthetic method |
|---|---|---|---|---|
| 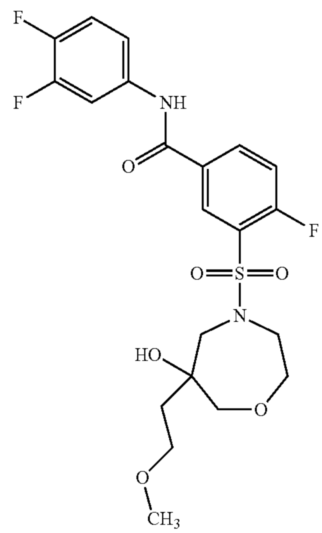 [SMILES: COCCC1(O)COCCN(S(=O)(=O)c2cc(C(=O)Nc3ccc(F)c(F)c3)ccc2F)C1] | 2515 | | 489 | GENERAL PROCEDURE A A62B02C03 |
| 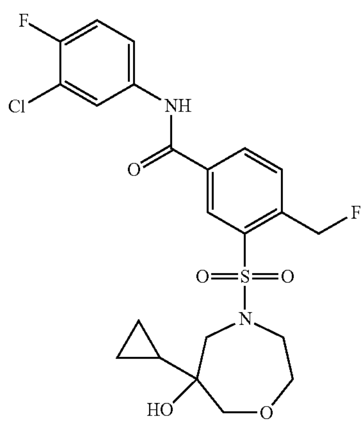 [SMILES: O=C(Nc1ccc(F)c(Cl)c1)c1ccc(CF)c(S(=O)(=O)N2CCOCC(O)(C3CC3)C2)c1] | 2504 | ¹HNMR (MeOD-d4, 400 MHz) δ 8.48 (s, 1H), 8.26 (d, J = 8.3 Hz, 1H), 8.00 (dd, J = 6.7, 2.5 Hz, 1H), 7.92 (d, J = 8.2 Hz, 1H), 7.64-7.68 (m, 1H), 7.28 (t, J = 9.0 Hz, 1H), 5.79-6.03 (m, 2H), 3.44-3.98 (m, 8H), 0.94-1.08 (m, 1H), 0.24-0.51 (m, 4H) | 501/503 | GENERAL PROCEDURE A A36B05C01 |
| 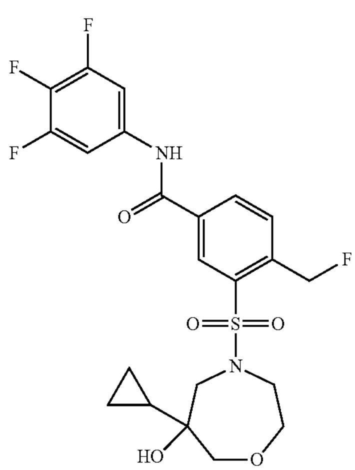 [SMILES: O=C(Nc1cc(F)c(F)c(F)c1)c1ccc(CF)c(S(=O)(=O)N2CCOCC(O)(C3CC3)C2)c1] | 2505 | | 503 | GENERAL PROCEDURE A A36B05C02 |

| Structure | Compound ID | ¹H NMR | MS(M + H)⁺ | Synthetic method |
|---|---|---|---|---|
| 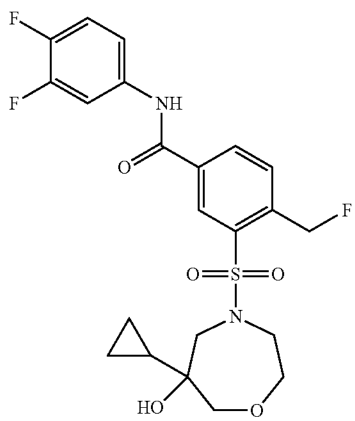 [SMILES: O=C(Nc1ccc(F)c(F)c1)c1ccc(CF)c(S(=O)(=O)N2CCOCC(O)(C3CC3)C2)c1] | 2506 | | 485 | GENERAL PROCEDURE A A36B05C03 |
| 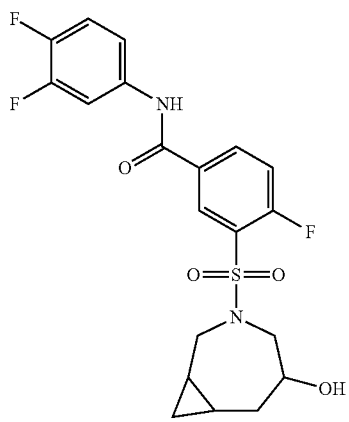 [SMILES: O=C(Nc1ccc(F)c(F)c1)c1ccc(F)c(S(=O)(=O)N2CC(O)CC3CC3C2)c1] | 2547 | | 441 | GENERAL PROCEDURE A A25B02C03 |
| 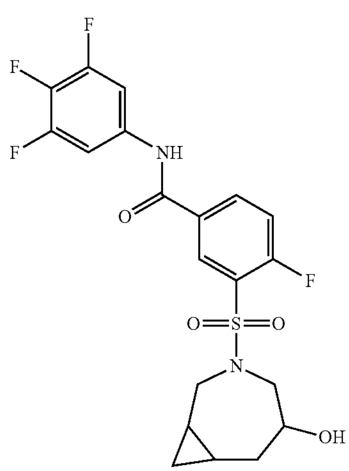 [SMILES: O=C(Nc1cc(F)c(F)c(F)c1)c1ccc(F)c(S(=O)(=O)N2CC(O)CC3CC3C2)c1] | 2548 | 1H NMR (400 MHz, MeOD) δ 8.47 (dd, J = 6.53, 2.01 Hz, 1H), 8.23 (ddd, J = 8.47, 4.45, 2.38 Hz, 1H), 7.61 (dd, J = 9.91, 6.40 Hz, 2H), 7.49 (t, J = 9.29 Hz, 1H), 4.27 (dd, J = 15.18, 5.90 Hz, 1H), 4.06 (d, J = 12.05 Hz, 1H), 3.82-3.93 (m, 1H), 2.57 (dd, J = 13.05, 10.04 Hz, 1H), 2.35-2.50 (m, 2H), 1.25-1.36 (m, 2H), 0.84-1.00 (m, 2H), 0.36 (q, J = 4.77 Hz, 1H). | 459 | GENERAL PROCEDURE A A25B02C02 |

TABLE 1-continued
| Structure | Compound ID | ¹H NMR | MS(M + H)⁺ | Synthetic method |
|---|---|---|---|---|
| 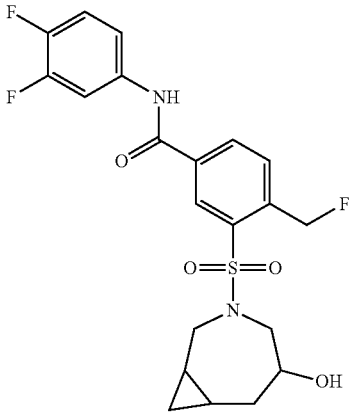 [SMILES: O=C(Nc1ccc(F)c(F)c1)c1ccc(CF)c(S(=O)(=O)N2CC(O)CC3CC3C2)c1] | 2549 | | 455 | GENERAL PROCEDURE A A25B05C03 |
| 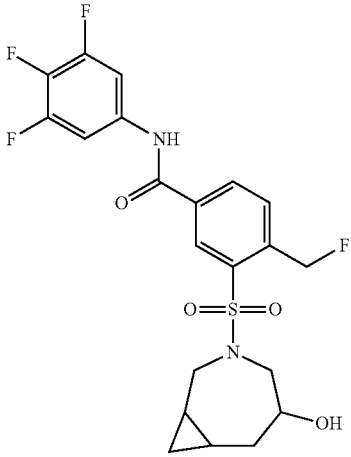 [SMILES: O=C(Nc1cc(F)c(F)c(F)c1)c1ccc(CF)c(S(=O)(=O)N2CC(O)CC3CC3C2)c1] | 2550 | | 473 | GENERAL PROCEDURE A A25B05C02 |
| 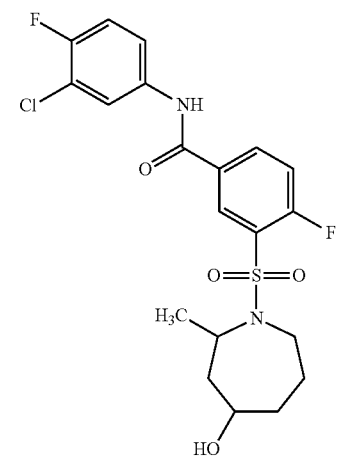 [SMILES: CC1CC(O)CCCN1S(=O)(=O)c1cc(C(=O)Nc2ccc(F)c(Cl)c2)ccc1F] | 1930 | | 459/461 | GENERAL PROCEDURE A A24B02C01 |

TABLE 1-continued

| Structure | Compound ID | ¹H NMR | MS(M + H)⁺ | Synthetic method |
|---|---|---|---|---|
| (structure) | 1936 | 1H NMR (400 MHz, METHANOL-d4) δ 8.37-8.53 (m, 1H), 8.12-8.28 (m, 1H), 7.76-7.91 (m, 1H), 7.37-7.55 (m, 2H), 7.18-7.33 (m, 1H), 4.25 (d, J = 6.65 Hz, 1H), 3.93-4.07 (m, 1H), 3.71 (s, 1H), 3.34-3.52 (m, 1H), 2.69-3.17 (m, 1H), 1.47-2.01 (m, 5H), 1.12 (d, J = 6.90 Hz, 2H), 0.88-1.03 (m, 1H) | 443 | GENERAL PROCEDURE A A24B02C03 |
| (structure) | 1942 | | 461 | GENERAL PROCEDURE A A24B02C02 |
| (structure) | 1931_D1 | 1H NMR (400 MHz, METHANOL-d4) δ 8.39-8.49 (m, 1H), 8.18-8.28 (m, 1H), 7.92-8.02 (m, 1H), 7.57-7.68 (m, 1H), 7.42-7.54 (m, 1H), 7.20-7.33 (m, 1H), 3.47-3.55 (m, 1H), 3.37-3.46 (m, 1H), 3.25-3.29 (m, 1H), 3.15-3.23 (m, 1H), 2.97-3.08 (m, 1H), 1.86-2.02 (m, 2H), 1.58-1.83 (m, 3H), 1.03 (d, J = 6.90 Hz, 3H) | 459/461 | GENERAL PROCEDURE A A24B02C01 |

TABLE 1-continued

| Structure | Compound ID | ¹H NMR | MS(M + H)⁺ | Synthetic method |
|---|---|---|---|---|
| 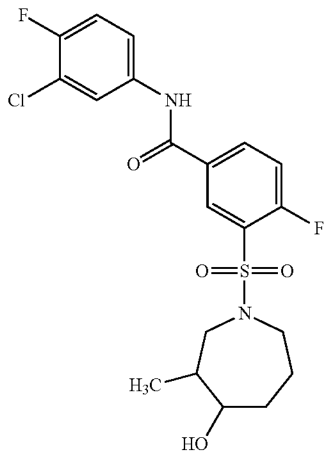 [SMILES: CC1CN(S(=O)(=O)c2cc(C(=O)Nc3ccc(F)c(Cl)c3)ccc2F)CCCC1O] | 1931_D2 | 1H NMR (400 MHz, METHANOL-d4) δ 8.40-8.46 (m, 1H), 8.18-8.26 (m, 1H), 7.93-8.00 (m, 1H), 7.58-7.65 (m, 1H), 7.43-7.51 (m, 1H), 7.20-7.29 (m, 1H), 3.84-3.93 (m, 1H), 3.47-3.60 (m, 1H), 3.37-3.44 (m, 1H), 3.09-3.26 (m, 2H), 1.87-2.06 (m, 3H), 1.65-1.80 (m, 2H), 0.93-1.03 (m, 3H) | 459/461 | GENERAL PROCEDURE A A22B02C01 |
| 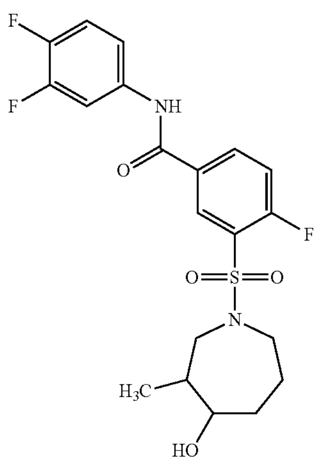 [SMILES: CC1CN(S(=O)(=O)c2cc(C(=O)Nc3ccc(F)c(F)c3)ccc2F)CCCC1O] | 1937_D1 | | 443 | GENERAL PROCEDURE A A22B02C03 |
| 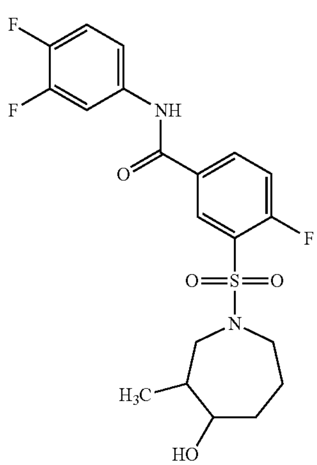 [SMILES: CC1CN(S(=O)(=O)c2cc(C(=O)Nc3ccc(F)c(F)c3)ccc2F)CCCC1O] | 1937_D2 | | 443 | GENERAL PROCEDURE A A22B02C03 |

TABLE 1-continued

| Structure | Compound ID | ¹H NMR | MS(M + H)⁺ | Synthetic method |
|---|---|---|---|---|
| (structure) | 1943_D1 | | 461 | GENERAL PROCEDURE A A22B02C02 |
| (structure) | 1943_D2 | | 461 | GENERAL PROCEDURE A A22B02C02 |
| (structure) | 1933 | | 459/461 | GENERAL PROCEDURE A A23B02C01 |

TABLE 1-continued

| Structure | Compound ID | ¹H NMR | MS(M + H)⁺ | Synthetic method |
|---|---|---|---|---|
| 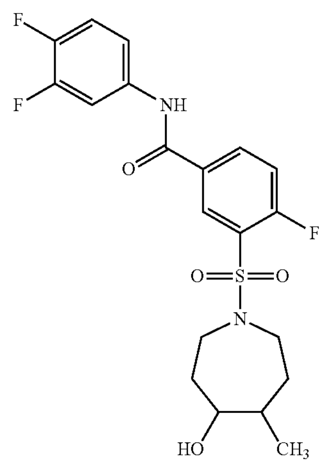 [SMILES: CC1CCN(S(=O)(=O)c2cc(C(=O)Nc3ccc(F)c(F)c3)ccc2F)CCC1O] | 1939 | | 443 | GENERAL PROCEDURE A A23B02C03 |
| 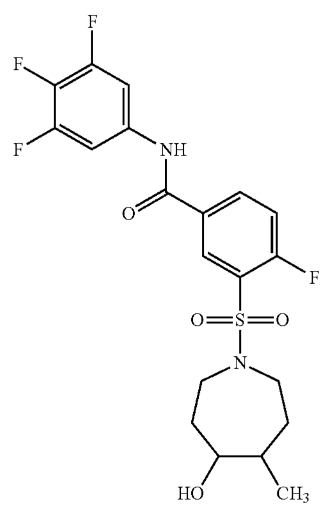 [SMILES: CC1CCN(S(=O)(=O)c2cc(C(=O)Nc3cc(F)c(F)c(F)c3)ccc2F)CCC1O] | 1945 | 1H NMR (400 MHz, METHANOL-d4) δ 8.39-8.46 (m, 1H), 8.18-8.25 (m, 1H), 7.54-7.64 (m, 2H), 7.44-7.52 (m, 1H), 3.81-3.89 (m, 1H), 3.32-3.57 (m, 4H), 1.79-1.98 (m, 4H), 1.55-1.64 (m, 1H), 1.02-1.09 (m, 3H) | 461 | GENERAL PROCEDURE A A23B02C02 |
| 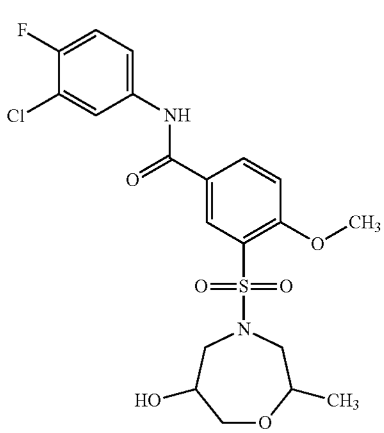 [SMILES: COc1ccc(C(=O)Nc2ccc(F)c(Cl)c2)cc1S(=O)(=O)N1CC(O)COC(C)C1] | 2096_D1 | | 473/475 | GENERAL PROCEDURE A A64B06C01 |

TABLE 1-continued

| Structure | Compound ID | ¹H NMR | MS(M + H)⁺ | Synthetic method |
|---|---|---|---|---|
| 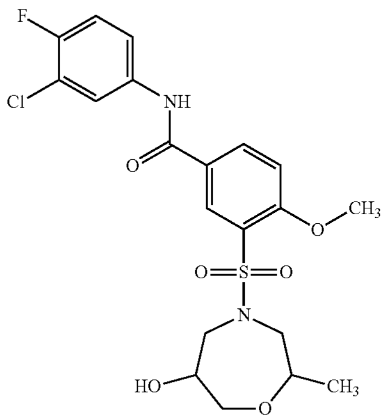 [SMILES: COc1ccc(C(=O)Nc2ccc(F)c(Cl)c2)cc1S(=O)(=O)N1CC(O)COC(C)C1] | 2096_D2 | | 473/475 | GENERAL PROCEDURE A A64B06C01 |
| 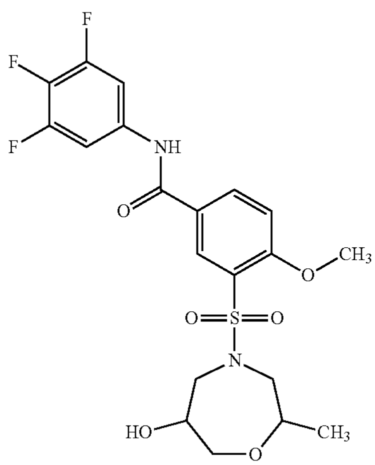 [SMILES: COc1ccc(C(=O)Nc2cc(F)c(F)c(F)c2)cc1S(=O)(=O)N1CC(O)COC(C)C1] | 2097_D1 | | 475 | GENERAL PROCEDURE A A64B06C02 |
| 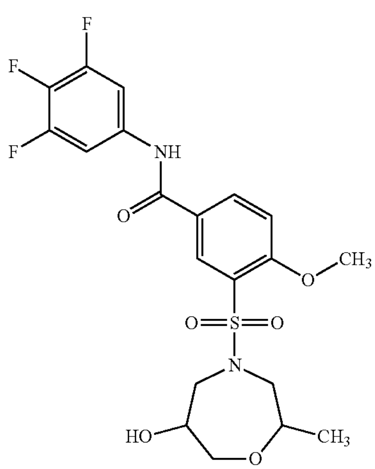 [SMILES: COc1ccc(C(=O)Nc2cc(F)c(F)c(F)c2)cc1S(=O)(=O)N1CC(O)COC(C)C1] | 2097_D2 | | 475 | GENERAL PROCEDURE A A64B06C02 |

TABLE 1-continued

| Structure | Compound ID | ¹H NMR | MS(M + H)⁺ | Synthetic method |
|---|---|---|---|---|
| 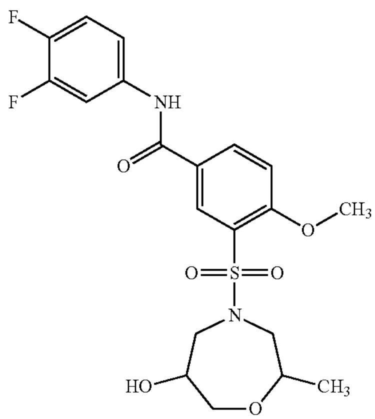 [SMILES: COc1ccc(C(=O)Nc2ccc(F)c(F)c2)cc1S(=O)(=O)N1CC(O)COC(C)C1] | 2098_D1 | 1H NMR (400 MHz, METHANOL-d4) δ 8.45-8.52 (m, 1H), 8.16-8.25 (m, 1H), 1.76-7.90 (m, 1H), 7.39-7.46 (m, 1H), 7.32-7.37 (m, 1H), 7.20-7.30 (m, 1H), 4.05 (s, 4H), 3.87-3.96 (m, 1H), 3.76-3.86 (m, 1H), 3.55-3.67 (m, 2H), 3.42-3.52 (m, 2H), 2.86-2.96 (m, 1H), 1.13 (d, J = 6.40 Hz, 3H) | 457 | GENERAL PROCEDURE A A64B06C03 |
| 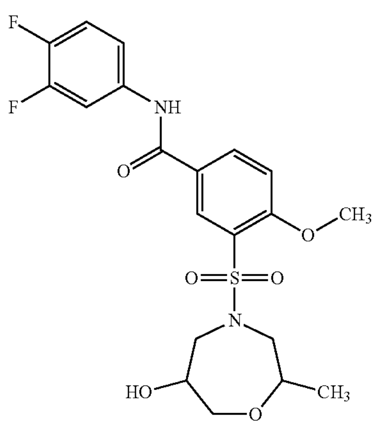 [SMILES: COc1ccc(C(=O)Nc2ccc(F)c(F)c2)cc1S(=O)(=O)N1CC(O)COC(C)C1] | 2098_D2 | 1H NMR (400 MHz, METHANOL-d4) δ 8.43-8.51 (m, 1H), 8.16-8.25 (m, 1H), 7.76-7.86 (m, 1H), 7.39-7.45 (m, 1H), 7.33-7.37 (m, 1H), 7.20-7.30 (m, 1H), 4.06 (s, 4H), 3.88-4.02 (m, 3H), 3.80-3.87 (m, 1H), 3.64-3.75 (m, 1H), 2.83-2.92 (m, 1H), 2.71-2.80 (m, 1H), 1.14 (d, J = 6.27 Hz, 3H) | 457 | GENERAL PROCEDURE A A64B06C03 |
| 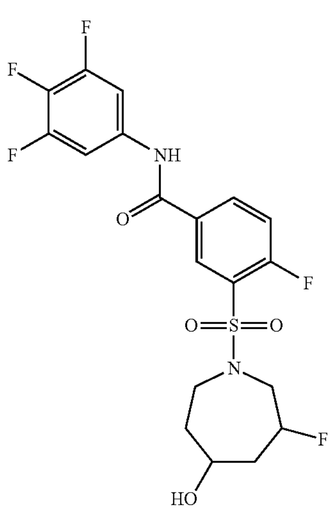 [SMILES: O=C(Nc1cc(F)c(F)c(F)c1)c1ccc(F)c(S(=O)(=O)N2CCC(O)CC(F)C2)c1] | 1835_D1 | | 465 | GENERAL PROCEDURE A A28B02C02 |

TABLE 1-continued

| Structure | Compound ID | ¹H NMR | MS(M + H)⁺ | Synthetic method |
|---|---|---|---|---|
| (structure) | 1835_D2 | | 465 | GENERAL PROCEDURE A A28B02C02 |
| (structure) | 1836_D1 | | 447 | GENERAL PROCEDURE A A28B02C03 |
| (structure) | 1836_D2 | | 447 | GENERAL PROCEDURE A A28B02C03 |

TABLE 1-continued
| Structure | Compound ID | ¹H NMR | MS(M + H)⁺ | Synthetic method |
|---|---|---|---|---|
| 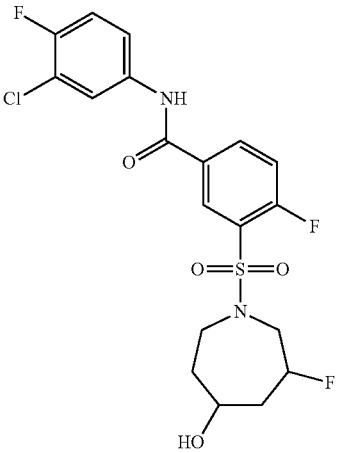 [SMILES: O=C(Nc1ccc(F)c(Cl)c1)c1ccc(F)c(S(=O)(=O)N2CCC(O)CC(F)C2)c1] | 1837_D1 | 1H NMR (400 MHz, METHANOL-d4) δ 8.42-8.49 (m, 1H), 8.21-8.30 (m, 1H), 7.91-8.02 (m, 1H), 7.58-7.67 (m, 1H), 7.46-7.55 (m, 1H), 7.20-7.30 (m, 1H), 4.53-4.77 (m, 1H), 3.81-3.93 (m, 1H), 3.56-3.75 (m, 2H), 3.43-3.56 (m, 1H), 3.24-3.30 (m, 1H), 2.28-2.43 (m, 1H), 1.94-2.12 (m, 2H), 1.78-1.93 (m, 1H) | 463/465 | GENERAL PROCEDURE A A28B02C01 |
| 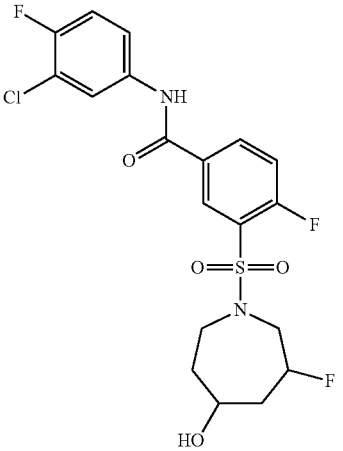 [SMILES: O=C(Nc1ccc(F)c(Cl)c1)c1ccc(F)c(S(=O)(=O)N2CCC(O)CC(F)C2)c1] | 1837_D2 | 1H NMR (400 MHz, METHANOL-d4) δ 8.41-8.48 (m, 1H), 8.20-8.29 (m, 1H), 7.93-8.00 (m, 1H), 7.58-7.66 (m, 1H), 7.45-7.54 (m, 1H), 7.21-7.30 (m, 1H), 4.97-5.08 (m, 1H), 4.54-4.71 (m, 1H), 4.07-4.21 (m, 1H), 3.56-3.84 (m, 2H), 3.39-3.54 (m, 1H), 3.33-3.38 (m, 1H), 2.04-2.32 (m, 3H), 1.67-1.86 (m, 1H) | 463/465 | GENERAL PROCEDURE A A28B02C01 |
| 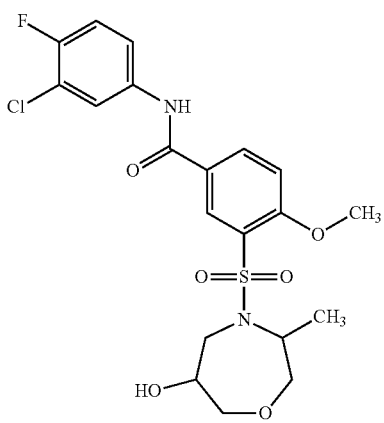 [SMILES: COc1ccc(C(=O)Nc2ccc(F)c(Cl)c2)cc1S(=O)(=O)N1CC(O)COCC1C] | 2093 | | 473/475 | GENERAL PROCEDURE A A65B06C01 |

TABLE 1-continued

| Structure | Compound ID | ¹H NMR | MS(M + H)⁺ | Synthetic method |
|---|---|---|---|---|
| 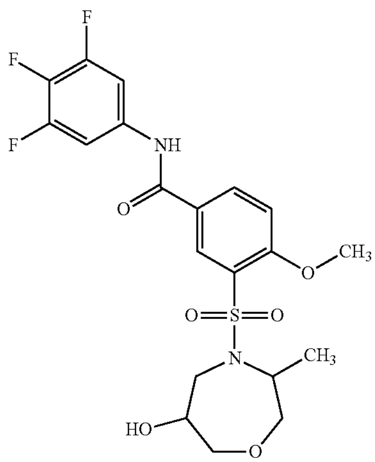 [SMILES: COc1ccc(C(=O)Nc2cc(F)c(F)c(F)c2)cc1S(=O)(=O)N1CC(O)COCC1C] | 2094 | 1H NMR (400 MHz, METHANOL-d4) δ 8.52-8.54 (m, 1H), 8.19-8.22 (m, 1H), 7.59-7.63 (m, 2H), 7.34-7.37 (m, 1H), 4.20-4.30 (m, 1H), 4.07 (s, 1H), 3.79-3.92 (m, 4H), 3.58-3.63 (m, 2.5H), 3.14-3.50 (m, 0.5H), 0.97-1.00 (m, 3H) | 475 | GENERAL PROCEDURE A A65B06C02 |
| 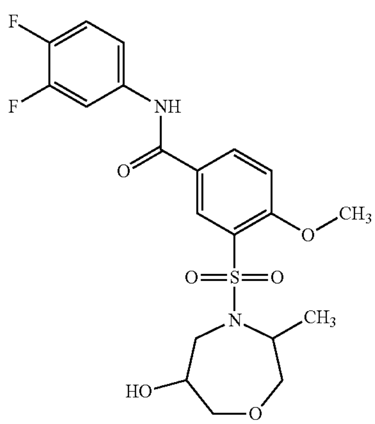 [SMILES: COc1ccc(C(=O)Nc2ccc(F)c(F)c2)cc1S(=O)(=O)N1CC(O)COCC1C] | 2095 | | 457 | GENERAL PROCEDURE A A65B06C03 |
| 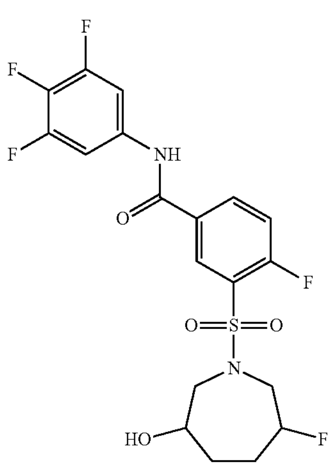 [SMILES: O=C(Nc1cc(F)c(F)c(F)c1)c1ccc(F)c(S(=O)(=O)N2CC(O)CCC(F)C2)c1] | 1826_D1 | | 465 | GENERAL PROCEDURE A A26B02C02 |

TABLE 1-continued

| Structure | Compound ID | ¹H NMR | MS(M + H)⁺ | Synthetic method |
|---|---|---|---|---|
| 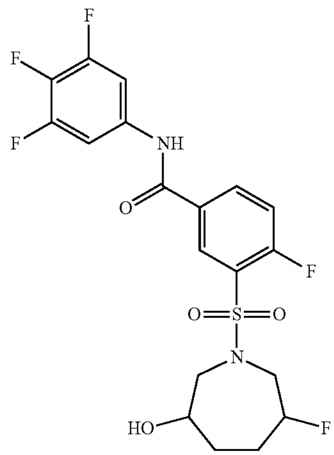 [SMILES: O=C(Nc1cc(F)c(F)c(F)c1)c1ccc(F)c(S(=O)(=O)N2CC(O)CCC(F)C2)c1] | 1826_D2 | | 465 | GENERAL PROCEDURE A A26B02C02 |
| 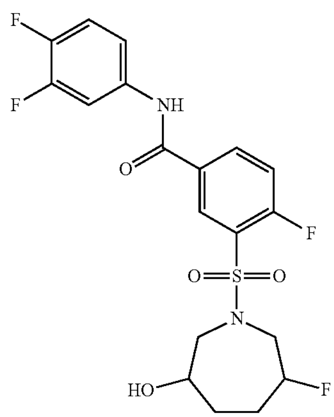 [SMILES: O=C(Nc1ccc(F)c(F)c1)c1ccc(F)c(S(=O)(=O)N2CC(O)CCC(F)C2)c1] | 1827_D1 | | 447 | GENERAL PROCEDURE A A26B02C03 |
| 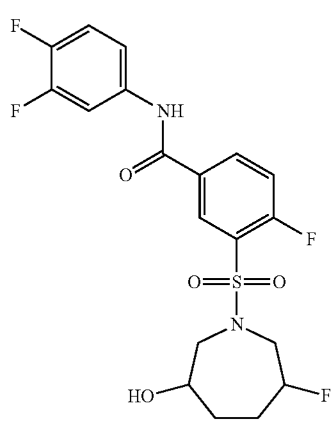 [SMILES: O=C(Nc1ccc(F)c(F)c1)c1ccc(F)c(S(=O)(=O)N2CC(O)CCC(F)C2)c1] | 1827_D2 | | 447 | GENERAL PROCEDURE A A26B02C03 |

TABLE 1-continued

| Structure | Compound ID | $^1$H NMR | MS(M + H)$^+$ | Synthetic method |
|---|---|---|---|---|
| 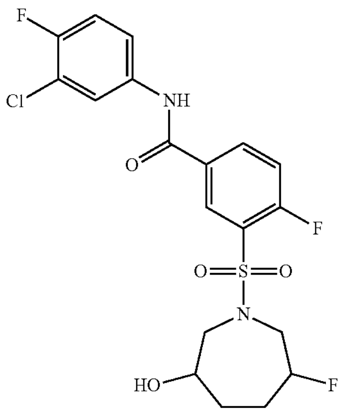 [SMILES: O=C(Nc1ccc(F)c(Cl)c1)c1ccc(F)c(S(=O)(=O)N2CC(O)CCC(F)C2)c1] | 1828_D1 | 1H NMR (400 MHz, METHANOL-d4) δ 8.48-8.50 (m, 1H), 8.26-8.29 (m, 1H), 7.98-8.00 (m, 1H), 7.63-7.64 (m, 1H), 7.50-7.54 (m, 1H), 7.25-7.30 (m, 1H), 4.76-4.88 (m, 1H), 4.01-4.02 (m, 1H), 3.75-3.85 (m, 1H), 3.71-3.74 (m, 1H), 3.46-3.50 (m, 1H), 2.96-3.01 (m, 1H), 2.10-2.18 (m, 2H), 1.78-1.85 (m, 1H), 1.54-1.60 (m, 1H) | 463/465 | GENERAL PROCEDURE A A26B02C01 |
| 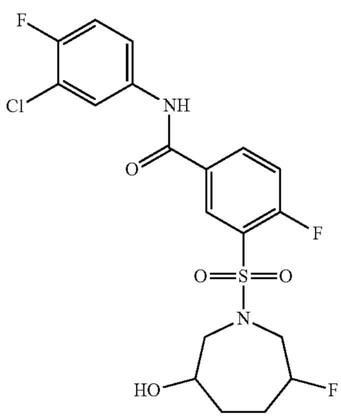 [SMILES: O=C(Nc1ccc(F)c(Cl)c1)c1ccc(F)c(S(=O)(=O)N2CC(O)CCC(F)C2)c1] | 1828_D2 | | 463/465 | GENERAL PROCEDURE A A26B02C01 |
| 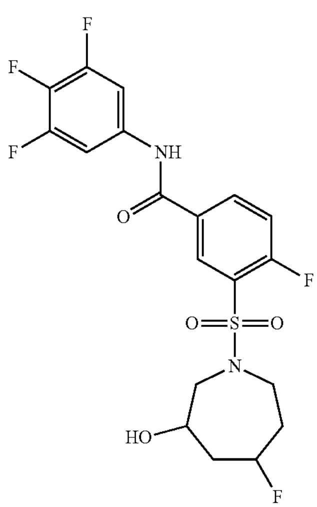 [SMILES: O=C(Nc1cc(F)c(F)c(F)c1)c1ccc(F)c(S(=O)(=O)N2CCC(F)CC(O)C2)c1] | 1823 | | 465 | GENERAL PROCEDURE A A27B02C02 |

TABLE 1-continued

| Structure | Compound ID | ¹H NMR | MS(M + H)⁺ | Synthetic method |
|---|---|---|---|---|
| 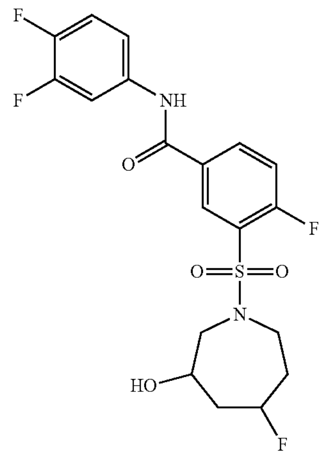 [SMILES: O=C(Nc1ccc(F)c(F)c1)c1ccc(F)c(S(=O)(=O)N2CCC(F)CC(O)C2)c1] | 1824 | | 447 | GENERAL PROCEDURE A A27B02C03 |
| 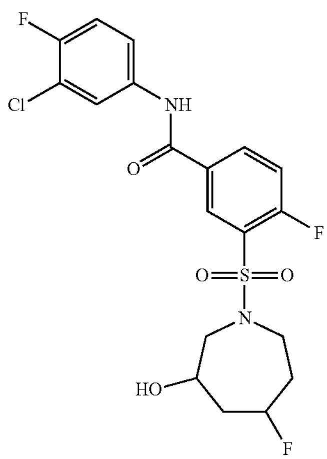 [SMILES: O=C(Nc1ccc(F)c(Cl)c1)c1ccc(F)c(S(=O)(=O)N2CCC(F)CC(O)C2)c1] | 1825 | | 463/465 | GENERAL PROCEDURE A A27B02C01 |
| 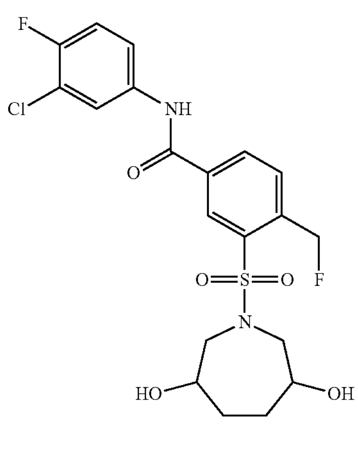 [SMILES: O=C(Nc1ccc(F)c(Cl)c1)c1ccc(CF)c(S(=O)(=O)N2CC(O)CCC(O)C2)c1] | 2434 | 1H NMR (400 MHz, METHANOL-d4) δ 8.40-8.44 (m, 1H), 8.24-8.26 (m, 1H), 8.00-8.02 (m, 1H), 7.90-7.92 (m, 1H), 7.64-7.67 (m, 1H), 7.26-7.30 (m, 1H), 5.82-5.98 (m, 2H), 3.76-3.98 (m, 3H), 3.56-3.61 (m, 1H), 3.28-3.30 (m, 1H), 3.00-3.06 (m, 1H), 1.86-1.87 (m, 3H), 1.55-1.56 (m, 1H) | 475/477 | GENERAL PROCEDURE A A68B05C01 |

TABLE 1-continued

| Structure | Compound ID | ¹H NMR | MS(M + H)⁺ | Synthetic method |
|---|---|---|---|---|
| 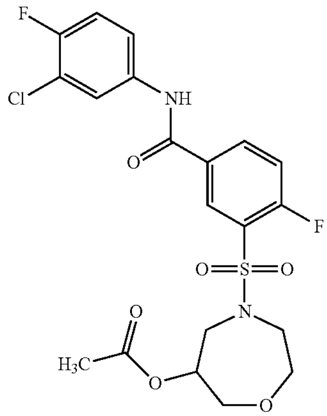 [SMILES: CC(=O)OC1COCCN(S(=O)(=O)c2cc(C(=O)Nc3ccc(F)c(Cl)c3)ccc2F)C1] | 2027 | | 489/491 | GENERAL PROCEDURE A A37B02C01 |
| 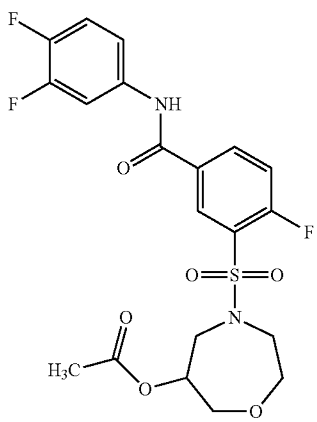 [SMILES: CC(=O)OC1COCCN(S(=O)(=O)c2cc(C(=O)Nc3ccc(F)c(F)c3)ccc2F)C1] | 2028 | | 473 | GENERAL PROCEDURE A A37B02C03 |
| 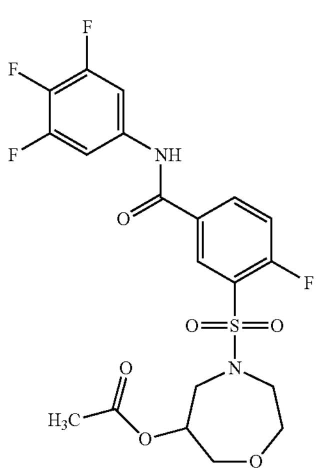 [SMILES: CC(=O)OC1COCCN(S(=O)(=O)c2cc(C(=O)Nc3cc(F)c(F)c(F)c3)ccc2F)C1] | 2029 | | 491 | GENERAL PROCEDURE A A37B02C02 |

TABLE 1-continued

| Structure | Compound ID | ¹H NMR | MS(M + H)⁺ | Synthetic method |
|---|---|---|---|---|
| 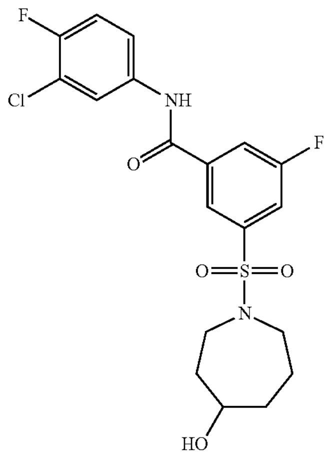 [SMILES: O=C(Nc1ccc(F)c(Cl)c1)c1cc(F)cc(S(=O)(=O)N2CCCC(O)CC2)c1] | 2014 | | 445/447 | GENERAL PROCEDURE F A02B11C01 |
| 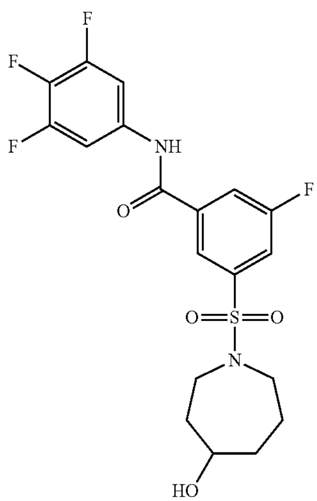 [SMILES: O=C(Nc1cc(F)c(F)c(F)c1)c1cc(F)cc(S(=O)(=O)N2CCCC(O)CC2)c1] | 2016 | | 447 | GENERAL PROCEDURE F A02B11C02 |
| 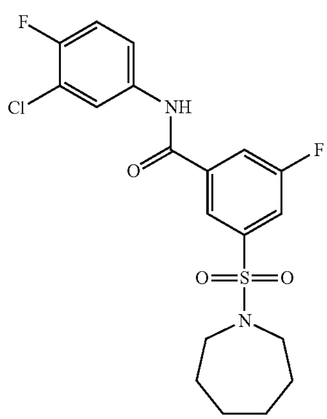 [SMILES: O=C(Nc1ccc(F)c(Cl)c1)c1cc(F)cc(S(=O)(=O)N2CCCCCC2)c1] | 2049 | | 429/431 | GENERAL PROCEDURE F A53B11C01 |

TABLE 1-continued

| Structure | Compound ID | ¹H NMR | MS(M + H)⁺ | Synthetic method |
|---|---|---|---|---|
| 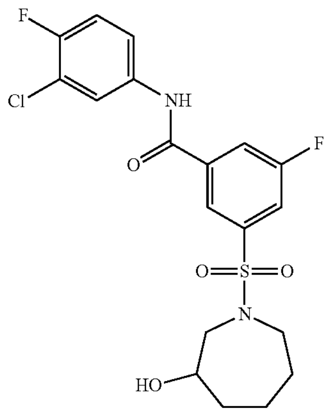 [SMILES: O=C(Nc1ccc(F)c(Cl)c1)c1cc(F)cc(S(=O)(=O)N2CCCCC(O)C2)c1] | 2053 | | 445/447 | GENERAL PROCEDURE F A01B11C01 |
| 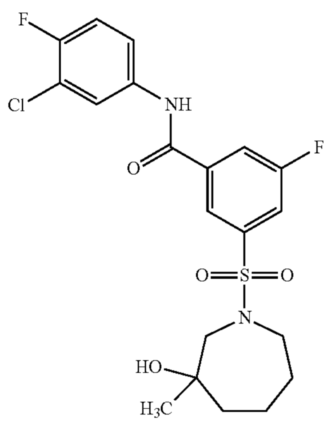 [SMILES: CC1(O)CCCCN(S(=O)(=O)c2cc(F)cc(C(=O)Nc3ccc(F)c(Cl)c3)c2)C1] | 2054 | | 459/461 | GENERAL PROCEDURE F A05B11C01 |
| 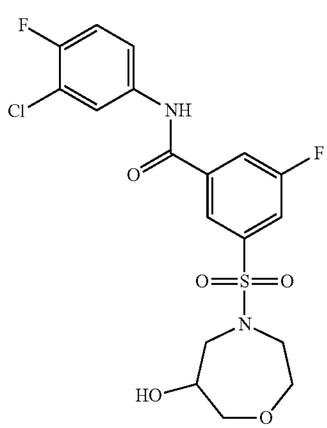 [SMILES: O=C(Nc1ccc(F)c(Cl)c1)c1cc(F)cc(S(=O)(=O)N2CCOCC(O)C2)c1] | 2055 | | 447/449 | GENERAL PROCEDURE F A13B11C01 |

| Structure | Compound ID | ¹H NMR | MS(M + H)⁺ | Synthetic method |
|---|---|---|---|---|
| 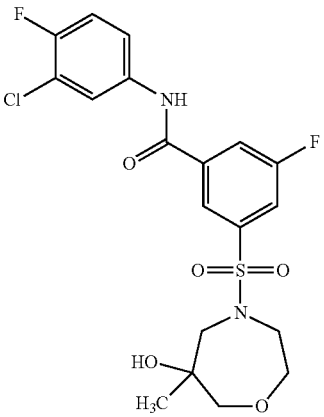 [SMILES: CC1(O)COCCN(S(=O)(=O)c2cc(F)cc(C(=O)Nc3ccc(F)c(Cl)c3)c2)C1] | 2056 | | 461/463 | GENERAL PROCEDURE F A35B11C01 |
| 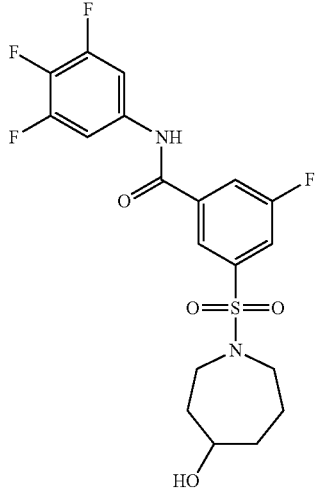 [SMILES: O=C(Nc1cc(F)c(F)c(F)c1)c1cc(F)cc(S(=O)(=O)N2CCCC(O)CC2)c1] | 2057 | | 447 | GENERAL PROCEDURE F A02B11C02 |
| 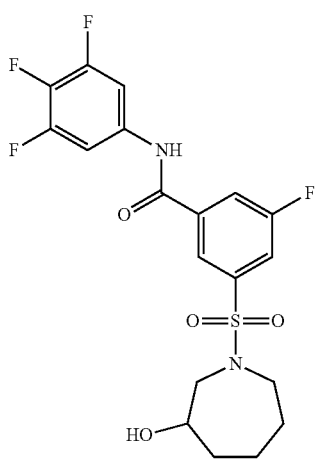 [SMILES: O=C(Nc1cc(F)c(F)c(F)c1)c1cc(F)cc(S(=O)(=O)N2CCCCC(O)C2)c1] | 2061 | 1H NMR (400 MHz, METHANOL-d4) δ = 8.22 (s, 1H), 7.99 (d, J = 8.7 Hz, 1H), 7.83 (d, J = 7.8 Hz, 1H), 7.63 (dd, J = 6.4, 10.0 Hz, 2H), 3.95-3.86 (m, 1H), 3.67 (dd, J = 4.6, 14.2 Hz, 1H), 3.54 (td, J = 6.4, 13.3 Hz, 1H), 3.24-3.13 (m, 1H), 3.00 (dd, J = 8.2, 14.1 Hz, 1H), 1.97 (ddd, J = 4.4, 8.1, 12.6 Hz, 1H), 1.91-1.65 (m, 3H), 1.64-1.46 (m, 2H) | 447 | GENERAL PROCEDURE F A02B11C03 |

TABLE 1-continued

| Structure | Compound ID | ¹H NMR | MS(M + H)⁺ | Synthetic method |
|---|---|---|---|---|
| 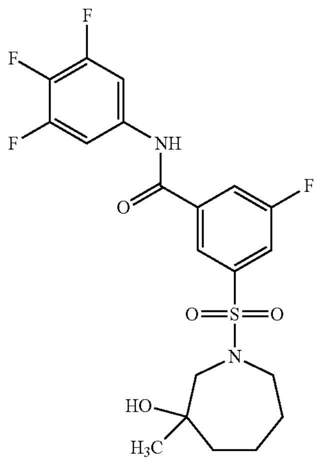 [SMILES: CC1(O)CCCCN(S(=O)(=O)c2cc(F)cc(C(=O)Nc3cc(F)c(F)c(F)c3)c2)C1] | 2062 | | 461 | GENERAL PROCEDURE F A05B11C02 |
| 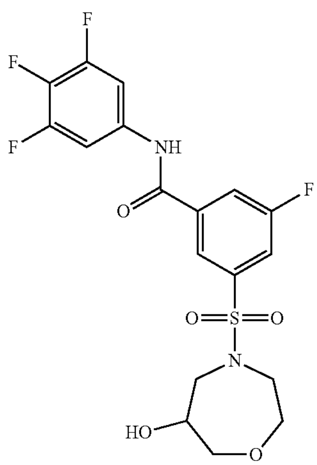 [SMILES: O=C(Nc1cc(F)c(F)c(F)c1)c1cc(F)cc(S(=O)(=O)N2CCOCC(O)C2)c1] | 2063 | 1H NMR (400 MHz, METHANOL-d4) δ = 8.25 (s, 1H), 8.01 (td, J = 2.1, 8.7 Hz, 1H), 7.87 (td, J = 1.9, 7.8 Hz, 1H), 7.63 (dd, J = 6.5, 10.0 Hz, 2H), 4.02 (dd, J = 5.1, 7.0 Hz, 1H), 3.94-3.84 (m, 2H), 3.80-3.57 (m, 4H), 3.32-3.27 (m, 1H), 3.21 (dd, J = 7.2, 14.2 Hz, 1H) | 449 | GENERAL PROCEDURE F A13B11C02 |
| 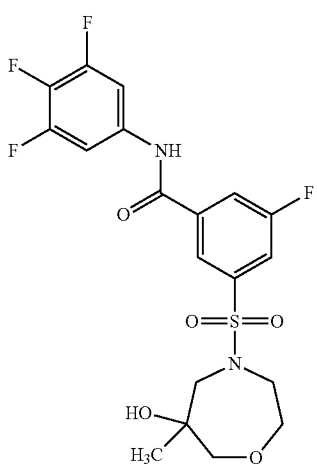 [SMILES: CC1(O)COCCN(S(=O)(=O)c2cc(F)cc(C(=O)Nc3cc(F)c(F)c(F)c3)c2)C1] | 2064 | | 463 | GENERAL PROCEDURE F A35B11C02 |

TABLE 1-continued

| Structure | Compound ID | ¹H NMR | MS(M + H)⁺ | Synthetic method |
|---|---|---|---|---|
| (structure) | 2045 | 1H NMR (400 MHz, METHANOL-d4) δ = 8.47 (d, J = 6.7 Hz, 1H), 8.24 (br. s., 1H), 7.99 (d, J = 6.5 Hz, 1H), 7.64 (d, J = 8.5 Hz, 1H), 7.50 (t, J = 9.2 Hz, 1H), 7.27 (t, J = 8.8 Hz, 1H), 3.62 (dd, J = 4.7, 14.2 Hz, 1H), 3.51-3.39 (m, 4H), 3.14 (dd, J = 8.8, 14.0 Hz, 1H), 1.98-1.78 (m, 4H), 1.75-1.51 (m, 2H), 1.42-1.30 (m, 1H) | 459/461 | GENERAL PROCEDURE A A50B02C01 |
| (structure) | 2046_D1 | 1H NMR (400 MHz, METHANOL-d4) δ = 8.46 (dd, J = 2.4, 6.7 Hz, 1H), 8.24 (ddd, J = 2.4, 4.5, 8.7 Hz, 1H), 7.99 (dd, J = 2.6, 6.7 Hz, 1H), 7.68-7.61 (m, 1H), 7.54-7.47 (m, 1H), 7.27 (t, J = 9.0 Hz, 1H), 3.76-3.67 (m, 1H), 3.60 (dd, J = 4.5, 13.9 Hz, 1H), 3.52-3.41 (m, 1H), 3.15 (dd, J = 10.2, 13.7 Hz, 1H), 1.95-1.84 (m, 3H), 1.82-1.75 (m, 1H), 1.68 (d, J = 5.0 Hz, 1H), 1.55-1.43 (m, 3H), 1.16 (d, J = 6.4 Hz, 3H) | 473/475 | GENERAL PROCEDURE A A51B02C01 |
| (structure) | 2046_D2 | 1H NMR (400 MHz, METHANOL-d4) δ = 8.47 (dd, J = 2.3, 6.6 Hz, 1H), 8.24 (ddd, J = 2.4, 4.6, 8.6 Hz, 1H), 7.99 (dd, J = 2.6, 6.7 Hz, 1H), 7.67-7.61 (m, 1H), 7.50 (dd, J = 8.8, 9.7 Hz, 1H), 7.27 (t, J = 9.0 Hz, 1H), 3.71-3.62 (m, 2H), 3.44-3.36 (m, 2H), 3.21 (dd, J = 9.1, 14.1 Hz, 1H), 1.95-1.79 (m, 3H), 1.78-1.61 (m, 2H), 1.60-1.48 (m, 1H), 1.46-1.35 (m, 1H), 1.18 (d, J = 6.4 Hz, 3H) | 473/475 | GENERAL PROCEDURE A A51B02C01 |

TABLE 1-continued

| Structure | Compound ID | ¹H NMR | MS(M + H)⁺ | Synthetic method |
|---|---|---|---|---|
| 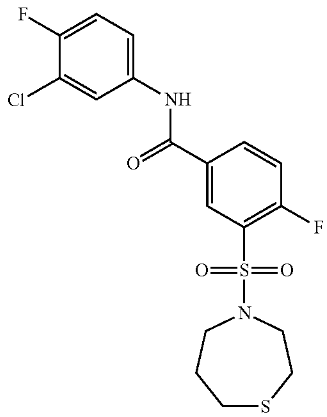 [SMILES: O=C(Nc1ccc(F)c(Cl)c1)c1ccc(F)c(S(=O)(=O)N2CCCSCC2)c1] | 2076 | | 447/449 | GENERAL PROCEDURE A A67B02C01 |
| 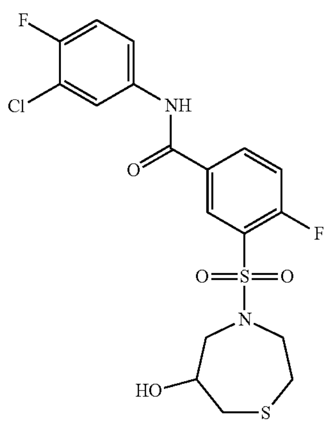 [SMILES: O=C(Nc1ccc(F)c(Cl)c1)c1ccc(F)c(S(=O)(=O)N2CCSCC(O)C2)c1] | 2077 | 1H NMR (400 MHz, METHANOL-d4) δ = 8.48 (dd, J = 2.3, 6.7 Hz, 1H), 8.30-8.23 (m, 1H), 7.98 (dd, J = 2.5, 6.7 Hz, 1H), 7.64 (td, J = 3.3, 8.9 Hz, 1H), 7.52 (t, J = 9.4 Hz, 1H), 7.27 (t, J = 9.0 Hz, 1H), 4.29-4.21 (m, 1H), 3.99 (td, J = 4.5, 14.1 Hz, 1H), 3.82 (dd, J = 5.5, 14.9 Hz, 1H), 3.27 (dd, J = 8.1, 15.1 Hz, 2H), 3.04 (dd, J = 4.3, 15.1 Hz, 1H), 2.89-2.76 (m, 3H) | 463/465 | GENERAL PROCEDURE A A43B02C01 |
| 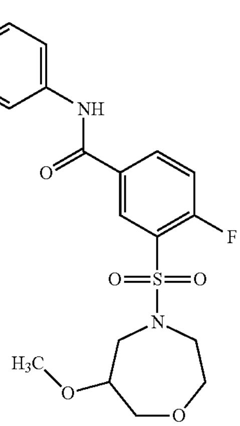 | 2159 | | 461/463 | GENERAL PROCEDURE A A38B02C01 |

TABLE 1-continued

| Structure | Compound ID | ¹H NMR | MS(M + H)⁺ | Synthetic method |
|---|---|---|---|---|
| 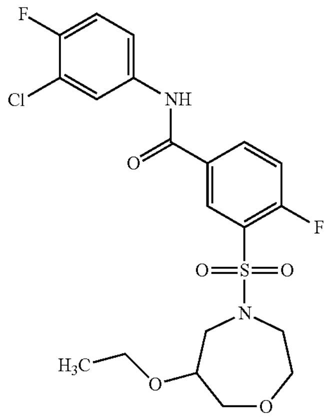 [SMILES: CCOC1COCCN(S(=O)(=O)c2cc(C(=O)Nc3ccc(F)c(Cl)c3)ccc2F)C1] | 2160 | | 475/477 | GENERAL PROCEDURE A A39B02C01 |
| 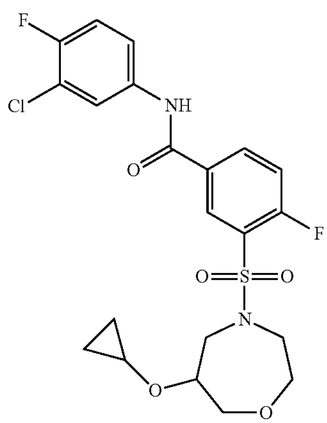 [SMILES: O=C(Nc1ccc(F)c(Cl)c1)c1ccc(F)c(S(=O)(=O)N2CCOCC(OC3CC3)C2)c1] | 2161 | | 487/489 | GENERAL PROCEDURE A A42B02C01 |
| 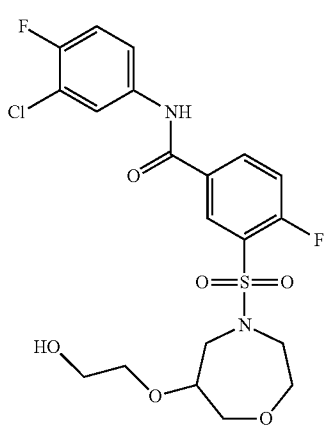 [SMILES: O=C(Nc1ccc(F)c(Cl)c1)c1ccc(F)c(S(=O)(=O)N2CCOCC(OCCO)C2)c1] | 2162 | | 491/493 | GENERAL PROCEDURE A A41B02C01 |

TABLE 1-continued

| Structure | Compound ID | ¹H NMR | MS(M + H)⁺ | Synthetic method |
|---|---|---|---|---|
| 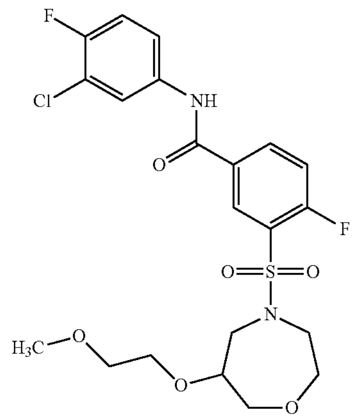 [SMILES: COCCOC1COCCN(S(=O)(=O)c2cc(C(=O)Nc3ccc(F)c(Cl)c3)ccc2F)C1] | 2163 | | 505/507 | GENERAL PROCEDURE A A40B02C01 |
| 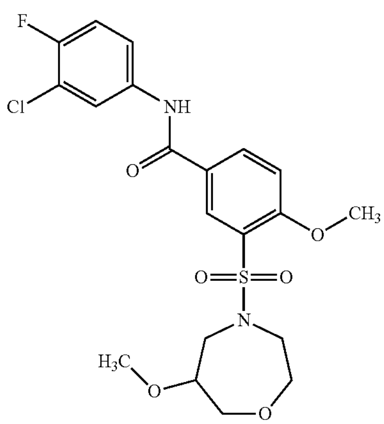 [SMILES: COc1ccc(C(=O)Nc2ccc(F)c(Cl)c2)cc1S(=O)(=O)N1CCOCC(OC)C1] | 2164 | | 473/475 | GENERAL PROCEDURE A A38B06C01 |
| 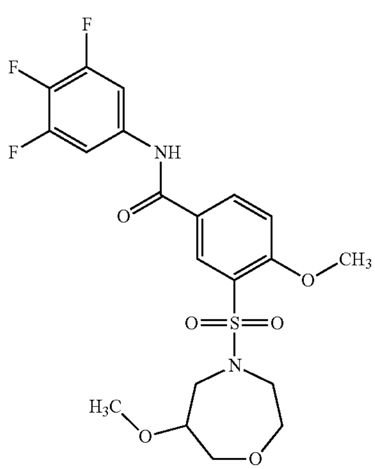 [SMILES: COc1ccc(C(=O)Nc2cc(F)c(F)c(F)c2)cc1S(=O)(=O)N1CCOCC(OC)C1] | 2165 | | 475 | GENERAL PROCEDURE A A38B06C02 |

TABLE 1-continued
| Structure | Compound ID | ¹H NMR | MS(M + H)⁺ | Synthetic method |
|---|---|---|---|---|
| 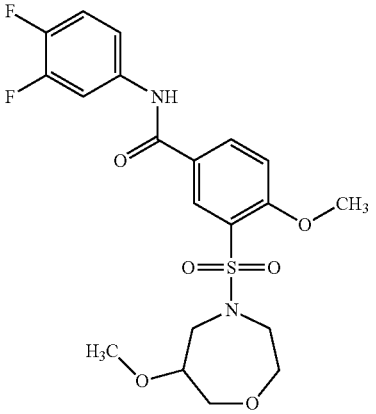 [SMILES: COc1ccc(C(=O)Nc2ccc(F)c(F)c2)cc1S(=O)(=O)N1CCOCC(OC)C1] | 2166 | | 457 | GENERAL PROCEDURE A A38B06C03 |
| 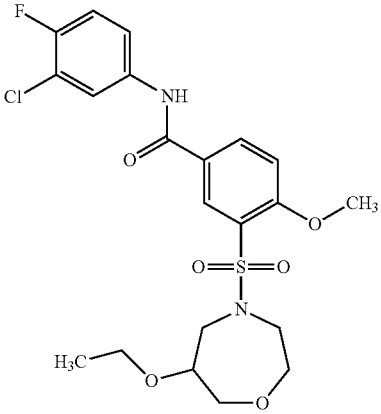 [SMILES: CCOC1COCCN(S(=O)(=O)c2cc(C(=O)Nc3ccc(F)c(Cl)c3)ccc2OC)C1] | 2167 | | 487/489 | GENERAL PROCEDURE A A39B06C01 |
| 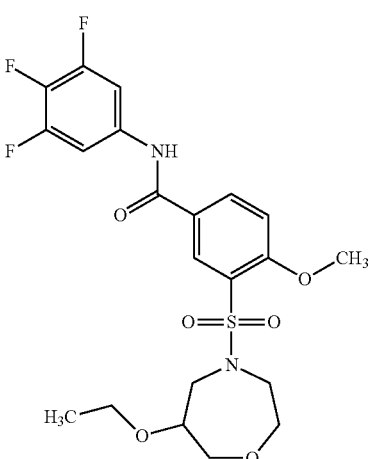 | 2168 | | 489 | GENERAL PROCEDURE A A39B06C02 |

TABLE 1-continued

| Structure | Compound ID | ¹H NMR | MS(M + H)⁺ | Synthetic method |
|---|---|---|---|---|
| 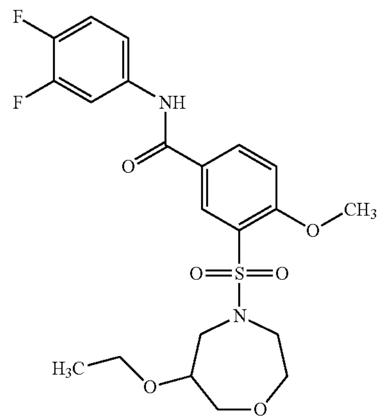 [SMILES: CCOC1COCCN(S(=O)(=O)c2cc(C(=O)Nc3ccc(F)c(F)c3)ccc2OC)C1] | 2169 | | 471 | GENERAL PROCEDURE A A39B06C03 |
| 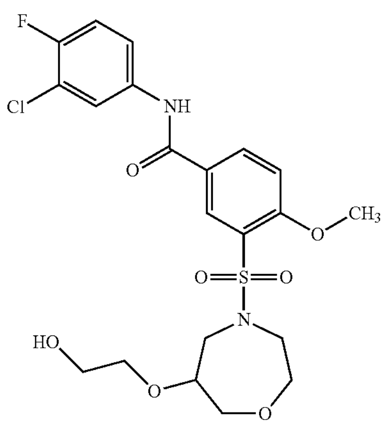 [SMILES: COc1ccc(C(=O)Nc2ccc(F)c(Cl)c2)cc1S(=O)(=O)N1CCOCC(OCCO)C1] | 2173 | | 503/505 | GENERAL PROCEDURE A A41B06C01 |
| 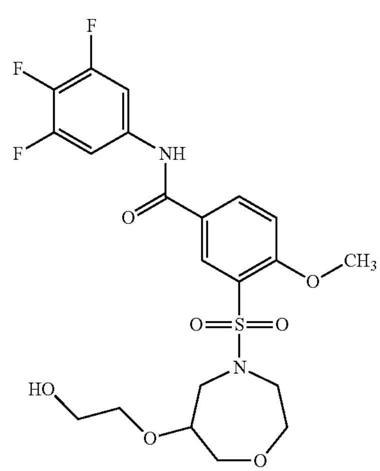 [SMILES: COc1ccc(C(=O)Nc2cc(F)c(F)c(F)c2)cc1S(=O)(=O)N1CCOCC(OCCO)C1] | 2174 | | 505 | GENERAL PROCEDURE A A41B06C02 |

TABLE 1-continued

| Structure | Compound ID | ¹H NMR | MS(M + H)⁺ | Synthetic method |
|---|---|---|---|---|
| 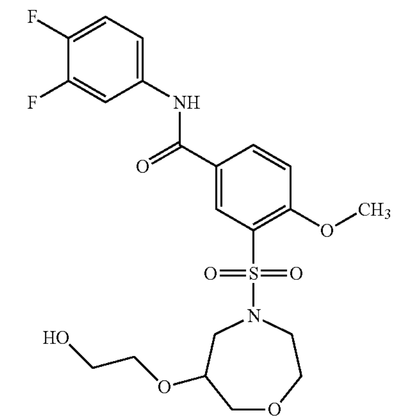 [SMILES: COc1ccc(C(=O)Nc2ccc(F)c(F)c2)cc1S(=O)(=O)N1CCOCC(OCCO)C1] | 2175 |  | 487 | GENERAL PROCEDURE A A41B06C03 |
| 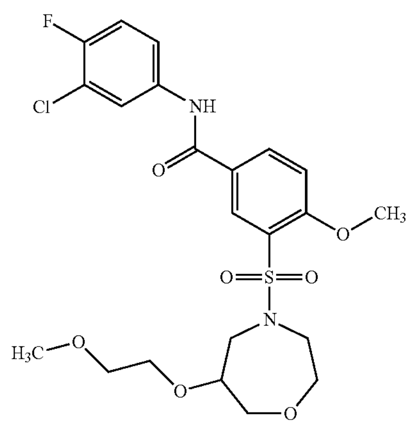 | 2176 |  | 517/519 | GENERAL PROCEDURE A A40B06C01 |
| 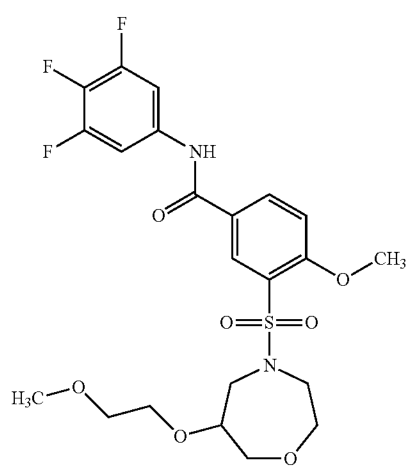 | 2177 |  | 519 | GENERAL PROCEDURE A A40B06C02 |

TABLE 1-continued

| Structure | Compound ID | ¹H NMR | MS(M + H)⁺ | Synthetic method |
|---|---|---|---|---|
| 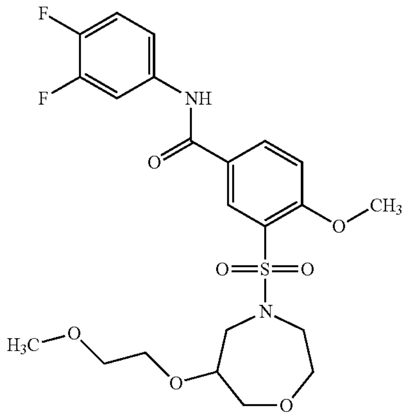 | 2178 | | 501 | GENERAL PROCEDURE A A40B06C03 |
| 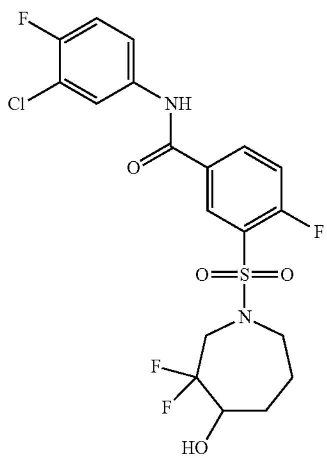 [SMILES: O=C(Nc1ccc(F)c(Cl)c1)c1ccc(F)c(S(=O)(=O)N2CCCC(O)C(F)(F)C2)c1] | 2197 | | 481/483 | GENERAL PROCEDURE A A45B02C01 |
| 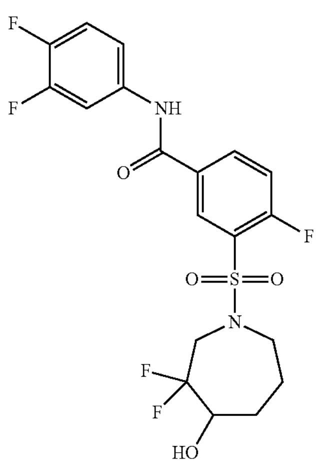 [SMILES: O=C(Nc1ccc(F)c(F)c1)c1ccc(F)c(S(=O)(=O)N2CCCC(O)C(F)(F)C2)c1] | 2198 | 1H NMR (400 MHz, METHANOL-d4) δ = 8.47 (dd, J = 2.4, 6.7 Hz, 1H), 8.27 (ddd, J = 2.4, 4.6, 8.5 Hz, 1H), 7.84 (ddd, J = 2.6, 7.4, 12.8 Hz, 1H), 7.56-7.42 (m, 2H), 7.34-7.23 (m, 1H), 4.05-3.89 (m, 2H), 3.80-3.65 (m, 1H), 3.58-3.47 (m, 1H), 3.20 (ddd, J = 5.8, 7.7, 13.3 Hz, 1H), 2.07-1.76 (m, 4H) | 465 | GENERAL PROCEDURE A A45B02C03 |

TABLE 1-continued

| Structure | Compound ID | ¹H NMR | MS(M + H)⁺ | Synthetic method |
|---|---|---|---|---|
| 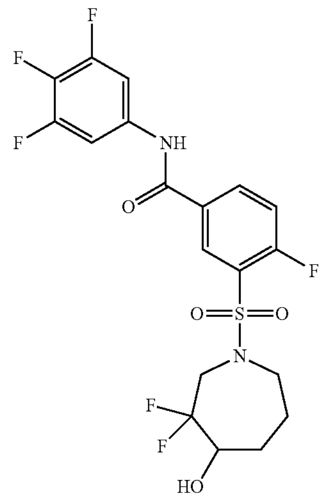 [SMILES: O=C(Nc1cc(F)c(F)c(F)c1)c1ccc(F)c(S(=O)(=O)N2CCCC(O)C(F)(F)C2)c1] | 2199 | 1H NMR (400 MHz, METHANOL-d4) δ = 8.46 (dd, J = 2.4, 6.7 Hz, 1H), 8.26 (ddd, J = 2.4, 4.6, 8.6 Hz, 1H), 7.61 (dd, J = 6.4, 10.0 Hz, 2H), 7.52 (dd, J = 8.7, 10.0 Hz, 1H), 4.05-3.88 (m, 2H), 3.79-3.65 (m, 1H), 3.58-3.47 (m, 1H), 3.19 (ddd, J = 5.8, 7.6, 13.3 Hz, 1H), 2.10-1.74 (m, 4H) | 483 | GENERAL PROCEDURE A A45B02C02 |
| 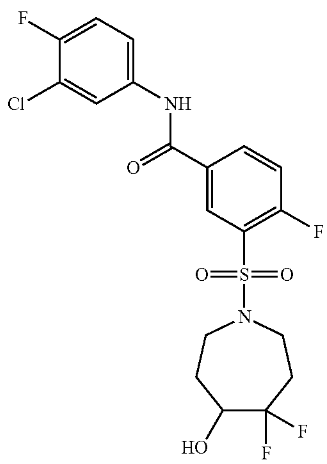 [SMILES: O=C(Nc1ccc(F)c(Cl)c1)c1ccc(F)c(S(=O)(=O)N2CCC(O)C(F)(F)CC2)c1] | 2200 | ¹HNMR (400 MHz, METHANOL) δ = 8.44 (dd, J = 2.3, 6.5 Hz, 1H), 8.23 (m, 1H), 7.96 (dd, J = 2.5, 6.8 Hz, 1H), 7.65-7.57 (m, 1H), 7.49 (t, J = 9.3 Hz, 1H), 7.25 (t, J = 8.9 Hz, 1H), 4.03-3.94 (m, 1H), 3.62-3.47 (m, 4H), 2.49-2.32 (m, 1H), 2.28-2.11 (m, 1H), 2.08-1.87 (m, 2H) | 481/483 | GENERAL PROCEDURE A A44B02C01 |
| 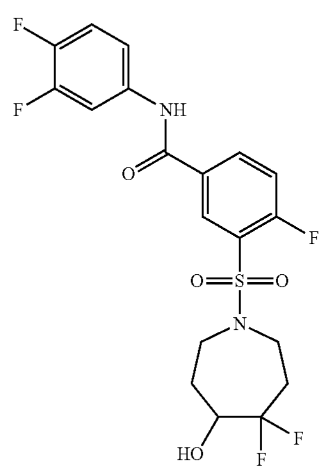 [SMILES: O=C(Nc1ccc(F)c(F)c1)c1ccc(F)c(S(=O)(=O)N2CCC(O)C(F)(F)CC2)c1] | 2201 | ¹HNMR (400 MHz, METHANOL) δ = 8.44 (dd, J = 2.1, 6.7 Hz, 1H), 8.28-8.20 (m, 1H), 7.83 (m, 1H), 7.53-7.38 (m, 2H), 7.32-7.20 (m, 1H), 3.99 (d, J = 7.8 Hz, 1H), 3.53 (br. s., 4H), 2.46-2.33 (m, 1H), 2.27-2.14 (m, 1H), 2.06-1.92 (m, 2H) | 465/467 | GENERAL PROCEDURE A A44B02C03 |

| Structure | Compound ID | ¹H NMR | MS(M + H)⁺ | Synthetic method |
|---|---|---|---|---|
| 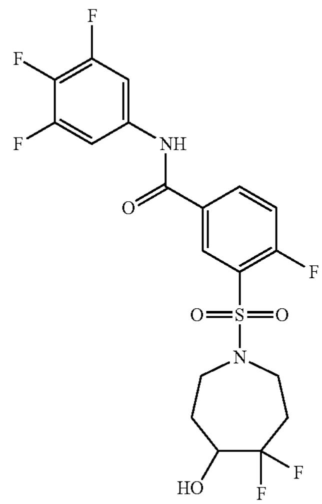 [SMILES: O=C(Nc1cc(F)c(F)c(F)c1)c1ccc(F)c(S(=O)(=O)N2CCC(O)C(F)(F)CC2)c1] | 2202 | | 483/485 | GENERAL PROCEDURE A A44B02C02 |
| 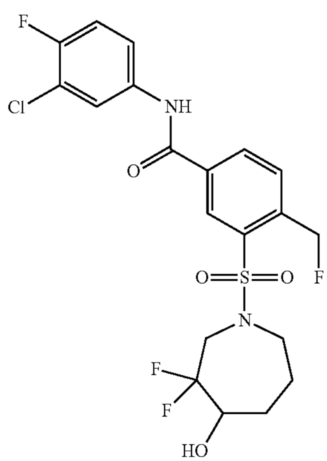 [SMILES: O=C(Nc1ccc(F)c(Cl)c1)c1ccc(CF)c(S(=O)(=O)N2CCCC(O)C(F)(F)C2)c1] | 2221 | 1H NMR (400 MHz, METHANOL-d4) δ = 8.43 (s, 1H), 8.27 (dd, J = 1.8, 8.0 Hz, 1H), 8.00 (dd, J = 2.6, 6.7 Hz, 1H), 7.92 (d, J = 8.0 Hz, 1H), 7.66 (ddd, J = 2.6, 4.1, 9.0 Hz, 1H), 7.28 (t, J = 9.0 Hz, 1H), 5.91 (s, 1H), 5.79 (s, 1H), 4.04-3.89 (m, 2H), 3.86-3.71 (m, 1H), 3.54-3.43 (m, 1H), 3.23 (ddd, J = 5.8, 7.7, 13.4 Hz, 1H), 2.10-1.72 (m, 4H) | 495/497 | GENERAL PROCEDURE A A45B05C01 |
| 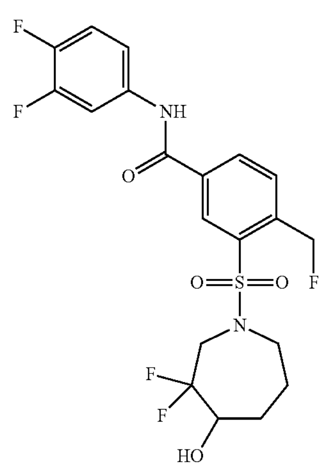 [SMILES: O=C(Nc1ccc(F)c(F)c1)c1ccc(CF)c(S(=O)(=O)N2CCCC(O)C(F)(F)C2)c1] | 2222 | | 479 | GENERAL PROCEDURE A A45B05C03 |

TABLE 1-continued

| Structure | Compound ID | ¹H NMR | MS(M + H)⁺ | Synthetic method |
|---|---|---|---|---|
| 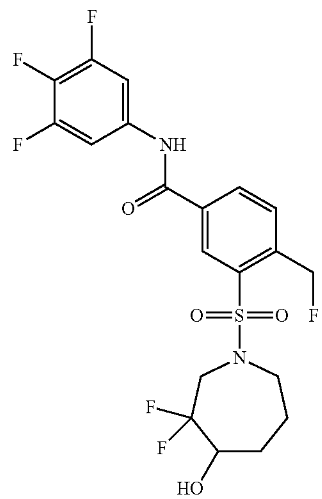 [SMILES: O=C(Nc1cc(F)c(F)c(F)c1)c1ccc(CF)c(S(=O)(=O)N2CCCC(O)C(F)(F)C2)c1] | 2223 | | 497 | GENERAL PROCEDURE A A45B05C02 |
| 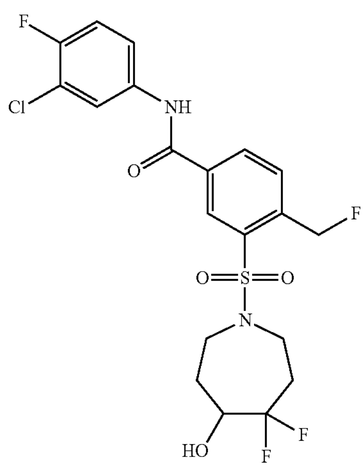 [SMILES: O=C(Nc1ccc(F)c(Cl)c1)c1ccc(CF)c(S(=O)(=O)N2CCC(O)C(F)(F)CC2)c1] | 2224 | ¹HNMR (400 MHz, METHANOL-d₄) δ = 8.38 (s, 1H), 8.23 (d, J = 8.0 Hz, 1H), 7.98 (dd, J = 2.5, 6.8 Hz, 1H), 7.89 (d, J = 8.0 Hz, 1H), 7.67-7.60 (m, 1H), 7.26 (t, J = 9.0 Hz, 1H), 5.92 (s, 1H), 5.81 (s, 1H), 4.05-3.94 (m, 1H), 3.64-3.45 (m, 4H), 2.45-2.29 (m, 1H), 2.25-2.09 (m, 1H), 2.08-1.90 (m, 2H) | 495/497 | GENERAL PROCEDURE A A44B05C01 |
| 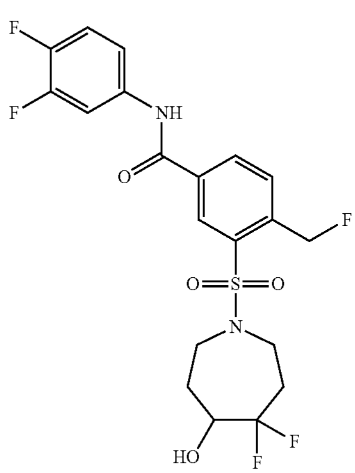 [SMILES: O=C(Nc1ccc(F)c(F)c1)c1ccc(CF)c(S(=O)(=O)N2CCC(O)C(F)(F)CC2)c1] | 2225 | | 479/481 | GENERAL PROCEDURE A A44B05C03 |

TABLE 1-continued

| Structure | Compound ID | ¹H NMR | MS(M + H)⁺ | Synthetic method |
|---|---|---|---|---|
| 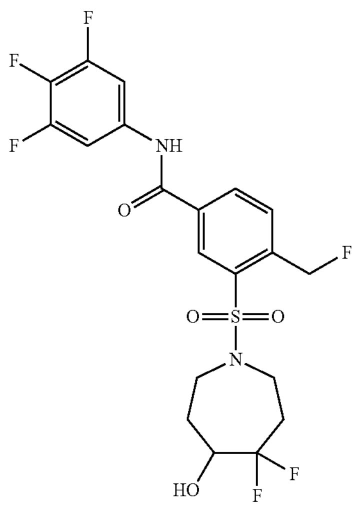 [SMILES: O=C(Nc1cc(F)c(F)c(F)c1)c1ccc(CF)c(S(=O)(=O)N2CCC(O)C(F)(F)CC2)c1] | 2226 | | 497/499 | GENERAL PROCEDURE A A44B05C02 |
| 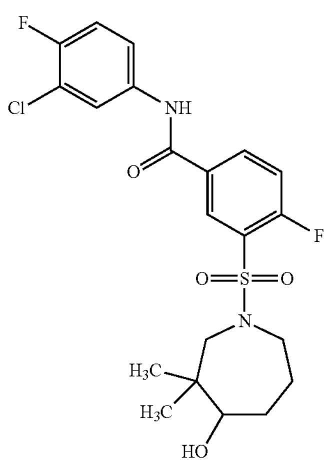 [SMILES: CC1(C)CN(S(=O)(=O)c2cc(C(=O)Nc3ccc(F)c(Cl)c3)ccc2F)CCCC1O] | 2421 | | 473/475 | GENERAL PROCEDURE A A46B02C01 |
| 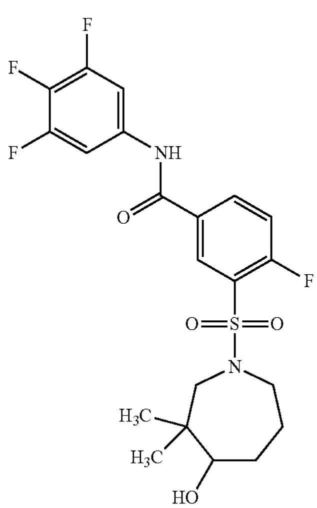 [SMILES: CC1(C)CN(S(=O)(=O)c2cc(C(=O)Nc3cc(F)c(F)c(F)c3)ccc2F)CCCC1O] | 2422 | | 475 | GENERAL PROCEDURE A A46B02C02 |

TABLE 1-continued

| Structure | Compound ID | ¹H NMR | MS(M + H)⁺ | Synthetic method |
|---|---|---|---|---|
| 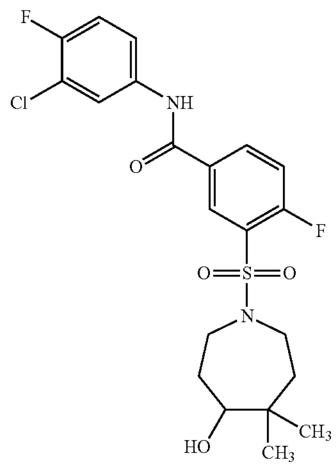 [SMILES: CC1(C)CCN(S(=O)(=O)c2cc(C(=O)Nc3ccc(F)c(Cl)c3)ccc2F)CCC1O] | 2425 | 1H NMR (400 MHz, METHANOL-d4) δ = 8.43 (dd, J = 2.3, 6.6 Hz, 1H), 8.24 (ddd, J = 2.4, 4.6, 8.6 Hz, 1H), 7.98 (dd, J = 2.6, 6.7 Hz, 1H), 7.66-7.60 (m, 1H), 7.49 (dd, J = 8.8, 9.8 Hz, 1H), 7.26 (t, J = 9.0 Hz, 1H), 3.58-3.49 (m, 1H), 3.45-3.34 (m, 4H), 2.03-1.94 (m, 1H), 1.91-1.78 (m, 2H), 1.50 (ddd, J = 4.6, 8.0, 15.3 Hz, 1H), 1.01 (d, J = 19.1 Hz, 6H) | 473/475 | GENERAL PROCEDURE A A47B02C01 |
| 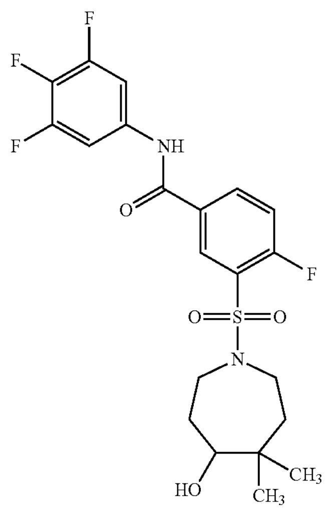 [SMILES: CC1(C)CCN(S(=O)(=O)c2cc(C(=O)Nc3cc(F)c(F)c(F)c3)ccc2F)CCC1O] | 2426 | | 475 | GENERAL PROCEDURE A A47B02C02 |
| 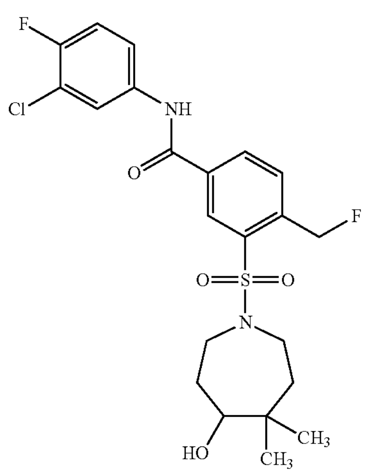 [SMILES: CC1(C)CCN(S(=O)(=O)c2cc(C(=O)Nc3ccc(F)c(Cl)c3)ccc2CF)CCC1O] | 2427 | | 487/489 | GENERAL PROCEDURE A A47B05C01 |

TABLE 1-continued

| Structure | Compound ID | ¹H NMR | MS(M + H)⁺ | Synthetic method |
|---|---|---|---|---|
| 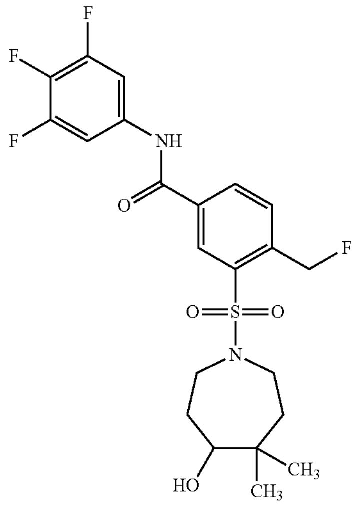 [SMILES: CC1(C)CCN(S(=O)(=O)c2cc(C(=O)Nc3cc(F)c(F)c(F)c3)ccc2CF)CCC1O] | 2428 | | 489 | GENERAL PROCEDURE A A47B05C02 |
| 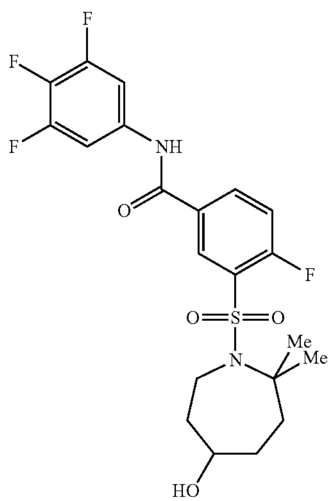 [SMILES: CC1(C)CCC(O)CCN1S(=O)(=O)c1cc(C(=O)Nc2cc(F)c(F)c(F)c2)ccc1F] | 2529 | | 475 | GENERAL PROCEDURE A A48B02C02 |
| 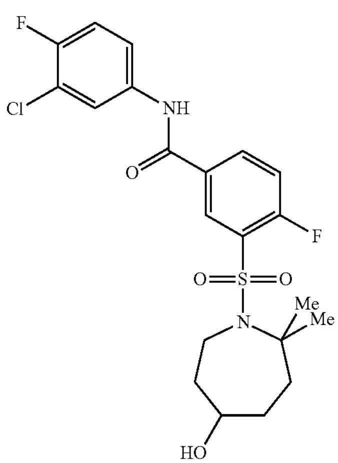 [SMILES: CC1(C)CCC(O)CCN1S(=O)(=O)c1cc(C(=O)Nc2ccc(F)c(Cl)c2)ccc1F] | 2530 | | 473/475 | GENERAL PROCEDURE A A48B02C01 |

TABLE 1-continued
| Structure | Compound ID | ¹H NMR | MS(M + H)⁺ | Synthetic method |
|---|---|---|---|---|
| 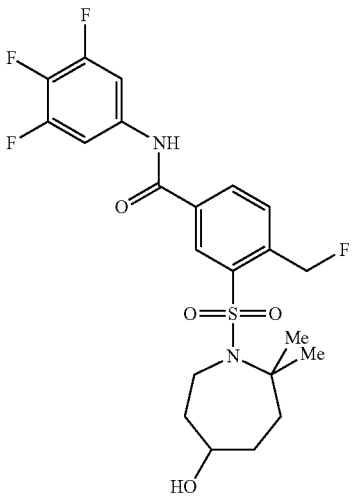 [SMILES: CC1(C)CCC(O)CCN1S(=O)(=O)c1cc(C(=O)Nc2cc(F)c(F)c(F)c2)ccc1CF] | 2531 | | 489 | GENERAL PROCEDURE A A48B05C02 |
| 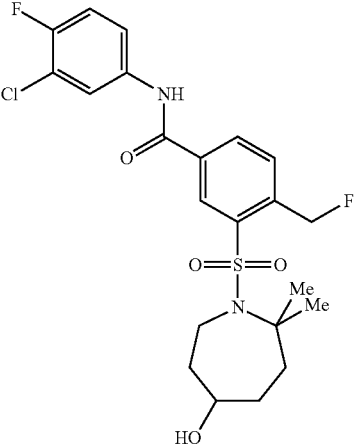 [SMILES: CC1(C)CCC(O)CCN1S(=O)(=O)c1cc(C(=O)Nc2ccc(F)c(Cl)c2)ccc1CF] | 2532 | | 487/489 | GENERAL PROCEDURE A A48B05C01 |
| 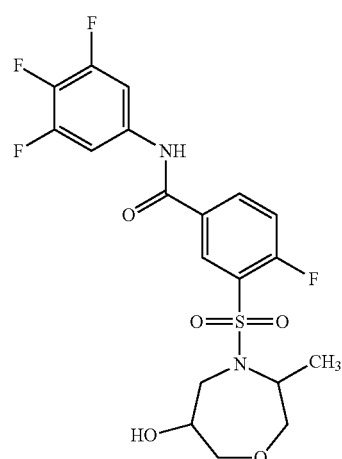 | 2537_D1 | | 463 | GENERAL PROCEDURE A A65B02C02 |

TABLE 1-continued

| Structure | Compound ID | ¹H NMR | MS(M + H)⁺ | Synthetic method |
|---|---|---|---|---|
| (structure) | 2537_D2 | | 463 | GENERAL PROCEDURE A A65B02C02 |
| (structure) | 2538_D1 | | 461 | GENERAL PROCEDURE A A65B02C01 |
| (structure) | 2538_D2 | | 461 | GENERAL PROCEDURE A A65B02C01 |

TABLE 1-continued

| Structure | Compound ID | $^1$H NMR | MS(M + H)$^+$ | Synthetic method |
|---|---|---|---|---|
| 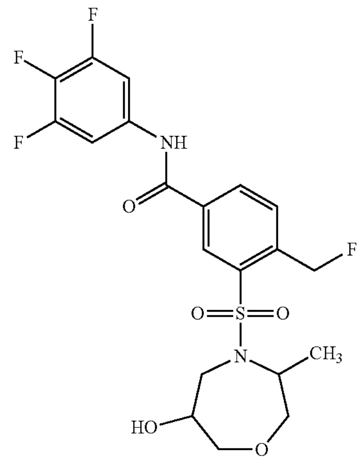 [SMILES: CC1COCC(O)CN1S(=O)(=O)c1cc(C(=O)Nc2cc(F)c(F)c(F)c2)ccc1CF] | 2539_D1 | | 477/499 | GENERAL PROCEDURE A A65B05C02 |
| 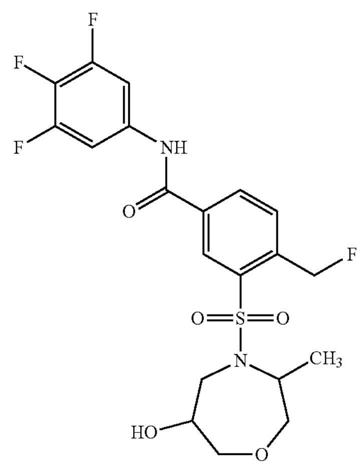 [SMILES: CC1COCC(O)CN1S(=O)(=O)c1cc(C(=O)Nc2cc(F)c(F)c(F)c2)ccc1CF] | 2539_D2 | | 477/499 | GENERAL PROCEDURE A A65B05C02 |
| 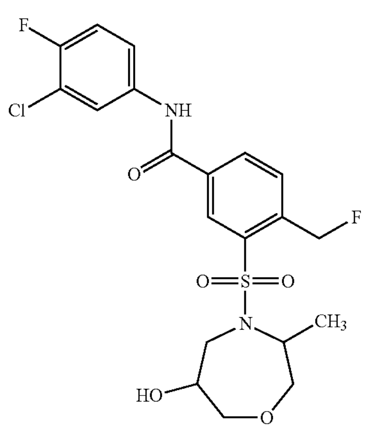 [SMILES: CC1COCC(O)CN1S(=O)(=O)c1cc(C(=O)Nc2ccc(F)c(Cl)c2)ccc1CF] | 2540_D1 | $^1$H NMR (400 MHz, MeOD) δ 8.56 (S, 1H), 8.26-8.24 (dd, 1H), 8.00-7.97 (dd, 1H), 7.91-7.89 (m, 1H), 7.66-7.62 (m, 1H), 7.28-7.24 (t, 1H), 5.93-5.92 (m, 1H), 5.81-5.80 (m, 1H), 4.19-4.14 (m, 1H), 3.97-3.91 (m, 2H), 3.78-3.67 (m, 2H), 3.48-3.39 (m, 2H), 3.29-3.23 (m, 1H), 1.04-1.03 (d, 3H). | 475 | GENERAL PROCEDURE A A65B05C01 |

TABLE 1-continued

| Structure | Compound ID | ¹H NMR | MS(M + H)⁺ | Synthetic method |
|---|---|---|---|---|
| 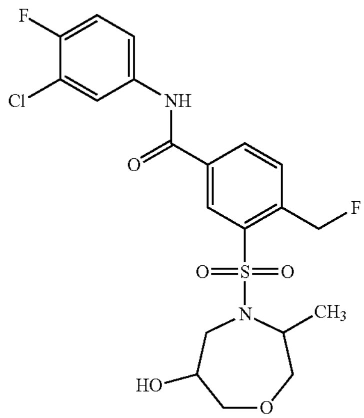 [SMILES: CC1COCC(O)CN1S(=O)(=O)c1cc(C(=O)Nc2ccc(F)c(Cl)c2)ccc1CF] | 2540_D2 | | 475 | GENERAL PROCEDURE A A65B05C01 |
| 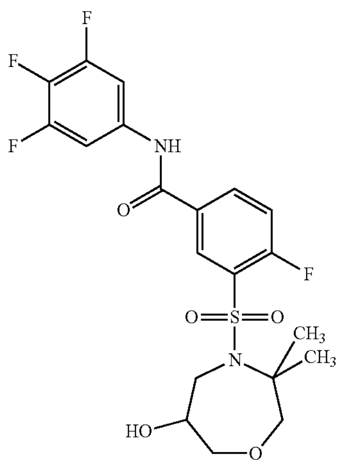 [SMILES: CC1(C)COCC(O)CN1S(=O)(=O)c1cc(C(=O)Nc2cc(F)c(F)c(F)c2)ccc1F] | 2541 | ¹H NMR (400 MHz, MeOD) δ 8.52-8.50 (dd, 1H), 8.25-8.23 (m, 1H), 7.61-7.57 (m, 2H), 7.50-7.47 (m, 1H), 3.94-3.89 (m, 3H), 3.60-3.47 (m, 4H), 1.41 (s, 3H), 1.28 (s, 3H). | 477 | GENERAL PROCEDURE A A66B02C02 |
| 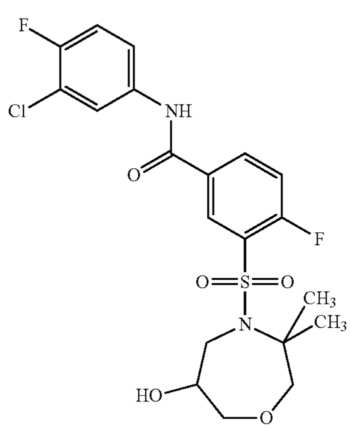 [SMILES: CC1(C)COCC(O)CN1S(=O)(=O)c1cc(C(=O)Nc2ccc(F)c(Cl)c2)ccc1F] | 2542 | ¹H NMR (400 MHz, MeOD) δ 8.53-8.51 (dd, 1H), 8.25-8.22 (m, 1H), 7.96-7.94 (m, 1H), 7.63-7.59 (m, 1H), 7.49-7.45 (t, 1H), 7.26-7.22 (t, 1H), 3.99-3.89 (m, 2H), 3.83-3.77 (m, 1H), 3.63-3.45 (m, 4H), 1.41 (s, 3H), 1.28 (s, 3H). | 475 | GENERAL PROCEDURE A A66B02C01 |

TABLE 1-continued

| Structure | Compound ID | ¹H NMR | MS(M + H)⁺ | Synthetic method |
|---|---|---|---|---|
| 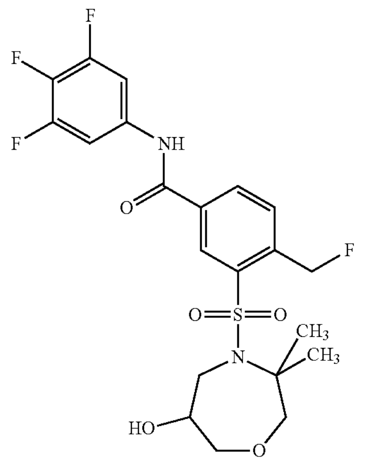 [SMILES: CC1(C)COCC(O)CN1S(=O)(=O)c1cc(C(=O)Nc2cc(F)c(F)c(F)c2)ccc1CF] | 2543 | ¹H NMR (400 MHz, MeOD) δ 8.43-8.46 (m, 1H), 8.23-8.25 (m, 1H), 7.80-7.86 (m, 1H), 7.44-7.53 (m, 2H), 7.26-7.31 (m, 1H), 4.41-4.53 (m, 1H), 3.77-3.81 (m, 1H), 3.41-3.72 (m, 4H), 1.73-2.25 (m, 4H). | 447 | GENERAL PROCEDURE A A66B05C02 |
| 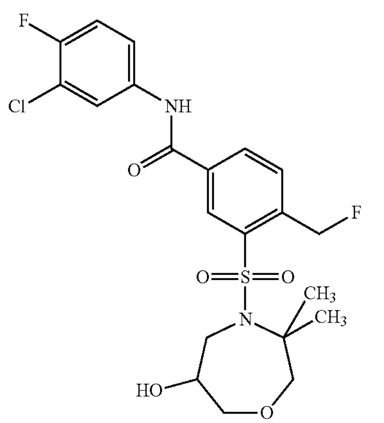 [SMILES: CC1(C)COCC(O)CN1S(=O)(=O)c1cc(C(=O)Nc2ccc(F)c(Cl)c2)ccc1CF] | 2544 | | 463/465 | GENERAL PROCEDURE A A66B05C01 |
| 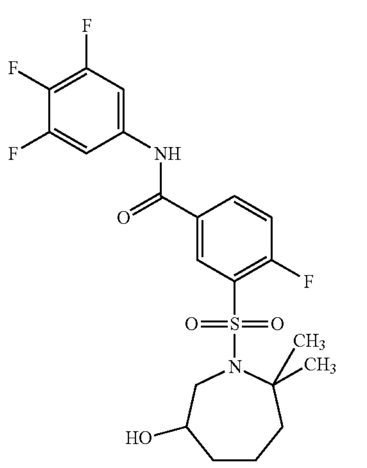 [SMILES: CC1(C)CCCC(O)CN1S(=O)(=O)c1cc(C(=O)Nc2cc(F)c(F)c(F)c2)ccc1F] | 2545 | | 475 | GENERAL PROCEDURE A A49B02C02 |

TABLE 1-continued

| Structure | Compound ID | ¹H NMR | MS(M + H)⁺ | Synthetic method |
|---|---|---|---|---|
| 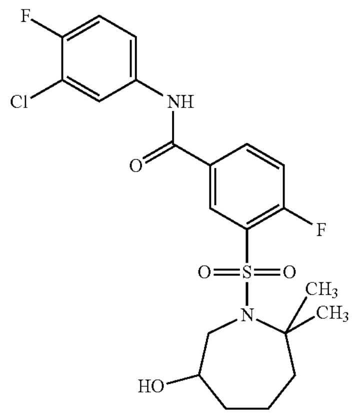 [SMILES: CC1(C)CCCC(O)CN1S(=O)(=O)c1cc(C(=O)Nc2ccc(F)c(Cl)c2)ccc1F] | 2546 | | 473/475 | GENERAL PROCEDURE A A49B02C01 |
| 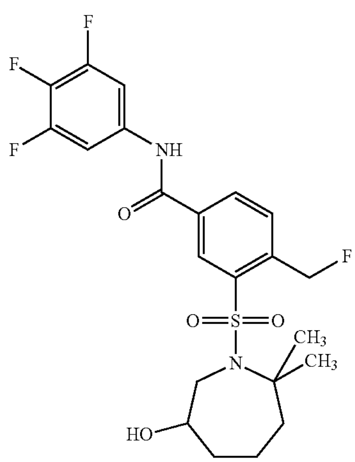 [SMILES: CC1(C)CCCC(O)CN1S(=O)(=O)c1cc(C(=O)Nc2cc(F)c(F)c(F)c2)ccc1CF] | 2535 | | 489 | GENERAL PROCEDURE A A49B05C02 |
| 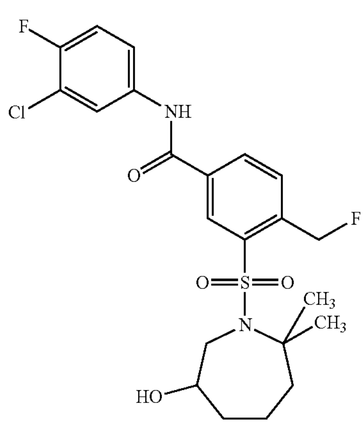 [SMILES: CC1(C)CCCC(O)CN1S(=O)(=O)c1cc(C(=O)Nc2ccc(F)c(Cl)c2)ccc1CF] | 2536 | | 487/489 | GENERAL PROCEDURE A A49B05C01 |

TABLE 1-continued

| Structure | Compound ID | ¹H NMR | MS(M + H)⁺ | Synthetic method |
|---|---|---|---|---|
| 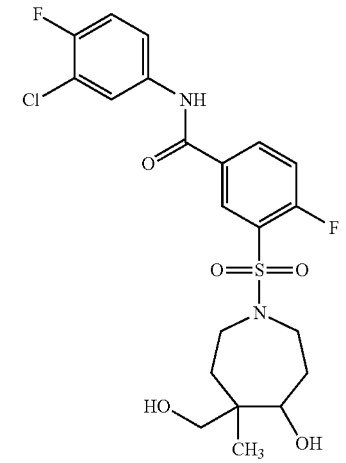 [SMILES: CC1(CO)CCN(S(=O)(=O)c2cc(C(=O)Nc3ccc(F)c(Cl)c3)ccc2F)CCC1O] | 2494_D1 | | 489/491 | GENERAL PROCEDURE A A51B02C01 |
| 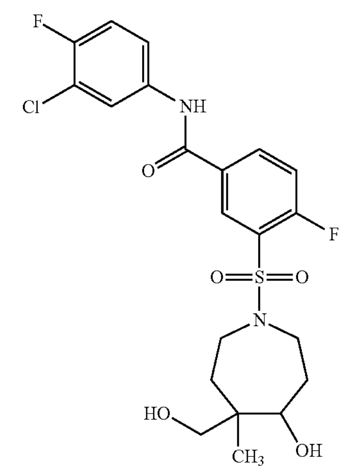 [SMILES: CC1(CO)CCN(S(=O)(=O)c2cc(C(=O)Nc3ccc(F)c(Cl)c3)ccc2F)CCC1O] | 2494_D2 | | 489/491 | GENERAL PROCEDURE A A51B02C01 |
| 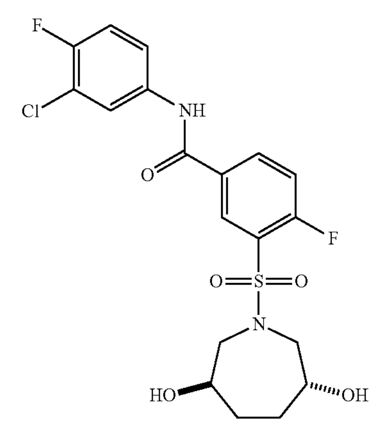 [SMILES: O=C(Nc1ccc(F)c(Cl)c1)c1ccc(F)c(S(=O)(=O)N2C[C@H](O)CC[C@@H](O)C2)c1] | 2433_D1 | ¹H NMR (400 MHz, DMSO-d$_6$) ppm 10.69 (s, 1H) 8.38 (dd, J = 6.78, 2.26 Hz, 1H), 8.30 (ddd, J = 8.66, 4.64, 2.26 Hz, 1H), 8.03 (dd, J = 6.84, 2.57 Hz, 1H), 7.65-7.73 (m, 2H), 7.44 (t, J = 9.16 Hz, 1H), 4.93 (d, J = 4.27 Hz, 2H), 3.68-3.82 (m, 4H), 2.66-2.75 (m, 2H), 1.67 (br. s., 4H). | 461/463 | GENERAL PROCEDURE A A68B02C01 Separated by Pre-HPLC for mixture |

TABLE 1-continued

| Structure | Compound ID | ¹H NMR | MS(M + H)⁺ | Synthetic method |
|---|---|---|---|---|
| 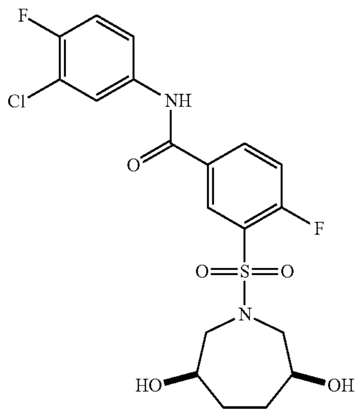 [SMILES: O=C(Nc1ccc(F)c(Cl)c1)c1ccc(F)c(S(=O)(=O)N2C[C@H](O)CC[C@H](O)C2)c1] | 2433_D2 | ¹H NMR (400 MHz, DMSO-d6) ppm 10.69 (s, 1H), 8.38 (dd, J = 6.78, 2.26 Hz, 1H), 8.30 (ddd, J = 8.66, 4.64, 2.26 Hz, 1H), 8.03 (dd, J = 6.84, 2.57 Hz, 1H), 7.65-7.73 (m, 2H), 7.44 (t, J = 9.16 Hz, 1H), 4.93 (d, J = 4.27 Hz, 2H), 3.68-3.82 (m, 4H), 2.66-2.75 (m, 2H), 1.67 (br, 4H). | 461/463 | GENERAL PROCEDURE A A68B02C01 Separated by Pre-HPLC for mixture in the first synthesis; Made from A68_Cis in the second run. |
| 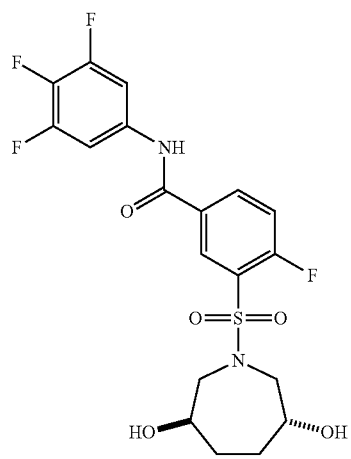 [SMILES: O=C(Nc1cc(F)c(F)c(F)c1)c1ccc(F)c(S(=O)(=O)N2C[C@H](O)CC[C@@H](O)C2)c1] | 2617_D1 | ¹H NMR (400 MHz, METHANOL-d₄) ppm 8.45 (dd, J = 6.59, 2.32 Hz, 1H), 8.24 (ddd, J = 8.66, 4.64, 2.38 Hz, 1H), 7.55-7.64 (m, 2H), 7.50 (dd, J = 10.04, 8.66 Hz, 1H), 3.92-4.01 (m, 2H), 3.87 (dd, J = 14.31, 5.90 Hz, 2H), 2.84 (dd, J = 13.80, 8.41 Hz, 2H), 1.80-1.91 (m, 4H), | 463 | GENERAL PROCEDURE A A68B02C02 Made from A68_Trans |
| 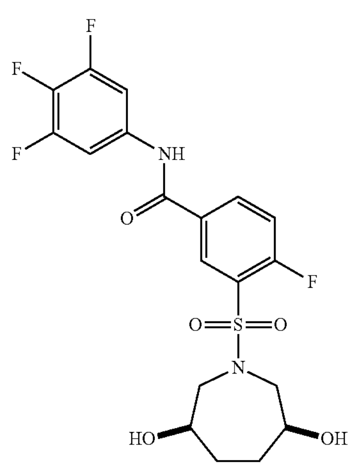 [SMILES: O=C(Nc1cc(F)c(F)c(F)c1)c1ccc(F)c(S(=O)(=O)N2C[C@H](O)CC[C@H](O)C2)c1] | 2617_D2 | ¹H NMR (400 MHz, METHANOL-d₄) ppm 8.45 (dd, J = 6.59, 2.32 Hz, 1H), 8.24 (ddd, J = 8.66, 4.64, 2.38 Hz, 1H), 7.55-7.64 (m, 2H), 7.50 (dd, J = 10.04, 8.66 Hz, 1H), 3.92-4.01 (m, 2H), 3.87 (dd, J = 14.31, 5.90 Hz, 2H), 2.84 (dd, J = 13.80, 8.41 Hz, 2H), 1.80-1.91 (m, 4H), | 463 | GENERAL PROCEDURE A A68B02C02 Made from A68_Cis |

TABLE 1-continued

| Structure | Compound ID | ¹H NMR | MS(M + H)+ | Synthetic method |
|---|---|---|---|---|
| 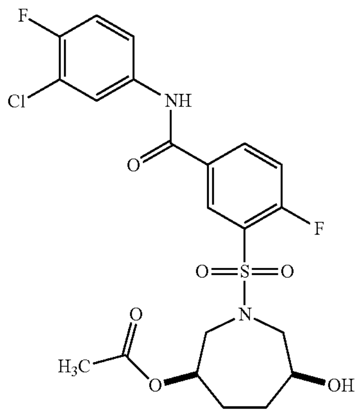 [SMILES: CC(=O)O[C@@H]1CC[C@H](O)CN(S(=O)(=O)c2cc(C(=O)Nc3ccc(F)c(Cl)c3)ccc2F)C1] | 2619_D2 | ¹H NMR (400 MHz, DMSO-d$_6$) ppm 10.69 (s, 1H) 8.38 (dd, J = 6.78, 2.26 Hz, 1H) 8.27-8.34 (m, 1H) 8.04 (dd, J = 6.90, 2.51 Hz, 1H) 7.66-7.74 (m, 2H) 7.44 (t, J = 9.10 Hz, 1H) 4.99 (d, J = 4.27 Hz, 1H) 4.90 (br. s., 1H) 3.67-3.80 (m, 2H) 3.59 (dd, J = 13.80, 5.27 Hz, 1H) 3.20 (dd, J = 14.68, 7.03 Hz, 1H) 2.94 (dd, J = 13.80, 8.03 Hz, 1H) 1.81-1.93 (m, 1H) 1.66-1.78 (m, 3H) | 503/505 | GENERAL PROCEDURE H A67B02C01 Made from 2433_D2 |
| 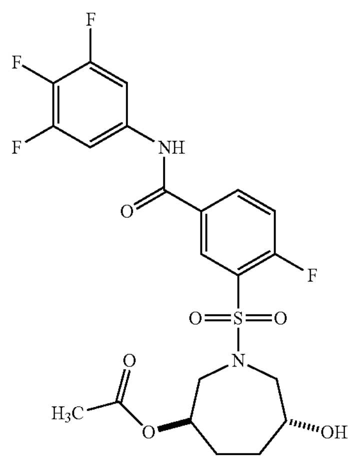 [SMILES: CC(=O)O[C@@H]1CC[C@@H](O)CN(S(=O)(=O)c2cc(C(=O)Nc3cc(F)c(F)c(F)c3)ccc2F)C1] | 2618_D1 | ¹H NMR (400 MHz, DMSO-d$_6$) ppm 10.82 (s, 1H), 8.37 (dd, J = 6.65, 2.26 Hz, 1H), 8.30 (ddd, J = 8.56, 4.61, 2.38 Hz, 1H), 7.65-7.75 (m, 3H), 4.96 (d, J = 4.14 Hz, 1H), 4.85 (dd, J = 7.15, 4.02 Hz, 1H), 3.81 (br, 1H), 3.72 (dd, J = 14.87, 3.70 Hz, 1H), 3.61 (dd, J = 13.87, 5.33 Hz, 1H), 3.40 (dd, J = 15.12, 3.95 Hz, 1H), 2.79 (dd, J = 14.05, 8.16 Hz, 1H), 1.86-2.04 (m, 5H), 1.41-1.62 (m, 2H). | 505 | GENERAL PROCEDURE H A67B02C02 Made from 2617_D1 |
| 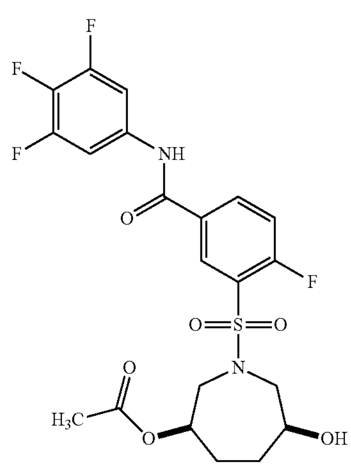 [SMILES: CC(=O)O[C@@H]1CC[C@H](O)CN(S(=O)(=O)c2cc(C(=O)Nc3cc(F)c(F)c(F)c3)ccc2F)C1] | 2618_D2 | ¹H NMR (400 MHz, METHANOL-d$_4$) ppm 8.45 (dd, J = 6.65, 2.26 Hz, 1H), 8.24 (ddd, J = 8.66, 4.64, 2.38 Hz, 1H), 7.54-7.64 (m, 2H) 7.50 (dd, J = 9.91, 8.78 Hz, 1H), 4.99-5.08 (m, 1H), 3.88-3.97 (m, 1H) 3.76 (td, J = 15.25, 5.40 Hz, 2H), 3.27 (d, J = 6.65 Hz, 1H), 3.05 (dd, J = 14.18, 7.78 Hz, 1H), 1.95-2.08 (m, 4H), 1.80-1.92 (m, 3H). | 505 | GENERAL PROCEDURE H A67B02C02 Made from 2617_D2 |

TABLE 1-continued

| Structure | Compound ID | ¹H NMR | MS(M + H)⁺ | Synthetic method |
|---|---|---|---|---|
| 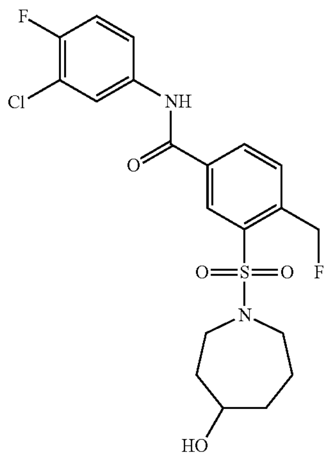 [SMILES: O=C(Nc1ccc(F)c(Cl)c1)c1ccc(CF)c(S(=O)(=O)N2CCCC(O)CC2)c1] | 1916 | | 459/461 | GENERAL PROCEDURE A A02B05C01 |
| 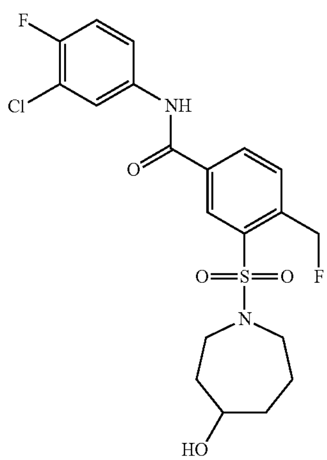 [SMILES: O=C(Nc1ccc(F)c(Cl)c1)c1ccc(CF)c(S(=O)(=O)N2CCCC(O)CC2)c1] | 1819 | | 459/461 | GENERAL PROCEDURE A A02B05C01 |
| 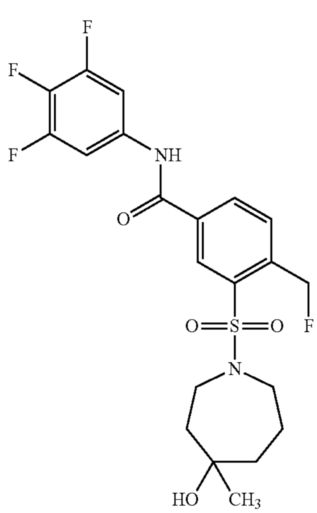 [SMILES: CC1(O)CCCN(S(=O)(=O)c2cc(C(=O)Nc3cc(F)c(F)c(F)c3)ccc2CF)CC1] | 1829-2 | | 475 | GENERAL PROCEDURE A A06B05C02 |

TABLE 1-continued

| Structure | Compound ID | $^1$H NMR | MS(M + H)$^+$ | Synthetic method |
|---|---|---|---|---|
| 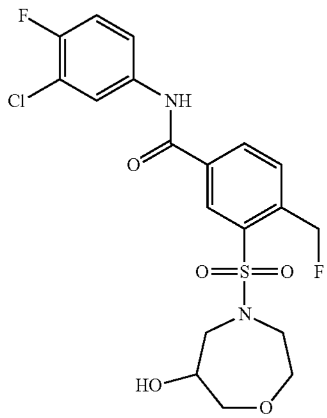 [SMILES: O=C(Nc1ccc(F)c(Cl)c1)c1ccc(CF)c(S(=O)(=O)N2CCOCC(O)C2)c1] | 1983 | | 461/463 | GENERAL PROCEDURE A A13B05C01 |
| 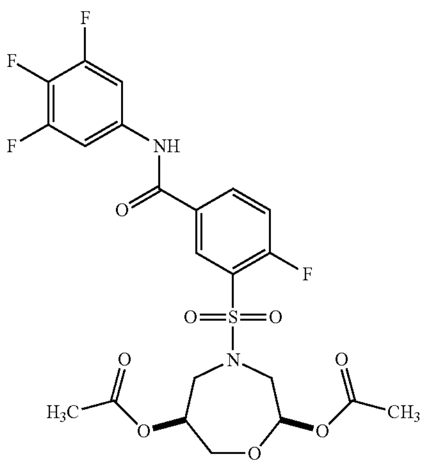 [SMILES: CC(=O)O[C@@H]1CO[C@H](OC(C)=O)CN(S(=O)(=O)c2cc(C(=O)Nc3cc(F)c(F)c(F)c3)ccc2F)C1] | 2625_D2 | $^1$H NMR (400 MHz, DMSO-d$_6$) ppm 10.80 (s, 1H) 8.26-8.37 (m, 2H) 7.65-7.76 (m, 3H) 4.89 (d, J = 3.89 Hz, 2H) 3.54-3.63 (m, 2H) 3.43-3.51 (m, 2H) 1.86-2.04 (m, 8H) 1.73-1.85 (m, 2H) | 547.1 | GENERAL PROCEDURE H A68B02C02 Made from 2617_D2 |
| 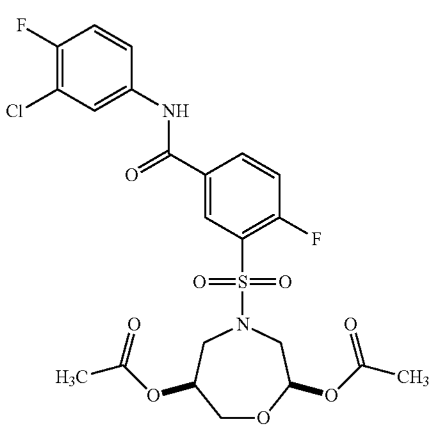 [SMILES: CC(=O)O[C@@H]1CO[C@H](OC(C)=O)CN(S(=O)(=O)c2cc(C(=O)Nc3ccc(F)c(Cl)c3)ccc2F)C1] | 2626_D2 | $^1$H NMR (400 MHz, DMSO-d6) ppm 10.70 (s, 1H), 8.39-8.27 (m, 2H), 8.04 (dd, J = 2.5, 6.8 Hz, 1H), 7.74-7.66 (m, 2H), 7.44 (t, J = 9.1 Hz, 1H), 4.89 (d, J = 4.0 Hz, 2H), 3.63-3.53 (m, 2H), 3.51-3.42 (m, 2H), 2.05-1.86 (m, 8H), 1.86-1.73 (m, 2H) | 545.1/547.1 | GENERAL PROCEDURE H A68B02C01 Made from 2433_D2 |

TABLE 1-continued

| Structure | Compound ID | ¹H NMR | MS(M + H)⁺ | Synthetic method |
|---|---|---|---|---|
| 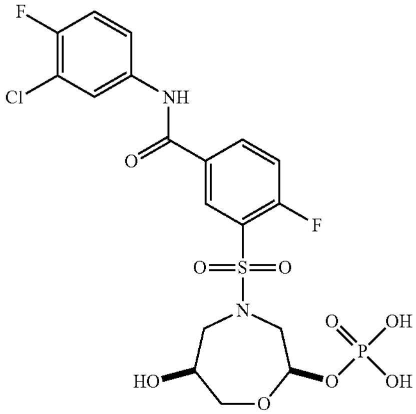 [SMILES: O=C(Nc1ccc(F)c(Cl)c1)c1ccc(F)c(S(=O)(=O)N2C[C@H](O)CO[C@H](OP(=O)(O)O)C2)c1] | 2632 | ¹H NMR (400 MHz, MeOD) δ 8.49 (dd, J = 6.65, 2.13 Hz, 1H), 8.21-8.31 (m, 1H), 8.02 (dd, J = 6.65, 2.64 Hz, 1H), 7.61-7.70 (m, 1H), 7.52 (t, J = 9.29 Hz, 1H), 7.27 (t, J = 8.91 Hz, 1H), 4.58 (br. s., 1H), 3.87-4.13 (m, 3H), 3.03 (dd, J = 14.56, 7.78 Hz, 1H), 2.88 (dd, J = 13.80, 9.03 Hz, 1H), 2.10 (dd, J = 11.67, 6.15 Hz, 1H), 1.80-2.01 (m, 3H) | 541/543 | GENERAL PROCEDURE I A68B02C01 Made from 2433_D2 |
| | 2634 | ¹H NMR (400 MHz, MeOD) δ 9.14 (s, 1H), 8.51 (d, J = 4.52 Hz, 1H), 8.23 (brs, 1H), 8.04 (dd, J = 6.59, 2.45 Hz, 1H), 7.63-7.75 (m, 1H), 7.50 (t, J = 9.32 Hz, 1H), 7.25 (t, J = 8.95 Hz, 1H), 4.49 (brs, 1H), 3.79-4.07 (m, 5H), 3.70 (t, J = 8.85 Hz, 1H), 3.34-3.47 (m, 2H) | 527/529 | GENERAL PROCEDURE I A13B02C01 Made from 1893 | or pharmaceutically acceptable salts thereof.

In yet another embodiment of Formula I provided herein, the compound of Formula V, or a pharmaceutically acceptable salt thereof, is selected from:

TABLE 2

1763_E1

TABLE 2-continued

1763_E2

TABLE 2-continued
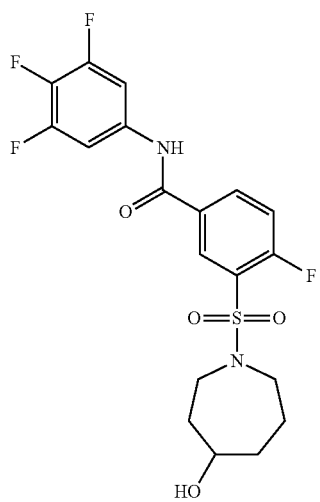 [SMILES: O=C(Nc1cc(F)c(F)c(F)c1)c1ccc(F)c(S(=O)(=O)N2CCCC(O)CC2)c1]
1765
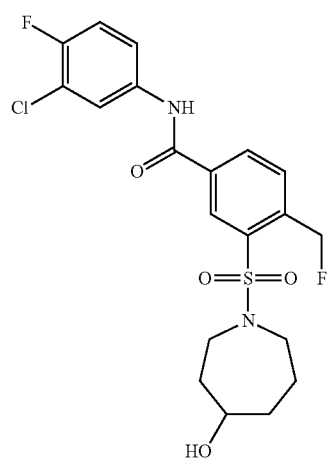
1819
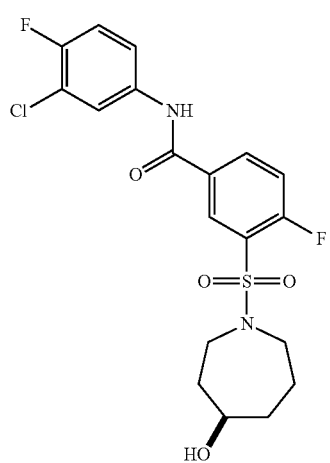 [SMILES: O=C(Nc1ccc(F)c(Cl)c1)c1ccc(F)c(S(=O)(=O)N2CCC[C@@H](O)CC2)c1]
1766_E1
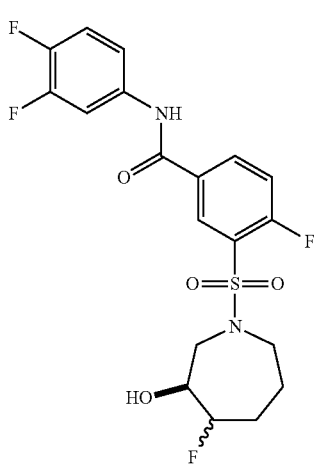
1821_D1
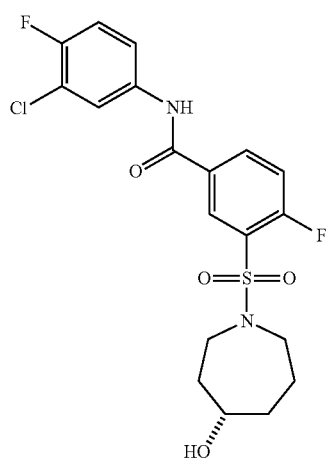 [SMILES: O=C(Nc1ccc(F)c(Cl)c1)c1ccc(F)c(S(=O)(=O)N2CCC[C@H](O)CC2)c1]
1766_E2
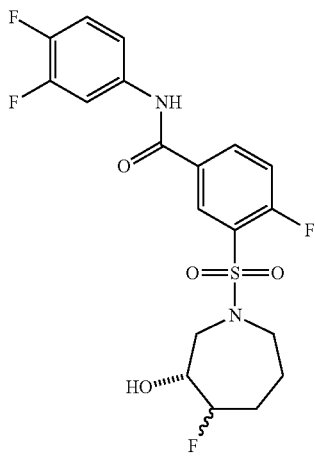 [SMILES: O=C(Nc1ccc(F)c(F)c1)c1ccc(F)c(S(=O)(=O)N2CCCC(F)[C@H](O)C2)c1]
1821_D2

TABLE 2-continued
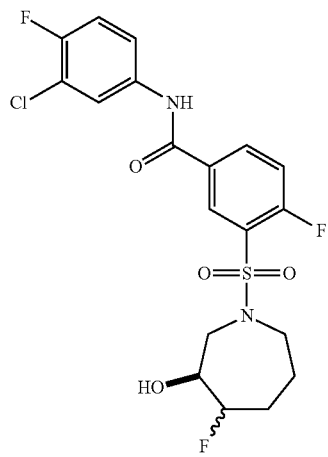 [SMILES: O=C(Nc1ccc(F)c(Cl)c1)c1ccc(F)c(S(=O)(=O)N2CCCC(F)[C@@H](O)C2)c1]
1822_D1
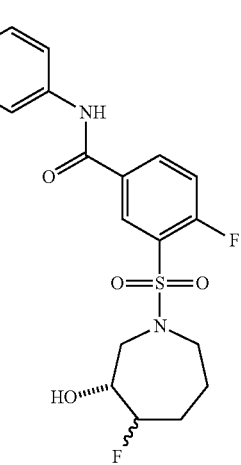
1822_D2
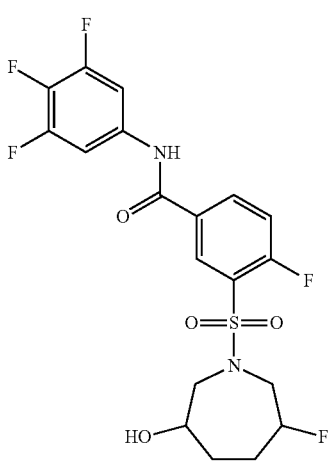 [SMILES: O=C(Nc1cc(F)c(F)c(F)c1)c1ccc(F)c(S(=O)(=O)N2CC(O)CCC(F)C2)c1]
1826_D2
TABLE 2-continued
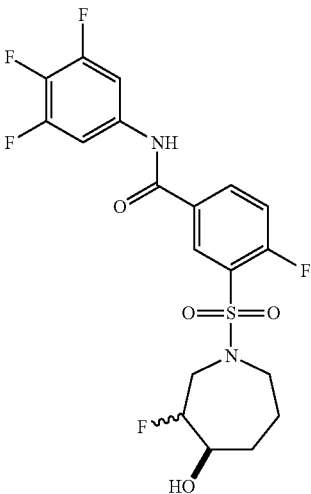 [SMILES: O=C(Nc1cc(F)c(F)c(F)c1)c1ccc(F)c(S(=O)(=O)N2CCC[C@@H](O)C(F)C2)c1]
1829_D1
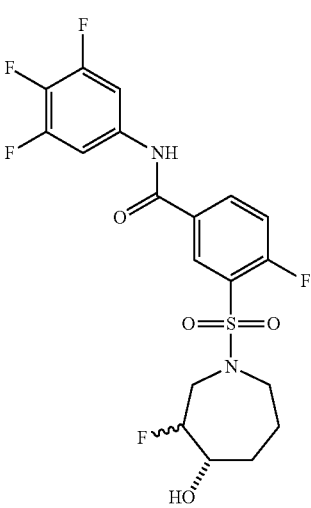 [SMILES: O=C(Nc1cc(F)c(F)c(F)c1)c1ccc(F)c(S(=O)(=O)N2CCC[C@H](O)C(F)C2)c1]
1829_D2
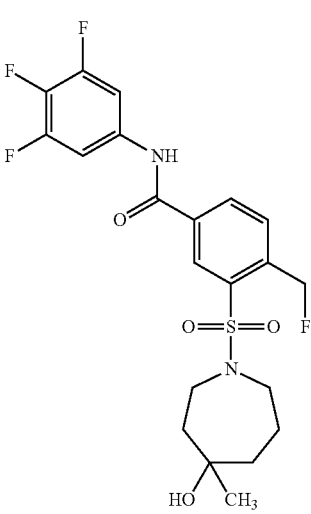 [SMILES: CC1(O)CCCN(S(=O)(=O)c2cc(C(=O)Nc3cc(F)c(F)c(F)c3)ccc2CF)CC1]
1829-2

TABLE 2-continued
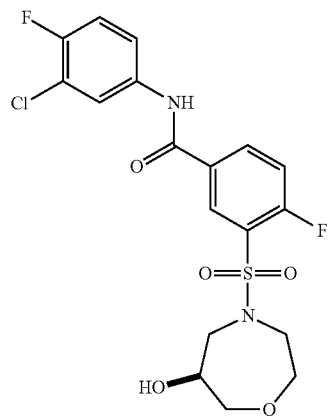 [SMILES: O=C(Nc1ccc(F)c(Cl)c1)c1ccc(F)c(S(=O)(=O)N2CCOC[C@@H](O)C2)c1]
1893_E1
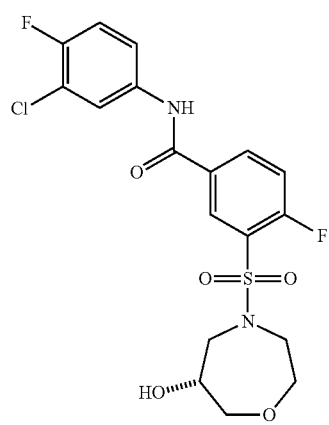 [SMILES: O=C(Nc1ccc(F)c(Cl)c1)c1ccc(F)c(S(=O)(=O)N2CCOC[C@H](O)C2)c1]
1893_E2
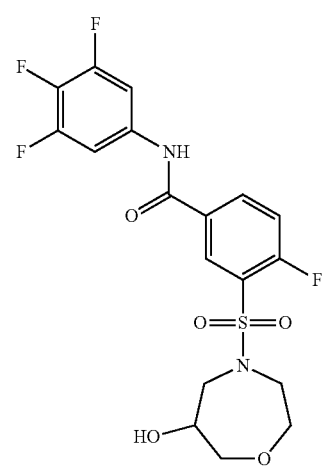 [SMILES: O=C(Nc1cc(F)c(F)c(F)c1)c1ccc(F)c(S(=O)(=O)N2CCOCC(O)C2)c1]
1895
TABLE 2-continued
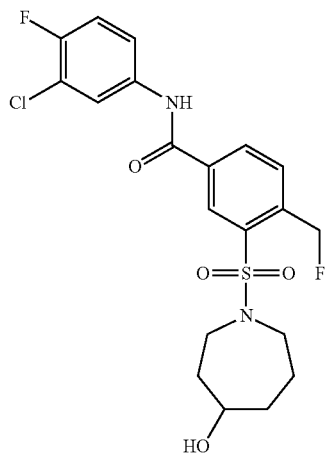 [SMILES: O=C(Nc1ccc(F)c(Cl)c1)c1ccc(CF)c(S(=O)(=O)N2CCCC(O)CC2)c1]
1916
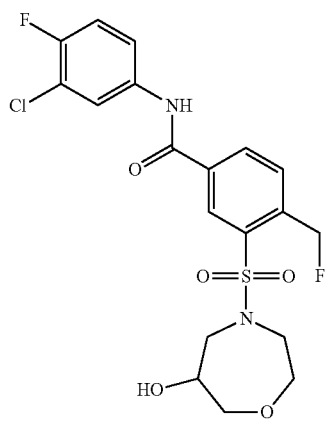 [SMILES: O=C(Nc1ccc(F)c(Cl)c1)c1ccc(CF)c(S(=O)(=O)N2CCOCC(O)C2)c1]
1983
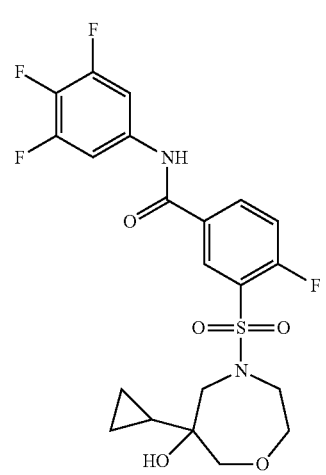 [SMILES: O=C(Nc1cc(F)c(F)c(F)c1)c1ccc(F)c(S(=O)(=O)N2CCOCC(O)(C3CC3)C2)c1]
1987

TABLE 2-continued
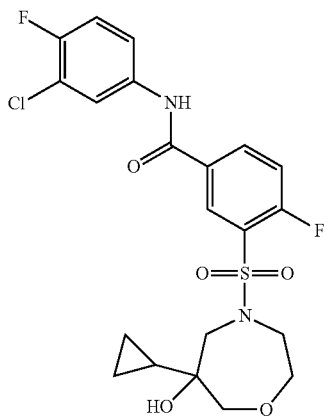 [SMILES: O=C(Nc1ccc(F)c(Cl)c1)c1ccc(F)c(S(=O)(=O)N2CCOCC(O)(C3CC3)C2)c1]
1989
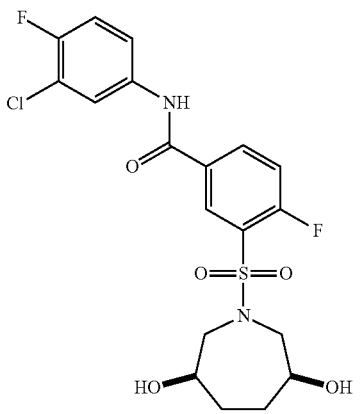
2433_D2
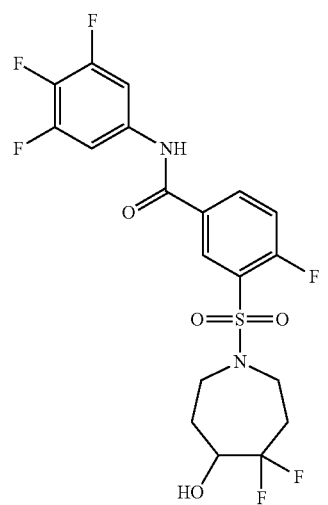 [SMILES: O=C(Nc1cc(F)c(F)c(F)c1)c1ccc(F)c(S(=O)(=O)N2CCC(O)C(F)(F)CC2)c1]
2202
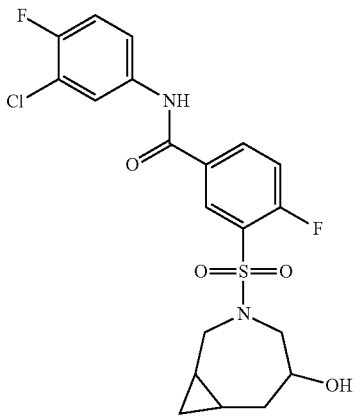 [SMILES: O=C(Nc1ccc(F)c(Cl)c1)c1ccc(F)c(S(=O)(=O)N2CC(O)CC3CC3C2)c1]
2492
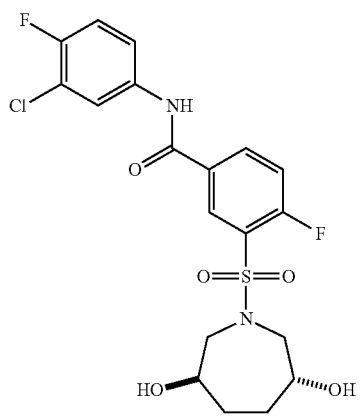
2433_D1
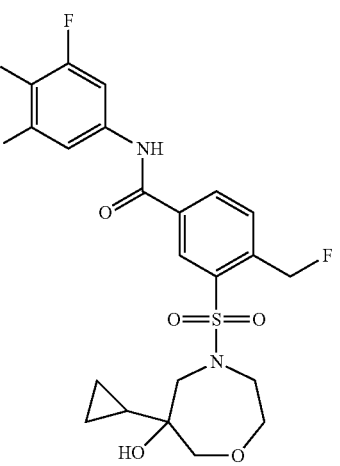
2505

TABLE 2-continued
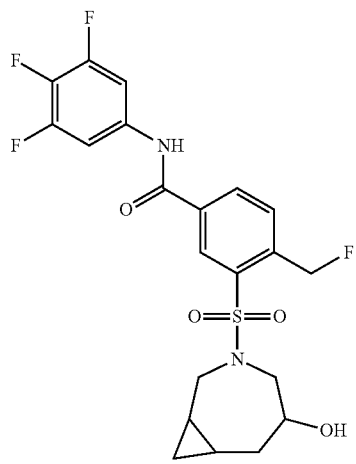 [SMILES: O=C(Nc1cc(F)c(F)c(F)c1)c1ccc(CF)c(S(=O)(=O)N2CC(O)CC3CC3C2)c1]
2550
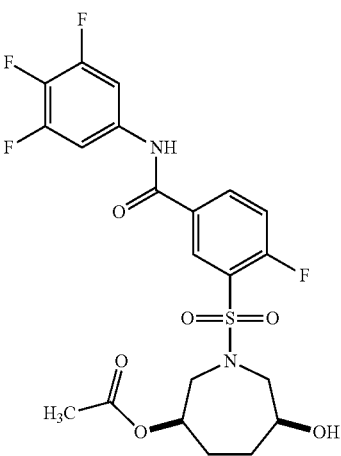
2618_D2
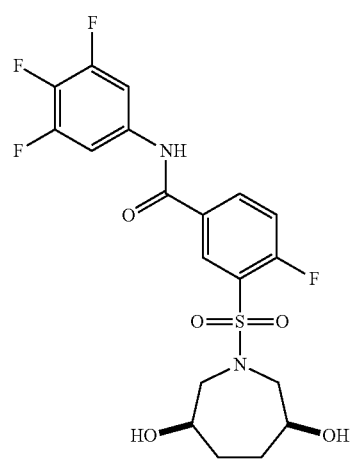
2617_D2
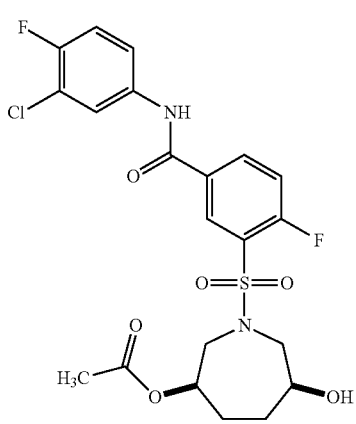
2619_D2
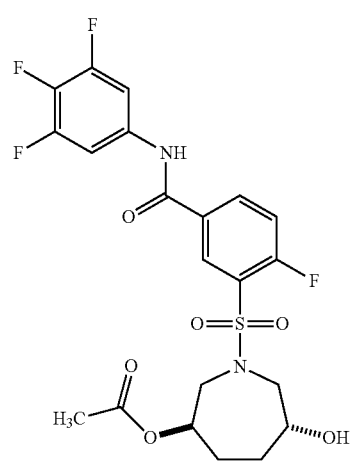
2618_D1
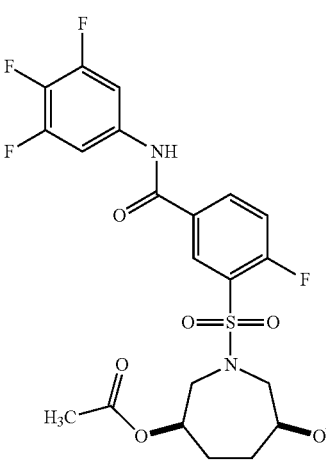
2625_D2

TABLE 2-continued

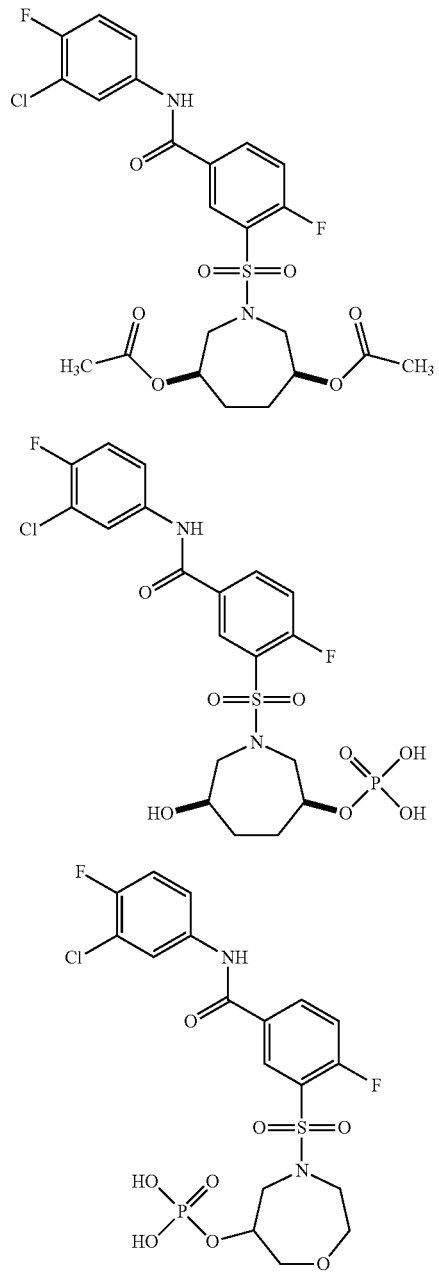

or pharmaceutically acceptable salts thereof.

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

In one embodiment, the compounds of the invention may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

Methods of the Invention

The invention provides a method of treating an HBV infection in an individual in need thereof, comprising administering to the individual a therapeutically effective amount of a compound of the invention.

The invention also provides a method of eradicating an HBV infection in an individual in need thereof, comprising administering to the individual a therapeutically effective amount of a compound of the invention.

The invention also provides a method of reducing viral load associated with an HBV infection in an individual in need thereof, comprising administering to the individual a therapeutically effective amount of a compound of the invention.

The invention further provides a method of reducing reoccurrence of an HBV infection in an individual in need thereof, comprising administering to the individual a therapeutically effective amount of a compound of the invention.

The invention also provides a method of reducing an adverse physiological impact of an HBV infection in an individual in need thereof, comprising administering to the individual a therapeutically effective amount of a compound of the invention.

The invention further provides a method of reducing, slowing, or inhibiting an HBV infection in an individual in need thereof, comprising administering to the individual a therapeutically effective amount of a compound of the invention.

The invention also provides a method of inducing remission of hepatic injury from an HBV infection in an individual in need thereof, comprising administering to the individual a therapeutically effective amount of a compound of the invention.

The invention further provides a method of reducing the physiological impact of long-term antiviral therapy for HBV infection in an individual in need thereof, comprising administering to the individual a therapeutically effective amount of a compound of the invention.

The invention further provides a method of prophylactically treating an HBV infection in an individual in need thereof, wherein the individual is afflicted with a latent HBV infection, comprising administering to the individual a therapeutically effective amount of a compound of the invention.

In one embodiment, the methods described herein further comprise administering at least one additional therapeutic agent selected from the group consisting of nucleotide/nucleoside analogs, entry inhibitors, fusion inhibitors, and any combination of these or other antiviral mechanisms. In another embodiment, the compound of the invention and the at least one additional therapeutic agent are co-formulated. In yet another embodiment, the compound of the invention and the at least one additional therapeutic agent are co-administered.

In one embodiment, the individual is refractory to other therapeutic classes of HBV drugs (e.g, HBV polymerase inhibitors, interferons, viral entry inhibitors, viral maturation inhibitors, literature-described capsid assembly modulators, antiviral compounds of distinct or unknown mechanism, and the like, or combinations thereof). In another embodiment, the method of the invention reduces viral load in an individual suffering from an HBV infection to a greater extent or at a faster rate compared to the extent that other therapeutic classes of HBV drugs reduce viral load in the individual.

In one embodiment, the administering of a compound of the invention, or a pharmaceutically acceptable salt thereof, allows for administering of the at least one additional therapeutic agent at a lower dose or frequency as compared to the administering of the at least one additional therapeutic agent alone that is required to achieve similar results in prophylactically treating an HBV infection in an individual in need thereof.

In one embodiment, the administering of a compound of the invention, or a pharmaceutically acceptable salt thereof, reduces the viral load in the individual to a greater extent or at a faster rate compared to the administering of a compound selected from the group consisting of a HBV polymerase inhibitor, interferon, viral entry inhibitor, viral maturation inhibitor, distinct capsid assembly modulator, antiviral compounds of distinct or unknown mechanism, and any combination thereof.

In one embodiment, the method of the invention reduces viral load in an individual suffering from an HBV infection, thus allowing lower doses or varying regimens of combination therapies to be used.

In one embodiment, the method of the invention causes a lower incidence of viral mutation and/or viral resistance compared to other classes of HBV drugs, thereby allowing for long term therapy and minimizing the need for changes in treatment regimens.

In one embodiment, the administering of a compound the invention, or a pharmaceutically acceptable salt thereof, causes a lower incidence of viral mutation and/or viral resistance than the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In one embodiment, the method of the invention increases the seroconversion rate beyond that of current treatment regimens.

In one embodiment, the method of the invention increases and/or normalizes and/or restores normal health, elicits full recovery of normal health, restores life expectancy, and/or resolves the viral infection in the individual in need thereof.

In one embodiment, the method of the invention eradicates HBV from an individual infected with HBV, thereby obviating the need for long term and/or life-long treatment, or shortening the duration of treatment, and/or allowing for reduction in dosing of other antiviral agents.

In another embodiment, the method of the invention further comprises monitoring the HBV viral load of the subject, and wherein the method is carried out for a period of time such that the HBV virus is undetectable.

Accordingly, in one embodiment, provided herein is a method of treating an HBV infection in an individual in need thereof, comprising administering to the individual a therapeutically effective amount of a compound of Formula I, or a pharmaceutically acceptable salt thereof.

In another embodiment, provided herein is a method of treating an HBV infection in an individual in need thereof, comprising administering to the individual a therapeutically effective amount of compound of Formula II, or a pharmaceutically acceptable salt thereof.

In another embodiment, provided herein is a method of treating an HBV infection in an individual in need thereof, comprising administering to the individual a therapeutically effective amount of compound of Formula III, or a pharmaceutically acceptable salt thereof.

In another embodiment, provided herein is a method of treating an HBV infection in an individual in need thereof, comprising administering to the individual a therapeutically effective amount of compound of Formula IV, or a pharmaceutically acceptable salt thereof.

In another embodiment, provided herein is a method of treating an HBV infection in an individual in need thereof, comprising administering to the individual a therapeutically effective amount of compound of Formula V, or a pharmaceutically acceptable salt thereof.

In another embodiment, provided herein is a method of treating an HBV infection in an individual in need thereof, comprising administering to the individual a therapeutically effective amount of compound 1763_E1, or a pharmaceutically acceptable salt thereof.

In another embodiment, provided herein is a method of treating an HBV infection in an individual in need thereof, comprising administering to the individual a therapeutically effective amount of compound 1763_E2, or a pharmaceutically acceptable salt thereof.

In another embodiment, provided herein is a method of treating an HBV infection in an individual in need thereof, comprising administering to the individual a therapeutically effective amount of compound 1765, or a pharmaceutically acceptable salt thereof.

In another embodiment, provided herein is a method of treating an HBV infection in an individual in need thereof, comprising administering to the individual a therapeutically effective amount of compound 1766_E1, or a pharmaceutically acceptable salt thereof.

In another embodiment, provided herein is a method of treating an HBV infection in an individual in need thereof, comprising administering to the individual a therapeutically effective amount of compound 1766_E2, or a pharmaceutically acceptable salt thereof.

In another embodiment, provided herein is a method of treating an HBV infection in an individual in need thereof, comprising administering to the individual a therapeutically effective amount of compound 1768, or a pharmaceutically acceptable salt thereof.

In another embodiment, provided herein is a method of treating an HBV infection in an individual in need thereof, comprising administering to the individual a therapeutically effective amount of compound 1769, or a pharmaceutically acceptable salt thereof.

In another embodiment, provided herein is a method of treating an HBV infection in an individual in need thereof, comprising administering to the individual a therapeutically effective amount of compound 1819, or a pharmaceutically acceptable salt thereof.

In another embodiment, provided herein is a method of treating an HBV infection in an individual in need thereof, comprising administering to the individual a therapeutically effective amount of compound 1820, or a pharmaceutically acceptable salt thereof.

In another embodiment, provided herein is a method of treating an HBV infection in an individual in need thereof, comprising administering to the individual a therapeutically effective amount of compound 1821, or a pharmaceutically acceptable salt thereof.

In another embodiment, provided herein is a method of treating an HBV infection in an individual in need thereof, comprising administering to the individual a therapeutically effective amount of compound 1821_D1, or a pharmaceutically acceptable salt thereof.

In another embodiment, provided herein is a method of treating an HBV infection in an individual in need thereof, comprising administering to the individual a therapeutically effective amount of compound 1821_D2, or a pharmaceutically acceptable salt thereof.

In another embodiment, provided herein is a method of treating an HBV infection in an individual in need thereof, comprising administering to the individual a therapeutically effective amount of compound 1822_D1, or a pharmaceutically acceptable salt thereof.

In another embodiment, provided herein is a method of treating an HBV infection in an individual in need thereof, comprising administering to the individual a therapeutically effective amount of compound 1822_D2, or a pharmaceutically acceptable salt thereof.

In another embodiment, provided herein is a method of treating an HBV infection in an individual in need thereof, comprising administering to the individual a therapeutically effective amount of compound 1826_D2, or a pharmaceutically acceptable salt thereof.

In another embodiment, provided herein is a method of treating an HBV infection in an individual in need thereof, comprising administering to the individual a therapeutically effective amount of compound 1829_D1, or a pharmaceutically acceptable salt thereof.

In another embodiment, provided herein is a method of treating an HBV infection in an individual in need thereof, comprising administering to the individual a therapeutically effective amount of compound 1829_D2, or a pharmaceutically acceptable salt thereof.

In another embodiment, provided herein is a method of treating an HBV infection in an individual in need thereof, comprising administering to the individual a therapeutically effective amount of compound 1829-2, or a pharmaceutically acceptable salt thereof.

In another embodiment, provided herein is a method of treating an HBV infection in an individual in need thereof, comprising administering to the individual a therapeutically effective amount of compound 1890, or a pharmaceutically acceptable salt thereof.

In another embodiment, provided herein is a method of treating an HBV infection in an individual in need thereof, comprising administering to the individual a therapeutically effective amount of compound 1891, or a pharmaceutically acceptable salt thereof.

In another embodiment, provided herein is a method of treating an HBV infection in an individual in need thereof, comprising administering to the individual a therapeutically effective amount of compound 1892, or a pharmaceutically acceptable salt thereof.

In another embodiment, provided herein is a method of treating an HBV infection in an individual in need thereof, comprising administering to the individual a therapeutically effective amount of compound 1893, or a pharmaceutically acceptable salt thereof.

In another embodiment, provided herein is a method of treating an HBV infection in an individual in need thereof, comprising administering to the individual a therapeutically effective amount of compound 1893_E1, or a pharmaceutically acceptable salt thereof.

In another embodiment, provided herein is a method of treating an HBV infection in an individual in need thereof, comprising administering to the individual a therapeutically effective amount of compound 1893_E2, or a pharmaceutically acceptable salt thereof.

In another embodiment, provided herein is a method of treating an HBV infection in an individual in need thereof, comprising administering to the individual a therapeutically effective amount of compound 1894, or a pharmaceutically acceptable salt thereof.

In another embodiment, provided herein is a method of treating an HBV infection in an individual in need thereof, comprising administering to the individual a therapeutically effective amount of compound 1895, or a pharmaceutically acceptable salt thereof.

In another embodiment, provided herein is a method of treating an HBV infection in an individual in need thereof, comprising administering to the individual a therapeutically effective amount of compound 1909, or a pharmaceutically acceptable salt thereof.

In another embodiment, provided herein is a method of treating an HBV infection in an individual in need thereof, comprising administering to the individual a therapeutically effective amount of compound 1910, or a pharmaceutically acceptable salt thereof.

In another embodiment, provided herein is a method of treating an HBV infection in an individual in need thereof, comprising administering to the individual a therapeutically effective amount of compound 1914, or a pharmaceutically acceptable salt thereof.

In another embodiment, provided herein is a method of treating an HBV infection in an individual in need thereof, comprising administering to the individual a therapeutically effective amount of compound 1915, or a pharmaceutically acceptable salt thereof.

In another embodiment, provided herein is a method of treating an HBV infection in an individual in need thereof, comprising administering to the individual a therapeutically effective amount of compound 1916, or a pharmaceutically acceptable salt thereof.

In another embodiment, provided herein is a method of treating an HBV infection in an individual in need thereof, comprising administering to the individual a therapeutically effective amount of compound 1917, or a pharmaceutically acceptable salt thereof.

In another embodiment, provided herein is a method of treating an HBV infection in an individual in need thereof, comprising administering to the individual a therapeutically effective amount of compound 1919, or a pharmaceutically acceptable salt thereof.

In another embodiment, provided herein is a method of treating an HBV infection in an individual in need thereof, comprising administering to the individual a therapeutically effective amount of compound 1938, or a pharmaceutically acceptable salt thereof.

In another embodiment, provided herein is a method of treating an HBV infection in an individual in need thereof, comprising administering to the individual a therapeutically effective amount of compound 1944, or a pharmaceutically acceptable salt thereof.

In another embodiment, provided herein is a method of treating an HBV infection in an individual in need thereof, comprising administering to the individual a therapeutically effective amount of compound 1975, or a pharmaceutically acceptable salt thereof.

In another embodiment, provided herein is a method of treating an HBV infection in an individual in need thereof, comprising administering to the individual a therapeutically effective amount of compound 1977, or a pharmaceutically acceptable salt thereof.

In another embodiment, provided herein is a method of treating an HBV infection in an individual in need thereof, comprising administering to the individual a therapeutically effective amount of compound 1979, or a pharmaceutically acceptable salt thereof.

In another embodiment, provided herein is a method of treating an HBV infection in an individual in need thereof, comprising administering to the individual a therapeutically effective amount of compound 1980, or a pharmaceutically acceptable salt thereof.

In another embodiment, provided herein is a method of treating an HBV infection in an individual in need thereof, comprising administering to the individual a therapeutically effective amount of compound 1981, or a pharmaceutically acceptable salt thereof.

In another embodiment, provided herein is a method of treating an HBV infection in an individual in need thereof, comprising administering to the individual a therapeutically effective amount of compound 1983, or a pharmaceutically acceptable salt thereof.

In another embodiment, provided herein is a method of treating an HBV infection in an individual in need thereof, comprising administering to the individual a therapeutically effective amount of compound 1986, or a pharmaceutically acceptable salt thereof.

In another embodiment, provided herein is a method of treating an HBV infection in an individual in need thereof, comprising administering to the individual a therapeutically effective amount of compound 1987, or a pharmaceutically acceptable salt thereof.

In another embodiment, provided herein is a method of treating an HBV infection in an individual in need thereof, comprising administering to the individual a therapeutically effective amount of compound 1989, or a pharmaceutically acceptable salt thereof.

In another embodiment, provided herein is a method of treating an HBV infection in an individual in need thereof, comprising administering to the individual a therapeutically effective amount of compound 2002, or a pharmaceutically acceptable salt thereof.

In another embodiment, provided herein is a method of treating an HBV infection in an individual in need thereof, comprising administering to the individual a therapeutically effective amount of compound 2004, or a pharmaceutically acceptable salt thereof.

In another embodiment, provided herein is a method of treating an HBV infection in an individual in need thereof, comprising administering to the individual a therapeutically effective amount of compound 2007, or a pharmaceutically acceptable salt thereof.

In another embodiment, provided herein is a method of treating an HBV infection in an individual in need thereof, comprising administering to the individual a therapeutically effective amount of compound 2024, or a pharmaceutically acceptable salt thereof.

In another embodiment, provided herein is a method of treating an HBV infection in an individual in need thereof, comprising administering to the individual a therapeutically effective amount of compound 2033, or a pharmaceutically acceptable salt thereof.

In another embodiment, provided herein is a method of treating an HBV infection in an individual in need thereof, comprising administering to the individual a therapeutically effective amount of compound 2114_D1, or a pharmaceutically acceptable salt thereof.

In another embodiment, provided herein is a method of treating an HBV infection in an individual in need thereof, comprising administering to the individual a therapeutically effective amount of compound 2114_D2, or a pharmaceutically acceptable salt thereof.

In another embodiment, provided herein is a method of treating an HBV infection in an individual in need thereof, comprising administering to the individual a therapeutically effective amount of compound 2121, or a pharmaceutically acceptable salt thereof.

In another embodiment, provided herein is a method of treating an HBV infection in an individual in need thereof, comprising administering to the individual a therapeutically effective amount of compound 2123, or a pharmaceutically acceptable salt thereof.

In another embodiment, provided herein is a method of treating an HBV infection in an individual in need thereof, comprising administering to the individual a therapeutically effective amount of compound 2199, or a pharmaceutically acceptable salt thereof.

In another embodiment, provided herein is a method of treating an HBV infection in an individual in need thereof, comprising administering to the individual a therapeutically effective amount of compound 2202, or a pharmaceutically acceptable salt thereof.

In another embodiment, provided herein is a method of treating an HBV infection in an individual in need thereof, comprising administering to the individual a therapeutically effective amount of compound 2205, or a pharmaceutically acceptable salt thereof.

In another embodiment, provided herein is a method of treating an HBV infection in an individual in need thereof, comprising administering to the individual a therapeutically effective amount of compound 2206, or a pharmaceutically acceptable salt thereof.

In another embodiment, provided herein is a method of treating an HBV infection in an individual in need thereof, comprising administering to the individual a therapeutically effective amount of compound 2433_D1, or a pharmaceutically acceptable salt thereof.

In another embodiment, provided herein is a method of treating an HBV infection in an individual in need thereof, comprising administering to the individual a therapeutically effective amount of compound 2433_D2, or a pharmaceutically acceptable salt thereof.

In another embodiment, provided herein is a method of treating an HBV infection in an individual in need thereof, comprising administering to the individual a therapeutically effective amount of compound 2492, or a pharmaceutically acceptable salt thereof.

In another embodiment, provided herein is a method of treating an HBV infection in an individual in need thereof, comprising administering to the individual a therapeutically effective amount of compound 2505, or a pharmaceutically acceptable salt thereof.

In another embodiment, provided herein is a method of treating an HBV infection in an individual in need thereof, comprising administering to the individual a therapeutically effective amount of compound 2547, or a pharmaceutically acceptable salt thereof.

In another embodiment, provided herein is a method of treating an HBV infection in an individual in need thereof, comprising administering to the individual a therapeutically effective amount of compound 2548, or a pharmaceutically acceptable salt thereof.

In another embodiment, provided herein is a method of treating an HBV infection in an individual in need thereof, comprising administering to the individual a therapeutically effective amount of compound 2550, or a pharmaceutically acceptable salt thereof.

In another embodiment, provided herein is a method of treating an HBV infection in an individual in need thereof, comprising administering to the individual a therapeutically effective amount of compound 2617_D2, or a pharmaceutically acceptable salt thereof.

In another embodiment, provided herein is a method of treating an HBV infection in an individual in need thereof, comprising administering to the individual a therapeutically effective amount of compound 2618_D1, or a pharmaceutically acceptable salt thereof.

In another embodiment, provided herein is a method of treating an HBV infection in an individual in need thereof, comprising administering to the individual a therapeutically effective amount of compound 2618_D2, or a pharmaceutically acceptable salt thereof.

In another embodiment, provided herein is a method of treating an HBV infection in an individual in need thereof, comprising administering to the individual a therapeutically effective amount of compound 2619_D2, or a pharmaceutically acceptable salt thereof.

In another embodiment, provided herein is a method of treating an HBV infection in an individual in need thereof, comprising administering to the individual a therapeutically effective amount of compound 2625_D2, or a pharmaceutically acceptable salt thereof.

In another embodiment, provided herein is a method of treating an HBV infection in an individual in need thereof, comprising administering to the individual a therapeutically effective amount of compound 2626_D2, or a pharmaceutically acceptable salt thereof.

In another embodiment, provided herein is a method of treating an HBV infection in an individual in need thereof, comprising administering to the individual a therapeutically effective amount of compound 2632, or a pharmaceutically acceptable salt thereof.

In another embodiment, provided herein is a method of treating an HBV infection in an individual in need thereof, comprising administering to the individual a therapeutically effective amount of compound 2634, or a pharmaceutically acceptable salt thereof.

Combination Therapies

The compounds of the present invention are intended to be useful in combination with one or more additional compounds useful for treating HBV infection. These additional compounds may comprise compounds of the present invention or compounds known to treat, prevent, or reduce the symptoms or effects of HBV infection. Such compounds include but are not limited to HBV polymerase inhibitors, interferons, viral entry inhibitors, viral maturation inhibitors, literature-described capsid assembly modulators, reverse transcriptase inhibitor, a TLR-agonist, and other agents with distinct or unknown mechanisms that affect the HBV life cycle and/or affect the consequences of HBV infection.

In non-limiting examples, the compounds of the invention may be used in combination with one or more drugs (or a salt thereof) selected from the group consisting of HBV reverse transcriptase inhibitors, and DNA and RNA polymerase inhibitors, including but not limited to: lamivudine (3TC, Zeffix, Heptovir, Epivir, and Epivir-HBV), entecavir (Baraclude, Entavir), adefovir dipivoxil (Hepsara, Preveon, bis-POM PMEA), tenofovir disoproxil fumarate (Viread, TDF or PMPA);

interferons, including but not limited to interferon alpha (IFN-α), interferon lambda (IFN-λ), and interferon gamma (IFN-γ);

viral entry inhibitors;

viral maturation inhibitors;

literature-described capsid assembly modulators, such as, but not limited to BAY 41-4109;

reverse transcriptase inhibitor;

a TLR-agonist; and agents of distinct or unknown mechanism, such as but not limited to AT-61 ((E)-N-(1-chloro-3-oxo-1-phenyl-3-(piperidin-1-yl)prop-1-en-2-yl)benzamide), AT-130 ((E)-N-(1-bromo-1-(2-methoxyphenyl)-3-oxo-3-(piperidin-1-yl)prop-1-en-2-yl)-4-nitrobenzamide), and similar analogs.

In one embodiment, the additional therapeutic agent is an interferon. The term "interferon" or "IFN" refers to any member the family of highly homologous species-specific proteins that inhibit viral replication and cellular proliferation, and modulate immune response. Human interferons are grouped into three classes; Type I, which include interferon-alpha (IFN-α), interferon-beta (IFN-β), and interferon-omega (IFN-ω), Type II, which includes interferon-gamma (IFN-γ), and Type III, which includes interferon-lambda (IFN-λ). Recombinant forms of interferons that have been developed and are commercially available are encompassed by the term "interferon" as used herein. Subtypes of interferons, such as chemically modified or mutated interferons, are also encompassed by the term "interferon" as used herein. Chemically modified interferons include pegylated interferons and glycosylated interferons. Examples of interferons include, but are not limited to, interferon-alpha-2a, interferon-alpha-2b, interferon-alpha-n1, interferon-beta-1a, interferon-beta-1b, interferon-lambda-1, interferon-lamda-2, and interferon-lamda-3. Examples of pegylated interferons include pegylated interferon-alpha-2a and pegylated interferson alpha-2b.

Accordingly, in one embodiment, the compounds of Formula I, Ia, Ib, II, III, IV, V, Vx, or Va can be administered in combination with an interferon selected from the group consisting of interferon alpha (IFN-α), interferon beta (IFN-β), interferon lambda (IFN-λ), and interferon gamma (IFN-γ). In one specific embodiment, the interferon is interferon-alpha-2a, interferon-alpha-2b, or interferon-alpha-n1. In another specific embodiment, the interferon-alpha-2a or interferon-alpha-2b is pegylated. In a preferred embodiment, the interferon-alpha-2a is pegylated interferon-alpha-2a (PEGASYS).

In another embodiment, the additional therapeutic agent is selected from immune modulator or immune stimulator therapies, which includes biological agents belonging to the interferon class.

Further, the additional therapeutic agent may be an agent of distinct or unknown mechanism including agents that disrupt the function of other essential viral protein(s) or host proteins required for HBV replication or persistence.

In another embodiment, the additional therapeutic agent is an antiviral agent that blocks viral entry or maturation or targets the HBV polymerase such as nucleoside or nucleotide or non-nucleos(t)ide polymerase inhibitors. In a further embodiment of the combination therapy, the reverse transcriptase inhibitor and/or DNA and/or RNA polymerase inhibitor is Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, cidofovir, Efavirenz, Nevirapine, Delavirdine, or Etravirine.

In one embodiment, the additional therapeutic agent is a TLR modulator or a TLR agonist, such as a TLR-7 agonist or TLR-9 agonist. In further embodiment of the combination therapy, the TLR-7 agonist is selected from the group consisting of SM360320 (9-benzyl-8-hydroxy-2-(2-methoxyethoxy)adenine) and AZD 8848 (methyl[3-({[3-(6-amino-2-butoxy-8-oxo-7,8-dihydro-9H-purin-9-yl)propyl][3-(4-morpholinyl)propyl]amino}methyl)phenyl]acetate).

In any of the methods provided herein, the method may further comprise administering to the individual at least one HBV vaccine, a nucleoside HBV inhibitor, an interferon or any combination thereof. In an embodiment, the HBV vaccine is at least one of RECOMBIVAX HB, ENGERIX-B, ELOVAC B, GENEVAC-B, or SHANVAC B.

In another aspect, provided herein is method of treating an HBV infection in an individual in need thereof, comprising reducing the HBV viral load by administering to the individual a therapeutically effective amount of a compound of the invention alone or in combination with a reverse transcriptase inhibitor; and further administering to the individual a therapeutically effective amount of HBV vaccine. The reverse transcriptase inhibitor may be one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, cidofovir, Efavirenz, Nevirapine, Delavirdine, or Etravirine.

For any combination therapy described herein, synergistic effect may be calculated, for example, using suitable methods such as the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

In another aspect, provided herein is pharmaceutical composition comprising a compound of the invention, or a pharmaceutically acceptable salt thereof, together with a pharmaceutically acceptable carrier.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of HBV infection in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments there between.

In some embodiments, the dose of a compound of the invention is from about 1 mg to about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., another drug for HBV treatment) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of HBV infection in a patient.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials:

Unless otherwise noted, all starting materials and resins were obtained from commercial suppliers and used without purification.

Library General Design

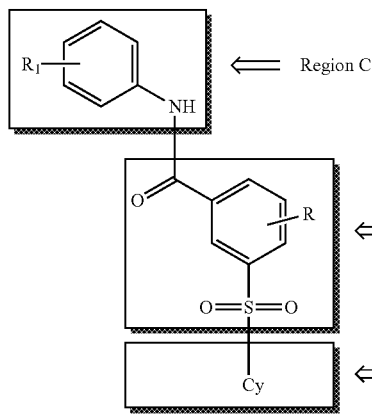

Region A:

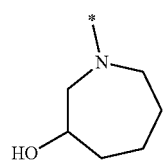 A01

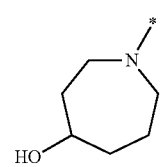 A02

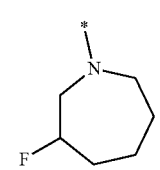 A03

-continued

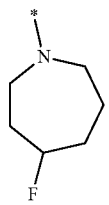 A04

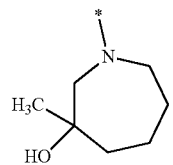 A05

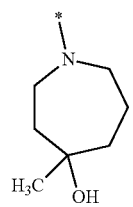 A06

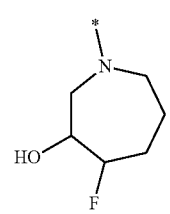 A07

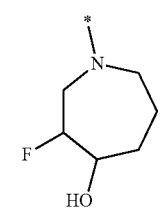 A08

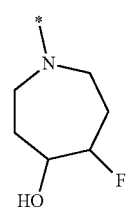 A09

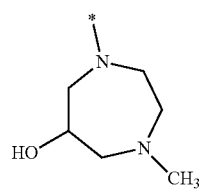 A10

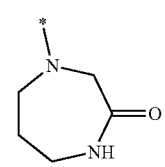 A11

275
-continued
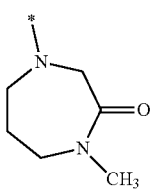 A12
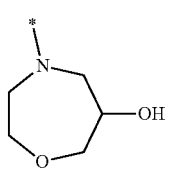 A13
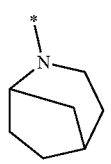 A14
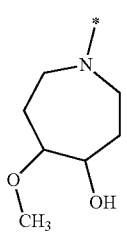 A15
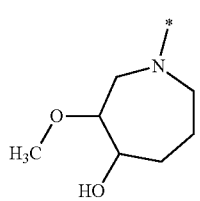 A16
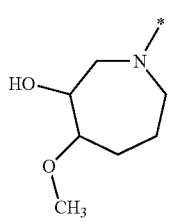 A17
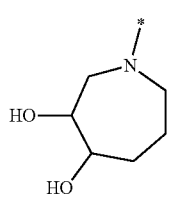 A18
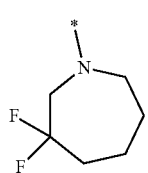 A19
276
-continued
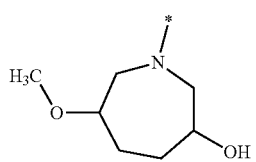 A20
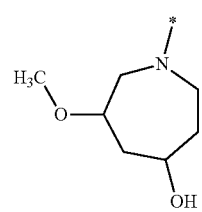 A21
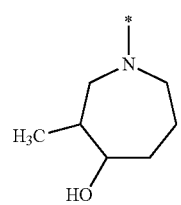 A22
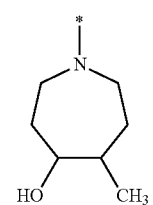 A23
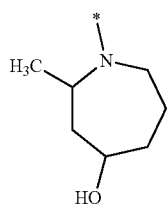 A24
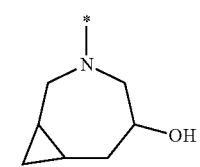 A25
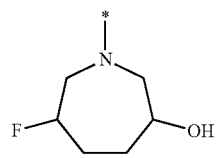 A26
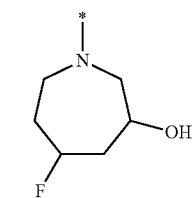 A27

277
-continued
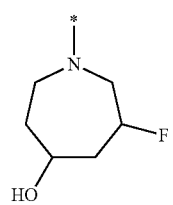 A28
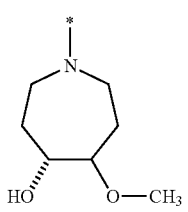 A29
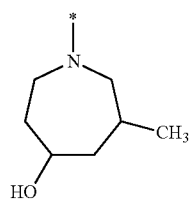 A30
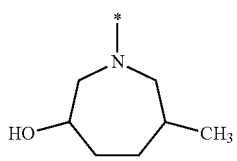 A31
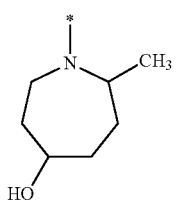 A32
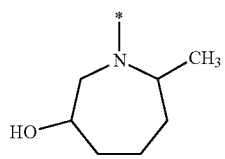 A33
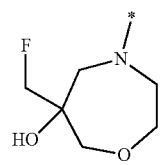 A34
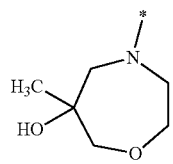 A35
278
-continued
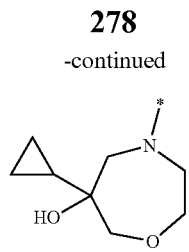 A36
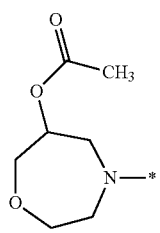 A37
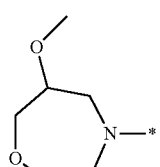 A38
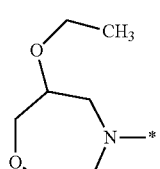 A39
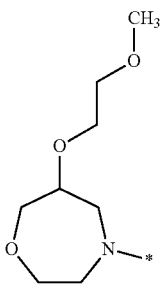 A40
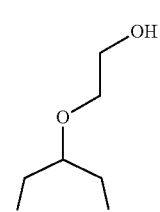 A41
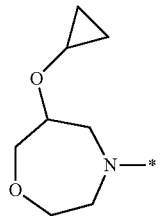 A42

-continued
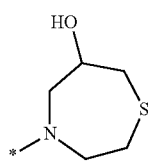 A43
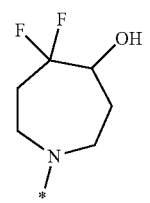 A44
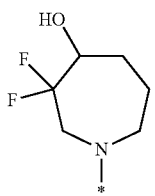 A45
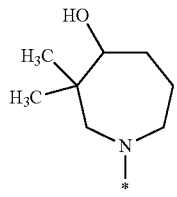 A46
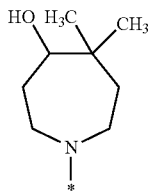 A47
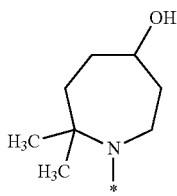 A48
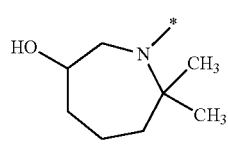 A49
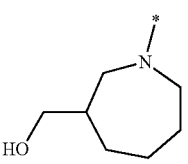 A50
-continued
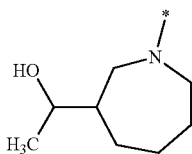 A51
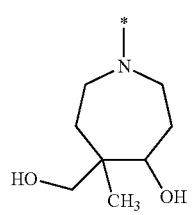 A51
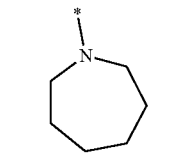 A53
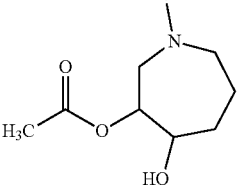 A54
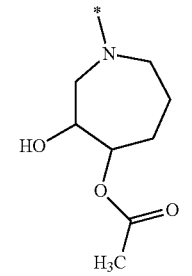 A55
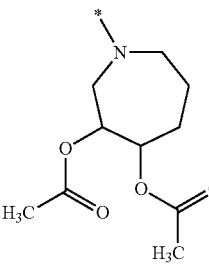 A56
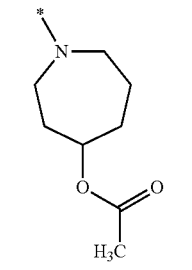 A57

281
-continued
| | | | |
|---|---|---|---|
| A58 | 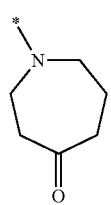 | | |
| A59 | 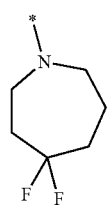 | B01 | 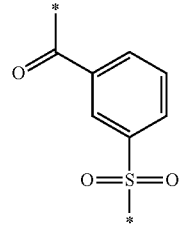 |
| A60 | 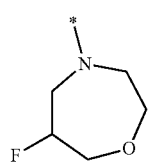 | B02 | 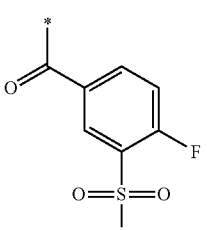 |
| A61 | 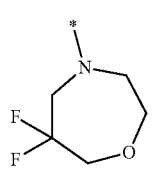 | B03 | 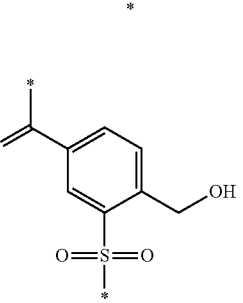 |
| A62 | 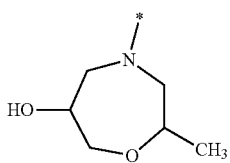 | B04 | 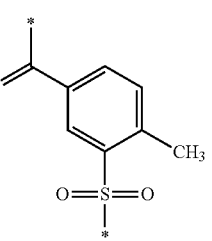 |
| A63 | 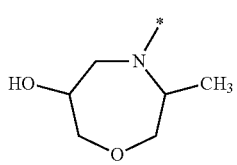 | B05 | 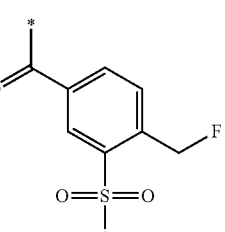 |
| A64 | 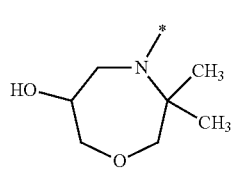 | B06 | 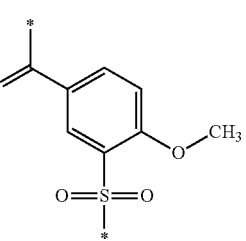 |
| A65 | 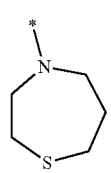 | | |
| A68 | 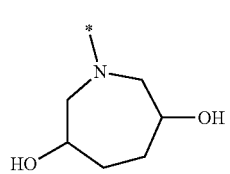 | | |
282
Region B:

B07 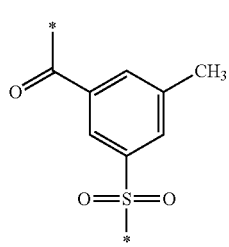
B08 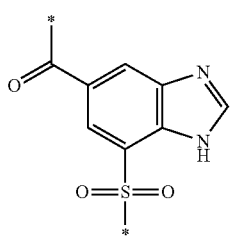
B09 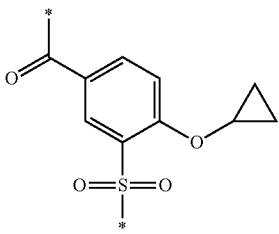
B10 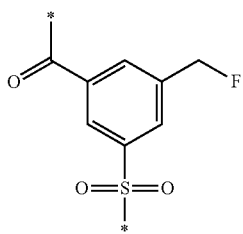
B11 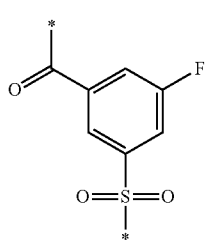
B12 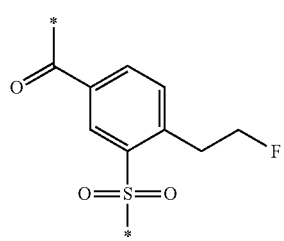
Region C:
C01 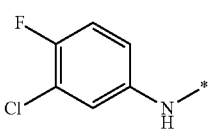
C02 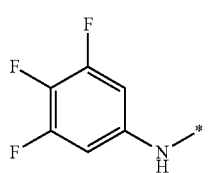
C03 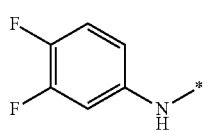
Part I Intermediate Synthesis (Regions A, B & C)
1 Preparation of Region a Intermediates
1.1 Preparation of A01/02
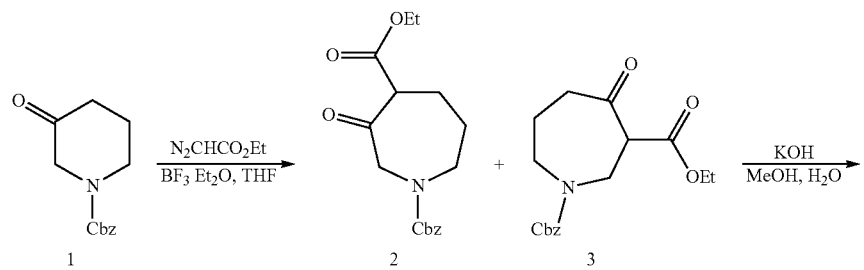

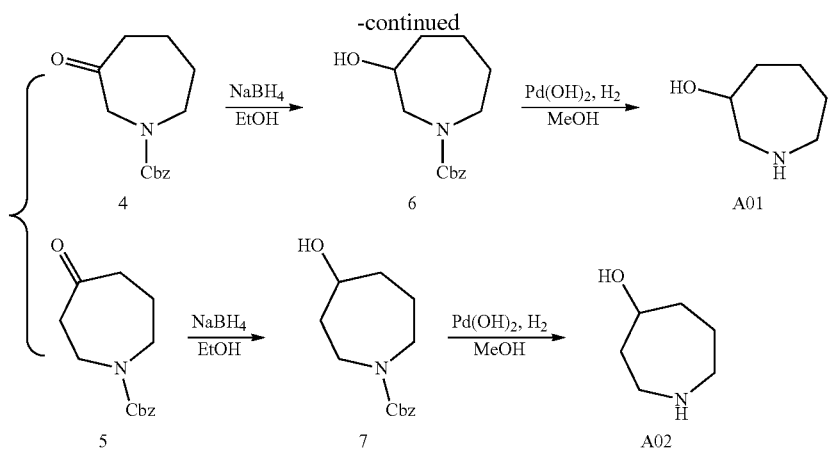

1.1.1 Preparation of Compound 2 and 3

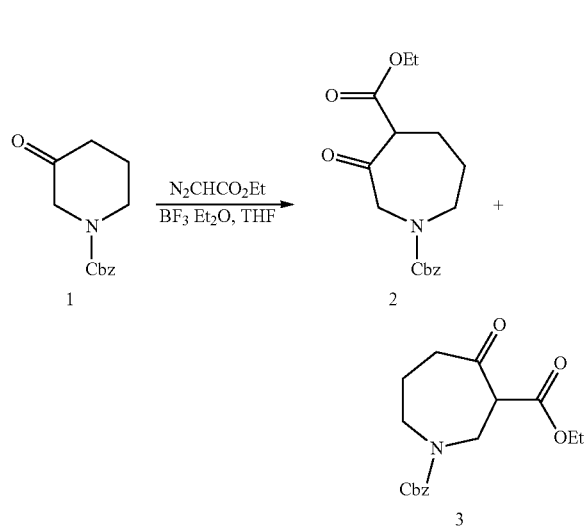

To a solution of Compound 1 (5.0 g, 21.5 mmol) and ethyl 2-diazoacetate (3.2 g, 28.1 mmol) in THF (100 mL) was added $BF_3\text{-}Et_2O$ (2.7 mL, 21.5 mmol) at −78° C. under $N_2$. The reaction mixture was stirred at −78° C. for 1.5 h, then warmed to 28° C. slowly and stirred for 1.5 h. The resulting mixture was quenched with $NaHCO_3$ (sat.) and extracted with EA (300 mL). The organic layer was dried over $Na_2SO_4$ and concentrated in vacuo to give a crude product, which was purified by flash column chromatography to give a mixture of Compound 2 and 3 (3.4 g, 50%). LCMS: 320.0 [M+1].

1.1.2 Preparation of Compound 4 and 5

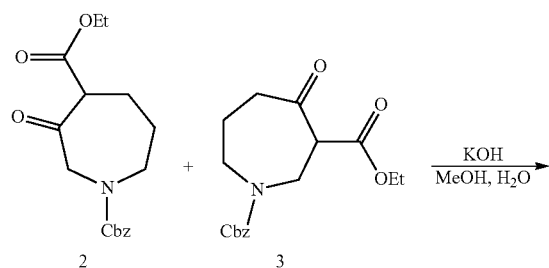

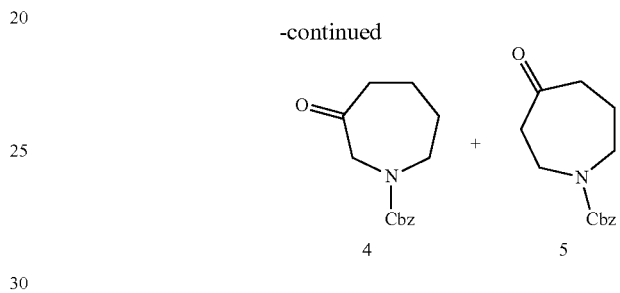

To a mixture of compound 2 and 3 (1 g, 3.1 mmol) dissolved $MeOH/H_2O$ (10 mL/2 mL) was added KOH (0.53 g, 9.3 mmol), and heated to 55° C. for 2 h. The mixture was diluted with EA (80 mL) and washed with brine (60 mL). The organic layer was dried over $Na_2SO_4$ and concentrated in vacuo to give a crude product, which was purified by flash column chromatography to give Compound 4 (0.32 g, 42%) and Compound 5 (0.22 g, 29%). LCMS: 248.0 [M+1]. Compound 4 $^1H$ NMR (400 MHz, CDCl3) δ 7.34-7.40 (m, 5H), 5.16-5.21 (m, 2H), 4.06-4.11 (m, 2H), 3.46-3.49 (m, 2H), 2.51-2.55 (m, 2H), 1.63-1.78 (m, 4H). Compound 5 $^1H$ NMR (400 MHz, CDCl3) δ 7.34-7.39 (m, 5H), 5.14 (s, 2H), 3.62-3.69 (m, 4H), 2.62-2.71 (m, 4H), 2.75-2.81 (m, 2H).

1.1.3 Preparation of Compound 6

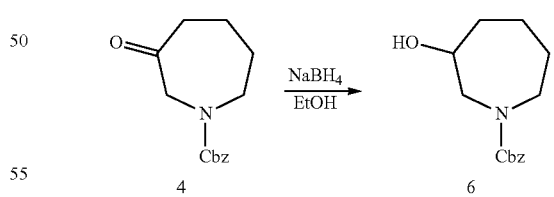

To a solution of compound 4 (0.32 g, 1.3 mmol) in EtOH (20 mL) was added $NaBH_4$ (74.2 mg, 1.9 mmol) at 0° C., and the mixture was stirred at 25° C. for 2 h. The resulting mixture was quenched with $NH_4Cl$ (sat.) and extracted with EA (80 mL). The organic layer was dried over $Na_2SO_4$ and concentrated in vacuo to give the crude product, which was purified by flash column chromatography to give the desired product (0.24 g, 74%). LCMS: 250.0 [M+1].

1.1.4 Preparation of Compound A01

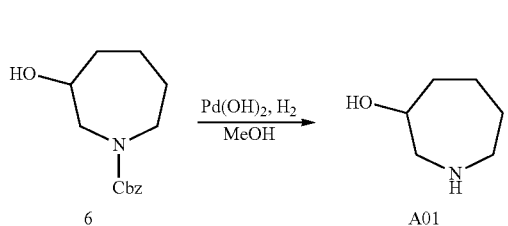

To a solution of Compound 6 (0.25 g, 1.0 mmol) in MeOH (25 mL) was added Pd(OH)₂/C (50 mg). The mixture was hydrogenated at 25° C. for 16 h under 25 Psi pressure. The catalyst was filtered and the filtrate was concentrated to give the crude product, which was used in the next step directly (0.1 g, 87%).

1.1.5 Preparation of Compound 7

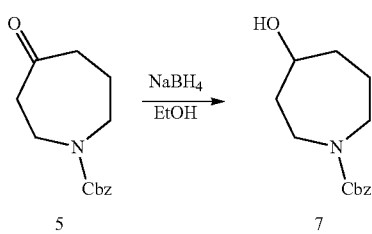 [SMILES: "EtOH" ; O=C1CCCN(C(=O)OCc2ccccc2)CC1 ; "NaBH4" ; O=C(OCc1ccccc1)N1CCCC(O)CC1]

To a solution of compound 5 (0.32 g, 1.3 mmol) in EtOH (20 mL) was added NaBH₄ (74.2 mg, 1.9 mmol) at 0° C., and the mixture was stirred at 25° C. for 2 h. The resulting mixture was quenched with NH₄Cl (sat.) and extracted with EA (80 mL). The organic layer was dried and concentrated to give the crude product, which was purified by flash column chromatography to give the desired product (0.24 g, 74%). LCMS: 250.0 [M+1].

1.1.6 Preparation of Compound A02

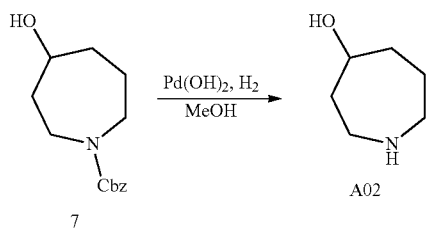

To a solution of Compound 5 (0.25 g, 1.0 mmol) in MeOH (25 mL) was added Pd(OH)₂/C (50 mg). The mixture was hydrogenated at 25° C. for 16 h under 25 psi pressure. The catalyst was filtered and the filtrate was concentrated to give the crude product, which was used in the next step directly (0.1 g, 87%).

1.2 Preparation of A03/04

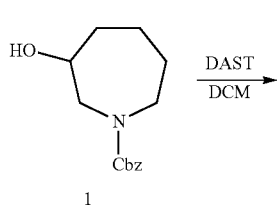

-continued

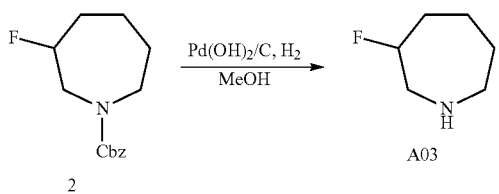

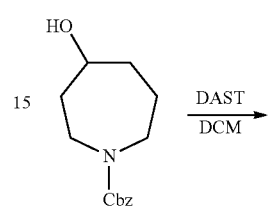

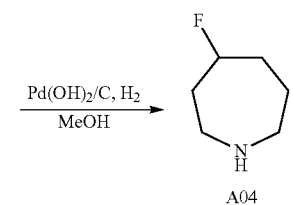

1.2.1 Preparation of Compound 2

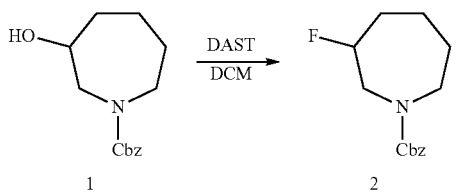

To a solution of Compound 1 (0.8 g, 3.2 mmol) in DCM (30 mL) was added DAST (1.1 g, 6.5 mmol) at −78° C. under N₂. The reaction mixture was stirred at −78° C. for 2 h and then warmed to 28° C. for 2 h. The resulting mixture was quenched with NaHCO₃ (sat.) and extracted with DCM (30 mL). The organic layer was dried and concentrated to give the crude product, which was purified by flash column chromatography PE:EA (30:1) to give the desired product (0.6 g, 74%). LCMS: 252.0 [M+1].

1.2.2 Preparation of Compound A03

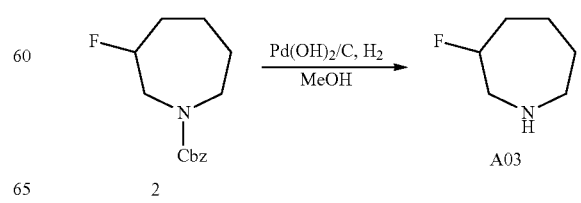

To a solution of Compound 2 (0.6 g, 2.4 mmol) in MeOH (25 mL) was added Pd(OH)$_2$/C (100 mg). The mixture was hydrogenated at 25° C. for 16 h under H$_2$ atmosphere. The catalyst was filtered and the filtrate was concentrated to give the crude product (0.3 g), which was used in the next step directly.

Amine A04 was prepared through the same procedure with amine A03 from benzyl 4-hydroxyazepane-1-carboxylate.

1.3 Preparation of A05/06

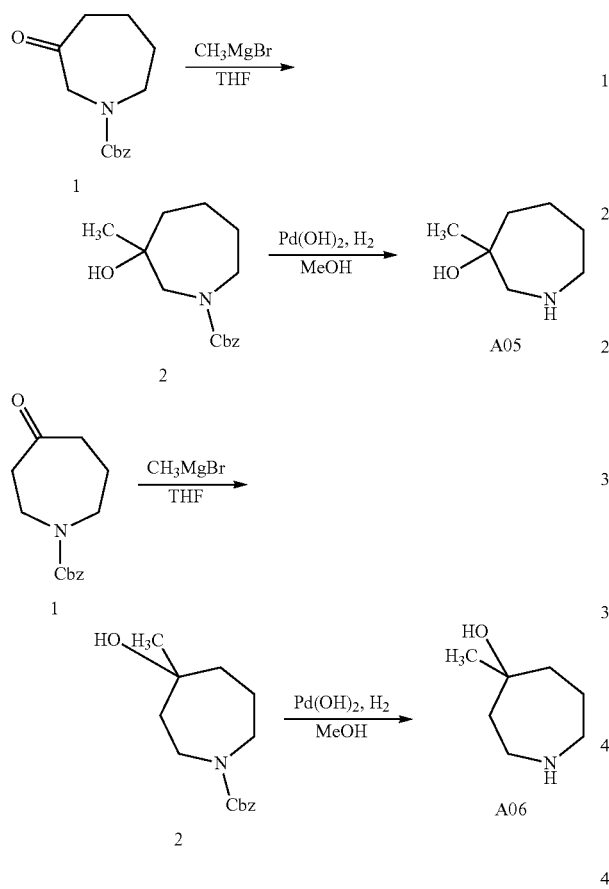

1.3.1 Preparation of Compound 2

To a solution of CH$_3$MgBr (14.2 mmol) in THF (10 mL) was added Compound 1 (0.7 g, 2.8 mmol) in THF (20 mL) at 0° C. under N$_2$. The reaction mixture was stirred at 0° C. for 2 h. The resulting mixture was quenched with NH$_4$Cl (sat.) and extracted with EtOAc (30 mL). The organic layer was dried and concentrated in vacuo to give the crude product, which was purified by flash column chromatography PE:EA (10:1) to give the desired product (0.2 g, 27%). LCMS: 264 [M+1].

1.3.2 Preparation of Compound A05

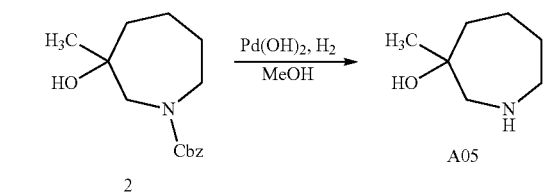

To a solution of Compound 2 (0.34 g, 1.3 mmol) in MeOH (25 mL) was added Pd(OH)$_2$/C (50 mg). The mixture was hydrogenated at 25° C. for 16 h under H$_2$ atmosphere. The catalyst was filtered and the filtrate was concentrated to give the crude product, which was used in the next step directly (0.16 g, 94%).

Amine A06 was prepared through the same procedure with amine A03 from benzyl 4-oxoazepane-1-carboxylate.

1.4 Preparation of A07/08

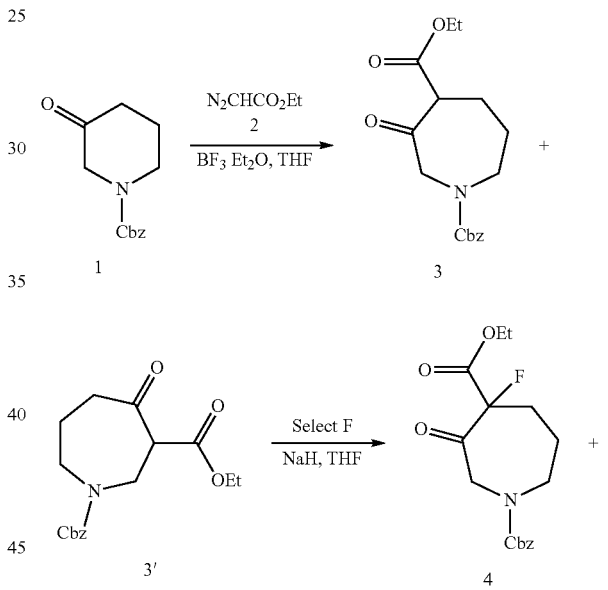

1.4.1.2 Preparation of Compound 4 and Compound 4'

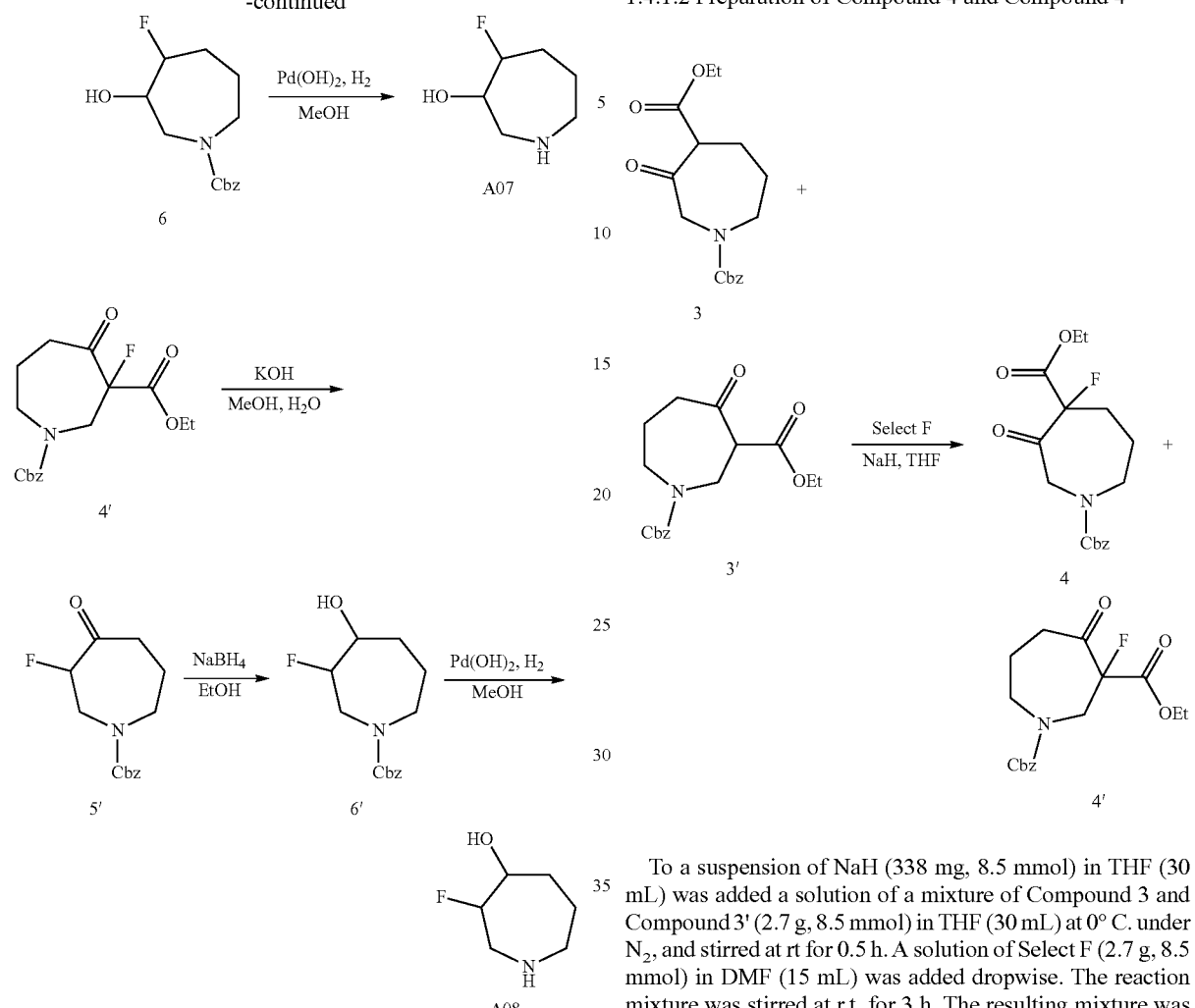

To a suspension of NaH (338 mg, 8.5 mmol) in THF (30 mL) was added a solution of a mixture of Compound 3 and Compound 3' (2.7 g, 8.5 mmol) in THF (30 mL) at 0° C. under $N_2$, and stirred at rt for 0.5 h. A solution of Select F (2.7 g, 8.5 mmol) in DMF (15 mL) was added dropwise. The reaction mixture was stirred at r.t. for 3 h. The resulting mixture was quenched with $NH_4Cl$ and extracted with EA (200 mL). The organic layer was washed with brine, dried over $Na_2SO_4$ and concentrated in vacuo to give the crude product, which was purified by flash column chromatography to give Compound 4 (1.0 g, 35%) and Compound 4'(0.9 g, 32%). Compound 4: $^1$H NMR (400 MHz, $CDCl_3$) δ=7.28-7.39 (m, 5H), 5.18 (s, 2H), 4.40-4.68 (m, 1H), 4.11-4.39 (m, 3H), 3.45-3.63 (m, 1H), 3.21-3.38 (m, 1H), 1.85-2.45 (m, 4H), 1.26-1.30 (m, 3H). Compound 4': $^1$H NMR (400 MHz, $CDCl_3$) δ=7.28-7.40 (m, 5H), 5.14-5.18 (m, 2H), 4.24-4.47 (m, 4H), 3.88-4.00 (m, 1H), 3.09-3.25 (m, 1H), 2.85-2.91 (m, 2H), 1.92-1.95 (m, 2H), 1.27-1.35 (m, 3H).

1.4.1.3 Preparation of Compound 5

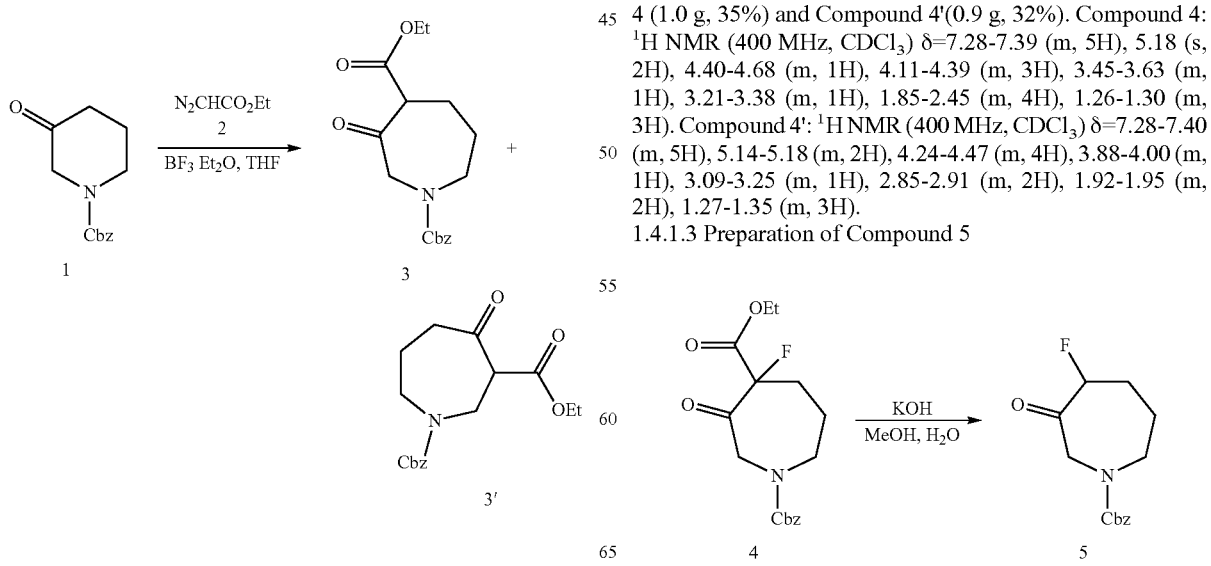

1.4.1.1 Preparation of Compound 3 and 3'

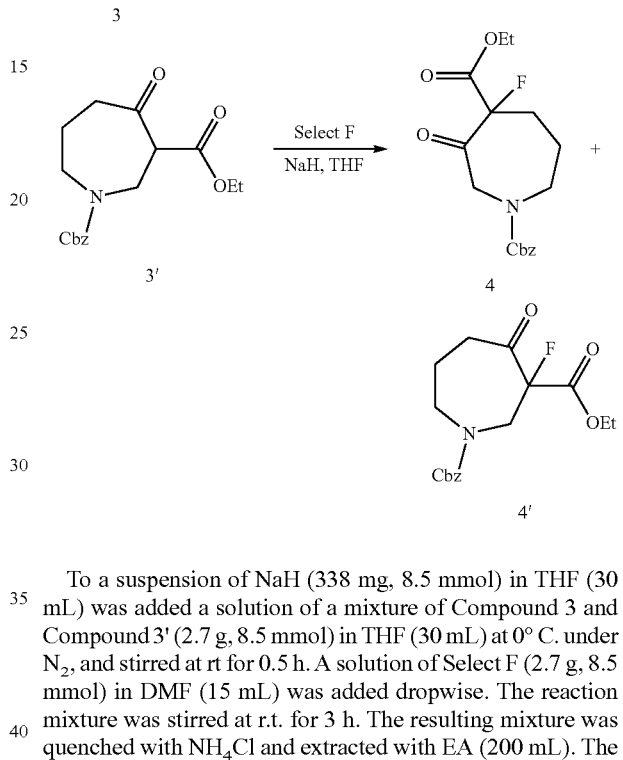

A mixture of compound 3 and 3' was prepared with the same procedure as 1.1.1.

A mixture of compound 4 (0.72 g, 2.1 mmol) and KOH (0.18 g, 3.2 mmol) in MeOH/H₂O (10 mL/2 mL) was heated to 55° C. for 2 h. The mixture was extracted with EA (80 mL) and washed with brine (60 mL). The organic layer was dried over Na₂SO₄ and concentrated in vacuo to give the crude product, which was used in the next step directly (0.54 g, crude). LCMS: 266.0 [M+1].

1.4.1.4 Preparation of Compound 6

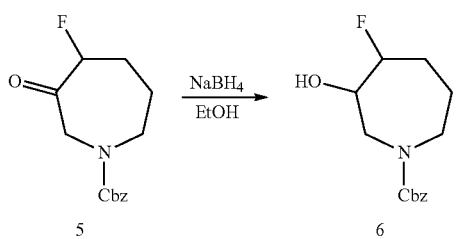 [SMILES: "EtOH" ; O=C1CN(C(=O)OCc2ccccc2)CCCC1F ; "NaBH4" ; O=C(OCc1ccccc1)N1CCCC(F)C(O)C1]

To a solution of compound 5 (0.54 g, 2.1 mmol) in EtOH (8 mL) was added NaBH₄ (0.12 g, 3.1 mmol) at 0° C., and the mixture was stirred at 25° C. for 2 h. The resulting mixture was quenched with NH₄Cl (Sat.) and extracted with EA (80 mL). The organic layer was dried over Na₂SO₄ and concentrated in vacuo to give the crude product, which was purified by flash column chromatography to give the desired product (0.22 g, 41%). LCMS: 268.0 [M+1].

1.4.1.5 Preparation of Compound A07

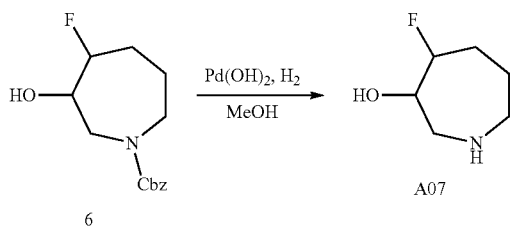

To a solution of Compound 6 (0.22 g, 0.8 mmol) in MeOH (25 mL) was added Pd(OH)₂/C (45 mg). The mixture was hydrogenated at 25° C. for 16 h under 25 Psi pressure. The catalyst was filtered and the filtrate was concentrated in vacuo to give the crude product, which was used in the next step directly (0.1 g, 91%).

1.4.1.6 Preparation of Compound 5'

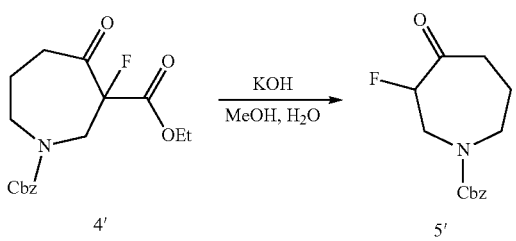

A mixture of compound 4' (0.89 g, 2.6 mmol) and KOH (0.22 g, 3.9 mmol) in MeOH/H₂O (10 mL/2 mL) was heated to 55° C. for 2 h. The mixture was diluted with EA (80 mL) and washed with brine (60 mL). The organic layer was dried over Na₂SO₄ and concentrated in vacuo to give the crude product, which was used in the next step directly (0.65 g, crude). LCMS: 266.0 [M+1].

1.4.1.7 Preparation of Compound 6'

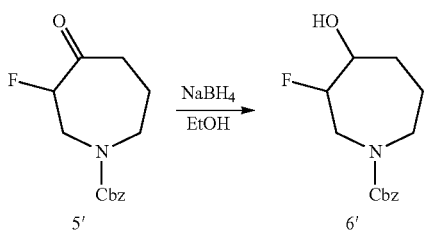

To a solution of compound 5' (0.65 g, 2.6 mmol) in EtOH (10 mL) was added NaBH₄ (0.15 g, 3.9 mmol) at 0° C., and the mixture was stirred at 25° C. for 2 h. The resulting mixture was quenched with NH₄Cl (sat.) and extracted with EA (80 mL). The organic layer was dried over Na₂SO₄ and concentrated in vacuo to give the crude product, which was purified by flash column chromatography to give the desired product (0.33 g, 50%). LCMS: 268.0 [M+1].

1.4.1.8 Preparation of Compound A08

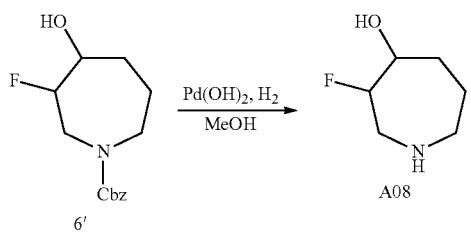

To a solution of Compound 6' (0.33 g, 1.2 mmol) in MeOH (30 mL) was added Pd(OH)₂/C (60 mg). The mixture was hydrogenated at 25° C. for 16 h under 25 Psi pressure. The catalyst was filtered and the filtrate was concentrated in vacuo to give the crude product, which was used in the next step directly (0.15 g, 91%).

Synthesis of the Diastereomers:

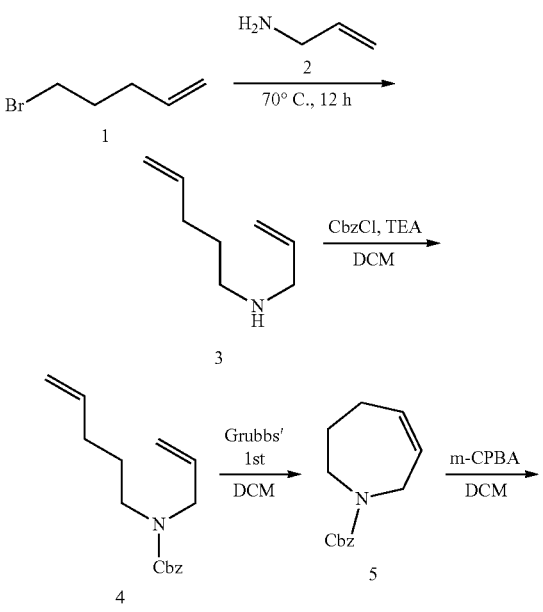

-continued

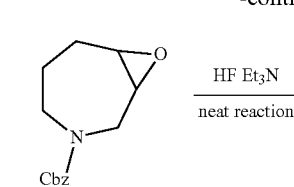 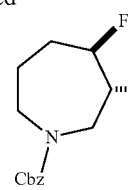

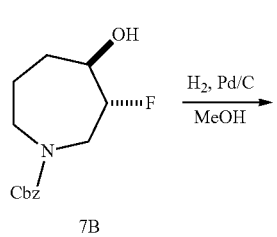 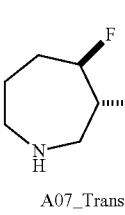

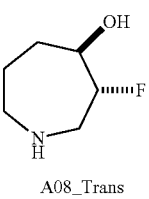

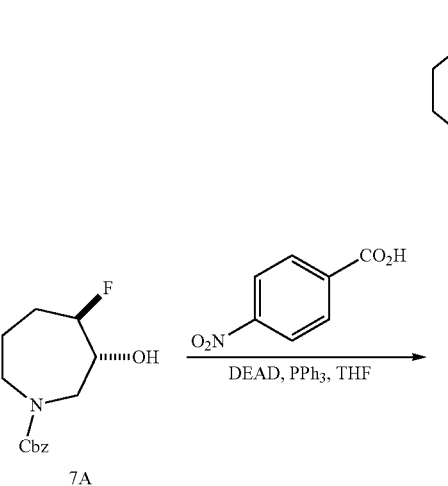

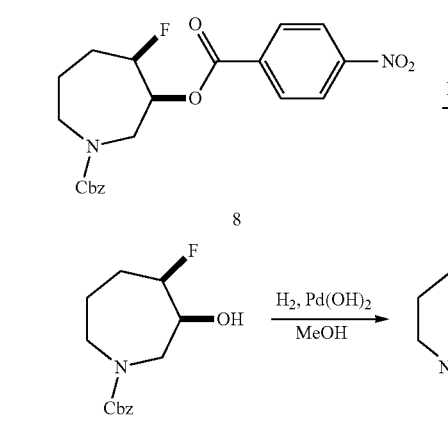

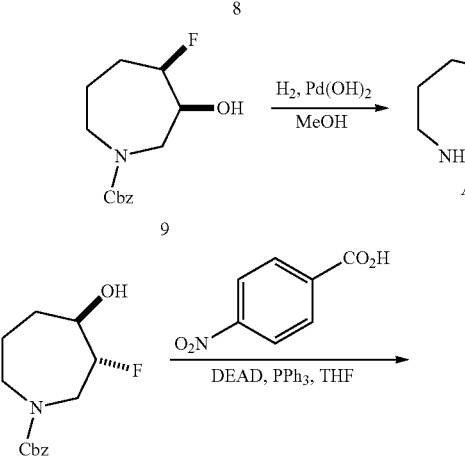

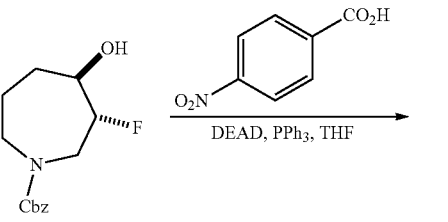

-continued

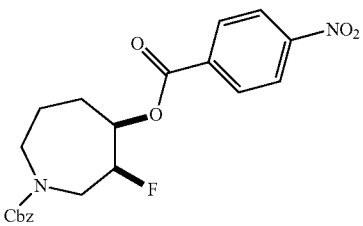

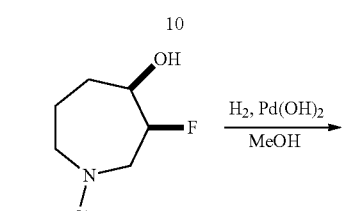

1.4.2.1 Preparation of Compound 3

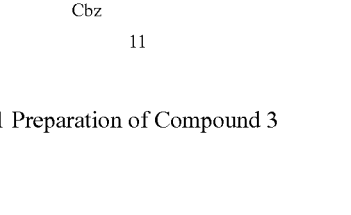

To a solution of Compound 1 (5.0 g, 33.7 mmol) was added prop-2-en-1-amine (6.0 g, 101.3 mmol), then the solution was stirred at 80° C. for 16 h. The mixture was concentrated in vacuum to give crude Compound 3 (6.6 g) for the next step directly.

1.4.2.2 Preparation of Compound 4

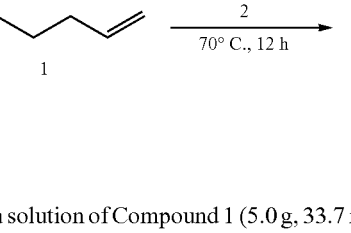

To a solution of Compound 3 (6.6 g, 52.71 mmol) in DCM (80 mL) was added TEA (10.67 g, 105.4 mmol) and CbzCl (13.49 g, 79.1 mmol) at 0° C., the solution was stirred at 25° C. for 2 h. The reaction was washed by water (100 mL) and extracted with DCM (100 mL), the organic layer was dried over $Na_2SO_4$ and concentrated in vacuum to give the crude product, which was purified by column chromatography on silica gel (PE:EA=10:1) to give Compound 4 (5.0 g, 36.6%).

$^1$H NMR (400 MHz, MeOD): δ ppm: 7.25-7.47 (m, 5H), 5.67-5.96 (m, 2H), 5.08-5.23 (m, 3H), 4.91-5.08 (m, 2H), 3.86-3.96 (m, 2H), 3.27 (t, J=7.5 Hz, 2H), 1.95-2.11 (m, 2H), 1.53-1.72 (m, 2H).

1.4.2.3 Preparation of Compound 5

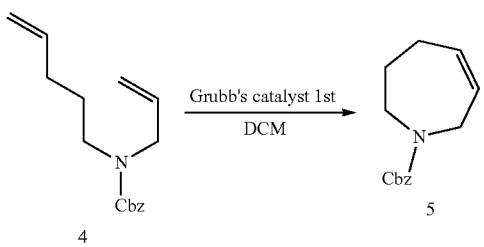 [SMILES: C=CCCCN(CC=C)C(=O)OCc1ccccc1 ; O=C(OCc1ccccc1)N1CC=CCCC1]

To a solution of Compound 4 (3.0 g, 11.57 mmol) in DCM (300 mL) was added Grubb's catalyst 1st (290 mg, 0.35 mmol), then the solution was stirred at 55° C. for 16 h under $N_2$ atmosphere. The mixture was concentrated in vacuum to give the crude product, which was purified by column chromatography on silica gel (PE:EA=20:1) to give Compound 5 (1.9 g, 71%) as darkness liquid.

$^1$H NMR (400 MHz, $CDCl_3$): δ ppm: 7.30-7.43 (m, 5H), 5.69-5.89 (m, 2H), 5.09-5.24 (m, 2H), 3.90-4.08 (m, 2H), 3.47-3.72 (m, 3H), 2.16-2.43 (m, 3H), 1.76-1.94 (m, 2H).

1.4.2.41 Preparation of Compound 6

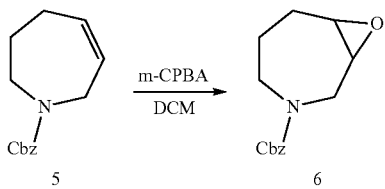 [SMILES: O=C(OCc1ccccc1)N1CC=CCCC1 ; O=C(OCc1ccccc1)N1CCCC2OC2C1]

To a solution of Compound 5 (1.0 g, 4.3 mmol) in DCM (15 mL) was added m-CPBA (1.49 g, 8.65 mmol), then the solution was stirred at 23° C. for 16 h. TLC showed the starting materials were consumed completely. The solution was washed with aq. $Na_2SO_3$ and extracted with DCM (20 mL), the organic layer was dried over $Na_2SO_4$ and concentrated in vacuum to give the crude product, which was purified by column chromatography on silica gel (PE:EA=3:1) to give Compound 6 (420 mg, 40%) as colorless liquid.

1.4.2.4 Preparation of Compound 7A and 7B

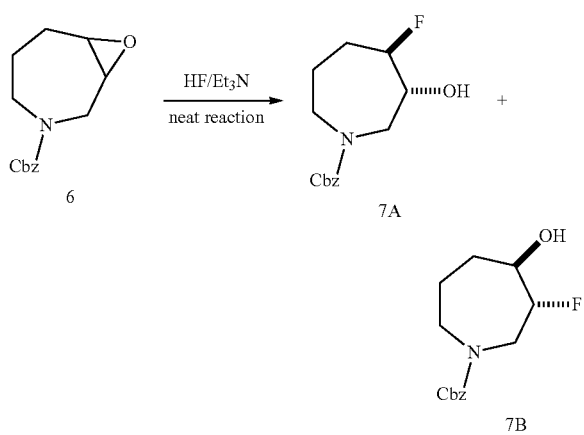

The compound 6 (800.00 mg, 3.24 mmol) was dissolved in HF/Et3N (522.32 mg, 6.48 mmol) a 50 mL single-necked round bottom flask. The mixture was stirred at 100° C. for 14 h under $N_2$. After cooled to 20° C., LCMS showed the starting material was consumed. The residue was washed by aq. $NaHCO_3$ (80 mL), and extracted by EA (70 mL*2), the organic layers were dried, contracted in vacuum to get the crude product. The crude mixture was further purification by column chromatography (PE/EA=4:1) to give compound 7A (320.00 mg, 37.04%) and 7B (70 mg, 8%) as yellow oil.

7A $^1$H NMR (400 MHz, $CDCl_3$): δ ppm: 7.30-7.45 (m, 5H), 5.11-5.27 (m, 2H), 4.28-4.64 (m, 1H), 3.21-4.05 (m, 5H), 1.60-2.20 (m, 4H).

7B $^1$H NMR (400 MHz, $CDCl_3$): δ ppm: 7.30-7.48 (m, 5H), 5.12-5.28 (m, 2H), 4.21-4.55 (m, 1H), 3.17-4.16 (m, 5H), 1.41-2.12 (m, 4H).

1.4.2.5 Preparation of Compound A07_Trans

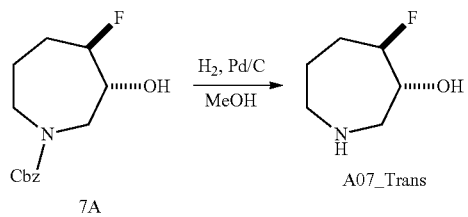 [SMILES: "MeOH" ; O=C(OCc1ccccc1)N1CCC[C@@H](F)[C@H](O)C1 ; O[C@@H]1CNCCC[C@H]1F]

To a solution of Compound 7A (460 mg, 1.72 mmol) in $CH_3OH$ (40 mL) was added $Pd(OH)_2$/C (85 mg). The formed mixture was hydrogenated 2.5 h under $H_2$ atmosphere. The catalyst was filtered and the filtrate was concentrated to give the desired product A07_Trans (220 mg, 96%). A08_Trans was prepared from 7B through the same procedure.

1.4.2.6 Preparation of Compound 8

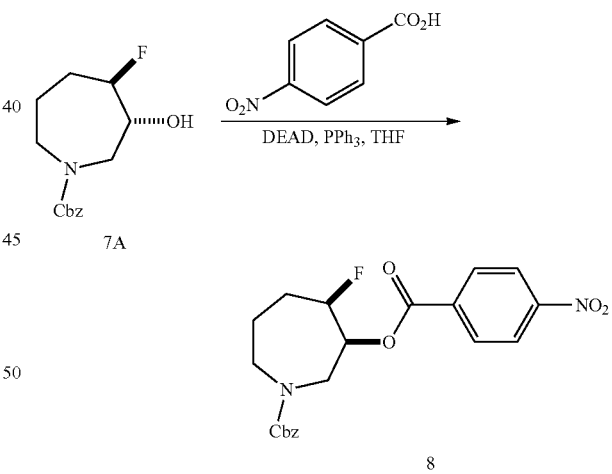

To a mixture of $PPh_3$ (471.00 mg, 1.80 mmol) in THF (2 mL) and DEAD (312.73 mg, 1.80 mmol) at 0° C., was added the 4-nitrobenzoic acid (300.10 mg, 1.80 mmol,) in THF (15 mL) dropwise, followed by a solution of compound 7A (400.00 mg, 1.50 mmol) in THF (2 mL). The reaction mixture was stirred at 25° C. for 12 h. TLC showed the starting material was consumed. Water (50 mL) was added. The reaction mixture was extracted by EA (35 ml*3). The organic layers were dried, concentrated in vacuo. The residue was purified by column chromatography (PE/EA=6/1, 4/1) to get the desired product compound 8 (200.00 mg, 32.10%). LCMS [M+1]: 417.

1.4.2.7 Preparation of Compound 9

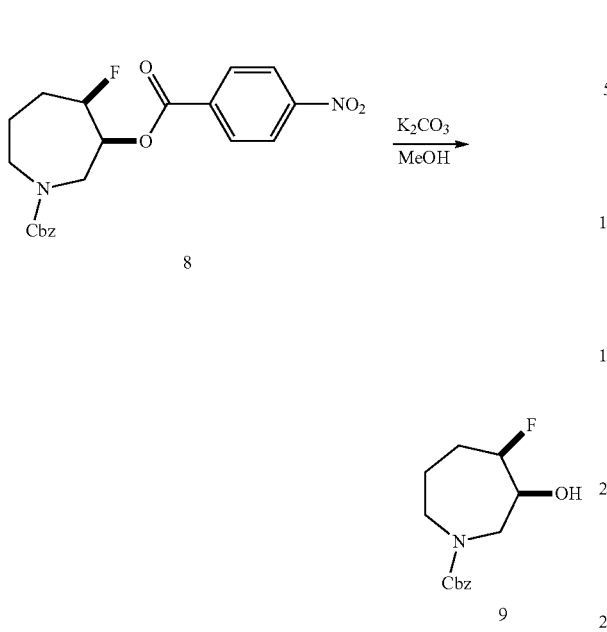

To a mixture of compound 8 (150.00 mg, 0.36 mmol) in MeOH (10 mL) was added K$_2$CO$_3$ (74.68 mg, 0.54 mmol). The mixture was stirred at 25° C. for 1.5 hr. TLC showed the reaction was completed. The mixture was purified directly by silica gel chromatography (PE/EA=6/1, 4/1) to afford compound 9 (70.00 mg, 72.70%) as yellow oil.

1.4.2.8 Preparation of Compound A07_Cis

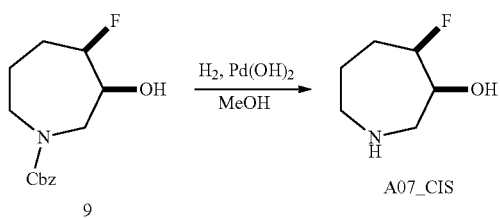

To a solution of Compound 9 (70 mg, 0.26 mmol) in CH$_3$OH (20 mL) was added Pd(OH)$_2$ (20 mg). The formed mixture was hydrogenated 2 h under H$_2$ atmosphere. The catalyst was filtered and the filtrate was concentrated to give the desired product C (34 mg, 97%).

A08_Cis was prepared from 7B through the same procedure.

1.5 Preparation of A09

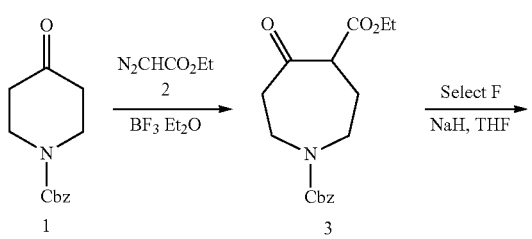

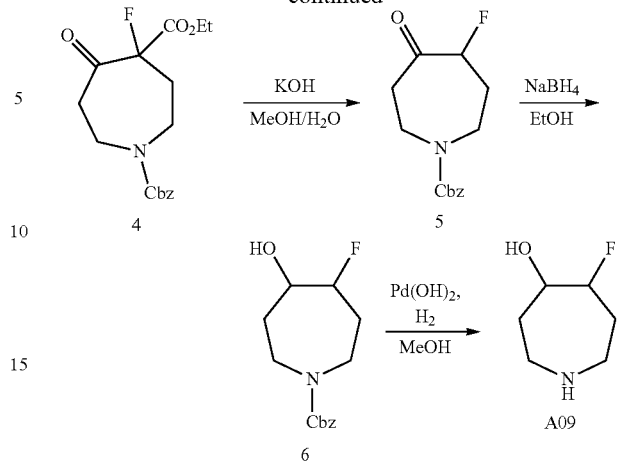

1.5.1.1 Preparation of Compound 3

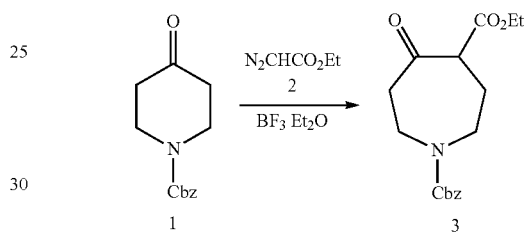

To a solution of Compound 1 (8.0 g, 34.3 mmol) and ethyl 2-diazoacetate (5.1 g, 44.7 mmol) in THF (160 mL) was added BF$_3$-Et$_2$O (4.3 mL, 34.3 mmol) at −78° C. under N$_2$. The reaction mixture was stirred at −78° C. for 1.5 h and then warmed to 28° C. slowly, and continued to stir for 1.5 h. The resulting mixture was quenched with NaHCO$_3$ and extracted with EA (500 mL). The organic layer was dried over Na$_2$SO$_4$ and concentrated in vacuo to give the crude product, which was purified by flash column chromatography to give the desired product (7.3 g, 67%). LCMS: 320.0 [M+1].

1.5.1.2 Preparation of Compound 4

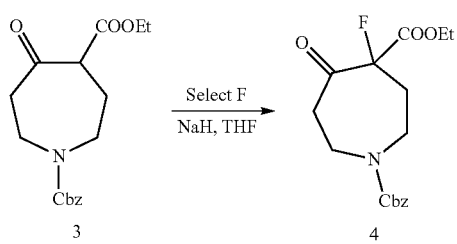 [SMILES: CCOC(=O)C1CCN(C(=O)OCc2ccccc2)CCC1=O ; CCOC(=O)C1(F)CCN(C(=O)OCc2ccccc2)CCC1=O]

To a suspension of NaH (464 mg, 11.6 mmol) in THF (40 mL) was added a solution of Compound 3 (3.7 g, 11.6 mmol) in THF (40 mL) at 0° C. under N$_2$, followed by a solution of Select F (4.4 g, 11.6 mmol) in DMF (20 mL) after 0.5 h. The reaction mixture was stirred at r.t. for 3 h. The resulting mixture was quenched with NH$_4$Cl (Sat.) and extracted with EA (300 mL). The organic layer was washed with brine, dried over Na$_2$SO$_4$ and concentrated in vacuo to give the crude product, which was purified by flash column chromatography to give the desired product (2.5 g, 64%). LCMS: 338.0 [M+1].

1.5.1.3 Preparation of Compound 5

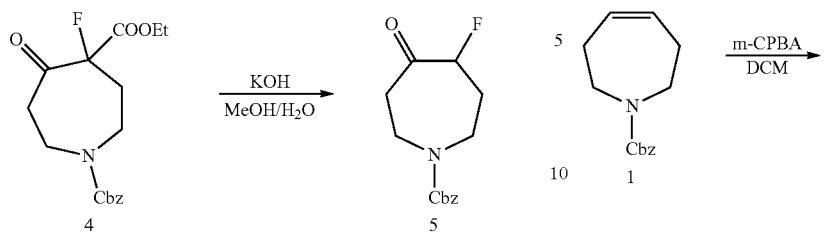

A mixture of compound 4 (2.5 g, 7.4 mmol) and KOH (0.62 g, 11.1 mmol) in MeOH/H$_2$O (20 mL/4 mL) was heated to 55° C. for 2 h. The mixture was diluted with EA (100 mL) and washed with brine (80 mL). The organic layer was dried over Na$_2$SO$_4$ and concentrated in vacuo to give the crude product, which was used in the next step directly (1.8 g, crude). LCMS: 266.0 [M+1].

1.5.1.4 Preparation of Compound 6

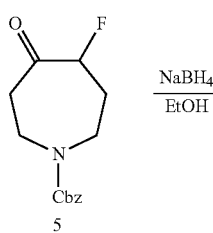

To a solution of compound 5 (1.8 g, 6.8 mmol) in EtOH (30 mL) was added NaBH$_4$ (0.39 g, 10.3 mmol) at 0° C., and the mixture was stirred at 25° C. for 2 h. The resulting mixture was quenched with NH$_4$Cl (sat.) and extracted with EA (150 mL). The organic layer was dried over Na$_2$SO$_4$ and concentrated in vacuo to give the crude product, which was purified by flash column chromatography to give the desired product (1.2 g, 66%). LCMS: 268.0 [M+1].

1.5.1.5 Preparation of Compound A09

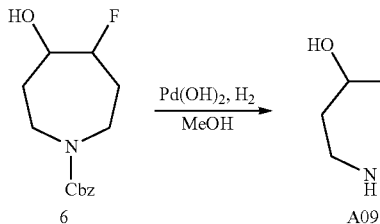

To a solution of Compound 6 (1.2 g, 4.5 mmol) in MeOH (50 mL) was added Pd(OH)$_2$/C (0.24 g). The mixture was hydrogenated at 25° C. for 16 h under 25 Psi pressure. The catalyst was filtered and the filtrate was concentrated in vacuo to give the crude product, which was used in the next step directly (0.59 g, 98%).

Synthesis of the Diastereomers:

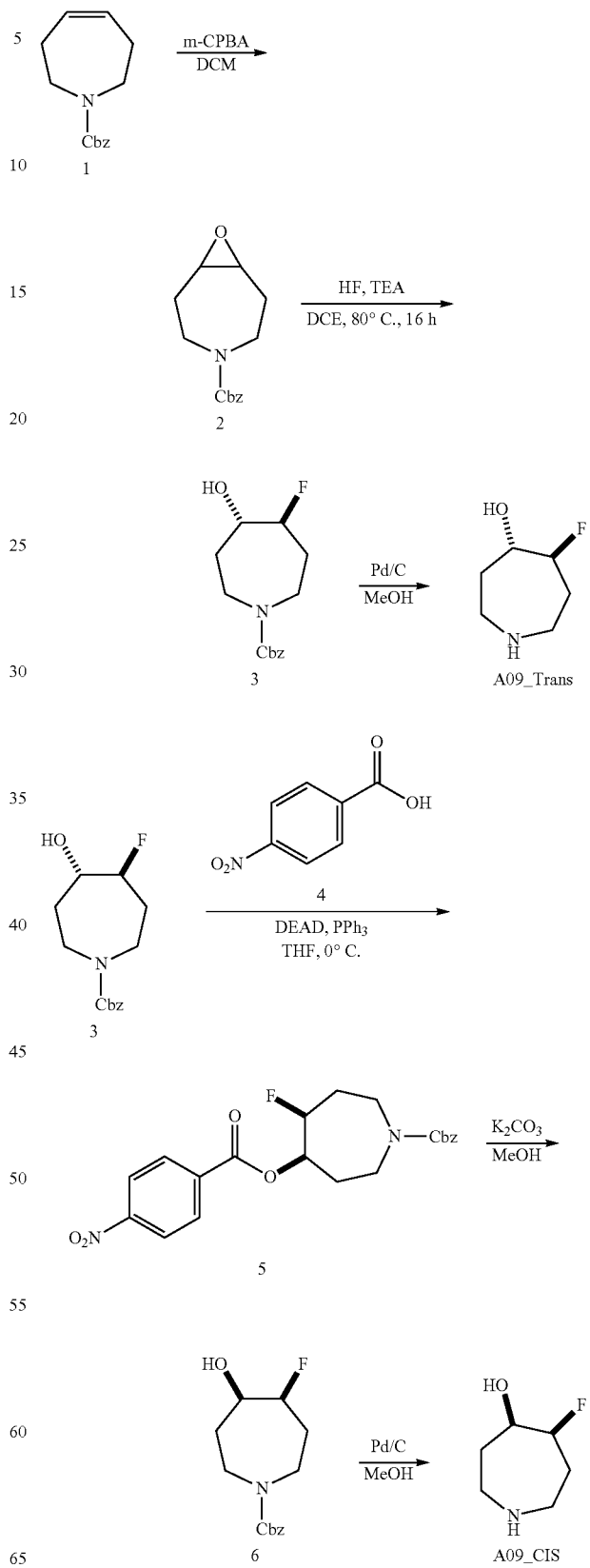

5.1.2.1 Preparation of Compound 2

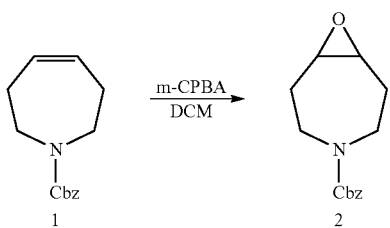

To a mixture of benzyl compound 1 (5.00 g, 21.62 mmol) in CH$_2$Cl$_2$ (100 mL) was added m-CPBA (9.33 g, 54.05 mmol) in one portion. The mixture was stirred at 25° C. for 1 h. The mixture was concentrated and the residue was purified by silica gel chromatography to afford compound 2 (2.70 g, 10.92 mmol, 50.50% yield) as yellow soil. $^1$H NMR (400 MHz, CHLOROFORM-d) δ=7.41-7.30 (m, 5H), 5.18-5.07 (m, 2H), 4.00-3.79 (m, 2H), 3.20 (t, J=4.5 Hz, 2H), 2.91-2.71 (m, 2H), 2.34-2.18 (m, 3H), 2.15-2.03 (m, 1H).

5.1.2.2 Preparation of Compound 3

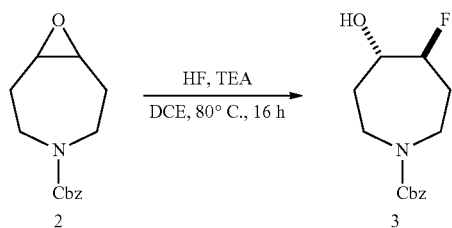 [SMILES: O=C(OCc1ccccc1)N1CCC2OC2CC1 ; O=C(OCc1ccccc1)N1CC[C@H](O)[C@@H](F)CC1]

Compound 2 (2.20 g, 8.90 mmol, 1.00 Eq) and HF-Et$_3$N (2.15 g, 13.35 mmol) were charged in a 100 mL single-necked round bottom flask. The mixture was stirred at 100° C. for 16 h under N$_2$. TLC showed the reaction was complete. Then it was diluted with DCM (100 mL), washed with brine (100 mL×2), dried over Na$_2$SO$_4$ and concentrated in vacuo. The residue was purified with column chromatography on silica gel (PE:EA=1:1) to give compound 3 (1.5 g, 5.61 mmol) as colorless oil. $^1$H NMR (400 MHz, CHLOROFORM-d) δ=7.42-7.28 (m, 5H), 5.14 (s, 2H), 4.51-4.29 (m, 1H), 3.90-3.58 (m, 3H), 3.48-3.25 (m, 2H), 2.29-2.07 (m, 2H), 1.99-1.84 (m, 1H), 1.72 (dt, J=5.0, 10.2 Hz, 1H).

5.1.2.3 Preparation of A09_Trans

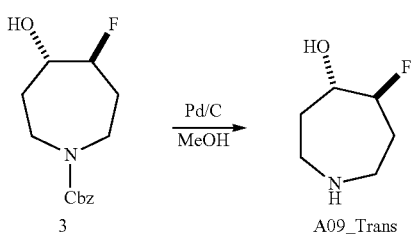 [SMILES: "MeOH" ; O=C(OCc1ccccc1)N1CC[C@H](O)[C@@H](F)CC1 ; O[C@H]1CCNCC[C@@H]1F]

To a solution of compound 3 (100.0 mg, 374.11 umol, 1.00 Eq) in MeOH (5 mL) was added Pd (OH)$_2$ (0.02 g) under N$_2$. The suspension was degassed under vacuum and purged with H$_2$ several times. The mixture was stirred under H$_2$ (50 psi) at 25° C. for 16 hours. The reaction mixture was filtered and the filter was concentrated to give A09_Trans (40.00 mg, 300.39 umol, 80.29% yield) as yellow solid.

5.1.2.4 Preparation of Compound 5

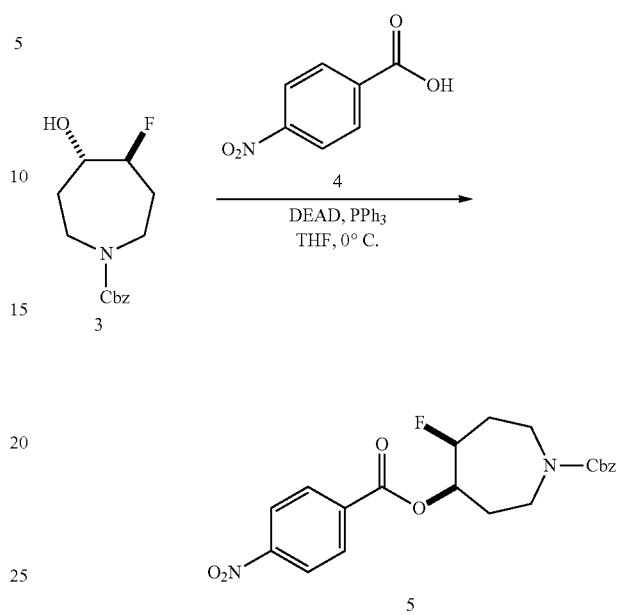

To a solution of compound 3 (400 mg, 1.5 mmol), compound 4 (0.3 g, 1.8 mmol) and PPh3 (0.47 g, 1.8 mmol) in THF (10 mL) was added DEAD (0.312 g, 1.8 mmol) in dry THF (10 mL) at 0° C. The reaction mixture was stirred for 16 h at 25° C. TLC showed reaction completed. The mixture was evaporated and the residue was purified with column chromatography on silica gel (PE:EA=10:1) to give compound 4 (0.5 g, 80%) as white solid.

5.1.2.5 Preparation of Compound 6

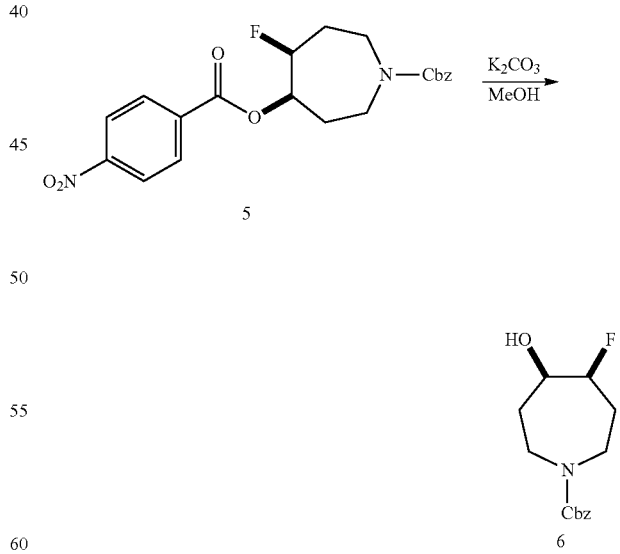

To a solution of compound 5 (500 mg, 1.2 mmol) in MeOH (10 mL) was added K$_2$CO$_3$ (165 mg, 1.2 mmol). The reaction mixture was stirred for 1 h at 25° C. TLC showed it was complete. The mixture was concentrated to give compound 6 (300 mg, crude) as yellow oil.

5.1.2.6 Preparation of A09_CIS

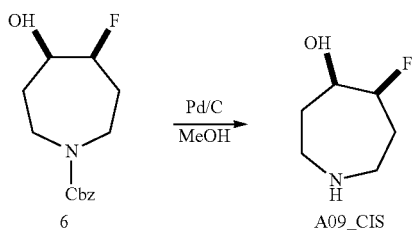 [SMILES: "MeOH" ; O=C(OCc1ccccc1)N1CC[C@@H](O)[C@@H](F)CC1 ; O[C@@H]1CCNCC[C@@H]1F]

To a solution of compound 6 (100.00 mg, 374.11 umol, 1.00 Eq) in MeOH (5 mL) was added Pd/C (0.02 g) under $N_2$. The suspension was degassed under vacuum and purged with $H_2$ several times. The mixture was stirred under $H_2$ (50 psi) at 25° C. for 16 hours. TLC (PE:EtOAc=1:1) showed the starting material was consumed completely. The reaction mixture was filtered and the filter was concentrated to give A09_CIS (40.00 mg, 300.39 umol, 80.29% yield) as colorless oil.

1.6 Preparation of A10

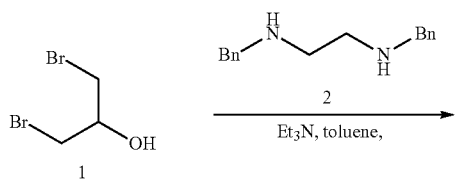

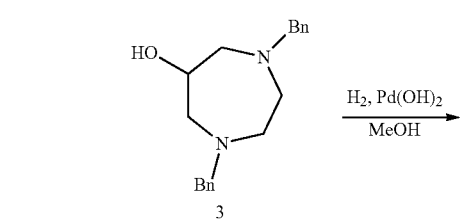

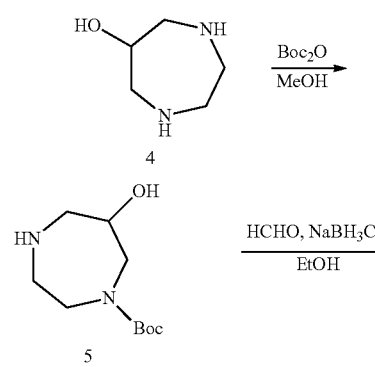

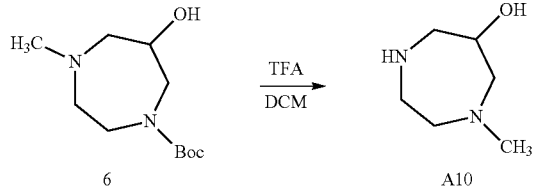

1.6.1 Preparation of Compound 3

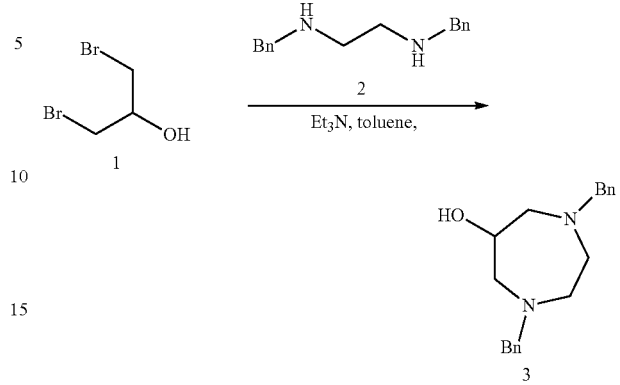

To a stirred solution of compound 1 (12.37 g, 56.5 mmol) and compound 2 (13.56 g, 56.5 mmol) in toluene (800 mL) was added $Et_3N$ (17.17 g, 170 mmol). The mixture was heated to 120° C. and stirred for 48 h. TLC showed starting material was consumed completely. The mixture was washed by saturated $NH_4Cl$ (100 mL) and concentrated in vacuo. The residue was purified by silica gel chromatography (PE:EA=2:1) to give compound 3 as yellow solid (6.9 g, yield: 41.2%). $^1$H NMR (400 MHz, $CDCl_3$) δ 7.47-7.21 (m, 10H), 3.87-3.61 (m, 5H), 2.97-2.41 (m, 8H).

LCMS: 297 [M+1].

1.6.2 Preparation of Compound 4

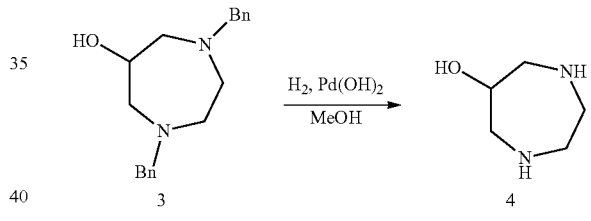

Compound 3 (2.2 g, 7.5 mmol) was dissolved in MeOH (80 mL), then $Pd(OH)_2$/C (500 mg) was added. The resulting mixture was hydrogenated overnight under $H_2$ atmosphere. TLC showed starting material was consumed completely. The catalyst was filtered and the filtrate was concentrated to give the desired compound 4 (0.8 g, 100%) as colorless oil. $^1$H NMR (400 MHz, MeOD) δ 3.89-3.71 (m, 1H), 2.97-2.63 (m, 8H).

1.6.3 Preparation of Compound 5

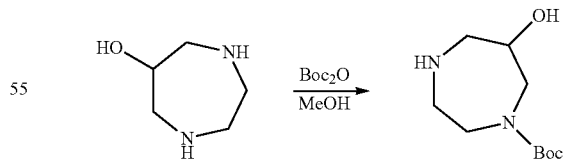

Compound 4 (522 mg, 4.5 mmol) was dissolved in MeOH (30 mL), then $Boc_2O$ (972 mg, 4.5 mmol) and $Et_3N$ (546 mg, 5.4 mmol) was added. The mixture was stirred at 15° C. for 12 hours. TLC showed starting material was consumed completely. The mixture was concentrated in vacuo. The residue was purification through silica gel column chromatography to give the desired compound 5 (860 mg, 92%) as colorless oil.

1.6.4 Preparation of Compound 6

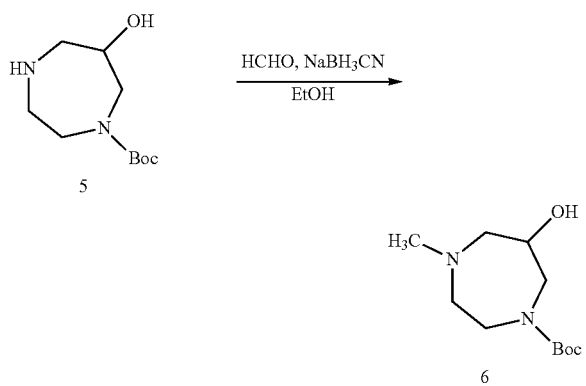

To a solution of compound 5 (972 mg, 4.5 mmol) in EtOH (20 mL) were added NaBH₃CN (837 mg, 13.5 mmol) and HCHO (1.5 g, 18 mmol) at room temperature, then the mixture was stirred at 15° C. for 4 h. TLC showed starting material was consumed completely. The mixture was concentrated in vacuo. The residue was purified by silica gel column (DCM: MeOH=20:1) to give compound 6 as colorless oil (610 mg, 59%). ¹H NMR (400 MHz, CDCl₃) δ 3.99-3.85 (m, 1H), 3.73-3.27 (m, 4H), 2.97-2.51 (m, 4H), 2.46-2.31 (m, 4H), 1.51 (s, 9H).

1.6.5 Preparation of Compound A10

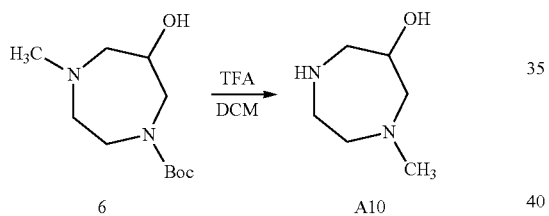

Compound 6 (300 mg, 1.3 mmol) was dissolved in DCM (20 mL), Then TFA (20 mL) was added. The resulting mixture was stirred at room temperature for 2 hours. TLC showed starting material was consumed completely. The solution was concentrated to give crude compound A10 (420 mg, crude) as TFA salt.

1.7 Preparation of A11/12

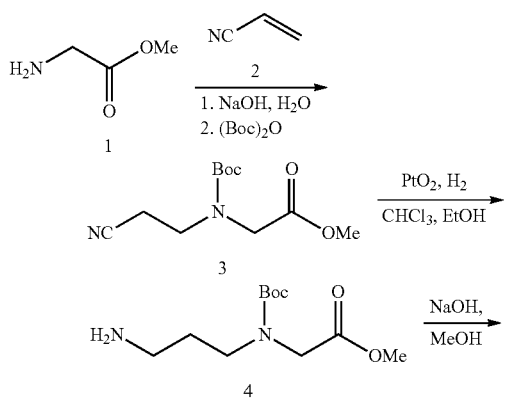

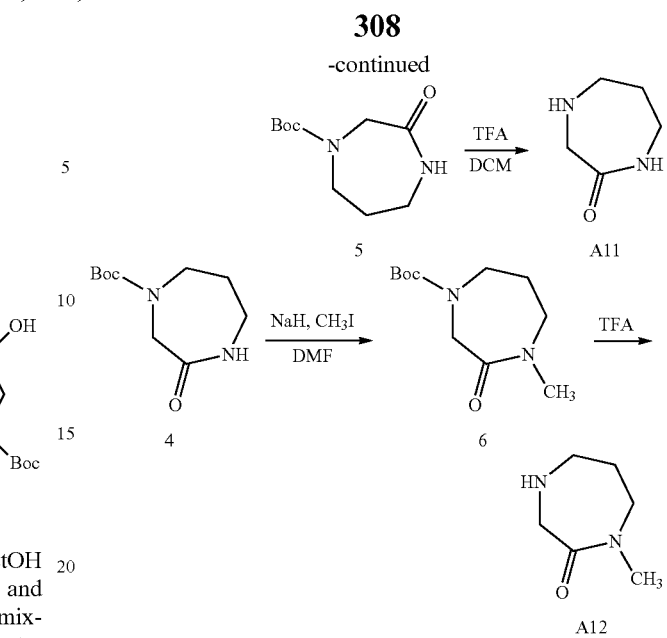

1.7.1 Preparation of Compound 3

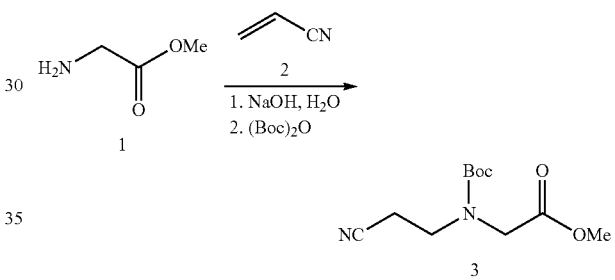

To a solution of Compound 1 (10 g, 80.0 mmol) and NaOH (3.6 g, 90.0 mmol) in H₂O (160 mL) was added Compound 2 (5.0 g, 100 mmol) at 0° C. The reaction mixture was heated to 75° C. for 3 h and then cooled to 25° C. (Boc)₂O (21 g, 100 mmol) was added and the mixture was continued to stir for 16 h. The reaction mixture was diluted with water, and extracted with EA (200 mL*2). The organic layer was dried over Na₂SO₄ and concentrated in vacuo to give the crude product, which was purified by flash column chromatography to give the desired product (11.2 g, 57%). ¹H NMR (400 MHz, CDCl₃): δ ppm: 4.03 (s, 2H), 3.78-3.77 (m, 3H), 3.60-3.57 (m, 2H), 2.72-2.67 (m, 2H), 1.51-1.45 (m, 9H).

1.7.2 Preparation of Compound 4

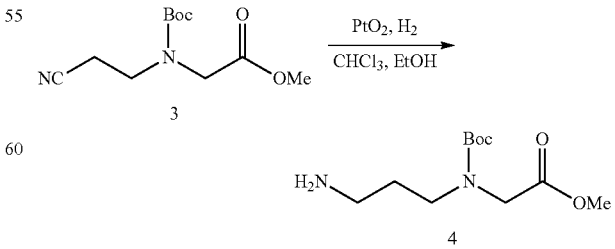

To a solution of Compound 3 (11.2 g, 46 mmol) in EtOH—CHCl₃ (200 mL/10 mL) was added PtO2 (1.0 g). The mixture was hydrogenated at 25° C. for 16 h under 50 Psi pressure of H2 atmosphere. The catalyst was filtered and the filtrate was concentrated to give the crude product, which was used in the next step directly (11.3 g, 99%). 1H NMR (400 MHz, CDCl$_3$): δ ppm: 8.45-8.43 (m, 2H), 3.91-3.89 (m, 2H), 3.76-3.73 (m, 3H), 3.51-3.48 (m, 2H), 3.21-3.19 (m, 2H), 2.10-1.99 (m, 2H), 1.50-1.44 (m, 9H).

1.7.3 Preparation of Compound 5

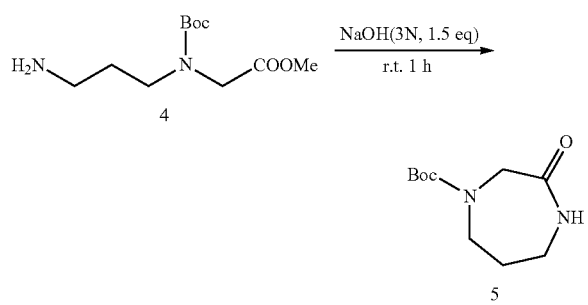

A solution of compound 4 (2.3 g, 9.3 mmol) in MeOH (20 mL) and NaOH (3N, 4 mL) was stirred at 25° C. for 2 h. TLC monitored that the reaction completed. The mixture was diluted with EA (150 mL) and washed with brine (100 mL). The organic layer was dried and concentrated to give the crude product, which was purified by column chromatography to give the desired product (1.25 g, 63%). $^1$H NMR (400 MHz, CDCl$_3$): δ ppm: 4.10-4.05 (m, 2H), 3.60-3.58 (m, 2H), 3.31-3.28 (m, 2H), 1.91-1.85 (m, 2H), 1.63-1.45 (m, 9H).

1.7.4 Preparation of Compound A11

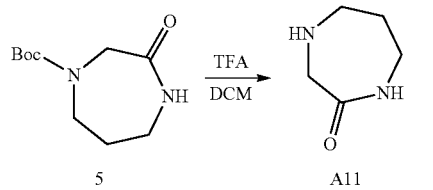

To a solution of compound 5 (0.5 g, 2.3 mmol) in DCM (5 mL) was added TFA (5 mL), and stirred at 25° C. for 2 h. TLC monitored that the reaction completed. The mixture was concentrated to give the crude product (780 mg, crude).

1.7.5 Preparation of Compound 6

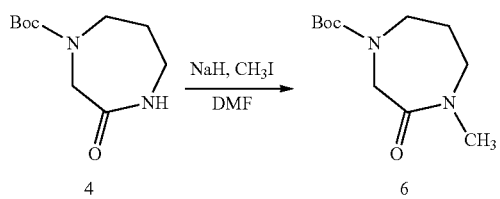

To a solution of compound 4 (800 mg, 3.7 mmol) in THF (20 mL) was added NaH (224 mg, 5.6 mmol), and stirred at 25° C. for 0.5 h. Then, MeI (795 mg, 5.6 mmol) was added. The mixture was stirred at room temperature until TLC monitored that the reaction completed. The mixture was quenched with water, diluted with EA (50 mL) and washed with brine (30 mL). The organic layer was dried and concentrated to give the crude product, which was purified by column chromatography to give the desired product (720 mg, 63%).

1.7.6 Preparation of Compound A12

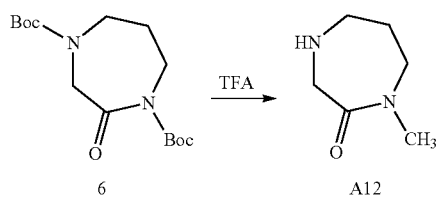

To a solution of compound 6 (720 mg, 2.3 mmol) in DCM (5 mL) was added TFA (5 mL), and stirred at 25° C. for 2 h. TLC monitored that the reaction completed. The mixture was concentrated to give the crude product (960 mg, crude).

1.8 Preparation of A13

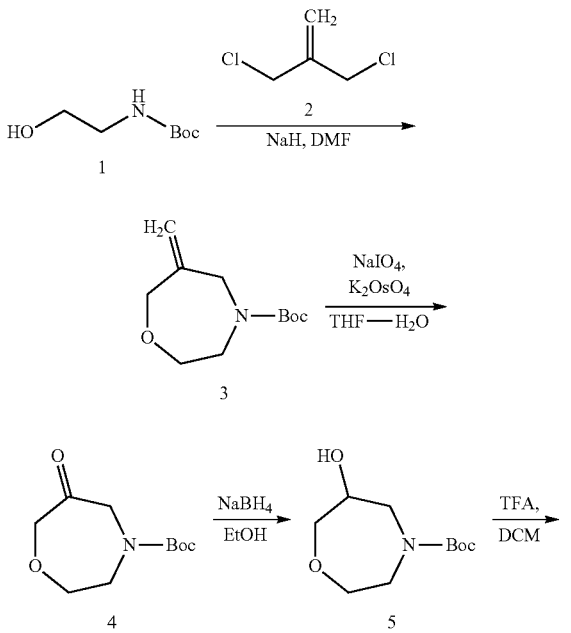

1.8.1 Preparation of Compound 3

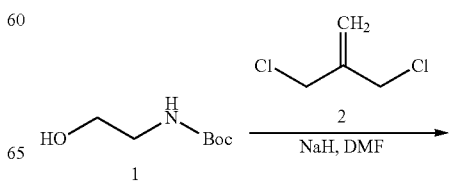

1.8.4 Preparation of Compound A13

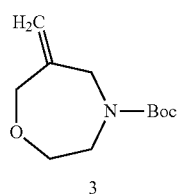

3

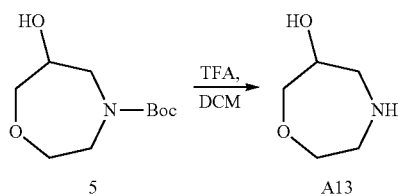

To a solution of Compound 1 (1.32 g, 10.5 mmol) in DMF (20 mL) was added NaH (960 mg, 24 mmol) at 0° C., the mixture was stirred at 0° C. for 30 min. Then compound 2 (1.61 g, 10 mmol) was added at 0° C. The mixture was stirred at 15° C. for 2 hours. TLC showed that starting material was consumed completely. Saturated NH$_4$Cl (100 mL) was added to quench the reaction. The solvent was removed in vacuo and the residue was extracted with EA (100 mL*2). The organic layer was concentrated and purified by silica gel column (PE:EA=4:1) to give compound 3 (1.1 g, yield: 51%) as colorless oil. $^1$H NMR (400 MHz, CDCl$_3$): δ: 5.12-4.91 (m, 2H), 4.29-4.03 (m, 4H), 3.76-3.45 (m, 4H), 1.47 (s, 9H).

Compound 5 (420 mg, 2 mmol) was dissolved in DCM (20 mL), Then TFA (20 mL) was added. The resulting mixture was stirred at room temperature for 2 hours. TLC showed starting material was consumed completely. The solution was concentrated to give desired crude compound 5 (620 mg, 100%) as TFA salt, used in next step directly.

1.9 Preparation of A15

1.8.2 Preparation of Compound 4

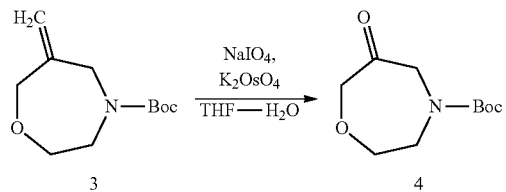

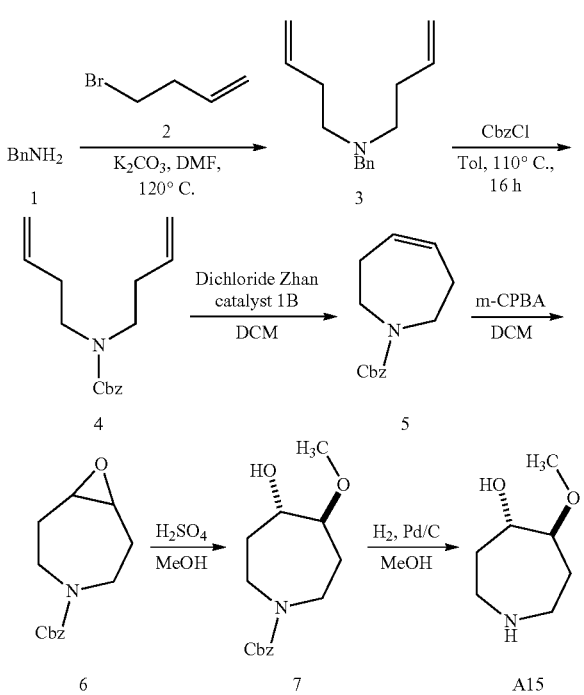

To a solution of compound 3 (212 mg, 1 mmol) in THF/H$_2$O (3 mL/3 mL) were added K$_2$OsO$_4$·2H$_2$O (18 mg, 0.05 mmol) and NaIO$_4$ (491 mg, 2.3 mmol) at room temperature, then the mixture was stirred at 15° C. for 4 h. TLC showed starting material was consumed completely. The mixture was concentrated in vacuo. The residue was purified by silica gel column (PE:EA=5:1) to give compound 4 as yellow oil (170 mg, 77%). LCMS: 216 [M+1].

1.8.3 Preparation of Compound 5

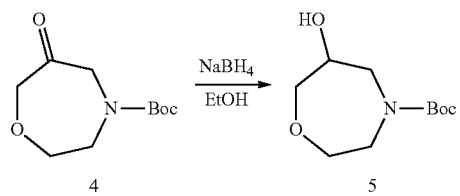 [SMILES: "EtOH" ; CC(C)(C)OC(=O)N1CCOCC(=O)C1 ; "NaBH4" ; CC(C)(C)OC(=O)N1CCOCC(O)C1]

1.9.1 Preparation of Compound 3

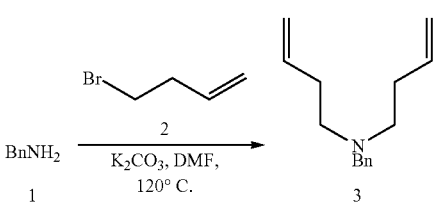

To a solution of compound 4 (425 mg, 2 mmol) in EtOH (10 mL) was added NaBH$_4$ (150 mg, 4 mmol). The mixture was stirred at 15° C. for 4 h. TLC showed starting material was consumed. Saturated NH$_4$Cl (20 mL) was added to quench the reaction. The mixture was concentrated in vacuo. The residue was extracted with EA (50 mL), dried over Na$_2$SO$_4$ and concentrated in vacuo to give the desired compound 5 (370 mg, 87%) as colorless oil.

A mixture of Compound 1 (8.7 g, 65.7 mmol), Compound 2 (3.5 g, 32.7 mmol) and K$_2$CO$_3$ (9.06 g, 65.7 mmol) in DMF (120 mL) was heated to 100° C. for 16 h. The mixture was diluted with EA (100 mL), and washed with H$_2$O (100 mL*3). The organic phase was dried over Na$_2$SO$_4$ and concentrated in vacuo to give the crude product, which was purified by column chromatography to give the desired product 3 as colorless oil (5.1 g, 72.5%). LCMS: 256 [M+1].

1.9.2 Preparation of Compound 4

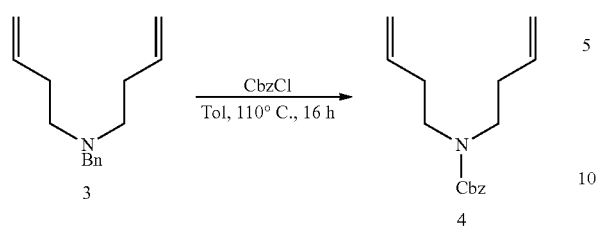

To a solution of Compound 3 (1.5 g, 6.97 mmol) in toluene (15 mL) was added CbzCl (1.42 g, 8.37 mmol). The mixture was heated to 110° C. for 16 h. The mixture was concentrated in vacuo. The residue was dissolved with water and EA. The organic layer was washed with aq. Na₂CO₃, dried over Na₂SO₄ and concentrated in vacuo to give the crude product, which was purified by column chromatography to give the desired product 4 as colorless oil (1.24 g, Yield: 68.9%). LCMS: 260 [M+1].

1.9.3 Preparation of Compound 5

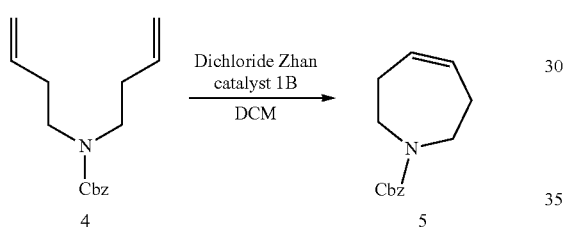

To a solution of Compound 4 (1.0 g, 3.86 mmol) in DCM (60 mL) was added Dichloride Zhan catalyst 1B (150 mg, CAS: 918870-76-5). The mixture was purged with N₂ for 10 min and stirred at 20° C. for 16 h. The mixture was concentrated in vacuo to give the crude product, which was purified by column chromatography to give the desired product 5 as colorless oil (800 mg, Yield: 89.7%). LCMS: 232 [M+1].

1.9.4 Preparation of Compound 6

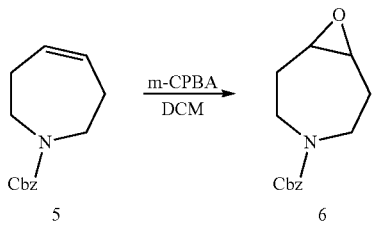 [SMILES: O=C(OCc1ccccc1)N1CCC=CCC1 ; "m-CPBA" ; O=C(OCc1ccccc1)N1CCC2OC2CC1]

To a solution of compound 5 (800 mg, 3.46 mmol) in DCM (30 mL), was added m-CPBA (774 mg, 4.5 mmol). The mixture stirred at room temperature for 5 hours. The solution was quenched by aq. Na₂SO₃, and extracted with DCM (60 mL*2). The organic combined phase was dried over Na₂SO₄, and concentrated to give desired compound 7 as colorless oil (812 mg, Yield: 95.9%). LCMS: 248 [M+1].

1.9.5 Preparation of Compound 7

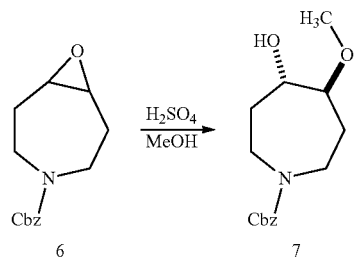

Compound 6 (812 mg, 3.31 mmol) was dissolved in MeOH (10 mL), then concentrated H₂SO₄ (200 mg) was added. The mixture stirred at room temperature for 1 h. The solution was neutralized with aq.Na₂CO₃ to pH=7. The resulting mixture was concentrated in vacuo. The residue was extracted with EA (60 mL*2). The combined organic phase was dried over Na₂SO₄, and concentrated in vacuo to give the crude product, which was purified by column chromatography to give the desired product 8 as colorless oil (778 mg, Yield: 84.9%). LCMS: 280 [M+1].

1.9.6 Preparation of Compound A15

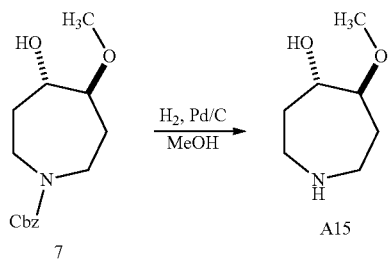

To a solution of Compound 7 (778 mg, 2.8 mmol) in MeOH (70 mL) was added Pd(OH)₂/C (100 mg) under N₂. The mixture was stirred under H₂ balloon at 23° C. for 2 h. The mixture was filtrated. The filtrates was concentrated to give the desired product 8 (310 mg, Yield: 78%).

1.10 Preparation of A16/17/18

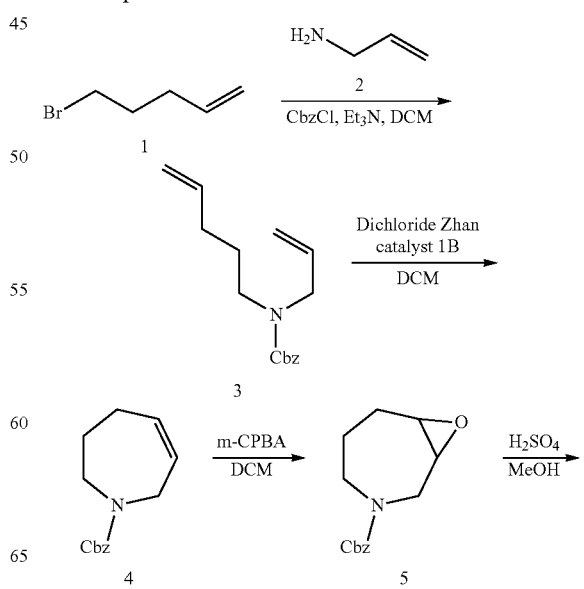

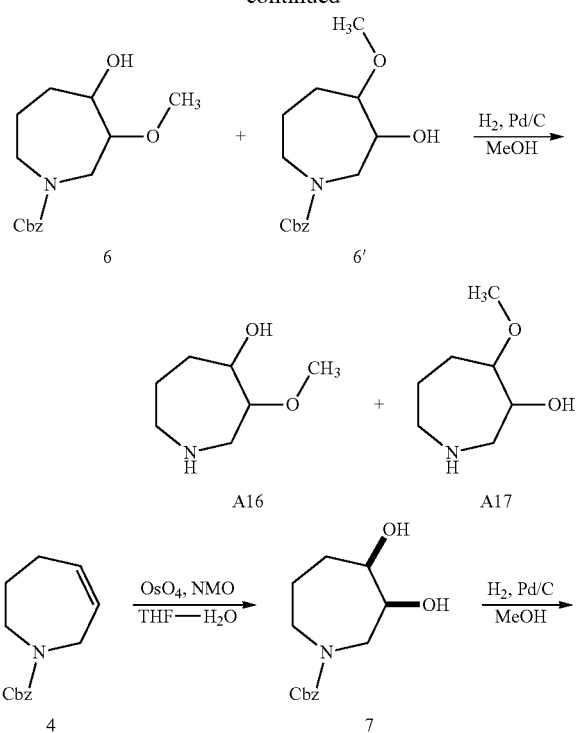

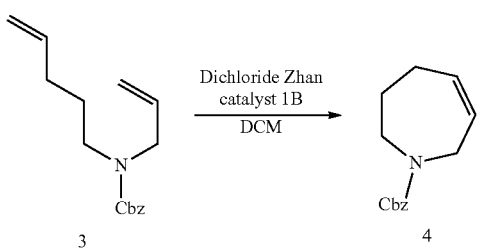

1.10.1 Preparation of Compound 3

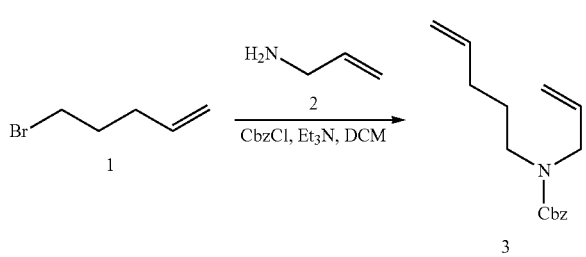

A mixture of Compound 1 (5.0 g, 33.7 mmol) and Compound 2 (6.0 g, 101.3 mmol) was heat to 80° C. for 16 h. The mixture was concentrated in vacuo. The residue was dissolved with DCM (100 mL). Et$_3$N (7.6 g, 75.6 mmol) followed by CbzCl (12.8 g, 75.6 mmol) at 0° C. The reaction mixture was stirred at rt for 16 h. The mixture was diluted with DCM (100 mL) and washed with water (100 mL). The organic layer was dried over Na$_2$SO$_4$ and concentrated in vacuo to give the crude product which was purified by column chromatography on silica gel (PE:EA=10:1) to give Compound 4 (4.4 g, 34%). LCMS: 260 [M+1]. $^1$H NMR (400 MHz, MeOD) δ 7.49-7.22 (m, 5H), 5.95-5.67 (m, 2H), 5.13 (s, 4H), 5.08-4.91 (m, 2H), 3.91 (d, J=5.6 Hz, 2H), 3.31-3.23 (m, 2H), 2.02 (s, 2H), 1.74-1.57 (m, 2H).

1.10.3 Preparation of Compound 4

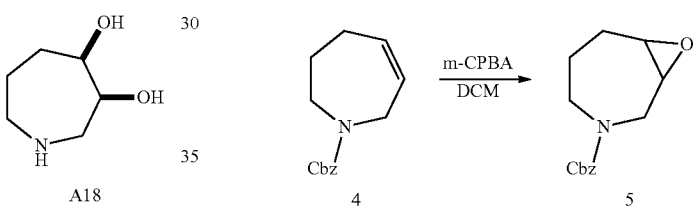

To a solution of Compound 3 (2.0 g, 7.7 mmol) in DCM (100 mL) was added Dichloride Zhan catalyst 1B (236 mg, CAS: 918870-76-5). The reaction mixture was stirred at rt for 16 h under N$_2$ atmosphere. The mixture was concentrated in vacuo to give the crude product which was purified by column chromatography on silica gel (PE:EA=10:1) to give Compound 4 (1.28 g, 72%) as darkness liquid. LCMS: 232 [M+1]. $^1$H NMR (400 MHz, MeOD) δ 7.40-7.27 (m, 5H), 5.95-5.62 (m, 2H), 5.13 (d, J=3.5 Hz, 2H), 3.99 (d, J=2.8 Hz, 2H), 3.63 (d, J=6.1 Hz, 2H), 2.28-2.19 (m, 3H), 1.89-1.75 (m, 2H).

1.10.4 Preparation of Compound 5

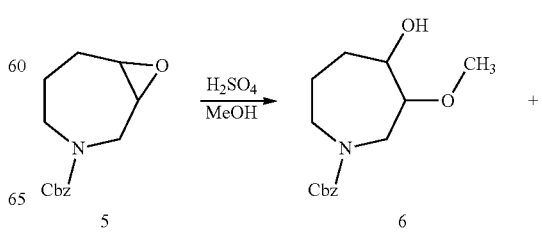

To a solution of Compound 5 (900 mg, 3.9 mmol) in DCM (40 mL) was added m-CPBA (1.34 g, 7.8 mmol), and stirred at rt for 16 h. TLC showed materials was consumed completed. The reaction mixture was quenched with Na$_2$SO$_3$ solution and extracted with DCM (20 mL). The organic layer was dried over Na$_2$SO$_4$ and concentrated in vacuo to give the crude product which was purified by column chromatography on silica gel (PE:EA=30:1) to give Compound 6 (900 mg, 83%) as colorless liquid. LCMS: 248 [M+1]. $^1$H NMR (400 MHz, MeOD) δ 7.37 (s, 6H), 5.19-5.08 (m, 2H), 4.32-4.18 (m, 1H), 3.86-3.74 (m, 1H), 3.56-3.38 (m, 1H), 3.19-3.08 (m, 2H), 2.80-2.66 (m, 1H), 2.31-2.17 (m, 1H), 2.02-1.94 (m, 1H), 1.79-1.51 (m, 2H).

1.10.5 Preparation of Compound 6 and 6'

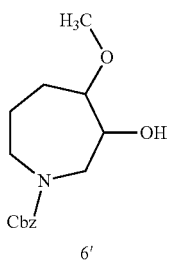

To a solution of Compound 6 (700 mg, 2.83 mmol) in MeOH (40 mL) was added concentrated H₂SO₄ (0.1 mL) at rt and the solution was stirred for 1 h. TLC showed materials was consumed completed. An aqueous solution of NaHCO₃ (1 mL) was added to neutralize the reaction mixture. The resulting mixture was concentrated in vacuo, then EtOAc (40 mL) and water (20 mL) was added to dissolve the residue. The organic layer was dried over Na₂SO₄ and concentrated in vacuo to give the crude product which was purified by column chromatography on silica gel (PE:EA=10:1) to give a mixture of Compound 7B and 7C (700 mg, yield 88.6%) as colorless liquid.

1.10.6 Preparation of Compound A16 and A11

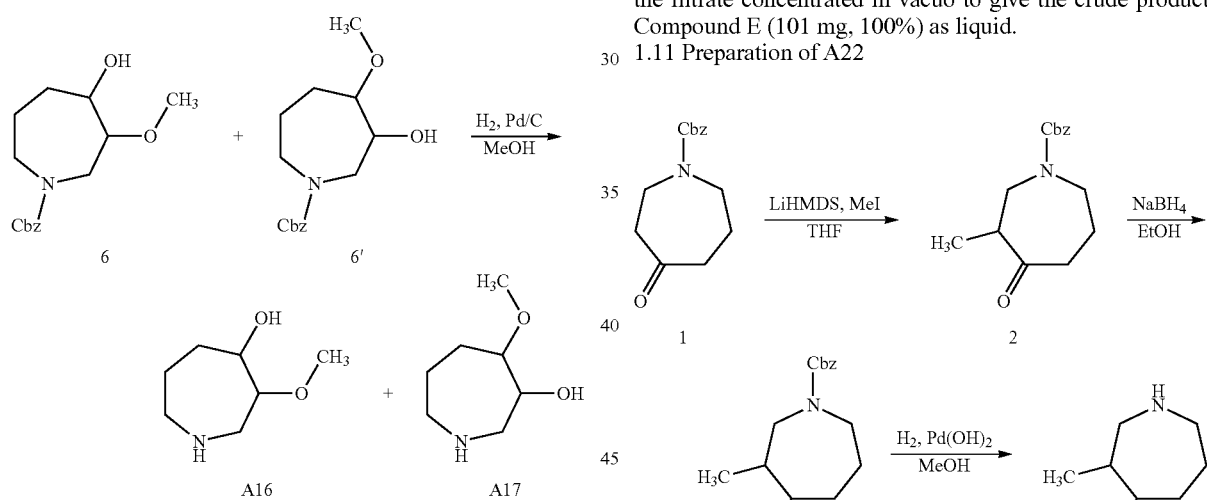

To a solution of a mixture of Compound 7B and 7C (800 mg, 2.86 mmol) in MeOH (20 mL) was added Pd(OH)₂/C (200 mg) and the mixture was stirred for 4 h under H₂ balloon. TLC showed materials was consumed completed the solution was filtered and the filtrate concentrated in vacuum to give a mixture of Compound C and D (370 mg, yield 88%) as liquid.

1.10.7 Preparation of Compound 7

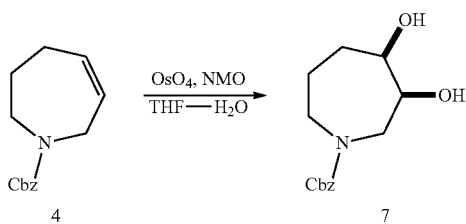

To a solution of Compound 4 (260 mg, 1.12 mmol) in THF (5 mL) and water (2 mL) was added OsO₄ (60 mg), followed by NMO (131 mg). The reaction was stirred at rt for 3 h. TLC showed materials was consumed completed. The mixture was diluted with water and extracted with EtOAc (30 mL). The organic layer was dried over Na₂SO₄ and concentrated in vacuo to give the crude product Compound 8 (186 mg, 62%) as colorless liquid. LCMS: 266 [M+1]. ¹H NMR (400 MHz, MeOD) δ 7.43-7.29 (m, 5H), 5.21-5.07 (m, 2H), 3.88-3.81 (m, 1H), 3.81-3.65 (m, 3H), 3.32-3.17 (m, 2H), 2.02-1.87 (m, 2H), 1.74-1.45 (m, 2H).

1.10.8 Preparation of Compound A18

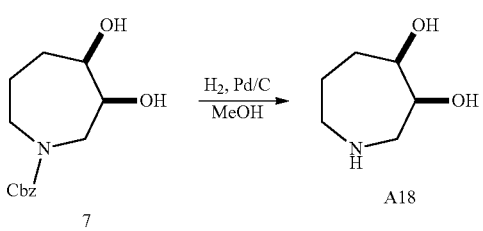

To a solution of Compound 7 (186 mg, 0.77 mmol) in MeOH (20 mL) was added Pd(OH)₂/C (40 mg) at rt and was stirred for 4 h under H₂ balloon. The mixture was filtered and the filtrate concentrated in vacuo to give the crude product Compound E (101 mg, 100%) as liquid.

1.11 Preparation of A22

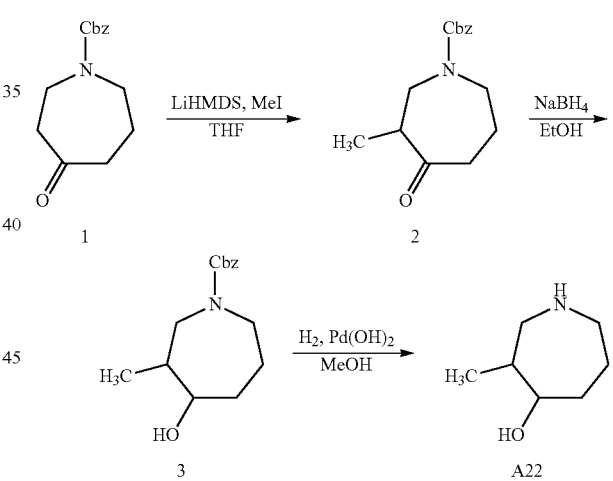

1.11.1 Preparation of Compound 2

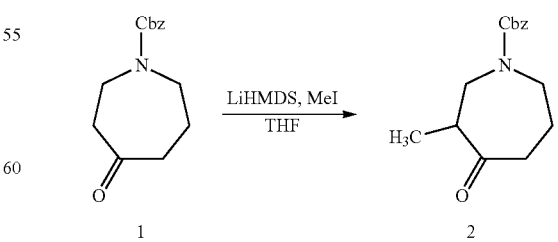

To a solution of Compound 1 (0.5 g, 2.0 mmol) in THF (30 mL) was added LiHMDS (4.0 mL, 4.0 mmol) at −78° C. under N₂. The reaction mixture was stirred at −78° C. for 2 h.

MeI (0.86 g, 6.0 mmol) was added to the mixture at −78° C., then warmed to 28° C. slowly and stirred for 1.5 h.

The resulting mixture was quenched with H₂O and extracted with EA (50 mL). The organic layer was dried over Na₂SO₄ and concentrated in vacuo to give a crude product, which was purified by flash column chromatography to give Compound 2 (0.4 g, 75%). 1H NMR (400 MHz, CHLOROFORM-d) δ 7.29-7.41 (m, 1H), 5.03-5.23 (m, 1H), 3.84-4.22 (m, 1H), 2.60-3.23 (m, 2H), 2.46-2.59 (m, 1H), 1.69-1.90 (m, 2H), 1.09 (dd, J=6.84, 15.12 Hz, 3H), LCMS: 262.0 [M+1].

1.11.3 Preparation of Compound 3

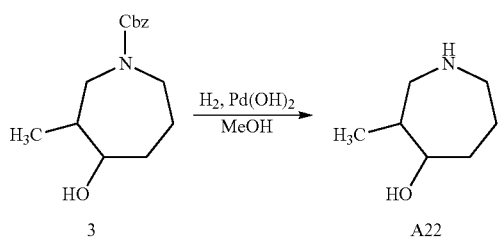

To a solution of compound 2 (1.2 g, 4.6 mmol) in EtOH (20 mL) was added NaBH₄ (259 mg, 6.8 mmol) at 0° C., and the mixture was stirred at 25° C. for 2 h. The resulting mixture was quenched with NH₄Cl (sat.) and extracted with EA (80 mL). The organic layer was dried over Na₂SO₄ and concentrated in vacuo to give the crude product, which was purified by flash column chromatography to give the desired product (650 mg, 54%). LCMS: 264.0 [M+1].

1.11.4 Preparation of Compound A22

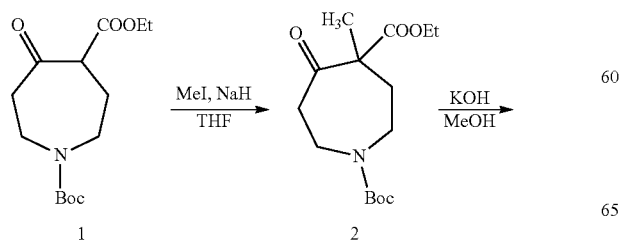

To a solution of Compound 3 (0.26 g, 1.0 mmol) in MeOH (25 mL) was added Pd(OH)₂ (50 mg). The mixture was hydrogenated at 25° C. for 16 h under 25 Psi pressure. The catalyst was filtered and the filtrate was concentrated to give the crude product, which was used in the next step directly (0.1 g, 77%).

1.12 Preparation of A23

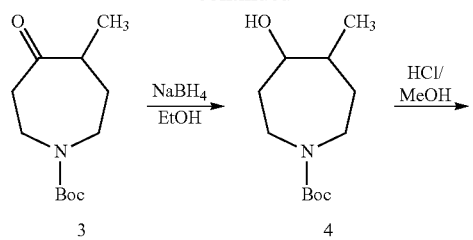

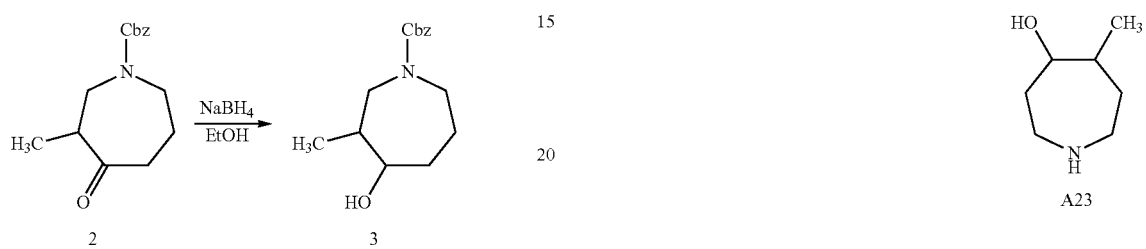

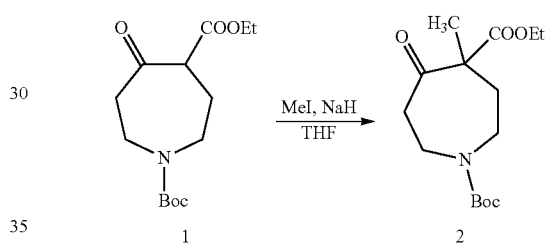

1.12.1 Preparation of Compound 2

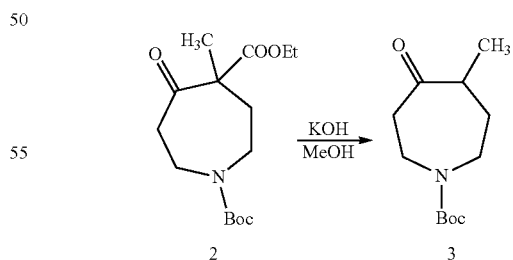

To a solution of Compound 1 (2.0 g, 7.0 mmol) in THF (50 mL) was added NaH (336 mg, 8.4 mmol) at 0° C. under N₂. The reaction mixture was stirred at 0° C. for 0.5 h. MeI (1.5 g, 10.5 mmol) was added to the mixture at 0° C., then warmed to 28° C. slowly and stirred for 16 h. The resulting mixture was quenched with H₂O and extracted with EA (50 mL). The organic layer was dried over Na₂SO₄ and concentrated in vacuo to give a crude product, which was purified by flash column chromatography to give Compound 2 (1.5 g, 71.4%).

1.12.2 Preparation of Compound 3

A mixture of compound 2 (1.5 g, 5 mmol) and KOH (0.5 g, 9.0 mmol) in MeOH/H₂O (20 mL/4 mL) was heated to 55° C. for 2 h. The mixture was diluted with EA (80 mL) and washed with brine (60 mL). The organic layer was dried over Na₂SO₄ and concentrated in vacuo to give a crude product, which was used in the next step directly (1.5 g, 94%).

1.12.3 Preparation of Compound 4

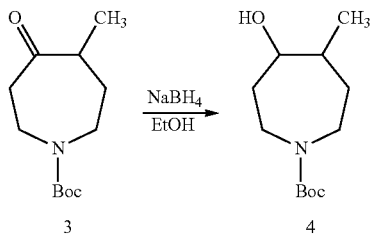

To a solution of compound 3 (1.3 g, 5.7 mmol) in EtOH (20 mL) was added NaBH₄ (260 mg, 6.9 mmol) at 0° C., and the mixture was stirred at 25° C. for 2 h. The formed mixture was quenched with NH₄Cl (Sat.) and extracted with EA (80 mL). The organic layer was dried over Na₂SO₄ and concentrated in vacuo to give a crude product, which was purified by flash column chromatography to give the desired product (821 mg, 63%).

1.12.4 Preparation of Compound A23

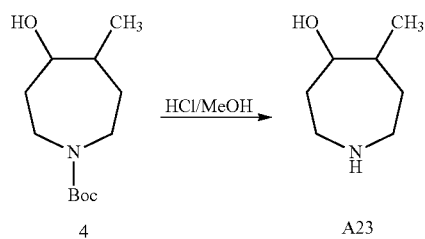

To a solution of Compound 4 (0.82 g, 3.6 mmol) in MeOH (10 mL) was added HCl/MeOH (4 mL, 4 M). The mixture was stirred at 25° C. for 2 h. The mixture was concentrated to give the crude HCl salt, which was used in the next step directly (760 mg, crude HCl salt).

1.13 Preparation of A24

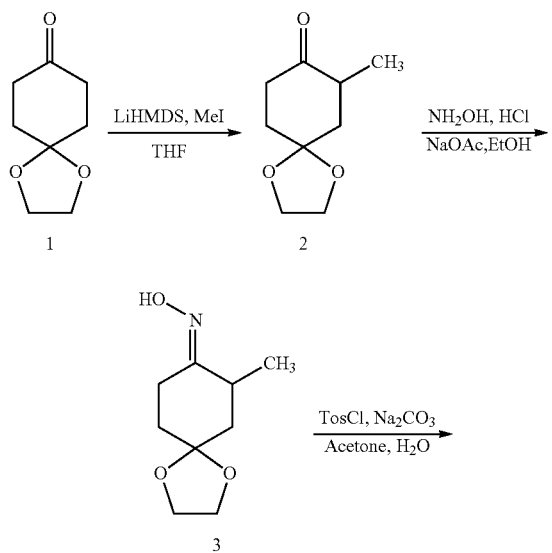

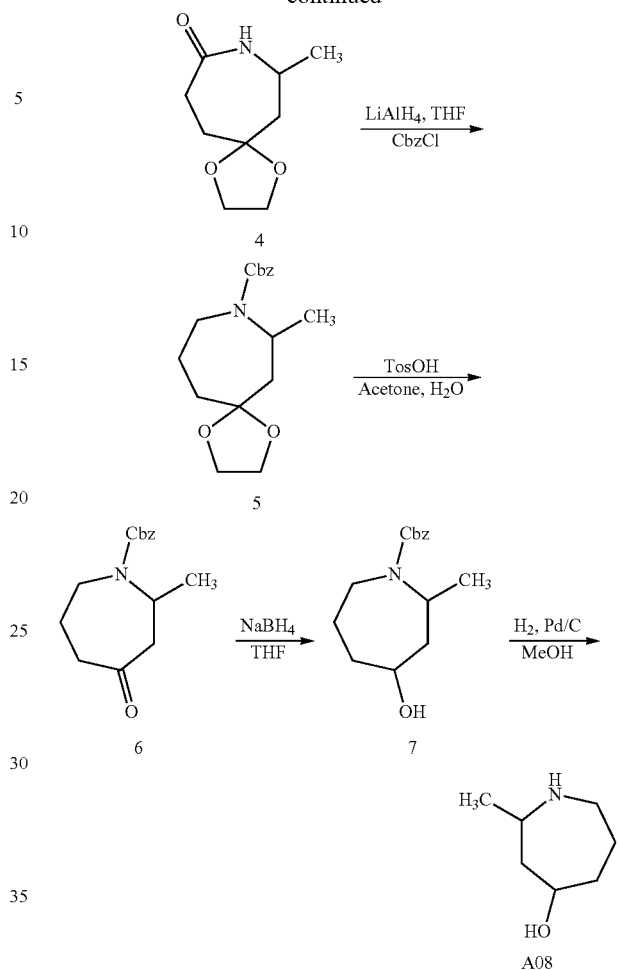

1.13.1 Preparation of Compound 2

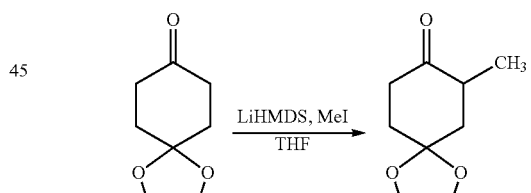

To a solution of Compound 1 (1 g, 6.4 mmol) in THF (30 mL) was added LiHMDS (12.8 mL, 12.8 mmol) at −78° C. under N₂. The reaction mixture was stirred at −78° C. for 2 h. MeI (2.7 g, 19.2 mmol) was added to the mixture at −78° C., then warmed to 28° C. slowly and stirred for 15 h. The resulting mixture was quenched with H₂O and extracted with EA (50 mL). The organic layer was dried over Na₂SO₄ and concentrated in vacuo to give a crude product, which was purified by flash column chromatography to give Compound 2 (0.62 g, 57%). ¹H NMR (400 MHz, CHLOROFORM-d) δ 3.92-4.17 (m, 4H), 2.55-2.83 (m, 2H), 2.31-2.43 (m, 1H), 1.87-2.13 (m, 3H), 1.69-1.81 (m, 1H), 1.04 (d, J=6.65 Hz, 3H). LCMS: 171.0 [M+1].

1.13.2 Preparation of Compound 3

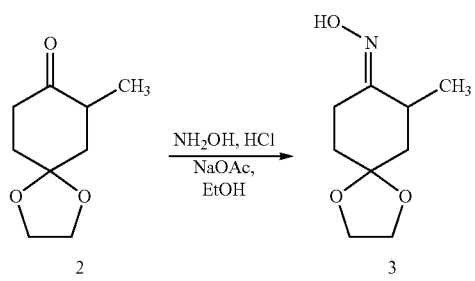

To a solution of Compound 2 (0.5 g, 2.9 mmol) in EtOH/H₂O (20/1 mL) was added NH₂OH.HCl (1.0 g, 14.7 mmol) and NaOAc (0.7 g, 8.8 mmol). The mixture was stirred at 25° C. for 16 h. The resulting mixture was diluted with EA (80 mL) and washed with brine (60 mL). The organic layer was dried over Na₂SO₄ and concentrated in vacuo to give a crude product, which was purified by flash column chromatography to give Compound 3 (0.4 g, 73%). LCMS: 186.0 [M+1].

1.13.3 Preparation of Compound 4

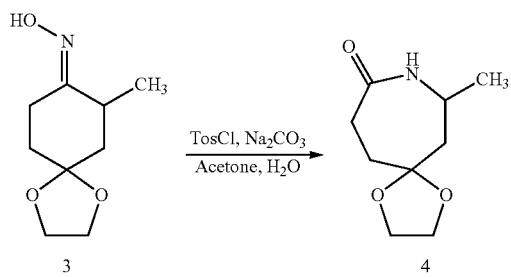

To a solution of Compound 3 (1.0 g, 5.4 mmol) in Actone (20 mL) was added TosCl (1.5 g, 8.1 mmol). NaOAc (1.7 g, 16.2 mmol) in H₂O (30 mL) was added to the mixture. The mixture was stirred at 16° C. for 2 h, then warmed to 40° C. slowly and stirred for 16 h. The resulting mixture was diluted with DCM (200 mL) and washed with brine (60 mL). The organic layer was dried over Na₂SO₄ and concentrated in vacuo to give a crude product, which was purified by flash column chromatography to give Compound 4 (0.9 g, 83%).

1.13.4 Preparation of Compound 5

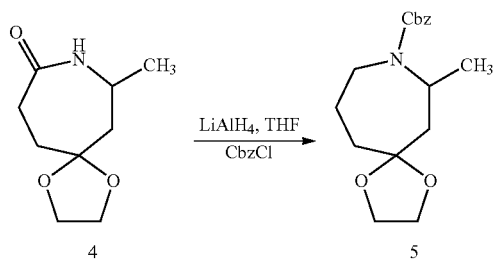 [SMILES: "CbzCl" ; CC1CC2(CCC(=O)N1)OCCO2 ; CC1CC2(CCCN1C(=O)OCc1ccccc1)OCCO2]

To a solution of Compound 4 (0.9 g, 4.8 mmol) in THF (15 mL) was added LiAlH₄ (0.27 g, 7.2 mmol) at 16° C. The mixture was stirred at 16° C. for 5 h. The mixture was quenched with water and filtered, then CbzCl (1.2 g, 7.2 mmol) was added to the solution. The mixture was stirred at 40° C. for 12 h. The resulting mixture was diluted with EA (20 mL) and washed with brine (20 mL). The organic layer was dried over Na₂SO₄ and concentrated in vacuo to give a crude product, which was purified by flash column chromatography to give Compound 5 (0.75 g, 60%).

1.13.4 Preparation of Compound 5

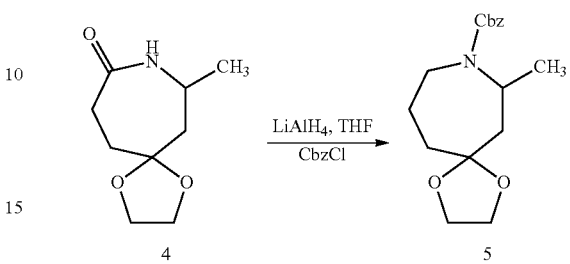

To a solution of Compound 4 (0.9 g, 4.8 mmol) in THF (15 mL) was added LiAlH₄ (0.27 g, 7.2 mmol) at 16° C. The mixture was stirred at 16° C. for 5 h. The mixture was quenched with water and filtered. t CbzCl (1.2 g, 7.2 mmol) was added to the filtrate. The mixture was stirred at 40° C. for 12 h. The resulting mixture was diluted with EA (20 mL) and washed with brine (20 mL). The organic layer was dried over Na₂SO₄ and concentrated in vacuo to give a crude product, which was purified by flash column chromatography to give Compound 5 (0.75 g, 60%).

1.13.5 Preparation of Compound 6

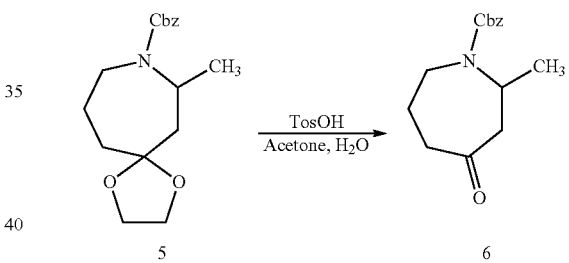

To a solution of Compound 5 (0.75 g, 2.3 mmol) in acetone (15 mL) and water (5 mL) was added TosOH (0.6 g, 3.4 mmol) at 16° C. The mixture was stirred at 40° C. for 12 h. The resulting mixture was diluted with EA (20 mL) and washed with brine (20 mL). The organic layer was dried over Na₂SO₄ and concentrated in vacuo to give a crude product, which was purified by flash column chromatography to give Compound 6 (0.3 g, 50%).

1.13.6 Preparation of Compound 7

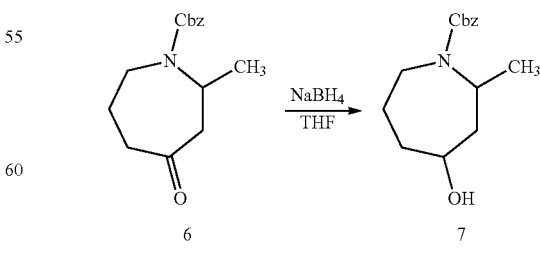

To a solution of Compound 6 (0.30 g, 1.1 mmol) in THF (15 mL), was added NaBH₄ (50 mg, 1.3 mmol) at 16° C. The mixture was stirred at 16° C. for 3 h. The resulting mixture was diluted with EA (20 mL) and washed with brine (20 mL). The organic layer was dried over Na$_2$SO$_4$ and concentrated in vacuo to give Compound 7 (0.30 g, 98%).

1.13.8 Preparation of Compound A24

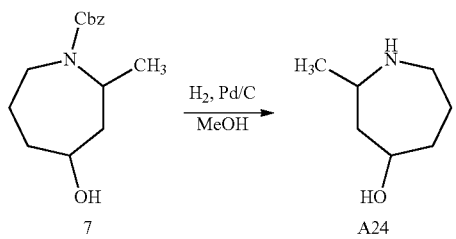

To a solution of Compound 7 (0.30 g, 1.1 mmol) in MeOH (25 mL) was added Pd/C (50 mg). The mixture was hydrogenated at 25° C. for 16 h under H$_2$ atmosphere. The catalyst was filtered and the filtrate was concentrated to give the crude product, which was used in the next step directly (0.14 g, 98%).

1.14 Preparation of A25

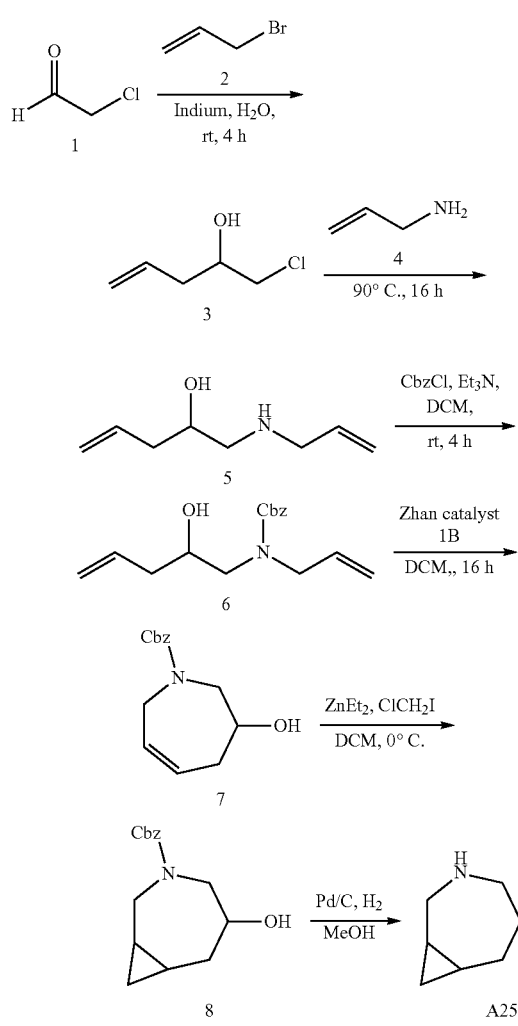

1.14.1 Preparation of Compound 3

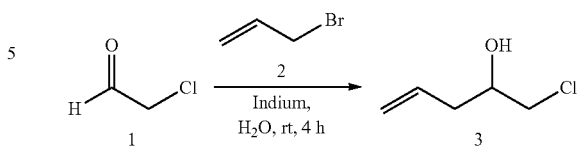

To a mixture of Indium (19.75 g, 172.03 mmol, 1.30 Eq) and 3-bromoprop-1-ene (20.81 g, 172.03 mmol, 1.30 Eq) in H$_2$O (400 mL), was added 2-chloroacetaldehyde (25.97 g, 132.33 mmol, 1.00 Eq) in one portion at 25° C. under N$_2$. The mixture was stirred at 25° C. for 16 hr. Then the mixture was filtered, the filtrate was extracted with EtOAc, the combined organic layer was dried over anhydrous Na$_2$SO$_4$, concentrated to afford 1-chloropent-4-en-2-ol (13.00 g, 107.81 mmol, 81.47% yield) as yellow oil. $^1$H NMR (400 MHz, CDCl3) δ5.79-5.89 (m, 1H), 5.13-5.25 (m, 2H), 3.86-3.97 (m, 1H), 3.62-3.70 (m, 1H), 3.50-3.59 (m, 1H), 2.32-2.46 (m, 2H), 2.24 (brs, 1H).

1.14.2 Preparation of Compound 5

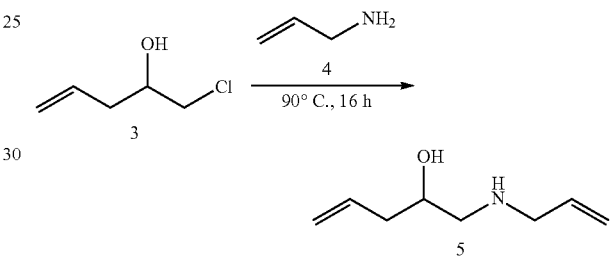

A mixture of 1-chloropent-4-en-2-ol (23.40 g, 194.06 mmol, 1.00 Eq) and prop-2-en-1-amine (33.00 g, 578.03 mmol, 2.98 Eq) was stirred at 90° C. for 16 hr. The mixture was cooled to 25° C. and concentrated in reduced pressure at 60° C. The residue was poured into ice-water (w/w=1/1) (150 mL) and stirred for 20 min. The aqueous phase was extracted with EA. The combined organic phase was washed with saturated brine (200 mL*2), dried with anhydrous Na$_2$SO$_4$, filtered and concentrated in vacuum. The residue was purified by silica gel chromatography (DCM:MeOH=30/1 to 10/1) to afford 1-(allylamino)pent-4-en-2-ol (16.00 g, 113.31 mmol, 58.39% yield) as yellow oil.

1.14.3 Preparation of Compound 6

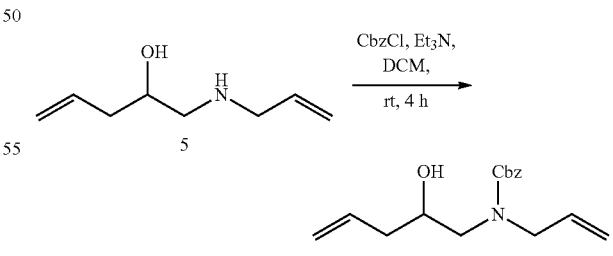

To a solution of 1-(allylamino)pent-4-en-2-ol (4.23 g, 29.96 mmol, 1.00 Eq) in DCM (50 mL) was added CbzCl (6.13 g, 35.95 mmol, 1.20 Eq) and TEA (6.06 g, 59.92 mmol, 2.00 Eq). The mixture was stirred at 25° C. for 4 hr. TLC detected the material was consumed completely, the mixture was washed with water, the aqueous layer was extracted with DCM, the combined organic layer was dried over anhydrous Na₂SO₄, concentrated and purified by silica gel chromatography (eluting with PE:EA=10:1) to afford desired product benzyl N-allyl-N-(2-hydroxypent-4-enyl) carbamate (6.10 g, 22.15 mmol, 73.95% yield) as yellow oil. LCMS: 276.0 [M+1].

1.14.4 Preparation of Compound 7

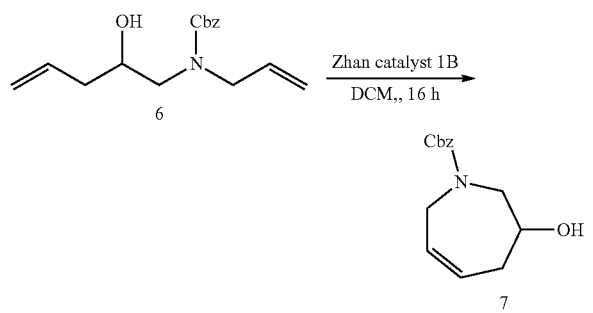

To a solution of benzyl N-allyl-N-(2-hydroxypent-4-enyl) carbamate (6.10 g, 22.15 mmol, 1.00 Eq) in DCM (400 mL) was added Zhan catalyst 1B (812.63 mg, 1.11 mmol, 0.05 Eq) under N₂ protection. The mixture was stirred at 25° C. for 16 hr under N₂ protection. Then TLC detected the reaction was completed, the solvent was evaporated, the residue was purified by chromatography (silica gel, eluting with PE:EA=2:1) to afford benzyl 3-hydroxy-2,3,4,7-tetrahydroazepine-1-carboxylate (2.60 g, 10.51 mmol, 47.47% yield) as yellow oil. $^1$H NMR (400 MHz, CDCl3) δ 7.30-7.46 (m, 5H), 5.63-5.89 (m, 2H), 5.19 (s, 2H), 3.96-4.13 (m, 2H), 3.74-3.90 (m, 2H), 3.54-3.70 (m, 1H), 2.43 (m, 2H).

1.14.5 Preparation of Compound 8

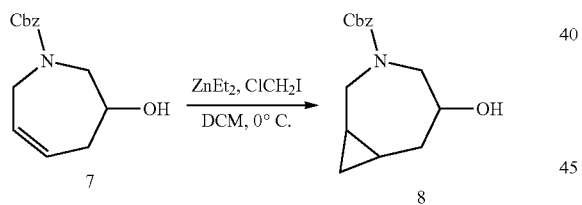

To a solution of benzyl 3-hydroxy-2,3,4,7-tetrahydroazepine-1-carboxylate (300.00 mg, 1.21 mmol, 1.00 Eq) in DCM (10 mL) was added ZnEt₂ (2 M, 1.21 mL, 2.00 Eq) at 0° C. under N₂ protection. Then the mixture was stirred at 0° C. for 30 mins, and ClCH₂I (533.55 mg, 3.03 mmol, 2.50 Eq) was added. The resulting mixture was stirred at 25° C. for 16 hrs. LCMS detected 75% desired product and 15% material remained. The mixture was poured into NH₄Cl solution, and extracted with EA, the combined organic layer was dried over Na₂SO₄, concentrated, the residue was diluted in THF (3 mL) and H₂O (3 mL), NaIO₄ (258.81 mg, 1.21 mmol, 1.00 Eq) and K₂OsO₄ (230.21 mg, 1.21 mmol, 1.00 Eq) was added, the mixture was stirred at 25° C. for 30 mins, then the reaction was quenched by saturated Na₂SO₃, extracted with EA, the combined organic layer was dried over Na₂SO₄, concentrated, the residue was purified by silica gel chromatography (PE:EA=3:1) to afford benzyl 3-hydroxy-5-azabicyclo[5.1.0]octane-5-carboxylate (110.00 mg, 420.94 umol, 34.79% yield) as colorless oil. LCMS: 262.0 [M+1].

1.14.6 Preparation of Compound A25

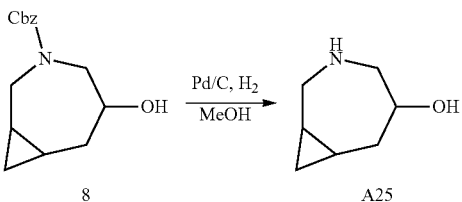

To a solution of benzyl 3-hydroxy-5-azabicyclo[5.1.0]octane-5-carboxylate (110.00 mg, 420.94 umol, 1.00 Eq) in MeOH (10 mL) was added Pd—C under N₂. The suspension was degassed under vacuum and purged with H₂ several times. The mixture was stirred under H₂ at 25° C. for 4 hr. TLC showed the starting material was consumed completely. The reaction mixture was filtered and the filter was concentrated to give 5-azabicyclo[5.1.0]octan-3-ol (37.00 mg, 290.93 umol, 69.11% yield) as colorless oil.

1.15 Preparation of A26/A27

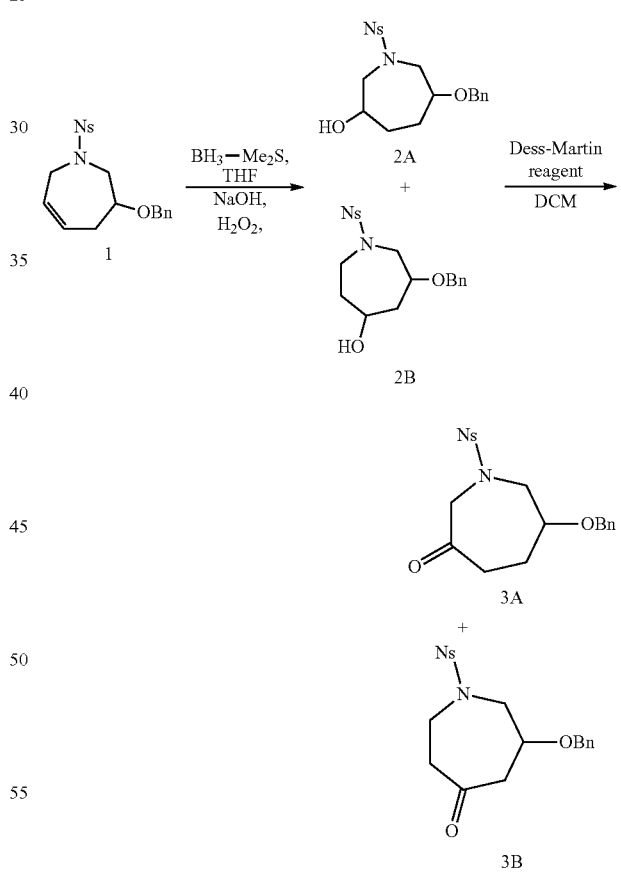

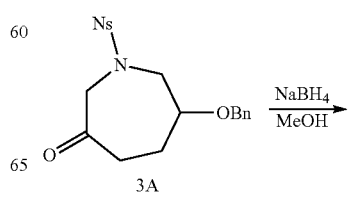

329
-continued

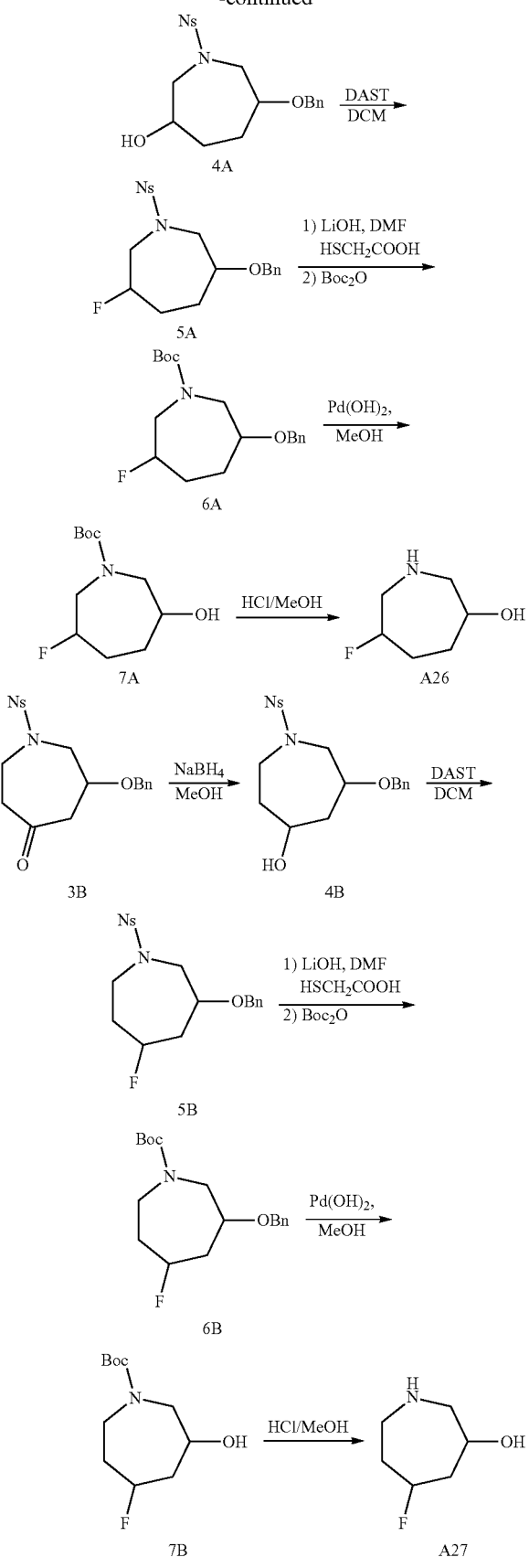

330

1.15.1 Preparation of Compound 2A and 2B

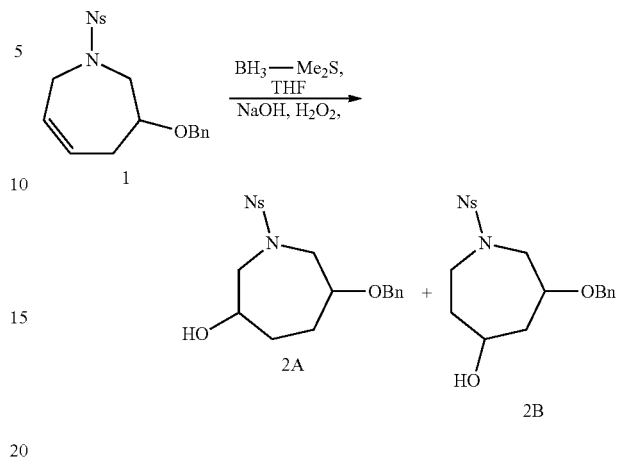

At ice bath, to a solution of compound 1 (9.0 g, 23.2 mmol)) in THF (135 mL) was added BH$_3$-Me$_2$S (7.0 mL, 70.0 mmol). After the solution stirring at rt overnight, 3 M NaOH (9.3 mL, 27.8 mmol) and H$_2$O$_2$ (14.7 g, 116.0 mmol) were added in turn at ice bath and stirred at rt for 2 hrs. The mixture was quenched with Na$_2$SO$_3$ solution, extracted with EtOAc (200 mL*2) and the organic layer was concentrated to give a crude mixed product, which was used for the next step directly (9.36 g, 99.6%).

1.15.2 Preparation of Compound 3A and 3B

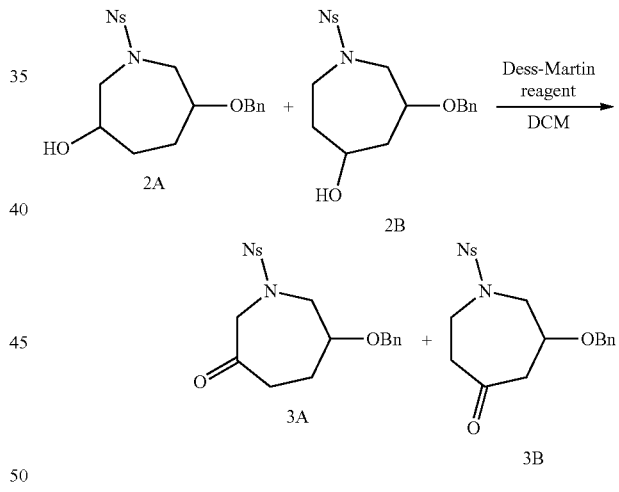

A mixture of Compound 2A and 2B (9.36 g, 23.0 mmol) and Dess-Martin reagent (11.72 g, 27.6 mmol) in DCM (160 mL) was stirred at rt under N$_2$ overnight. The mixture was quenched with Na$_2$SO$_3$ solution, extracted with DCM (150 mL*2) and the organic layer was concentrated to give the crude product, which was purified by Biotage chromatography to give the Compound 3A (4.6 g) and Compound 3B (2.2 g). LCMS: 427 [M+23].

Compound 10A $^1$H NMR (400 MHz, CDCl$_3$, 10A): δ ppm: 8.27-8.30 (m, 2H), 7.93-7.96 (m, 2H), 7.36-7.43 (m, 5H), 4.60-4.67 (m, 2H), 4.05 (d, J=18.2 Hz, 1H), 3.82-3.87 (m, 1H), 3.75 (d, J=18.2 Hz, 1H), 3.62-3.66 (dd, J=14.6 Hz, 3.0 Hz, 1H), 3.32-3.37 (dd, J=14.6 Hz, 7.0 Hz, 1H), 2.63-2.67 (m, 2H), 2.06-2.09 (m, 1H), 1.82-1.86 (m, 1H).

Compound 10B $^1$H NMR (400 MHz, CDCl$_3$, 10B): δ ppm: 8.18-8.21 (m, 2H), 7.94-7.97 (m, 2H), 7.27-7.37 (m, 5H), 4.62 (d, J=11.2 Hz, 1H), 4.51 (d, J=11.2 Hz, 1H), 3.75-3.93 (m, 3H), 3.49-3.56 (m, 2H), 3.02-3.08 (m, 1H), 2.91-2.95 (m, 1H), 2.56-2.71 (m, 2H).

1.15.3 Preparation of Compound 4A

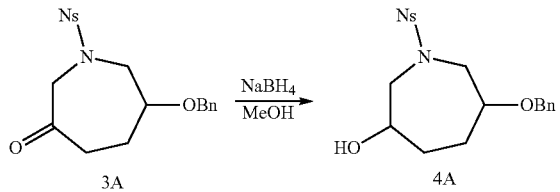

A solution of Compound 3A (4.6 g, 11.4 mmol) and NaBH$_4$ (0.43 g, 11.4 mmol) in MeOH (40 mL) and THF (20 mL) was stirred at rt for 30 minutes. The mixture was quenched with NH$_4$Cl solution, evaporated the solvent, extracted with EA (150 mL*2) and the organic layer was concentrated to give the crude product, which was purified by Biotage chromatography to give the desired product as a white solid (4.21 g, 91%).

$^1$H NMR (400 MHz, CDCl$_3$): δ ppm: 8.28-8.34 (m, 2H), 7.98-8.00 (m, 2H), 7.28-7.38 (m, 5H), 4.48-4.58 (m, 2H), 4.00-4.04 (m, 1H), 3.77-3.84 (m, 1.4H), 3.54-3.57 (m, 1.6H), 3.28-3.38 (m, 1H), 3.17-3.23 (m, 0.6H), 3.03-3.09 (m, 0.4H), 2.42-2.67 (m, 1H), 1.60-2.14 (m, 4H).

1.15.4 Preparation of Compound 5A

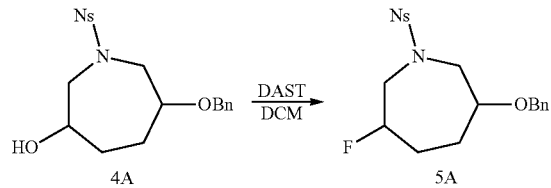

To a solution of Compound 5A (1.8 g, 4.4 mmol) in DCM (20 mL) was added DAST (1.78 g, 11 mmol) at −60° C. under N$_2$. The solution was stirred at ice bath for 2 hrs. Quenched with NaHCO3 solution, extracted with DCM (100 mL*2) and the organic layer was concentrated to give the crude product, which was purified by Biotage chromatography to give the desired product as a white solid (480 mg, 26.7%).

$^1$H NMR (400 MHz, CDCl$_3$): δ ppm: 8.25 (d, J=8.8 Hz, 2H), 7.99 (d, J=8.8 Hz, 2H), 7.31-7.40 (m, 5H), 4.80-4.93 (m, 1H), 4.50-4.57 (m, 2H), 3.40-3.75 (m, 5H), 1.78-2.07 (m, 4H).

1.15.5 Preparation of Compound 6A

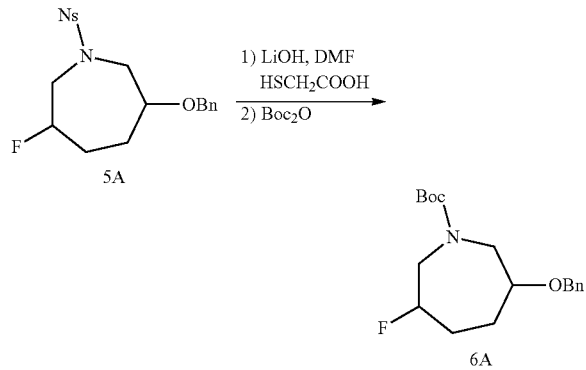

At ice bath, to a solution of Compound 5A (480 mg, 1.17 mmol) in DMF (8 mL) was added LiOH (296 mg, 7.06 mmol), followed by HSCH$_2$CO$_2$H (216 mg, 2.35 mmol) under N$_2$. The mixture was stirred at rt for 2 hrs. Boc$_2$O (279 mg, 1.29 mmol) was added and stirred at rt for another 30 minutes. The mixture was quenched with NaClO solution, extracted with EA (50 mL*2) and the organic layer was concentrated to give the crude product, which was purified by silica gel chromatography to give the desired product as an oil (300 mg, 79.3%). LCMS: 346 [M+23].

1.15.6 Preparation of Compound 7A

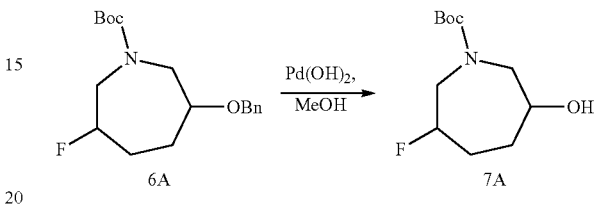

To a solution of Compound 6A (300 mg, 0.9 mmol) in CH$_3$OH (50 mL) was added Pd(OH)$_2$/C (300 mg). The mixture was hydrogenated at 60° C. under 50 Psi of hydrogen pressure overnight. The catalyst was filtered and the filtrate was concentrated to give the desired product as oil (160 mg, 73.7%).

1.15.6 Preparation of Compound 26A

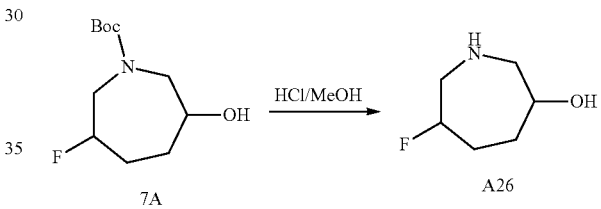

4M HCl-MeOH (10 mL) was added to Compound 13A (160 mg, 0.68 mmol). Then the solution was stirred at rt for 10 minutes. The solvent was evaporated and the residue was basified with Et$_3$N. It was used for the next step directly.

1.15.7 Preparation of Compound 4B

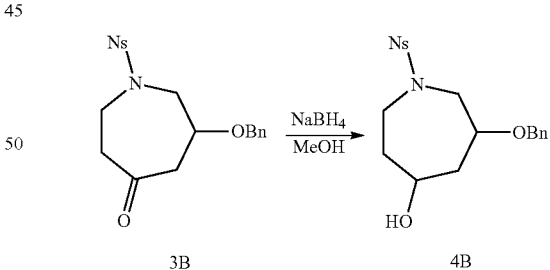

A solution of Compound 3B (2.2 g, 5.4 mmol) and NaBH$_4$ (0.20 g, 5.4 mmol) in MeOH (20 mL) and THF (10 mL) was stirred at rt for 1 hr. The mixture was quenched with NH$_4$Cl solution, evaporated the solvent, extracted with EA (50 mL*2) and the organic layer was concentrated to give the crude product, which was purified by Biotage chromatography to give the desired product as an oil (1.79 g, 81%).

$^1$H NMR (400 MHz, CDCl$_3$, 9B): δ ppm: 8.27-8.33 (m, 2H), 7.94-7.97 (m, 2H), 7.27-7.35 (m, 5H), 4.52-4.58 (m, 2H), 4.11-4.17 (m, 1H), 3.92-3.95 (m, 1H), 3.54-3.72 (m, 2H), 3.17-3.41 (m, 2H), 1.84-2.21 (m, 4H).

1.15.8 Preparation of Compound 5B

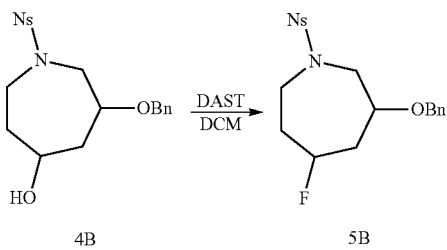

To a solution of Compound 4B (2.16 g, 5.3 mmol) in DCM (30 mL) was added DAST (2.14 g, 13.3 mmol) at −60° C. under $N_2$. The solution was stirred at rt for 3 hrs. The mixture was quenched with $NaHCO_3$ solution, extracted with DCM (100 mL*2) and the organic layer was concentrated to give the crude product, which was purified by silica gel chromatography to give the desired product as a slight yellow solid (1.48 g, 68%).

$^1$H NMR (400 MHz, $CDCl_3$): δ ppm: 8.30-8.33 (m, 2H), 7.94-7.99 (m, 2H), 7.31-7.40 (m, 5H), 4.75-5.04 (m, 1H), 4.51-4.66 (m, 2H), 3.11-3.96 (m, 5H), 2.01-2.27 (m, 4H).

1.15.9 Preparation of Compound 6B

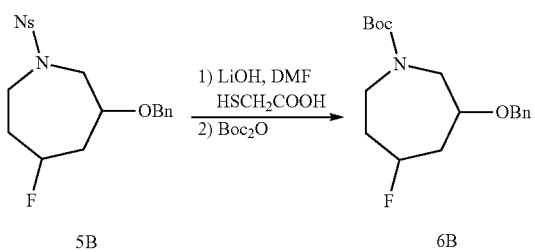

At ice bath, to a solution of Compound 5B (560 mg, 1.37 mmol) in DMF (8 mL) was added LiOH (346 mg, 8.23 mmol), followed by 2-mercaptoacetic acid (252 mg, 2.74 mmol) under $N_2$. The mixture was stirred at rt for 1 hr. $Boc_2O$ (444 mg, 2.06 mmol) was added and stirred at rt for another 30 minutes. Quenched with NaClO solution, extracted with EA (50 mL*2) and the organic layer was concentrated to give the crude product, which was purified by silica gel chromatography to give the desired product as an oil (300 mg, 67.8%).

$^1$H NMR (400 MHz, $CDCl_3$): δ ppm: 7.30-7.40 (m, 5H), 4.94-5.05 (m, 1H), 4.57-4.65 (m, 2H), 3.59-4.09 (m, 3H), 2.95-3.32 (m, 2H), 1.99-2.40 (m, 4H), 1.43-1.49 (m, 9H).

1.15.10 Preparation of Compound 7B

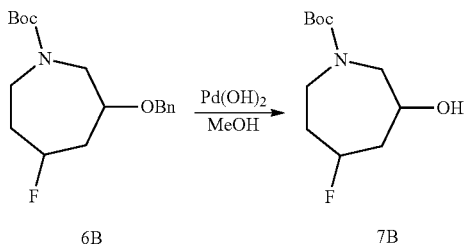

To a solution of Compound 6B (300 mg, 0.9 mmol) in $CH_3OH$ (20 mL) was added $Pd(OH)_2$ (200 mg). The mixture was hydrogenated at 60° C. under 50 Psi of hydrogen pressure overnight. The catalyst was filtered and the filtrate was concentrated to give the desired product as oil (200 mg, 91.7%).

1.15.11 Preparation of Compound A27

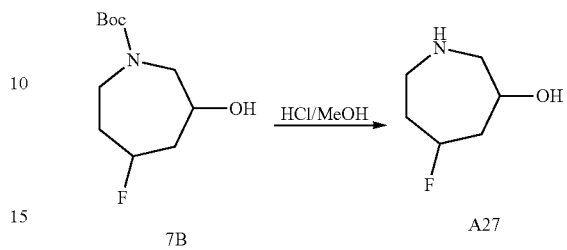

4M HCl-MeOH (10 mL) was added to Compound 7B (190 mg, 0.81 mmol). Then the solution was stirred at rt for 10 minutes. The solvent was evaporated and the residue was basified with $Et_3N$. It was used for the next step directly.

1.16 Preparation of A28

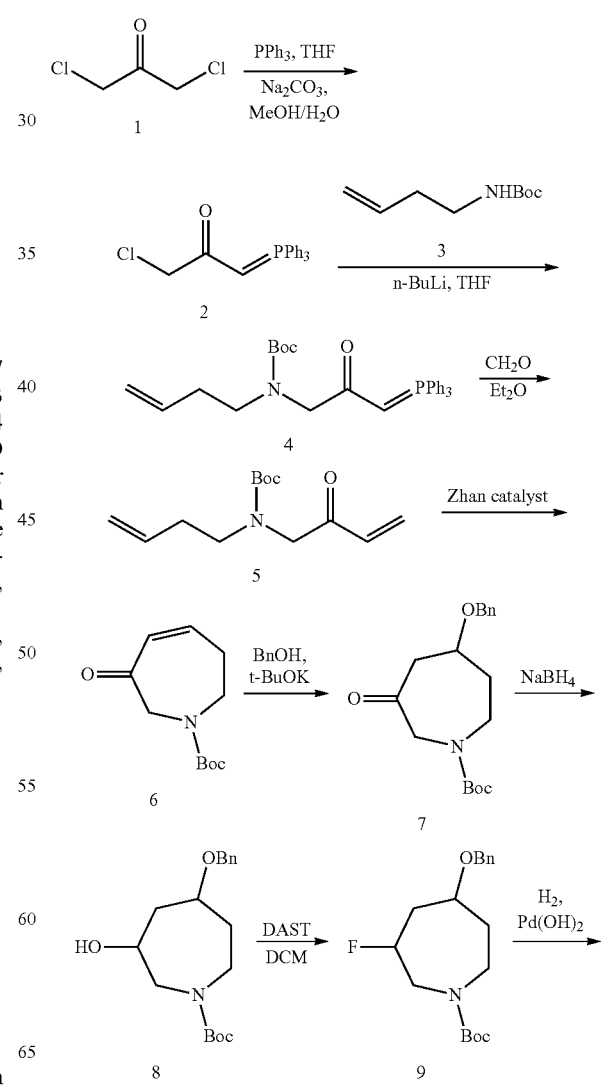

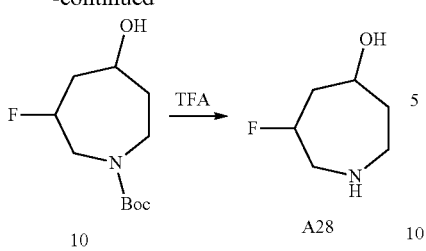

1.16.3 Preparation of Compound 5

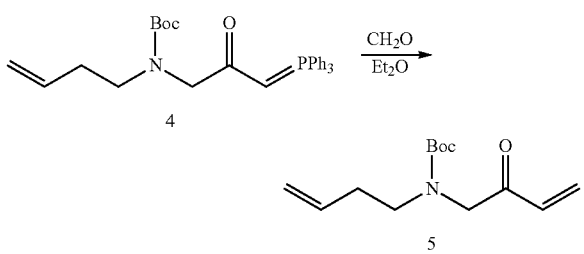

1.16.1 Preparation of Compound 2

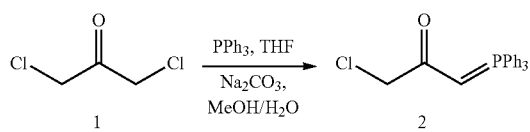

To a mixture of 1,3-dichloropropan-2-one (20.00 g, 157.52 mmol, 1.00 Eq) in THF (94 mL), was added PPh₃ (37.18 g, 141.77 mmol, 0.90 Eq) in one portion at 14° C. The mixture was stirred at 80° C. for 18 hr. The monophosphonium chloride thus formed was isolated by filtration and then treated with a solution of Na₂CO₃ (20.03 g, 189.02 mmol, 1.20 Eq)/MeOH (250 mL)—H2O (250 mL) at 14° C. After 18 hr, a precipitate appeared, and was filtered from the solution to give compound 2 (55.57 g, 82.78%) as white solid.

1.16.2 Preparation of Compound 4

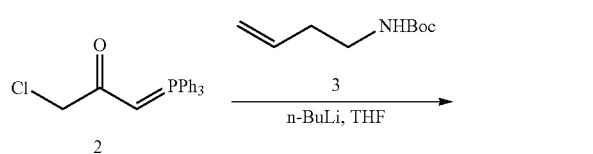

To a mixture of tert-butyl N-but-3-enylcarbamate (3.16 g, 18.42 mmol, 1.30 Eq) in THF (20 mL), was added n-BuLi (2.5 M, 14.74 mL, 2.60 Eq) at −78° C. under $N_2$. The mixture was stirred at −20° C. for 1 hr. Then 1-chloro-3-(triphenyl phosphoranylidene)propan-2-one (5.00 g, 14.17 mmol, 1.00 Eq) in THF (20 mL) was added to the mixture at −78° C. under $N_2$. The mixture was stirred at −20° C. for 3 hr. The resulting mixture was poured into water (30 mL) and stirred for 20 min. The aqueous phase was extracted with EA (10 mL). The combined organic phase was washed with saturated brine (20 mL*2), dried with anhydrous Na₂SO₄, filtered and concentrated in vacuum. The residue was purified by silica gel chromatography (PE/EA=1/1) to afford ttert-butyl but-3-en-1-yl(2-oxo-3-(triphenylphosphoranylidene)propyl)carbamate (5.80 g, 11.90 mmol, 83.98% yield) as yellow solid.

To a mixture of tert-butyl N-but-3-enyl-N-[2-oxo-3-(triphenyl-phosphanylidene) propyl]carbamate (5.80 g, 11.90 mmol, 1.00 Eq) in THF (30 mL), was added HCHO (96.58 g, 1.19 mol, 100.00 Eq) in one portion at 18° C. The mixture was stirred at 18° C. for 15 hr. TLC showed the reaction was completed. The mixture was extracted with PE (100 mL*3). The combined organic phase was washed with saturated brine (200 mL*2), dried with anhydrous Na₂SO₄, filtered and concentrated in vacuum. The residue was purified by silica gel chromatography (PE/EA=50/1, 40/1) to afford tert-butyl N-but-3-enyl-N-(2-oxobut-3-enyl)carbamate (1.40 g, 5.85 mmol, 49.16% yield) as yellow solid.

1.16.4 Preparation of Compound 6

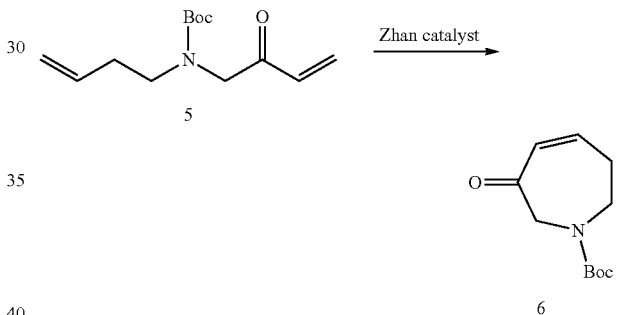

To a mixture of tert-butyl N-but-3-enyl-N-(2-oxobut-3-enyl)carbamate (1.50 g, 6.27 mmol, 1.00 Eq) in DCM (250 mL), was added Zhan catalyst 1B (150.00 mg, 204.43 umol, 0.03 Eq) in one portion at 18° C. under $N_2$. The mixture was stirred at 18° C. for 10 hr. TLC showed the reaction was completed. The mixture was concentrated in vacuum. The residue was purified by silica gel chromatography (PE/EA=30/1, 20/1) to afford tert-butyl 6-oxo-3,7-dihydro-2H-azepine-1-carboxylate (850.00 mg, 4.02 mmol, 64.17% yield) as yellow solid. ¹H NMR (400 MHz, CHLOROFORM-d) 6.36-6.64 (m, 1H), 5.88-6.14 (m, 1H), 4.23-4.35 (m, 1H), 4.16 (s, 1H), 3.51-3.68 (m, 2H), 2.62-2.78 (m, 2H), 1.46 (d, J=17.32 Hz, 1H).

1.16.5 Preparation of Compound 7

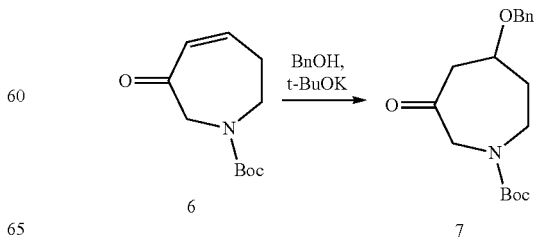

To a mixture of tert-butyl 6-oxo-3,7-dihydro-2H-azepine-1-carboxylate (540.00 mg, 2.56 mmol, 1.00 Eq) in BnOH (2.76 g, 25.56 mmol, 10.00 Eq), was added t-BuOK (28.68 mg, 255.61 umol, 0.10 Eq) in one portion under N$_2$. The mixture was stirred at 20° C. for 12 hours. LCMS showed the reaction was completed. The mixture was poured into water (100 mL) and stirred for 20 min. The aqueous phase was extracted with EA (40 mL*2). The combined organic phase was washed with saturated brine (20 mL*3), dried with anhydrous Na$_2$SO$_4$, filtered and concentrated in vacuum to afford tert-butyl 5-benzyloxy-3-oxo-azepane-1-carboxylate (1.50 g, crude) as yellow oil.

1.16.6 Preparation of Compound 8

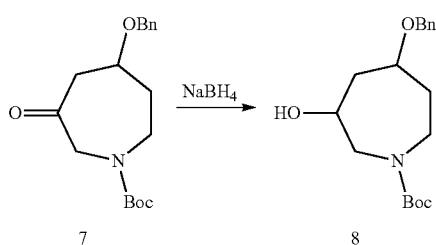

To a mixture of tert-butyl tert-butyl 5-benzyloxy-3-oxo-azepane-1-carboxylate (700.00 mg, 2.19 mmol, 1.00 Eq) in EtOH (30 mL) was added NaBH$_4$ (99.49 mg, 2.63 mmol, 1.20 Eq) in one portion under N$_2$. The mixture was stirred at 18° C. for 6 hours. TLC showed the reaction was completed. The mixture was poured water (150 mL) and stirred for 20 min. The aqueous phase was extracted with EA (90 mL*2). The combined organic phase was washed with saturated brine (80 mL*2), dried with anhydrous Na$_2$SO$_4$, filtered and concentrated in vacuum. The residue was purified by silica gel chromatography (PE/EA=10/1, 2/1) to afford tert-butyl 5-benzyloxy-3-hydroxy-azepane-1-carboxylate (510.00 mg, 1.59 mmol, 72.55% yield) as yellow oil, which was purified by pre-HPLC (FA) to afford 193 mg (D1) and 190 mg (D2).

1.16.7 Preparation of Compound 9

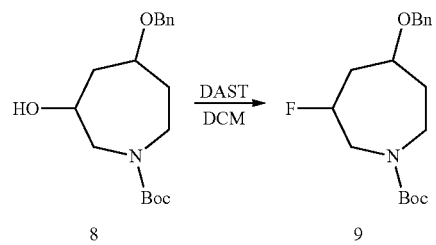

To a mixture of tert-butyl 5-benzyloxy-3-hydroxy-azepane-1-carboxylate (200.00 mg, 622.26 umol, 1.00 Eq, D2) in DCM (20 mL), was added DAST (200.60 mg, 1.24 mmol, 2.00 Eq) at −78° C. under N$_2$. The mixture was stirred at −78° C. for 1 hr. TLC showed the reaction was completed. The mixture was poured into saturated NaHCO$_3$ (10 mL) and stirred for 5 min. The aqueous phase was extracted with DCM (10 mL*2). The combined organic phase was washed with NaClO$_4$ (5 mL), dried with anhydrous Na$_2$SO$_4$, filtered and concentrated in vacuum. The residue was purified by silica gel chromatography (Petroleum ether/Ethyl acetate=15/1) to afford tert-butyl 5-benzyloxy-3-fluoro-azepane-1-carboxylate (163.00 mg, 504.02 umol, 81.00% yield, D2) as yellow oil.

1.16.8 Preparation of Compound 10

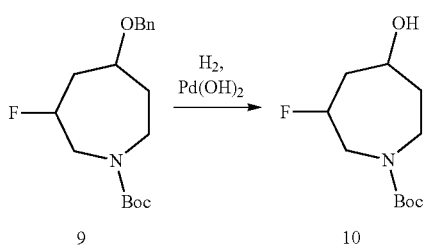 [SMILES: CC(C)(C)OC(=O)N1CCC(OCc2ccccc2)CC(F)C1 ; CC(C)(C)OC(=O)N1CCC(O)CC(F)C1]

To a solution of tert-butyl 5-benzyloxy-3-fluoro-azepane-1-carboxylate (163.00 mg, 504.02 umol, 1.00 Eq, D2) in MeOH (20 mL) was added Pd(OH)$_2$ (30.00 mg, N/A) under N$_2$. The suspension was degassed under vacuum and purged with H$_2$ several times. The mixture was stirred under H$_2$ (15 psi) at 20° C. for 12 hours. TLC (Petroleum ether/Ethyl acetate=3:1) showed the starting material was consumed completely. The reaction mixture was filtered and the filter was concentrated to give tert-butyl 3-fluoro-5-hydroxy-azepane-1-carboxylate (115.00 mg, 492.97 umol, 97.81% yield, D2) as yellow oil.

1.16.9 Preparation of A28

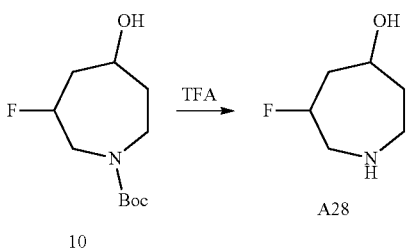 [SMILES: CC(C)(C)OC(=O)N1CCC(O)CC(F)C1 ; OC1CCNCC(F)C1 ; "A28"]

To a mixture of tert-butyl 3-fluoro-5-hydroxy-azepane-1-carboxylate (115.00 mg, 492.97 umol, 1.00 Eq, D2) in DCM (3 mL), was added TFA (1 mL) at 25° C. under N$_2$. The mixture was stirred at 25° C. for 2 hr. TLC showed the reaction was completed. The mixture was concentrated in vacuum to afford 6-fluoroazepan-4-ol (240.00 mg, crude, D2) as yellow oil.

1.17 Preparation of A29

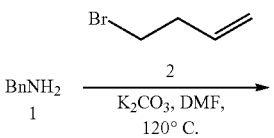

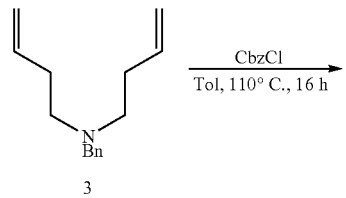

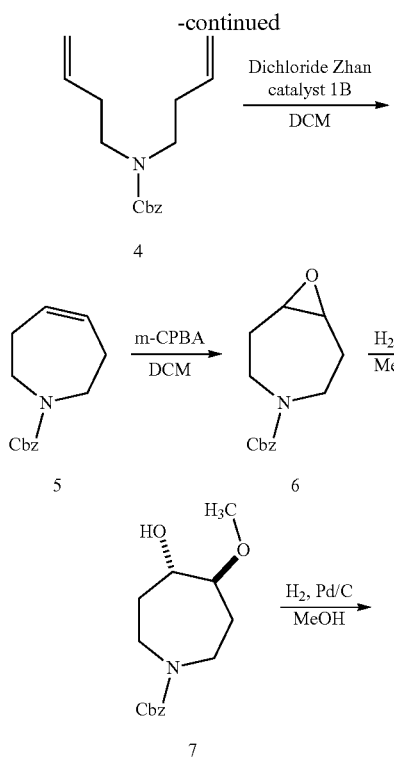

1.17.1 Preparation of Compound 3

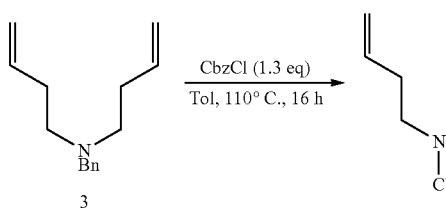

To a solution of Compound 1 (8.7 g, 65.7 mmol) in DMF (120 mL) was added Compound 2 (3.5 g, 32.7 mmol) followed by $K_2CO_3$ (9.06 g, 65.7 mmol). The mixture was heated to 100° C. for 16 h. The mixture was diluted with EA (100 mL), and washed with $H_2O$ (100 mL×3). The organic phase was dried over $Na_2SO_4$ and concentrated in vacuo to give the crude product, which was purified by column chromatography to give the desired product 3 as colorless oil (5.1 g, 72.5%). LCMS: 256 [M+1].

1.17.2 Preparation of Compound 4

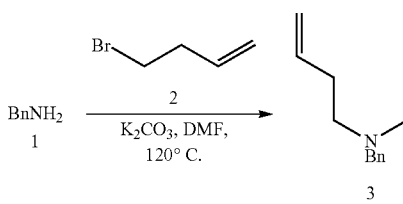

To a solution of Compound 3 (1.5 g, 6.97 mmol) in tolene (15 mL) was added CbzCl (1.42 g, 8.37 mmol). The mixture was heated to 110° C. for 16 h. The mixture was concentrated in vacuo. The residue was dissolved with water and EA. The organic layer was washed with aq. $Na_2CO_3$, dried over $Na_2SO_4$ and concentrated in vacuo to give the crude product, which was purified by column chromatography to give the desired product 4 as colorless oil (1.24 g, Yield: 68.9%). LCMS: 260 [M+1].

1.17.3 Preparation of Compound 5

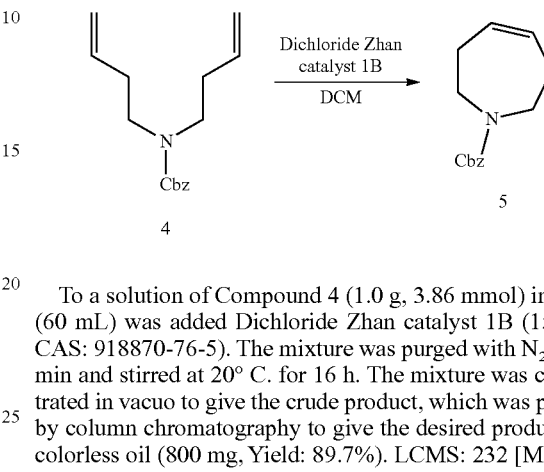

To a solution of Compound 4 (1.0 g, 3.86 mmol) in DCM (60 mL) was added Dichloride Zhan catalyst 1B (150 mg, CAS: 918870-76-5). The mixture was purged with $N_2$ for 10 min and stirred at 20° C. for 16 h. The mixture was concentrated in vacuo to give the crude product, which was purified by column chromatography to give the desired product 5 as colorless oil (800 mg, Yield: 89.7%). LCMS: 232 [M+1].

1.17.4 Preparation of Compound 6

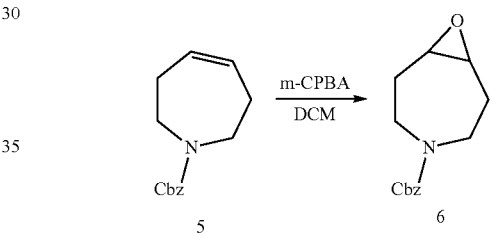

To a solution of compound 5 (800 mg, 3.46 mmol) in DCM (30 mL), was added m-CPBA (774 mg, 4.5 mmol). The mixture stirred at room temperature for 5 hours. The solution was quenched by aq. $Na_2SO_3$, and extracted with DCM (60 mL*2). The organic combined phase was dried over $Na_2SO_4$, and concentrated to give desired compound 7 as colorless oil (812 mg, Yield: 95.9%). LCMS: 248 [M+1].

1.17.5 Preparation of Compound 7

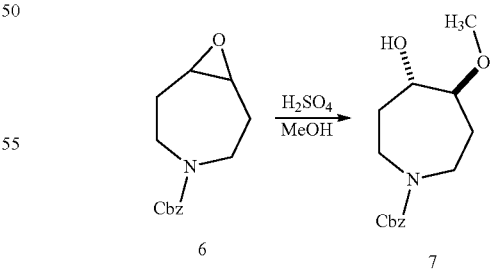

Compound 7 (812 mg, 3.31 mmol) was dissolved in MeOH (10 mL), then concentrated $H_2SO_4$ (200 mg) was added. The mixture stirred at room temperature for 1 h. The solution was neutralized with aq.$Na_2CO_3$ to pH=7. The resulting mixture was concentrated in vacuo. The residue was extracted with EA (60 mL*2). The combined organic phase was dried over Na$_2$SO$_4$, and concentrated in vacuo to give the crude product, which was purified by column chromatography to give the desired product 8 as colorless of (778 mg, Yield: 84.9%).
LCMS: 280 [M+1].

1.17.6 Preparation of A29

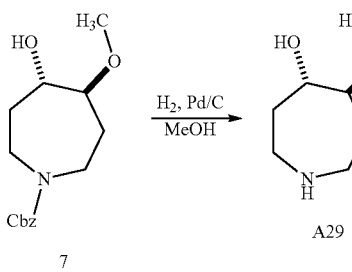

To a solution of Compound 7 (778 mg, 2.8 mmol) in MeOH (70 mL) was added Pd(OH)$_2$/C (100 mg) under N$_2$. The mixture was stirred under H$_2$ balloon at 23° C. for 2 h. The mixture was filtrated, the filtrate was concentrated to give the desired product 8 (310 mg, Yield: 78%).

1.18 Preparation of A20/A21

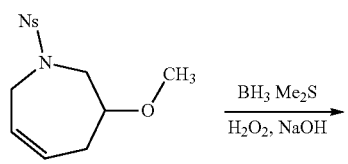

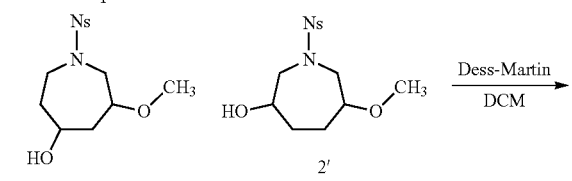

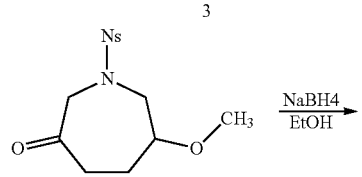

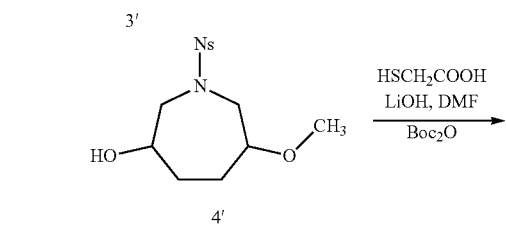

-continued

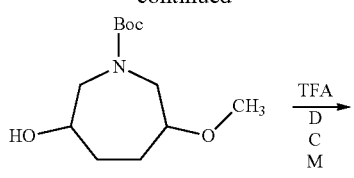

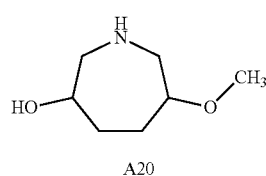

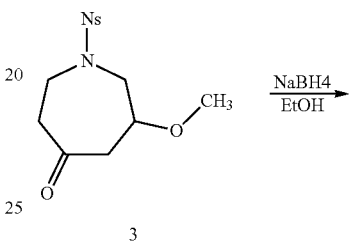

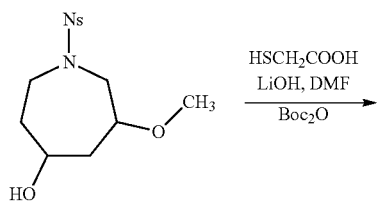

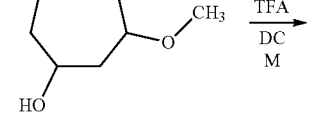

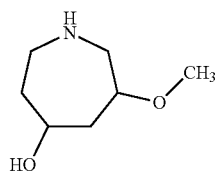

1.18.1 Preparation of Compound 2/2'

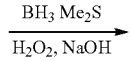

-continued

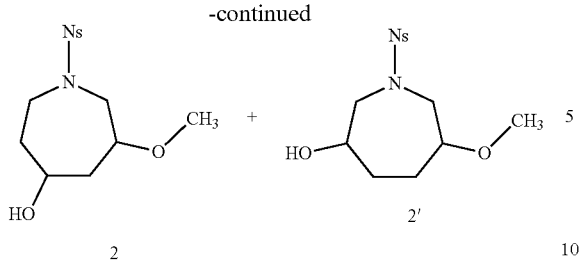

To a solution of Compound 1 (1.8 g, 5.8 mmol) in THF (40 mL) was added BH$_3$.Me$_2$S (1.2 mL, 10 M) at 0° C., and the mixture was stirred at 16° C. for 12 h. To the reaction mixture was added NaOH (2.3 mL, 3 M) and H$_2$O$_2$ (3.3 g, 29.0 mmol) at 0° C., and the mixture was stirred at 16° C. for 12 h. The resulting mixture was quenched with Na$_2$SO$_3$ (Sat.) and extracted with EA (150 mL). The organic layer was dried over Na$_2$SO$_4$ and concentrated in vacuo to give compound 2 and compound 2' (1.8 g, crude), which was used in the next step directly.

1.18.2 Preparation of Compound 3/3'

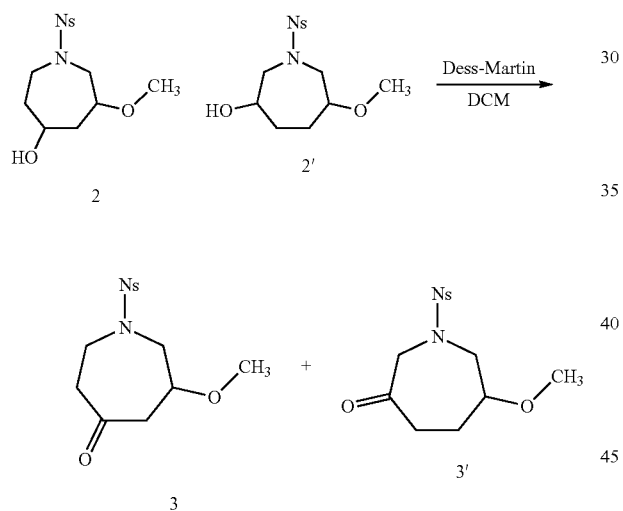

To a solution of Compound 2 and Compound 2'(1.8 g, crude) in DCM (40 mL) was added Dess-Martin (3.5 g, 8.2 mmol) at 0° C., and the mixture was stirred at 16° C. for 16 h. The resulting mixture was quenched with Na$_2$SO$_3$ (Sat.) and extracted with DCM (100 mL). The organic layer was dried over Na$_2$SO$_4$ and concentrated in vacuo to give the crude product, which was purified by flash column chromatography to give compound 3 (0.58 g, 32%) $^1$H NMR (400 MHz, CDCl$_3$) δ=8.39-8.42 (m, 2H), 8.02-8.05 (m, 2H), 3.73-3.78 (m, 1H), 3.60-3.65 (m, 2H), 3.51-3.56 (m, 2H), 3.38 (s, 3H), 2.90-2.97 (m, 2H), 2.67-2.70 (m, 2H) and compound 3' (0.86 g, 48%). $^1$H NMR (400 MHz, CDCl$_3$) δ=8.39-8.43 (m, 2H), 8.02-8.05 (m, 2H), 4.04-4.09 (m, 1H), 3.72-3.77 (m, 1H), 3.64-3.68 (m, 2H), 3.38 (s, 3H), 3.20-3.30 (m, 1H), 2.63-2.69 (m, 2H), 2.09-2.19 (m, 1H), 1.76-1.79 (m, 1H).

1.18.3 Preparation of Compound 4'

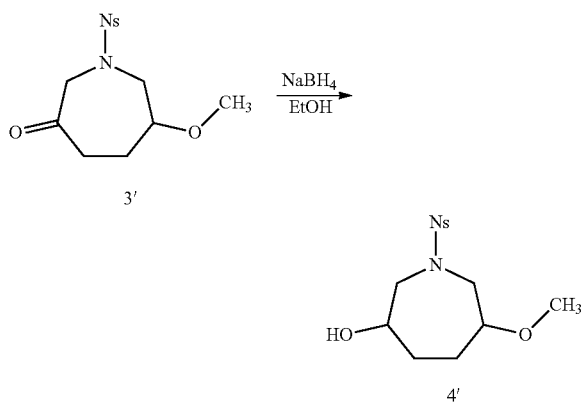

To a solution of Compound 3'(0.86 g, 2.6 mmol) in EtOH (15 mL) was added NaBH$_4$ (0.15 g, 3.9 mmol) at 0° C., and the mixture was stirred at 18° C. for 1 h. The resulting mixture was quenched with NH$_4$Cl (Sat.) and extracted with EA (100 mL). The organic layer was dried over Na$_2$SO$_4$ and concentrated in vacuo to give compound 4'(0.86 g, crude), which was used in the next step directly.

1.18.4 Preparation of Compound 5'

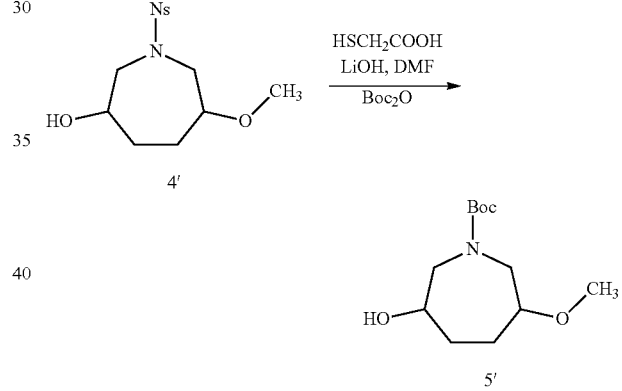

To a solution of Compound 4'(0.86 g, 2.6 mmol) in DMF (10 mL) was added LiOH.H$_2$O (0.64 g, 15.6 mmol) and HSCH$_2$COOH (0.48 g, 5.3 mmol) at 0° C., and the mixture was stirred at 16° C. for 2 h. Then Boc$_2$O (0.85 g, 5.3 mmol) was added, and the mixture was stirred for another 1 h. The resulting mixture was quenched with NaClO (aq.) and extracted with EA (100 mL). The organic layer was dried over Na$_2$SO$_4$ and concentrated in vacuo to give the crude product, which was purified by flash column chromatography to give the desired product (0.39 g, 61%).

1.18.5 Preparation of A20

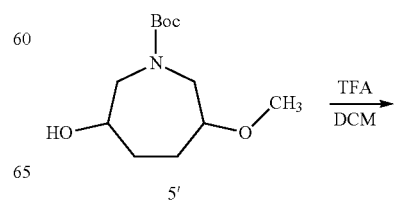

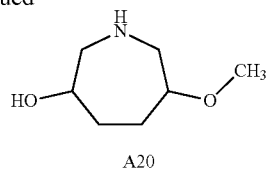

A20

To a solution of Compound 5'(390 mg, 1.6 mmol) in DCM (5 mL) was added TFA (3 mL) and stirred at 16° C. for 0.5 h. The reaction mixture was concentrated in vacuo to give the crude product (360 mg, contained TFA).

1.18.6 Preparation of Compound 4

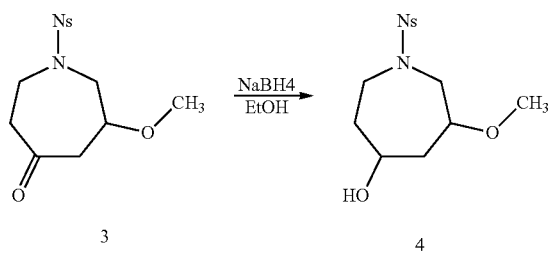

To a solution of Compound 3 (0.58 g, 1.8 mmol) in EtOH (10 mL) was added NaBH$_4$ (0.10 g, 2.7 mmol) at 0° C., and the mixture was stirred at 18° C. for 1 h. The resulting mixture was quenched with NH$_4$Cl (Sat.) and extracted with EA (100 mL). The organic layer was dried over Na$_2$SO$_4$ and concentrated in vacuo to the crude product, which was purified by flash column chromatography to give the desired product (0.47 g, 81%).

1.18.7 Preparation of Compound 5

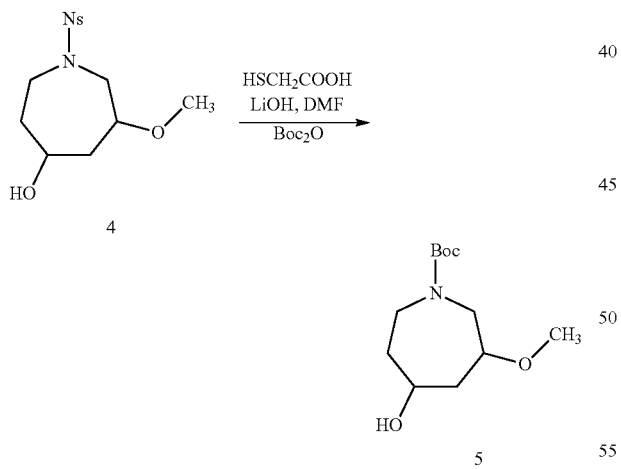

To a solution of Compound 4 (0.47 g, 1.4 mmol) in DMF (10 mL) was added LiOH.H$_2$O (0.35 g, 8.5 mmol) and HSCH$_2$COOH (0.26 g, 2.8 mmol) at 0° C., and the mixture was stirred at 16° C. for 2 h. Then Boc$_2$O (0.47 g, 2.1 mmol) was added, and the mixture was stirred for another 1 h. The resulting mixture was quenched with NaClO (aq.) and extracted with EA (100 mL). The organic layer was dried over Na$_2$SO$_4$ and concentrated in vacuo to give the crude product, which was purified by flash column chromatography to give the desired product (0.20 g, 57%).

1.18.8 Preparation of A21

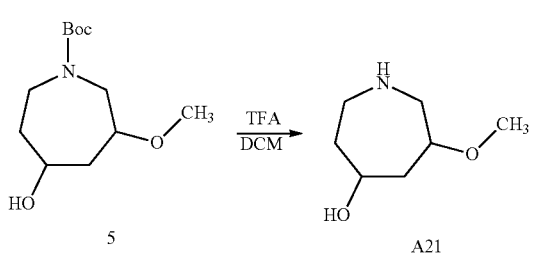

To a solution of Compound 5 (201 mg, 0.82 mmol) in DCM (3 mL) was added TFA (3 mL) and stirred at 16° C. for 0.5 h. The reaction mixture was concentrated in vacuo to give the crude product (182 mg, TFA).

1.19 Preparation of Compound A34

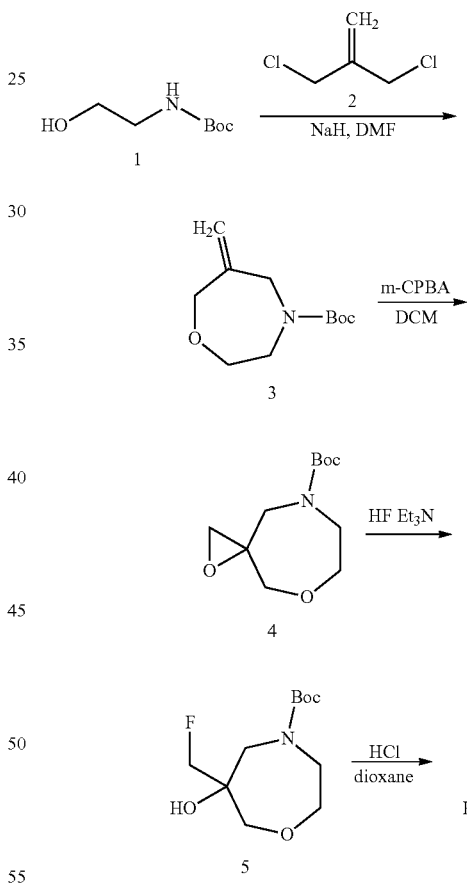

1.19.1 Preparation of Compound 3

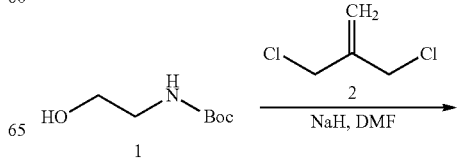

-continued

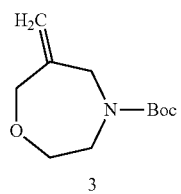

3

To a solution of Compound 1 (50.00 g, 310.17 mmol, 1.00 Eq) in DMF (500 mL), the mixture was cooled to −10° C., then NaH (27.29 g, 682.37 mmol, 2.20 Eq) was added, the mixture was stirred for 40 min at 0° C., and compound 2 (38.77 g, 310.17 mmol, 1.00 Eq) was dropwised at −5~0° C., the mixture was stirred at 18° C. for 3 hr, TLC (PE:EA=3:1) shown the reaction was completed, the reaction solution was poured into ice-water, extracted with EA (200 mL) and the organic phase was washed with more water (300*3), dried over NaSO4, concentrated, The residue was purified by silica gel chromatography (PE/EA=5/1) to afford Compound 3 (30.00 g, 140.67 mmol, 45.35% yield) as yellow solid.

1.19.2 Preparation of Compound 4

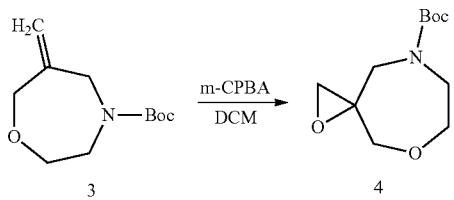 [SMILES: C=C1COCCN(C(=O)OC(C)(C)C)C1 ; CC(C)(C)OC(=O)N1CCOCC2(CO2)C1]

To a solution of Compound 3 (1.00 g, 4.69 mmol, 1.00 Eq) in DCM (10 mL) was added m-CPBA (1.21 g, 7.04 mmol, 1.50 Eq), the mixture was stirred at 18° C. for 2 hr, TLC (PE:EA=3:1) shown the reaction was completed, the mixture was washed with NaSO₃ (30 mL*5), the organic phase was dried and concentrated, The residue was purified by silica gel chromatography (PE/EA=10/1) to afford compound 4 (700.00 mg, 3.05 mmol, 65.10% yield) as colorless oil. ¹H NMR (400 MHz, CDCl3) δ3.91-3.54 (m, 8H), 2.78-2.73 (m, 2H), 1.48 (s, 9H).

1.19.3 Preparation of Compound 5

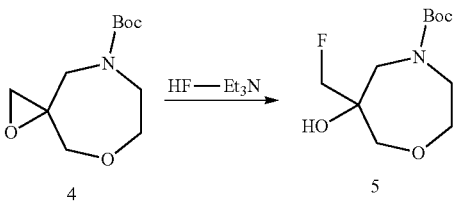

Compound 4 (600.00 mg, 2.62 mmol, 1.00 Eq) was added into HF-Et3N (15 mL), the mixture was stirred at 18° C. for 12 hr, TLC (PE:EA=3:1) shown the reaction was almost completed, the mixture was poured into ice sat.NaHCO₃ (80 mL), extracted with EA (80 mL*2), washed with brine, The residue was purified by silica gel chromatography (PE/EA=7/1) to afford Compound 5 (190.00 mg, 762.20 umol, 29.09% yield) as colorless oil.

1.19.4 Preparation of Compound A34

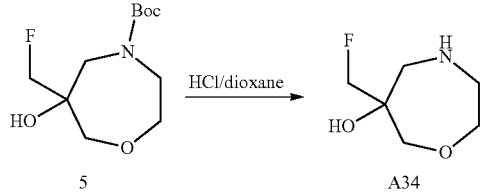

Compound 5 (190.00 mg, 762.20 umol, 1.00 Eq) was added HCl-dioxane (5 mL) and stirred for 30 min at 17° C., TLC (PE:EA=1:1) shown the reaction was completed, the mixture was concentrated to give compound B (100.00 mg, 670.42 umol, 87.96% yield).

1.20 Preparation of Compound A35/36

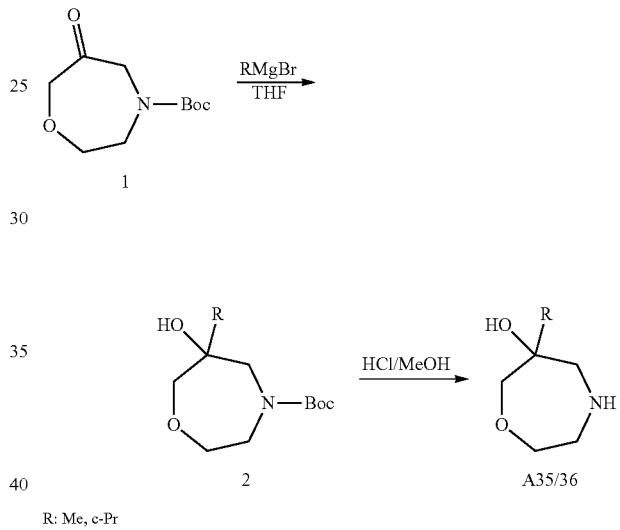

R: Me, c-Pr 1.20.1 Preparation of Compound 2

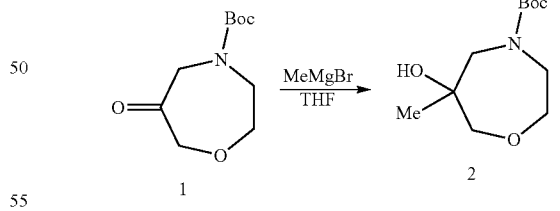

To a solution of methylmagnesium bromide (2.5 M, 4.46 mL, 3.00 Eq) in THF (30 mL) under N₂ at 0° C., was added compound 1 (800.00 mg, 3.72 mmol, 1.00 Eq) and remained the temperature was 0-5° C., the mixture was stirred at room temperature for 2 hr, TLC (PE:EA=3:1) shown the reaction was almost completed, the solution was poured into ice sat.NH₄Cl (50 mL), extracted with EA and concentrated. The residue was purified by silica gel chromatography (PE/EA=5/1, to afford compound 2 (560.00 mg, 2.42 mmol, 65.09% yield) as colorless oil.

1.20.2 Preparation of Compound A35

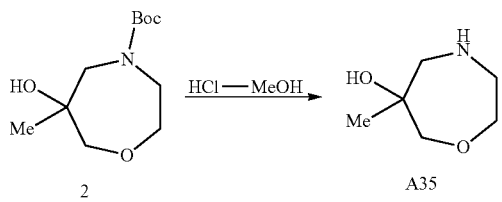

To a solution of compound 2 (560.00 mg, 2.42 mmol, 1.00 Eq) in MeOH (10 mL) was added HCl-MeOH (10 mL), the mixture was stirred at room temperature for 30 min, TLC (PE:EA=1:1) shown the reaction was completed, the mixture was concentrated to give compound A (530.00 mg, crude) as a light yellow solid.

1.21 Preparation of A62

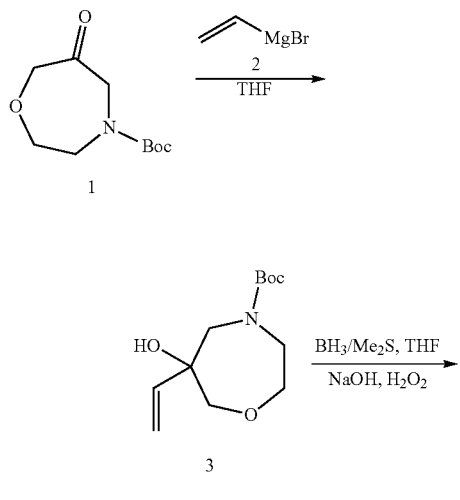

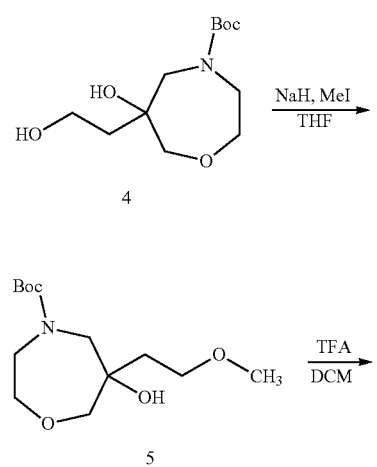

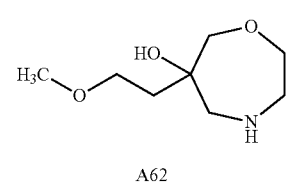

1.21.1 Preparation of Compound 3

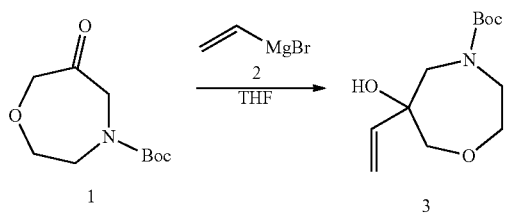

To a solution of Vinylmagnesium Bromide (9.15 g, 69.69 mmol) in THF (20 mL) was added Compound 1 (3.0 g, 13.94 mmol) under $N_2$ at −10° C. Then the mixture was stirred at 25° C. for 3 h. TLC monitored that the reaction completed. The mixture was poured into aq. $NH_4Cl$ (300 mL) and stirred for 20 min. The aqueous phase was extracted with EA (100 mL*3). The combined organic phase were dried with anhydrous $Na_2SO_4$, filtered and concentrated in vacuum. The residue was purified by silica gel chromatography (PE/EA=6/1, 5/1) to afford the desired product compound 3 (2.05 g, 8.43 mmol, 60.44%) as yellow oil.

$^1$H NMR (400 MHz, CDCl$_3$): δ ppm: 5.93 (dd, J=17.1, 10.7 Hz, 1H), 5.39-5.56 (m, 1H), 5.19 (d, J=10.8 Hz, 1H), 3.63-3.97 (m, 5H), 3.08-3.59 (m, 3H), 1.41-1.60 (m, 9H).

1.21.2 Preparation of Compound 4

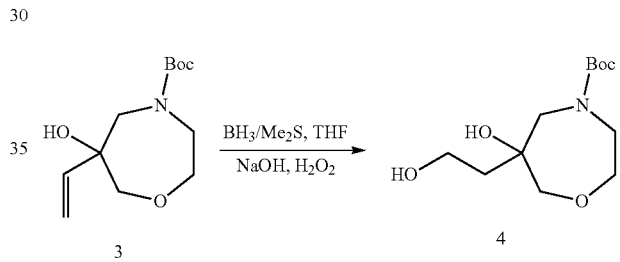

To a solution of Compound 3 (500 mg, 2.06 mmol) in THF (10 mL) was added $BH_3/Me_2S$ (0.5 mL, 5.14 mmol, 10M) at 0° C., then warmed slowly to 25° C., and the reaction mixture was stirred at 25° C. for 12 h. The solution was poured into aq. NaOH (3.0 mL, 10.3 mmol, 3M), followed by $H_2O_2$ (1.17 g, 10.3 mmol, 30%) at 0° C. the mixture was stirred at 25° C. for 1 h, TLC monitored that the reaction was completed. The reaction mixture was washed by aq. $Na_2SO_3$ (50 mL*2), extracted by EA (80 mL*3). The organic layers were concentrated to give the crude product, which was purified by column chromatography (PE:EA=5:1, 2:1) to give the desired product (210 mg, 39%).

$^1$H NMR (400 MHz, CDCl$_3$): δ ppm: 3.31-4.02 (m, 9H), 3.06-3.29 (m, 2H), 1.69-1.93 (m, 2H), 1.46-1.54 (m, 9H).

1.21.3 Preparation of Compound 5

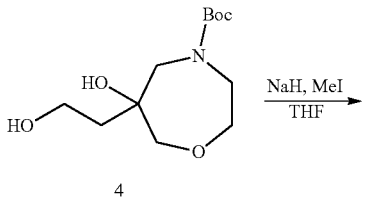

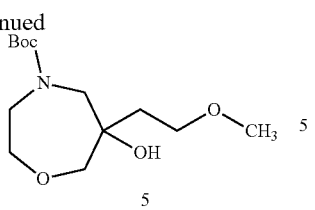

To a solution of Compound 4 (210 mg, 0.8 mmol) in THF (8 mL) was added NaH (48 mg, 1.2 mmol, 60%) at 0° C. After stirring for 30 min, a solution of MeI (0.8 mmol) in THF (2 mL) was added dropwise, and stirred at 25° C. for 2 h. TLC monitored that the reaction was completed.

The mixture was poured into water and extracted with EA. The combined organic phase was dried over $Na_2SO_4$, and concentrated in vacuum. The residue was purified through column chromatography (PE/EA=5/1, 3/1) to give the desired product compound 5 (90 mg, 41%).

$^1$H NMR (400 MHz, $CDCl_3$): δ ppm: 3.25-3.94 (m, 14H), 1.75-1.89 (m, 3H), 1.43-1.56 (m, 9H).

1.21.4 Preparation of Amine A62

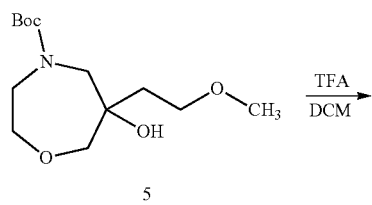

To a solution of compound 5 (350 mg, 1.27 mmol) in DCM (2 mL) was added TFA (2 mL). The formed mixture was stirred for 2 h, and concentrated to give the desired product which was used for the next step directly (210 mg, 94%).

1.22 Preparation of A37

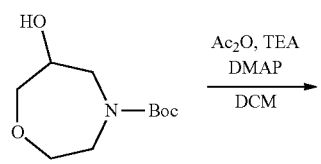

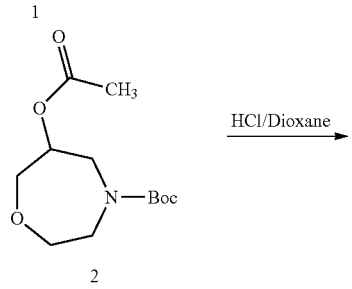

1.22.1 Preparation of Compound 2

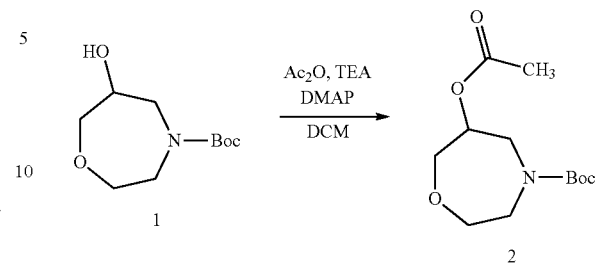

To a solution of compound 1 (400 mg, 1.84 mmol) in DCM (4 mL) added TEA (557.5 mg, 5.52 mmol), $Ac_2O$ (376 mg, 3.69 mmol) followed by DMAP (44.9 mg, 0.33 mmol). The mixture was stirred at 12° C. for 2 h. The mixture was extracted with EA (50 mL*2). The combined organic layer was dried over $Na_2SO_4$, concentrated to give the crude product, which was purified by chromatography on silica gel to give compound 2 as colorless oil (450 mg, 94.4%).

1.22.2 Preparation of A37

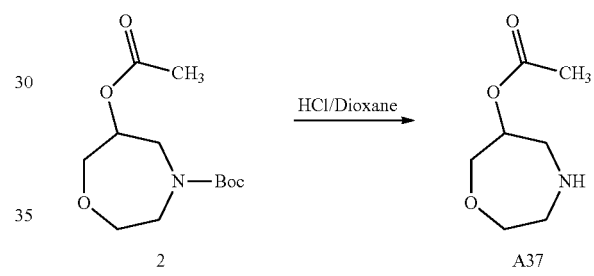

Compound 2 was treated with HCl/dioxane (4 M) to afford compound 3.

1.23 Preparation of A38-41

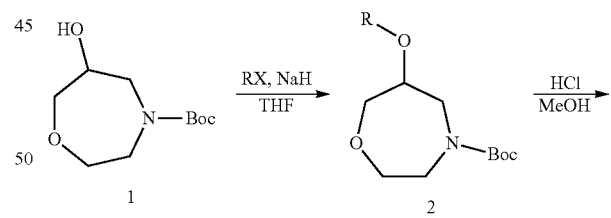

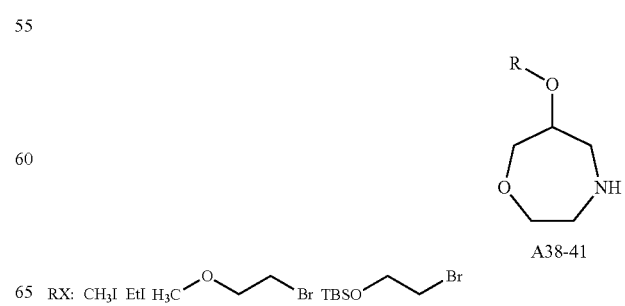

RX: $CH_3I$ EtI $H_3C{\sim}O{\sim}Br$ $TBSO{\sim}Br$

1.23.1 Preparation of Compound 2

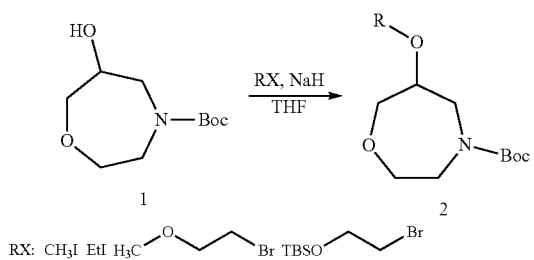

To a solution of Compound 1 (2.36 g, 10.95 mmol) in DMF (23 mL) added NaH (1.26 g, 31.5 mmol) portion-wise at 0° C. The mixture was attired at 0° C. for 40 min. RX (219 mmol) added dropwise at 0° C. The mixture was attired at 19° C. for 1 h. The mixture was poured into ice-water, extracted with EA. The combined organic layer was washed with $H_2O$, dried over $Na_2SO_4$, and concentrated in vacuo. The residue was purified through a silica gel column to give Compound 2.

1.23.2 Preparation of A38-41

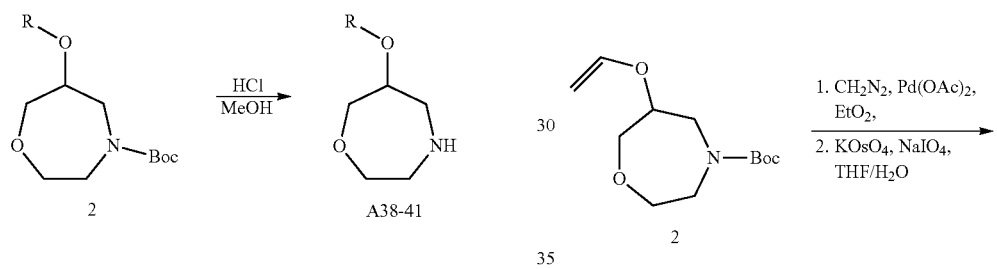

To a solution of Compound 2 (7.73 mmol) in Dioxane (2 mL) added HCl/Dioxane (4M) (2 mL). The mixture was stirred at 19° C. for 1 h. The mixture was concentrated in vacuo to give Compound A38-41.

1.24 Procedure for Preparation of A42

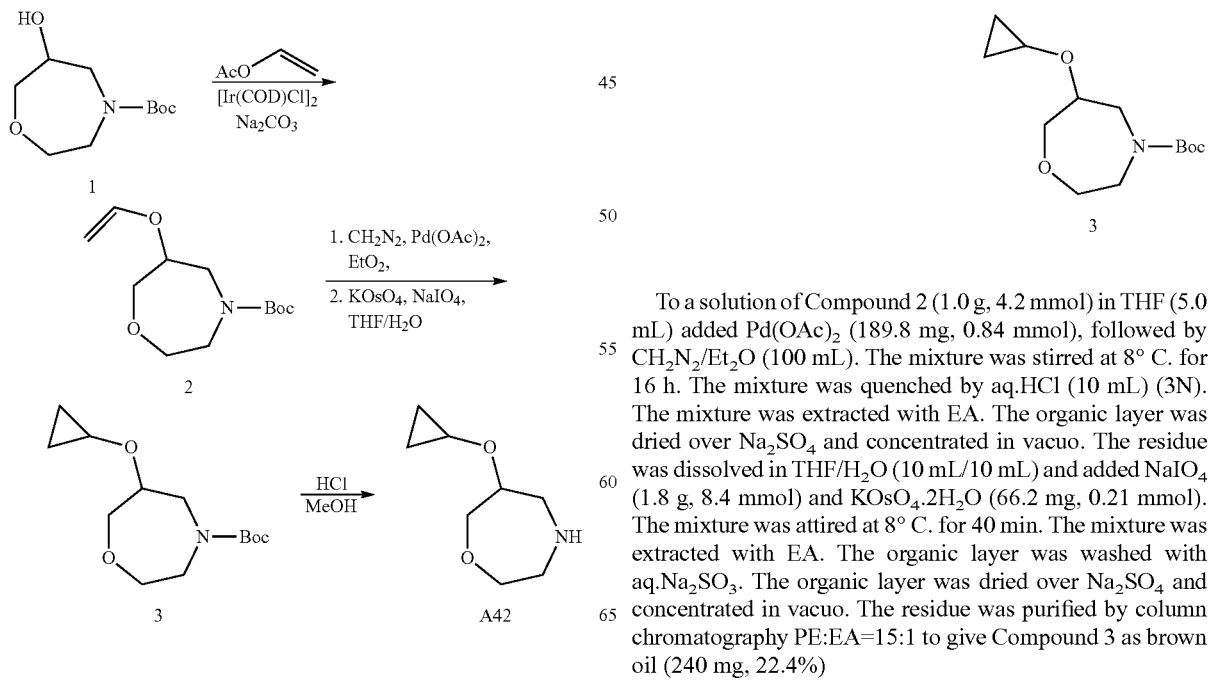

1.24.1 Preparation of Compound 2

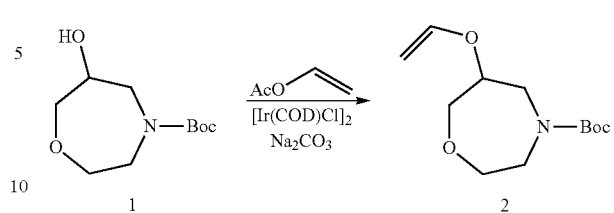

To a solution of Compound 1 (3.0 g, 13.9 mmol) in Toluene (30 mL) added $Na_2CO_3$ (736.7 mg, 69.5 mmol) followed by $[Ir(COD)Cl]_2$ (189 mg, 0.28 mmol). The mixture was degassed under vacuo and purged with $N_2$ several times. Vinyl acetate (4.78 g, 55.5 mmol) added by syringe. The reaction mixture was heated to 110° C. for 16 h. The mixture was cooled to 11° C. and extracted with EA. The combined organic layer was dried over $Na_2SO_4$ and concentrated. The residue was purified by column chromatography to give Compound 1 as colorless oil (1.0 g, 29.8%).

1.24.2 Preparation of Compound 3

To a solution of Compound 2 (1.0 g, 4.2 mmol) in THF (5.0 mL) added $Pd(OAc)_2$ (189.8 mg, 0.84 mmol), followed by $CH_2N_2/Et_2O$ (100 mL). The mixture was stirred at 8° C. for 16 h. The mixture was quenched by aq.HCl (10 mL) (3N). The mixture was extracted with EA. The organic layer was dried over $Na_2SO_4$ and concentrated in vacuo. The residue was dissolved in $THF/H_2O$ (10 mL/10 mL) and added $NaIO_4$ (1.8 g, 8.4 mmol) and $KOsO_4 \cdot 2H_2O$ (66.2 mg, 0.21 mmol). The mixture was attired at 8° C. for 40 min. The mixture was extracted with EA. The organic layer was washed with aq.$Na_2SO_3$. The organic layer was dried over $Na_2SO_4$ and concentrated in vacuo. The residue was purified by column chromatography PE:EA=15:1 to give Compound 3 as brown oil (240 mg, 22.4%)

1.24.3 Preparation of A42

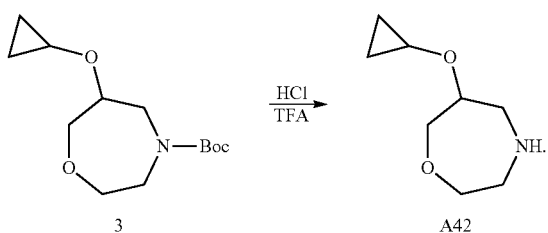

To a solution of Compound 3 (100 mg, 0.39 mmol) in DCM (2 mL) added TFA (2 mL). The mixture was stirred at 8° C. for 2 h. The mixture was concentrated in vacuum to give Compound 3 as brown oil (91 mg, crude).

1.25 Procedure for A43

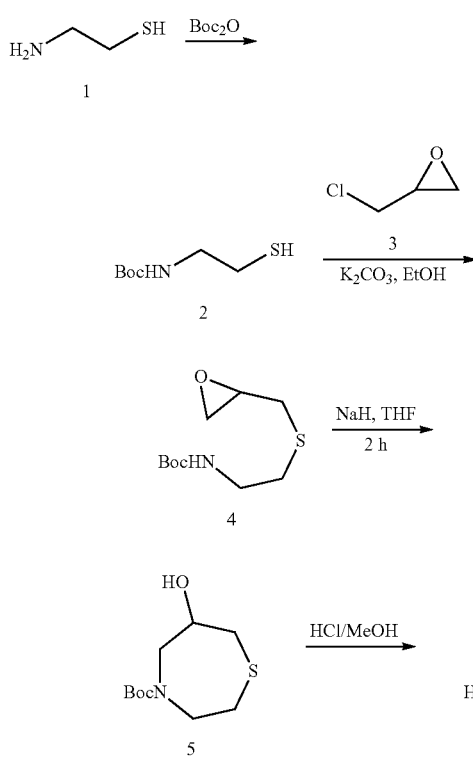

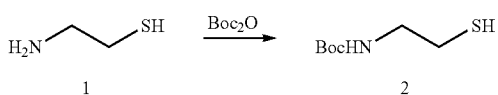

1.25.1 Preparation of Compound 2

To a solution of compound 1 (10 g, 129.8 mmol) in DCM (150 mL) added Boc$_2$O (28 g, 129.8 mmol) followed by TEA (19.7 g, 194.7 mmol). The mixture was stirred at 12° C. for 16 h. The mixture was concentrated to give the crude product, which was purified by chromatography on silica gel PE:EA (10:1) to give compound 2 as colorless oil (18.3 g, 79.9%).

1.25.2 Preparation of Compound 4

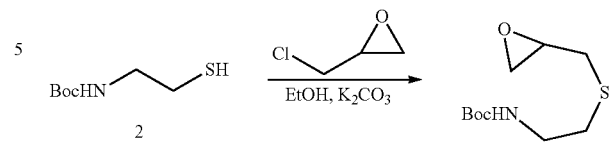

Compound 2 (1.0 g, 6.2 mmol) and compound 3 (960.8 mg, 10.5 mmol) in EtOH (12 mL) were cooled to 0° C. and treated with K$_2$CO$_3$ (960.8 mg, 6.96 mmol). The mixture was stirred at 12° C. for 16 h. The mixture was diluted with EA (100 mL) and filtered through celite. The volatiles were removed under reduced pressure to give compound 4 as colorless oil (1.4 g, 83.8%).

1.25.3 Preparation of Compound 5

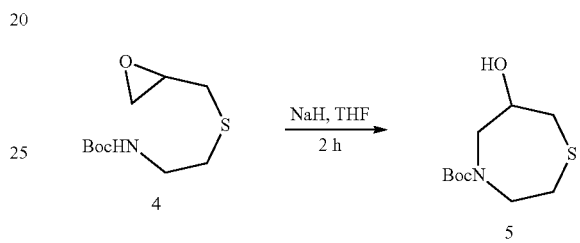

To a solution of compound 4 (500 mg, 2.14 mmol) in DMF (6 mL) added NaH (246.7 mg, 6.4 mmol) portionwise at −5° C. After stirring for 30 min at 0° C., the mixture was allowed to stir at 16° C. for 2 h. The mixture was poured into ice-water with stirring, extracted with EA (30 mL*2). The combined organic layer was dried over Na$_2$SO$_4$, concentrated to give the crude product, which was purified by chromatography on silica gel PE:EA (15:1) to give compound 5 as brown oil (140 mg, crude).

1.25.4 Preparation of A42

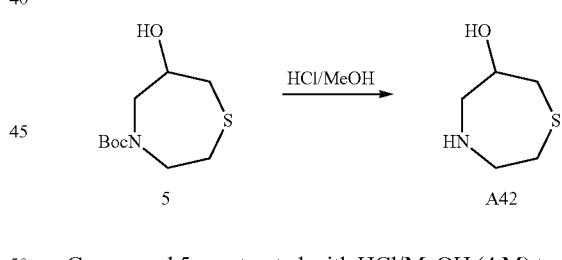

Compound 5 was treated with HCl/MeOH (4 M) to afford compound D.

1.26 Procedure for A44

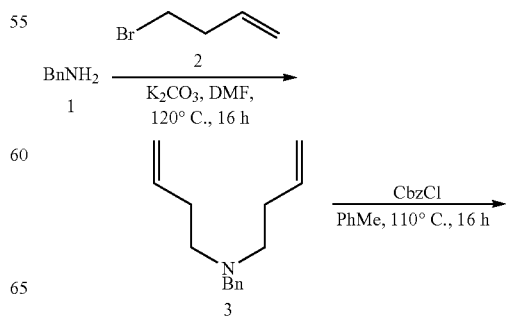

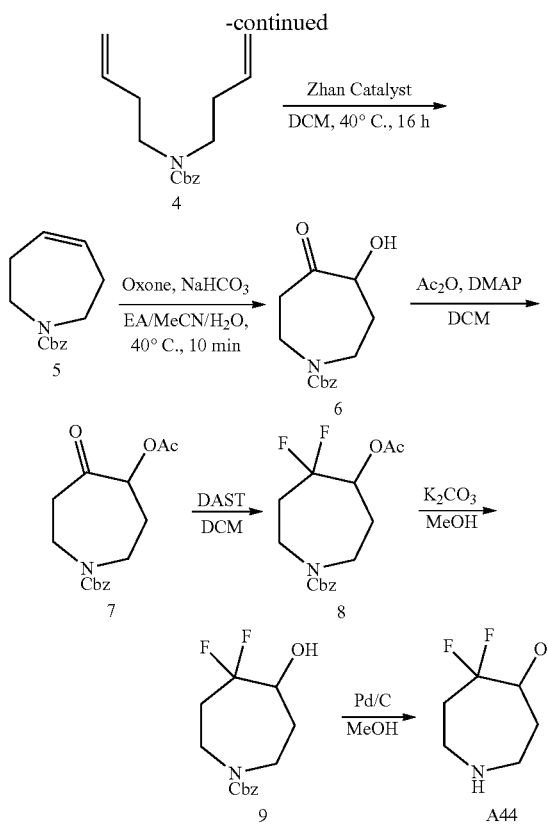

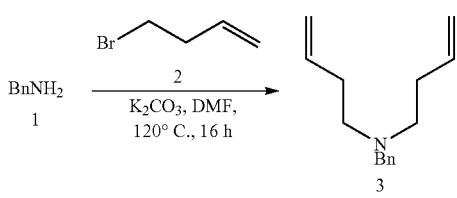

1.26.1 Preparation of Compound 3

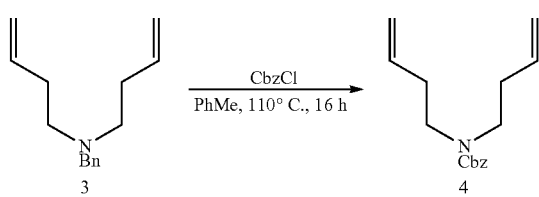

A mixture of Compound 1 (4.0 g, 37.3 mmol) and Compound 2 (10 g, 74.7 mmol), $K_2CO_3$ (12.9 g, 93.4 mmol) in DMF (100 mL) was heated at 120° C. for 16 hrs. The mixture was poured into water (200 mL), extracted with EA (100 mL×3), and the organic layer was washed with brine (150 mL), dried over $Na_2SO_4$ and concentrated to dryness. The residue was purified by silica gel chromatography (PE:EA=1:1 to PE:EA=1:0) to give desired compound 3 (5.1 g, 63.5%) as brown oil.

1.26.2 Preparation of Compound 4

A solution of Compound 3 (5.1 g, 23.7 mmol) and CbzCl (4.4 g, 26.1 mmol) in toluene (100 mL) was heated at 110° C. for 16 hrs. Then the mixture was concentrated to dryness, the residue was purified by silica gel chromatography (PE: EA=5:1 to PE:EA=2:1) to give desired compound 4 (4.5 g, 72.5%) as brown oil.

1.26.3 Preparation of Compound 5

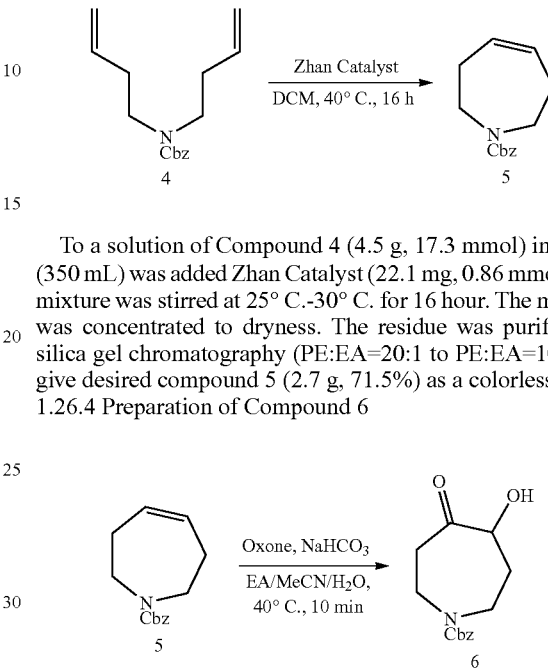

To a solution of Compound 4 (4.5 g, 17.3 mmol) in DCM (350 mL) was added Zhan Catalyst (22.1 mg, 0.86 mmol), the mixture was stirred at 25° C.-30° C. for 16 hour. The mixture was concentrated to dryness. The residue was purified by silica gel chromatography (PE:EA=20:1 to PE:EA=10:1) to give desired compound 5 (2.7 g, 71.5%) as a colorless oil.

1.26.4 Preparation of Compound 6

A mixture of $NaHCO_3$ (2.43 g, 29.1 mmol) and $RuCl_3$ (200 mg, 1.08 mmol) in EA/MECN/H2O (72 ml/72 ml/12 ml) was added oxone (35.3 g, 58.0 mmol), then compound 5 (2.7 g, 11.6 mmol) was added into the above mixture. And the reaction was stirred at 40° C. for 10 min, the mixture was filtered and the filtrate was washed with $Na_2SO_3$ (100 ml), the organic layer was dried over $Na_2SO_4$ and concentrated to dryness. The residue was purified with column chromatography on silica gel (PE:EA=5:1 to 1:1) to give compound 6 (1.7 g, 54.5%) as colorless oil. $^1$H NMR (400 MHz, CHLOROFORM-d) δ=7.41-7.28 (m, 5H), 5.21-5.06 (m, 2H), 4.45 (t, J=10.0 Hz, 1H), 4.32-4.16 (m, 1H), 4.16-4.00 (m, 2H), 3.84 (d, J=15.1 Hz, 1H), 3.34-3.10 (m, 2H), 3.00-2.55 (m, 2H), 2.18-2.07 (m, 1H), 1.81-1.62 (m, 1H).

1.26.5 Preparation of Compound 7

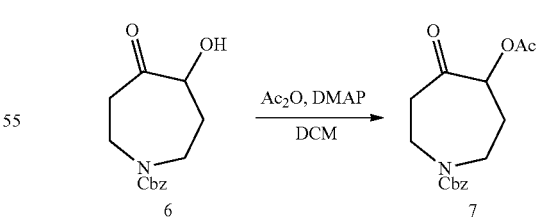

To a mixture of compound 6 (1.7 g, 6.50 mmol) in DCM (20 mL) was added DMAP (1.2 g, 9.7 mmol) in one portion, followed by $Ac_2O$ (0.8 g, 7.8 mmol). The mixture was stirred at 40° C. for 16 h. The mixture was concentrated to dryness. The residue was purified with column chromatography on silica gel (PE:EA=5:1 to 3:1) to give compound 7 (1.5 g, 79.5%) as colorless oil. $^1$H NMR (400 MHz, CHLORO- FORM-d) δ=7.43-7.30 (m, 5H), 5.30-5.23 (m, 1H), 5.18-5.07 (m, 2H), 4.10-3.89 (m, 2H), 3.75 (t, J=6.5 Hz, 1H), 3.53-3.30 (m, 2H), 2.89-2.61 (m, 2H), 2.04-1.90 (m, 2H), 1.86 (td, J=3.3, 6.5 Hz, 1H).

1.26.6 Preparation of Compound 8

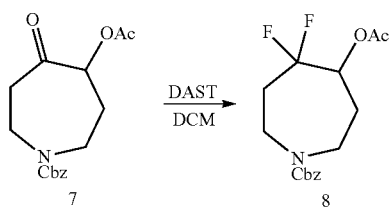

To a solution of compound 7 (1.7 g, 4.9 mmol) in DCM (15 mL) was added a solution of DAST (3.18 g, 19.6 mmol) in DCM (5 mL) drop-wise at −60° C. over a period of 30 mins under N₂. The reaction mixture was stirred at 40° C. for another 12 hrs. TLC (PE:EtOAc=1:1) showed the starting material was consumed completely. The reaction was poured into waster and then extracted with DCM (50 mL*3). The combined organic phase was washed with saturated brine (50 mL*2), dried over anhydrous Na₂SO₄, filtered and concentrated in vacuo. The residue was purified by silica gel chromatography silica gel (PE/EA=3/1, 1/1) to afford compound 8 (0.71 g, 44.31% yield) as yellow soil. ¹H NMR (400 MHz, CHLOROFORM-d) δ=7.42-7.30 (m, 5H), 5.25-5.14 (m, 3H), 3.75-3.58 (m, 2H), 3.52-3.33 (m, 2H), 2.50-2.29 (m, 1H), 2.28-1.98 (m, 6H).

1.26.7 Preparation of Compound 9

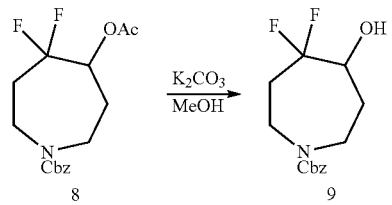

To a mixture of compound 8 (770 mg, 2.35 mmol) in MeOH (10 mL) was added K₂CO₃ (260 mg, 1.8 mmol) in one portion, the mixture was stirred at 40° C. for 1 h. The mixture poured into water (20 ml), extracted with EtOAc (20 ml), the combined organic layers were washed with brine (20 ml) and concentrated to dryness to give compound 9 (560 mg, 83.3%).

1.26.8 Preparation of A44

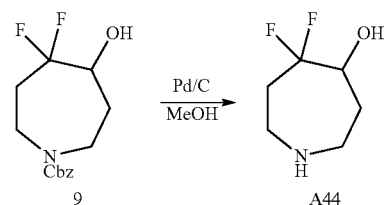

To a solution of compound 9 (560 mg, 1.96 mmol) in MeOH (10 mL) was added Pd(OH)₂/C (10%, 56 mg) under N₂. The suspension was degassed under vacuum and purged with H₂ several times. The mixture was stirred under H₂ (50 psi) at 40° C. for 16 hours. TLC (PE:EtOAc=1:1) showed the starting material was consumed completely. The reaction mixture was filtered and the filter was concentrated to give compound B (280 mg, 95.53% yield) as yellow solid.

1.27 Preparation of A45

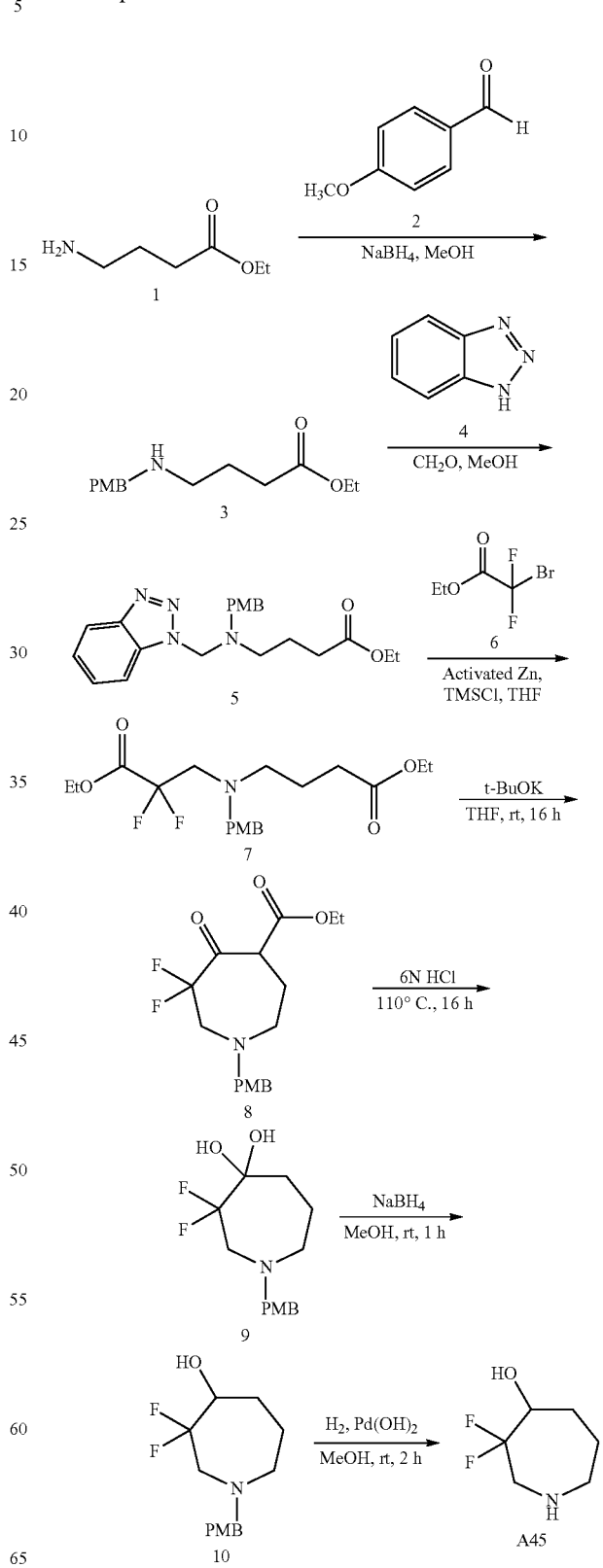

1.27.1 Preparation of Compound 3

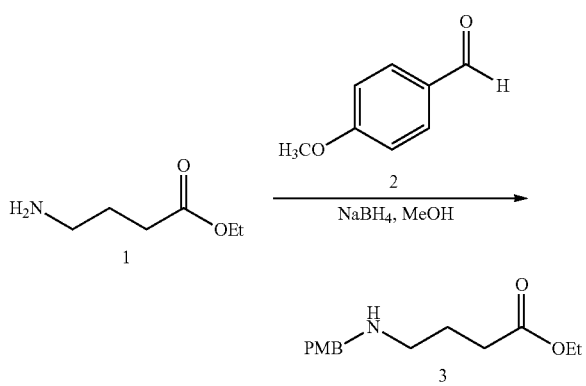

To a mixture of compound 1 (20.00 g, 119.31 mmol, HCl salt) in MeOH (200 mL) was added TEA (12.07 g, 119.31 mmol) and compound 2 (12.66 g, 119.31 mmol, 1.00 Eq) in one portion at 16° C. The mixture was stirred at 16° C. for 16 h. The mixture was added NaBH$_4$ (2.71 g, 71.59 mmol) portion-wise at 0° C. The mixture was stirred at 16° C. for 1 h. The mixture was quenched by H$_2$O (50 mL). The mixture was concentrated and purified by flash chromatography to give compound 3 as white solid (15.60 g, 50.73% yield).

1.27.2 Preparation of Compound 5

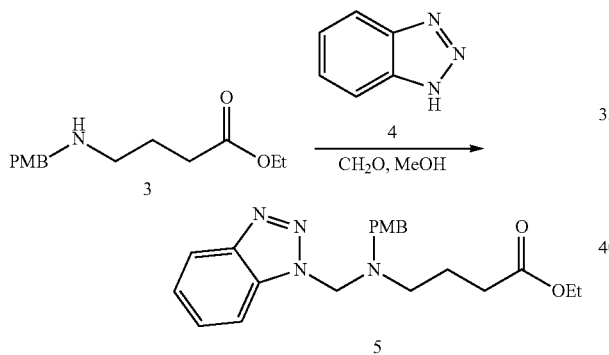

To a mixture of compound 3 (9.00 g, 31.27 mmol,) and compound 4 (3.73 g, 31.27 mmol) in MeOH (90 mL)/H$_2$O (10 mL) was added Na$_2$CO$_3$ (3.98 g, 37.53 mmol) followed by formalin (3.30 g, 40.66 mmol) in one portion at 16° C. under N$_2$. The mixture was stirred at 16° C. for 16 h. The mixture was extracted with EA (400 mL*3). The combined organic phase was dried with anhydrous Na$_2$SO$_4$, filtered and concentrated in vacuum to afford compound 5 as brown oil (8.90 g, 74.42%).

1.27.3 Preparation of Compound 7

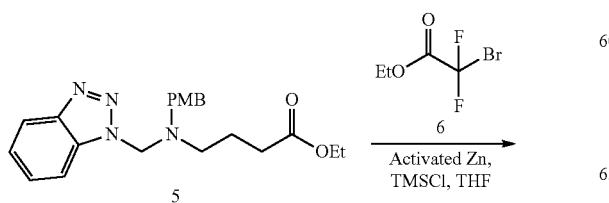

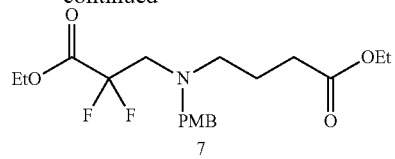

To a mixture of Zn (3.08 g, 47.06 mmol) in THF (90 mL) was added TMSCl (2.68 g, 24.71 mmol, 1.05 Eq) slowly below 30° C. under N$_2$. The mixture was stirred at 20° C. for 10 min. Compound 6 (5.25 g, 25.89 mmol, 1.10 Eq) was added slowly below 30° C. under N$_2$. The mixture was stirred at 20° C. for another 10 min. A solution of compound 5 (9.00 g, 23.53 mmol, 1.00 Eq) in THF (10 mL) added slowly. While keep inner temperature was below 30° C. The mixture was stirred at 20° C. for another 16 h. The mixture was quenched by aq.NaHCO$_3$ (5 mL). The precipitate was removed by filtration. The filtrate was extracted with EA (100 mL*2). The combined organic phase was washed with 1M HCl (10 mL*2), dried with anhydrous Na$_2$SO$_4$, filtered and concentrated in vacuum. The residue was purified by silica gel chromatography to afford compound 7 as colorless oil (4.00 g, 44%).

1.27.4 Preparation of Compound 8

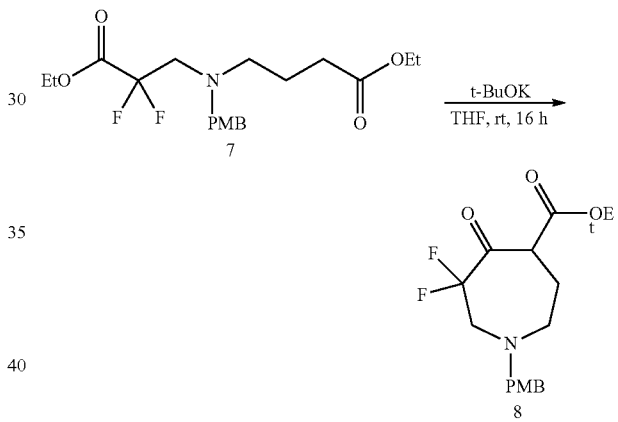

To a solution of compound 7 (4.00 g, 10.32 mmol) in THF (80 mL) was added t-BuOK (1.74 g, 15.49 mmol) in one portion at 15° C. The mixture was stirred at 15° C. for 3 hr. The mixture was poured into aq.NH$_4$Cl and extracted with EA (10 mL*2). The combined organic phase was washed with saturated brine (200 mL*2), dried with anhydrous Na$_2$SO$_4$, filtered and concentrated in vacuum. The residue was purified by silica gel chromatography to afford compound 8 as yellow oil (2.50 g, 70.97%).

1.27.5 Preparation of Compound 9

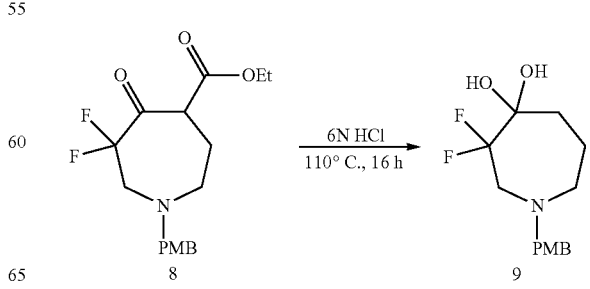

Compound 8 (2.50 g, 7.32 mmol) was dissolved in HCl (50 mL). The mixture was heated to 100° C. and stirred for 16 hours. The mixture was cooled to 25° C. and concentrated in vacuo to afford compound 9 as brown oil (1.52 g, 72%).

1.27.6 Preparation of Compound 10

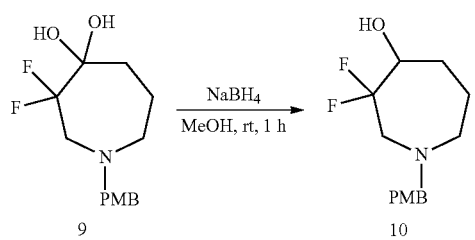

To a solution of compound 9 (1.52 g, 5.29 mmol) in MeOH (5 mL) was added NaBH$_4$ (200.14 mg, 5.29 mmol) portionwise at 0° C. The mixture was stirred at 15° C. for 16 hr. Then the mixture was poured into aq.NH$_4$Cl and extracted with EA (10 mL*2). The combined organic phase was dried with anhydrous Na$_2$SO$_4$, filtered and concentrated in vacuum to afford compound 10 as yellow oil (1.39 g, 96.85%).

1.27.7 Preparation of Compound A45

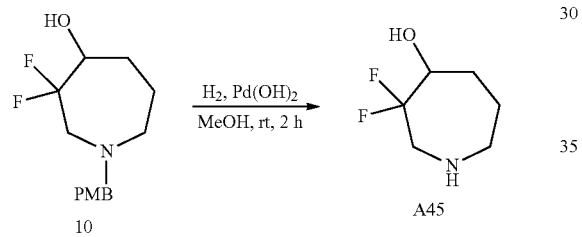

To a solution of compound 10 (1.39 g, 5.12 mmol) in MeOH (60 mL) was added Pd(OH)$_2$/C (10%, 0.2 g) under N$_2$. The suspension was degassed under vacuum and purged with H$_2$ several times. The mixture was stirred under H$_2$ (15 psi) at 15° C. for 3 hours. TLC (PE:EtOAc=3:1) showed the starting material was consumed completely. The reaction mixture was filtered and the filter was concentrated. The crude product was purified by silica gel chromatography to give compound A as colorless oil (511.00 mg, 66.03%).

1.27 Preparation of A46

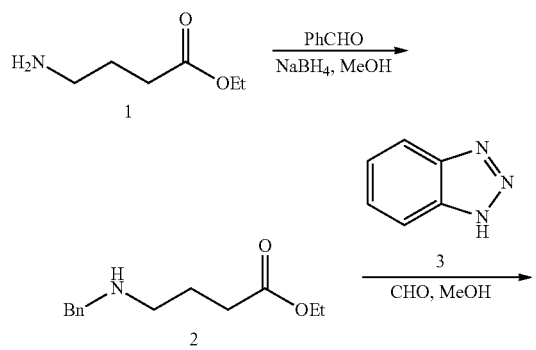

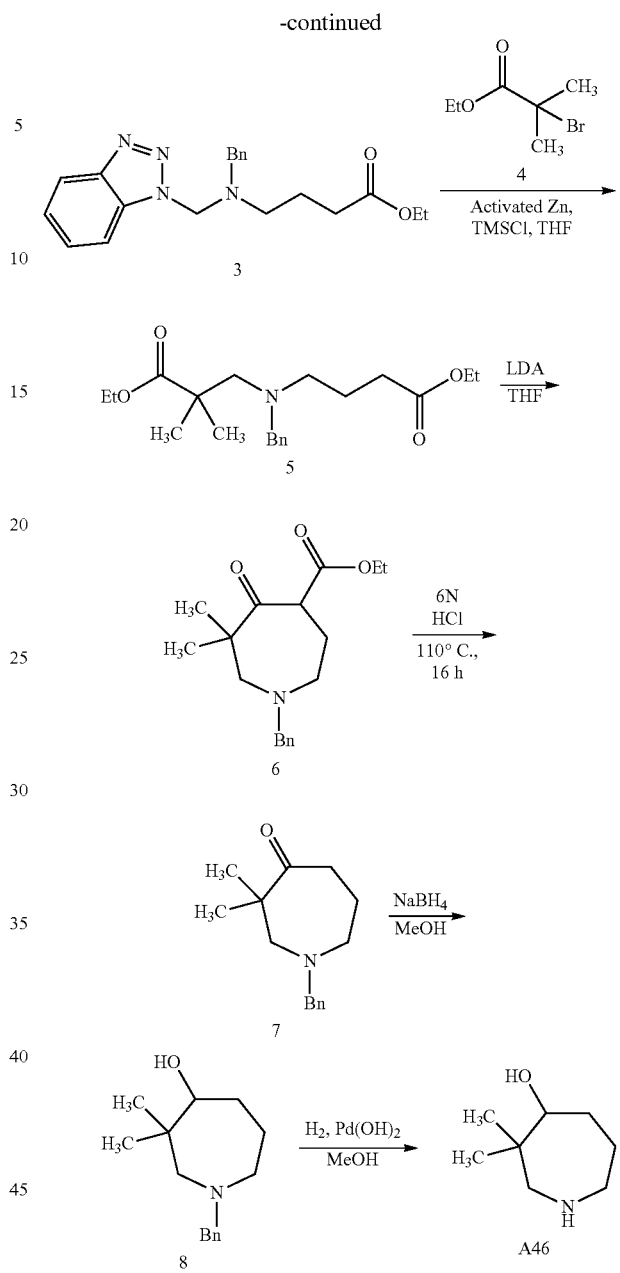

The procedure for preparation of amine B was the similar with amine A. LDA was used to cyclization step from compound 5 to compound 6.

1.28 Preparation of A47

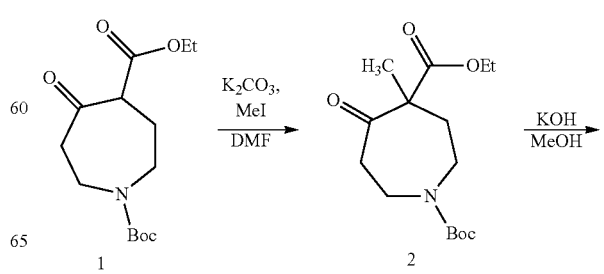

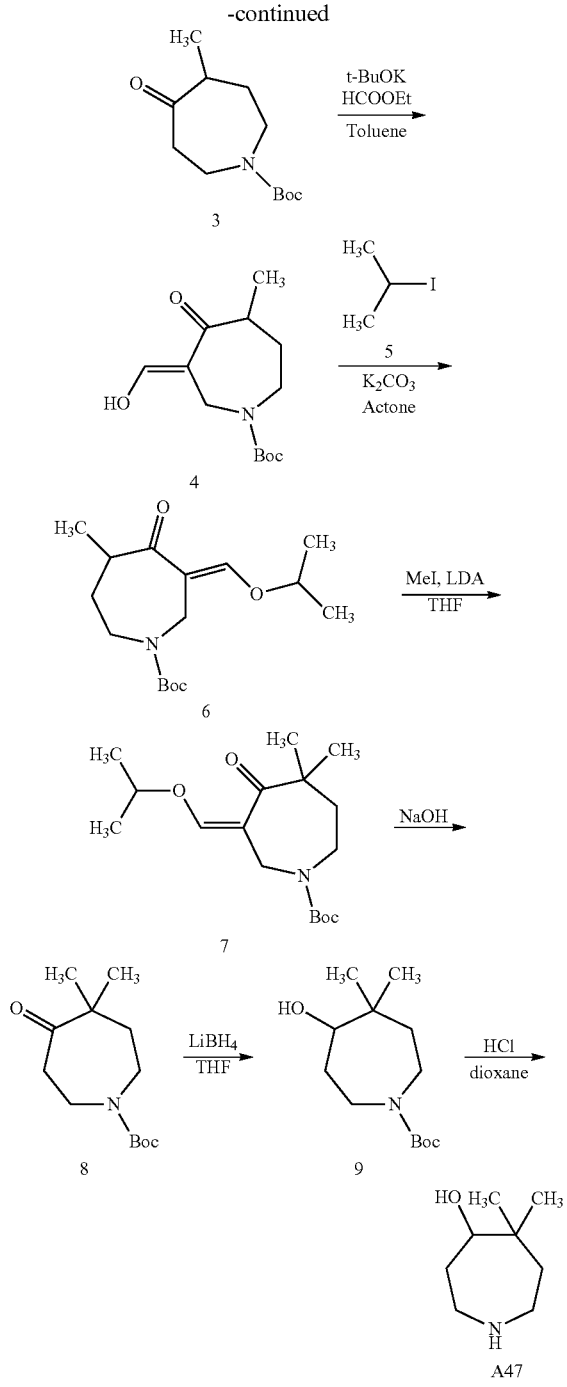

1.28.1 Preparation of Compound 2

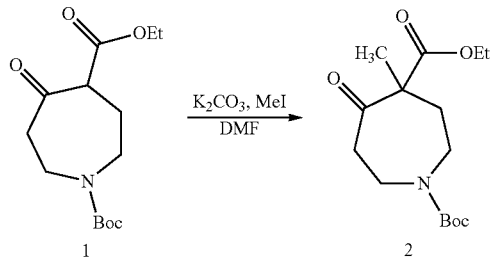

To a solution of compound 1 (5.00 g, 17.52 mmol,) in DMF (50 mL) was added $K_2CO_3$ (4.84 g, 35.04 mmol) followed by MeI (3.73 g, 26.28 mmol) portion-wise at 0° C. The mixture was stirred at r.t. for 16 hr. TLC showed the reaction was completed. The mixture was cooled to r.t. and concentrated in reduced pressure at 60° C. The residue was poured into ice-water (w/w=1/1) (150 mL) and stirred for 20 min. The aqueous phase was extracted with EA (400 mL*3). The combined organic phase was washed with saturated brine (200 mL*2), dried with anhydrous $Na_2SO_4$, filtered and concentrated in vacuum. The residue was purified by silica gel chromatography to afford compound 2 as yellow solid (3.60 g, 68.64%).

1.28.2 Preparation of Compound 3

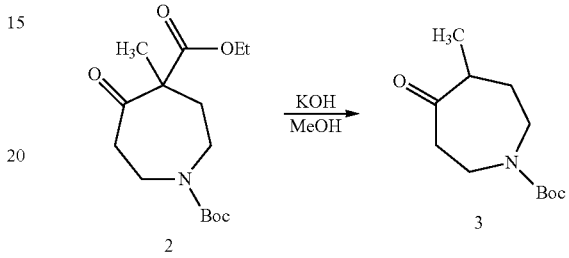

To a solution of compound 2 (15.00 g, 50.11 mmol, 1.00 Eq) in MeOH (100 mL) was added KOH (5.62 g, 100.21 mmol, 2.00 Eq) in $H_2O$ (35 mL). The mixture was heated to 60° C. for 3 hr. The mixture was cooled to r.t. and poured into aq.$NH_4Cl$. The mixture was extracted with EA (50 mL*3). The combined organic phase was dried with anhydrous $Na_2SO_4$, filtered and concentrated in vacuo to afford compound 3 as brown oil (9.00 g, 79.02%).

1.28.3 Preparation of Compound 4

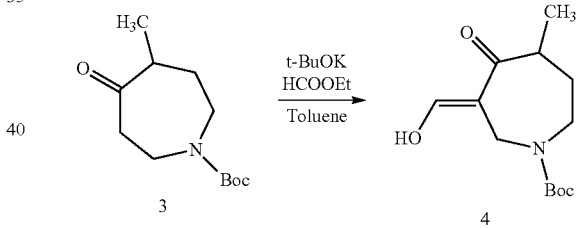

To a solution of compound 3 (10.00 g, 43.99 mmol) in toluene (100 mL) was added t-BuOK (7.40 g, 65.99 mmol at 0° C. The mixture was stirred at 15° C. for 16 hr. The mixture was extracted with EA. The EA layer was washed with 10% aq.NaOH (50 mL*3). Combined the water layer and adjust PH=4 and extracted with EA (100 mL*3). The EA layer was dried over $Na_2SO_4$, filtered and concentrated in vacuum to afford compound 4 as yellow oil (10.00 g, 89.04%).

1.28.4 Preparation of Compound 6

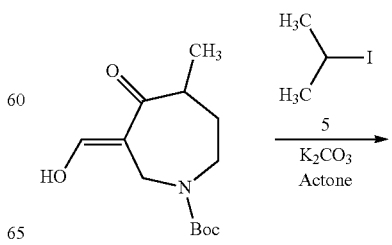

1.28.6 Preparation of Compound 8

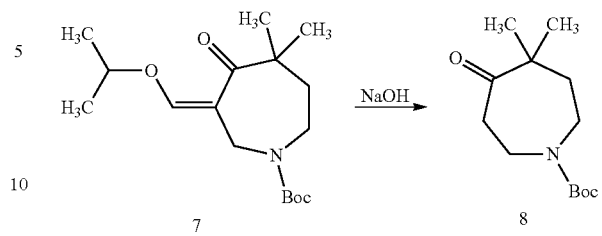

To a solution of compound 7 (800.00 mg, 2.6 mmol) in EtOH (10 mL) was added NaOH (205.69 mg, 5.22 mmol,) in H$_2$O (0.8 mL). The mixture was stirred at 90° C. for 16 hr. TLC showed the starting material was consumed. The mixture was adjust pH=7 and extracted with DCM. The organic layer was concentrated in vacuum to give compound 8 (900.00 mg, crude).

1.28.7 Preparation of Compound 9

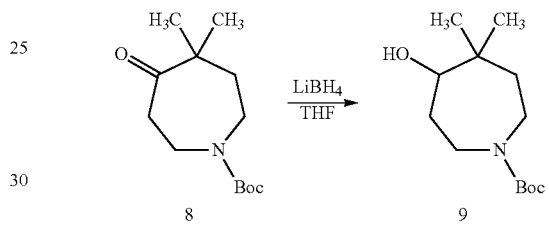

To a solution of compound 8 (900.00 mg, 3.73 mmol) in THF (10 mL) was added LiBH4 (243.72 mg, 11.19 mmol) in one portion at 0° C. The mixture was stirred at 20° C. for 1 hr. Then the mixture was quenched by aq.NH4Cl and extracted with EA (50 mL*2). The combined organic phase was dried with anhydrous Na$_2$SO$_4$, filtered and concentrated in vacuum. The residue was purified by silica gel chromatography to afford compound 9 as yellow oil (570.00 mg, 62.80%).

1.28.8 Preparation of A47

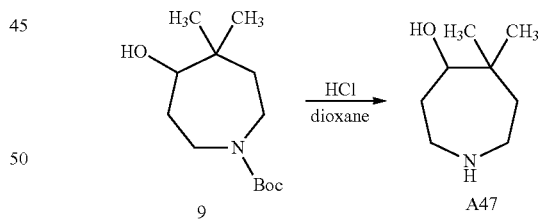

Compound 5 was treated with HCl/dioxane (4 M) to afford compound B.

1.29 Preparation of A48/49:

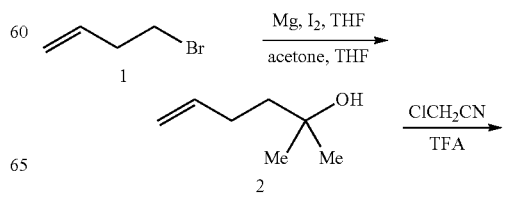

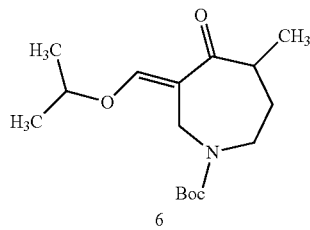

To a solution of compound 4 (9.00 g, 35.25 mmol) in ACETONE (100 mL) was added K2CO3 (9.74 g, 70.50 mmol) followed by compound 5 (8.99 g, 52.88 mmol). The mixture was refluxed at 60° C. for 16 hr. TLC showed the reaction was completed. The mixture was extracted with EA (100 mL*3). The combined organic layer was dried over Na$_2$SO$_4$, filtrated and concentrated to give the residue product, which was purified by flash chromatography to give compound 6 as yellow oil (7.80 g, 74.41%).

1.28.5 Preparation of Compound 7

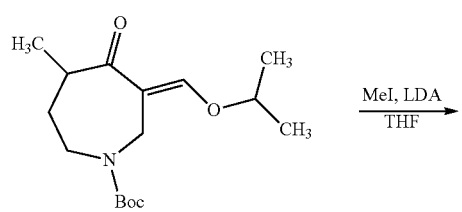

To a solution of diisopropylamine (6.18 g, 61.03 mmol) in THF (80 mL) was added n-BuLi (2.5 M, 22.19 mL) dropwise at −70° C. The mixture was stirred at −10° C. for 30 min under N2. Compound 6 (5.50 g, 18.49 mmol) in THF (80 mL) was added dropwise at −70° C. When added completely, the mixture was stirred at −30–−20° C. for 30 min. Then CH$_3$I (7.88 g, 55.48 mmol, 3.00 Eq) was added dropwise at −70° C. The mixture was allowed to stir at 20° C. for 3 hr. TLC showed starting material was nearly consumed. The mixture was poured into aq.NH4Cl and extracted with EA (40 mL*3). The combined organic phase was washed with saturated brine (20 mL*2), dried with anhydrous Na$_2$SO$_4$, filtered and concentrated in vacuum to the crude product, which was purified by flash chromatography to afford compound 7 as yellow oil (1.50 g, 26.07%).

369
-continued

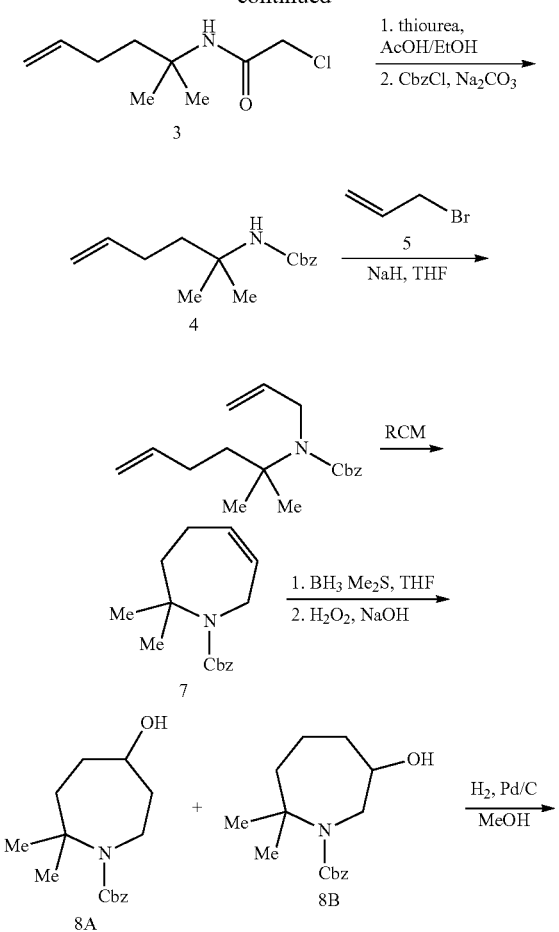

1.29.1 Preparation of Compound 2

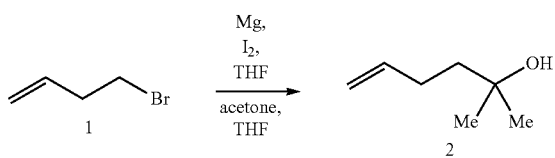

To a mixture of Mg (31.20 g, 1.30 mol) and $I_2$ (10 mmol) in THF (700 mL) was added compound 1 (130.00 g, 963 mmol) in THF (700 mL) dropwise at 40° C. When added completely after 1.5 hr. The mixture was stirred at 50° C. for 1 hr. Acetone (75.50 g, 1.30 mol) in THF (700 mL) was added dropwise at −10° C. Then the mixture was stirred at 20° C. for another 2 hr. The mixture was quenched by aq.NH4Cl and extracted with DCM (200 mL). The mixture was distilled at ordinary pressure (190° C.) to afford compound 2 as colorless oil (60.00 g, 52.55%).

370

1.29.2 Preparation of Compound 3

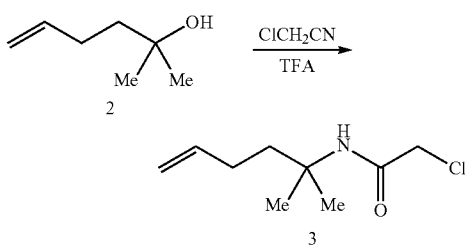

To a solution of compound 2 (7.00 g, 61.30 mmol) in TFA (104.84 g, 919.50 mmol, 15.00 Eq) was added 2-chloroacetonitrile (13.88 g, 183.90 mmol) in one portion. The mixture was heated to 70° C. for 16 hr. The mixture was adjust pH=7 with aq.$Na_2CO_3$ and extracted with EA. The organic layer was concentrated and purified by FLASH CHROMATOGRAPHY to give compound 3 as yellow oil (4.20 g, 36%).

1.29.3 Preparation of Compound 4

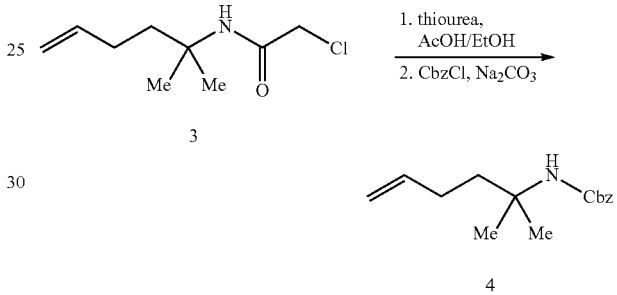

To a solution of compound 3 (4.20 g, 22.14 mmol) in EtOH (40 mL) was added THIOUREA (2.02 g, 26.57 mmol). The mixture was stirred at 100° C. for 2 hr. Then the mixture was detected by TLC. TLC showed SM was consumed. The mixture was added HOAc (8 mL) and heated to 90° C. for 16 hours. The mixture was adjust PH=12 with aq.$Na_2CO_3$ and added CbzCl (7.55 g, 44.28 mmol) The mixture was stirred at 25° C. for 2 hr. The mixture was detected by TLC). TLC showed have DP. The mixture was extracted with EA (500 mL*2). The combined organic phase was dried with anhydrous $Na_2SO_4$, filtered and concentrated in vacuum. The residue was purified by silica gel chromatography to afford compound 4 as yellow oil (5.10 g, 93.14%).

1.29.4 Preparation of Compound 6

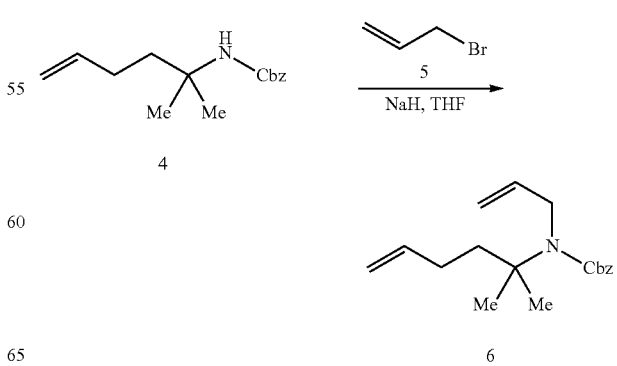

To a solution of compound 4 (5.00 g, 20.22 mmol) in DMF (50 mL) was added NaH (1.37 g, 34.37 mmol) portion-wise at 0° C. under N$_2$. When added completely. The mixture was stirred at 5° C. for 30 min. compound 5 (4.89 g, 40.44 mmol, 2.00 Eq) was added dropwise at 0° C. The mixture was stirred at 27° C. for 4 h. The mixture was detected by TLC. TLC showed SM was consumed incompletely. The mixture was continued to stir at 27° C. for 2 hr. The mixture was poured into ice-water and extracted with EA (200 mL*2). The combined organic layer was washed water (100 mL*3) dried with anhydrous Na$_2$SO$_4$, filtered and concentrated in vacuum. The residue was purified by silica gel chromatography to afford compound 6 as yellow solid (3.20 g, 55.07%).

1.29.5 Preparation of Compound 7

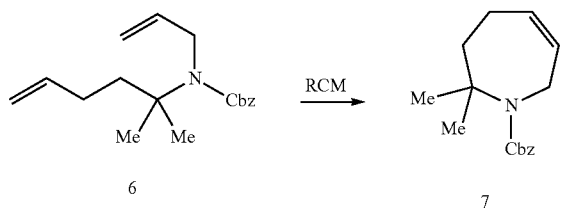 [SMILES: C=CCCC(C)(C)N(CC=C)C(=O)OCc1ccccc1 ; CC1(C)CCC=CCN1C(=O)OCc1ccccc1]

To a solution of compound 6 (3.20 g, 11.13 mmol) in DCM (60 mL) was added Grubb's 2st (320.00 mg, 388.85 umol) under N$_2$. The mixture was stirred at 28° C. for 16 hr under N2. The mixture was detected by TLC. TLC showed SM was consumed completely. The mixture was filtrated. The filtrate was concentrated in vacuum to give the residue, which was purified by silica gel chromatography to afford compound 7 as yellow oil (2.70 g, 93.54%).

1.29.6 Preparation of Compound 8A,8B

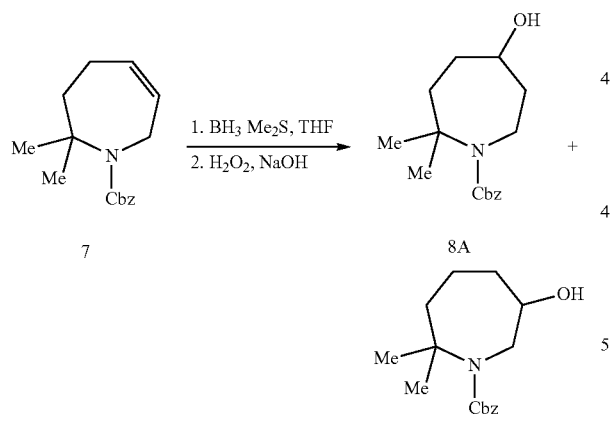

To a solution of compound 7 (2.70 g, 10.41 mmol) in THF (30 mL) was added BH3-Me2S (10 M, 3.12 mL) drop-wise at 0° C. under N$_2$. The mixture was stirred at 29° C. for 16 hr. Then the mixture was added into aq.NaOH (2.08 g, 52.05 mmol, 5.00 Eq) in H$_2$O (4 mL) dropwise at 0° C. H2O2 (N/A, 52.05 mmol, 5.00 Eq) was added into the mixture slowly. Then the mixture was stirred at 29° C. for 3 hr. The mixture was detected by TLC. TLC showed SM was consumed completely. The mixture was quenched by aq.Na$_2$SO$_3$ and extracted with EA (60 mL*2). The combined organic layer was dried over Na$_2$SO$_4$, filtrated and concentrated in vacuum.

The residue product was purified by column chromatography to give compound 8A as colorless oil (700.00 mg, 24.24%) and Compound 8B as colorless oil (1.20 g, 41.56%).

1.29.7 Preparation of Compound A48

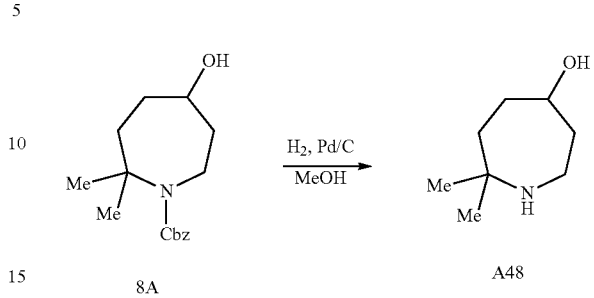

To a solution of f compound 8A (700.00 mg, 2.52 mmol) in MeOH (40 mL) was added Pd/C (10%, 80 mg) under N$_2$. The suspension was degassed under vacuum and purged with H$_2$ several times. The mixture was stirred under H$_2$ (15 psi) at 27° C. for 2 hours. TLC (Petroleum ether/Ethyl acetate=1:1) showed the starting material was consumed completely. The reaction mixture was filtered and the filter was concentrated to give compound A48 as yellow oil (320.00 mg, 88.66%).

Compound A49 was hydrogenated from 8B.

1.30 Preparation of A50

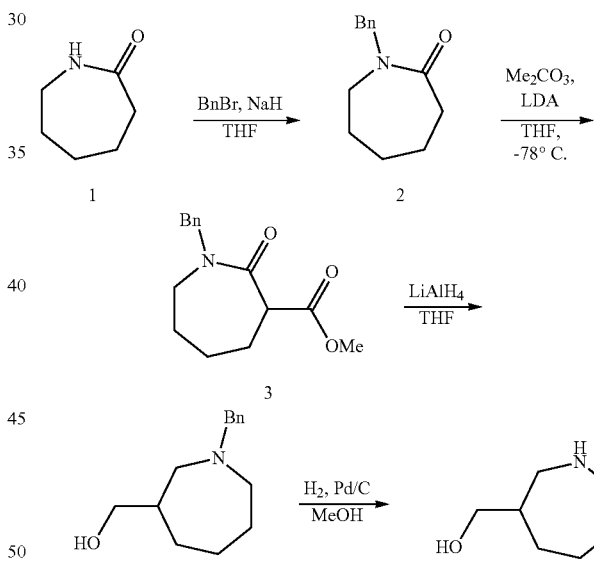

1.30.1 Preparation of Compound 2

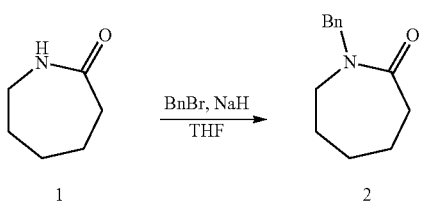 [SMILES: O=C1CCCCCN1 ; O=C1CCCCCN1Cc1ccccc1 ; "THF"]

To a solution of compound 1 (5.0 g, 44.2 mmol) in THF (100 mL) added NaH (2.6 g, 66.3 mmol) portionwise at −5°

C., while keeping inner temperature between −5~0° C. After stirring for 30 min at 0° C., BnBr (6.8 mL) was added dropwise. The mixture was stirred at 16° C. for 16 h. The mixture was poured into ice-water with stirring, extracted with EA (100 mL*2). The combined organic layer was dried over Na$_2$SO$_4$, concentrated to give the crude product, which was purified by chromatography on silica gel PE:EA (10:1) to give compound 2 as colorless oil (6.3 g, 70.8%).

1.30.2 Preparation of Compound 3

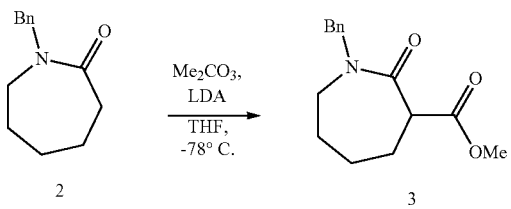 [SMILES: O=C1CCCCCN1Cc1ccccc1 ; "THF,-78° C." ; COC(=O)C1CCCCN(Cc2ccccc2)C1=O]

To a solution of compound 2 (2.03 g, 10.0 mmol) in THF (50 mL) added LDA (10 mL) dropwise at −78° C. under N$_2$ atmosphere. After stirring for 1 h at −78° C., dimethyl carbonate (1.8 g, 20.0 mmol) was added dropwise at −78° C. The mixture was stirred at 16° C. for 2 h. The mixture was quenched by aq.NH$_4$Cl, and extracted with EA (100 mL*2). The combined organic layer was dried over Na$_2$SO$_4$, concentrated to give the crude product, which was purified by chromatography on silica gel PE:EA (1:1) to give compound 4 as colorless oil (800 mg, 30.6%).

1.30.3 Preparation of Compound 5

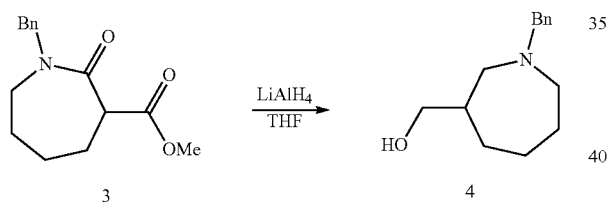

To a solution of LiAlH$_4$ (340 mg, 9.2 mmol) in THF (10 mL) was added a solution of compound 4 (800 mg, 3.06 mmol) in THF (10 mL) at −5° C., while keeping inner temperature between −5~10° C. The mixture was stirred at 0° C. for 3 h. H$_2$O (0.5 mL) was added slowly, followed by NaOH (15%, 0.5 mL) and H$_2$O (1.5 mL). The resulting mixture was filtrated. The filtrate was extracted with EA (50 mL*2). The combined organic layer was dried over Na$_2$SO$_4$, concentrated to give compound 4 as colorless oil (488 mg, 72.5%).

1.30.4 Preparation of Compound A50

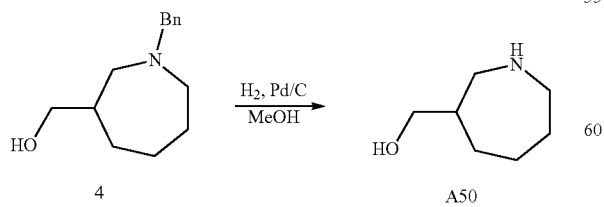

To a solution of Compound 4 (488 mg, 2.23 mmol) in MeOH (60 mL) was added Pd(OH)$_2$ (10%, 50 mg) under N$_2$. The suspension was degassed under vacuum and purged with H$_2$ several times. The mixture was stirred under H$_2$ (15 Psi) at 12° C. for 16 h. The mixture was filtrated, the filtrates was concentrated to give Compound A (220 mg, 76.6%).

1.31 Preparation of A51

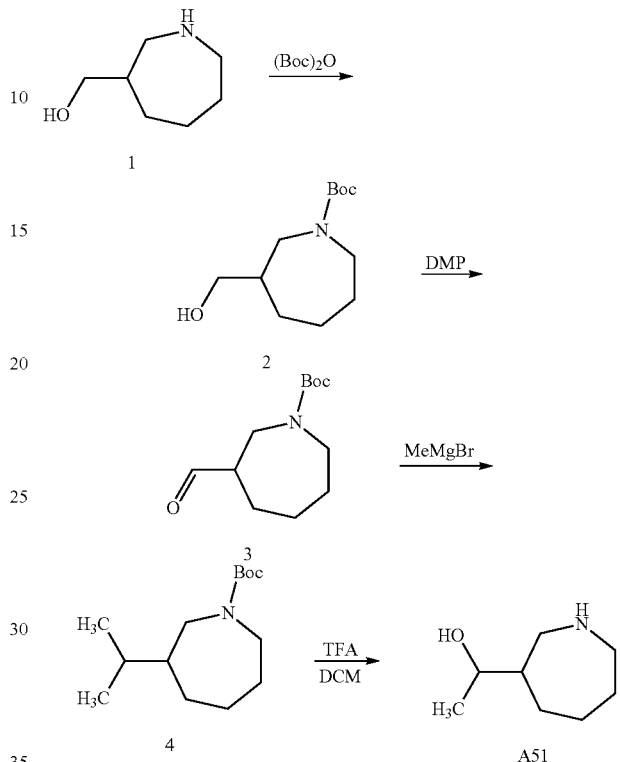

1.31.1 Preparation of Compound 4

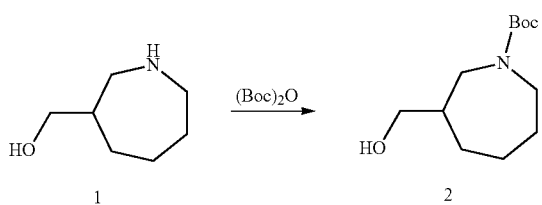

To a solution of Compound 1 (250 mg, 2.0 mmol) in DCM (5 mL) was added TEA (0.3 mL) followed by Boc$_2$O (426 mg, 2.0 mmol). The mixture was stirred at 12° C. for 2 h. The mixture was concentrated and purified by fish chromatography to give Compound 2 (350 mg, 76.6%).

1.31.2 Preparation of Compound 5

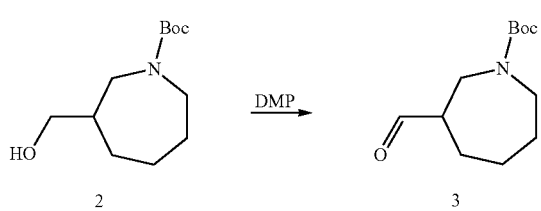

To a solution of Compound 3 (350 mg, 1.5 mmol) in DCM (5 mL) was added Dess-Martin reagent (190 mg, 1.95 mmol).

The mixture was stirred at 12° C. for 2 h. The mixture was extracted with DCM (50 mL) and washed with aq.NaHSO3 several times and concentrated to give Compound 5 (410 mg, crude).

1.31.3 Preparation of Compound 4

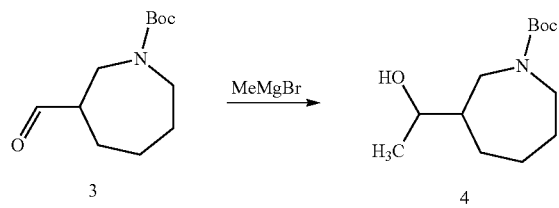

To a solution of MeMgBr (1.8 mL, 3M) in THF (3 mL) was added a solution of Compound 3 (410 mg, crude) in THF (3 mL) dropwise at 0° C. The mixture was stirred at 12° C. for 2 h. The mixture was quenched by aq.NH4Cl and extracted with DCM (50 mL), dried over $Na_2SO_4$ and concentrated to give Compound 6 (340 mg, crude).

1.31.4 Preparation of Compound B

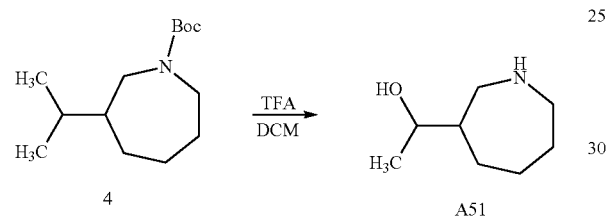

Compound 2 was treated with TFA/DCM (1:1) to afford compound B 1.32 Preparation of A52

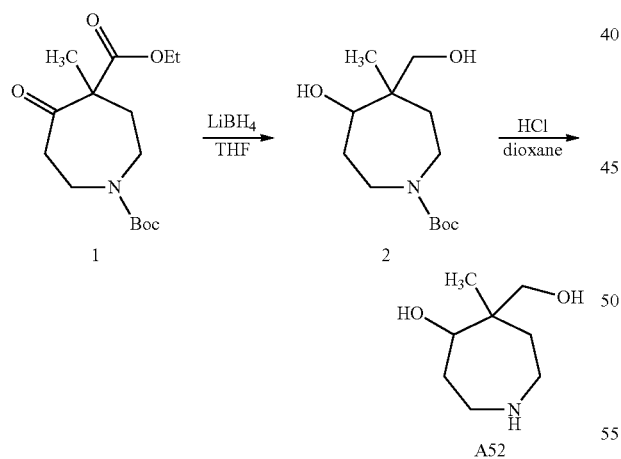

To a solution of compound 1 (2.60 g, 8.69 mmol) in THF (30 mL) was added LiBH4 (756.65 mg, 34.74 mmol) in one portion at 0° C. The mixture was stirred at 15° C. for 16 hr. TLC showed the reaction was completed. The mixture was quenched by aq.NH4Cl and extracted with EA (50 mL*3). The combined organic phase was dried with anhydrous $Na_2SO_4$, filtered and concentrated in vacuum. The residue was purified by silica gel chromatography to afford compound 2 as colorless oil (2.10 g, 93.18%). The resulting solid was treated with HCl/dioxane to give HCl salt.

1.33 Preparation of A64

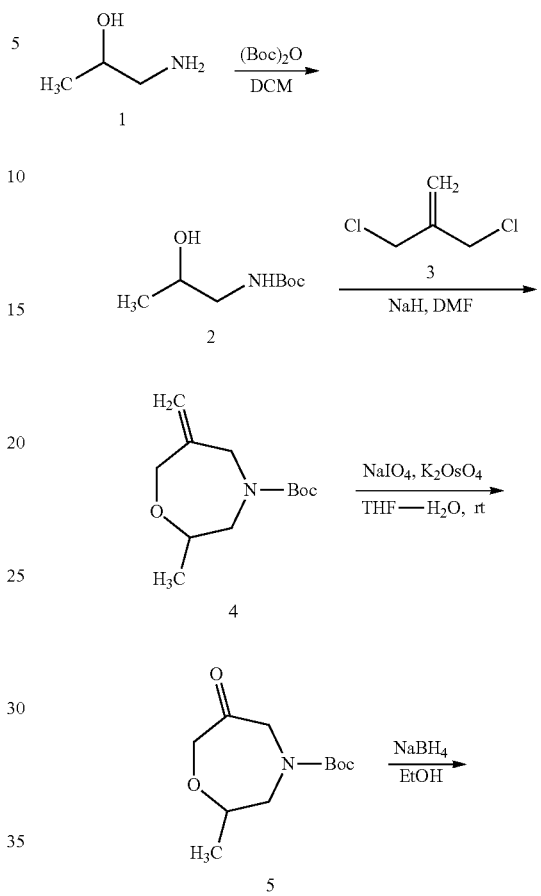

1.33.1 Preparation of Compound 2

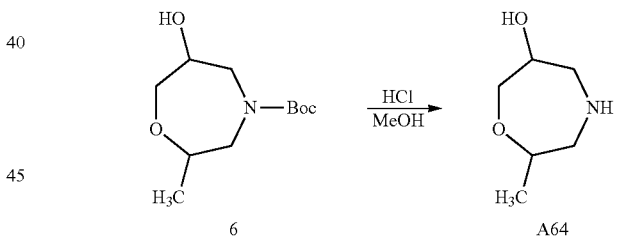

To a mixture of 1-aminopropan-2-ol (10.00 g, 133.14 mmol, 1.00 eq) in DCM, was added Boc2O (29.06 g, 133.14 mmol, 1.00 eq) in one portion at 30° C. under $N_2$. The mixture was stirred at 30° C. for 5 hours. TLC showed the reaction was completed. The mixture was concentrated in to afford tert-butyl N-(2-hydroxypropyl) carbamate (23.00 g, 131.26 mmol, 98.59% yield) as yellow oil.

1.33.2 Preparation of Compound 4

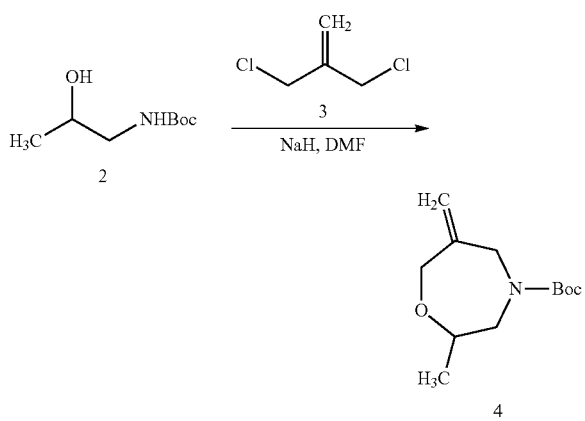

To a mixture of tert-butyl N-(2-hydroxypropyl)carbamate (5.00 g, 28.54 mmol, 1.00 eq) in DMF (100.00 mL), was added NaH (2.51 g, 62.79 mmol, 2.20 eq) in one portion at 0° C. under $N_2$. The mixture was stirred at 0° C. for 1 hr, then 3-chloro-2-(chloromethyl)prop-1-ene (3.57 g, 28.54 mmol, 1.00 eq) was added to the mixture, the mixture was stirred at 0° C. for 4 hr. TLC showed the reaction was completed. The mixture was poured into water (100 mL) and stirred for 5 min. The aqueous phase was extracted with ethyl acetate (100 mL*2). The combined organic phase was washed with saturated brine (100 mL*2), dried with anhydrous $Na_2SO_4$, filtered and concentrated in vacuum. The residue was purified by silica gel chromatography (Petroleum ether/Ethyl acetate=10/1) to afford tert-butyl 2-methyl-6-methylene-1,4-oxazepane-4-carboxylate (2.20 g, 9.68 mmol, 33.91% yield) as yellow oil.

1.33.3 Preparation of Compound 5

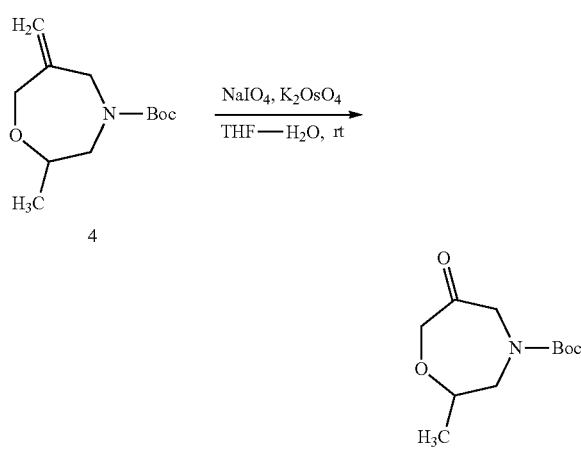

To a mixture of tert-butyl 2-methyl-6-methylene-1,4-oxazepane-4-carboxylate (2.40 g, 10.56 mmol, 1.00 eq) in THF (50.00 mL), was added NaIO4 (4.97 g, 23.23 mmol, 2.20 eq) and K2OSO4 (401.83 mg, 2.11 mmol, 0.20 eq) in one portion at 30° C. under $N_2$. The mixture was stirred at 30° C. for 5 hours. TLC showed the reaction was completed. The mixture was poured into saturated $NaSO_3$ (100 mL) and stirred for 5 min. The aqueous phase was extracted with ethyl acetate (30 mL*2). The combined organic phase was washed with saturated brine (30 mL*2), dried with anhydrous $Na_2SO_4$, filtered and concentrated in vacuum. The residue was purified by silica gel chromatography (Petroleum ether/Ethyl acetate=8/1) to afford tert-butyl 2-methyl-6-oxo-1,4-oxazepane-4-carboxylate (1.90 g, 8.29 mmol, 78.48% yield) as yellow oil.

1.33.4 Preparation of Compound 6

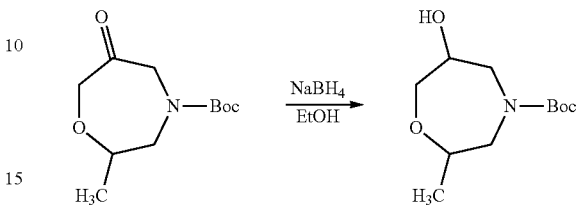

To a mixture of tert-butyl 2-methyl-6-oxo-1,4-oxazepane-4-carboxylate (1.90 g, 8.29 mmol, 1.00 eq) in EtOH (20.00 mL), was added NaBH4 (376.33 mg, 9.95 mmol, 1.20 eq) in one portion at 30° C. under $N_2$. The mixture was stirred at 30° C. for 5 hours. TLC showed the reaction was completed. The mixture was poured into saturated water (100 mL) and stirred for 5 min. The aqueous phase was extracted with ethyl acetate (30 mL*2). The combined organic phase was washed with saturated brine (30 mL*2), dried with anhydrous $Na_2SO_4$, filtered and concentrated in vacuum. The residue was purified by silica gel chromatography (Petroleum ether/Ethyl acetate=5/1) to afford two point, the first point D1:494 mg; the second point D2:656 mg.

1.33.5 Preparation of A64

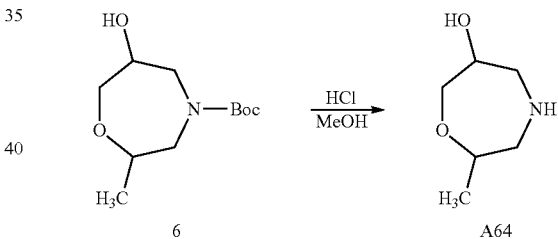

To a mixture of tert-butyl 6-hydroxy-2-methyl-1,4-oxazepane-4-carboxylate (D1, 494.00 mg, 2.14 mmol, 1.00 eq) in MeOH (5.00 mL), was added HCl/MeOH (15.00 mL) in one portion at 30° C. under $N_2$. The mixture was stirred at 30° C. for 5 hours. TLC showed the reaction was completed. The mixture was concentrated in vacuum to afford 2-methyl-1,4-oxazepan-6-ol (385.00 mg, crude) as yellow oil.

1.34 Preparation of A65

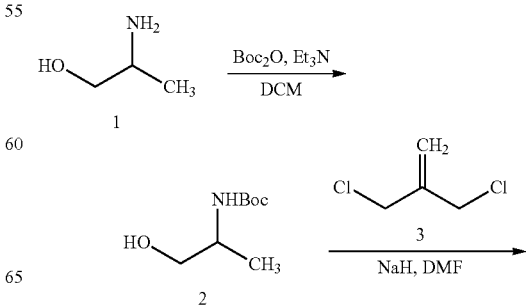

-continued

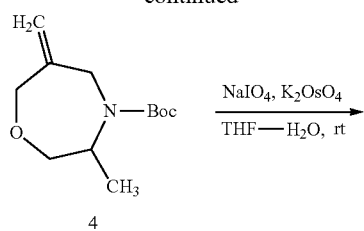

4

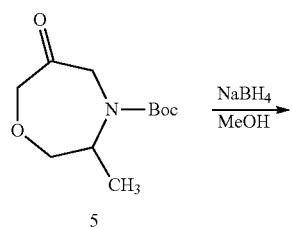

5

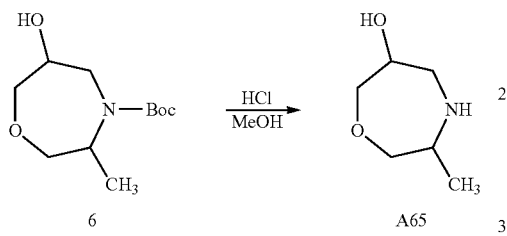

1.34.1 Procedure for Preparation of Compound 2

At ice bath, to a solution of Compound 1 (18 g, 0.24 mol) and Et3N (29 g, 0.28 mol) in DCM (180 mL) was added Boc$_2$O (65 g, 0.28 mol). Then the mixture was stirred at rt for 30 minutes. Washed with water and concentrated to give the crude product, which was purified by silica gel chromatography to give the desired product as a white solid (38.1 g, 90.7%).

1.34.2 Procedure for Preparation of Compound 4

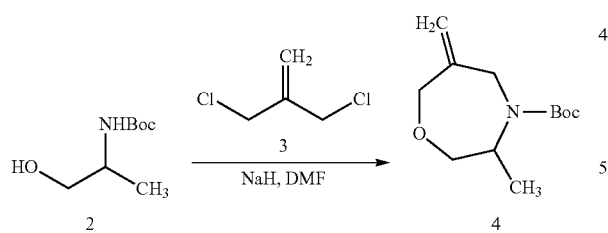

At ice bath, a solution of Compound 2 (3.5 g, 20 mmol) in DMF (30 mL) was added into a mixture of NaH (1.76 g, 44 mmol) in DMF (20 mL). After the mixture stirring for 30 minutes, Compound 3 (2.5 g, 20 mmol) was added and stirred at rt for 2 hrs. Quenched with NH4Cl solution, extracted with EA, washed with water and concentrated to give the crude product, which was purified by silica gel chromatography to give the pure product as an oil (780 mg, 17.2%).

$^1$H NMR (400 MHz, CDCl$_3$): δ ppm: 4.94-5.10 (m, 2H), 4.29-4.53 (m, 3H), 4.07 (d, J=10.0 Hz, 1H), 3.66-3.71 (m, 3H), 1.43 (m, 9H), 1.21 (d, J=7.1 Hz, 3H).

1.34.3 Procedure for preparation of compound 5

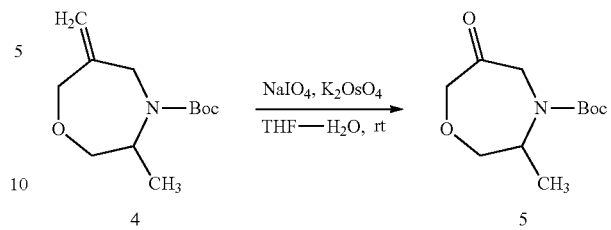

A mixture of Compound 4 (780 mg, 3.43 mmol), K2OsO$_4$ (54 mg, 0.20 mmol) and NaIO4 (1.69 mg, 7.90 mmol) in THF-H$_2$O (1:1, 20 mL) was stirred at rt for 2 hrs. The mixture was extracted with EtOAc (50 mL*2) and the organic layer was concentrated to give the crude product as an oil (790 mg).

1.34.4 Procedure for Preparation of Compound 6

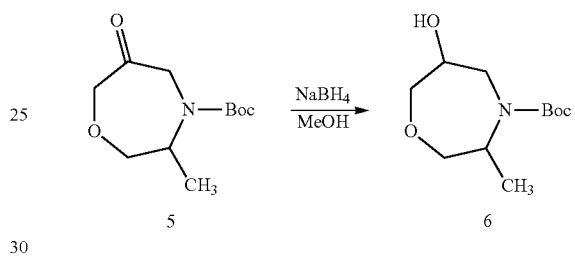

A solution of Compound 5 (787 mg, 3.43 mmol) and NaBH4 (130 mg, 3.43 mmol) in MeOH (15 mL) was stirred at rt for 30 minutes. Quenched with NH$_4$Cl solution, evaporated the solvent, extracted with EA (50 mL*2) and the organic layer was concentrated to give the crude product, which was purified by silica gel chromatography to give the desired product as an oil (517 mg, 65.2%).

$^1$H NMR (400 MHz, CDCl$_3$): δ ppm: 3.92-4.23 (m, 5H), 3.02-3.47.53 (m, 3H), 1.50 (d, J=6.4 Hz, 9H), 1.01-1.04 (m, 3H).

1.34.5 Preparation of A65

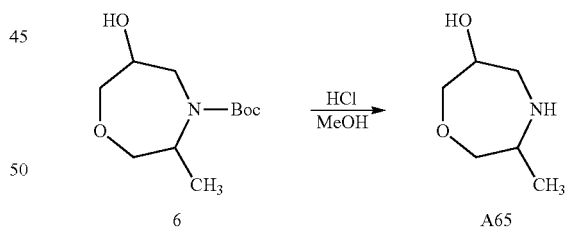

4M HCl-dioxane (10 mL) was added to Compound 6 (500 mg, 2.16 mmol). Then the solution was stirred at rt for 30 minutes. The solvent was evaporated in vacuo to give a HCl salt, which is used in the next step directly.

1.35 Preparation of A66

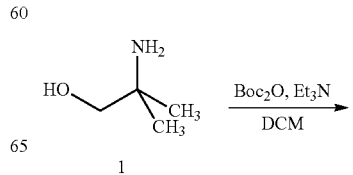

1

-continued

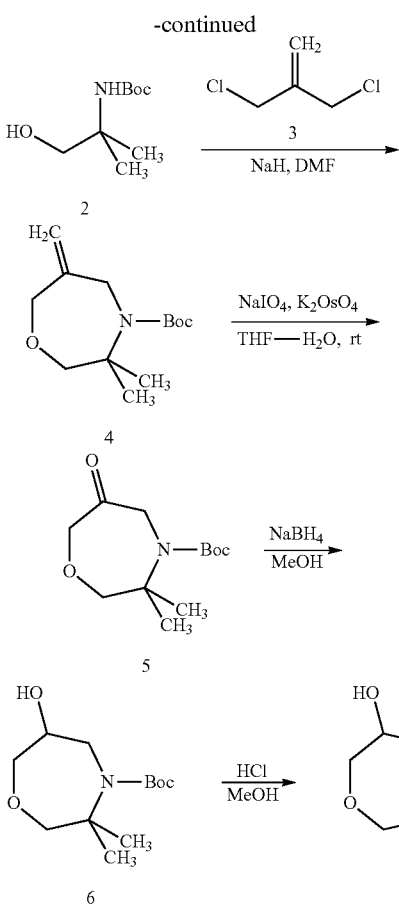

1.35.1 Preparation of Compound 2

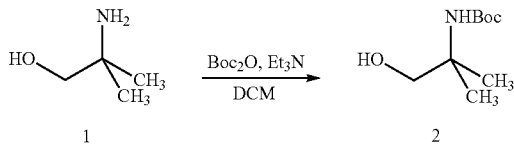

To a solution of compound 1 (10.00 g, 112.18 mmol, 1.00 Eq) in DCM (200 mL) was added Et₃N (23.00 g, 227.30 mmol, 2.03 Eq). The mixture was cooled to 0° C. and Boc₂O (38.40 g, 175.95 mmol, 1.57 Eq) was added, the mixture was stirred at 20° C. for 1 hr. The mixture was diluted with EA and washed with water. The organic phase was concentrated in vacuo. The residue was purified by silica gel chromatography (Petroleum ether/Ethyl acetate=15/1) to afford compound 2 (16.00 g, 84.54 mmol, 75.36% yield) as white solid.

1.35.2 Preparation of Compound 4

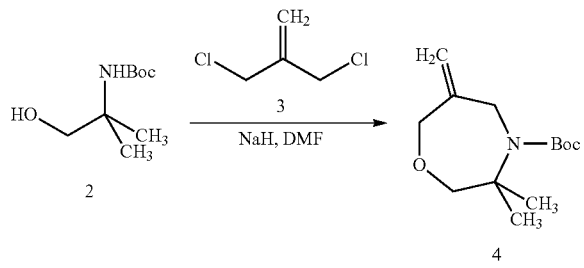

To a solution of compound 2 (2.00 g, 10.57 mmol, 1.00 Eq) in DMF (60 mL), the mixture was cooled to −10° C. Then NaH (930.16 mg, 23.25 mmol, 2.20 Eq) was added, the mixture was stirred for 40 min at 0° C., and compound 3 (1.59 g, 12.68 mmol, 1.20 Eq) was added dropwise at −5-0° C. The mixture was stirred at 20° C. for 3 hr. TLC (PE:EA=5:1) shown the reaction was completed. The reaction solution was poured into ice-water, extracted with EA and the organic phase was washed with more water, dried over Na₂SO4, and concentrated in vacuo. The residue was purified through silica gel chromatography (PE/EA=15/1) to afford compound 4 (1.00 g, 4.14 mmol, 39.20% yield) as yellow solid. ¹H NMR (400 MHz, CDCl₃) δ 5.02-4.98 (d, 2H), 4.15-4.08 (d, 4H), 3.64 (s, 2H), 1.47 (s, 9H), 1.40 (s, 6H).

1.35.3 Preparation of Compound 5

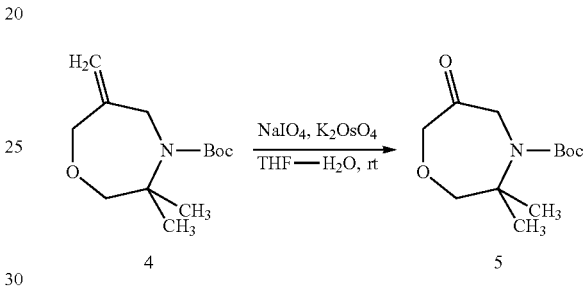

To a mixture of compound 4 (1.00 g, 4.14 mmol, 1.00 Eq) in THF (5 mL) and H₂O (5 mL) was added NaIO₄ (2.04 g, 9.52 mmol, 2.30 Eq), followed by K₂OsO₄.2H₂O (76.18 mg, 207.00 umol, 0.05 Eq). The mixture was stirred at 20° C. for 1 hr. TLC shown the reaction was completed. The reaction solution was diluted with EA, washed with Na₂SO₃ and brine, the organic phase was concentrated to give product compound 5 (1.10 g, crude) as yellowed oil.

1.35.4 Preparation of Compound 6

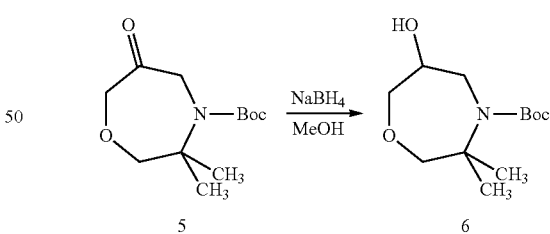

To a solution of compound 5 (1.10 g, 4.52 mmol, 1.00 Eq) in MeOH (10 mL) was added NaBH₄ (512.97 mg, 13.56 mmol, 3.00 Eq) at 0° C. The mixture was stirred at 20° C. for 1 h, TLC shown the reaction was completed, the reaction mixture was poured into ice sat.NH₄Cl and extracted with EA, the organic phase was concentrated, the residue was purified by silica gel chromatography (PE:EA=6:1) to give product compound 6 (700.00 mg, 2.85 mmol, 63.13% yield) as colorless oil.

1.35.5 Preparation of A66

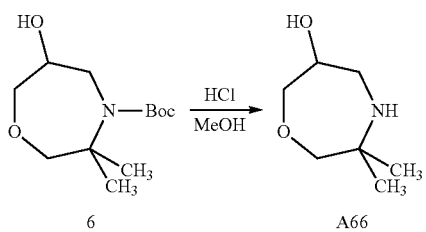

To a solution of compound 6 (700.00 mg, 2.85 mmol, 1.00 Eq) in dioxane (5 mL) was added HCl/dioxane (5 mL), the mixture was stirred at 23° C. for 1 hr. TLC shown the reaction was completed, the mixture was concentrated to give product compound D (600.00 mg, crude) as light yellow solid. ¹H NMR (400 MHz, CDCl₃) δ 4.45 (s, 1H), 3.93-3.92 (m, 2H), 3.88-3.87 (m, 1H), 3.77-3.74 (m, 2H), 3.52-3.48 (m, 1H), 1.53-1.49 (m, 6H).

1.36 Preparation of A52:

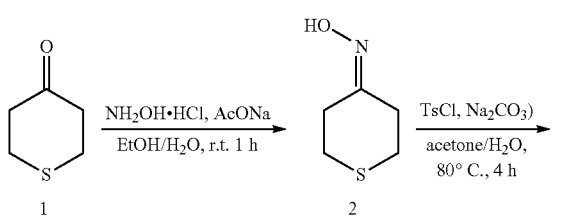

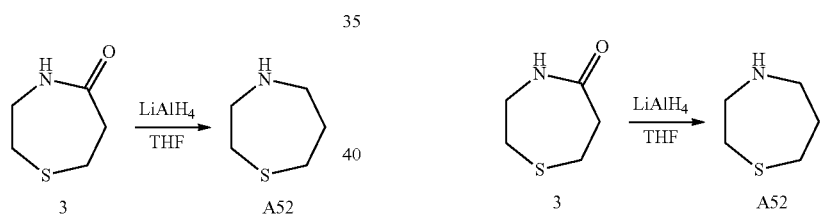

1.36.1 Preparation of Compound 2

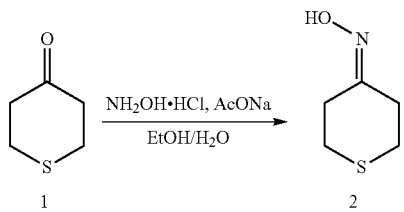

A mixture of Compound I (1.0 g, 8.6 mmol) and NH₂OH.HCl (3.0 g, 43 mmol), AcONa (2.1 g, 25.8 mmol) in EtOH/H₂O (20 mL/20 mL) was stirred at 25° C. for 1 hour. Then the mixture was extracted with EA (150 mL×3), the organic layer was dried over Na₂SO₄, and concentrated to give compound 2 (1.0 g, 89.2%).

1.36.2 Preparation of Compound 3

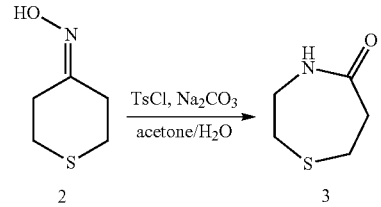

To a solution of compound 2 (1.0 g, 7.6 mmol) in acetone/H₂O (20 mL/20 mL) was added TsCl (2.16 g, 11.4 mmol) and Na₂CO₃ (1.2 g, 23.2 mmol). The resulting mixture was stirred at 60° C. for 16 hours. The mixture was concentrated to remove solvents. The residue was extracted with EA (20 mL×3). The organic layer was dried over Na₂SO₄, filtered, the filtrates were concentrated to give compound 3 (740 mg, 74%) as white solid.

1.36.3 Preparation of A52

To a suspension of LiAlH₄ (200 mg, 5.2 mmol) in THF (5 mL) was added compound 3 (370 mg, 2.8 mmol). The mixture was stirred at 60° C. for 2 hours. The reaction was quenched with H₂O (0.2 mL), dried over Na₂SO₄, filtered, and the filtrates were concentrated to give desired compound 4 (250 mg, 75.7%) as a yellow oil. ¹H NMR (400 MHz, CHLOROFORM-d) δ=3.08-3.02 (m, 1H), 2.99-2.92 (m, 1H), 2.89-2.82 (m, 1H), 2.81-2.66 (m, 5H), 2.00-1.85 (m, 2H).

1.37 Preparation of A68:

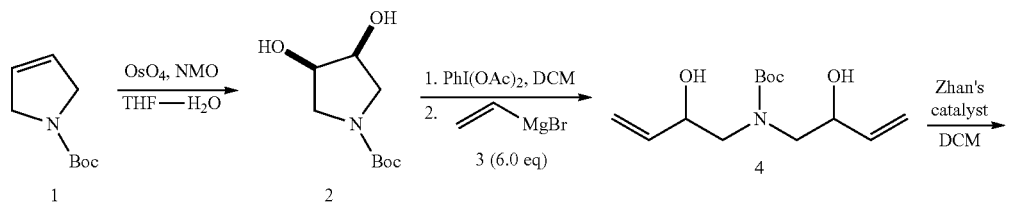

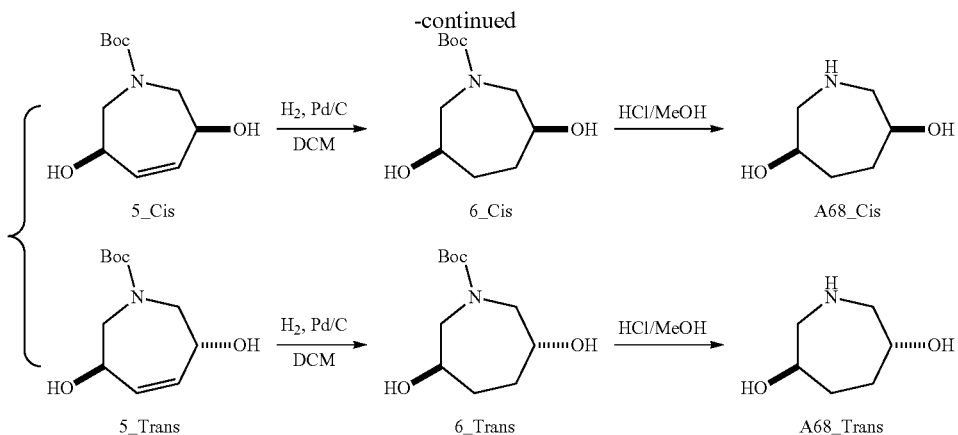

1.37.2.1 Preparation of Compound 2

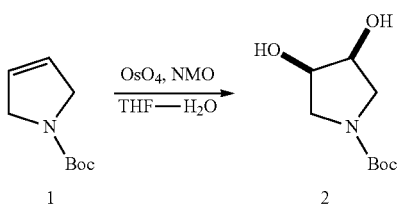

To a solution of Compound 1 (45.00 g, 265.93 mmol, 1.00 Eq) in THF (225 mL) and H₂O (450 mL) was added NMO (71.65 g, 611.64 mmol, 2.30 Eq) and OsO₄ (500.00 mg, 1.97 mmol, 0.01 Eq), the mixture was stirred at 28° C. for 16 hr. TLC showed the reaction was completed. The reaction solution was diluted with EA, washed with sat.Na₂SO₃ and brine. The organic phase was concentrated in vacuo. The residue was purified by silica gel chromatography (PE:EA=3:1) to give compound 2 (33.00 g, 162.38 mmol, 61.06% yield). $^1$H NMR (400 MHz, CHLOROFORM-d) ppm 4.23 (d, J=2.38 Hz, 2H), 3.52-3.63 (m, 2H), 3.34 (t, J=12.11 Hz, 2H), 3.13 (br, 1H), 2.97 (br, 1H), 1.45 (s, 9H).

1.37.2.2 Preparation of Compound 4

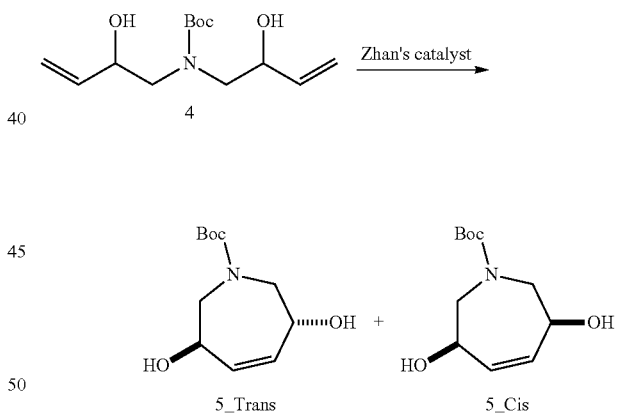

To a solution of Compound 2 (33.00 g, 162.38 mmol, 1.00 Eq) in DCM (330 mL) was added [acetoxy(phenyl)-iodanyl] acetate (78.45 g, 243.57 mmol, 1.50 Eq) at 0° C., the mixture was stirred for 1 hr from 0° C. to 28° C. Then the mixture was cooled to −60° C. and bromo(vinyl)magnesium (1 M, 974.28 mL, 6.00 Eq) in THF was added, the mixture was stirred for 2 hr from −60° C. to 28° C. TLC showed the reaction was completed, the mixture was diluted with EA and washed with sat.NH4Cl and brine. The organic phase was concentrated, the residue was purified by silica gel chromatography (PE: EA=10:1) to give Compound 4 (17.00 g, 66.06 mmol, 40.68% yield) as colorless oil. $^1$H NMR (400 MHz, CHLOROFORM-d) ppm 5.73-5.92 (m, 2H), 5.25-5.40 (m, 2H), 5.16 (dd, J=10.48, 1.19 Hz, 2H), 4.22-4.50 (m, 2H), 3.56-3.75 (m, 1H), 3.38 (d, J=11.17 Hz, 2H), 2.82-2.98 (m, 1H), 1.42-1.53 (m, 9H).

1.37.2.3 Preparation of Compound 5_Trans and 5_Cis

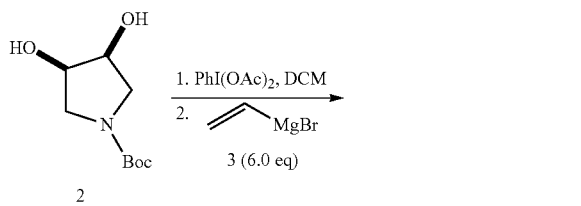

To a solution of Compound 4 (13.00 g, 50.52 mmol, 1.00 eq) in DCM (1.80 L) was added Zhan catalyst 1B (1.20 g, 1.64 mmol, 0.03 eq) under N₂, the mixture was stirred at 30° C. for 30 hr. TLC showed the reaction was completed, the reaction mixture was concentrated, the residue was purified by silica gel chromatography (PE:EA=2:1) to give both cis isomer 5_Cis (2.80 g, 12.22 mmol, 24.22% yield) with lower polarity and trans isomer 5_Trans (2.80 g, 12.22 mmol, 24.22% yield) with higher polarity. 5_Cis: $^1$HNMR (400 MHz, CHLOROFORM-d) ppm 5.83 (d, J=1.63 Hz, 2H) 4.26-4.43 (m, 2H) 3.67 (d, J=13.55 Hz, 2H) 3.38 (dd, J=13.68, 8.28 Hz, 2H) 1.48 (s, 9H). 5_Trans: $^1$H NMR (400 MHz, CHLOROFORM-d) ppm 5.82 (s, 2H) 4.46 (br. s., 2H) 3.53-3.79 (m, 3H) 3.34-3.46 (m, 1H) 1.48 (s, 9H).

1.37.2.4 Preparation of 6_Cis

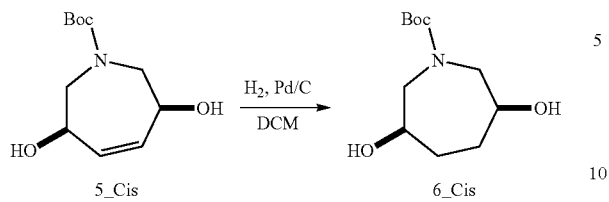

To a solution of Compound 5_Cis (2.80 g, 12.21 mmol, 1.00 eq) in MeOH (100.00 mL) was added Pd/C (300.00 mg) under Ar. The suspension was degassed under vacuum and purged with $H_2$ several times. The mixture was stirred under $H_2$ (50 psi) at 30° C. for 16 hours. TLC showed the reaction was completed. The mixture was filtered and the filtrate was concentrated, the residue was purified by silica gel chromatography (PE:EA=1:1) to give compound 6_Cis (1.50 g, 6.49 mmol, 53.12% yield) as colorless oil. $^1$H NMR (400 MHz, CHLOROFORM-d) ppm 3.95-4.08 (m, 2H) 3.68-3.85 (m, 2H) 3.25 (ddd, J=14.56, 9.98, 4.08 Hz, 2H) 3.10 (br, 1H) 2.02 (br, 1H) 1.84-1.98 (m, 2H) 1.66-1.76 (m, 2H) 1.49 (s, 9H).

1.37.2.5 Preparation of A68_Cis

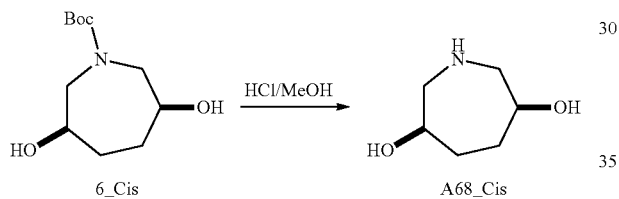

To a solution of Compound 6_Cis (500.00 mg, 2.16 mmol, 1.00 eq) in dioxane (10.00 mL) was added HCl dioxane (20.00 mL), the mixture was stirred at 30° C. for 2 hr, TLC showed the reaction was completed, the mixture was concentrated to give A68_Cis (250.00 mg, 1.91 mmol, 88.24% yield) as yellow solid.

A68_Trans was prepared from compound 5_Trans through the same procedure.

Part II General Procedure for Targets

General Procedure A

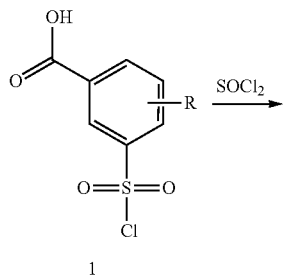

1.1 General Procedure for Preparation of Compound 2

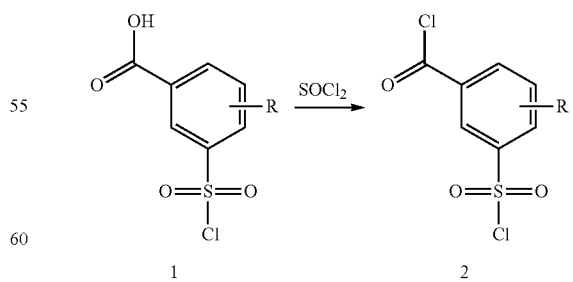

A mixture of Compound 1 (4.53 mmol) in $SOCl_2$ (10 mL) was heated to reflux overnight. The mixture was concentrated to give the crude product, which was used for the next step directly.

1.2 General Procedure for Preparation of Compound 3

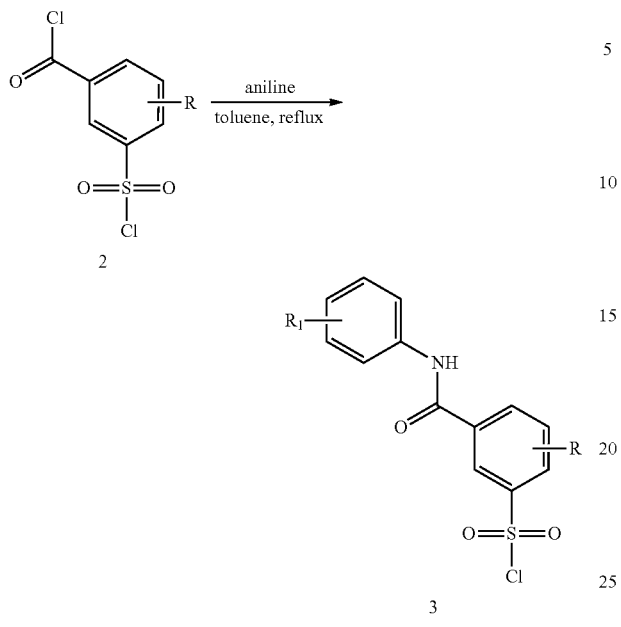

To a boiled solution of Compound 2 (1.08 g, 4.52 mmol) in toluene (10 mL) was added aniline (4.52 mmol), and refluxed for 2 h. The mixture was concentrated in vacuo to give a solid, which was used for the next step directly.

1.3 General Procedure for Preparation of iii

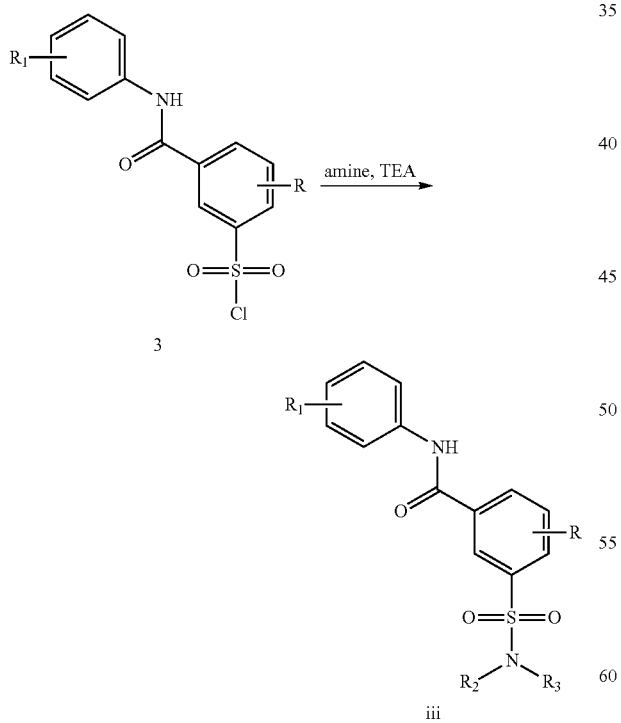

To a solution of Compound 3 (0.3 mmol) in MeCN (3 mL) was added amine (0.3 mmol) and Et$_3$N (30 mg, 0.33 mmol) at rt, and the mixture was stirred at rt for 2 h. The mixture was diluted with CH$_2$Cl$_2$ (20 mL) and washed with water. The organic phase was concentrated in vacuo to give the crude product, which was purified by prep-HPLC to give the desired product.

General Procedure B

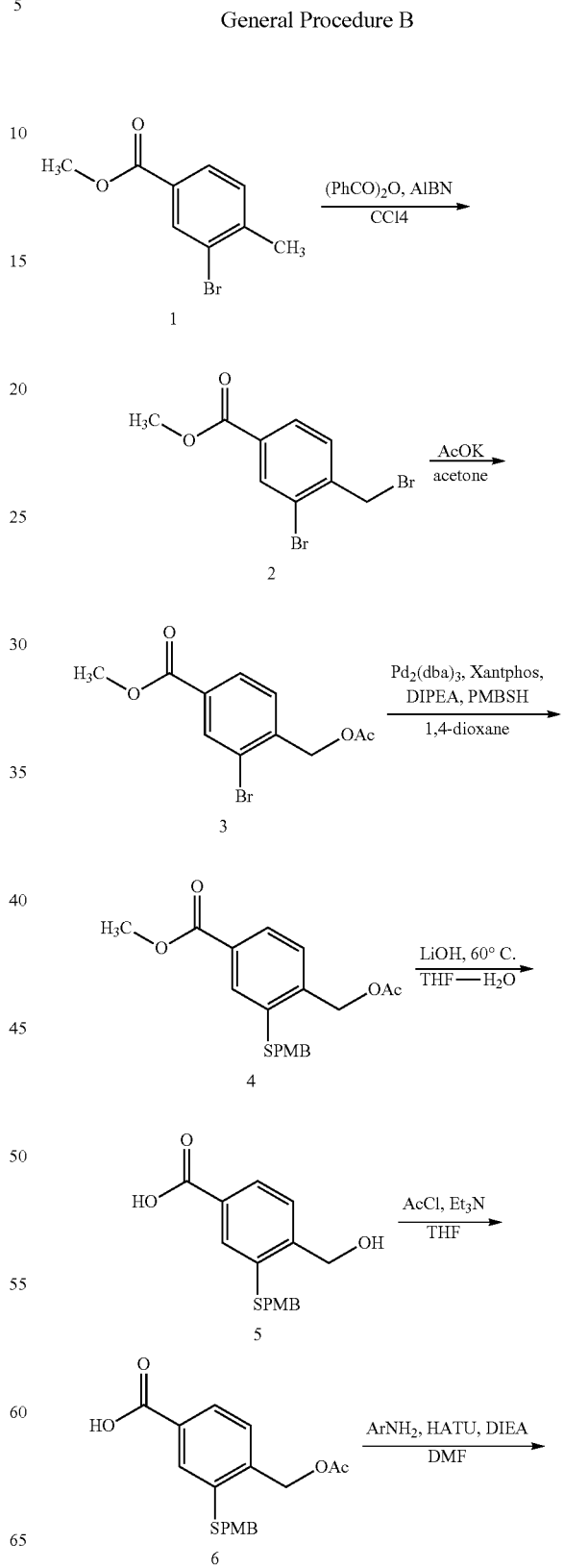

1.2 Preparation of Compound 3

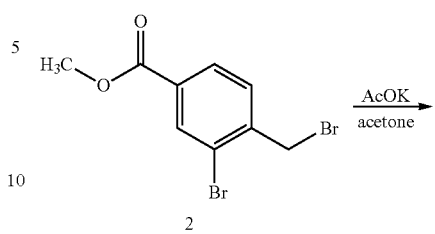

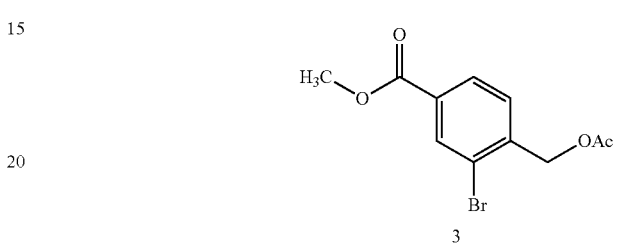

A mixture of compound 2 (1 g, 3.24 mmol) and AcOK (3.18 g, 32.4 mmol) in acetone (20 mL) was stirred for 18 hours. Then the mixture was filtered and washed with acetone. The filtrate was concentrated under vacuum to give the compound 3 (0.7 g, 78%). 1H NMR (400 MHz, CDCl$_3$) δ 8.26 (d, J=1.6 Hz, 1H), 7.99-8.01 (m, 1H), 7.48-7.50 (d, J=8 Hz, 1H), 5.24 (s, 2H), 3.95 (s, 3H), 2.19 (s, 3H).

1.3 Preparation of Compound 4

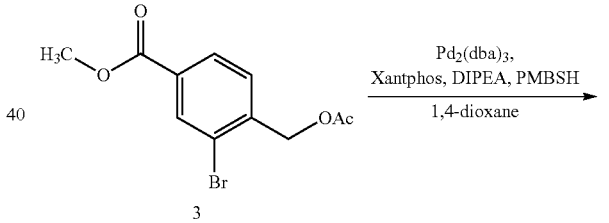

A mixture of compound 3 (7.5 g, 0.026 mol), PMBSH (5.25 g, 0.034 mol), Pd$_2$(dba)$_3$ (3.65 g, 5.2 mmol), Xantphos (3 g, 5.2 mmol) and DIPEA (6.7 g, 5.2 mmol) in 1,4-dioxane (80 mL) was heated to 100° C. for 18 hours. Then the mixture was concentrated under vacuum, and purified by column chromatography (PE:AcOEt=10:1) to give the compound 4 (6.9 g, 73%). 1H NMR (400 MHz, CDCl$_3$) δ 8.08 (d, J=1.6 Hz, 1H), 7.86-7.89 (m, 1H), 7.42-7.44 (d, J=8 Hz, 1H), 7.19-7.21 (m, 2H), 6.81-6.84 (m, 2H), 5.17 (s, 2H), 4.13 (s, 2H), 3.94 (s, 3H), 3.80 (s, 3H), 2.13 (s, 3H).

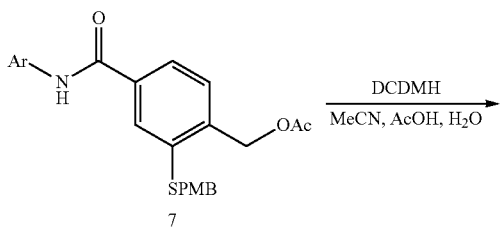

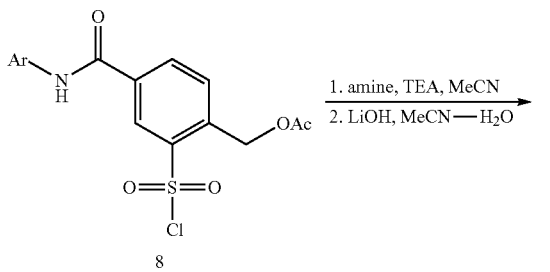

1.1 Preparation of Compound 2

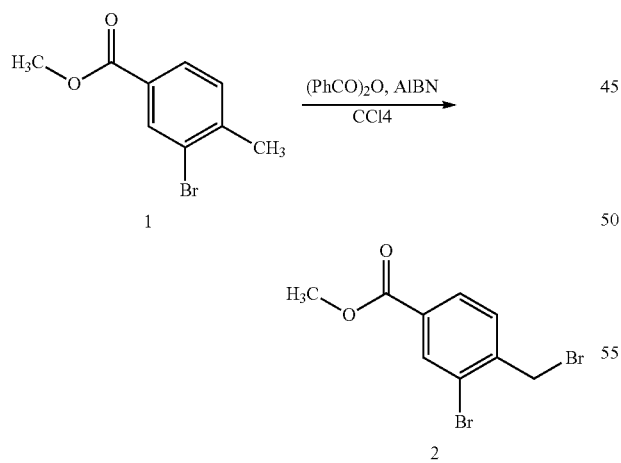

A mixture of compound 1 (9.5 g, 0.04 mol), NBS (8.3 g, 0.044 mol) and (PhCO)$_2$O (1.9 g, 8 mmol) in CCl$_4$ (100 mL) was heated to reflux for 5 hours. Then the mixture was concentrated under vacuum, and the residue was purified by column chromatography (PE:AcOEt=20:1) to give the compound 2 (4 g, 31%).

1.4 Preparation of Compound 5

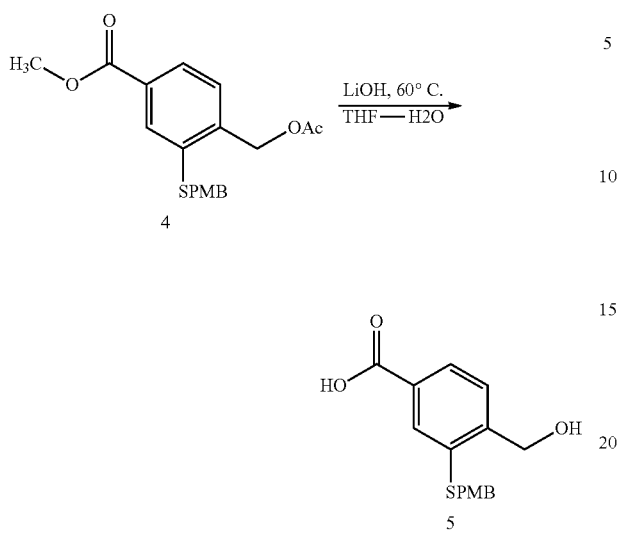

A mixture of compound 4 (3.60 g, 10 mmol) and LiOH (4.20 g, 100 mmol) in THF/H$_2$O (50 mL/10 mL) was heated to 60° C. for 14 hours. The reaction mixture was adjusted to pH=6.0 with HCl (1N), extracted with AcOEt. The organic phase was dried over Na$_2$SO$_4$ and concentrated to give the compound 5 (2.40 g, 80%). 1H NMR (400 MHz, CD$_3$OD) δ 8.02 (d, J=1.2 Hz, 1H), 7.87-7.89 (m, 1H), 7.56-7.58 (d, J=8 Hz, 1H), 7.17-7.20 (m, 2H), 6.81-6.83 (m, 2H), 4.65 (s, 2H), 4.12 (s, 2H), 3.74 (s, 3H).

1.5 Preparation of Compound 6

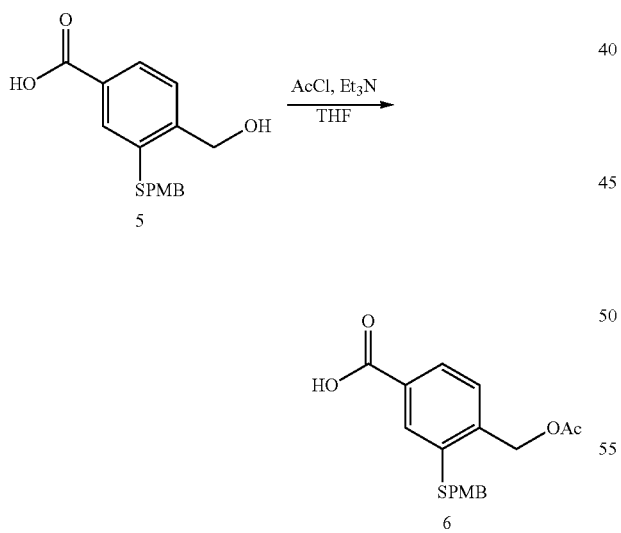

To a solution of compound 5 (1.0 g, 3.4 mmol) in THF (20 mL) was added TEA (1.0 mg, 10 mmol) and AcCl (540 mg, 6.8 mmol) at 0° C. The resulting mixture was stirred at rt for 14 hours. The mixture was diluted with water, and extracted with AcOEt. The organic phase was dried over Na$_2$SO$_4$, concentrated under vacuum to give the crude product, used in the next step directly.

1.6 Preparation of Compound 7

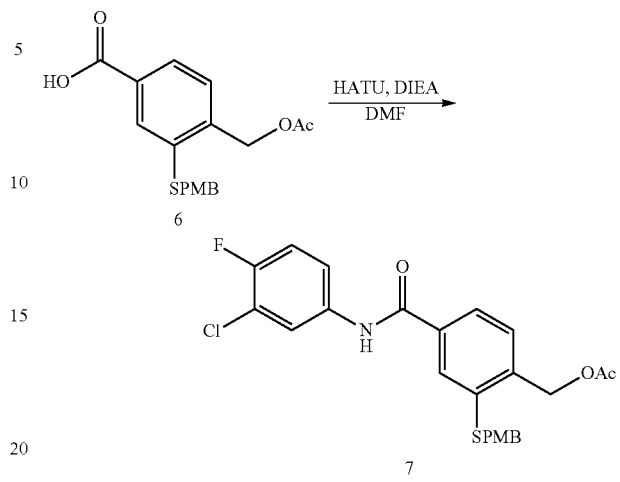

A mixture of compound 6 (100 mg, 0.28 mmol), HATU (126 mg, 0.33 mmol), DIPEA (164 g, 0.43 mmol), 3-chloro-4-fluoroaniline (63 mg, 0.43 mmol) in DMF (5 mL) was stirred at rt for 4 hours. The mixture was diluted with AcOEt and water, and combined organic layers were separated, dried over Na$_2$SO$_4$ and concentrated. Then the residue was purified by column chromatography (PE:AcOEt=5:1) to give the compound 5 (110 m g, 74%).

1H NMR (400 MHz, CD$_3$OD) δ 7.96-7.99 (m, 2H), 7.79 (d, J=1.6 Hz, 1H), 7.49-7.51 (d, J=8 Hz, 1H), 7.16-7.28 (m, 3H), 6.80-6.82 (m, 2H), 5.16 (s, 2H), 4.17 (s, 2H), 3.74 (s, 3H), 2.11 (s, 3H).

1.7 Preparation of Compound 8

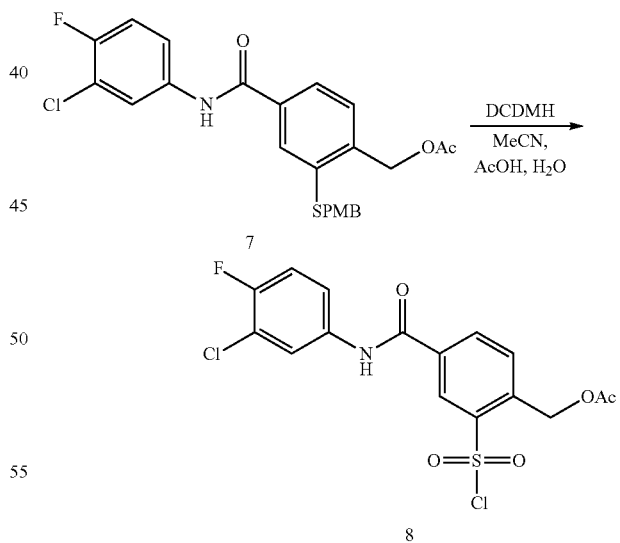

To a solution of compound 7 (150 mg, 0.32 mmol) in MeCN (8 mL), AcOH (0.1 mL) and H$_2$O (0.2 mL) was added 1,3-dichloro-5,5-dimethylimidazolidine-2,4-dione (89 mg, 0.45 mmol) at −15° C. and stirred for 4 hours. Then the mixture was diluted with water and extracted with DCM. The combined organic layer was dried over Na$_2$SO$_4$ and concentrated in vacuo to give a crude product (134 mg, crude), used directly in the next step.

1.8 Preparation of iiii

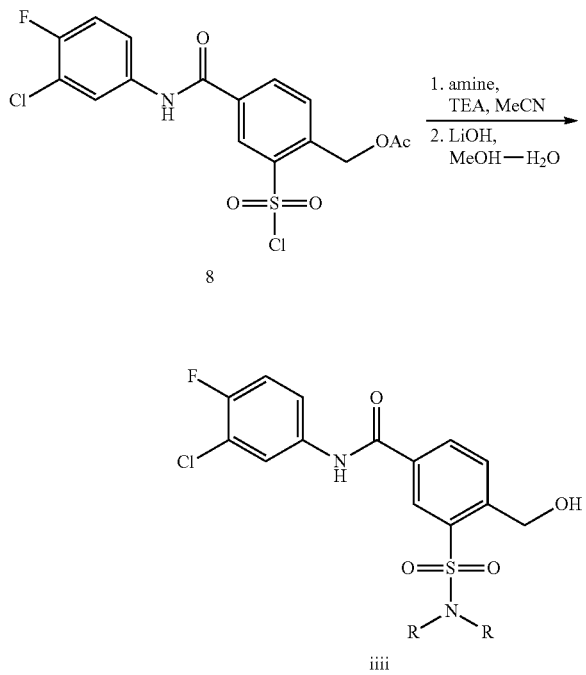

To a solution of compound 8 (134 mg, 0.32 mmol, crude) in MeCN (2 mL) was added TEA (106 mg, 1.05 mmol) and amine (0.84 mmol). The resulting mixture was stirred at rt until the starting material was consumend. Then, to the resulting mixture was added a mixture of LiOH (150 mg, 3.6 mmol) in MeOH/H₂O (2 mL/0.5 mL) and stirred for 14 hours. The mixture was diluted with water, and extracted with EA. The combined organic layers were dried over Na₂SO₄ and concentrated in vacuo. The residue was preparative HPLC to give the product.

General Procedure C

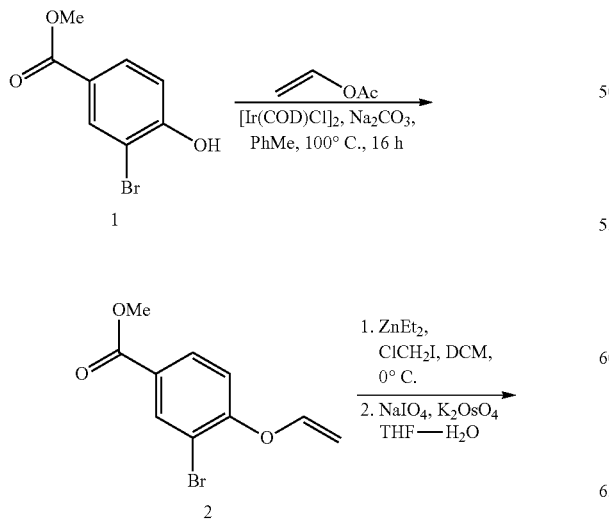

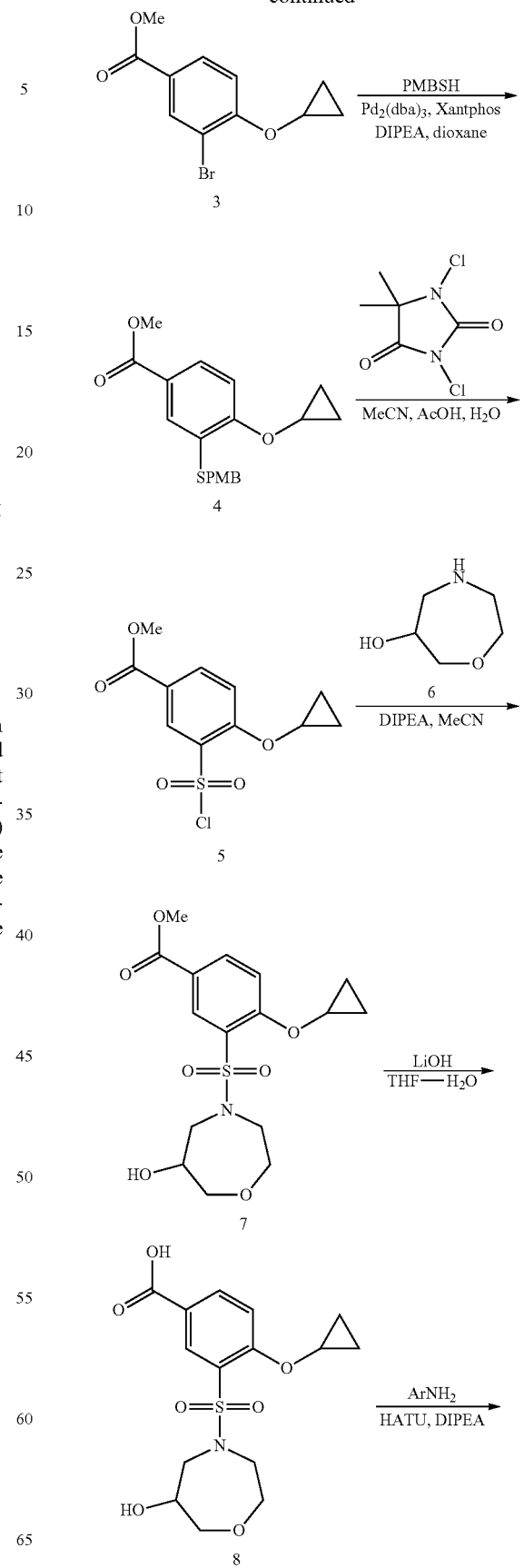

-continued

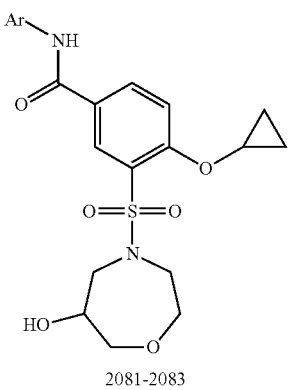

2081-2083

1.1 Preparation of Compound 2

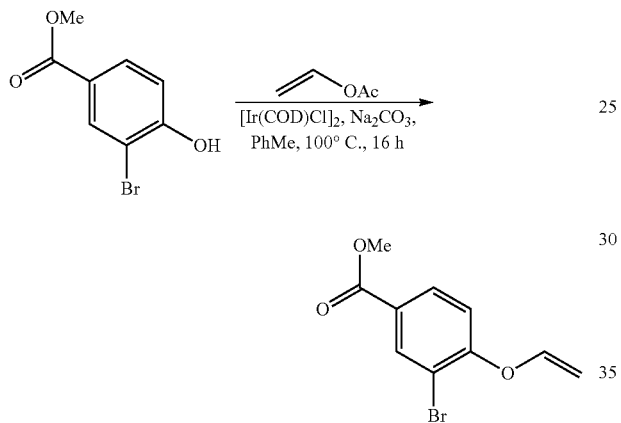

To a solution of methyl 3-bromo-4-hydroxy-benzoate (1.00 g, 4.33 mmol, 1.00 eq) in toluene (15.00 mL) were added vinyl acetate (745.54 mg, 8.66 mmol, 2.00 eq), Chloro (1,5-cyclooctadiene)iridium(I) dimer (29.08 mg, 43.30 umol, 0.01 eq) and Na$_2$CO$_3$ (229.47 mg, 2.17 mmol, 0.50 eq). The mixture was stirred at 100° C. for 16 hr under N$_2$ protection. TLC detected the reaction was complete, the solvent was evaporated, the residue was purified by chromatography (silica gel, eluting with PE:EA=10:1) to afford product methyl 3-bromo-4-vinyloxy-benzoate (730.00 mg, 2.84 mmol, 65.58% yield) as colorless oil. $^1$H NMR (400 MHz, CDCl$_3$) δ 8.29 (d, J=1.76 Hz, 1H), 7.99 (dd, J=8.53, 2.01 Hz, 1H), 7.06 (d, J=8.53 Hz, 1H), 6.65 (dd, J=13.80, 6.02 Hz, 1H), 4.98 (dd, J=13.80, 2.01 Hz, 1H), 4.70 (dd, J=5.90, 1.88 Hz, 1H), 3.93 (s, 3H).

1.2 Preparation of Compound 3

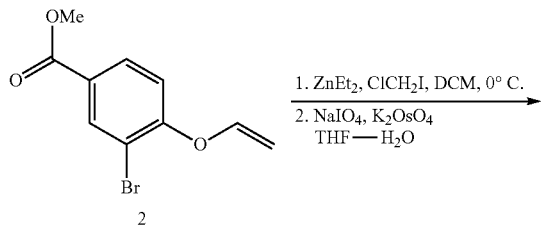

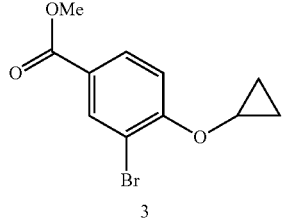

To a solution of methyl 3-bromo-4-vinyloxy-benzoate (1.00 g, 3.89 mmol, 1.00 eq) in DCM (15.00 mL) was added ZnEt$_2$ (960.91 mg, 7.78 mmol, 2.00 eq) at 0° C. under N$_2$ protection. Then the mixture was stirred at 0° C. for 30 min, and ClCH$_2$I (1.72 g, 9.73 mmol, 2.50 eq) was added. The formed mixture was stirred at 25° C. for 16 hrs. The mixture was poured into NH$_4$Cl solution, and extracted with EA, the combined organic layer was dried over Na$_2$SO$_4$, concentrated, the residue was diluted in THF (5.00 mL) and H$_2$O (5.00 mL), NaIO$_4$ (832.00 mg, 3.89 mmol, 1.00 eq) and K$_2$OsO$_4$ (74.01 mg, 389.00 umol, 0.10 eq) was added, the mixture was stirred at 25° C. for 30 min, then the reaction was quenched by saturated Na$_2$SO$_3$, extracted with EA, the combined organic layer was dried over Na$_2$SO$_4$, concentrated, the residue was purified by silica gel chromatography (PE:EA=10:1) to afford product methyl 3-bromo-4-(cyclopropoxy)benzoate (530.00 mg, 1.95 mmol, 50.26% yield) as colorless oil. $^1$H NMR (400 MHz, CDCl$_3$) δ 8.23 (d, J=2.01 Hz, 1H), 8.00 (dd, J=8.78, 2.01 Hz, 1H), 7.28-7.33 (m, 1H), 3.92 (s, 3H), 3.88 (t, J=4.39 Hz, 1H), 0.76-0.99 (m, 4H).

1.3 Preparation of Compound 4

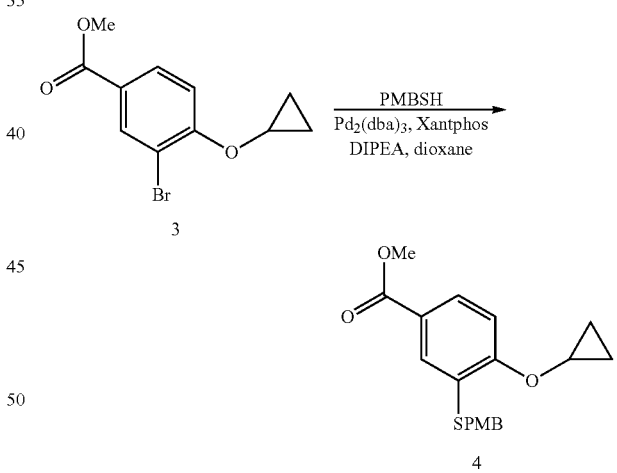

To a solution of methyl 3-bromo-4-(cyclopropoxy)benzoate (530.00 mg, 1.95 mmol, 1.00 eq) and (4-methoxyphenyl)methanethiol (451.12 mg, 2.93 mmol, 1.50 eq) in toluene (10.00 mL) were added Pd$_2$(dba)$_3$ (89.28 mg, 97.50 umol, 0.05 eq), Xantphos (112.83 mg, 195.00 umol, 0.10 eq) and DIPEA (504.04 mg, 3.90 mmol, 2.00 eq) under N$_2$ protection. Then the mixture was stirred at 100° C. for 16 hr N$_2$ protection. TLC detected the reaction was complete, the solvent was evaporated, the residue was washed with water, the aqueous layer was extracted with EA, the combined organic layer was dried over Na$_2$SO$_4$, concentrated, the residue was purified by silica gel chromatography (PE:EA=5:1) to afford product methyl 4-(cyclopropoxy)-3-[(4-methoxyphenyl)methylsulfanyl]benzoate (600.00 mg, 1.74 mmol, 89.34% yield) as white solid. LCMS: 345 [M+1].

1.4 Preparation of Compound 5

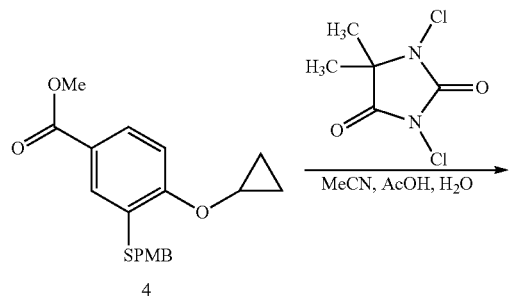

To a suspension of methyl 4-(cyclopropoxy)-3-[(4-methoxyphenyl)methylsulfanyl]benzoate (1.00 g, 2.90 mmol, 1.00 eq) in MeCN (8.00 mL), AcOH (100.00 uL) and H₂O (200.00 uL) at −15° C. was added 1,3-dichloro-5,5-dimethyl-imidazolidine-2,4-dione (914.17 mg, 4.64 mmol, 1.60 eq), the mixture was stirred at −15° C. for 2 hours. The residue was washed with water, the aqueous layer was extracted with EA, the combined organic layer was dried over Na₂SO₄, concentrated to afford crude product, which was used in the next step directly.

1.1.5 Preparation of Compound 7

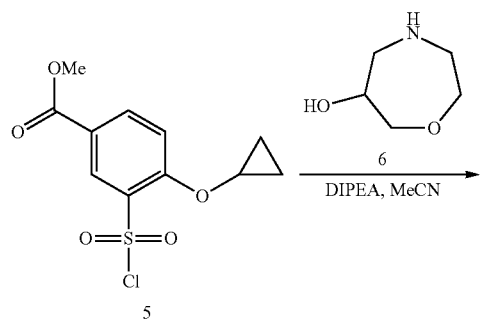

To a solution of methyl 3-chlorosulfonyl-4-(cyclopropoxy)benzoate (840.00 mg, crude, 2.89 mmol, 1.00 eq) in MeCN (10.00 mL) were added 1,4-oxazepan-6-ol (338.49 mg, 2.89 mmol, 1.00 eq) and TEA (584.88 mg, 5.78 mmol, 2.00 eq). The resulting mixture was stirred at 28° C. until the starting material was consumed. The solvent was removed and the residue was purified by chromatography (silica gel, eluting with PE:EA=3:1) to give desired compound methyl 4-(cyclopropoxy)-3-[(6-hydroxy-1,4-oxazepan-4-yl)sulfonyl]benzoate (620.00 mg, 1.67 mmol, 57.76% yield) as white solid. LCMS: 372 [M+1].

1.6 Preparation of Compound 8

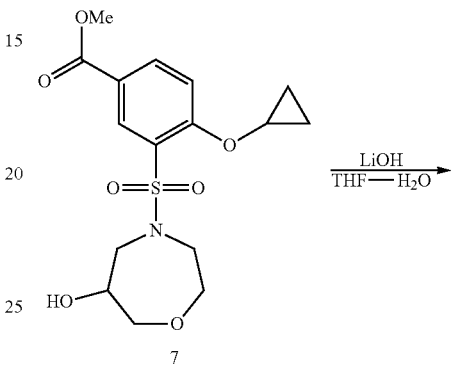

To a solution of methyl 4-(cyclopropoxy)-3-[(6-hydroxy-1,4-oxazepan-4-yl)sulfonyl]benzoate (620.00 mg, 1.67 mmol, 1.00 eq) in THF (5.00 mL) and H₂O (1.00 mL). The formed mixture was stirred at 50° C. for 3 hr. The reaction mixture was neutralized with 1N HCl solution and extracted with EA, the combined organic layer was dried over Na₂SO₄, concentrated to afford crude product 4-(cyclopropoxy)-3-[(6-hydroxy-1,4-oxazepan-4-yl)sulfonyl]benzoic acid (510.00 mg, 1.43 mmol, 85.45% yield) as white solid.

1.7 Preparation of Compound 2081

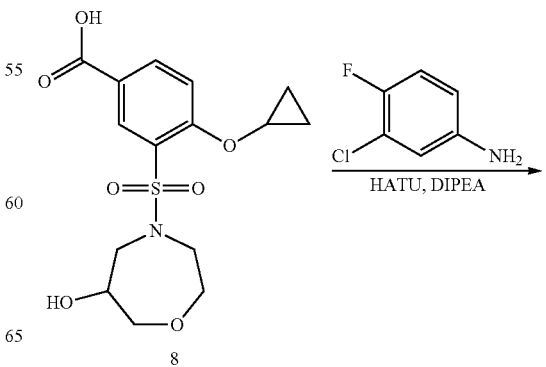

401

-continued

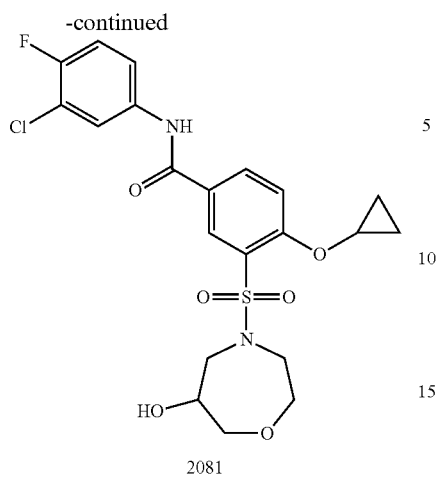

2081

To a solution of 4-(cyclopropoxy)-3-[(6-hydroxy-1,4-oxazepan-4-yl)sulfonyl]benzoic acid (170.00 mg, 475.68 umol, 1.00 eq) and 3-chloro-4-fluoro-aniline (69.24 mg, 475.68 umol, 1.00 eq) in DMF (5.00 mL) were added HATU (180.87 mg, 475.68 umol, 1.00 eq) and DIPEA (122.95 mg, 951.36 umol, 2.00 eq). The mixture was stirred at 25° C. for 16 hr. TLC detected the reaction was complete, the mixture was poured into water, extracted with EA, the combined organic layer was dried over anhydrous Na2SO4, concentrated, the residue was purified by prep-HPLC (FA) to afford product N-(3-chloro-4-fluoro-phenyl)-4-(cyclopropoxy)-3-[(6-hydroxy-1,4-oxazepan-4-yl)sulfonyl]benzamide (94.10 mg, 194.05 umol, 40.79% yield) as white solid. $^1$H NMR (400 MHz, MeOD) δ 8.48 (d, J=2.01 Hz, 1H), 8.23 (dd, J=8.66, 2.13 Hz, 1H), 7.96 (dd, J=6.78, 2.51 Hz, 1H), 7.70 (d, J=8.78 Hz, 1H), 7.59-7.65 (m, 1H), 7.27 (t, J=8.91 Hz, 1H), 4.07-4.13 (m, 1H), 4.03 (t, J=6.53 Hz, 1H), 3.77-3.97 (m, 4H), 3.61-3.73 (m, 2H), 3.21-3.30 (m, 1H), 3.11 (dd, J=14.56, 7.53 Hz, 1H), 0.84-1.04 (m, 4H). LCMS: 485/487 [M+1].

2082/2083 were prepared through the same procedure as 2081.

General Procedure D

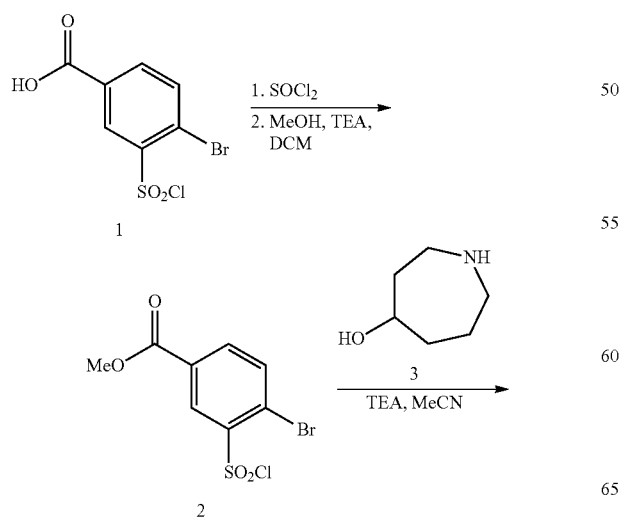

402

-continued

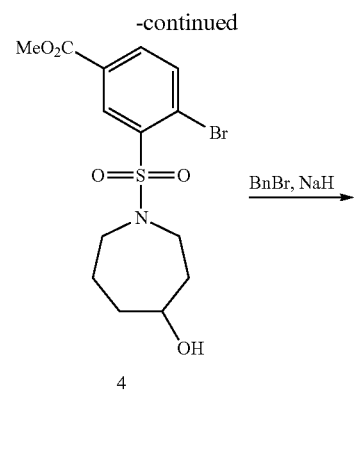

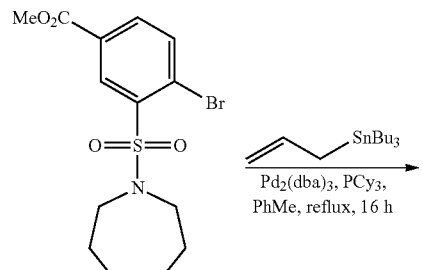

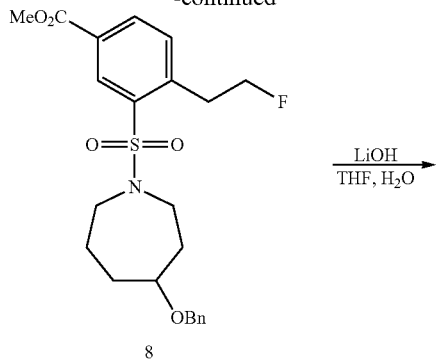

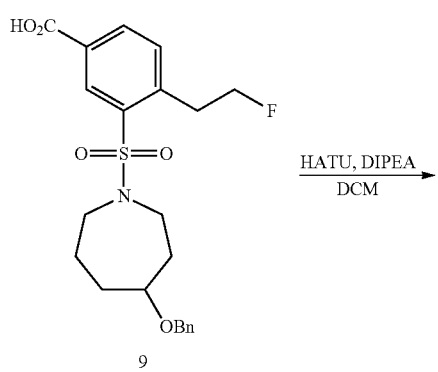

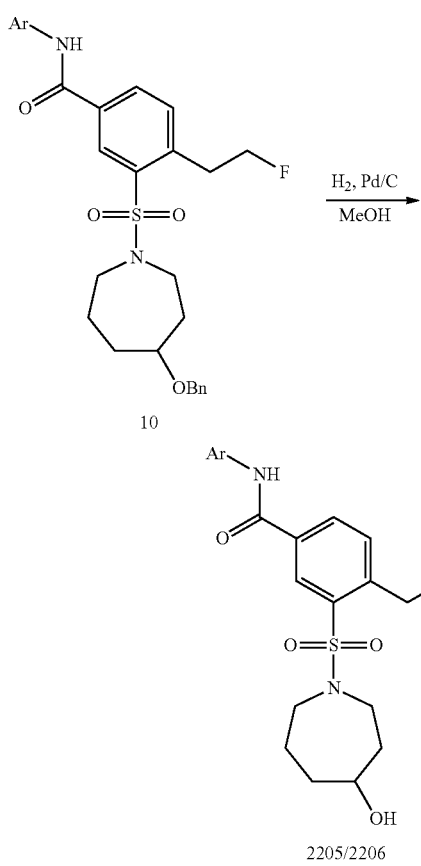

1.1 Preparation of Compound 2

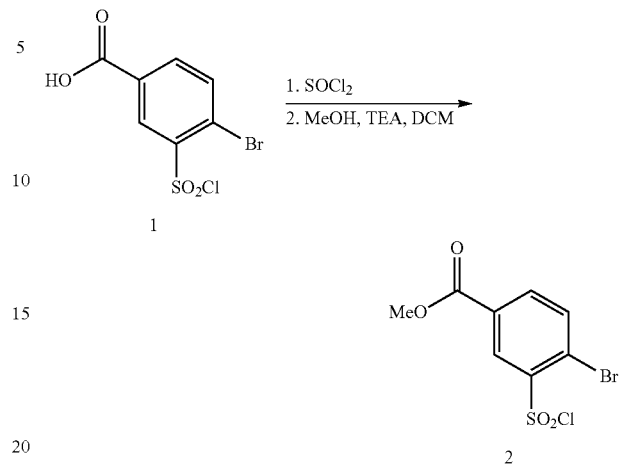

A mixture of 4-bromo-3-chlorosulfonyl-benzoic acid (6.90 g, 23.04 mmol, 1.00 Eq) in $SOCl_2$ (27.41 g, 230.40 mmol, 10.00 Eq) was stirred at 80° C. for 3 hr. Then the solvent was evaporated. The residue was diluted in TOLUENE (50 mL), and MeOH (959.66 mg, 29.95 mmol, 1.30 Eq) was added, the formed mixture was stirred at 110° C. for 2 hr. Solid was formed, and the solvent was evaporated, the solid was washed with PE, and filtered to afford product methyl 4-bromo-3-chlorosulfonyl-benzoate (7.22 g, 23.03 mmol, 99.94% yield) as white solid.

1.2 Preparation of Compound 4

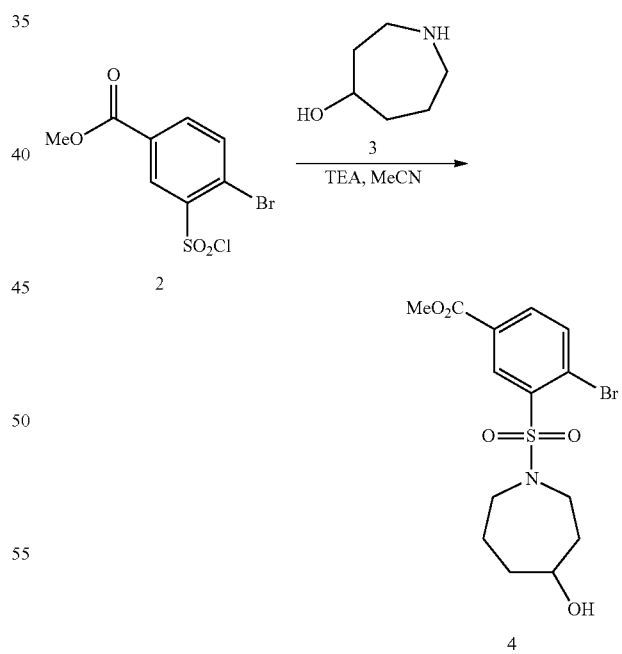

To a solution of methyl 4-bromo-3-chlorosulfonyl-benzoate (7.22 g, 23.03 mmol, 1.00 Eq) in DCM (100 mL) was added azepan-4-ol (2.65 g, 23.03 mmol, 1.00 Eq) and TEA (2.33 g, 23.03 mmol, 1.00 Eq). The resulting mixture was stirred at 25° C. until the starting material was consumed. The solvent was removed and the residue was purified by silica gel chromatography (PE:EA=1:1) to give desired compound methyl 4-bromo-3-(4-hydroxyazepan-1-yl)sulfonyl-benzoate (7.00 g, 17.85 mmol, 77.49% yield). LCMS: 393/395 [M+1].

1.3 Preparation of Compound 5

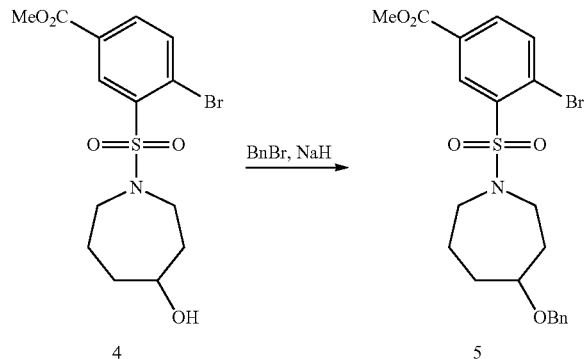 [SMILES: COC(=O)c1ccc(Br)c(S(=O)(=O)N2CCCC(O)CC2)c1 ; COC(=O)c1ccc(Br)c(S(=O)(=O)N2CCCC(OCc3ccccc3)CC2)c1]

To a mixture of methyl 4-bromo-3-(4-hydroxyazepan-1-yl)sulfonyl-benzoate (1.00 g, 2.55 mmol, 1.00 Eq) in DMF (15 mL), was added NaH (153.00 mg, 3.82 mmol, 1.50 Eq) in portions at 0° C. under $N_2$. The mixture was stirred at 25° C. for 30 min. Then bromomethylbenzene (654.19 mg, 3.82 mmol, 1.50 Eq) was added and stirred at 25° C. for 16 hours. TLC showed the reaction was completed. The mixture was poured into $NH_4Cl$ aqueous and extracted with EA. The combined organic phase was washed with saturated brine, dried with anhydrous $Na_2SO_4$, filtered and concentrated in vacuum. The residue was purified by silica gel chromatography (eluting with PE/EA=10/1, 2/1) to afford methyl 3-(4-benzyloxyazepan-1-yl)Sulfonyl-4-bromo-benzoate (550.00 mg, 1.14 mmol, 44.71% yield) as white solid. LCMS: 482/484 [M+1].

1.4 Preparation of Compound 6

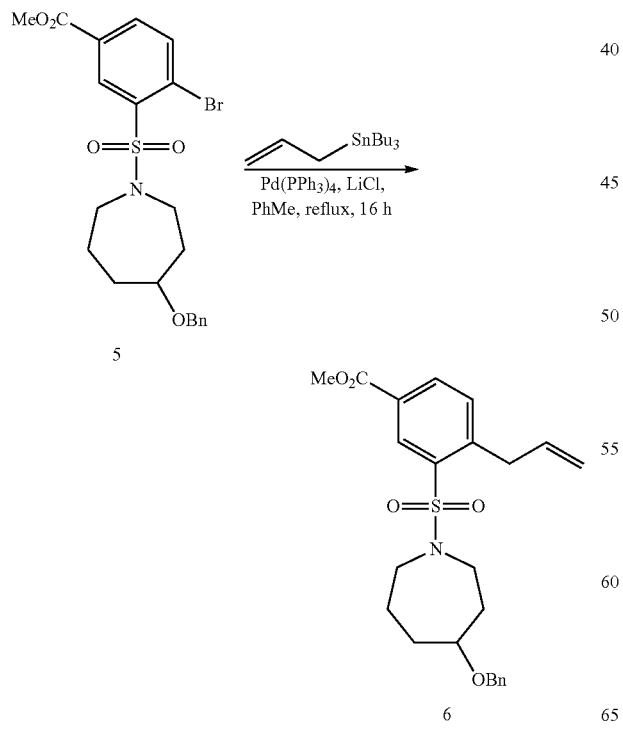

Methyl 3-(4-benzyloxyazepan-1-yl)sulfonyl-4-bromo-benzoate (1.30 g, 2.69 mmol, 1.00 Eq), allyl(tributyl)stannane (1.07 g, 3.23 mmol, 1.20 Eq) LiCl (136.83 mg, 3.23 mmol, 1.20 Eq) and Pd(PPh3)4 (310.85 mg, 269.00 umol, 0.10 Eq) in TOLUENE (20 mL) was de-gassed and then heated to 110° C. for 16 hr under $N_2$. TLC (PE:EtOAc=1:1) showed the starting material and the product was the same spot. The reaction mixture was poured into $H_2O$, extracted with EA. The organic phase was dried over anhydrous $Na_2SO_4$, concentrated in vacuum to give a residue, which was purified by column chromatography (silica gel, eluting with PE:EA=1:1) to afford the pure methyl 4-allyl-3-(4-benzyloxyazepan-1-yl)sulfonyl-benzoate (630.00 mg, 1.42 mmol, 52.80% yield) as light yellow solid.

1.5 Preparation of Compound 7

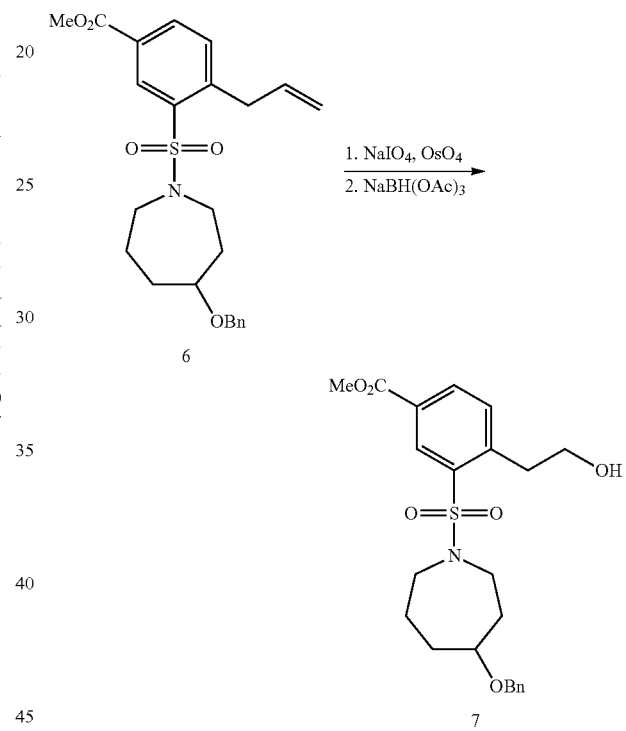

To a solution of methyl 4-allyl-3-(4-benzyloxyazepan-1-yl)sulfonyl-benzoate (630.00 mg, 1.42 mmol, 1.00 Eq) in THF (10 mL) and $H_2O$ (2 mL) were added $OsO_4$ (36.10 mg, 142.00 umol, 0.10 Eq) and $NaIO_4$ (607.45 mg, 2.84 mmol, 2.00 Eq) at 0° C. The mixture was stirred at 25° C. for 3 hr. TLC detected the reaction was complete, the mixture was poured into saturated $Na_2S_2O_3$ solution, extracted with DCM, the combined organic layer was dried over anhydrous $Na_2SO_4$, concentrated, the residue was diluted in MeOH (10 mL), to the formed mixture was added $NaBH_3CN$ (88.86 mg, 1.41 mmol, 1.00 Eq). The mixture was stirred at 25° C. for 3 hr. TLC detected the reaction was complete, the reaction was quenched with water, extracted with EA, the combined organic layer was dried over anhydrous $Na_2SO_4$, concentrated, the residue was purified by chromatography (silica gel, eluting with PE:EA=3:1 to 1:1) to afford product methyl 3-(4-benzyloxyazepan-1-yl)sulfonyl-4-(2-hydroxyethyl) benzoate (340.00 mg, 759.71 umol, 53.88% yield). LCMS: 448 [M+1].

1.6 Preparation of Compound 8

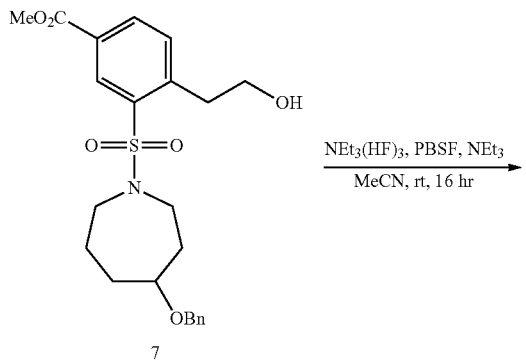

7

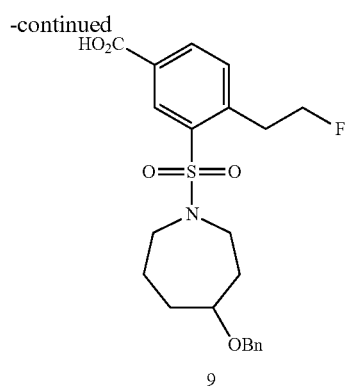

9

To a solution of methyl 3-(4-benzyloxyazepan-1-yl)sulfonyl-4-(2-fluoroethyl)benzoate (180.00 mg, 400.42 umol, 1.00 Eq) in THF (5 mL) and H$_2$O (1 mL). The formed mixture was stirred at 25-50° C. for 3 hr. The reaction mixture was neutralized with 1N HCl solution and concentrated to give the crude product 3-(4-benzyloxyazepan-1-yl)sulfonyl-4-(2-fluoroethyl)benzoic acid (160.00 mg, 367.39 umol, 91.75% yield).

1.8 Preparation of Compound 10

8

To a solution of methyl 3-(4-benzyloxyazepan-1-yl)sulfonyl-4-(2-hydroxyethyl)benzoate (340.00 mg, 759.71 umol, 1.00 Eq) in MeCN (10 mL) were added PBSF (458.86 mg, 1.52 mmol, 2.00 Eq), N,N-diethylethanamine; trihydrofluoride (244.95 mg, 1.52 mmol, 2.00 Eq) and TEA (307.50 mg, 3.04 mmol, 4.00 Eq). The mixture was stirred at 28° C. for 16 hr under N$_2$ protection. TLC detected the reaction was complete, the mixture was poured into water, extracted with EA, the combined organic layer was dried over anhydrous Na$_2$SO$_4$, concentrated, the residue was purified by chromatography (silica gel, eluting with PE:EA=1:1) to afford product methyl 3-(4-benzyloxyazepan-1-yl)sulfonyl-4-(2-fluoroethyl)benzoate (180.00 mg, 400.42 umol, 52.71% yield) as colorless oil.

1.7 Preparation of Compound 9

8

9

10

To a solution of 3-(4-benzyloxyazepan-1-yl)sulfonyl-4-(2-fluoroethyl)benzoic acid (80.00 mg, 183.69 umol, 1.00 Eq) and aniline (202.06 umol, 1.10 Eq) in MeCN (5 mL) were added HATU (76.83 mg, 202.06 umol, 1.10 Eq) and DIEA (47.48 mg, 367.38 umol, 2.00 Eq). The mixture was stirred at 25° C. for 16 hr. TLC detected the reaction was complete, the mixture was poured into water, extracted with EA, the combined organic layer was dried over anhydrous Na2SO4, concentrated, the residue was purified by prep-TLC (eluting with PE:EA=2:1) to afford product 3-(4-benzyloxyazepan-1-yl)sulfonyl-N-(3-chloro-4-fluoro-phenyl)-4-(2-fluoroethyl)benzamide (65.00 mg, 115.44 umol, 62.85% yield) as white solid.

1.9 Preparation of 2205/2206

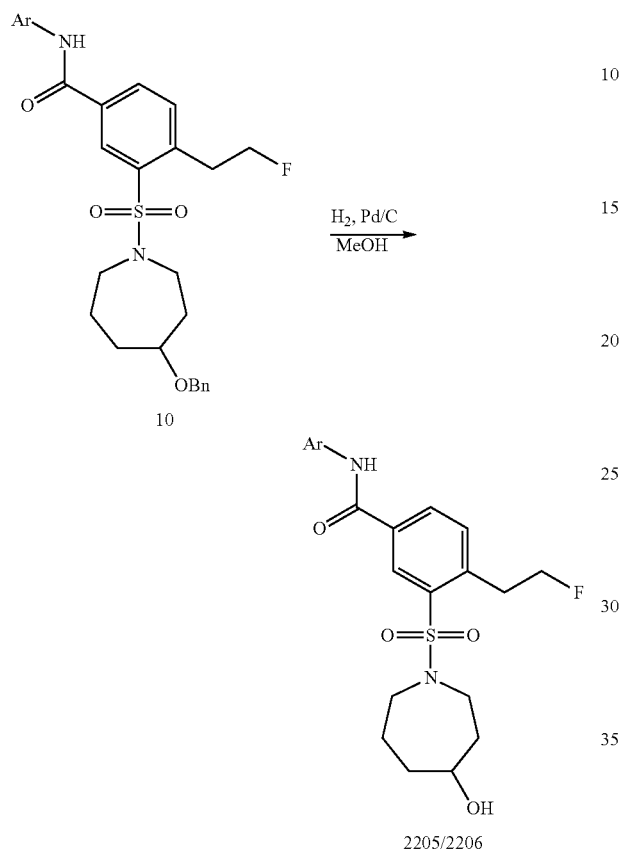

To a solution of 3-(4-benzyloxyazepan-1-yl)sulfonyl-N-(3-chloro-4-fluoro-phenyl)-4-(2-fluoroethyl)benzamide (65.00 mg, 115.44 umol, 1.00 Eq) in MeOH (15 mL) was added Pd/C (30.00 mg, 115.44 umol, 1.00 Eq) under $N_2$. The suspension was degassed under vacuum and purged with $H_2$ several times. The mixture was stirred under $H_2$ at 25° C. for 16 hr. TLC showed the starting material was consumed completely. The reaction mixture was filtered and the filter was concentrated, purified by prep-TLC (eluting with PE:EA=1:1) to afford product N-(3-chloro-4-fluoro-phenyl)-4-(2-fluoroethyl)-3-(4-hydroxyazepan-1-yl)sulfonyl-benzamide (24.00 mg, 50.75 umol, 43.96% yield) as white solid.

General Procedure F

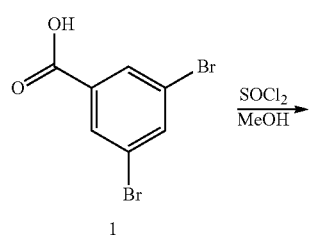

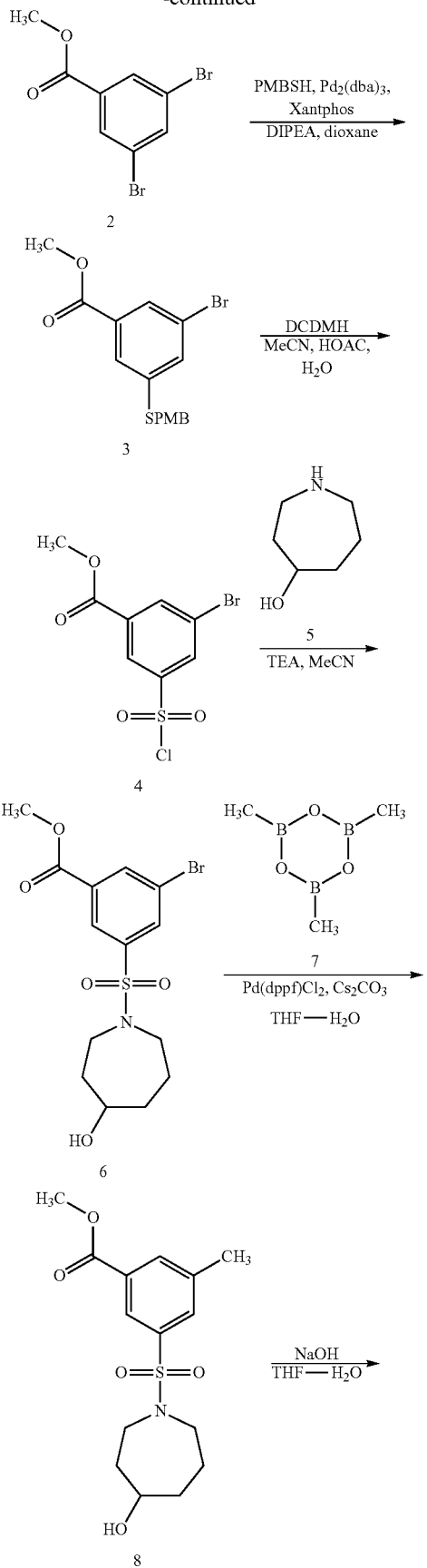

411

-continued

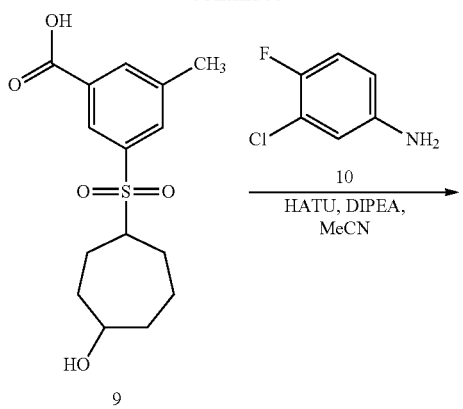

9

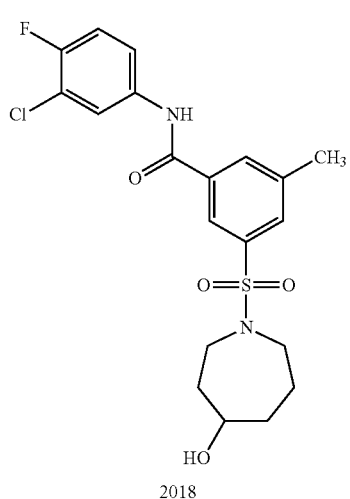

2018

1.1 Preparation of Compound 2

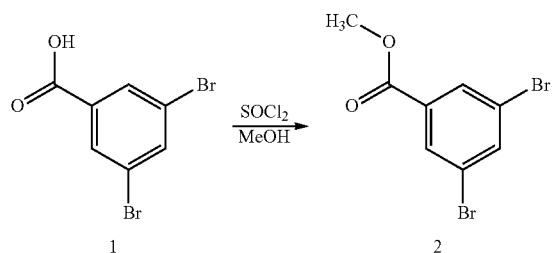

To a solution of Compound I (6.0 g, 21.6 mmol) in MeOH (80 mL) was added SOCl$_2$ (10.2 g, 86.5 mmol) at 0° C. under N$_2$. The reaction mixture was heated to 85° C. for 3 h. The resulting mixture was concentrated in vacuo to give compound 2 (6.2 g, crude), which was used for the next step directly. $^1$H NMR (400 MHz, DMSO) δ=8.17-8.19 (m, 1H), 8.03-8.05 (m, 2H), 3.88 (s, 3H).

412

1.2 Preparation of Compound 3

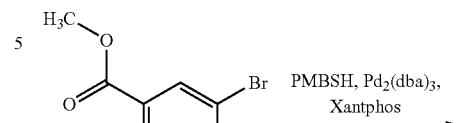

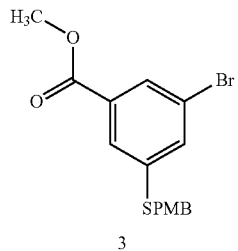

A mixture of compound 2 (5.6 g, 19.2 mmol), PMBSH (3.8 g, 24.7 mmol), Pd$_2$(dba)$_3$ (1.7 g, 1.9 mmol), Xantphos (2.2 g, 3.8 mmol) and DIPEA (4.9 g, 38.0 mmol) in 1,4-dioxane (100 mL) was heated to 100° C. for 16 h. The reaction mixture was concentrated under vacuum, and purified by column chromatography to give the compound 3 (3.9 g, 56%).

1.3 Preparation of Compound 4

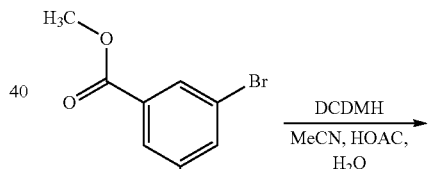

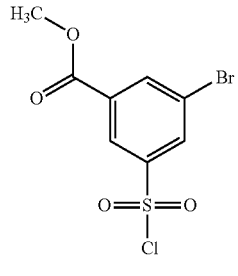

To a solution of compound 3 (1.2 g, 3.3 mmol) in MeCN/HOAc/H$_2$O (16/0.2/0.4, mL) was added 1,3-dichloro-5,5-dimethylimidazolidine-2,4-dione (0.97 g, 4.9 mmol) at −15° C. and stirred for 3 h. The reaction mixture was diluted with water and extracted with EA. The combined organic layer was dried over Na$_2$SO$_4$ and concentrated in vacuo to give a crude product, which was used in the next step directly (1.0 g, crude).

1.4 Preparation of Compound 6

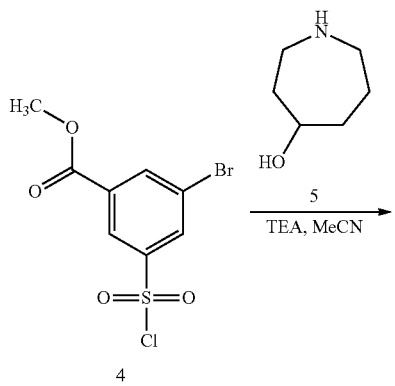

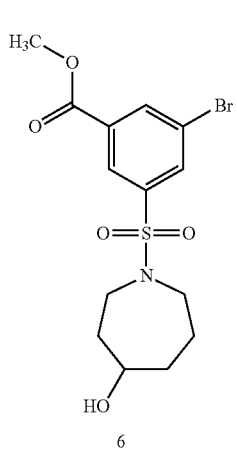

To a solution of Compound 4 (1.0 g, 3.2 mmol) in MeCN (10 mL) was added Compound 5 (553 mg, 4.8 mmol) and Et₃N (810 mg, 8.0 mmol) at 25° C. and stirred for 1 h. The mixture was diluted with EA (100 mL) and washed with water (80 mL). The organic phase was concentrated in vacuo to give the crude product, which was purified by flash column chromatography to give the desired product (0.54 g, 43%). LCMS: 392.0 [M+1].

1.5 Preparation of Compound 8

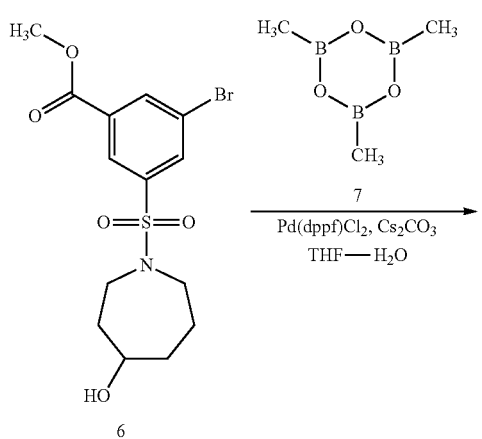

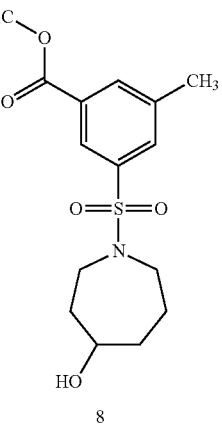

A mixture of compound 6 (540 mg, 1.4 mmol), compound 7 (261 mg, 2.1 mmol), Cs₂CO₃ (898 mg, 2.8 mmol) and Pd(dppf)Cl₂ (140 mg, 0.2 mmol) in THF/H₂O (10/1, mL) was heated to 80° C. for 16 h. The reaction mixture was diluted with EA (100 mL), and washed with brine (60 mL). The organic phase was concentrated under vacuum to give a crude product, which was used in the next step directly (451 mg, crude).

1.6 Preparation of Compound 9

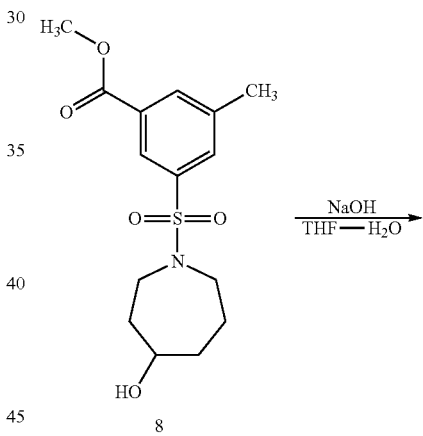

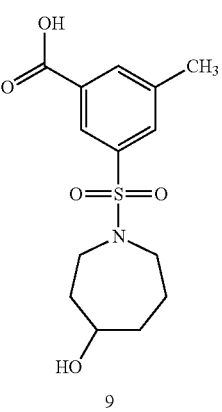

A mixture of compound 8 (451 mg, 1.4 mmol) and NaOH (112 mg, 2.8 mmol) in THF/H₂O (5/1, mL) was heated to 35° C. for 16 h. The reaction mixture was diluted with water (80 mL), and extracted with EA (80 mL). The aqueous phase was adjusted to pH=6.0 with HCl (2 M), and extracted with EA (80 mL). The organic phase was dried over $Na_2SO_4$ and concentrated to give the crude product, which was used in the next step directly (305 mg, 71%).

1.7 Preparation of 2018

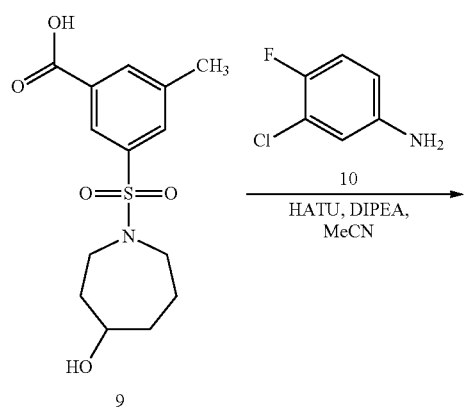

A mixture of compound 9 (143 mg, 0.46 mmol), HATU (209 mg, 0.55 mmol), DIPEA (119 mg, 0.92 mmol), compound 9 (80 mg, 0.55 mmol) in MeCN (5 mL) was heated to 50° C. for 3 h. The mixture was diluted with EA (80 mL), and washed with water (60 mL). The organic layer was dried over $Na_2SO_4$ and concentrated in vacuo to give the crude product, which was purified Prep-HPLC to give the desired product (149.64 mg, 74%). LCMS: 441.0 [M+1].

General Procedure F

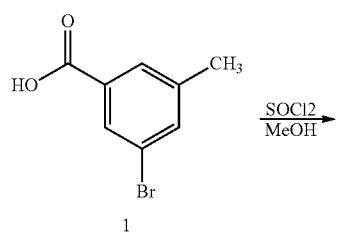

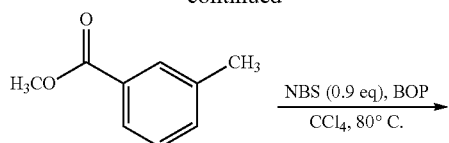

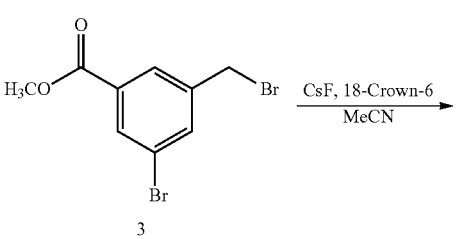

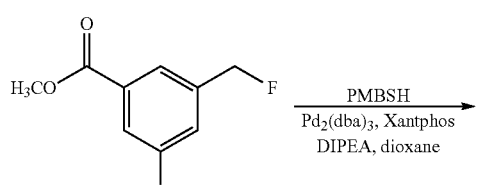

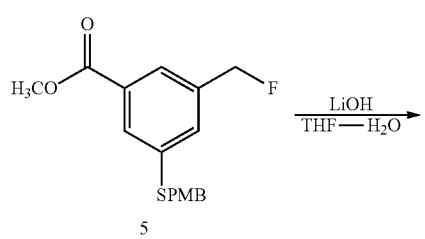

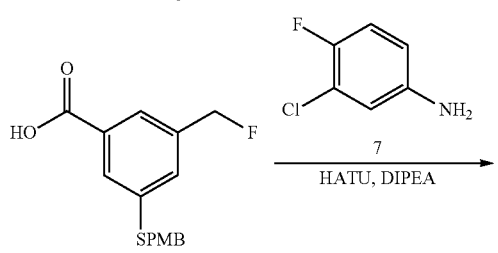

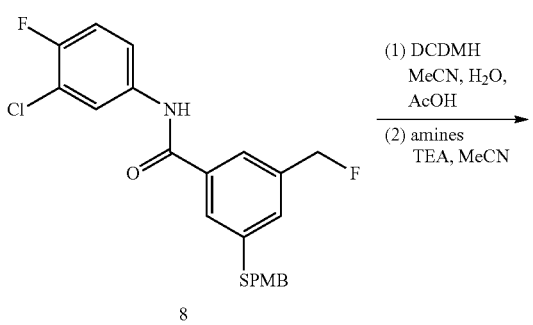

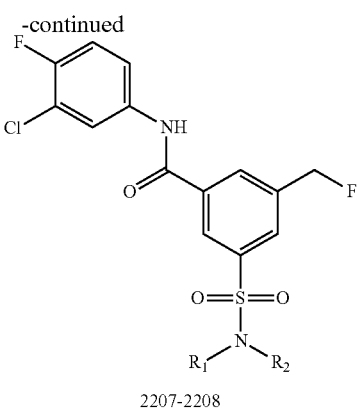

2207-2208

1.1 Preparation of Compound 2

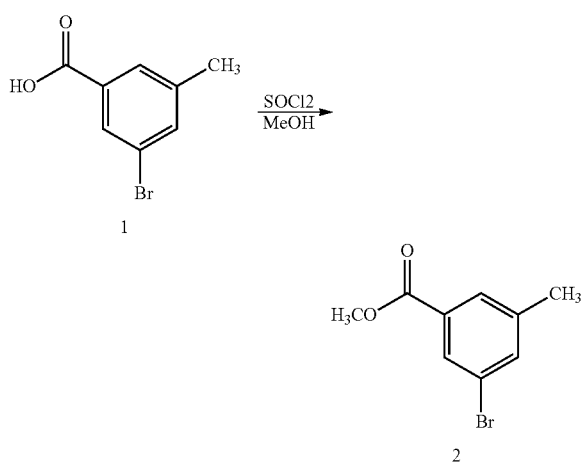

To a solution of Compound 1 (5 g, 0.023 mol) in SOCl2 (30 mL) was added MeOH (1.104 g, 0.035 mol) under 0° C. And the solution was stirred at 80° C. for 2 h. Then the solution was cooled to 18° C. and concentrated to remove the solvent. It was washed with water (20 mL) and extracted with EA (100 mL), dried over $Na_2SO_4$, concentrated to give compound 2 (5.3 g, 93.8%).

LCMS: 229 [M+1].

1.2 Preparation of Compound 3

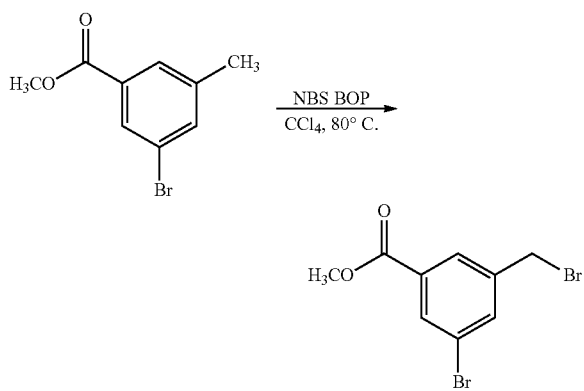

A solution of Compound 2 (5.3 g, 0.023 mol) in CCl4 (50 mL) was added NBS (3.72 g, 0.021 mol), BPO (557 mg, 0.002 mol) in one portion under N2. The mixture was heated to 80° C. for 2 h. The mixture was washed with saturated $Na_2SO_3$ (50 mL) and extracted with EA (100 mL*2). The combined organic layer was dried over $Na_2SO_4$ and concentrated in vacuum. The residue was purified by PE to give compound 3 (6.2 g, crude).

1.3 Preparation of Compound 4

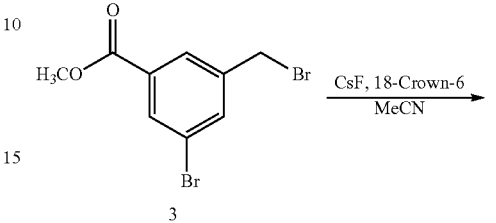

To a solution of Compound 3 (6.2 g, 0.02 mol) in MeCN (100 mL) was added CsF (18.35 g, 0.121 mol), 18-Crown-6 (1.06 g, 4.03 mmol) in one portion and it was heated to 90° C. for 16 hours. The mixture was filtered and concentrated in reduced pressure at 40° C. The residue was purified by column chromatography on silica gel (PE/EA=30/1, 20/1, 10/1) to give compound 4 (360.00 mg, 7.24% for two steps) as solid. $^1$H NMR (400 MHz, METHANOL-$d_4$)=8.16-8.10 (m, 1H), 8.05-7.99 (m, 1H), 7.86-7.80 (m, 1H), 5.54-5.49 (m, 1H), 5.42-5.37 (m, 1H), 3.95 (s, 3H).

1.4 Preparation of Compound 5

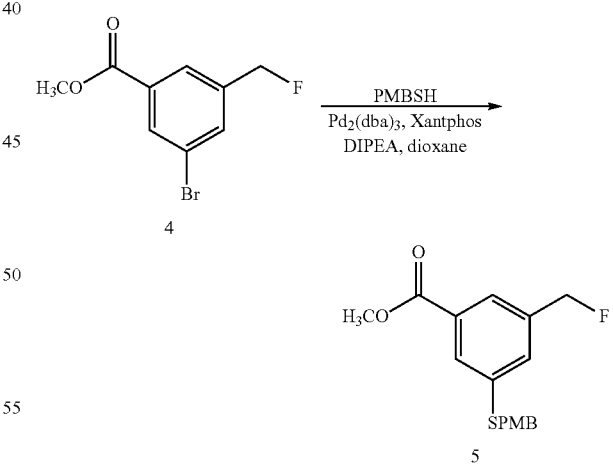

To a solution of Compound 4 (0.36 g, 1.46 mmol) in 1,4-dixoane (40 mL) was added PMBSH (0.338 g, 2.19 mmol), DIPEA (0.337 g, 2.92 mmol), Xantphos (42.24 mg, 0.073 mmol) at 18° C. Then $Pd_2(dba)_3$ (66.85 mg, 0.073 mmol) was added to the solution and it was heated to 120° C. for 16 h. The mixture solution was concentrated and purified by column chromatography on silica gel (PE/EA=30/1, 20/1, 10/1) to give compound 5 (0.464 g, 99.2%)

LCMS: 321 [M+1].

1.5 Preparation of Compound 6

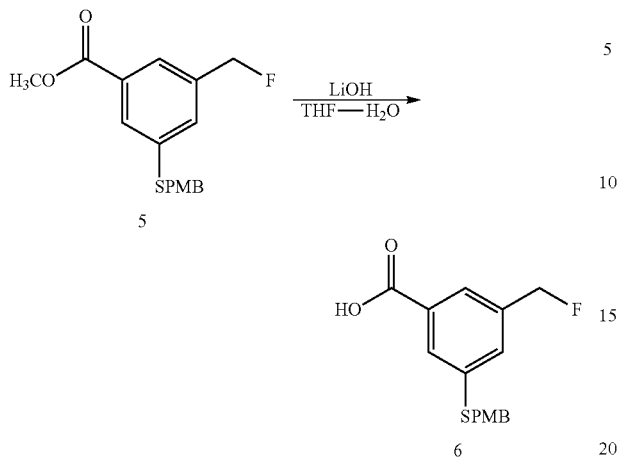

To a solution of compound 5 (0.464 g, 1.45 mmol) in THF (20 mL) was added a solution of LiOH (694.55 mg, 29.00 mmol) in H$_2$O (5 mL). The mixture solution was heated to 60° C. for 2 h. The solution was adjusted to pH<3 by adding HCl (3M). Then it was extracted by EtOAc (200 mL), dried over Na$_2$SO$_4$, concentrated to give compound 6 (0.5 g, crude).

LCMS: 307 [M+1].

1.6 Preparation of Compound 8

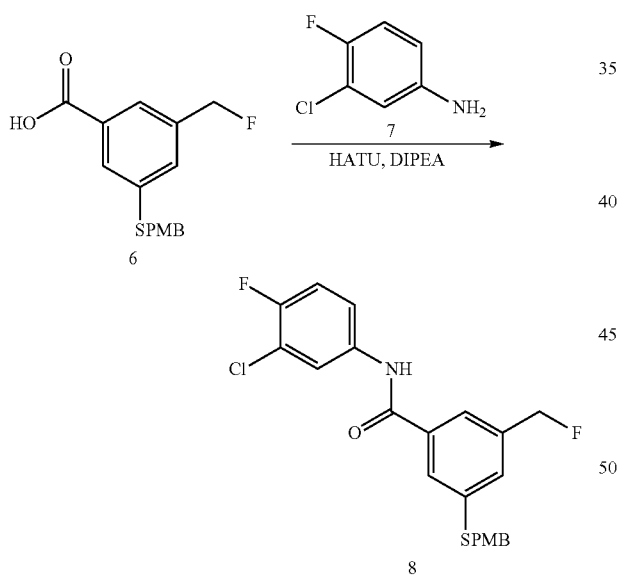

To a solution of compound 6 (0.5 g, 1.63 mmol) in DCM (20 mL) was added DIPEA (0.421 g, 3.26 mmol), HATU (0.93 g, 2.45 mmol). The mixture solution was stirred at 20° C. for 1 h. Then compound 7 (0.285, 1.96 mmol) was added to the mixture and it was stirred at 20° C. for 16 hours. The solution was washed with saturated NH$_4$Cl (50 mL), extracted by EtOAc (100 mL*2), dried over Na$_2$SO$_4$, concentrated to give crude product which was purified by column chromatography on silica gel (PE/EA=20/1, 10/1, 3/1) to give compound 8 (0.7 g, 98.97%)

LCMS: 435 [M+23].

1.7 Preparation of 2207-2208

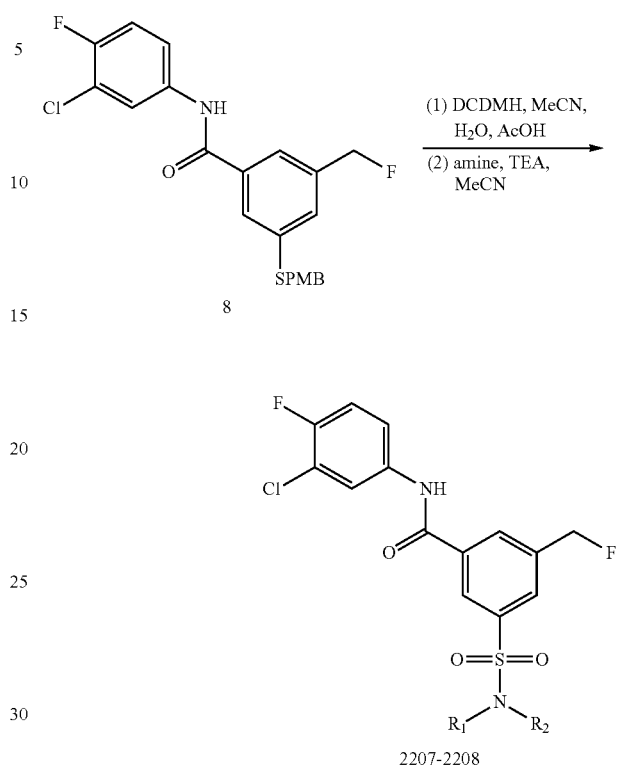

To a solution of compound 8 (100 mg, 0.23 mmol) in MeCN/AcOH/H2O (10 mL, 80:1:2) was added DCDMH (90.81 mg, 0.46 mmol) under −5° C. It was stirred at −5° C. for 2 h. Then amine (0.35 mmol), Et$_3$N (69.96 mg, 0.69 mmol) was added to the solution. It was stirred at 18° C. for 0.5 h. Then it was concentrated to give crude product which was purified by pre-HPLC to give desired product.

General Procedure G

Preparation of 2032 is Exemplified

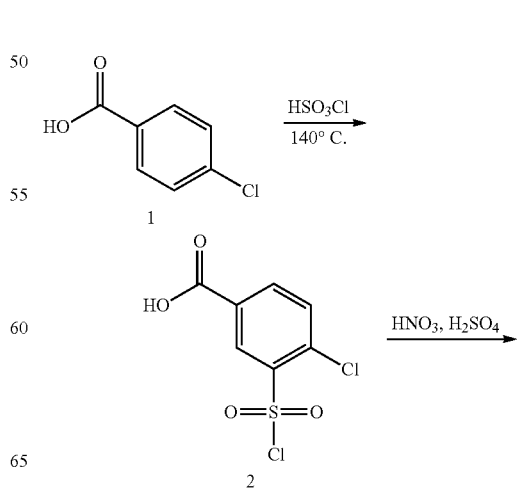

1.1 Preparation of Compound 2

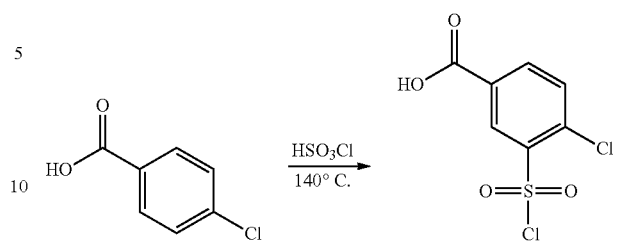

To HSO$_3$Cl (80 mL) was added Compound 1 (20.0 g, 0.13 mol) portionwise at 0° C., then the resulting mixture was heated to 140° C. for 4 hours. After cooled to room temperature, the mixture was poured into ice-water. The resulting precipitate was collected by filtration and dried to give desired compound 2 (25.0 g, 76%) as white solid.

1.2 Preparation of Compound 3

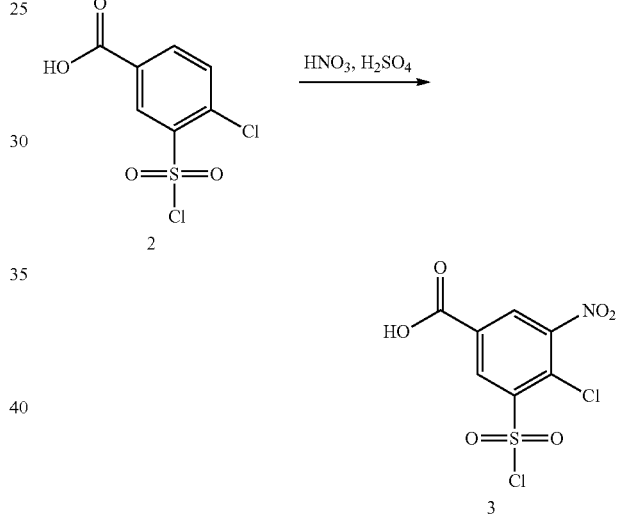

Compound 2 (3.0 g, 11.7 mmol) was added to a mixture of HNO$_3$ (4 mL) in H$_2$SO$_4$ (20 mL), and heated to 90° C. for 4 hours. After cooled to room temperature, the mixture was added to ice-water slowly. The resulting precipitate was collected by filtration and dried to give desired Compound 3 (1.3 g, 38%) as white solid. $^1$H NMR (CDCl$_3$, 400 MHz): δ 9.05 (d, J=2.0 Hz, 1H), 8.76 (d, J=2.0 Hz, 1H).

1.3 Preparation of Compound 4

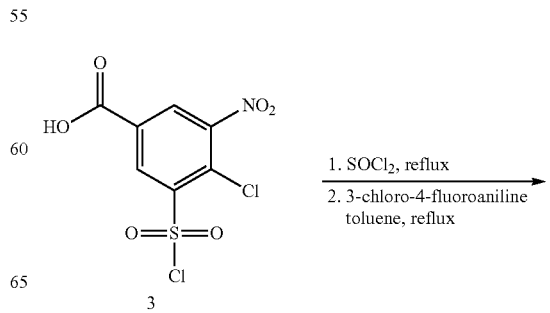

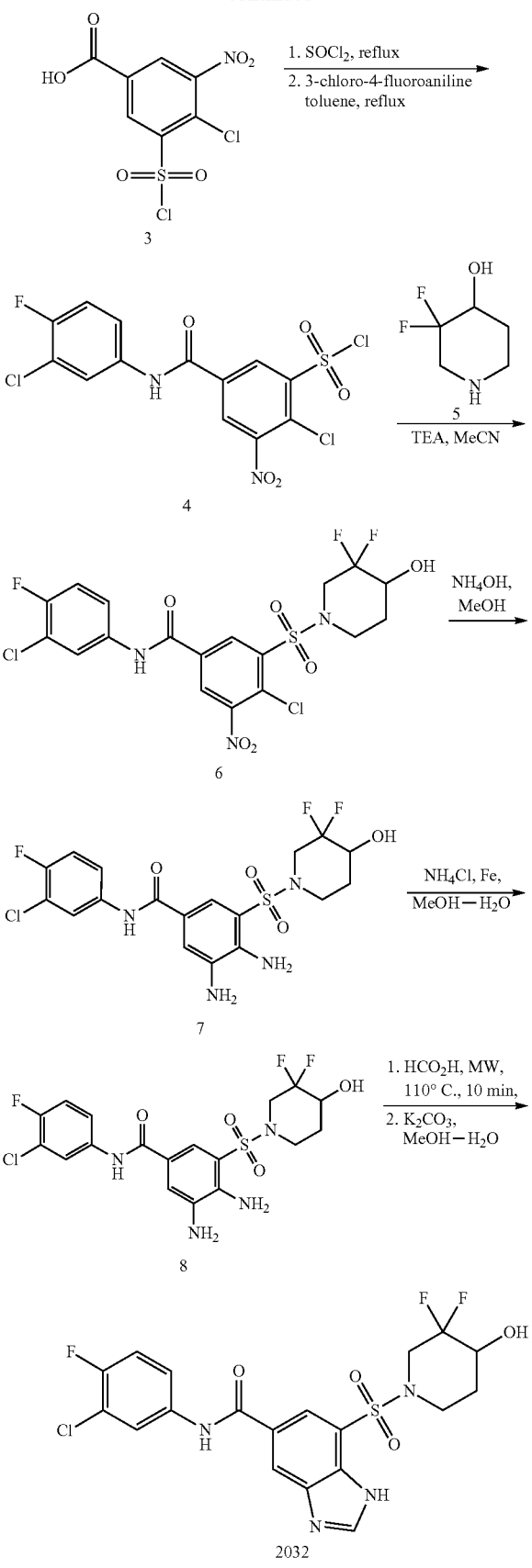

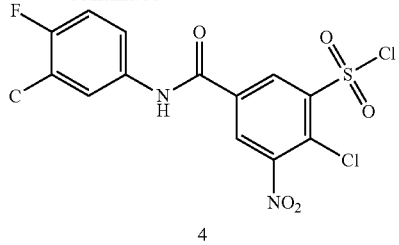

4

A mixture of Compound 3 (1.3 g, 4.3 mmol) and $SOCl_2$ (40 mL) was heated to 90° C. for 4 hours. The mixture was concentrated in vacuo. The residue was dissolved with toluene (10 mL) and heated to 90° C. 3-chloro-4-fluoroaniline (1.2 mg, 3.9 mmol) was added and the mixture was continued to heat to reflux for 4 hours. The mixture was concentrated to give desired compound 4 (1.6 g, crude) as yellow solid, which was used for the next step without further purification.

1.4 Preparation of Compound 6

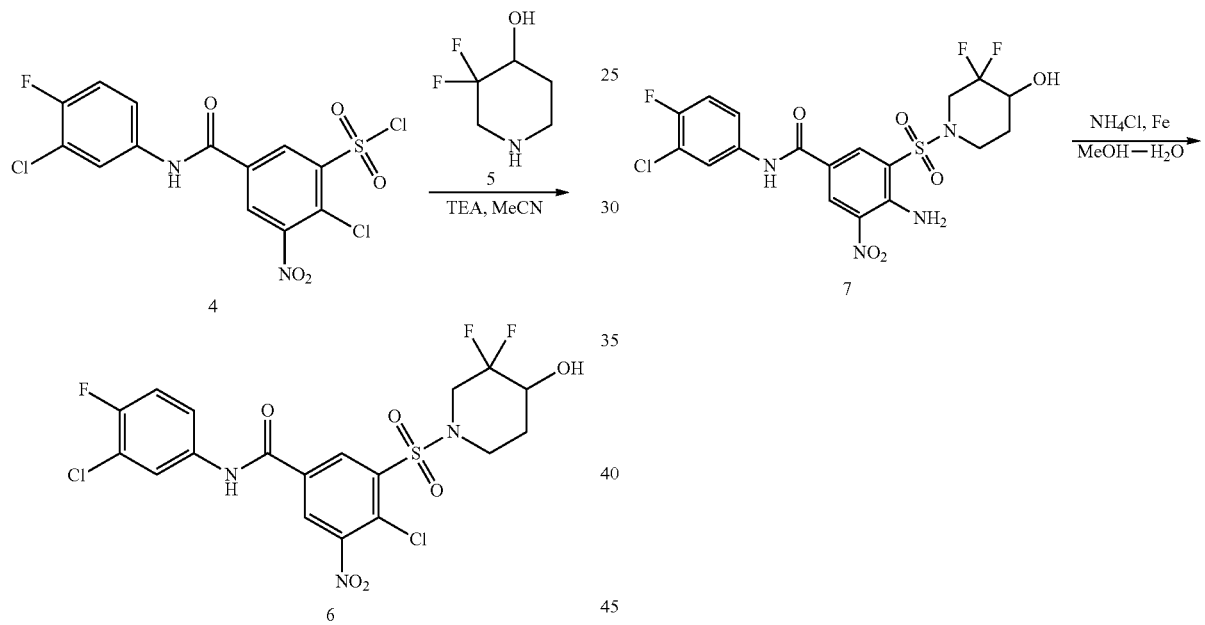

To a mixture of Compound 4 (0.8 g, crude) and 5 (256 mg, 1.8 mmol) in $CH_3CN$ (10 mL), was added $Et_3N$ (566 mg, 5.6 mmol), and stirred at room temperature for 4 hours. The mixture was diluted with EA (50 mL), the organic layer was washed with $NH_4Cl$ (50 mL*2) and concentrated to give desired compound 6 (0.5 g, crude) as a yellow solid, which was used for the next step without further purification.

1.5 Preparation of Compound 7

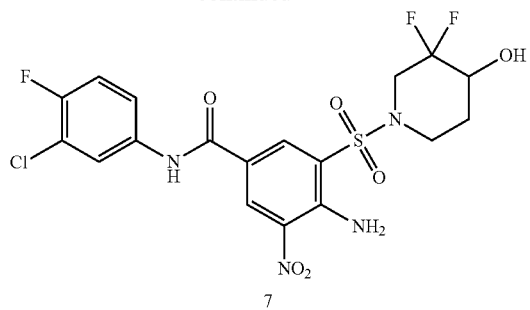

To a solution of Compound 6 (0.1 g, crude) in MeOH (10 mL) was added ammonia (0.5 mL, 28%), and the mixture was heated to 70° C. for 4 hours. The mixture was concentrated in vacuo to give desired compound 7 (80 mg, crude) as yellow solid, which was used for the next step without purification.

1.6 Preparation of Compound 8

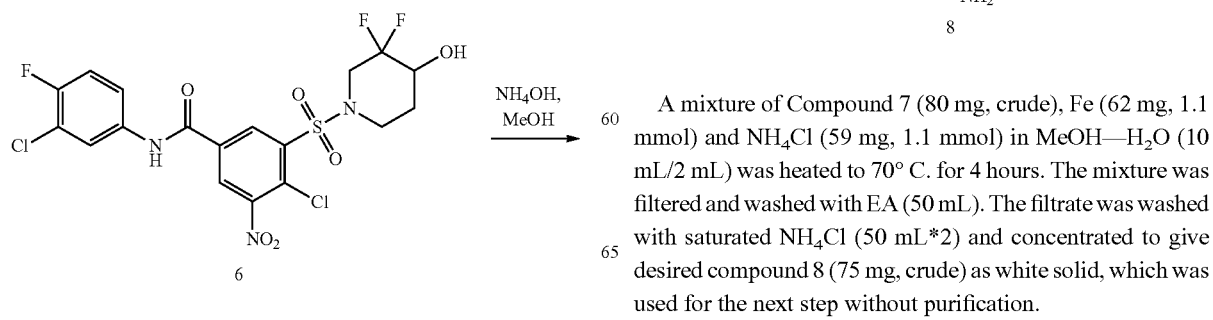

A mixture of Compound 7 (80 mg, crude), Fe (62 mg, 1.1 mmol) and $NH_4Cl$ (59 mg, 1.1 mmol) in MeOH—$H_2O$ (10 mL/2 mL) was heated to 70° C. for 4 hours. The mixture was filtered and washed with EA (50 mL). The filtrate was washed with saturated $NH_4Cl$ (50 mL*2) and concentrated to give desired compound 8 (75 mg, crude) as white solid, which was used for the next step without purification.

1.7 Preparation of 2032

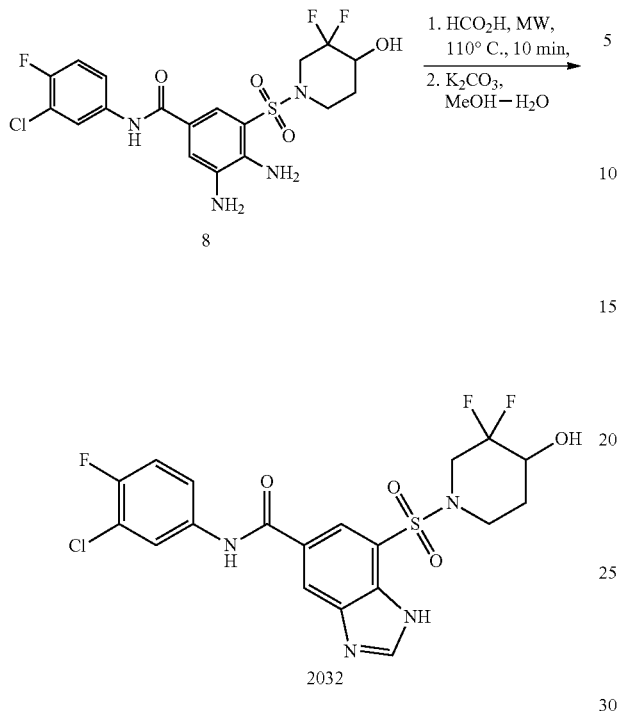

A mixture of Compound 8 (75 mg, crude) in formic acid (10 mL) was microwaved to 110° C. for 10 mins. The mixture was concentrated in vacuo. The residue was dissolved in MeOH—H$_2$O (10 mL/2 mL), and K$_2$CO$_3$ (57 mg, 0.4 mmol) was added. The mixture was heated to 80° C. for 2 hours. After LCMS showed the reaction was finished, the mixture was concentrated in vacuo and extracted with EA. The organic phase was concentrated in vacuo and the residue was purified via acid prep-HPLC to give 2032 (65.89 mg, yield 64.2%) as a white solid.

General Procedure H

Preparation of 2619_D2, 2626_D2 Exemplified

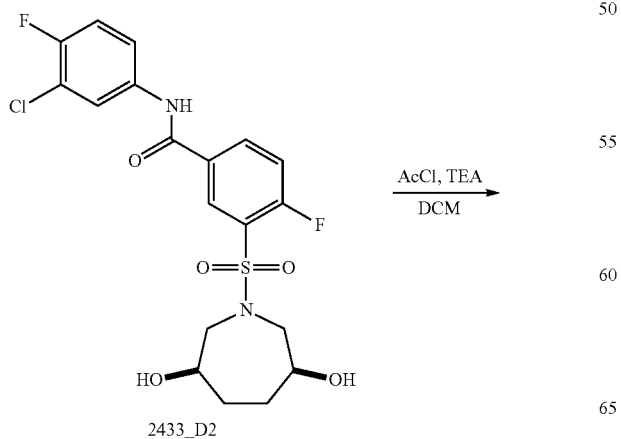

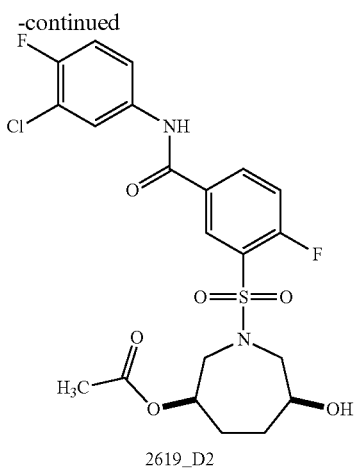

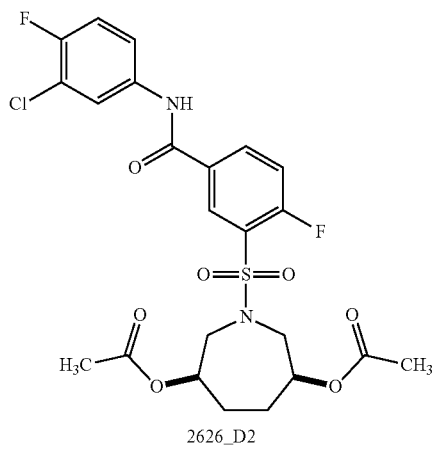

To a solution of N-(3-chloro-4-fluoro-phenyl)-3-(3,6-di-hydroxyazepan-1-yl)sulfonyl-4-fluoro-benzamide (300.00 mg, 650.93 umol, 1.00 eq), TEA (65.87 mg, 650.93 umol, 1.00 eq) and DMAP (79.52 mg, 650.93 umol, 1.00 eq) in DCM (30.00 mL), was dropwise added acetyl chloride (51.10 mg, 650.93 umol, 1.00 eq) at 0° C. The mixture was stirred for 1 hr. LCMS showed 30% 2433_D2 and 32% 2626_D2 produced, and 25% starting material remained. The reaction mixture was washed with water. The organic layer was dried and concentrated. The residue was purified by pre-HPLC to give 2619_D2 (95.00 mg, 188.90 umol, 29.02% yield) as white solid and 2626_D2 (90.00 mg, 165.15 umol, 25.37% yield) as white solid.

General Procedure I

Preparation of 2632, 2634 Exemplified

1 Procedure for Preparation of 2632
1.1 General Scheme:

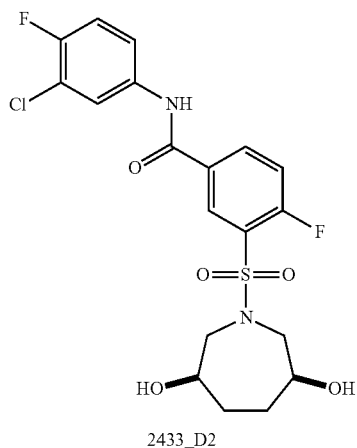

2433_D2

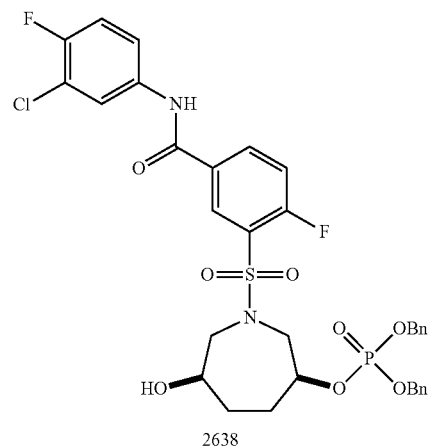

2638

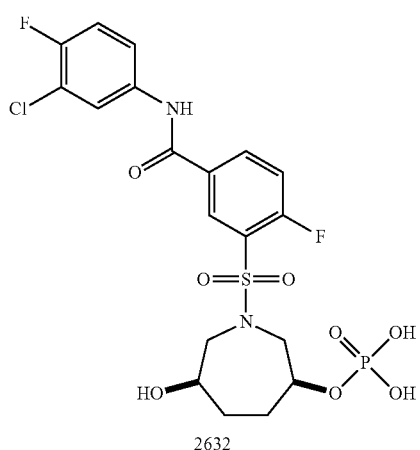

2632

1.1.1 Preparation of 2638

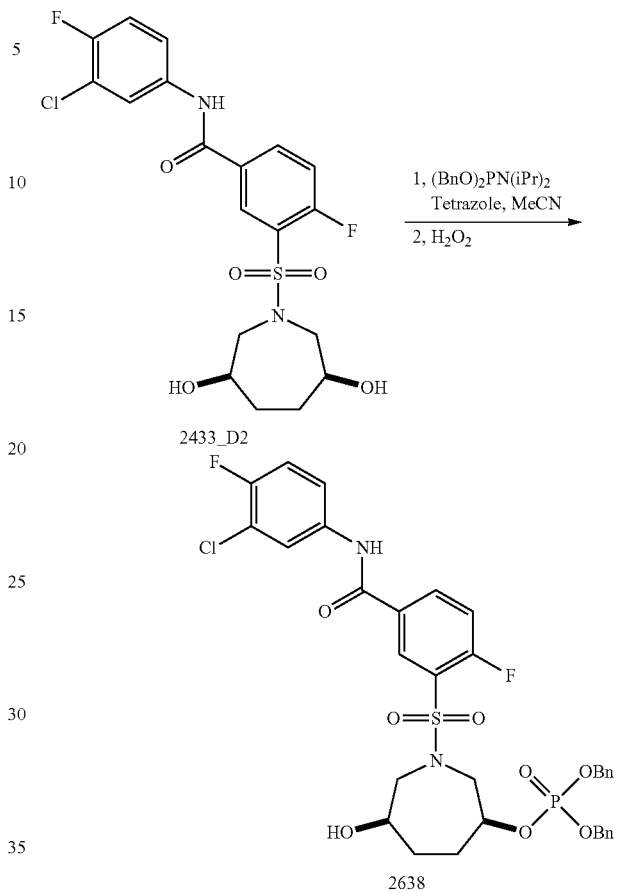

2433_D2

2638

To a solution of N-(3-chloro-4-fluoro-phenyl)-3-(3,6-dihydroxyazepan-1-yl)sulfonyl-4-fluoro-benzamide (500.00 mg, 1.08 mmol, 1.00 eq) in MeCN (30.00 mL) were added 1H-TETRAZOLE (455.98 mg, 6.51 mmol, 6.00 eq) and N-dibenzyloxyphosphanyl-N-isopropyl-propan-2-amine (1.12 g, 3.25 mmol, 3.00 eq). The mixture was stirred at 30° C. for 2 hr. Then $H_2O_2$ (737.94 mg, 6.51 mmol, 6.00 eq) was added, and the mixture was stirred at 30° C. for 16 hr. TLC showed the material was remained, and ~1/3 desired product detected. The mixture was poured into saturated $Na_2SO_3$ (20 mL), extracted with ethyl acetate (20 mL*3), the combined organic layer was dried over anhydrous $Na_2SO_4$, concentrated in vacuum. The residue was purified by chromatography (silica gel, eluting with Petroleum ether/Ethyl acetate=10/1-1/2) to afford dibenzyl[1-[5-[(3-chloro-4-fluoro-phenyl)carbamoyl]-2-fluoro-phenyl]sulfonyl-6-hydroxy-azepan-3-yl]phosphate (105.00 mg, 139.22 umol, 12.89% yield, 95.61% purity) as white solid. $^1$H NMR (400 MHz, MeOD) δ 8.46 (dd, J=6.59, 2.26 Hz, 1H), 8.23-8.31 (m, 1H), 7.98 (dd, J=6.78, 2.45 Hz, 1H), 7.60-7.68 (m, 1H), 7.52 (t, J=9.32 Hz, 1H), 7.20-7.43 (m, 11H), 5.07 (d, J=9.04 Hz, 4H), 4.63 (br. s., 1H), 3.92 (br. s., 1H), 3.71-3.85 (m, 2H), 3.18 (dd, J=15.07, 7.16 Hz, 1H), 2.98 (dd, J=14.32, 7.54 Hz, 1H), 1.96-2.09 (m, 1H), 1.72-1.90 (m, 3H). LCMS: 721/723 [M+1].

1.1.2 Preparation of Compound 2632

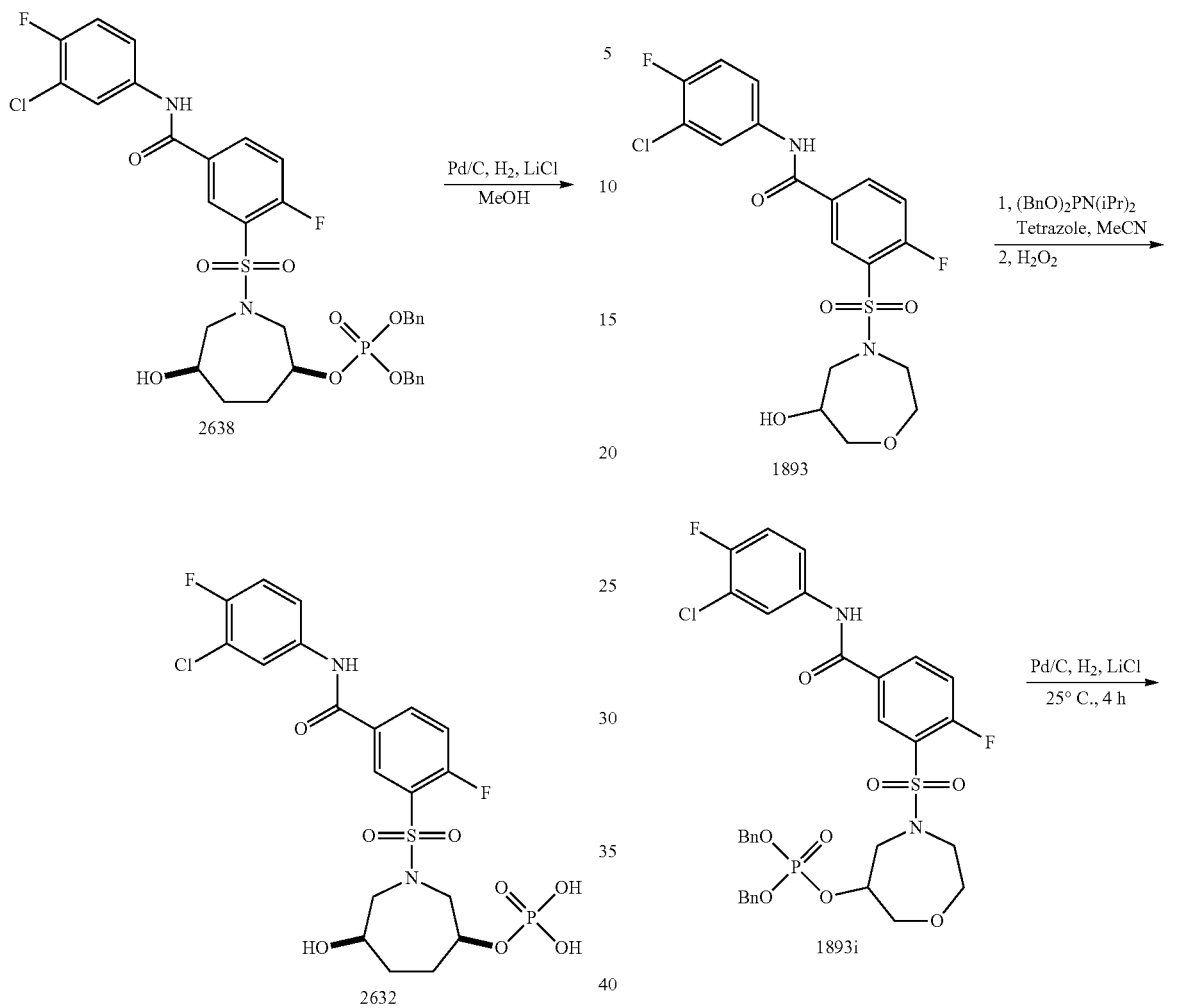

2 Procedure for Preparation of 2634

2.1 General Scheme:

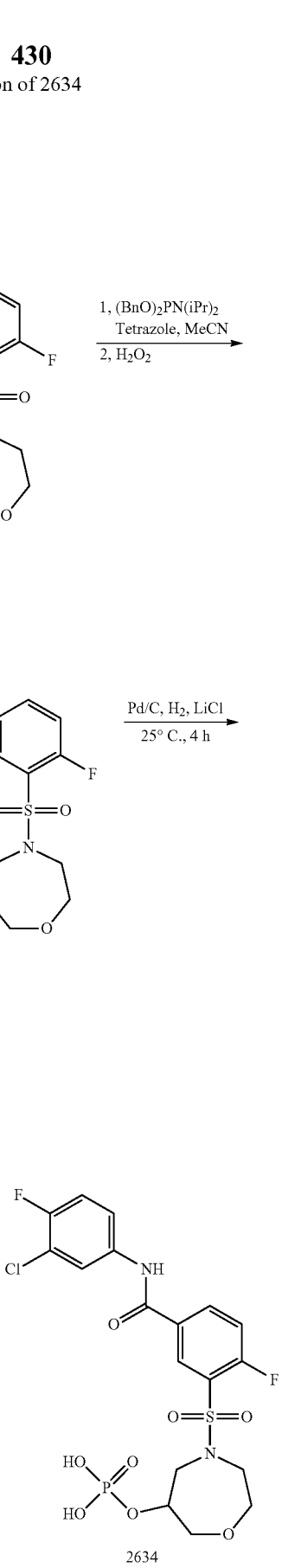

To a solution of dibenzyl[1-[5-[(3-chloro-4-fluoro-phenyl)carbamoyl]-2-fluoro-phenyl]sulfonyl-6-hydroxy-azepan-3-yl]phosphate (210.00 mg, 291.22 umol, 1.00 eq) in MeOH (10.00 mL) was added LiCl (12.34 mg, 291.22 umol, 1.00 eq) and Pd/C (10%, 20 mg) under $N_2$ atmosphere. The suspension was degassed and purged with $H_2$ for 3 times. The mixture was stirred under $H_2$ (15 Psi) at 15° C. for 1 hour. TLC showed the material was consumed completely. The reaction mixture was filtered and the filtrate was concentrated. The residue was purified by pre-HPLC (FA) to afford product 1-((5-((3-chloro-4-fluorophenyl)carbamoyl)-2-fluorophenyl) sulfonyl)-6-hydroxyazepan-3-yl dihydrogen phosphate (110.30 mg, 192.35 umol, 66.05% yield, 94.32% purity) as white solid. $^1$H NMR (400 MHz, MeOD) δ 8.49 (dd, J=6.65, 2.13 Hz, 1H), 8.21-8.31 (m, 1H), 8.02 (dd, J=6.65, 2.64 Hz, 1H), 7.61-7.70 (m, 1H), 7.52 (t, J=9.29 Hz, 1H), 7.27 (t, J=8.91 Hz, 1H), 4.58 (br. s., 1H), 3.87-4.13 (m, 3H), 3.03 (dd, J=14.56, 7.78 Hz, 1H), 2.88 (dd, J=13.80, 9.03 Hz, 1H), 2.10 (dd, J=11.67, 6.15 Hz, 1H), 1.80-2.01 (m, 3H). LCMS: 527/529 [M+1].

2.1.1 Preparation of Compound 1893i

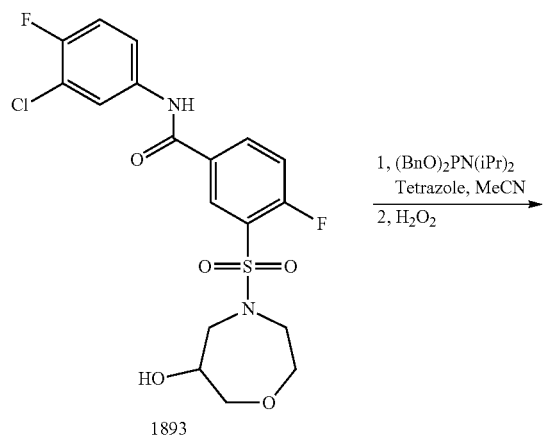

2.1.2 Preparation of 2634

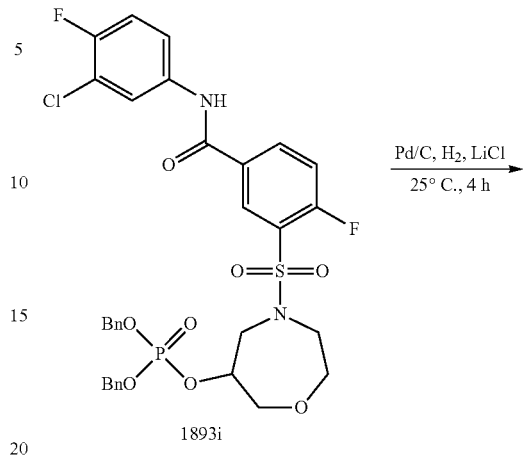

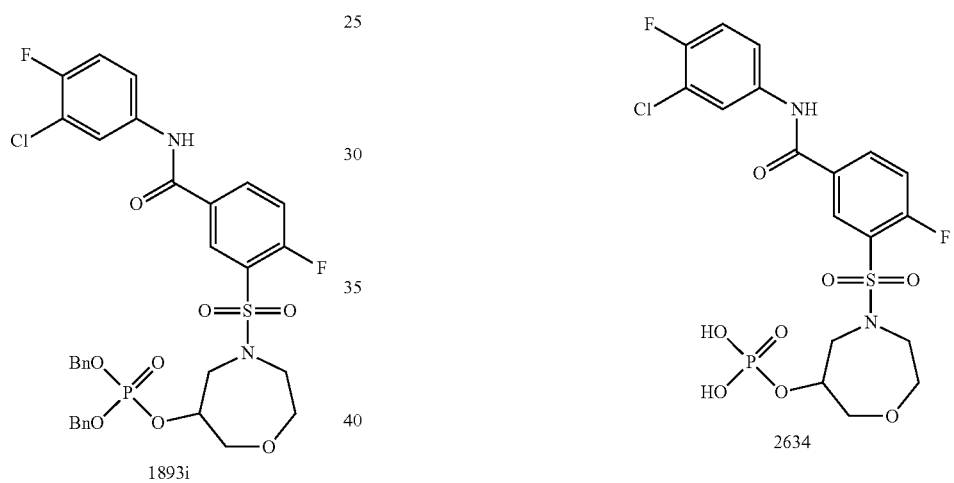

A solution of N-(3-chloro-4-fluoro-phenyl)-4-fluoro-3-[(6-hydroxy-1,4-oxazepan-4-yl)sulfonyl]benzamide (500.00 mg, 1.12 mmol, 1.00 eq) and N-dibenzyloxyphosphanyl-N-isopropyl-propan-2-amine (772.99 mg, 2.24 mmol, 2.00 eq) in MeCN (7.50 mL) was added 2H-tetrazole (0.45 M, 7.46 mL, 3.00 eq). The mixture was stirred at 25° C. for 4 hr. Then $H_2O_2$ (152.22 mg, 1.34 mmol, 3.00 eq) was added, the reaction was stirred at 25° C. for 1 hr. TLC showed the reaction was completed. The mixture quenched by saturated $Na_2SO_3$ (10 mL), extracted with EA (20 mL*3), the combined organic layer was dried over anhydrous $Na_2SO_4$, concentrated. The residue was purified by chromatography (silica gel, eluting with PE:EA=2:1 to 1:1) to afford product dibenzyl[4-[5-[(3-chloro-4-fluoro-phenyl)carbamoyl]-2-fluoro-phenyl]sulfonyl-1,4-oxazepan-6-yl]phosphate (1.00 g, 1.41 mmol, 89.92% yield) as white solid. $^1$H NMR (400 MHz, MeOD) δ 9.86 (brs, 1H), 8.42 (dd, J=6.53, 2.26 Hz, 1H), 8.13-8.26 (m, 1H), 7.95 (dd, J=6.53, 2.51 Hz, 1H), 7.71 (dt, J=7.15, 4.20 Hz, 1H), 7.24-7.39 (m, 10H), 7.11 (t, J=8.78 Hz, 1H), 5.07 (t, J=9.66 Hz, 2H), 4.91-5.01 (m, 2H), 4.40 (d, J=6.27 Hz, 1H), 3.73-3.98 (m, 5H), 3.57-3.69 (m, 2H), 3.32 (dd, J=13.18, 6.40 Hz, 1H). LCMS: 707/709 [M+1].

To a solution of dibenzyl[4-[5-[(3-chloro-4-fluoro-phenyl)carbamoyl]-2-fluoro-phenyl]sulfonyl-1,4-oxazepan-6-yl]phosphate (1.00 g, 1.41 mmol, 1.00 eq) in MeOH (20.00 mL) was added LiCl (60 mg, 1.41 mmol, 1.00 eq), followed by Pd/C (15.00 mg) under N2. The suspension was degassed under vacuum and purged with $H_2$ several times. The mixture was stirred under $H_2$ (15 psi) at 25° C. for 1 hours. LCMS showed the reaction was completed. The reaction mixture was filtered and the filter was concentrated. The residue was purified by pre-HPLC (FA) to afford [4-[5-[(3-chloro-4-fluoro-phenyl)carbamoyl]-2-fluoro-phenyl]sulfonyl-1,4-oxazepan-6-yl]dihydrogen phosphate (433.00 mg, 821.90 umol, 58.29% yield) as white solid. $^1$H NMR (400 MHz, MeOD) δ 9.14 (s, 1H), 8.51 (d, J=4.52 Hz, 1H), 8.23 (brs, 1H), 8.04 (dd, J=6.59, 2.45 Hz, 1H), 7.63-7.75 (m, 1H), 7.50 (t, J=9.32 Hz, 1H), 7.25 (t, J=8.95 Hz, 1H), 4.49 (brs, 1H), 3.79-4.07 (m, 5H), 3.70 (t, J=8.85 Hz, 1H), 3.34-3.47 (m, 2H). LCMS: 527/529 [M+1].

Resolution of Chiral Compounds

Chiral resolution of selected compounds of the invention was performed according to the conditions listed in Table 3.

TABLE 3

| Structure | Compound ID | Supercritical Fluid Chromatography Resolution condition |
|---|---|---|
| 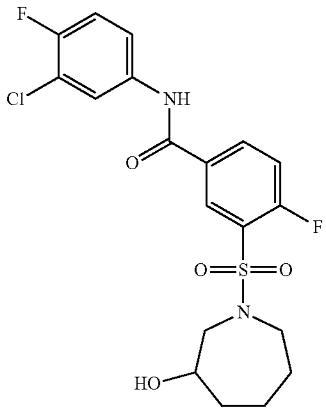 [SMILES: O=C(Nc1ccc(F)c(Cl)c1)c1ccc(F)c(S(=O)(=O)N2CCCCC(O)C2)c1] | 1763 | Column: AD-10 um(CHIRAL PAK)<br>Mobile Phase A: $CO_2$<br>Mobile Phase B: 0.1% $NH_3H_2O$ in EtOH<br>Gradient(% B): 30%<br>Flow Rate: 60 g/min.<br>Wavelength: 220 nm<br>Column Temp.: 35° C.<br>Back Pressure: 100 Bar<br>Elution time(min): 6.3-7.5; 8.3-10.0 |
| 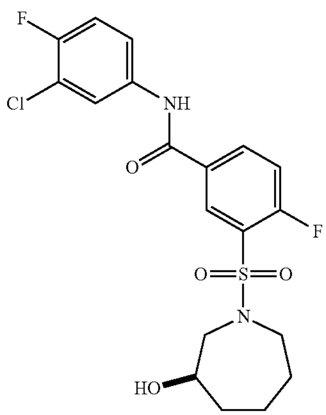 [SMILES: O=C(Nc1ccc(F)c(Cl)c1)c1ccc(F)c(S(=O)(=O)N2CCCC[C@@H](O)C2)c1] | 1763_E1 | |
| 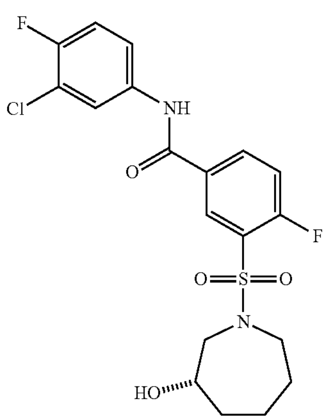 [SMILES: O=C(Nc1ccc(F)c(Cl)c1)c1ccc(F)c(S(=O)(=O)N2CCCC[C@H](O)C2)c1] | 1763_E2 | |

TABLE 3-continued
| Structure | Compound ID | Supercritical Fluid Chromatography Resolution condition |
|---|---|---|
| 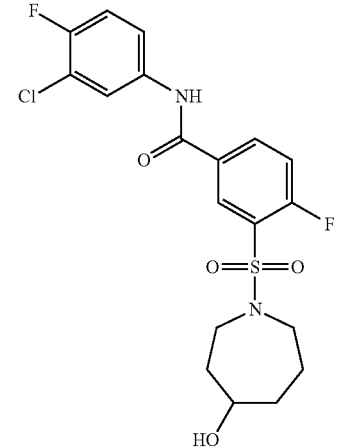 [SMILES: O=C(Nc1ccc(F)c(Cl)c1)c1ccc(F)c(S(=O)(=O)N2CCCC(O)CC2)c1] | 1766 | Column: AD-5 um(CHIRAL PAK)<br>Mobile Phase A: $CO_2$<br>Mobile Phase B: 0.1% $NH_3H_2O$ in IPA<br>Gradient(% B): 30%<br>Flow Rate: 60 g/min.<br>Wavelength: 220 nm<br>Column Temp.: 35° C.<br>Back Pressure: 100 Bar<br>Elution time(min): 5.2-6.8; 7.2-8.9 |
| 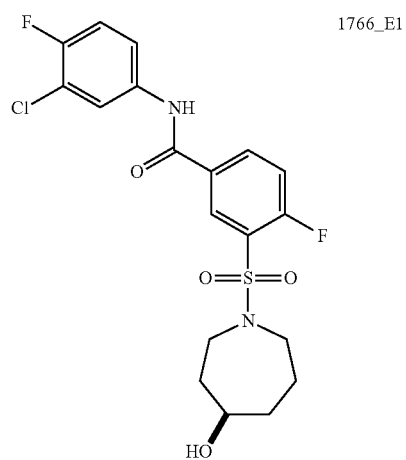 | 1766_E1 | |
| 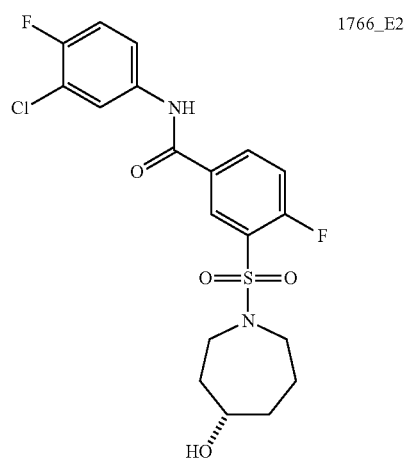 | 1766_E2 | |

TABLE 3-continued

| Structure | Compound ID | Supercritical Fluid Chromatography Resolution condition |
|---|---|---|
| 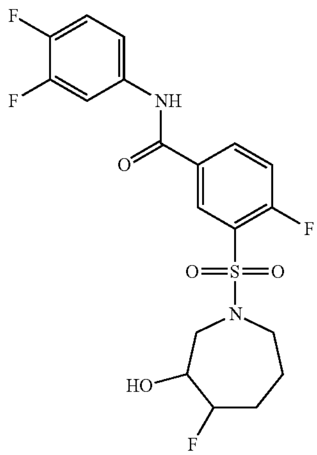 [SMILES: O=C(Nc1ccc(F)c(F)c1)c1ccc(F)c(S(=O)(=O)N2CCCC(F)C(O)C2)c1] | 1821 | Column: AD-10 um(CHIRAL PAK)<br>Mobile Phase A: $CO_2$<br>Mobile Phase B: 0.1% $NH_3H_2O$ in EtOH<br>Gradient(% B): 30%<br>Flow Rate: 60 g/min.<br>Wavelength: 220 nm<br>Column Temp.: 35° C.<br>Back Pressure: 100 Bar<br>Elution time(min): 3.6-4.2; 4.6-5.6 |
| 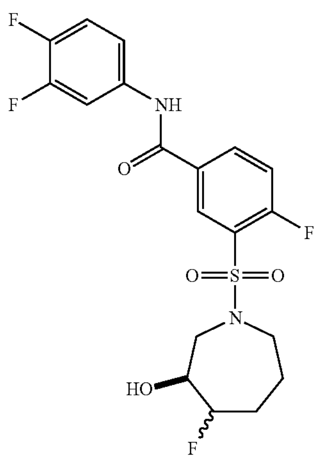 [SMILES: O=C(Nc1ccc(F)c(F)c1)c1ccc(F)c(S(=O)(=O)N2CCCC(F)[C@@H](O)C2)c1] | 1821_D1 | |
| 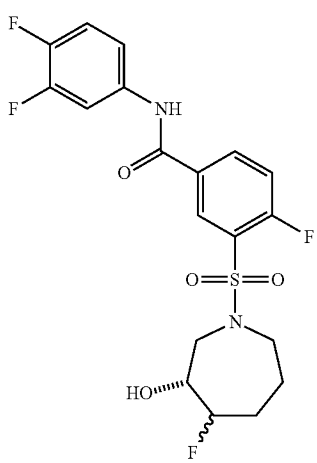 [SMILES: O=C(Nc1ccc(F)c(F)c1)c1ccc(F)c(S(=O)(=O)N2CCCC(F)[C@H](O)C2)c1] | 1821_D2 | |

TABLE 3-continued

| Structure | Compound ID | Supercritical Fluid Chromatography Resolution condition |
|---|---|---|
| 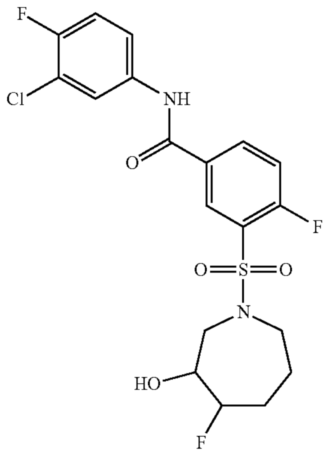 [SMILES: O=C(Nc1ccc(F)c(Cl)c1)c1ccc(F)c(S(=O)(=O)N2CCCC(F)C(O)C2)c1] | 1822 | Column: AD-10 um(CHIRAL PAK)<br>Mobile Phase A: $CO_2$<br>Mobile Phase B: 0.1% $NH_3H_2O$ in EtOH<br>Gradient(% B): 30%<br>Flow Rate: 60 g/min.<br>Wavelength: 220 nm<br>Column Temp.: 35° C.<br>Back Pressure: 100 Bar<br>Elution time(min): 8.9-11.0; 11.9-14.6 |
| 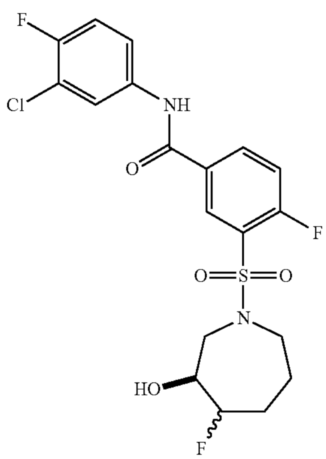 [SMILES: O=C(Nc1ccc(F)c(Cl)c1)c1ccc(F)c(S(=O)(=O)N2CCCC(F)[C@@H](O)C2)c1] | 1822_D1 | |
| 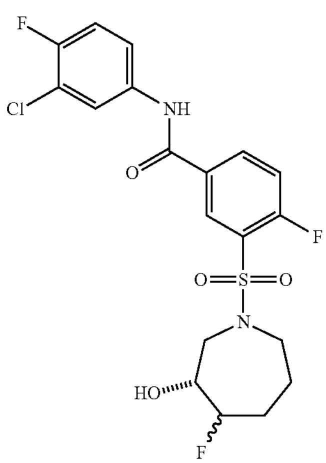 [SMILES: O=C(Nc1ccc(F)c(Cl)c1)c1ccc(F)c(S(=O)(=O)N2CCCC(F)[C@H](O)C2)c1] | 1822_D2 | |

TABLE 3-continued

| Structure | Compound ID | Supercritical Fluid Chromatography Resolution condition |
|---|---|---|
| (structure) | 1829 | Column: AD-5 um(CHIRAL PAK)<br>Mobile Phase A: $CO_2$<br>Mobile Phase B: 30% 0.1% $NH_3H_2O$ in IPA<br>Gradient(% B): 40%<br>Flow Rate: 60 g/min.<br>Wavelength: 220 nm<br>Column Temp.: 35° C.<br>Back Pressure: 100 Bar<br>Elution time(min): 5.9-7.4; 7.9-9.7 |
| (structure) | 1829_D1 | |
| (structure) | 1829_D2 | |

TABLE 3-continued

| Structure | Compound ID | Supercritical Fluid Chromatography Resolution condition |
|---|---|---|
| 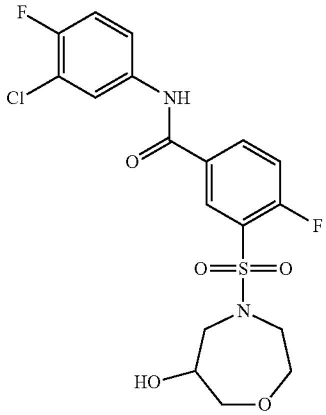 [SMILES: O=C(Nc1ccc(F)c(Cl)c1)c1ccc(F)c(S(=O)(=O)N2CCOCC(O)C2)c1] | 1893 | Column: AD-10 um(CHIRAL PAK)<br>Mobile Phase A: $CO_2$<br>Mobile Phase B: 0.1% $NH_3H_2O$ in MeOH<br>Gradient(% B): 40%<br>Flow Rate: 70 g/min.<br>Wavelength: 220 nm<br>Column Temp.: 35° C.<br>Back Pressure: 100 Bar<br>Elution time(min): 4.5-5.1; 5.5-6.5 |
| 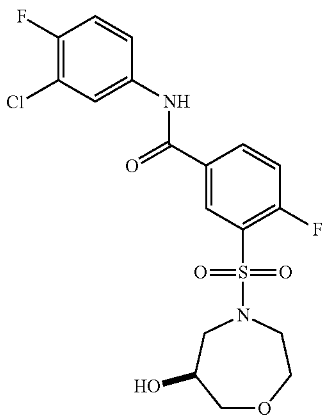 [SMILES: O=C(Nc1ccc(F)c(Cl)c1)c1ccc(F)c(S(=O)(=O)N2CCOC[C@@H](O)C2)c1] | 1893_E1 | |
| 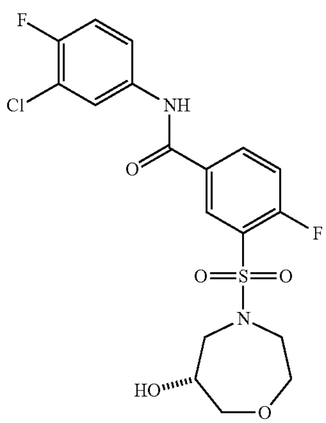 [SMILES: O=C(Nc1ccc(F)c(Cl)c1)c1ccc(F)c(S(=O)(=O)N2CCOC[C@H](O)C2)c1] | 1893_E2 | |

Example

HBV Assembly Assay

The fluorescence quenching in vitro assembly HBV assay was developed according to a method described by Zlotnick and coworkers (Nature Biotechnology 2006, 24:358). The assay is based on the observation that the C-termini of the HBV core protein cluster together during capsid formation. This assay utilizes a mutant C150 HBV capsid protein where all wild-type cysteines are mutated to alanines, but a C-terminal cysteine residue is preserved and is labeled with fluorescent BoDIPY-FL dye. HBV C150Bo protein is highly fluorescent, however the fluorescence is drastically reduced during the capsid assembly process. Thus, the assay measures the ability and potency of test compounds to modulate capsid assembly by monitoring the fluorescence of the labeled capsid C150Bo protein.

In a typical assay, the mutant HBV C150 protein (amino acids 1-150, C49A, C61A, C107A, 150C) is cloned into a T7 RNA-polymerase based expression vector, expressed in *E. coli* and purified to homogeneity as a dimer. The purified HBV core protein is desalted and labeled with BODIPY-FL Dye.

In a non-limiting embodiment, the assembly assay is conducted in 96-well plate format. The assembly reactions are carried out in 50 mM Hepes buffer, pH 7.5 and 150 mM NaCl. The compounds are pre-incubated with the HBV CA protein for 15 min, and the assembly reactions are initiated by addition of NaCl. The reaction is allowed to continue for 1 hour at room temperature.

To determine the effect on capsid assembly, each test compound is initially screened at least 4 different concentrations in duplicates. Primary hits are compounds that show activity in the assembly assay at 10 uM. Identified primary hits are confirmed in follow-up studies as described elsewhere herein. Known modulators of HBV CA assembly, such as HAP-1 and BAY 41-4109, are used as control compounds in these experiments and exhibited $EC_{50}$ values consistent with the literature. $EC_{50}$ values for test compounds are determined via analysis of the dose-response curve.

Selected compounds of the invention were assayed in the HBV assembly assay, as described above. The assembly assay was conducted in 96-well plate format. The assembly reactions were carried out in 50 mM Hepes buffer, pH 7.5 and 150 mM NaCl. The compounds were pre-incubated with the HBV CA protein for 15 min, and the assembly reactions were initiated by addition of NaCl. The reaction was allowed to continue for 1 hour at room temperature. The 96-well plate assembly assay consistently had Z' factors greater than 0.7 and were robust and reproducible both from plate-to-plate and day-to-day.

To determine the effect on capsid assembly, each test compound was initially screened at 5 different concentrations: about 30 μM, 10 μM, 3 μM, 1 μM, and 0.3 μM in duplicates. Primary hits were compounds that show >50% activity in the assembly assay at about 10 μM and a representative group of these active compounds is shown in Table 4.

TABLE 4

HBV assembly assay ('+' indicates >50% activity at about 10 μM)

| Compound | Activity |
|---|---|
| 1763_E1 | + |
| 1763_E2 | + |
| 1765 | + |
| 1766_E1 | + |
| 1766_E2 | + |
| 1768 | + |
| 1769 | + |
| 1819 | + |
| 1820 | + |
| 1821 | + |
| 1821_D1 | + |
| 1821_D2 | + |
| 1822_D1 | + |
| 1822_D2 | + |
| 1826_D2 | + |
| 1829_D1 | + |
| 1829_D2 | + |
| 1829-2 | + |
| 1890 | + |
| 1891 | + |
| 1892 | + |
| 1893 | + |
| 1893_E1 | + |
| 1893_E2 | + |
| 1894 | + |
| 1895 | + |
| 1909 | + |
| 1910 | + |
| 1914 | + |
| 1915 | + |
| 1916 | + |
| 1917 | + |

TABLE 4-continued

HBV assembly assay ('+' indicates >50% activity at about 10 μM)

| Compound | Activity |
|---|---|
| 1919 | + |
| 1938 | + |
| 1944 | + |
| 1975 | + |
| 1977 | + |
| 1979 | + |
| 1980 | + |
| 1981 | + |
| 1983 | + |
| 1986 | + |
| 1987 | + |
| 1989 | + |
| 2002 | + |
| 2004 | + |
| 2007 | + |
| 2024 | + |
| 2033 | + |
| 2114_D1 | + |
| 2114_D2 | + |
| 2121 | + |
| 2123 | + |
| 2199 | + |
| 2202 | + |
| 2205 | + |
| 2206 | + |
| 2433_D1 | + |
| 2433_D2 | + |
| 2492 | + |
| 2505 | + |
| 2547 | + |
| 2548 | + |
| 2550 | + |
| 2617_D2 | + |
| 2618_D1 | + |
| 2618_D2 | + |
| 2619_D2 | + |
| 2625_D2 | + |
| 2626_D2 | + |

Example

Inhibition of HBV Replication Dot-Blot Assay

Compounds active in the HBV assembly assay are tested for their activity and toxicity in cellular assay. In the first anti-viral assay, the ability of compounds to inhibit HBV replication in an HBV-producing hepatoma cell line using the dot-blot method is evaluated.

Briefly, confluent monolayers of HepG2-2.2.15 cells are incubated with complete medium containing various concentrations of a test compound. Three days later, the culture medium is replaced with fresh medium containing the appropriately diluted test compound. Six days following the initial administration of the test compound, the cell culture supernatant is collected, and cell lysis is performed. The samples are applied onto Nylos membranes and DNA is immobilized to the membrane by UV cross-linking. After pre-hybridization, the HBV probe is added and the hybridization is performed overnight. The membranes are exposed to the Kodak films; antiviral activity is calculated from the reduction in HBV DNA levels ($EC_{50}$). The $EC_{50}$ for antiviral activity is calculated from the dose response curves of active compounds. Assay performance over time is monitored by the use of the standard positive control compounds ETV, BAY 41-4109, and HAP-1.

Compound cytotoxicity ($TC_{50}$) is measured in this same HepG2-2.2.15 cell line using a CellTiter Blue-based cytotoxicity assay employed as recommended by manufacturer (Promega). To confirm and expand these results, a second antiviral assay is carried out on active compounds using the stable HBV cell line HepG2.2.15 and measuring anti-HBV potency by real-time PCR and cytotoxicity by CellTiter Blue. In this assay, 24 hours after cell seeding, HepG2-2.2.15 cells are incubated with complete medium containing various concentrations of a test compound with BAY 41-4109 and HAP-1 used as positive controls. After three days, the culture medium is replaced with fresh medium containing the appropriately diluted test compound. The cell culture is collected six days following the initial administration of the test compound, followed by HBV DNA extraction using QIAamp 96 DNA Blood Kit (Qiagen). The extracted HBV DNA is diluted and analyzed by Real-Time PCR. A standard curve is generated by plotting Ct value vs the amount of HBV plasmid standard. Cytotoxicity is determined similarly to the above described method by applying a dye uptake method (CellTiter Blue kit, Promega).

Selected compounds were tested for their activity and toxicity in cellular assay. In the first anti-viral assay, the ability of compounds to inhibit HBV replication in an HBV-producing hepatoma cell line using the dot-blot method was evaluated.

Confluent monolayers of HepG2-2.2.15 cells were incubated with complete medium containing various concentrations of a test compound. Three days later, the culture medium was replaced with fresh medium containing the appropriately diluted test compound. Six days following the initial administration of the test compound, the cell culture supernatant was collected, and cell lysis was performed. The samples were applied onto Nylos membranes and DNA was immobilized to the membrane by UV cross-linking. After pre-hybridization, the HBV probe was added and the hybridization was performed overnight. The membranes were exposed to the Kodak films; antiviral activity was calculated from the reduction in HBV DNA levels ($EC_{50}$). The $EC_{50}$ for antiviral activity was calculated from the dose response curves of active compounds. Assay performance over time was monitored by the use of the standard positive control compounds ETV, BAY 41-4109, and HAP-1. Results for selected compounds of the invention are illustrated in Table 5.

Cytotoxicity ($CC_{50}$) was measured in this same HepG2-2.2.15 cell line using a CellTiter Blue-based cytotoxicity assay employed as recommended by manufacturer (Promega).

TABLE 5

"Activity" represents activity in dot-blot-assay ('+' indicates >50% activity at 10 μM)

| Compound | Activity |
| --- | --- |
| 1763_E1 | + |
| 1763_E2 | + |
| 1765 | + |
| 1766_E1 | + |
| 1766_E2 | + |
| 1768 | + |
| 1769 | + |
| 1819 | + |
| 1820 | + |
| 1821 | + |
| 1821_D1 | + |
| 1821_D2 | + |
| 1822_D1 | + |
| 1822_D2 | + |
| 1826_D2 | + |
| 1829_D1 | + |
| 1829_D2 | + |
| 1829-2 | + |
| 1890 | + |
| 1891 | + |
| 1892 | + |
| 1893 | + |
| 1893_E1 | + |
| 1893_E2 | + |
| 1894 | + |
| 1895 | + |
| 1909 | + |
| 1910 | + |
| 1914 | + |
| 1915 | + |
| 1916 | + |
| 1917 | + |
| 1919 | + |
| 1938 | + |
| 1944 | + |
| 1975 | + |
| 1977 | + |
| 1979 | + |
| 1980 | + |
| 1981 | + |
| 1983 | + |
| 1986 | + |
| 1987 | + |
| 1989 | + |
| 2002 | + |
| 2004 | + |
| 2007 | + |
| 2024 | + |
| 2033 | + |
| 2114_D1 | + |
| 2114_D2 | + |
| 2121 | + |
| 2123 | + |
| 2199 | + |
| 2202 | + |
| 2205 | + |
| 2206 | + |
| 2433_D1 | + |
| 2433_D2 | + |
| 2492 | + |
| 2505 | + |
| 2547 | + |
| 2548 | + |
| 2550 | + |
| 2617_D2 | + |
| 2618_D1 | + |
| 2618_D2 | + |
| 2619_D2 | + |
| 2625_D2 | + |
| 2626_D2 | + |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of treating an HBV infection in an individual in need thereof, comprising administering to the individual a therapeutically effective amount of a compound of Formula Va:

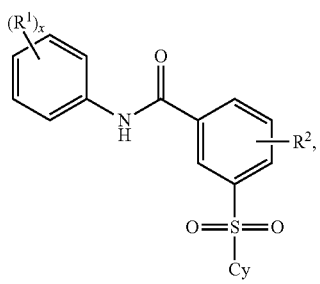

or a pharmaceutically acceptable salt thereof;
wherein
each $R^1$ is, independently at each occurrence, halo, OH, —$C_1$-$C_6$ alkyl, or —O—$C_1$-$C_6$ alkyl, wherein the alkyl groups are optionally substituted 1-3 times with halo or OH;
each $R^2$ is, independently at each occurrence, halo, OH, —$C_1$-$C_6$ alkyl, or —O—$C_1$-$C_6$ alkyl, wherein the alkyl groups are optionally substituted 1-3 times with halo or OH;
x is 2 or 3;
Cy is

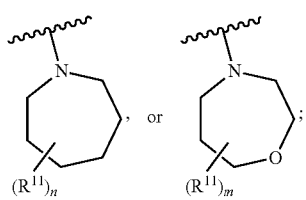

and $R^{11}$ is, independently at each occurrence, —OH, halo, —$C_1$-$C_6$ alkyl, —OC(O)CH$_3$, or —H$_2$PO$_4$, wherein n and m are 1, 2, or 3, and at least one $R^{11}$ is

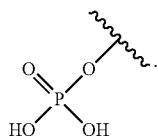

2. The method of claim 1, further comprising administering to the individual at least one additional therapeutic agent selected from the group consisting of a HBV polymerase inhibitor, immunomodulatory agents, pegylated interferon, viral entry inhibitor, viral maturation inhibitor, BAY 41-4109, reverse transcriptase inhibitor, a cyclophilin/TNF inhibitor, a TLR-agonist, and an HBV vaccine, and a combination thereof.

3. The method of claim 2, wherein the therapeutic agent is a reverse transcriptase inhibitor, and is at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, cidofovir, Efavirenz, Nevirapine, Delavirdine, and Etravirine.

4. The method of claim 2, wherein the therapeutic agent is a TLR agonist, and wherein the TLR agonist is a TLR-7 agonist selected from the group consisting of SM360320 (9-benzyl-8-hydroxy-2-(2-methoxy-ethoxy)adenine) and AZD 8848 (methyl[3-({[3-(6-amino-2-butoxy-8-oxo-7,8-dihydro-9H-purin-9-yl)propyl][3-(4-morpholinyl)propyl]amino}methyl)phenyl]acetate).

5. The method of claim 2, wherein the therapeutic agent is an interferon selected from the group consisting of interferon alpha (IFN-α), interferon beta (IFN-β), interferon lambda (IFN-λ), and interferon gamma (IFN-γ).

6. The method of claim 5, wherein the interferon is interferon-alpha-2a, interferon-alpha-2b, or interferon-alpha-n1.

7. The method of claim 6, wherein the interferon-alpha-2a or interferon-alpha-2b is pegylated.

8. The method of claim 6, wherein the interferon-alpha-2a is pegylated interferon-alpha-2a (PEGASYS).

9. The method of claim 1, further comprising administering to the individual at least one HBV vaccine, a nucleoside HBV inhibitor, an interferon or any combination thereof.

10. The method of claim 9, wherein the HBV vaccine is selected from the group consisting of RECOMBIVAX HB, ENGERIX-B, ELOVAC B, GENEVAC-B, and SHANVAC B.

11. A method of treating an HBV infection in an individual in need thereof, comprising reducing the HBV viral load by administering to the individual a therapeutically effective amount of a compound alone or in combination with a reverse transcriptase inhibitor; and further administering to the individual a therapeutically effective amount of HBV vaccine; wherein the compound is a compound of Formula Va:

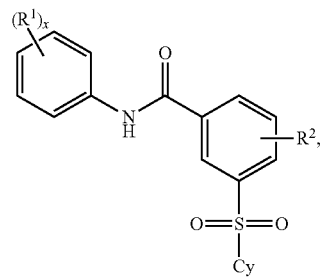

or a pharmaceutically acceptable salt thereof;
wherein
each $R^1$ is, independently at each occurrence, halo, OH, —$C_1$-$C_6$ alkyl, or —O—$C_1$-$C_6$ alkyl, wherein the alkyl groups are optionally substituted 1-3 times with halo or OH;
each $R^2$ is, independently at each occurrence, halo, OH, —$C_1$-$C_6$ alkyl, or —O—$C_1$-$C_6$ alkyl, wherein the alkyl groups are optionally substituted 1-3 times with halo or OH;
x is 2 or 3;
Cy is

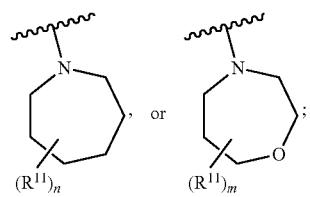

and $R^{11}$ is, independently at each occurrence, —OH, halo, —$C_1$-$C_6$ alkyl, —OC(O)CH$_3$, or —H$_2$PO$_4$, wherein n and m are 1, 2, or 3, and at least one $R^{11}$ is

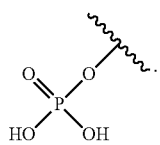

12. The method of claim 1 further comprising monitoring the HBV viral load of the subject, and wherein the method is carried out for a period of time such that the HBV virus is undetectable.

13. The method of claim 1, wherein each $R^1$ is, independently at each occurrence, halo.

14. The method of claim 1, wherein each $R^2$ is, independently at each occurrence, halo or —$C_1$-$C_6$ alkyl, wherein the alkyl is optionally substituted 1-3 times with halo.

15. The method of claim 1, wherein the compound is selected from:

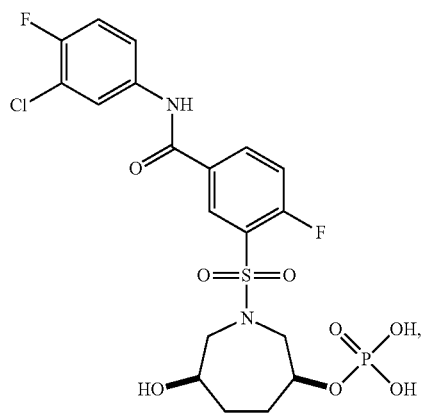

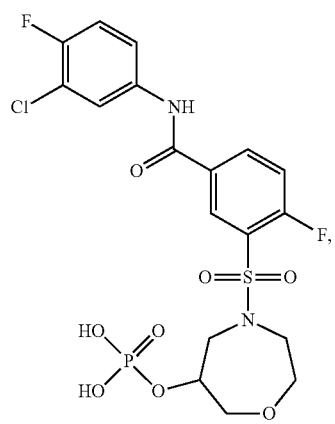

or
a pharmaceutically acceptable salt thereof.

16. The method of claim 1, wherein the compound is

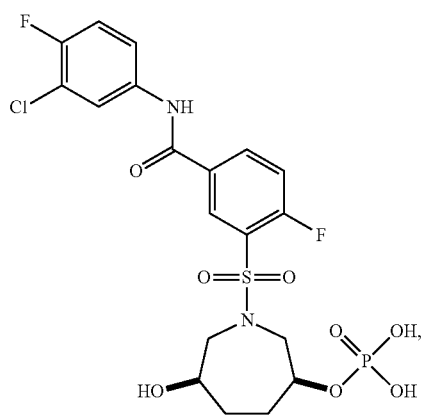

or a pharmaceutically acceptable salt thereof.

17. The method of claim 11, wherein each $R^1$ is, independently at each occurrence, halo.

18. The method of claim 11, wherein each $R^2$ is, independently at each occurrence, halo or —$C_1$-$C_6$ alkyl, wherein the alkyl is optionally substituted 1-3 times with halo.

19. The method of claim 11, wherein the compound is selected from:

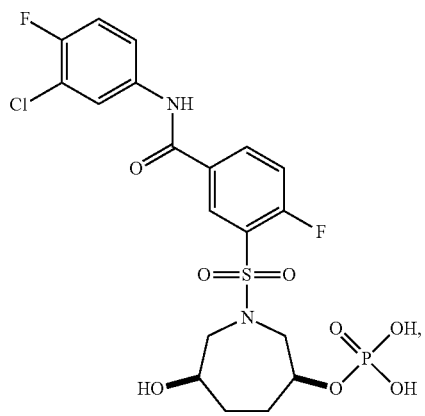

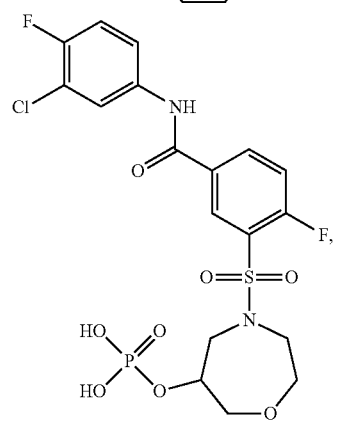

or
a pharmaceutically acceptable salt thereof.

20. The method of claim 11, wherein the compound is
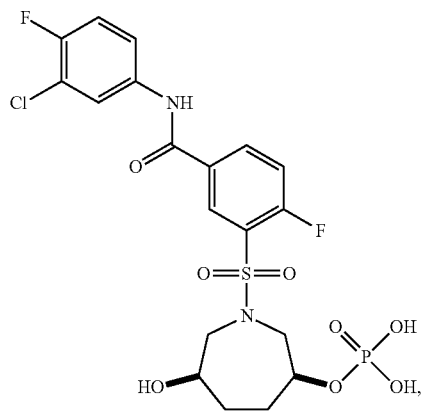 [SMILES: O=C(Nc1ccc(F)c(Cl)c1)c1ccc(F)c(S(=O)(=O)N2C[C@H](O)CC[C@H](OP(=O)(O)O)C2)c1]
or a pharmaceutically acceptable salt thereof.